United States Patent
Westphal et al.

(10) Patent No.: US 10,532,083 B2
(45) Date of Patent: Jan. 14, 2020

(54) METHODS FOR INDUCING DIFFERENTIATION OR CONVERSION OF WHITE ADIPOCYTES AND/OR PREADIPOCYTES TO BROWN ADIPOCITES USING FGF8

(71) Applicant: Technische Universität München, München (DE)

(72) Inventors: Sören Westphal, Ulm (DE); Tobias Fromme, Freising (DE); Martin Klingenspor, Freising (DE)

(73) Assignee: Technische Universität München, München (DE)

( * ) Notice: Subject to any disclaimer, the term of this patent is extended or adjusted under 35 U.S.C. 154(b) by 0 days.

(21) Appl. No.: 15/118,365

(22) PCT Filed: Feb. 13, 2015

(86) PCT No.: PCT/EP2015/053165
§ 371 (c)(1),
(2) Date: Aug. 11, 2016

(87) PCT Pub. No.: WO2015/121457
PCT Pub. Date: Aug. 20, 2015

(65) Prior Publication Data
US 2017/0258874 A1    Sep. 14, 2017

(30) Foreign Application Priority Data
Feb. 13, 2014 (EP) .................................... 14155088

(51) Int. Cl.
*A61K 38/18* (2006.01)
*A61K 45/06* (2006.01)
*A61K 8/64* (2006.01)
*A61Q 19/06* (2006.01)

(52) U.S. Cl.
CPC .......... *A61K 38/1825* (2013.01); *A61K 45/06* (2013.01); *A61K 8/64* (2013.01); *A61Q 19/06* (2013.01)

(58) Field of Classification Search
None
See application file for complete search history.

(56) References Cited

U.S. PATENT DOCUMENTS
6,037,329 A    3/2000    Baird et al.

FOREIGN PATENT DOCUMENTS

| EP | 2 359 843 | 8/2011 |
| WO | WO 2001-000662 | 1/2001 |
| WO | WO 2013-006486 | 1/2013 |
| WO | WO 2013-138795 | 9/2013 |
| WO | WO 2013-149258 | 10/2013 |

OTHER PUBLICATIONS

Korner et al. N. Engl. J. Med. 349(10): 926-928, 2003.*
Science. 280: 1363-1387, 1998.*
Kanasaki et al. J. Biomed. Biotech. vol. 2011, Article ID 197636, 11 pages, 2011.*
Lutz et al. Curr. Protoc. Pharmacol. Chapter: Unit 5.61, 2012.*
Beenken et al., "The FGF family: biology, pathophysiology and therapy," *Nature Reviews*, 8(3):235-253, 2009.
Kharitonenkov et al., "FGF-21 as a novel metabolic regulator," *Journal of Clinical Investigation*, 115(6):1627-1635, 2005.
PCT International Preliminary Report on Patentability issued in International Application No. PCT/EP2015/053165, dated Aug. 25, 2016.
PCT International Search Report and Written Opinion issued in International Application No. PCT/EP2015/053165, dated May 26, 2015.

* cited by examiner

Primary Examiner — Christine J Saoud
(74) *Attorney, Agent, or Firm* — Parker Highlander PLLC

(57) ABSTRACT

The present invention relates to polypeptides for use in treating diseases or disorders of energy homeostasis such as obesity, dyslipidemia, diabetes, insulin resistance, hyperglycemia or the metabolic syndrome. The invention also relates to polynucleotides encoding said polypeptides for use in treating diseases or disorders of energy homeostasis. Also provided by the present invention are pharmaceutical compositions comprising said polypeptides and polynucleotides for use in treating diseases or disorders of energy homeostasis. Said polypeptides, polynucleotides and pharmaceutical compositions may be administered locally, in particular locally into the visceral adipose tissue. Another aspect of the invention relates to a cosmetic product and the use of said cosmetic product for reducing body weight, in particular for reducing abdominal adipose tissue.

16 Claims, 24 Drawing Sheets

Specification includes a Sequence Listing.

FIGS. 1B-C
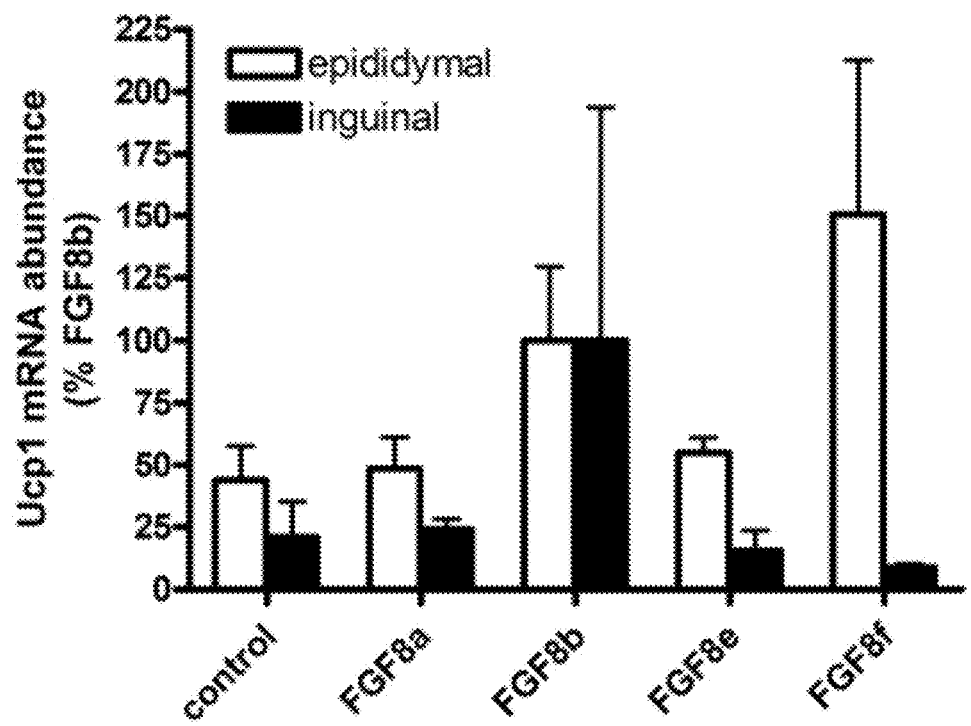
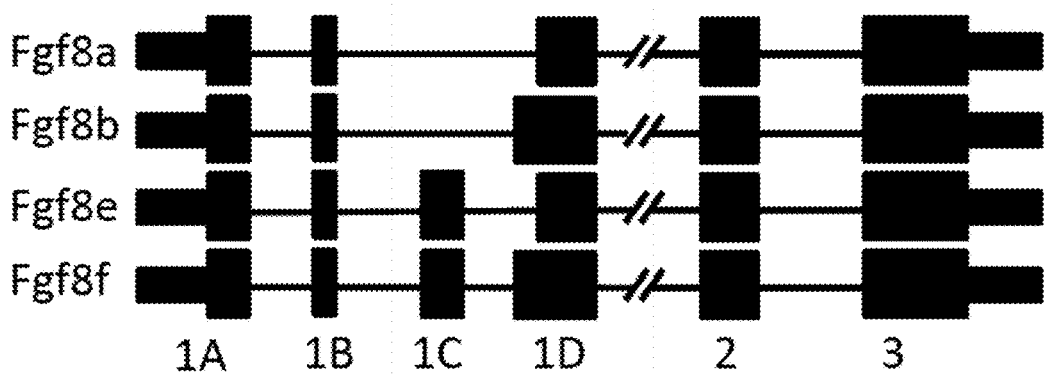

FIGS. 4A-D
A
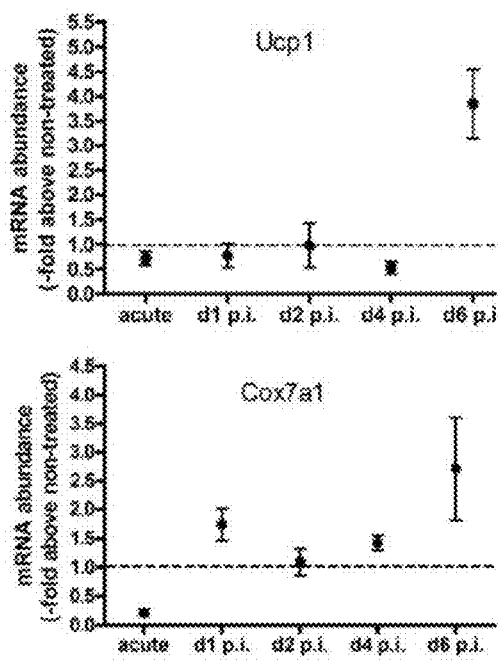
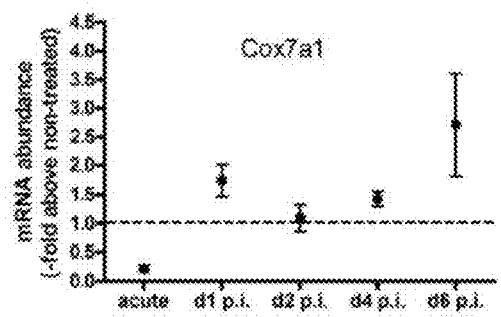
B
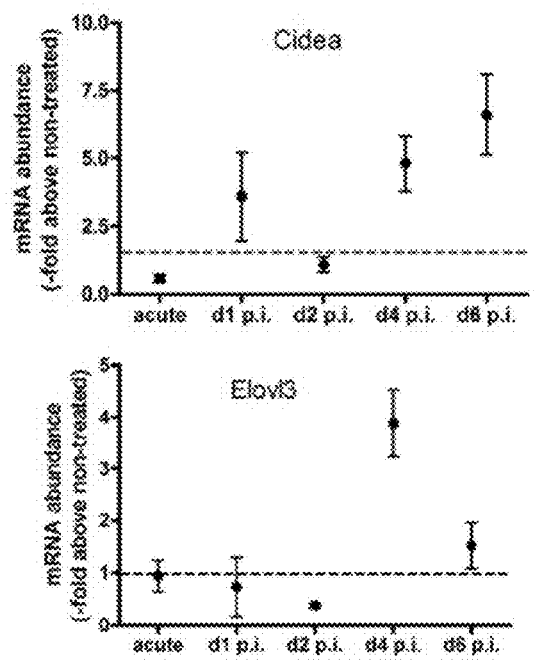
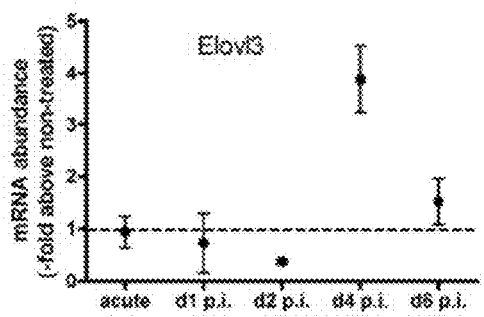
C
D

FIGS. 4E-H
E
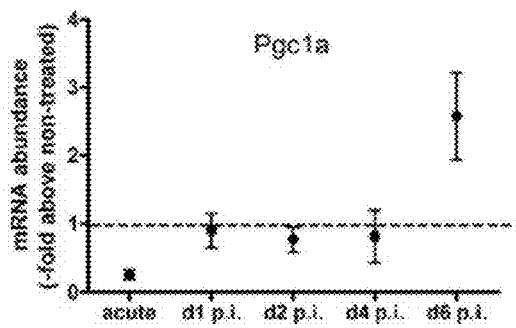
F
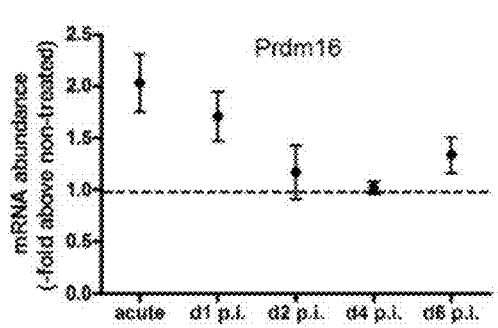
G
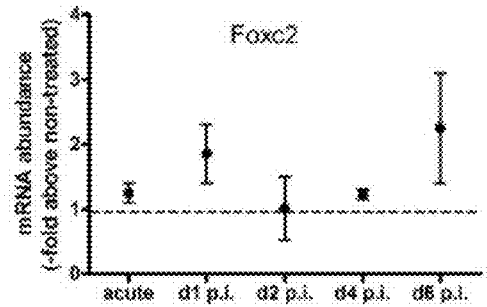
H
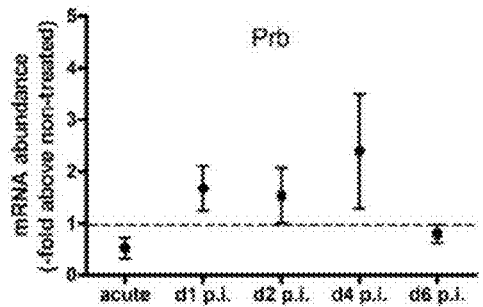

FIGS. 5A-B
A
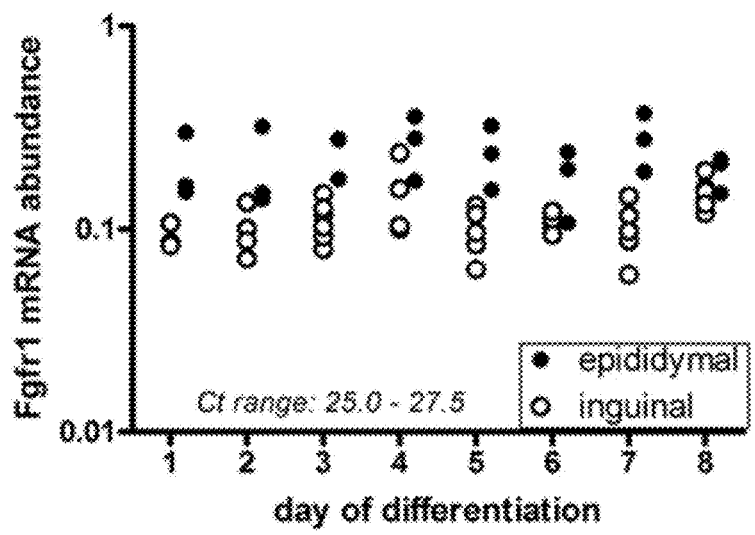
B
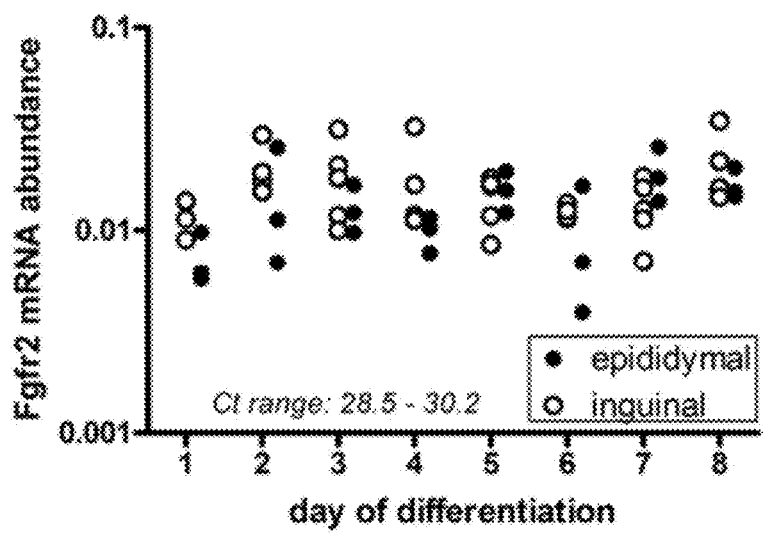

FIGS. 5C-D
C
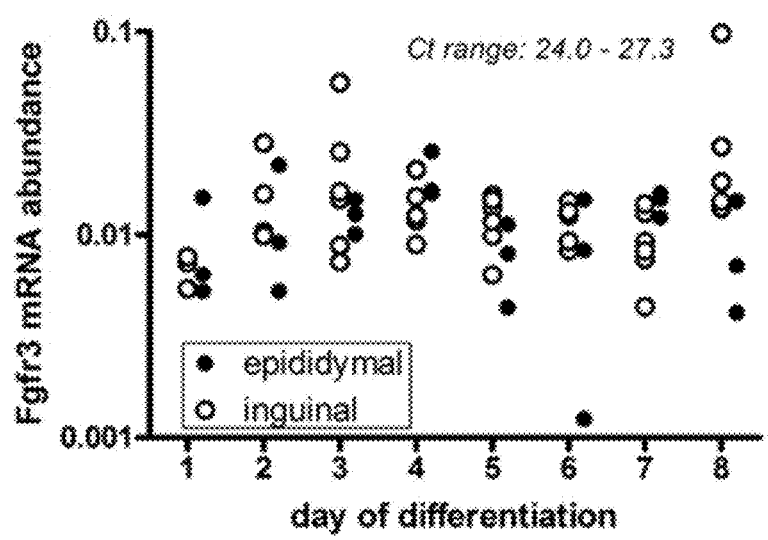
D
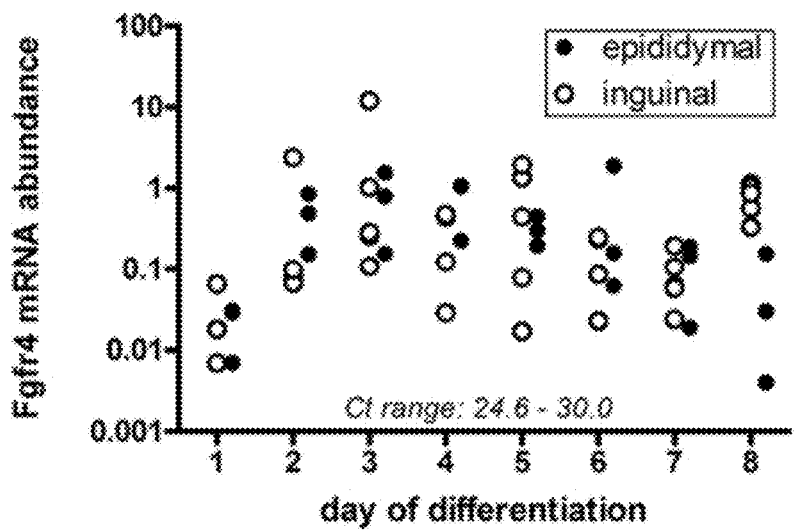

FIGS. 5E-F
E
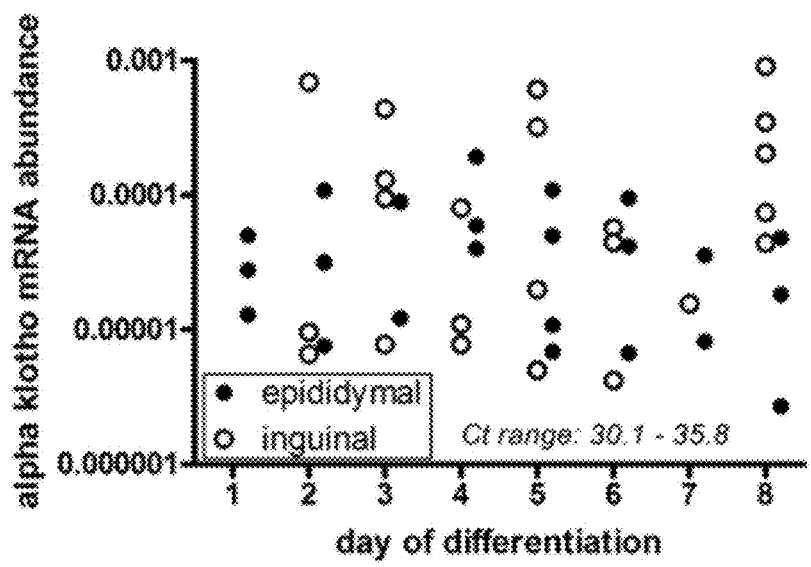
F
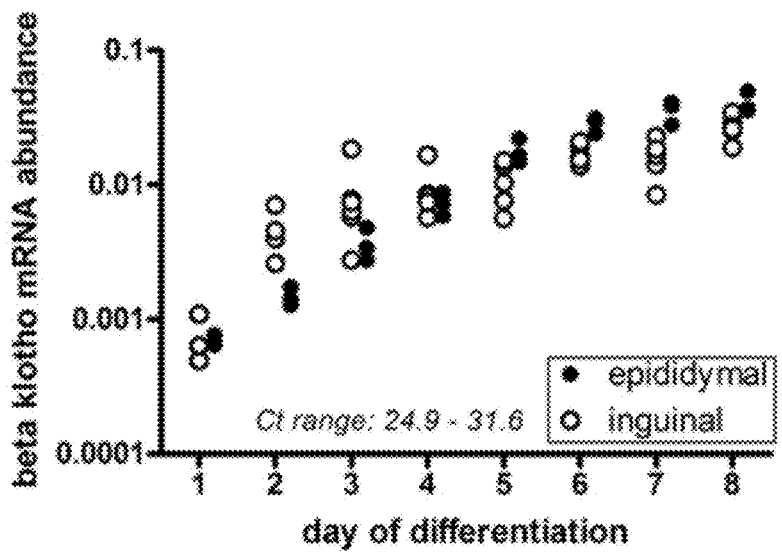

FIGS. 6A-B
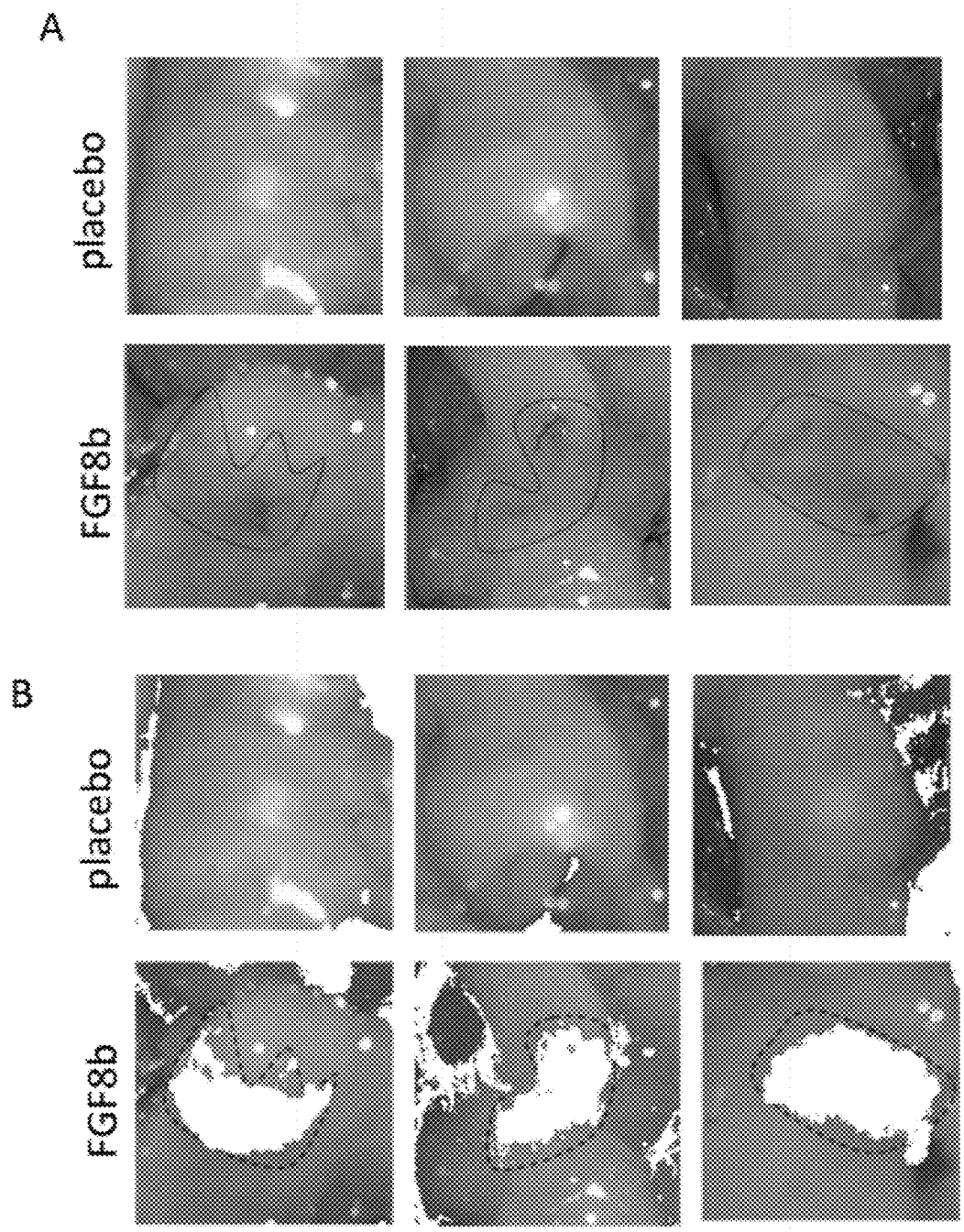

Figure 7E:
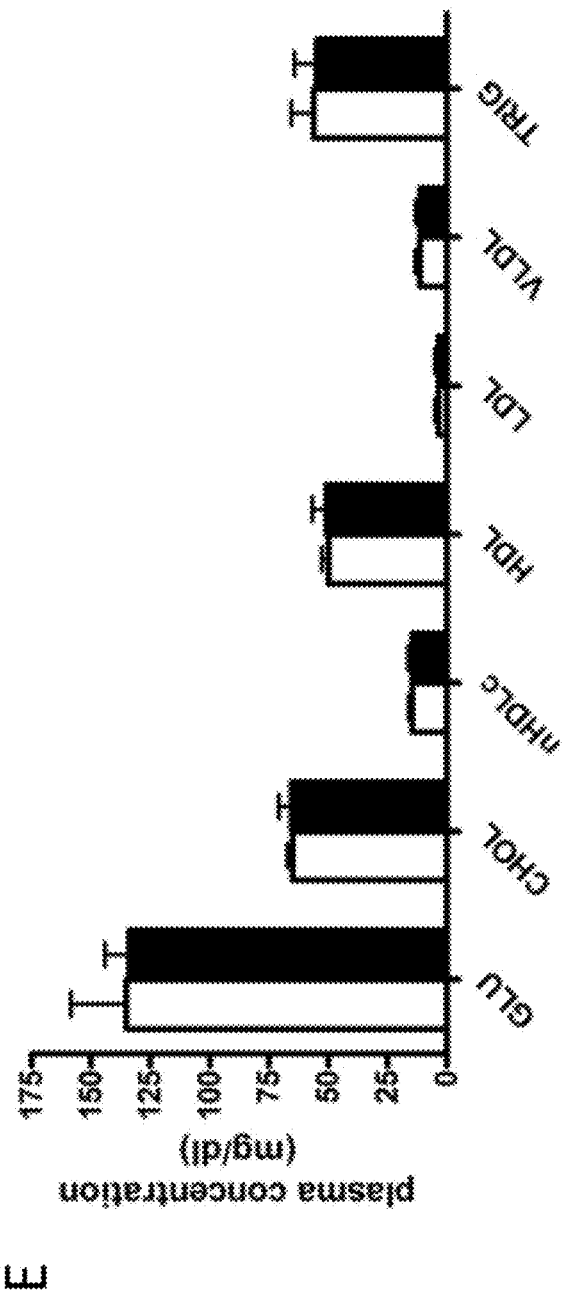

FIGS. 7A-B
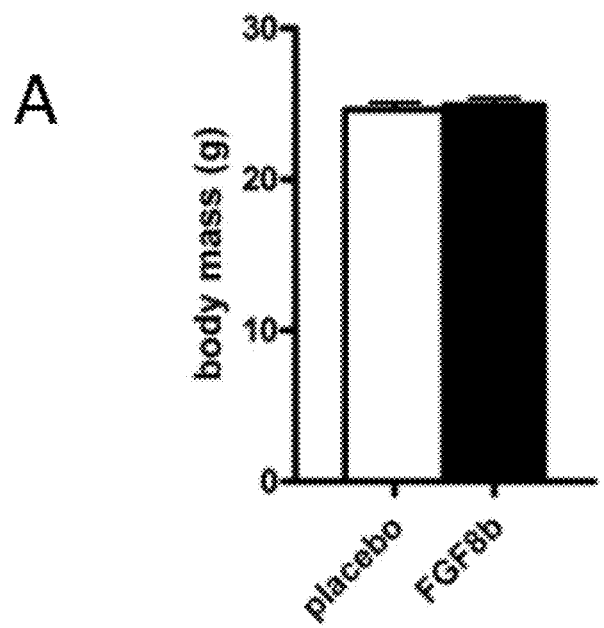
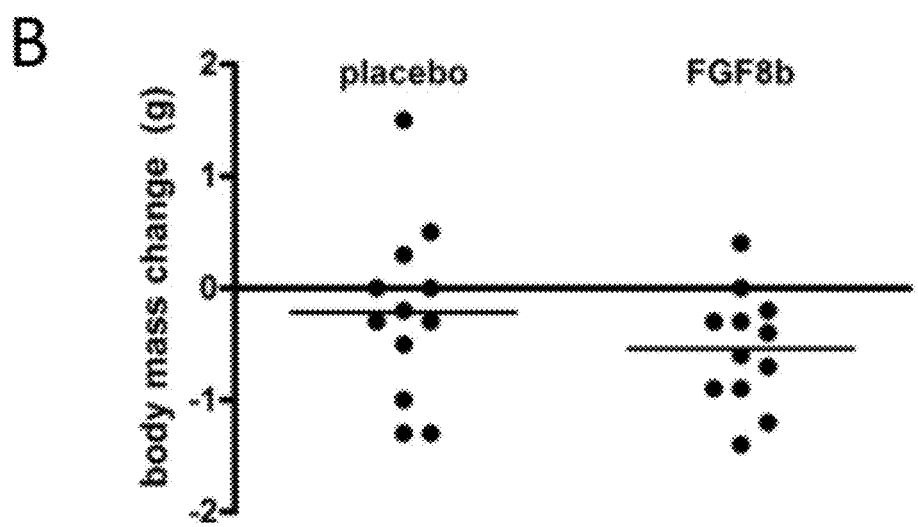

FIGS. 7C-D
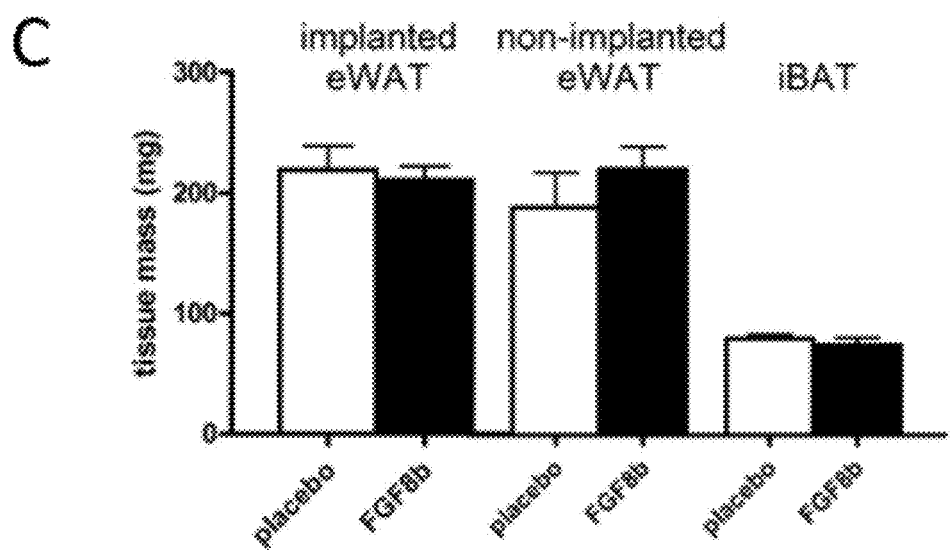
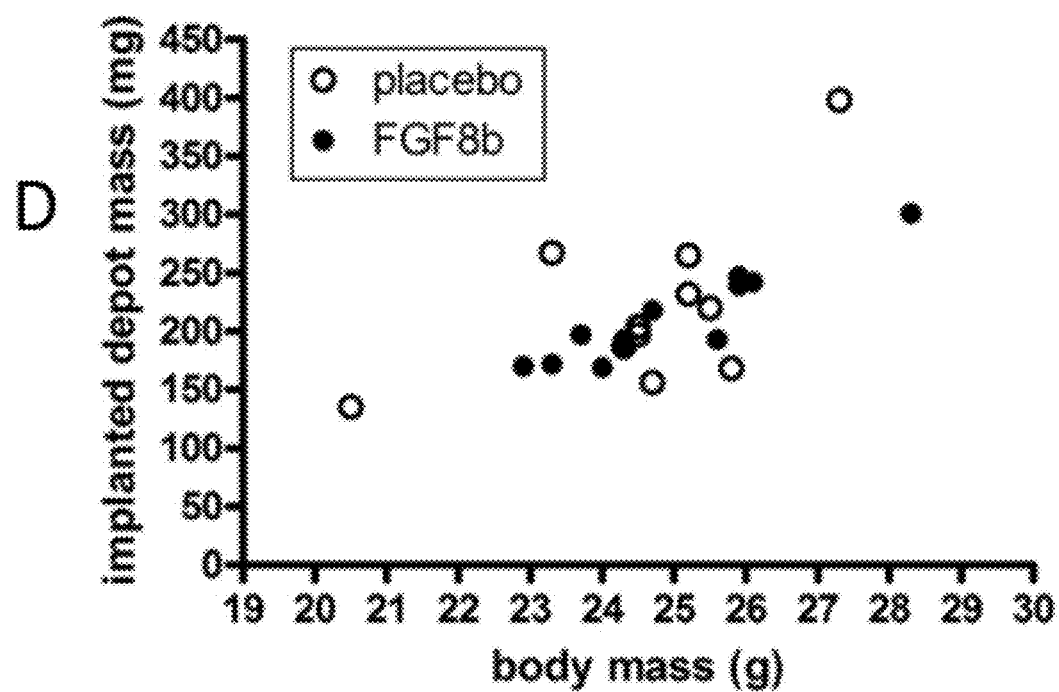

FIGS. 8A-B
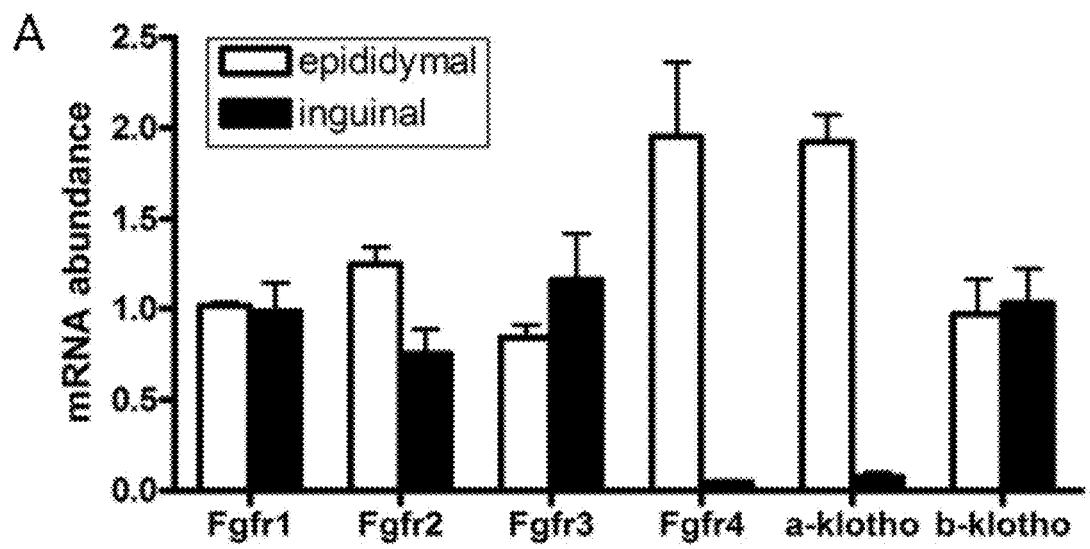
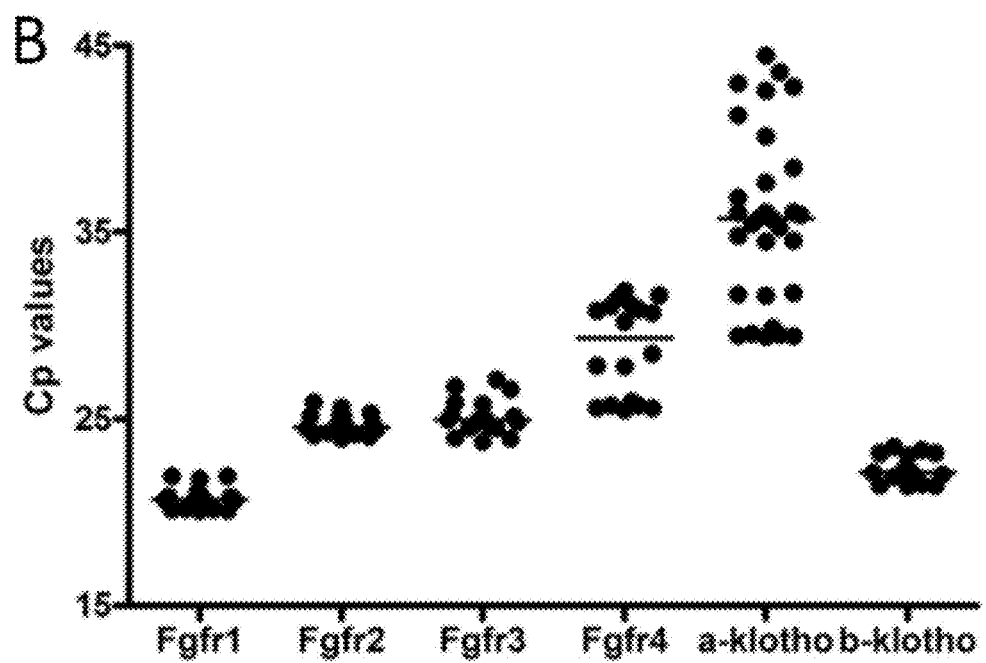

METHODS FOR INDUCING DIFFERENTIATION OR CONVERSION OF WHITE ADIPOCYTES AND/OR PREADIPOCYTES TO BROWN ADIPOCITES USING FGF8

This application is a national phase application under 35 U.S.C. § 371 of International Application No. PCT/EP2015/053165, filed Feb. 13, 2015, which claims priority to European Application No. 14155088.9, filed Feb. 13, 2014, the entire contents of each of which are incorporated herein by reference.

The present invention relates to polypeptides for use in treating diseases or disorders of energy homeostasis such as obesity, dyslipidemia, diabetes, insulin resistance, hyperglycemia and/or the metabolic syndrome. The invention also relates to polynucleotides encoding said polypeptides for use in treating diseases or disorders of energy homeostasis. Also provided by the present invention are pharmaceutical compositions comprising said polypeptides and/or polynucleotides for use in treating diseases or disorders of energy homeostasis. Said polypeptides, polynucleotides and/or pharmaceutical compositions may be administered locally, in particular locally into the visceral adipose tissue. Another aspect of the invention relates to a cosmetic product and the use of said cosmetic product for reducing body weight, in particular for reducing abdominal adipose tissue.

Obesity is a medical condition in which excess body fat has accumulated to an extent that it has an adverse effect on health, leading to reduced life expectancy and/or increased health problems. For example, obesity is associated with various metabolic disturbances, such as type 2 diabetes, insulin resistance, hyperglycemia, dyslipidemia, high blood pressure and metabolic syndrome. Obesity is most commonly the consequence of a misbalanced energy homeostasis caused by a misbalance of food energy intake and physical activity. However, the misbalanced energy homeostasis leading to obesity can also be the result of genetic susceptibility, endocrine disorders, medications and/or psychiatric illness.

Diseases of energy homeostasis such as obesity and secondary diseases of obesity (like diabetes, insulin resistance, hyperglycemia, dyslipidemia, high blood pressure and metabolic syndrome) are considered a major health issue. For example, obesity has emerged as a global health problem with more than 1.1 billion adults to be classified as overweight or obese (Oh, Curr Top Med Chem (2009), 9: 466-481). Nevertheless, treatment of diseases of energy homeostasis (such as obesity) is so far not satisfactory.

Mammals have two types of adipose tissue (i.e. fat), brown adipose tissue (BAT, also called brown fat) and white adipose tissue (WAT, also called white fat). The primary function of brown adipose tissue is to produce body heat in mammals without the necessity to shiver. In brown adipose tissue, body heat is produced by signaling the mitochondria to allow protons to run back along the proton gradient without producing ATP (proton leak). This is realized by the uncoupling protein 1 (Ucp1 or thermogenin) which allows re-entry of protons from the intermembrane space into the matrix, thereby bypassing ATP synthase, and thus, uncoupling oxygen consumption from ATP production. This alternative route for protons uncouples oxidative phosphorylation and releases energy as heat.

Brown adipose tissue is highly specialized for non-shivering thermogenesis. For example, as compared to white adipocytes, brown adipocytes have a higher number of mitochondria and these mitochondria have a high concentration of Ucp1 in the inner membrane. The term brown adipocytes refers to all types of thermogenic, UCP1 expressing and/or multilocular cells. These are sometimes categorized into "classical brown" versus "beige" or "brite" and others. The term brown adipocytes is intended to encompass all of this, e.g. "brown adipocytes in white adipose tissue" is synonym to both "beige" and "brite".

Brown adipocytes are not restricted to uniform, classical BAT depots but are often found interspersed in white adipose tissue (WAT) depots. This second type of brown adipocyte has been termed beige or brite (brown in white) and seems to emerge from a different progenitor cell than classical brown fat cells (reviewed in (Pfeifer & Hoffmann, 2014)). To convert WAT into BAT by means of recruiting brite cells offers a possibility to massively increase the BAT amount accessible to therapeutic activation and at the same time decreases the amount of WAT, thereby replacing an energy-storing organ with an energy-dissipating one. This browning of white fat has been subject to intense research during the last years and several systemic interventions have been identified increasing the number of brite cells in mice, including cold exposure and treatment with β-adrenergic agonists or cardiac natriuretic peptides (Bordicchia et al., 2012; Fisher et al., 2012; Guerra, Koza, Yamashita, Walsh, & Kozak, 1998; Young, Arch, & Ashwell, 1984).

Brown adipose tissue is especially abundant in newborns and in hibernating mammals. However, this tissue and its ability to combust nutrient energy into heat has recently gained increased attention by the scientific community after the repeated and convincing demonstration that adult healthy humans possess appreciable amounts of metabolically active BAT. It is accepted in the art that physiological or pharmacological activation of BAT thermogenesis is effective in treating some of the most widespread diseases of our time including obesity, dyslipidemia, diabetes, insulin resistance, hyperglycemia and metabolic syndrome.

The thermogenic function of brown adipose tissue (BAT) has been known for more than 50 years and has been subject to intense study. The specific properties of this tissue and its utility in the treatment of human metabolic disease are well accepted in the field and documented in numerous studies. A recent review stated that "from the literature, it is clear that expansion or increased activity of BAT in rodents is associated with a metabolically healthy phenotype." (Lidell, (2014) J Int Med 276, 364-377). The presence of BAT is associated with low body mass index, low total adipose tissue content and a lower risk of type 2 diabetes mellitus (Lidell, loc. cit.). Thus, it is accepted in the art that expansion or increased activity of BAT is associated with a healthy phenotype in animals and adult humans. Vice versa, it is accepted that a defect in BAT in animals and adult humans is associated with or is a cause of metabolic disorders like diabetes and obesity (Himms-Hagen (1979) CMA Journal 121, 1361-1364; Rothwell (1979) Nature 281, 31-35). Indeed, recent studies documented the presence of substantial amounts of metabolically active brown adipose tissue in healthy adult humans, while BAT was significantly reduced in overweight or obese adult humans (Saito (2009) Diabetes; Lichtenbelt (2009) NEJM 360, 1500-1508, Virtanen (2009) NEJM 360, 1518-1525).

It is evident that the limiting factor for the therapy of metabolic diseases and disorders is the low amount of brown adipose tissue in adult, especially overweight, humans (Bartelt & Heeren, (2014) *Nat Rev Endocrinol,* 10(1), 24-36; Klingenspor, M., Fromme, T. (2012). Brown adipose tissue. In M. E. Symonds (Ed.), *Adipose Tissue Biology* (Vol. 414). Heidelberg: Springer; Saito et al., (2009) *Diabetes,* 58(7), 1526-1531; Virtanen et al., (2009) NEJM 360, 1518-1525). Animal experiments have indeed demonstrated that metabolic diseases and disorders like diabetes type I and II, obesity and hyperlipidemia can be treated by increasing the amount of active BAT (e.g. by converting white adipocytes into brown adipocytes); further it is accepted in the art that corresponding results can be obtained in therapy of humans suffering from metabolic diseases and disorders (Cinti (2006) Nutr Metabol Cardiovas Dis 16, 569-574; Bartelt (2011) Nature Medicine doi:10.1038/nm.2297); Gunawardana (2012) Diabetes 61, 674-682; Gunawardana (2014) World J Diabet 15, 420-430; Roman (2014) Translational Research, 1-15.

The properties of active brown adipose tissue that constitute its potential to counteract specific metabolic diseases are outlined in the following:

In relation to obesity and related disorders it is accepted that brown adipose tissue is characterized by its ability to release chemical energy as heat. Specific heat production is enormous and ranges from approx. 150 to 500 Watt/gram tissue in rodents. Increasing the mass of active brown adipose tissue necessarily leads to increased total energy expenditure and therefore to weight loss, assuming no compensation by increased food intake. The possibility to utilize active brown fat to counter obesity is generally accepted in the field and consequence of fundamental thermodynamics (Himms-Hagen, 1979; Klingenspor, 2012; Rothwell & Stock, 1979).

In relation to diabetes it is known that brown adipose tissue imports and combusts large amounts glucose from the blood stream. In fact, the first unambiguous demonstration of active brown fat in humans relied on a high uptake of labelled glucose and is thus a certain property of human brown fat (van Marken Lichtenbelt et al., 2009; Virtanen et al., 2009). This property can be applied to counter excessive glucose levels that are the primary manifestation of diabetes. In a rodent model, a brown adipose tissue transplant into a white adipose tissue depot even effectively cures diabetes (Gunawardana & Piston, 2012).

The following non-limiting references support the utility of BAT in the therapy of metabolic diseases and disorders, like obesity and diabetes as well as related disorders, such as insulin-resistance, hyperglycemia and metabolic syndrome. For example, Lidell et al. (2014, loc. cit.) disclosed that "pharmacologic interventions that activate and expand BAT would provide a very attractive means for weight reduction, especially in individuals unable to exercise" and that "data from rodents provide robust indications for amelioration of insulin resistance upon physiological or pharmacological stimulation of BAT." Gunawardana (2014, loc. cit) stated that "increasing the content of endogenous brown adipose tissue is known to combat obesity and type 2 diabetes in both humans and animal models." Roman et al., (2014, loc. cit.) confirmed that "ultimately, the long-term effect of increasing BAT is expected to improve energy expenditure, leading to weight loss and increased insulin sensitivity." "a BAT phenotype of the adipose organ in rodents is important for the prevention of obesity and diabetes. [ . . . ] in vivo and in vitro data suggest that the human adipose organ react similarly to the murine adipose organ."

In relation to dyslipidemia, it is known in the art that the excessive metabolic rate of active brown adipose tissue is mainly fueled by lipids which are partially imported from the blood stream. In the active state, brown adipose tissue is considered the master regulator of triglyceride rich lipoprotein clearance and blood lipid abundance (Bartelt et al., 2011). From these established properties it is evident that increased mass of active brown fat can be utilized to lower pathological levels of circulation lipoproteins and lipids. For example, Bartelt et al., (2011, loc. cit. disclose that "BAT activation is able to correct hyperlipidemia". Bartelt & Heeren (2014, loc. cit.) described the following in relation to hyperlipidaemia: "The activation of brown adipose tissue (BAT), the primary organ for heat production, confers beneficial effects on adiposity, insulin resistance and hyperlipidaemia, at least in mice. As the amount of metabolically active BAT seems to be particularly low in patients with obesity or diabetes mellitus who require immediate therapy, new avenues are needed to increase the capacity for adaptive thermogenesis."

Summarizing the above it is evident that an increase in active brown adipose tissue necessarily leads to an improvement in the primary manifestations of a disease or disorder of energy homeostasis, like obesity, diabetes, dyslipidemia, insulin resistance, hyperglycemia and metabolic syndrome.

The amount of human BAT, however, is limited and estimated to account for approximately 0.05-0.1% of body mass as compared to a far more than 10-fold higher specific amount in mice. Thus, to therapeutically use the unique capabilities of BAT in humans, not only acute activators may be required, but also agents that recruit a greater number of brown adipocytes.

Brown adipocytes are not restricted to uniform, classical BAT depots but are often found interspersed in otherwise white adipose tissue depots. This second type of brown adipocytes has been termed beige or brite (brown in white) and seems to emerge from a different progenitor cell than classical brown fat cells. To convert WAT into BAT by means of recruiting brite cells offers a possibility to massively increase the BAT amount accessible to therapeutic activation and at the same time would decrease the amount of WAT, thereby replacing an energy-storing tissue with an energy-dissipating one. This browning of white fat has been subject to intense research during the last years. Meanwhile, several systemic interventions are known which at least to a certain degree increase the number of brite cells in mice. These systemic interventions include cold exposure and treatment with β-adrenergic agonists, cardiac natriuretic peptides or fibroblast growth factor 21 (FGF21). However, these compounds act systemically which bears the risk of severe side effects. Moreover, these compounds mainly target subcutaneous adipose tissue, although particularly the visceral adipose tissue is known to correlate with secondary diseases arising from obesity such as diabetes, metabolic syndrome, cardiovascular disease and premature death (see, e.g., Fisher, Genes & Development (2012) 26, 271-281 and Bordicchia et al. (The Journal of clinical investigation (2012) 122, 1022-36).

Thus, there is a need for medical intervention of diseases or disorders of energy homeostasis.

Accordingly, the technical problem underlying the present invention is the provision of means and methods for the medical intervention of diseases or disorders of energy homeostasis, such as obesity, like central obesity.

This technical problem has been solved by the embodiments provided herein and as described in the claims and illustrated in the appended examples.

Accordingly, the present invention relates to a polypeptide for use in treating a disease or disorder of energy homeostasis, wherein said disease or disorder is obesity, dyslipidemia, diabetes, insulin resistance, hyperglycemia or metabolic syndrome, and wherein the polypeptide is selected from the group consisting of:
(a) a polypeptide comprising an amino acid sequence encoded by a nucleic acid molecule having the nucleic acid sequence as depicted in SEQ ID NO: 2 or the nucleic acid sequence comprising nucleic acid residues 67-648 in SEQ ID NO: 2;
(b) a polypeptide comprising an amino acid sequence as depicted in SEQ ID NO: 16 or an amino acid sequence comprising amino acids 23-215 in SEQ ID NO: 16;
(c) a polypeptide comprising an amino acid sequence encoded by a nucleic acid molecule hybridizing under stringent conditions to the complementary strand of a nucleic acid molecule as defined in (a) and encoding a functional polypeptide, wherein the function comprises the ability to induce differentiation or conversion of white adipocytes and/or preadipocytes to brown adipocytes;
(d) a polypeptide having at least 40% identity to the polypeptide of any one of (a) to (c), whereby said polypeptide is functional, wherein the function comprises the ability to induce differentiation or conversion of white adipocytes and/or preadipocytes to brown adipocytes; and
(e) a polypeptide comprising an amino acid sequence encoded by a nucleic acid molecule being degenerate as a result of the genetic code to the nucleotide sequence of a nucleic acid molecule as defined in (a) and (c).

The function of the above described polypeptide of the invention is the ability to induce differentiation or conversion of white adipocytes and/or preadipocytes (in particular white visceral adipocytes and/or white visceral preadipocytes) to brown adipocytes. The term "brown adipocytes" as used herein refers to all types of thermogenic, UCP1 expressing and/or multilocular cells. "Brown adipocytes" are in particular defined by expression of uncoupling protein 1 (herein also "UCP1", "UCP-1", "ucp-1". "Ucp1" or "Ucp1", i.e. abbreviations as used in the art). The sequence and function of Uncoupling protein 1 (UCP-1) is well documented in the art and disclosed, inter alia, in Aquila et al. (1985) EMBO J 4(9):2369-2376; Bouillaud et al. (1986). J Biol Chem 261(4):1487-1490; Cassard et al., J Cell Biochem. 1990 July; 43(3):255-64, Nedergaard et al. Biochim Biophys Acta. (2001) Mar. 1, 1504(1):82-106. Brown adipocytes are sometimes categorized into "classical brown" versus "beige" or "brite" and others. The term brown adipocytes is intended to encompass all of this, e.g. "brown adipocytes in white adipose tissue" is synonym to both "beige" and "brite".

The present invention solves the above identified technical problem since, as documented herein below and in the illustrative appended examples, it was surprisingly found that certain paracrine FGFs (including FGF8b, FGF8f and/or FGF17) induce browning of white adipose tissue.

Figure 1A:
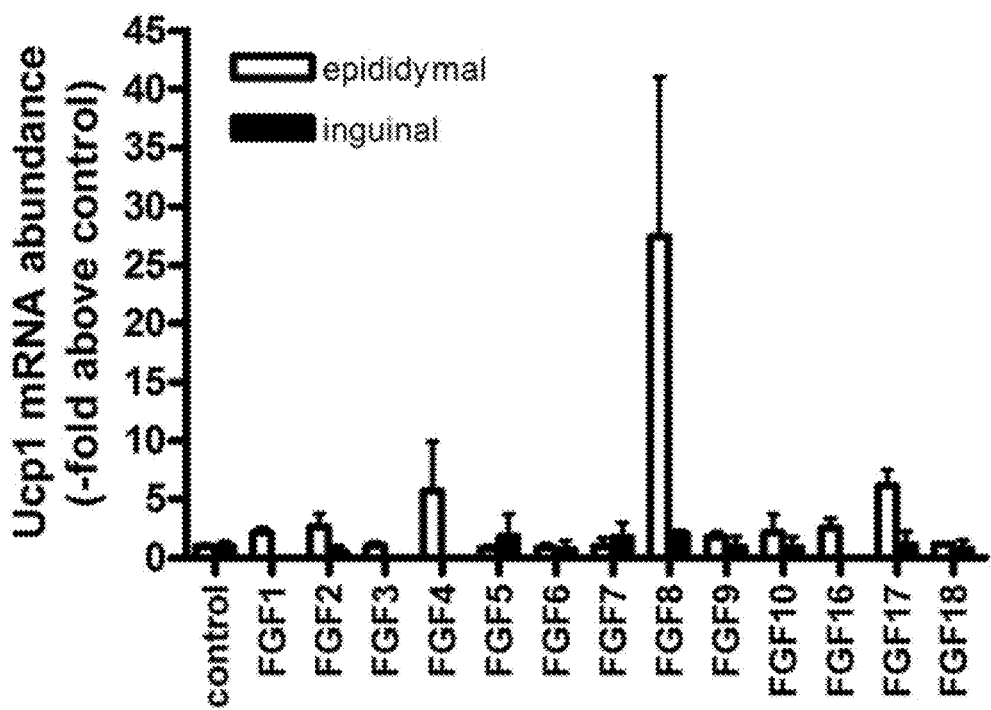

The appended examples show that paracrine FGF8 and FGF17 of murine origin induced the expression of brown adipocyte specific gene uncoupling protein 1 (Ucp1/UCP1) in white adipocyte cell lines derived from murine inguinal and epididymal adipose tissue depot; FIG. 1A. Brown adipocyte specific gene uncoupling protein 1 (Ucp1) is a recognized marker of brown adipocytes; see, for example, Sharp L Z, et al., PLOS ONE, 2012 "Human BAT possesses . . . ". In fact, the presence of thermogenic Ucp1 is the decisive hallmark of a functional brown adipocyte.

Murine FGF8 comprises 8 differently spliced transcripts leading to 8 different proteins FGF8a-h. Four of the eight murine FGF8 isoforms are also present in humans, i.e. FGF8a, b, e and f. Human and murine FGF8 isoforms have the following level of identity of amino acid sequences: FGF8a 100%, FGF8b 100%, FGF8e 98.28%, FGF8f 98.36%. Human and murine FGF8 isoforms have the following level of identity of nucleic acid level: FGF8a: 94.96%, FGF8b 95.22%, FGF8e 94.59%, FGF8f 94.83%.

FGF8 isoforms FGF8b and FGF8f are shown to induce Ucp1 mRNA expression in murine adipocytes, while isoforms Fgf8a and FGF8e did not induce Ucp1 mRNA expression; FIG. 1B. Fgf8b was highly effective in inducing Ucp1 expression in murine adipocytes of both inguinal and epididymal origin. FGF8f was only effective in inducing Ucp1 expression in adipocytes of epididymal adipocytes. Epididymal fat is viscerally located, while inguinal fat is subcutaneously located. Both paracrine FGFs are accordingly effective in viscerally located fat. In humans, omental fat is the dominant visceral adipose tissue depot and thus functionally comparable to the murine epididymal fat depot. Further, the presence of visceral fat is more dangerous in terms of health risk.

Figure 2A:
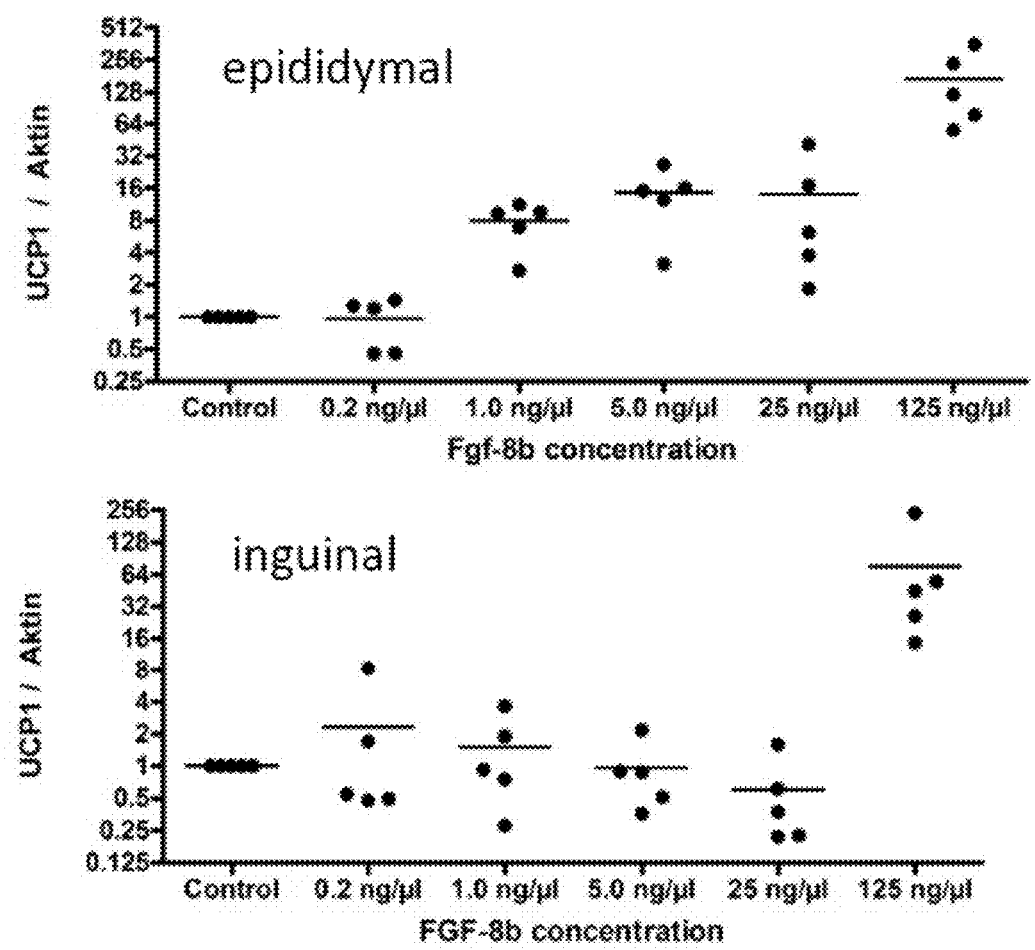
Figure 2B:
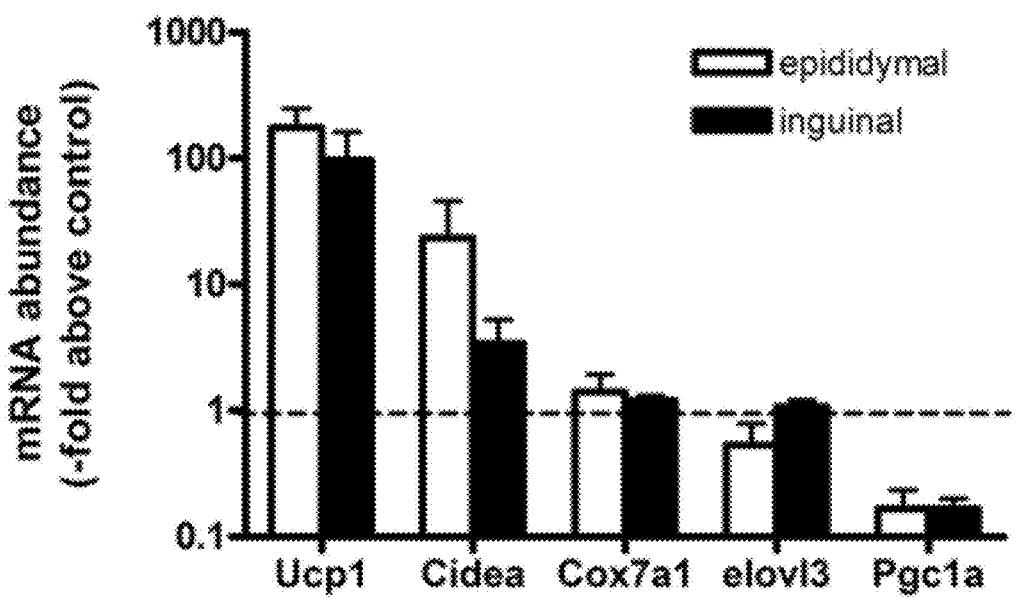

As documented in the appended examples, FGF8b could be shown as capable of increasing Ucp1 mRNA expression level in adipocytes of both inguinal and epididymal origin in a dose-response study; FIG. 2A. Further, FGF8b increased the expression level of cell death-inducing DNA fragmentation factor alpha like effector A (Cidea) in adipoocytes with a greater effect size in epididymal as compared to inguinal adiopcytes; FIG. 2B. Cell death-inducing DNA fragmentation factor alpha like effector A (Cidea) is a known marker of brown adipocytes; see, for example, Sharp L Z, et al., PLOS ONE, 2012 "Human BAT possesses . . . ". I Thus, the appended in vitro experiments show that paracrine FGFs (including FGF8b, FGF8f and/or FGF17, especially FGF8b,) induce the expression level of markers of brown adipocytes (like Ucp1 and Cidea).

Subsequent in vivo experiments as provided herein, document the capacity of FGF8b to induce differentiation or conversion of white adipocytes and/or preadipocytes to brown adipocytes. FGF8b was surprisingly shown herein to effectively transform epididymal white adipose tissue into brown adipose tissue; FIG. 6. To this end, pellets that release 100 ng FGF8 per day and placebo pellets were implanted into the epididymal white adipose tissue of adult mice. Brown adipocytes are not restricted to uniform, classical BAT depots but are often found interspersed in white adipose tissue (WAT) depots. This second type of brown adipocyte has been termed beige or brite (brown in white). To convert WAT into BAT by means of recruiting brite cells offers a possibility to massively increase the BAT amount.

Figure 6C:
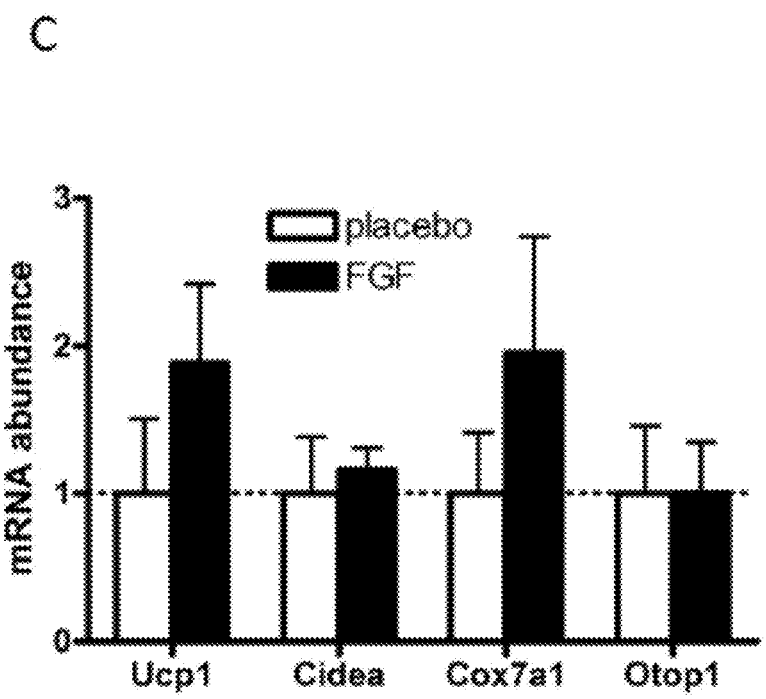

After three weeks the mice were sacrificed and the tissue analyzed. By visual inspection, the implantation site of FGF8b pellets and the surrounding tissue was of brown colour. By contrast, the non-implanted contralateral depot and the implantation site of placebo remained white; FIG. 6A. The "browning" effect is even more clearly shown in FIG. 6B. Here, the brown area of the images of FIG. 6A were digitally converted into white area. The browning effect of FGF8b is evident compared to placebo. Also brown adipocyte markers Ucp1 and Cox7a1 are increased in the depot; FIG. 6C. Cox7a1 is a marker for BAT; see Beige Adipocytes are a Distinct Type of Thermogenic Fat Cell in Mouse and Human" (Jun Wu et al, Cell (2012).

Thus, the in vivo experiments show that FGF8b is capable of increasing/inducing brown adipose tissue (BAT). Brown adipose tissue also comprises white adipose tissue (WAT) with interspersed brown adipocytes (beige or brite adipocytes). This documented increase/induction may be due to induction of differentiation/conversion of white adipocytes to brown adipocytes and/or differentiation of white preadipocytes to brown adipocytes or may be due to recruitment of brown adipocytes.

Therefore, the in vitro and in vivo experiments of the present invention demonstrate that paracrine FGFs, (including FGF8b, FGF8f and/or FGF17, preferably FGF8b) have the capacity to increase or induce brown adipose tissue (BAT). Thus, the data in the present application establish a causal link between paracrine FGFs (including FGF8b, FGF8f and/or FGF17, preferably FGF8b) and BAT.

As explained above, it is accepted in the art that an increase in active brown adipose tissue (BAT) necessarily leads to an improvement in the primary manifestations of a disease or disorder of energy homeostasis, like obesity, diabetes, dyslipidemia, insulin resistance, hyperglycemia and/or metabolic syndrome.

Therefore, the present application provides a clear and plausible teaching that paracrine FGFs, (including FGF8b, FGF8f and/or FGF17, preferably FGF8b) can be used in the therapy of diseases or disorders of energy homeostasis, like obesity, diabetes, dyslipidemia, insulin resistance, hyperglycemia and/or metabolic syndrome.

Thus, paracrine FGFs, (including FGF8b, FGF8f and/or FGF17, preferably FGF8b) are used as the active agent(s) (preferably as the therapeutic agent(s)) in accordance with the present invention.

Certain data provided herein do not show a difference in body weight or blood parameters including glucose, plasma lipids and liver enzymes between FGF8b- and placebo-treated animals. These data do, however, not challenge the finding that paracrine FGFs can suitably be used in the therapy of diseases or disorders of energy homeostasis, since the corresponding experiments were not designed to show an effect of FGF8b on body weight or blood parameters. The miniscule amount of recruited brown fat by implantation of a single pellet releasing FGF8b was not designed or expected to affect metabolic parameters in these particular experimental settings. In particular, the experiments were not conducted in disease models, but in healthy, lean mice. Accordingly, these experiments were not designed to detect amelioration of disease parameters (as they are absent to start with) and rather demonstrate the absence of unwanted effects on the healthy phenotype.

In contrast, in particular the in vivo experiments were designed to prove and document the capacity of FGF8b to recruit brown fat. The experiments of this invention successfully confirmed said capacity. Once the capacity to recruit brown fat is established and confirmed in vivo, the therapeutic effect is not only plausible but also credible since the art acknowledges the clear and evident (positive) link between BAT and therapy of disease or disorder of energy homeostasis, like obesity, diabetes, dyslipidemia, insulin resistance, hyperglycemia and/or metabolic syndrome.

The therapeutic effect of paracrine FGFs (including FGF8b, FGF8f and/or FGF17, preferably FGF8b) can be validated in suitable experiments. For example, it is known in the prior art that the amount of BAT which is described as therapeutically effective in the treatment of metabolic diseases, is in the range of 1% of body mass; see Klingenspor & Fromme (2012). The amount of BAT formed/recruited in the in vivo experiments in the present invention was far below this range. Therefore, a therapeutic effect is envisaged and expected (also in suitable animal models), if the amount of BAT is increased to the level (or above) reported in the prior art. This may, for example, be achieved by increasing the dose of paracrine FGFs, treatment time and pellet number.

FGF8b dose-dependently increases the expression of several markers of brown adipose tissue, including Ucp1. Moreover, the appended examples demonstrate that the paracrine FGFs of the invention (e.g. FGF8b) reprogram both, proliferating and differentiating preadipocytes. Accordingly, the present invention takes advantage of a known mammalian physiological mechanism. In particular, as mentioned above, brown adipose tissue can cause direct energy output in the form of heat which allows mammals to maintain their high body temperature in a cold environment. In this mechanism the uncoupling protein 1 (Ucp1) effects that stored energy is directly converted into heat. This reaction takes place in brown adipose tissue, which is also present in humans. Accordingly, the present invention provides means and methods for replacing an energy-storing organ with an energy-dissipating one, thereby paving the way for reliably reducing fat mass. Moreover, BAT displays a high uptake of both glucose and lipoproteins from the bloodstream. Since Diabetes mellitus has a prevalence of 8.3% worldwide and affects 382 million individuals in 2013 care providers are in desperate need of innovative therapeutic approaches for treating this condition. Especially diabetes mellitus type 2 is highly associated with obesity and its hallmark is peripheral insulin resistance especially in the obese. Furthermore, a high concentration of circulating free fatty acids in the overweight patients is toxic for insulin-producing beta-cells of the pancreas. Unfortunately there is nearly none—apart from metformin—established therapeutic agent in treating diabetes without increasing body weight. And even metformins impact on reducing body weight is only minor. All other medications, insulin in particular, result in rising body weight. Accordingly, by augmenting the amount of BAT the present invention thus provides means and methods for the reduction of glucose and lipid plasma levels in diabetic and dyslipidemia patients.

In general, brown adipose tissue removes glucose from the blood stream dependent on tissue mass and activation state. At a given sympathetic tone in white adipose tissue, increasing the mass of brown fat increases the amount of removed glucose. Additionally, the sympathetic tone can be increased (i.e. by fasting) or mimicked by acute co-administration of sympathomimetic drugs, such as indirect sympathomimetics (e.g. ephedrine, methylphenidate). In both cases, brown adipose tissue activity can be expected to not only actively remove glucose, but also increase the insulin sensitivity of other tissues (Lidell et al., 2014, loc. cit.).

Different forms of application can be envisioned in the therapy of diabetes:

First, therapy with paracrine FGFs, preferably FGF8b, can be used to improve insulin sensitivity in combination with insulin and/or alternative diabetes drugs like the biguanids metformin, phenformin, buformin, and proguanil, the glitazones like rosiglitazone, pioglitazone, lobeglitazone, troglitazone, netoglitazone, and rivoglitazone, the glucagon-like Peptide-1 (GLP-1)-receptor agonists like exenatide, liraglutide, lixisenatide, albiglutide, dulaglutide, and taspoglutide, the dipeptidyl-Peptidase-4 (DPP-4) inhibitors like sitagliptin, vildagliptin, saxagliptin, linagliptin, anagliptin, teneligliptin, alogliptin, gemigliptin, dutogliptin, berberine, and lupeol, the group of the sulfonyl ureas like carbutamid, tolbutamid, glibenclamid, glibornurid, gliclazid, glipizide, gliquidon, glisoxepid, glycodiazin, and glimepiride, the alpha-glucosidase inhibitor arcabose, and miglitol, and the group of the sodium dependent glucose transporter (SGLT)-2 inhibitors like canagliflozin, empagliflozin, ipragliflozin, and tofogliflozin. The intended outcome of such therapy would be the reduction of previous, combined medication. In less severe cases this may ultimately lead to complete replacement.

Second, by combination of paracrine FGF treatment, preferably FGF8b treatment, with a sympathomimetic drug (such as indirect sympathomimetics (e.g. ephedrine, methylphenidate), patient may be able to regulate glucose disposal specifically to their individual need and thus replace insulin treatment.

The herein provided therapy with paracrine FGFs is suitable for the treatment of both diabetes type 1 and diabetes type 2. Primarily, the therapy effects a lowering/decrease of glucose levels in the blood. Moreover, an increased amount of BAT improves/increases insulin sensitivity which is of primary benefit in the treatment of diabetes type 2. In relation to diabetes type 1 it may be conceivable to use the herein provided therapy with paracrine FGFs in emergency cases, like acute hyperglycemia.

Previously known therapeutic approaches for the treatment of obesity (and secondary diseases arising from obesity) mainly consist of the reduction in caloric intake (e.g. through diets, pharmacotherapy with appetite suppressants, operational or mechanical measures, inhibition of food adsorption, etc.) and the increase of calorie consumption (e.g. by physical activity). These treatments, however, often do not lead to the desired and long-term weight reduction.

In contrast, with the help of the means and methods provided by the present invention, effective and lasting weight reduction can be achieved. In particular, the amount and duration of administration of the herein provided paracrine FGFs (e.g. FGF8b, FGF8f or FGF17) may be controlled, and thereby the body weight may be reduced up to normal or ideal weight. The ideal human body weight has been a topic of debate forever, is changing over times and is different between cultures. A lot of formulas and theories have been invented, but a broadly accepted answer is still not found. Generally speaking, the ideal weight should be unique for everyone. The major factors that contribute to a person's ideal weight are height, gender, age, body composition, body type, fat distribution and others. From a medical standpoint the ideal weight is the individual body weight without negative influence on health. i.e. a normal height/body mass equation along with regular body mass composition, especially body fat composition. In addition, by constant or repeated administration of the paracrine FGFs of the invention, a lasting weight reduction can be achieved. A method for reliably and sustainable reducing body weight is of high value in the treatment of obesity or secondary diseases of obesity, such as metabolic syndrome which goes along with severe health problems. In addition, using the paracrine FGFs of the present invention for reducing body weight makes it possible to prevent the occurrence of both, obesity (and obesity-related diseases such as the metabolic syndrome), and its short- and long-term health effects (such as atherosclerosis, strokes and heart attacks). Thus, the means and methods provided herein may significantly increase quality of life and life expectancy of overweight or obese individuals.

In the prior art, $\beta_3$-adrenergic receptor (also called $\beta_3$-adrenoceptor or $\beta_3$-adrenoreceptor) agonists have been shown to be effective thermogenic anti-obesity and insulin-sensitizing agents in rodents. However, due to severe side effects and very complex receptor specificity in humans, $\beta_3$-adrenergic receptor agonists could not be brought to market (Arch, European Journal of Pharmacology 440 (2002) 99-107). As shown in the appended examples, the paracrine FGFs provided by the present invention (e.g. FGF8b, FGF8f and/or FGF17) offer the possibility to achieve brown fat recruitment by a different signaling route. In particular, the illustrative appended examples demonstrate that FGF8b effectively induces conversion of white visceral adipose tissue into brown adipose tissue in mice, wherein a panel of blood parameters including glucose, plasma lipids and liver enzymes do not differ between FGF8b and placebo treated animals.

WO 01/00662 speculates that human FGF8 might be used in the therapy of neurological disorders, such as neuropathy associated with diabetes. WO 01/00662 attributes a neuroprotective property to FGF8. By contrast, the present invention demonstrated an increase in BAT by paracrine FGFs. Furthermore, it is contemplated herein that paracrine FGFs can directly lower the blood glucose level. Thus, the paracrine FGFs can, in contrast to WO 01/00662, directly interfere with the primary cause of metabolic diseases, e.g. obesity and related disorders, rather than trying to cure a secondary symptom like neuropathy associated with diabetes. Thus, the mechanism described in WO 01/00662 underlying the therapy of neurological disorders is completely unrelated to that of the therapy provided in the present invention. Furthermore, diabetic neuropathy is a neuron disorder and not diabetes. Rather, diabetic neuropathy is, like diabetic nephropathy, diabetic osteopathy or diabetic retinopathy, a secondary disorder that may be caused by untreated diabetes or diabetes that is associated with average high glucose levels in the blood. These disorders are not regarded as the pathological condition known as diabetes but rather as pathological conditions that may result from diabetes.

WO 2013/138795 describes a technology to deliver antibodies or antibody-like moieties into a cell by complexing them with a polypeptide having positive surface charge (so termed Surf+ peptides). WO 2013/138795 aims at providing a means for delivery antibodies or antibody-like moieties into a cell. FGF is one of the Surf+ peptides disclosed in WO 2013/138795. Thus, FGF is intended to serve as a carrier while the therapeutic effect is conferred by the antibody. By contrast, the paracrine FGFs, particularly FGF8b, are the active agent (preferably therapeutic agent) to be used in accordance with the present invention. Further, it is preferred herein that the herein provided paracrine FGFs are not fused to (an)other protein(s) or peptide(s), particularly where the protein(s)/peptide(s) confer a further biological activity distinct from that of the paracrine FGF(s).

U.S. Pat. No. 6,037,329 discloses therapeutic compositions comprising FGF-8. However, U.S. Pat. No. 6,037,329 aims at providing a gene therapy, wherein FGF8 is to be used as a carrier for delivery of nucleic acids (the latter are the therapeutic agent in U.S. Pat. No. 6,037,329). By contrast, the paracrine FGFs, particularly FGF8b, are the active (therapeutic) agent to be used in accordance with the present invention.

WO 2013/149258 discloses a treatment of a metabolic syndrome related disorder by administering a compound that increases the activity and/or protein level of follistatin and/or uncoupling protein 1 (UCP-1). WO 2013/149258 proposes many chemical compounds that might be useful to increase the activity and/or protein level of follistatin and/or uncoupling protein 1 (UCP-1). Yet, WO 2013/149258 does neither disclose nor propose a use of paracrine FGFs, like FGF8, in the treatment of a metabolic syndrome related disorder. WO 2013/149258 merely vaguely mentions by reference to Alexandre et al. ((2006) Development) that Follistatin modulators such as FGF8 may be used to modulate fat mobilization. Yet, WO 2013/149258 does not provide any evidence that FGF8 would be a Follistatin activator as required for the therapy of metabolic disorders in WO 2013/149258, let alone any evidence that FGF8 might therapeutically effective in the therapy of a metabolic syndrome related disorder.

WO 2013/149258 does not provide a full citation of the Alexandre et al. paper. It appears that they referred to Alexandre et al. ((2006) Development 133, 2905-2913). Alexandre et al. (loc. cit.) does not support the notion in WO 2013/149258 that FGF8 may be used to modulate fat mobilization. In fact, Alexandre et al. is completely silent on a potential role of FGF8 in the modulation of fat mobilization. Alexandre et al. merely report on positive and negative regulations by FGF8 to midbrain roof plate developmental plasticity in white leghorn chick and Japanese quail embryos. Thus, WO 2013/149258 has incorrectly summarized the content of Alexandre et al.

Further, Alexandre et al. reports that FGF8 might negatively regulate follistatin in the therein dissected brains of embryos. Thus, Alexandre et al. discloses that FGF8 is a negative regulator, i.e. inhibitor, of follistatin. According to WO 2013/149258 a treatment of a metabolic syndrome related disorder requires however a compound that increases the activity and/or protein level of follistatin. Alexandre et al. discloses that FGF8 is not suitable for said purpose and its teaching is thus not compatible with that of WO 2013/149258. Therefore, Alexandre et al. teaches away from the use of FGF8 in the therapy of metabolic syndrome related disorders.

The prior art has shown that FGF21 may play a role in the browning of white adipose tissue in adaptive thermogenesis (Fisher, Genes & Development 26 (2012) 271-281). However, amino acid sequences and mechanism of action of members of the FGF family are extremely diverse (Itoh et al. Developmental Dynamics 237:18-27, 2008, Itoh et al. J. Biochem 2011; 149(2):121-130). Thus, one cannot assume that other endocrine members of the FGF family might have a similar effect as FGF21, let alone paracrine or intracellular FGFs. FGF21 belongs to the group of endocrine FGFs and therefore exhibits a systemic effect on multiple target tissues. Systemic action bears a high risk of undesired side effects. In contrast to the prior art, the FGFs provided by the present invention (e.g. FGF8b, FGF8f and/or FGF17) are paracrine FGFs. Paracrine FGFs have a protein domain binding to extracellular matrix components and are thereby less mobile and not found in circulation. Their matrix anchor also serves to stabilize interaction with FGF receptors, while endocrine FGFs require an additional cofactor of the klotho family for that purpose. Accordingly, the paracrine FGFs of the present invention (e.g. FGF8b, FGF8f and/or FGF17) act locally on the target tissue they are released into. This local action may for example be accomplished by a local infusion or by pushing an implantable drug depot (e.g. an erodible implant or a minipump) into the target fat depot. Optionally, application of paracrine FGFs may be performed during visceral surgery, e.g. during the implementation of gastric banding or gastric bypass.

Local action is advantageous, since it is accompanied with fewer side effects than systemic action. In addition, the (positive and negative) effects of a local acting agent are better controllable as compared to a systemic agent. Especially for reducing adipose tissue local action is beneficial, as an adipose tissue depot (in a specific region of the body) can be chosen and specifically be targeted by the paracrine FGFs of the present invention (e.g. FGF8b, FGF8f and/or FGF17). As mentioned above, insertion of an implantable drug depot (e.g. an erodible implant or a minipump), which releases one or several of the paracrine FGFs of the invention, may be performed during visceral surgery, e.g. during the implementation of gastric banding or gastric bypass. A further advantage of local acting agents is that local action combined with a local and continuous administration (e.g. via an erodible implant or a minipump) enables a constant level of the polypeptides of the invention (e.g. FGF8b, FGF8f and/or FGF17) within the target adipose tissue over a desired period of time. Said period may be as long as the desired reduction of adipose tissue has been achieved. For example, said treatment period may be, e.g., at least 1 day, at least 2 days, at least 3 days, at least 4 days, at least 5 days or at least 6 days. Said treatment period may also be at least 1 week, at least 2 weeks, at least 3 weeks or at least 4 weeks. Said treatment period may also be at least 1 month, at least 1.5 months, at least 2 months, at least 2.5 months, at least 3 months, at least 3.5 months, at least 4 months, at least 4.5 months, at least 5 months, at least 5.5 months, at least 0.5 years, at least 1 year, at least 1.5 years, at least 2 years or more. For example, the treatment period may be three weeks.

As mentioned above, the prior art has shown that $\beta_3$-adrenergic receptor agonists are able to produce brown adipose cells in white adipose tissue. However, these $\beta_3$-adrenergic receptor agonists mainly act in subcutaneous adipose depots. It was reported that FGF19 has a positive impact on BAT mass and recruitment state and transgene FGF19 mice seem to exhibit more BAT than wildtype littermates. However, white adipose tissue was not examined for the presence of brown adipocates in this study. With regard to FGF21, Fisher et al. (Genes & Development 26 (2012) 271-281) describe that treatment with this factor increases the appearance of brown-like adipocytes in subcutaneous white adipose tissue.

An advantage of the present invention over the prior art is the fact that the herein provided polypeptides are particularly active in visceral adipose tissue (such as mammal visceral adipose tissue). For example, as documented in the appended illustrative examples, in fully differentiated white adipocyte cell lines, FGF8b increases Ucp1 mRNA abundance 2.1-fold in subcutaneous (inguinal) adipose tissue and 27.4-fold in visceral (epididymal) adipose tissue. In addition, the appended examples further show that in visceral (epididymal) adipose cells, FGF8b induces Ucp1 mRNA abundance in a dose dependent manner, while in subcutaneous (inguinal) adipose cells only the highest dose increased Ucp1 expression. Moreover, abundance of the brown adipocyte marker cell death-inducing DNA fragmentation factor alpha like effector A (Cidea) mRNA was increased by FGF8b treatment similarly to Ucp1 with a greater effect size in visceral (epididymal) as compared to subcutaneous (inguinal) adipocytes. Furthermore, as also shown in the appended examples, FGF8f specifically targets visceral adipocytes (such as mammal adipocytes). Furthermore, as also shown in the appended examples, in vivo treatment with FGF8b effectively recruits brown adipocytes in visceral adipose tissue (such as mammal adipose tissue) and not (or not detectably) in subcutaneous adipose tissue. In a variety of mammalian species, including both mice and men, a difference in characteristics between subcutaneous and visceral adipose tissue is established. Without being bound by theory, it is expected that these differences be causative for the different sensitivity to FGF8b. Accordingly, FGF8b treatment is effective in mammalian visceral adipose tissue, such as human visceral adipose tissue. The nucleic acid and amino acid sequences of the paracrine FGF family and its receptors are very conserved across mammalian species. For instance, human and murine FGF8b are 100 percent identical on the amino acid level, and 95 percent on the coding nucleic acid level. The same is true for the respective receptors, e.g. the identity between human and murine FGFR1 is 98 percent on the amino acid level, and 89 percent on a nucleotide acid level, respectively. The identity between the sequence of human and murine FGFR4 is 89 percent on the amino acid level, and 85 percent on a nucleotid acid level, respectively. In summary, the entire paracrine FGF signaling system is exceptionally well conserved between mice and humans and it is feasible and evident that also functionality is conserved.

The appended examples further show that adipocytes of subcutaneous (inguinal) origin are only responsive to FGF8b treatment in their fully differentiated state whereas visceral (epididymal) cells respond to early as well as late treatments during adipose differentiation. Thus, the herein provided paracrine FGFs (e.g. FGF8b, FGF8f and/or FGF17) are advantageous over the prior art as they specifically target visceral adipose tissue.

Particularly the visceral adipose tissue is known to correlate with secondary diseases arising from obesity. Visceral (or central) obesity is associated with metabolic abnormalities that increase the risk of type 2 diabetes and coronary heart disease (see, e.g., Després, Ann Med. 33 (2001) 534-41). Obese patients with a substantial accumulation of visceral adipose tissue are characterized by higher insulinaemic and glycaemic responses during an oral glucose challenge as well as by a deteriorated plasma lipoprotein-lipid profile compared with individuals with normal body weights or obese subjects with low levels of visceral adipose tissue. Results of the Quebec Cardiovascular Study have shown that the cluster of metabolic disturbances observed among subjects with visceral obesity (hyperinsulinaemia, hyperapolipoprotein B and small, dense low-density lipoprotein (LDL) particles) is associated with a 20-fold increase in the risk of coronary heart disease in a sample of middle-aged men followed over 5 years.

As the paracrine FGFs of the present invention (e.g. FGF8b, FGF8f and/or FGF17) reduce adipose tissue specifically in the visceral adipose depots, these polypeptides are particularly useful in the treatment (and/or prevention) of central obesity and secondary diseases of central obesity (such as metabolic syndrome, dyslipidemia, insulin resistance, type 2 diabetes, disturbed glucose tolerance, a pathological fasting blood sugar level, hypertension, coronary heart disease or hyperglycemia). The treatment of obesity in accordance with the present invention encompasses the therapy of secondary diseases of obesity (such as metabolic syndrome, dyslipidemia, insulin resistance, type 2 diabetes, disturbed glucose tolerance, a pathological fasting blood sugar level, hypertension, coronary heart disease or hyperglycemia). The treatment of central obesity in accordance with the present invention encompasses the therapy of secondary diseases of central obesity (such as metabolic syndrome, dyslipidemia, insulin resistance, type 2 diabetes, disturbed glucose tolerance, a pathological fasting blood sugar level, hypertension, coronary heart disease or hyperglycemia). Thus, the present invention paves the way for an efficient and sustainable weight reduction and the reduction of the risk for several secondary diseases of obesity. Furthermore, it gives rise to a method to prevent weight gain beforehand.

A "patient" or "subject" for the purposes of the present invention includes both humans and other animals, particularly mammals, and other organisms. Thus, the methods are applicable to both human therapy and veterinary applications. In the preferred embodiment the patient or subject to be treated is a mammal (like pets, such as cats or dogs), and in the most preferred embodiment the patient is a human patient. However, the present invention also encompasses the medical intervention of metabolic diseases (like obesity dyslipidemia, diabetes, insulin resistance, hyperglycemia or metabolic syndrome) by use of the compounds, means and methods as described herein in a veterinary setting.

Accordingly, the medical therapy of humans/human patients is preferred herein. Thus, it is preferred herein that paracrine FGFs as defined herein (including FGF8b, FGF8f and/or FGF17, preferably FGF8b) are for use in the treatment of a human patient suffering from or prone to suffering from a disease or disorder of energy homeostasis, particularly wherein said disease or disorder is obesity, dyslipidemia, diabetes, insulin resistance, hyperglycemia or metabolic syndrome. Diabetes includes, but is not limited to, diabetes type 1 and type 2, gestational diabetes, MODY (Maturity Onset Diabetes of the Young). Dyslipidemia includes, but is not limited to, LDL increase, HDL decrease, triglycerid increase and genetic forms of dyslipidemia, Moreover, as mentioned above, BAT displays a high uptake of both glucose and lipoproteins from the bloodstream. This is an important aspect of the present invention as diabetes mellitus (particularly diabetes mellitus type 2) is highly associated with obesity and its hallmark is peripheral insulin resistance especially in the obese and that a high concentration of circulating free fatty acids in the over-weight patients is toxic for insulin-producing beta-cells of the pancreas. As mentioned above, there is nearly none—apart from metformin—established therapeutic agent in treating diabetes without increasing body weight. And even metformins impact on reducing body weight is only minor. Accordingly, by augmenting the amount of BAT the present invention thus provides means and methods for the reduction of glucose and lipid plasma levels in diabetic and dyslipidemia patients. Therefore, the paracrine FGFs of the present invention (i.e. FGF8b, FGF8f and/or FGF17) may be used to treat diabetes. Furthermore, the paracrine FGFs of the present invention (i.e. FGF8b, FGF8f and/or FGF17) may be used to treat dyslipidemia.

Accordingly, the present invention advantageously provides for paracrine FGFs (e.g. FGF8b, FGF8f and/or FGF17) which are capable of converting disease causing visceral adipose tissue into the beneficial fat-burning brown adipose tissue, which is involved in the prevention of sustained and life threatening hypothermia in the cold. Thus, the invention relates to a paracrine FGF which is useful for the treatment of diseases or disorders of energy homeostasis (e.g. obesity, such as central obesity). This paracrine FGF of the invention may be FGF8b or FGF8f. FGF8, FGF8f and FGF17 are structurally very similar. Therefore, these factors may signal via the same receptor and/or via the same pathway. Preferably, the paracrine FGF of the invention is FGF8b or FGF8f. More preferably, the paracrine FGF of the invention is FGF8b.

The present invention relates in particular to the following items:

1. A polypeptide for use in treating a disease or disorder of energy homeostasis, wherein the polypeptide is selected from the group consisting of:
   (a) a polypeptide comprising an amino acid sequence encoded by a nucleic acid molecule having the nucleic acid sequence as depicted in SEQ ID NO:2 or the nucleic acid sequence comprising nucleic acid residues 67-648 in SEQ ID NO:2;

(b) a polypeptide comprising an amino acid sequence as depicted in SEQ ID NO:16 or an amino acid sequence comprising amino acids 23-215 in SEQ ID NO:16;

(c) a polypeptide encoded by a nucleic acid molecule encoding a polypeptide comprising an amino acid sequence having amino acids 23-215 in SEQ ID NO:16 or having an amino acid sequence as depicted in SEQ ID NO:16;

(d) a polypeptide comprising an amino acid sequence encoded by a nucleic acid molecule hybridizing under stringent conditions to the complementary strand of a nucleic acid molecule as defined in (a) or (c) and encoding a functional polypeptide, wherein the function comprises the ability to induce differentiation or conversion of white adipocytes and/or preadipocytes to brown adipocytes;

(e) a polypeptide having at least 40% identity to the polypeptide of any one of (a) to (d), whereby said polypeptide is functional, wherein the function comprises the ability to induce differentiation or conversion of white visceral adipocytes and/or preadipocytes to brown adipocytes; and (f) a polypeptide comprising an amino acid sequence encoded by a nucleic acid molecule being degenerate as a result of the genetic code to the nucleotide sequence of a nucleic acid molecule as defined in (a), (c) and (d).

2. A polynucleotide for use in treating a disease or disorder of energy homeostasis, wherein the polynucleotide encodes the polypeptide of item 1.

3. A pharmaceutical composition comprising the polypeptide of item 1 and/or the polynucleotide of item 2 for use in treating a disease or disorder of energy homeostasis, further comprising a pharmaceutically acceptable carrier and/or diluent.

4. A method of treating a disease or disorder of energy homeostasis by administering an effective dose of the polypeptide of item 1, the polynucleotide of item 2, or the pharmaceutical composition of item 3, to a subject in need of such treatment.

5. The polypeptide of item 1, the polynucleotide of item 2, the pharmaceutical composition of item 3, or the method of item 4, wherein said polypeptide binds to an FGF receptor.

6. The polypeptide of item 5, the polynucleotide of item 5, the pharmaceutical composition of item 5, or the method of item 5, wherein said FGF receptor is at least one FGF receptor selected from the group consisting of FGF receptor 4, FGF receptor 1, FGF receptor 2 and FGF receptor 3.

7. The polypeptide of any one of items 1, 5 or 6, the polynucleotide of any one of items 2, 5 or 6, the pharmaceutical composition of any one of items 3, 5 or 6, or the method of any one of items 4, 5 or 6, wherein said polypeptide, polynucleotide or pharmaceutical composition is to be administrated locally.

8. The polypeptide of item 7, the polynucleotide of item 7, the pharmaceutical composition of item 7, or the method of item 7, wherein said polypeptide, polynucleotide or pharmaceutical composition is to be administrated locally into the visceral adipose tissue.

9. The polypeptide of any one of items 1 and 5 to 8, the polynucleotide of any one of items 2 and 5 to 8, the pharmaceutical composition of any one of items 3 and 5 to 8, or the method of any one of items 4 to 8, wherein said polypeptide, polynucleotide or pharmaceutical composition is to be administered into the visceral adipose tissue.

10. The polypeptide of any one of items 1 and 5-9, the polynucleotide of any one of items 2 and 5 to 9, the pharmaceutical composition of any one of items 3 and 5 to 9, or the method of any one of items 4-9, wherein said polypeptide, polynucleotide or pharmaceutical composition is in the form of an erodible implant, an implantable drug release device, a gel for injection or a solution for injection.

11. The polypeptide of any one of items 1 and 5-10, the polynucleotide of any one of items 2 and 5-10, the pharmaceutical composition of any one of items 3 and 5-10, or the method of any one of items 4-10, wherein said polypeptide, polynucleotide or pharmaceutical composition is to be administered via a minipump.

12. The polypeptide of any one of items 1 and 5-11, the polynucleotide of any one of items 2 and 5-11, the pharmaceutical composition of any one of items 3 and 5-11, or the method of any one items 4-11, wherein said disease or disorder of energy homeostasis is at least one disease or disorder selected from the group consisting of obesity, dyslipidemia, diabetes, insulin resistance, hyperglycemia and metabolic syndrome.

13. The polypeptide of item 12, the polynucleotide of item 12, the pharmaceutical composition of item 12, or the method of item 12, wherein said obesity is central obesity.

14. The polypeptide of any one of items 1 and 5-13, the polynucleotide of any one of items 2 and 5-13, the pharmaceutical composition of any one of items 3 and 5-13, or the method of any one of items 4 and 5-13, wherein said polypeptide, polynucleotide or pharmaceutical composition is co-administered with at least one other active agent.

15. The polypeptide of item 14, the polynucleotide of item 14, the pharmaceutical composition of item 14, or the method of item 14, wherein said other active agent is at least one active agent selected from the group consisting of beta-adrenergic agonists (e.g. noradrenalin, isoproterenol, BRL 35135, ICI D7114, CGP-12177A, CL 316243), indirect sympathomimetics (e.g. ephedrine, methylphenidate), atrial natriuretic peptide (e.g. ANP, BNP) and ANP/BNP receptor agonists (e.g. AP-811).

16. The polypeptide of item 15, the polynucleotide of item 15, the pharmaceutical composition of item 15, or the method of item 15, wherein said beta-adrenergic agonist is a beta3-adrenergic agonist.

17. The polypeptide of item 16, the polynucleotide of item 16, the pharmaceutical composition of item 16, or the method of item 16, wherein said beta3-adrenergic agonist is CL 316243.

18. A method for the preparation of a pharmaceutical composition for use in treating a disease or disorder of energy homeostasis, wherein the method comprises the following steps:

(a) contacting the polypeptide of any one of items 1 and 5-17 and/or the polynucleotide of any one of items 2 and 5-17 with a liquid carrier or a solid carrier;

(b) optionally, adjusting the pH and/or the osmolarity of the product obtained in step (a);

(c) optionally, sterilizing the product obtained in step (a) or (b); and (d) formulating and/or packaging the product obtained in step (a), (b) or (c) as a finished medical product.

19. The method of item 18, wherein said carrier is at least one carrier selected from the group consisting of cellulose, lactose, water, saline, Ringer's solution, dextrose solution, a fixed oil, ethyl oleate and liposomes.

20. A cosmetic product comprising a polypeptide, wherein said polypeptide is selected from the group consisting of:
 (a) a polypeptide comprising an amino acid sequence encoded by a nucleic acid molecule having the nucleic acid sequence as depicted in SEQ ID NO:2 or the nucleic acid sequence comprising nucleic acid residues 67-648 in SEQ ID NO:2;
 (b) a polypeptide comprising an amino acid sequence as depicted in SEQ ID NO:16 or an amino acid sequence comprising amino acids 23-215 in SEQ ID NO:16;
 (c) a polypeptide encoded by a nucleic acid molecule encoding a polypeptide comprising an amino acid sequence having amino acids 23-215 in SEQ ID NO:16 or having an amino acid sequence as depicted in SEQ ID NO:16;
 (d) a polypeptide comprising an amino acid sequence encoded by a nucleic acid molecule hybridizing under stringent conditions to the complementary strand of a nucleic acid molecule as defined in (a) or (c) and encoding a functional polypeptide, wherein the function comprises the ability to induce differentiation or conversion of white adipocytes and/or preadipocytes to brown adipocytes;
 (e) a polypeptide having at least 40% identity to the polypeptide of any one of (a) to (d), whereby said polypeptide is functional, wherein the function comprises the ability to induce differentiation or conversion of white adipocytes and/or preadipocytes to brown adipocytes; and
 (f) a polypeptide comprising an amino acid sequence encoded by a nucleic acid molecule being degenerate as a result of the genetic code to the nucleotide sequence of a nucleic acid molecule as defined in (a), (c) and (d).
21. Use of the cosmetic product of item 20 for reducing body weight.
22. The cosmetic product of item 20, or the use of item 21, wherein said polypeptide binds to a FGF receptor.
23. The cosmetic product of item 22, or the use of item 22, wherein said FGF receptor is at least one FGF receptor selected from the group consisting of FGF receptor 4, FGF receptor 1c, FGF receptor 2c and FGF receptor 3c.
24. The cosmetic product of any one of items 20, 22 and 23, or the use of any one of items 21-23, wherein said cosmetic product reduces abdominal adipose tissue.
25. The cosmetic product of any one of items 20 and 22-24, or the use of any one of items 21-24, wherein said cosmetic product is in the form of a cream, salve or gel.
26. The cosmetic product of any one of items 20 and 22-25, or the use of any one of items 21-25, wherein said cosmetic product further comprises a chemical penetration enhancer.
27. The cosmetic product of item 26, or the use of item 26, wherein said chemical penetration enhancer is at least one chemical penetration enhancer selected from the group consisting of ethanol, isopropyl alcohol, decanol, hexanol, lauryl alcohol, myristyl alcohol, octanol, octyl dodecanol, oleyl alcohol, azone, ethyl acetate, octyl salicylate, 2-ethylhexyl 4-(dimethylamino)benzoate, ethyl oleate, glyceryl monooleate, glyceryl monocaprate, glyceryl tricaprylate, isopropyl myristate, isopropyl palmitate, propylene glycol monolaurate, propylene glycol monocaprylate, 2-(2-ethoxyethoxy)ethanol, lauric acid, linoleic acid, linolenic acid, myristic acid, oleic acid, palmitic acid, stearic acid, isostearic acid, dipropylene glycol, propylene glycol, 1,2-butylene glycol, 1,3-butylene glycol, N-methyl-2-pyrrolidone, 2-pyrrolidone, decylmethyl sulphoxide, dimethyl sulfoxide, sodium lauryl sulphate, alkyl dimethylbenzyl ammonium halides, alkyl trimethyl ammonium halides, alkyl pyridinium halides, 2-(dodecyloxy)ethanol, polyoxyethylen(20)-sorbitan-monooleat, eugenol, d-limonene, menthol, menthone, farnesol and neridol.

As mentioned, FGF8b, FGF8f and FGF17 are paracrine fibroblast growth factors. The nucleic acid and amino acid sequences of FGF8b, FGF8f and FGF17 are known in the art and also disclosed herein. In particular, the nucleic acid and amino acid sequences of FGF8b are disclosed herein as SEQ ID NO:2 and SEQ ID NO:16, respectively. The nucleic acid and amino acid sequences of FGF8f are disclosed herein as SEQ ID NO:4 and SEQ ID NO:18, respectively. In addition, the nucleic acid and amino acid sequences of FGF17 are disclosed herein as SEQ ID NO:9 and SEQ ID NO:23, respectively. The appended examples show that these paracrine FGFs are capable of inducing conversion of white visceral adipocytes to brown adipocytes.

Accordingly, the present invention relates to a paracrine FGF which has the ability to induce differentiation (or conversion) of white adipocytes and/or white preadipocytes to brown adipocytes (e.g. FGF8b, FGF8f and/or FGF17). In particular, the present invention relates to a paracrine FGF which has the ability to induce differentiation (or conversion) of white visceral adipocytes and/or white visceral preadipocytes to brown adipocytes (e.g. FGF8b, FGF8f and/or FGF17). Assays for testing whether a polypeptide has the ability to induce differentiation or conversion of white (visceral) adipocytes and/or preadipocytes to brown adipocytes are employed routinely in the art. For example, the polypeptide to be tested may be contacted with cultivated white adipocytes or white preadipocytes (e.g. cultivated white visceral adipocytes or cultivated white visceral preadipocytes); and (after differentiation of the white adipocytes or of the white preadipocytes) the expression of marker genes of brown adipose tissue (e.g. Ucp1) may be measured. Or, in other words, the potential of the polypeptide to be tested to induce the expression of brown adipocyte specific genes (e.g. Ucp1) in white visceral adipocyte cell lines may be tested.

For example, an assay for testing the ability to induce differentiation (or conversion) of white adipocytes and/or white preadipocytes (in particular white visceral adipocytes and/or white visceral preadipocytes) to brown adipocytes as used herein and comprising routine methodology is described as follows: immortalized white visceral adipocyte cell lines may be established from primary stromal-vascular cells isolated from the murine epididymal adipose tissue depot. Treatment of the cells with the polypeptide to be tested may be started after induction of adipocyte differentiation and continued for the entire differentiation period of 6 days. Adipocyte differentiation may be induced by complementing the medium with 250 µM indomethacin, 500 µM isobutylmethylxanthine and 2 µg/ml dexamethasone for 24 h after confluence. The concentration to be chosen for the polypeptide to be tested may be based on the biological $IC_{50}$ value determined in fibroblast proliferation assays by the supplier and ranged between 1 and 50 ng/ml.

To characterize whether a polypeptide (e.g. FGF8b, FGF8f and/or FGF17) has the ability to induce differentiation or conversion of either white adipocytes or preadipocytes (e.g. white visceral adipocytes or preadipocytes) to brown adipocytes, a sensitive time window for the conversion during the differentiation process can be identified (1) by treatment during several different time windows (for example, and without limitation, during two days of proliferation, two days of induction or every two day time span during differentiation) and (2) quantification of established BAT markers after full differentiation. Those established BAT markers include Cidea, Cox7a1, Elovl3, Pgc1a, Prdm16, Foxc2, Prb, and above all, Ucp1.

As mentioned above, the invention provides for a polypeptide for use in treating diseases or disorders of energy homeostasis (e.g. obesity). This polypeptide may have a length of 10-1000 amino acids, preferably of 30-800 amino acids, 50-700 amino acids or 70-500 amino acids; more preferably, of 90-300 amino acids, 110-280 amino acids, 150-200 amino acids or 170-270 amino acids; or, most preferably, of 200-230 amino acids. The term "polypeptide" also encompasses fragments and variants of the specific polypeptides provided herein that have the biological function/activity of the herein described polypeptides. Also the use of short peptides consisting of about 11 or less amino acids is envisaged. These peptides can consist of 10, 9, 8, 7, 6, 5 or 4 amino acids. Also these peptides are polypeptides for use in accordance with the present invention. In one particular aspect of the invention, the polypeptide of the invention has a length of 215 amino acids.

The invention further relates to a polynucleotide for use in treating a disease or disorder of energy homeostasis, wherein the polynucleotide encodes the polypeptide of the invention. The invention also relates to a pharmaceutical composition comprising the polypeptide of the invention and/or the polynucleotide of the invention for use in treating a disease or disorder of energy homeostasis, further comprising a pharmaceutically acceptable carrier and/or diluent. Thus, provided herein is a method of treating a disease or disorder of energy homeostasis by administering an effective dose of the polypeptide of the invention, the polynucleotide of the invention, or the pharmaceutical composition of the invention, to a subject in need of such treatment (e.g. an obese or diabetic or dyslipidemic human being).

The cellular response to FGFs is mediated by FGF receptors (FGFR). A variety of FGFRs is produced from four different genes by differential splicing (FGFR1-4). Thus, one aspect of the invention relates to the polypeptide of the invention, the polynucleotide of the invention, the pharmaceutical composition of the invention, or the method of the invention, wherein said polypeptide binds to a FGF receptor. Assays for testing whether a given polypeptide binds to a FGF receptor are routinely applied in the art. For example, surface plasmon resonance is commonly used to test whether a particular polypeptide binds to a FGF receptor. Alternatively, binding to a FGF receptor may be assayed by reducing the expression of the FGF receptor in question (e.g. by RNA interference) and analyzing whether the biological effect of the polypeptide to be analyzed (e.g. the conversion of white visceral adipocytes into brown adipocytes) is decreased or lost. A decrease or loss of said biological effect is indicative of a binding of the polypeptide to be analyzed to the FGF receptor in question.

The illustrative appended examples demonstrate that the FGF receptors 1-3 are well detectable in both, subcutaneous (inguinal) and visceral (epididymal) adipose tissue. Thus, the paracrine FGF of the invention (e.g. FGF8b, FGF8f and/or FGF17) may signal through binding to FGF receptor 1 (FGFR1), FGF receptor 2 (FGFR2) and/or FGF receptor 3 (FGFR3). FGFR1-3 each have the splice forms a, b and c. The murine and human nucleotide and amino acid sequences of FGFR1-4 are shown herein below as SEQ ID NOs:29 to 36 and 43 to 50. The nucleotide and amino acid sequences of alternative splice forms of FGFR1-3 are well known in the art and can be retrieved from databases like NCBI or EMBL, for example under the following accession numbers:

|  | Splice form b | Splice form c |
|---|---|---|
| Human |  |  |
| FGFR1 | FGFR1-020 ENST00000397108 | FGFR1-011 ENST00000397103 |
| FGFR2 | FGFR2-201 ENST00000351936 | FGFR2-010 ENST00000457416 |
| FGFR3 | FGFR3-201 ENST00000340107 | FGFR3-203 EN5T00000440486 |
| murine |  |  |
| Fgfr1 | FGFR1-201 ENSMUST00000178276 | FGFR1-202 ENSMUST00000179592 |
| Fgfr2 | FGFR2-011 ENSMUST00000119260 | FGFR2-012 ENSMUST00000117089 |
| Fgfr3 | FGFR3-201 ENSMUST00000114411 | FGFR3-202 ENSMUST00000169212 |

Exemplary murine and human nucleotide and amino acid sequences of FGFR3c are shown in SEQ ID NO:85/86 and 87/88. Exemplary human and murine amino acid sequences of alternative splice forms of FGFR1-3 are shown in SEQ ID NO:89 to 100. In a preferred aspect of the invention, the paracrine FGFs of the invention (e.g. FGF8b, FGF8f and/or FGF17) achieve browning of white adipose tissue through binding to the FGF receptor e.g. FGFR1c, FGFR2c, FGFR3c and/or FGFR4, particularly to FGFR3c and/or FGFR4. It is known in the art that FGFR1c is strongly expressed in adipose tissue. Thus, the paracrine FGFs of the invention may achieve browning of white adipose tissue through binding to FGFR1c. The appended examples also demonstrate that the FGF receptor 4 is only found in visceral (epididymal) and not in subcutaneous (inguinal) adipose tissue in appreciable amounts. Moreover, the appended examples show that FGF receptor 4 expression as well as FGF receptor 3c expression correlates with FGF8b sensitivity. These results suggest that the paracrine FGF of the invention (e.g. FGF8b, FGF8f and/or FGF17) accomplish the browning of white adipose tissue through binding to the FGF receptor, particularly FGF receptor 4 or 3c. Thus, the invention further relates to the polypeptide of the invention, the polynucleotide of the invention, the pharmaceutical composition of the invention, or the method of the invention, wherein said FGF receptor is at least one FGF receptor selected from the group consisting of FGF receptor 4, FGF receptor 1, FGF receptor 2 and FGF receptor 3. It is prioritized that the receptor is FGF receptor 1c, 2c or 3c. It is even more prioritized that the FGF receptor is FGF receptor 3c or 4.

The illustrative appended examples demonstrate that local administration of the therein provided paracrine FGFs (e.g. of FGF8b) into the visceral adipose tissue results in a considerable recruitment of brown adipocytes specifically in the visceral adipose tissue depot. Thus, the invention relates to the polypeptide of the invention, the polynucleotide of the invention, the pharmaceutical composition of the invention, or the method of the invention, wherein said polypeptide, polynucleotide or pharmaceutical composition is to be administrated locally. Local administration encompasses injection or implantation e.g. by using an implantable drug depot.

A further aspect of the invention relates to the polypeptide of the invention, the polynucleotide of the invention, the pharmaceutical composition of the invention, or the method of the invention, wherein said polypeptide, polynucleotide or pharmaceutical composition is to be administrated locally into the visceral adipose tissue. Thus, according to the invention, it is envisaged that the polypeptide of the invention, polynucleotide of the invention or pharmaceutical composition of the invention is to be administered into the visceral adipose tissue.

The illustrative appended examples show that the herein provided paracrine FGFs (e.g. FGF8b) have the ability to transform white adipose tissue into brown adipose tissue in vivo. More specifically, the appended examples show that the visceral adipose tissue can be effectively and specifically targeted by using an implantable drug depot comprising the herein provided paracrine FGFs (e.g. an implanted "pellet" comprising FGF8b) which is to be implanted directly into the visceral adipose tissue. Implantable drug depots include erodible implants. An example of an erodible implant is a "pellet" produced by Innovative Research of America, Sarasota, Fla., USA. The catalogue number of a customized "pellet" is Y-999. A further example for an implantable drug depot is an implantable drug release device (such as a minipump) or a single-rod implant. Implantable drug depots (such as a single-rod implant) are commonly known in the art and also used, e.g., for the delivery of contraceptives such as Nexplanon/Implanon. However, the herein provided paracrine FGFs may also be administered within a gel for injection or a solution for injection. For example, a ready-to-use gel for injection or a ready-to-use solution for injection can be used. Thus, the invention provides the polypeptide of the invention, the polynucleotide of the invention, the pharmaceutical composition of the invention, or the method of the invention, wherein said polypeptide, polynucleotide or pharmaceutical composition is in the form of an erodible implant, an implantable drug release device, a gel for injection or a solution for injection. It is also envisaged in context of the invention that said polypeptide, polynucleotide or pharmaceutical composition is to be administered via a minipump.

Thus, one embodiment of the invention relates to an implantable drug depot for use in administering the paracrine FGFs of the invention (i.e. the polypeptide of the invention, the polynucleotide of the invention or the pharmaceutical composition of the invention) for use in treating obesity and/or secondary diseases of obesity. Accordingly, the invention relates to the use of an implantable drug depot for administering the herein provided paracrine FGFs. The implantable drug depot described herein may be a minipump, such as an osmotic minipump.

The construction and function of a minipump (such as an osmotic minipump) is known in the art and described, e.g., in Theeuwes, Ann Biomed Eng (1976) 4, 343-353 and "http://www.alzet.com". Osmotic minipumps are also designated "miniature pumps" and are miniature, implantable pumps for research and therapy. These minipumps deliver drugs (such as the paracrine FGFs of the invention) continuous and in controlled rates, for durations ranging from one day to several weeks (e.g. six weeks), without the need for external connections or frequent handling. Their unattended operation eliminates the need for repeated nighttime or weekend dosing by the attending doctor.

The minipump of the invention may be designed as follows. The minipump of the invention may be an osmotic minipump and may consist of a cylindrical reservoir for the fluid (which contains the drug to be delivered, e.g., the paracrine FGF of the invention), surrounded by a layer of an osmotic driving agent which, in turn, is encapsulated by a semipermeable membrane. The reservoir material may be chemically inert to most aqueous drug formulations, dilute acids, bases and alcohols. The outer housing of the minipump, which is the membrane, may be highly compatible with tissues when the minipump is implanted in an animal (e.g. a human being). The minipump of the invention may have a total volume of approximately 0.6 ml, and an internal effective volume of approximately 0.2 ml. In the minipump, the active drug (e.g. the paracrine FGF of the invention) may be prepared in a homogenous solution, stable suspension or emulsion and may be contained in the drug reservoir which has a delivery orifice. A collapsible partition such as a diaphragm or bag may separate the drug formulation from the osmotic driving agent that provides the osmotic driving force. The osmotic driving agent may be isolated from the outside environment by a membrane that is permeable to water, but not to the osmotic driving agent. In one embodiment of the invention, the minipump is designed as shown in FIG. 1 of Theeuwes, Ann Biomed Eng (1976) 4, 343-353.

The osmotic minipump described herein operates because of an osmotic pressure difference between a compartment within the minipump, called the salt sleeve, and the tissue environment in which the minipump is implanted. The high osmolality of the salt sleeve causes water to flux into the minipump through a semipermeable membrane which forms the outer surface of the minipump. As the water enters the salt sleeve, it compresses the flexible reservoir, displacing the active agent (e.g. the paracrine FGF of the invention) from the minipump at a controlled, predetermined rate. In one aspect of the invention, the compressed reservoir cannot be refilled and the minipump is designed for single-use only.

The rate of delivery by a minipump of the invention may be controlled by the water permeability of the minipump's outer membrane. Thus, the delivery profile of the pump is independent of the drug formulation dispensed. Drugs of various molecular configurations, including ionized drugs and macromolecules, can be dispensed continuously in a variety of compatible vehicles at controlled rates. The molecular weight of a compound, or its physical and chemical properties, has no bearing on its rate of delivery by the minipumps of the invention. The volume delivery rate of the minipump of the invention may be fixed at manufacture. The (e.g. osmotic) minipump of the invention may have delivery rates between 0.1 and 10 μl/hr and delivery durations between 1 day and several (e.g. six) weeks. Although the volume delivery rate of the minipump of the invention may be fixed, different dosing rates can be achieved by varying the concentration of agent (e.g. FGF8b, FGF8f and/or FGF17) in the solution or suspension used to fill the minipump reservoir.

The implantable drug depot may also be an erodible implant (e.g. a "pellet" of Innovative Research of America, Sarasota, Fla., USA). Accordingly, this implantable drug depot may be fabricated from a biodegradable matrix. In particular, the implantable drug depot may be made of a matrix fused with an active product (i.e. the herein provided paracrine FGF(s)). For example, the ingredients of the implantable drug depot may comprise a hydrophilic matrix (e.g. cellulose), a surface-active emollient (e.g. cholesterol, phosphates and/or stearates) and filler (e.g. lactose). Thus, the implantable drug depot may be composed of cholesterol, cellulose, lactose, phosphates, stearates and the paracrine FGF(s) provided herein. In accordance with the invention, the implantable drug depot may work by the erosion of the implantable drug depot or by the diffusion of the active product. However, the implantable drug depot described herein may also work by the double process of erosion of the implantable drug depot and diffusion of the active product. The implantable drug depot may locally release 0.1 ng to 1000 mg per day. For example, the implantable drug depot may locally release 1 ng to 500 mg per day, 10 ng to 100 mg per day or 100 ng to 1 mg per day. In one aspect of the invention, the implantable drug depot locally releases 100 ng per day. In context of the invention, that implantable drug depot may locally release the paracrine FGF(s) of the invention (e.g. FGF8b, FGF8f and/or FGF17) for several days. For example, the implantable drug depot may release the paracrine FGF(s) of the invention for at least 1 day, at least 2 days, at least 3 days, at least 4 days, at least 5 days or at least 6 days. The implantable drug depot may also release the paracrine FGF(s) of the invention for at least 1 week, at least 2 weeks, at least 3 weeks or at least 4 weeks. The implantable drug depot may also release the paracrine FGF(s) of the invention for at least 1 month, at least 1.5 months, at least 2 months, at least 2.5 months, at least 3 months, at least 3.5 months, at least 4 months, at least 4.5 months, at least 5 months, at least 5.5 months, at least 0.5 years, at least 1 year, at least 1.5 years, at least 2 years or more. For example, the implantable drug depot may release the paracrine FGF(s) of the invention for three weeks. An example for an implantable drug depot is, as discussed herein above and herein below, a "pellet" (Innovative Research of America, Sarasota, Fla., USA). Again, dosages/releasing quantities for local release can be determined without further ado by the attending physician. The same holds true for the time frame of the treatment and/or corresponding dosage regimens.

The herein provided paracrine FGFs may also be administered by injecting a gel and/or a solution locally into the target tissue (e.g. into the visceral adipose tissue). Thus, a further embodiment of the invention relates to a gel or solution for use in injecting the polypeptide of the invention, the polynucleotide of the invention of the pharmaceutical composition of the invention locally into the target tissue (e.g. into the visceral adipose tissue) fur use in treating obesity and/or secondary diseases of obesity. Accordingly, one aspect of the invention relates to the use of a gel and/or solution for injecting the polypeptide of the invention, the polynucleotide of the invention or the pharmaceutical composition of the invention into the target tissue (e.g. into the visceral adipose tissue). In accordance with the invention, the gel for injection and/or the solution for injection usually comprise(s) a pharmaceutically acceptable carrier. Examples of non aqueous carriers are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Further carriers are sodium chloride solution, Ringer's dextrose, dextrose and sodium chloride, lactated Ringer's, or fixed oils, fluid and nutrient replenishers, electrolyte replenishers (such as those based on Ringer's dextrose), and the like. Preservatives and other additives may also be present in the herein defined gel for injection and/or solution for injection, such as antimicrobials, anti oxidants, chelating agents, inert gases and the like. The gel for injection may further comprise agents for thickening, such as hyaluronan.

As known in the art, the term "energy homeostasis" relates to any process involved in the balance between energy intake (food consumption) and energy expenditure. In particular, energy homeostasis is the relation between intake of food and output of energy that is positive when the body stores extra food as fats and negative when the body draws on stored fat to provide energy for work. A significant contributor to energy expenditure of mammals is the generation of heat for keeping the body temperature constant as well as muscular and metabolic activities.

Energy turnover in the human body includes the uptake and breakdown of chemical energy delivered by the macronutrients in food (fat, carbohydrate, protein). After resorption across the gut epithelium this chemical energy is either converted to heat and dissipated to the environment, transferred to the environment while conducting external work, excreted as indigestible material with feces and urine or stored mainly as triglycerides in adipose tissues. An adult organism with a healthy energy homeostasis compensates by food consumption the daily amount of energy leaving the body with an equal amount of daily energy uptake into the body. In a balanced state no surplus energy is stored in adipose tissues or elsewhere thus maintaining a stable body mass and body composition (i.e. are not obese). Although in these healthy individuals day-to-day fluctuations in energy stores are detected, these fluctuations are countered over periods of weeks to months by coordinated adjustments of food intake and energy expenditure (see, e.g., Schwartz, Diabetes 52 (2003) 232-238). Unfortunately in modern society, environmental circumstances (thermoneutrality, sedentary lifestyle etc.) and the constant availability of high caloric food counteracts a perfectly balanced energy homeostasis and often lead to a positive energy balance resulting in obesity and secondary diseases of obesity.

In accordance with the invention, a disease or disorder of energy homeostasis is preferably characterized by a positive energy homeostasis (wherein the body is storing energy as fat). Accordingly, the invention relates to the herein provided paracrine FGFs (e.g. FGF8b, FGF8f and/or FGF17) for use in treating a disease or disorder of energy homeostasis, wherein said disease or disorder is characterized by a positive energy homeostasis. Such diseases include, e.g., obesity, dyslipidemia, diabetes, insulin resistance, hyperglycemia and metabolic syndrome.

Moreover, BAT displays a high uptake of both glucose and lipoproteins from the bloodstream. This is an important aspect of the present invention as diabetes mellitus (particularly diabetes mellitus type 2) is highly associated with obesity and its hallmark is peripheral insulin resistance especially in the obese. Furthermore, a high concentration of circulating free fatty acids in the overweight patients is toxic for insulin-producing beta-cells of the pancreas. As mentioned above, there is nearly none—apart from metformin—established therapeutic agent in treating diabetes without increasing body weight. And even metformins impact on reducing body weight is only minor. All other medications, insulin in particular, result in rising body weight. Accordingly, by augmenting the amount of BAT the present invention thus provides means and methods for the reduction of glucose and lipid plasma levels in diabetic and dyslipidemia patients. Therefore, the paracrine FGFs of the present invention (i.e. FGF8b, FGF8f and/or FGF17) may be used to treat diabetes.

According to the International Statistical Classification of Diseases and Related Health Problems 10th Revision (ICD-10)-2015-WHO Version for 2015 "diabetes" may be classified as follows:

Diabetes Mellitus (E10-E14)

The following fourth-character subdivisions are for use with categories E10-E14:

.0 With coma
Incl.:
  Diabetic:
    coma with or without ketoacidosis
    hyperosmolar coma
    hypoglycaemic coma
  Hyperglycaemic coma NOS .1 With ketoacidosis
Incl.:
  Diabetic:
    acidosis
    ketoacidosis
    without mention of coma .2† With renal complications
Incl.:
  Diabetic nephropathy (N08.3*)
  Intracapillary glomerulonephrosis (N08.3*)
  Kimmelstiel-Wilson syndrome (N08.3*)

.3† With ophthalmic complications
Incl.:
  Diabetic:
    cataract (H28.0*)
    retinopathy (H36.0*)

.4† With neurological complications
Incl.:
  Diabetic:
    amyotrophy (G73.0*)
    autonomic neuropathy (G99.0*)
    mononeuropathy (G59.0*)
    polyneuropathy (G63.2*)
      autonomic (G99.0*)

.5 With peripheral circulatory complications
Incl.:
  Diabetic:
    gangrene
    peripheral angiopathy† (I79.2*)
    ulcer .6 With other specified complications
Incl.:
  Diabetic arthropathy† (M14.2*)
  Neuropathic diabetic arthropathy† (M14.6*)

.7 With multiple complications
.8 With unspecified complications
.9 Without complications E10 Type 1 Diabetes Mellitus
Modifier-Hint
[See before E10 for subdivisions]
Incl.:
diabetes (mellitus):
  brittle
  juvenile-onset
  ketosis-prone
ExcL:
diabetes mellitus (in):
  malnutrition-related (E12.-)
  neonatal (P70.2)
  pregnancy, childbirth and the puerperium (O24.-)
glycosuria:
  NOS (R81)
  renal (E74.8)
impaired glucose tolerance (R73.0)
postsurgical hypoinsulinaemia (E89.1)

E11 Type 2 Diabetes Mellitus
Modifier-Hint
[See before E10 for subdivisions]
Incl.:
diabetes (mellitus)(nonobese)(obese):
  adult-onset
  maturity-onset
  nonketotic
  stable
non-insulin-dependent diabetes of the young
ExcL:
diabetes mellitus (in):
  malnutrition-related (E12.-)
  neonatal (P70.2)
  pregnancy, childbirth and the puerperium (O24.-)
glycosuria:
  NOS (R81)
  renal (E74.8)
impaired glucose tolerance (R73.0)
postsurgical hypoinsulinaemia (E89.1)

E12 Malnutrition-Related Diabetes Mellitus
Modifier-Hint
[See before E10 for subdivisions]
Incl.:
malnutrition-related diabetes mellitus:
  type 1
  type 2
ExcL:
diabetes mellitus in pregnancy, childbirth and the puerperium (O24.-) glycosuria:
  NOS (R81)
  renal (E74.8)
impaired glucose tolerance (R73.0)
neonatal diabetes mellitus (P70.2)
postsurgical hypoinsulinaemia (E89.1)

E13 Other Specified Diabetes Mellitus
Modifier-Hint
[See before E10 for subdivisions]
ExcL:
diabetes mellitus (in):
  malnutrition-related (E12.-)
  neonatal (P70.2)
  pregnancy, childbirth and the puerperium (O24.-)
  type 1 (E10.-)
  type 2 (E11.-)
glycosuria:
  NOS (R81)
  renal (E74.8)
impaired glucose tolerance (R73.0)
postsurgical hypoinsulinaemia (E89.1)

E14 Unspecified Diabetes Mellitus
Modifier-Hint
[See before E10 for subdivisions]
Incl.:
diabetes NOS
ExcL:
diabetes mellitus (in):
  malnutrition-related (E12.-)
  neonatal (P70.2)
  pregnancy, childbirth and the puerperium (O24.-)
  Type 1 (E10.-)
  Type 2 (E11.-)
glycosuria:
  NOS (R81)
  renal (E74.8)

impaired glucose tolerance (R73.0)

postsurgical hypoinsulinaemia (E89.1)

The treatment of obese diabetes is preferred herein, particularly preferred obese diabetes type 2. The terms "obese diabetes", diabetes associated with obesity", "obesity associated with diabetes" and the like are used interchangeable herein. In this context "obesity" refers to "overweight" and "obese" as explained and defined herein. In a certain aspect, it is envisaged herein that the treatment of diabetes does not encompass secondary disorders related thereto. For example, it is envisaged that the treatment of diabetes does not encompass the treatment of disorders mentioned in subdivision .2† of the above WHO classification, such as renal complications, like Diabetic nephropathy (N08.3*), Intracapillary glomerulonephrosis (N08.3*) or Kimmelstiel-Wilson syndrome (N08.3*).

Furthermore, the paracrine FGFs of the present invention (i.e. FGF8b, FGF8f and/or FGF17) may be used to treat dyslipidemia.

As mentioned above, obesity is a disorder of energy homeostasis and is defined as an abnormal increase in body fat. Since the eighties of the twentieth century, the incidence of obesity is steadily increasing in countries with a Western lifestyle. For example, more than 30% of the American population is obese. The co-morbidities associated with obesity include dyslipidemia, diabetes, insulin resistance, hyperglycemia and metabolic syndrome.

As the paracrine FGFs provided herein have the ability to induce conversion of white adipocytes and preadipocytes (e.g. white visceral adipocytes and white visceral preadipocytes) to brown adipocytes, these paracrine FGFs are useful in the treatment (and/or prevention) of a disease of energy homeostasis such as obesity and secondary diseases of obesity. Thus, one aspect of the invention relates to the polypeptide of the invention, the polynucleotide of the invention, the pharmaceutical composition of the invention, or the method of the invention, wherein said disease or disorder of energy homeostasis is at least one disease or disorder selected from the group consisting of obesity, dyslipidemia, diabetes, insulin resistance, hyperglycemia (such as acute hyperglycemia, e.g. acute hyperglycemia associated with type 1 diabetes) and metabolic syndrome. Said diabetes may be type 2 diabetes. The diabetes may also be type 1 diabetes. The herein provided polypeptide, polynucleotide or method may also be used for treating further secondary disease of obesity such as cardiovascular disease, coronary heart disease, hypertension or stroke.

Obesity and insulin resistance are the core components of the metabolic syndrome which is defined by the World Health Organization (WHO) as the combination of insulin resistance, i.e. type 2 diabetes, impaired glucose tolerance or a pathological fasting blood sugar level, combined with arterial hypertension, dyslipidaemia and obesity (WHO 1998, evidence IV). The metabolic syndrome is also known as the deadly quartet, as it significantly correlates with increased cardiovascular morbidity and mortality (Go, Circulation 125 (2012) 188-97).

With regard to the body mass index (BMI), a measurement obtained by dividing a person's weight in kilograms by the square of the person's height in metres, individuals are considered to be obese when their BMI exceeds 30 kg/m$^2$, are considered to be overweight when the BMI lies above 25 and below 30 kg/m$^2$, and are considered to be of normal weight when their BMI is above 18.5 and below 25 kg/m$^2$. The term "obesity" as used herein encompasses "overweight" and "obese" as defined herein above. Due to the fact that the body composition differs from one human being to the other, the BMI is not necessarily sufficient to predict the individual health risk. Interestingly, close to half the women and more than half the men with normal BMI scores had excessive levels of internal fat deposited around the heart and liver, and streaked through under-used muscles. Therefore, distribution of different fat depots and other tissue masses are crucial.

The total amount of adipose tissue is distributed throughout the human body in a variety of different depots. A common categorization of depots by their localization is the discrimination into subcutaneous (i.e. between skin and abdominal wall) and visceral (i.e. within the abdominal cavity) depots. Subcutaneous adipose tissue is found in all parts of the body and contributes most to total fat mass, typically in the range of 80%.

Common obesity is a state of abdominal fat accumulation. The total amount of abdominal fat can be grouped into subcutaneous (SAT) and visceral (VAT) adipose tissue. The ratio between both is different in men and women. In women, VAT constitutes approx. 25% of SAT (e.g. 3.2 liters SAT; 1.4 l VAT). In men, VAT constitutes approx. 50% (age group under 40 years) to more than 75% (age group above 40 years) of SAT (e.g. 2.7 l SAT; 2.3 l VAT).

During the development of obesity VAT expands more than SAT. Especially VAT mass is associated with negative consequences on human health. Therefore, a human being is considered to be at risk for obesity-related diseases, e.g. dyslipidemia, diabetes, insulin resistance, hyperglycemia and/or the metabolic syndrome, when the individual suffers from increased central fat mass along with or without an above normal BMI.

A formula which takes this into account is the waist to hip ratio defined as the ratio of the circumference of the waist to that of the hips. Waist to hip ratio normal values differ between men and women and are considered to increase with age. The absolute waist circumference (>102 centimetres (40 inch) in men and >88 centimetres (35 inch) in women) and the waist-hip ratio (>0.9 for men and >0.85 for women) are both used as measures of central obesity. Therefore the waist to hip ratio predicts the individual metabolic health risk more accurately.

New imaging techniques, like computed tomography and magnetic resonance imaging, tried to calculate the abdominal fat mass even more precisely. Imaging of the abdomen and a cross-sectional scan of 10-mm thickness centered at the L4-L5 vertebral disc space are obtained with the participant in the supine position with both arms stretched above his/her head. Subsequently, the areas of visceral and subcutaneous adipose tissue (expressed in square centimeters) are calculated. Visceral fat area (VFA) and subcutaneous fat area (SFA) are summed to obtain the total abdominal fat area (TFA). Individuals with a VFA ≥100 cm$^2$ are considered to be obese and therefore at risk for adverse health conditions.

The latest and most sophisticated attempt is the 3D volumetric and body composition analysis by the Heartlands Hospital, a National Health Service (NHS) Obesity Centre in the United Kingdom. They use a 3D scanner to calculate the Body Volume Index (BVI). It looks at the relationship between mass and volume distribution, i.e. where different body mass is located in the body. It is expected, but not established sufficiently yet, that the BVI will predict the individual health risk for disorders of energy homeostasis most precisely.

As mentioned, the herein provided paracrine FGFs specifically target the visceral adipose tissue which is known to be responsible for several secondary diseases of obesity.

Accordingly, the obesity to be treated by the polypeptide of the invention, the polynucleotide of the invention, the pharmaceutical composition of the invention, or the method of the invention may be central obesity. "Central obesity", "abdominal obesity" or "belly fat" is the accumulation of abdominal fat resulting in an increase in waist size. There is a strong correlation between central obesity and cardiovascular disease. Central obesity, as mentioned above also, is characterized by an excess of visceral fat in the body in which the abdomen protrudes excessively. Central obesity can be diagnosed by taking waist and hip measurements. The absolute waist circumference (>102 centimetres in men and >88 centimetres in women) and the waist-hip ratio (>0.9 for men and >0.85 for women) are both used as measures of central obesity. Another measure of central obesity is the Index of Central Obesity (waist-to-height ratio—WHtR). For persons younger than 40 years, a WHtR ratio of >0.5 (i.e. a waist circumference at least half of the individual's height) is predictive of central obesity (and an increased risk for cardiovascular disease). For persons in the age between 40 and 50 years, a WHtR ratio between 0.5 and 0.6 is indicative of central obesity. For persons older than 50 years, a WHtR of >0.6 is indicative of central obesity. Another diagnosis of obesity is the analysis of intraabdominal fat. The increased amount of fat in this region relates to the higher levels of plasma lipid and lipoproteins. In addition, as described above, central obesity (or abdominal obesity) can also be diagnosed by using computed tomography and magnetic resonance imaging. In addition or alternatively, central obesity may be diagnosed by using 3D volumetric and body composition analysis as described above.

The appended examples demonstrate that the herein provided paracrine FGFs (e.g. FGF8b) have the ability to increase the total amount of brown adipocytes capable of uncoupled respiration and thus thermogenesis. In particular, the herein provided paracrine FGFs recruit thermogenic potential by inducing the neoformation of brown adipocytes. In accordance with the present invention, the activation of the brown adipose tissue may be accomplished by sympathetic innervation of the surrounding white adipose tissue which releases noradrenalin and stimulates the release of fatty acids of the deposited fat. In addition, the released noradrenalin also activates the newly generated BAT and thereby effectively assists the weight reduction. Sympathetic innervation of white adipose tissue can be activated through energy restriction, e.g. a dietary lifestyle intervention. However, the (newly generated) BAT may also be activated via the administration of pharmaceuticals. Thus, the herein provided paracrine FGFs (e.g. FGF8b, FGF8f and/or FGF17) may be co-administered with a pharmaceutical which activates BAT. The co-administration may be a simultaneous, sequential or separate administration. It is prioritized that the administration is sequential.

Thus, the invention relates to the polypeptide of the invention, the polynucleotide of the invention, the pharmaceutical composition of the invention, or the method of the invention, wherein said polypeptide, polynucleotide or pharmaceutical composition is co-administered with at least one other active agent. In accordance with the present invention, said other active agent is at least one active agent selected from the group consisting of beta-adrenergic agonists (e.g. noradrenalin, isoproterenol, BRL 35135, ICI D7114, CGP-12177A, CL 316243), indirect sympathomimetics (e.g. ephedrine, methylphenidate), atrial natriuretic peptide (e.g. ANP, BNP) and ANP/BNP receptor agonists (e.g. AP-811). Said noradrenalin may be native noradrenalin. Said beta-adrenergic agonist may be a beta3-adrenergic agonist and/or said beta3-adrenergic agonist may be CL 316243.

The therapeutic benefit of brown adipose tissue is a function of tissue mass and sympathetic tone (sympathetic catecholamines are activators of brown fat activity). The more brown fat is recruited in white adipose tissue with its specific, given sympathetic tone, the more therapeutic activity is expected. In addition to brown fat recruitment by a paracrine FGF, the sympathetic tone can be increased (e.g. by fasting) or mimicked by co-administration of sympathomimetic drugs. Exemplary sympathomimetic drugs are indirect sympathomimetics (e.g. ephedrine, methylphenidate).

Accordingly, provided herein is a combined preparation of the herein provided FGF (e.g. FGF8b, FGF8f and/or FGF17) and a pharmaceutical which activates BAT for simultaneous, sequential or separate use in therapy. As mentioned above, a pharmaceutical which activates BAT may be a beta-adrenergic agonist, noradrenalin, ephedrine, isoproterenol, methylphenidate, BRL 35135, ICI D7114, CGP-12177A and atrial natriuretic peptide (ANP).

In one aspect of the present invention, the co-administration of the paracrine FGF(s) as provided herein and the other active agent (e.g. an agent for activating brown adipose tissue) may lead to synergistic effects resulting in reduced symptoms and/or faster treatment of a disease or disorder of energy homeostasis (e.g. obesity) as compared to the administration of the inventive paracrine FGF(s) or the other active agent alone.

The term "synergistic effect" is commonly known in the art and used herein to describe a situation where the combined effect of two or more active agents is greater than the sum of the individual active agents. In other words, two or more active agents can interact in a way that the presence of one active agent enhances or magnifies the effect(s) of the second. In particular, synergistic effects may lead to more effective treatment of a disease or disorder of energy homeostasis (e.g. obesity, dyslipidemia, diabetes, insulin resistance, hyperglycemia and/or metabolic syndrome).

Another embodiment of the invention relates to a method for the preparation of a pharmaceutical composition for use in treating a disease or disorder of energy homeostasis, wherein the method comprises the following steps:
(a) contacting the polypeptide of the invention and/or the polynucleotide of the invention with a liquid carrier or a solid carrier;
(b) optionally, adjusting the pH and/or the osmolarity of the product obtained in step (a);
(c) optionally, sterilizing the product obtained in step (a) or (b); and
(d) formulating and/or packaging the product obtained in step (a), (b) or (c) as a finished medical product.

In this preparation method, said carrier may be at least one carrier selected from the group consisting of cellulose, lactose, water, saline, Ringer's solution, dextrose solution, a fixed oil, ethyl oleate and liposomes. For example, said carrier may be cellulose and/or lactose.

The carrier may contain minor amounts of additives such as substances that enhance isotonicity and/or chemical stability. Such materials are preferably non-toxic to recipients at the dosages and concentrations employed, and may include buffers such as phosphate, citrate, succinate, acetic acid, and other organic acids or their salts; antioxidants such as ascorbic acid; low molecular weight (less than about ten residues) (poly)peptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

In the preparation method described above, the resulting pharmaceutical composition may be in the form of an erodible implant, a gel, a liquid solution, a pill, a tablet, a capsule, a thin film, a powder, a solid crystal or liposomes. In the herein described method for the preparation of a pharmaceutical composition, the carrier may be at least one carrier selected from the group consisting of cellulose, lactose, water, saline (e.g. physiological saline), Ringer's solution, dextrose solution, a fixed oil, ethyl oleate and liposomes.

In step (b) of the herein described preparation method, the pH may be adjusted to be the pH of blood (e.g. a pH of 7.35-7.45) or to be the pH of adipose tissue (e.g. a pH of 7.1-7.4. In addition, in step (b) of the preparation method, the osmolarity of the product may be adjusted to be isotonic with blood or adipose tissue. For example, the NaCl content may be adjusted to be isosmotic with blood or adipose tissue. For example, the NaCl content may be adjusted to be 9 g/l NaCl (i.e. 308 mosmol/l).

In step (c) of the above described preparation method, the medical product is sterilized. Methods for sterilization are known in the art. For example, sterilization may be accomplished by, e.g., filtration through sterile filtration membranes (e.g., 0.2 micron membranes). Sterilization may also be accomplished by exposing the medical product to appropriate kind of radiation, id est alpha and beta particles, gamma rays, x-ray, ultraviolet radiation, and neutron radiation. Furthermore, heat, appropriate chemical substances, and plasmas can be used for sterilization.

In step (d) of the herein described preparation method, formulating of the pharmaceutical product is conducted. For example, the product may be shaped into the desired formulation (e.g. into an erodible implant, a gel, a liquid solution, a pill, a tablet, a capsule, a thin film, a powder, a solid crystal or liposomes). Finally, the pharmaceutical product may be packaged. For example, the pharmaceutical product may be placed into a minipump. Alternatively, the pharmaceutical product may be packed in unit or multi-dose containers, for example, sealed ampoules or vials. The method for the preparation of a pharmaceutical composition as described herein results in the production of a finished medical product. Such a product is a product which is ready for administration, sale and distribution. In addition, the package of the pharmaceutical composition may comprise instructions regarding the use of the pharmaceutical composition.

As mentioned above, provided herein are paracrine FGFs (e.g. FGF8b, FGF8f and/or FGF17) which are capable of converting white visceral adipocytes or preadipocytes to brown adipocytes. FGFs act by binding to and thereby eliciting a response from FGF receptors The activity of a particular FGF (e.g. FGF8b, FGF8f and/or FGF17) can be mimicked by the activation of the responsive FGF receptor. Accordingly, a small molecule which binds to (and activates) the target receptor of the paracrine FGFs provided herein (e.g. FGF8b, FGF8f and/or FGF17) may be used for treating a disease or disorder of energy homeostasis (e.g. obesity). Thus, one aspect of the present invention relates to a small molecule which simulates binding of the herein provided FGF(s) (e.g. FGF8b, FGF8f and/or FGF17) to its target receptor(s) for use in treating a disease or disorder of energy homeostasis (e.g. obesity).

The illustrative appended examples demonstrate that the FGF receptors 1-3 are well detectable in both, subcutaneous (inguinal) and visceral (epididymal) adipose tissue. The appended examples also show that the FGF receptor 4 is only found in visceral (epididymal) and not in subcutaneous (inguinal) adipose tissue in appreciable amounts and that FGF receptor 4 expression correlates with FGF8b sensitivity. Accordingly, one aspect of the present invention relates to a small molecule which activates at least one FGF receptor selected from the group consisting of FGF receptor 1c, FGF receptor 2c, FGF receptor 3c and FGF receptor 4 for use in treating a disease or disorder of energy homeostasis (e.g. obesity). Preferably, said small molecule activates FGF receptor 4.

As used herein, the term "small molecule" refers to a low molecular weight (<900 Daltons) compound. Small molecules can help to regulate a biological process and have usually a size in the order of $10^{-9}$ m.

As used herein, the term "polypeptide" relates to a peptide, a protein, or a polypeptide which encompasses amino acid chains of a given length, wherein the amino acid residues are linked by covalent peptide bonds. However, peptidomimetics of such proteins/polypeptides wherein amino acid(s) and/or peptide bond(s) have been replaced by functional analogs as well as polypeptides comprising other than the 20 gene-encoded amino acids (such as selenocysteine) are also encompassed by the invention. Peptides, oligopeptides and proteins may be termed polypeptides. The term polypeptide also refers to, and does not exclude, modifications of the polypeptide, e.g., glycosylation, acetylation, phosphorylation and the like. Such modifications are well described in the art.

The herein provided polypeptides comprise amino acid sequences e.g. the amino acid sequence as shown in SEQ ID NO:16, or the amino acid sequence comprising amino acids 34-215 of SEQ ID NO:16, or (a) fragment(s) thereof. As used herein, the term "amino acid" refers to any amino acid known in the art and comprises proteinogenic as well as non-proteinogenic amino acids as known in the art.

Proteinogenic amino acids comprise alanine (Ala; A), arginine (Arg; R), asparagine (Asn; N), aspartic acid (Asp; D), cysteine (Cys; C), glutamine (Gln; Q), glutamic acid (Glu; E), glycine (Gly; G), histidine (His; H), isoleucine (Ile, I), leucine (Leu; L), lysine (Lys; K), methionine (Met; M), phenylalanine (Phe; F), proline (Pro; P), serine (Ser; S), threonine (Thr; T), tryptophane (Trp; W), tyrosine (Tyr; Y), valine (Val; V), selenocysteine (Sec; U) and pyrrolysine (Pyl; O). Non-limiting examples for non-proteinogenic amino acids are hydroxyproline, selenomethionine, carnitine, gamma-aminobutyric acid (GABA), lanthionine, dehydroalanine, ornithine, or citrulline. As the skilled person is readily aware of, it is possible that in some cases also non-proteinogenic amino acids may be part of proteins. Amino acids are abbreviated herein by the one-letter code or the three-letter code as commonly used in the art and as also set forth hereinabove.

Without being bound by theory, it is believed that the capacity of paracrine FGFs, preferably FGF8, to induce differentiation or conversion of white adipocytes and/or preadipocytes to brown adipocytes or to recruit brown adipocytes, may be conferred by the amino acid sequence VTVQSSPNFTQ (SEQ ID NO:103) close to the n-terminal region of the protein. This is explained in more detail below. The corresponding nucleic acid sequence is "GTAACTGT-TCAGTCCTCACCTAATTTTACACAG" (SEQ ID NO:104).

The capacity of members of the FGF family to potentially activate UCP-1 mRNA gene expression during the differentiation of different adipocyte cell lines was screened FGF8b and FGF17 were demonstrated to enhance UCP1 mRNA expression in epididymal adipocytes (FIG. 1A). It is of note that FGF8 and FGF17 belong to the same subfamily within the FGF gene family, namely the FGF8 subfamily (Itoh et al. Developmental Dynamics 2008). The so called FGF8 subfamily consists of FGF8, FGF17, and FGF18.

FGF8 was demonstrated herein to be the most potent inducer of UCP1. Since the murine FGF8 gene gives rise to 8 differently spliced transcripts leading to 8 different peptides (FGFa-h) in rodents, the ability of the 4 murine isoforms that are also present in humans (FGF8a, b, e, and f) to induce Ucp1 mRNA abundance was assessed (FIG. 1B). In adipocytes of inguinal origin, FGF8b was the only isoform with browning potential, while in epididymal adipocytes Fgf8b and Fgf8f were both effective.

Notably, only FGF8b and FGF8f share the amino acid sequence VTVQSSPNFTQ (SEQ ID NO:103) close to the N-terminal region of the protein:

FGF8b and FGF17 both exhibit the short amino acid sequence SPNF (SEQ ID NO:107) around F32. This suggests that the potential biological activity of the polypeptides might be conferred by this amino acid sequence. Thus, it is preferred that the polypeptides to be used herein comprise the amino acid sequence SPNF (SEQ ID NO:107), preferably of from position 29 to position 32 of the respective

```
human FGF8 spliceforms
human_FGF8a    MGSPRSALSCLLLHLLVLCLQAQ---------------------------------------
human_FGF8b    MGSPRSALSCLLLHLLVLCLQAQ----------------------------VTVQSSPN
human_FGF8f    MGSPRSALSCLLLHLLVLCLQAQEGPGRGPALGRELASLFRAGREPQGVSQQVTVQSSPN
human_FGF8e    MGSPRSALSCLLLHLLVLCLQAQEGPGRGPALGRELASLFRAGREPQGVSQ---------
               ********************* human_FGF8a    ---HVREQSLVTDQLSRRLIRTYQLYSRTSGKHVQVLANKRINAMAEDGDPFAKLIVETD
human_FGF8b    FTQHVREQSLVTDQLSRRLIRTYQLYSRTSGKHVQVLANKRINAMAEDGDPFAKLIVETD
human_FGF8f    FTQHVREQSLVTDQLSRRLIRTYQLYSRTSGKHVQVLANKRINAMAEDGDPFAKLIVETD
human_FGF8e    --QHVREQSLVTDQLSRRLIRTYQLYSRTSGKHVQVLANKRINAMAEDGDPFAKLIVETD
                  ********************************************************* human_FGF8a    TFGSRVRVRGAETGLYICMNKKGKLIAKSNGKGKDCVFTEIVLENNYTALQNAKYEGWYM
human_FGF8b    TEGSRVRVRGAETGLYICMNKKGKLIAKSNGKGKDCVETEIVLENNYTALQNAKTEGWYM
human_FGF8f    TFGSRVRVRGAETGLYICMNKKGKLIAKSNGKGKDCVFTEIVLENNYTALQNAKYEGWYM
human_FGF8e    TFGSRVRVRGAETGLYICMNKKGKLTAKSNGKGKDCVETEIVLENNYTALQNAKYEGWYM
               ************************************************************* human_FGF8a    AFTRKGRPRKGSKTRQHQREVHFMKRLPRGHHTTEQSLRFEFLNYPPFTRSLRGSQRTWA
human_FGF8b    AFTRKGRPRKGSKTRQHQREVHFMKRLPRGHHTTEQSLRFEFLNYPPFTRSLRGSQRTWA
human_FGF8f    AFTRKGRPRKGSKTRQHQREVHFMKRLPRGHHTTEQSLRFEFLNYPPFTRSLRGSQRTWA
human_FGF8e    AFTRKGRPRKGSKTRQHQREVHFMKRLPRGHHTTEQSLRFEFLNYPPFTRSLRGSQRTWA
               ************************************************************* human_FGF8a    PEPR (SEQ ID NO: 15)
human_FGF8b    PEPR (SEQ ID NO: 16)
human_FGF8f    PEPR (SEQ ID NO: 17)
human_FGF8e    PEPR (SEQ ID NO: 18)
                
```

Therefore, these 11 amino acids on exon 1D (nomenclature by MacArthur et al. Development 1995) are likely sufficient to mediate a biological effect. Therefore, it is preferred that the polypeptides for use in accordance with the present invention comprise the amino acid sequence VTVQSSPNFTQ (SEQ ID NO:103) or related sequences like QVTVQSSPNFTQ (SEQ ID NO:105) or QVTVQSSP-NFT (SEQ ID NO:106) or fragments thereof that contribute to mediating the biological effect of the polypeptide.

Furthermore, the phenylalanine residue 32 (F32) of this short amino acid peptide has been shown to interact with the hydrophobic groove within the Ig domain III, i.e. the "c" variants of the FGF receptors (Olsen et al. 2013). The "c" spliceforms comprise FGFR1c, FGFR2c, FGFR3c, and FGFR4. Strikingly, FGF17, an endocrine FGF, is also active to induce UCP1 mRNA gene expression (FIG. 1A) and also shares F32:

amino acid sequence of FGF8b (exemplary amino acid sequence of FGF8b is shown in SEQ ID NO.16) or of from position 30 to position 33 of the respective amino acid sequence of FGF17 (exemplary amino acid sequence of FGF8b is shown in SEQ ID NO:18). And both FGF8b and FGF17 share the amino acid residue Q at position 34 of the respective amino acid sequence of FGF8b (exemplary amino acid sequence of FGF8b is shown in SEQ ID NO:16) or at position 35 of the respective amino acid sequence of FGF17 (exemplary amino acid sequence of FGF8b is shown in SEQ ID NO:18) Thus, they share the motif "SPNFXQ" (SEQ ID NO:108). Therefore, it is preferred that the polypeptides to be used herein comprise the amino acid sequence SPNFXQ (SEQ ID NO:108), preferably of from position 29 to position 34 of the respective amino acid sequence of FGF8b (exemplary amino acid sequence of FGF8b is shown in SEQ ID NO: 16) or of from position 30 to position 35 of the

```
human: FGF8b vs. FGF17
human_FGF8b MGSPRSALS-CLLLHLLVLCLQAQVTVQSSPNFTQHVREQSLVTDQLSRRLIRTYQLYSR
human_FGF17 MGAARLLPNLTLCLQLLILCCQTQGENHPSPNFNQYVRDQGAMTDQLSRRQIREYQLYSR
            **:.*   . * *:: *:*    :.****.*:**:*. :*****  ****** human_FGF8b TSGKHVQVLANKRINAMAEDGDPFAKLIVETDTFGSRVRVRGAETGLYICMNKKGKLIAK
human_FGF17 TSGKHVQVTG-RRISATAEDGNKFAKLIVETDTFGSRVRIKGAESEKYICMNKRGKLIGK
            ******  .:.* **. *************:.*.  ****.**.* human_FGF8b SNGKGKDCVFTEIVLENNYTALQNAKYEGWYMAFTRKGRPRKGSKTRQHQREVHFMKRLP
human_FGF17 PSGKSKDCVFTEIVLENNYTAFQNARHEGWFMAFTRQGRPRQASRSRQNQREAHFIKRLY
            .:.***********.*::*.*:**:.:*::*.:* human_FGF8b RG----HHTTEQSLRFEFLNYPPFTRSLRGSQRTWAPEPR-  (SEQ ID NO: 16)
human_FGF17 QGQLPFPNHAEKQKQFEFVGSAPTRR----TKRTRRPQPLT  (SEQ ID NO: 23)
            :*  :  : * . .:** *:. . * *  :** *:*
``` respective amino acid sequence of FGF17 (exemplary amino acid sequence of FGF8b is shown in SEQ ID NO:18). X may be T or N.

The literature describes that mutation of Phenylalanine F32 to Alanine A32 FGF8bF32A is sufficient to abrogate the organizer activity of FGF8b in the mid-hindbrain development (Olsen et al. 2013). Therefore, FGF8bF32A and FGF17F32A variants can be used to assess whether such variants are no longer capable of inducing differentiation or conversion of white adipocytes and/or preadipocytes to brown adipocytes or recruiting brown adipocytes.

Abrogation of marker expression, like UCP-1 mRNA expression, by exchange of phenylalanine to alanine would provide evidence for a crucial involvement of F32 in browning of white adipose tissue. Furthermore, fragments like QVTVQSSPNFT (SEQ ID NO:106), QVTVQSSPNFTQ (SEQ ID NO:105), VTVQSSPNFTQ (SEQ ID NO:103), SPNF (SEQ ID NO:107), SPNFXQ (SEQ ID NO:108) (wherein X may be T or N), or functional fragments thereof, can be used to assess if these short aa peptides are capable of mediating the browning effect. These peptides are also exemplary polypeptides to be used in accordance with the invention.

The following table shows annotations of the positions amino acid residues of the QVTVQSSPNFTQ (SEQ ID NO:105) (and fragments thereof) to exemplary amino acid sequences of FGF8b, FGF8f and FGF17:

| Q | V | T | V | Q | S | S | P | N | F | T N | (SEQ ID NO: 105 and SEQ ID NO: 110) |
|---|---|---|---|---|---|---|---|---|---|---|---|
| 23 | 24 | | | | | | 29 | | 32 | 34 | FGF8b (SEQ ID NO: 16) |
| 52 | 53 | | | | | | 58 | | 61 | 63 | FGF8f (SEQ ID NO: 18) |
| | | | | | | | 30 | | 33 | 35 | FGF17 (SEQ ID NO: 23) |

If polypeptides to be used in accordance with the present invention comprise amino acid sequences like QVTVQSSPNFT (SEQ ID NO:106), QVTVQSSPNFTQ (SEQ ID NO:105), VTVQSSPNFTQSPNF (SEQ ID NO:109), SPNFXQ (SEQ ID NO:108), SPNF (SEQ ID NO:107) or functional fragments thereof, it is understood that these sequences (i.e. QVTVQSSPNFT (SEQ ID NO:106), QVTVQSSPNFTQ (SEQ ID NO:105), VTVQSSPNFTQ (SEQ ID NO:103), SPNF (SEQ ID NO:107), SPNFXQ (SEQ ID NO:108), or functional fragments thereof) are invariable. In other words, the variation of the amino acid sequence of these polypeptides occurs outside of amino acid sequences like QVTVQSSPNFT (SEQ ID NO:106), QVTVQSSPNFTQ (SEQ ID NO:105), VTVQSSPNFTQSPNF (SEQ ID NO:109), SPNFXQ (SEQ ID NO:108), SPNF (SEQ ID NO:107) or functional fragments thereof. Variant polypeptides are, for example, polypeptides that are encoded by a nucleic acid molecule hybridizing under stringent conditions to the complementary strand of a nucleic acid molecule as defined herein (e.g. a nucleic acid molecule having a nucleic acid sequence as depicted in SEQ ID NO:2, 4 or 9 or a nucleic acid molecule encoding a paracrine FGF, like FGF8b, FGF8f or FGF17, e.g. a polypeptide comprising an amino acid sequence as depicted in SEQ ID NO:16, 18 or 23. Variant polypeptides are, for example, polypeptides having at least 40% identity to the paracrine FGF polypeptide as defined herein, like FGF8b, FGF8f or FGF17, e.g. a polypeptide comprising an amino acid sequence as depicted in SEQ ID NO:16, 18 or 23.

Further, different amino acid sequences from the n- and c-terminus of paracrine FGFs (such as FGF8 and/or FGF17) can be added to these fragments. For example, the heparin binding domains of the FGF8 subfamily might be added. The heparin binding domains are of importance because FGF8-subfamily members bind to heparin and are therefore tightly bound to heparansulfate proteoglycans, and subsequently, trapped in the extracellular matrix. This aspect is advantageous in context of the present invention, because this local entrapment of active peptides prevents potential side effects to have systemic consequences.

More than 100 heparin binding proteins have been identified, and the ability to bind heparin itself has, up to now, not been attributed to a specific sequence. Fromm et al. have reported that heparin binding sites frequently contain clusters of basic amino acids, like XBX, XBBX (SEQ ID NO:111), XBBBX (SEQ ID NO:112) (Fromm Arch Biochem Biophys 1997).

Figure 8C:
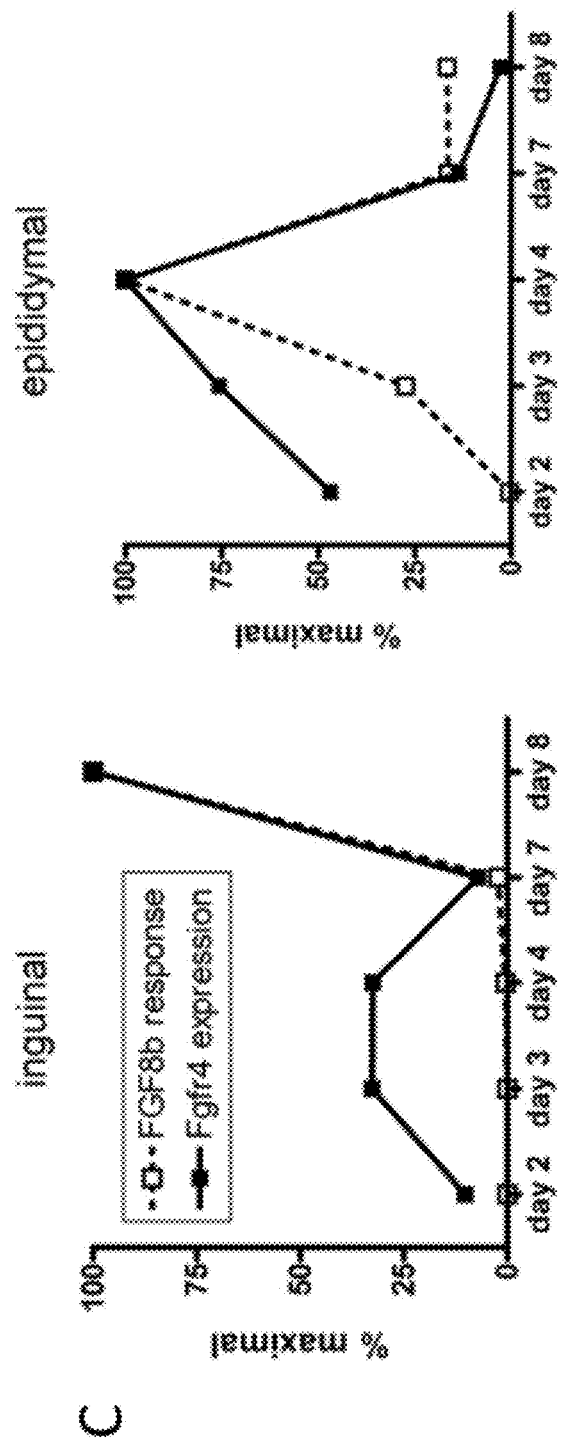
Figure 8D:
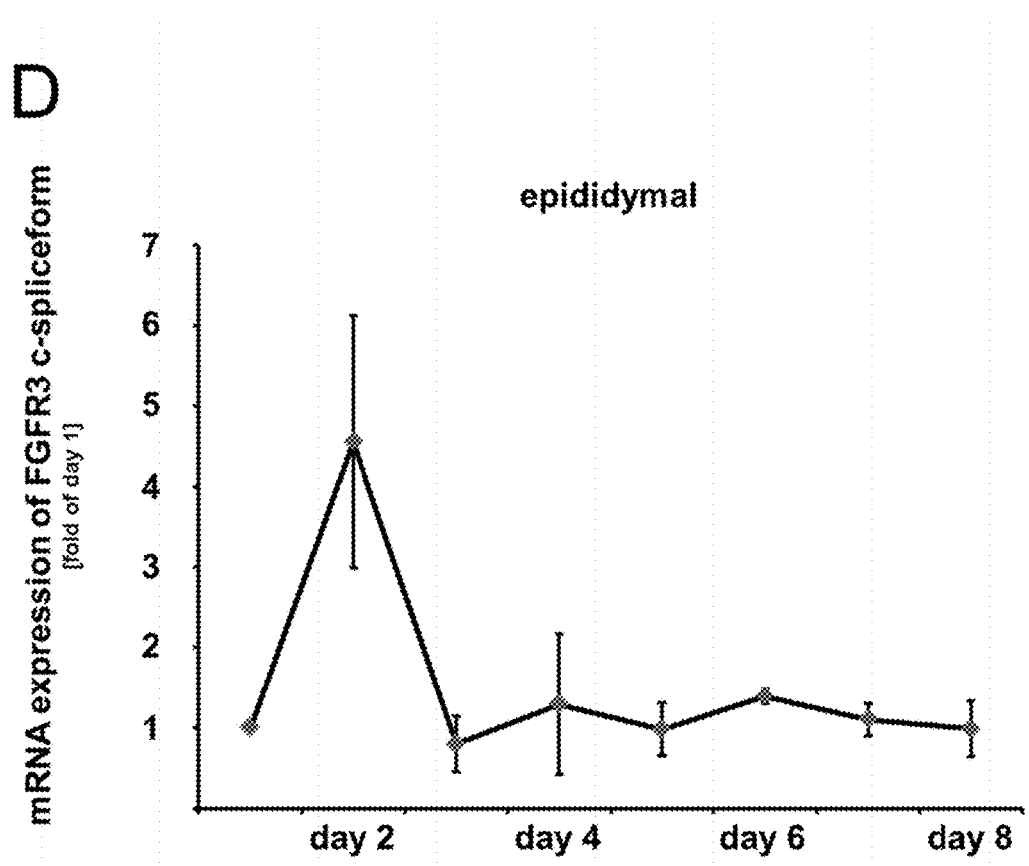
Figure 9:
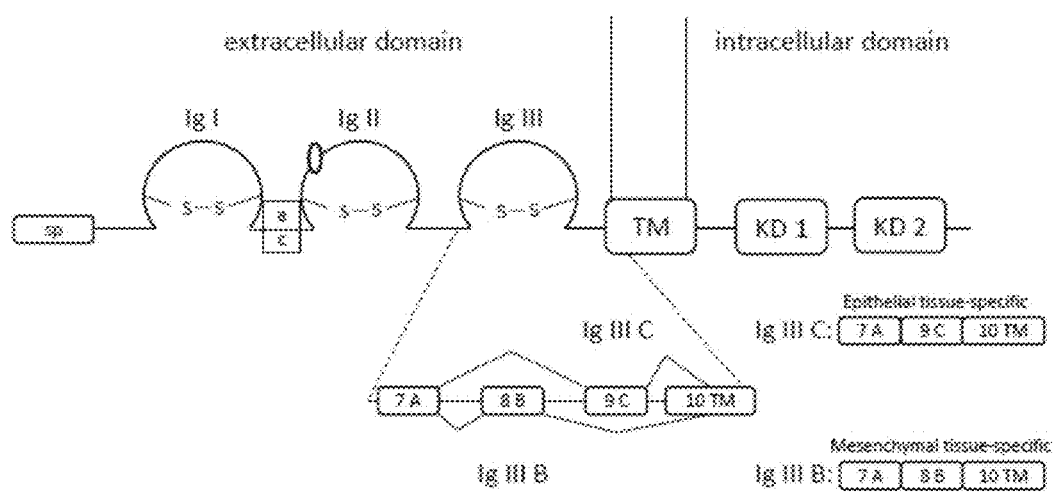

Apart from identifying heparin binding sites, the known splice variants of FGF8, i.e. FGF8a-h can be assessed. As shown in FIG. 8C FGF8b-mediated responsiveness correlated with Fgf receptor 4 mRNA abundance in immortalized inguinal as well as epididymal adipocytes. Zhang X et al. analysed receptor activation by FGF8, FGF17, and FGF18 by utilizing BaF3 cell mitogenic assay for b-spliced and c-spliced FGFR1, 2, and -3 als well as FGFR4. They observed a high receptor activation of c-spliced FGFRs and FGFR4 by the members of the FGF8-subfamily (Zhang (2006), J. Biol. Chem. 2006, 281:15694-15700). FGFR4 is considered to belong to the c-spliced FGFR family on a functional level. Als shown in FIGS. 8 C and 8 D data as provided herein show a similar correlation between the FGF8b-mediated responsiveness FGFR4 and other "c" variants of the FGF receptors, e.g. FGFR3c. Ig domain III "c" variants of the FGF receptor comprise exon 7, 9, and the transmembrane domain of the FGF receptors (FIG. 9). It is contemplated herein that the observed effect of FGF8b-mediated browning of white adipocytes is a FGF8-subfamily group effect based on interaction of FGF8-subfamily members with the "c" splice variants of the FGFR 1-3 and FGFR4.

Methods for synthesizing polypeptides are known in the art and comprise, e.g., standard FMOC-synthesis as described in the literature (e.g., solid phase peptide synthesis—"A practical approach" by E. Atherton, R. C. Sheppard, Oxford University press 1989) or liquid phase synthesis, where the peptides are assembled using a mixed strategy by BOC-chemistry and fragment condensation as described in the literature (E. Wunsch, "Synthese von Peptiden" in "Methoden der organischen Chemie" (Houben-Weyl), 15 Ausg. 4, Teil 1 and 2 Thieme, Stuttgart, 1974). Another method for synthesizing the polypeptide(s) of the invention is the generation of transgenic cells which express the polypeptide(s) of the invention. After expression of a desired polypeptide(s) by a transgenic cell, said polypeptide(s) may be purified.

The polypeptides to be used herein may be modified. Especially modifications are contemplated herein that alter the amino acid sequence of the naturally occurring polypeptides so that the polypeptides for use in the present invention are distinct from the naturally occurring polypeptides.

Exemplary modifications are explained below.

Phenylalanine is an aromatic, neutral, and nonpolar amino acid. The interaction domain of FGF8b-mediated UCP1 mRNA inducing effect seems to be dependent on interaction with the hydrophobic groove within in Ig III domain of the FGF receptors. Interaction stability might be enhanced by using alternating amino acids, like other natural or not natural aromatic amino acids. Natural amino acids of this group are Histidine, Tryptophan, and Tyrosine. Other nonpolar amino acids are Alanine, Cysteine, Glycine, Isoleucine, Leucine, Methionine, Proline, Tryptophan, and Valine. Likewise amino acids with similar characteristics (polar, nonpolar, aromatic, neural, negative, positive) can be used to influence interaction of amino acids, especially amino acids of the QVTVQSSPNFT (SEQ ID NO:106) motif and fragments thereof.

Apart from this strategy, peptide or protein engineering of FGF8-subfamily members might be necessary to develop a molecule suitable for clinical use.

Improvement by using and/or inclusion of disulfide bonds: To yield a biopharmaceutically improved variant of FGF8 it might be useful to stabilize the molecule by disulfide bonds. FGF8f, for example, exhibits various cysteine for this purpose (position 10, 19, 138, and 156). Functionally irrelevant aa could be exchanged by cysteines for artificial disulfide bonds.

Glycosylation may be modified, too. For example, w

Improvement by enhancing stability by preventing n-terminal proteolysis: Proteins are cleaved by ubiquitous and multiple intracellular and extracellular peptidases. High-temperature requirement A1 (Htra1a) serine peptidase 1a is a novel antagonist of FGF signalling via cleavage of FGF8 in the extracellular domain (Kim et al. Mol Cell Biol 2012). This protease was first identified in bacteria and is characterized by a highly conserved trypsin-like serine protease domain. In order to enhance stability of FGF8b and subsequent strengthen the effect of browning in the herein provided in vivo model Htra1a-mediated cleavage can be addressed by removal of the Htra1a target sequence.

Alternative optimization of the FGF8-mediated effect include introduction of a non-natural amino acid, p-acetyl-phenylalanine, for the site-specific attachment of polyethylene glycol (PEG), the so called PEGylation method. For example, FGF8 conjugates fused to SUMO, FGF8-CovX-body chimera, and/or fusion of FGF8 to the immunoglobulin Fc can be used to enhance therapeutic effectiveness of the described effect of FGF8-subfamily members to induce browning in white adipose tissue.

As mentioned above, the invention relates to "polynucleotides" for use in treating a disease or disorder of energy homeostasis, wherein the polynucleotides encode the polypeptides of the invention. These polynucleotides may be nucleic acids or nucleic acid analogues such as, e.g., DNA molecules, RNA molecules, oligonucleotide thiophosphates, substituted ribo-oligonucleotides, LNA molecules, PNA molecules, GNA (glycol nucleic acid) molecules, TNA (threose nucleic acid) molecules or morpholino polynucleotides. Furthermore, the term "polynucleotide" is to be construed equivalently with the term "nucleic acid molecule" in context of the present invention and may inter alia refer to DNA, RNA, PNA or LNA or hybrids thereof or any modification thereof that is known in the art (see, e.g., U.S. Pat. Nos. 5,525,711, 4,711,955, 5,792,608 or EP 302175 for examples of modifications). Nucleic acid residues comprised by the polynucleotides described and provided herein may be naturally occurring nucleic acid residues or artificially produced nucleic acid residues. Examples for nucleic acid residues are adenine (A), guanine (G), cytosine (C), thymine (T), uracil (U), xanthine (X), and hypoxanthine (HX). As understood by the person of skill in the art, thymine (T) and uracil (U) may be used interchangeably depending on the respective type of polynucleotide. For example, as the skilled person is aware of, a thymine (T) as part of a DNA corresponds to an uracil (U) as part of the corresponding transcribed mRNA. The polynucleotides described and provided herein may be single- or double-stranded, linear or circular, natural or synthetic.

The production of a desired polynucleotide is commonly known in the art. For example, the polynucleotide(s) of the invention may be synthesized by generating transgenic cells which express the polynucleotide(s) of the invention. After replication of (a) desired polynucleotide(s) by a transgenic cell, said polynucleotide(s) may be purified. Various means also exist to artificially accomplish the replication of naturally occurring DNA, or to create artificial gene sequences. For example, polymerase chain reaction (PCR) may be used to replicate a particular polynucleotide. Artificial gene synthesis is the process of synthesizing a gene in vitro without the need for initial template DNA samples. This may be achieved by oligonucleotide synthesis from digital genetic sequences and subsequent annealing of the resultant fragments.

The polynucleotides for use in treating a disease or disorder of energy homeostasis (e.g. obesity) provided herein may be cloned into a vector. Thus, the present invention also relates to a vector for use in treating a disease or disorder of energy homeostasis comprising the polynucleotide as described and provided herein. The term "vector" as used herein particularly refers to plasmids, cosmids, viruses, bacteriophages and other vectors commonly used in genetic engineering. Preferably, these vectors are suitable for the transformation of cells, like fungal cells, cells of microorganisms such as yeast, mammalian cells or prokaryotic cells. In a particularly preferred embodiment, such vectors are suitable for stable transformation of bacterial or eukaryotic cells, for example to express the polynucleotides provided herein.

Generally, expression vectors have been widely described in the literature. As a rule, they may not only contain a selection marker gene and a replication-origin ensuring replication in the host selected, but also a promoter, and in most cases a termination signal for transcription. Between the promoter and the termination signal there is preferably at least one restriction site or a polylinker which enables the insertion of a nucleic acid sequence/molecule desired to be expressed.

Non-limiting examples for the vector into which a polynucleotide for use in treating a disease or disorder of energy homeostasis may be cloned are adenoviral, adeno-associated viral (AAV), lentiviral, HIV-based lentiviral, or nonviral minicircle-vectors.

Furthermore, the herein described polynucleotides and/or vectors may be transduced, transformed or transfected or otherwise introduced into a host cell. Thus, the present invention also relates to a host cell comprising the polynucleotide and/or the vector as described and provided herein. For example, the host cell may be a prokaryotic cell, for example, a bacterial cell. As a non-limiting example, the host cell may also be a mammalian cell. The host cell described herein is intended to be particularly useful for generating the polypeptides provided herein. An overview of examples of different corresponding expression systems to be used for generating the host cell described herein is for instance contained in Methods in Enzymology 153, 1987, 385-516, in Bitter (Methods in Enzymology 153, 1987, 516-544), in Sawers (Applied Microbiology and Biotechnology 46, 1996, 1-9), Billman-Jacobe (Current Opinion in Biotechnology 7, 1996, 500-4), Hockney (Trends in Biotechnology 12, 1994, 456-463), and in Griffiths, (Methods in Molecular Biology 75, 1997, 427-440). The transformation or genetically engineering of the host cell with a polynucleotide or vector described and provided herein can be carried out by standard methods, as for instance described in Sambrook and Russell, 2001, Molecular Cloning: A Laboratory Manual, CSH Press, Cold Spring Harbor, N.Y., USA; Methods in Yeast Genetics, A Laboratory Course Manual, Cold Spring Harbor Laboratory Press, 1990.

In context of the present invention, the term "local", in particular "local action" means that the effect of an administered agent is restricted to a particular region of the body and does not have a systemic effect. For example, the effect of a polypeptide of the invention (e.g. FGF8b, FGF8f and/or FGF17) may be restricted to the tissue or organ to which said polypeptide has been administered. Since the herein provided paracrine FGFs (e.g. FGF8b, FGF8f and/or FGF17) may be administered into adipose tissue (such as visceral adipose tissue), "local action" of a polypeptide of the invention (i.e. of the paracrine FGFs of the invention) means that said polypeptide acts mainly or specifically on adipose tissue (such as visceral adipose tissue). In line with this, "local action" means that no systemic action can be observed. Furthermore, "local action" of a polypeptide of the invention (e.g. of FGF8b, FGF8f and/or FGF17) means that a particular adipose tissue depot (in a specific region of the body) is specifically targeted by said polypeptide. The adipose tissue depot which may completely or partly be converted into brown fat by the inventive polypeptides may have a particular size. The amount of visceral fat, comprising intraabdominal fat and retroperitoneal fat, in an individual with a BMI of 30 kg/m$^2$ may have a size 3 kg (1.4-4.9). The amount of subcutaneous fat may be 4.7 kg (3.2-7.1). The total amount of visceral and subcutaneous fat can be subdivided into specific adipose tissue depots. For example, said adipose tissue may be the mesenteric adipose tissue with a size of approximately 1 kg, the omentum majus with a size of approximately 0.5 kg, the peritoneal fat tissue with a size of approximately 0.5 kg, or superficial fat depots. The rate of conversion into brown adipose in a given depot may be 0.1% to 100% of the total amount of visceral or subcutaneous fat, e.g. 0.5% to 80%, 1% to 70%, 5% to 60%, 10% to 50% or 20% to 40% of the total amount of visceral or subcutaneous fat. The polypeptides of the invention (e.g. FGF8b, FGF8f and/or FGF17) act locally since these polypeptides are paracrine factors. Paracrine (signaling) factors are factors for the cell-cell communication which are produced by cells to induce changes in nearby cells to altering the behavior or differentiation of those cells. Signaling molecules known as paracrine factors diffuse over a relatively short distance (local action), as opposed to endocrine factors (hormones which travel considerably longer distances via the circulatory system) and juxtacrine interactions (autocrine signaling). Cells that produce paracrine factors secrete them into the immediate extracellular environment. The paracrine factors then travel to nearby cells in which the gradient of factor received determines the outcome. The distance a paracrine factor (such as FGF8b, FGF8f and/or FGF17) typically travels is in the range of a few cell diameters, e.g. from 1 µM to 1 mm.

The terms "white adipose tissue" (WAT, or white fat) and "brown adipose tissue" (BAT, or brown fat) are commonly known in the art and described herein above and below. White adipose tissue is the storage of food energy in the form of fat, brown adipose tissue is used for heat production in defense of body temperature against cold. Brown adipose tissue is characterized by an enormously high energy turnover. In particular brown adipose tissue consumes fat and sugar from the blood and can "burn" large amounts of energy.

Brown adipose tissue accounts for approximately 0.05-0.1% of body mass (i.e. 35-70 g in a 70 kg man). The performance of brown adipose tissue is in the order of 50 mW/g tissue and (if continuously activated) results in a weight loss of about 4 kg of fat per year. This relatively small theoretical weight loss could be increased by increasing the mass of brown adipose tissue (Klingenspor and Fromme, (2012) M. E. Symonds (ed.), Adipose Tissue Biology, Chapter 3, p. 39-69). Thus, an advantageous effect of the inventive polypeptides (e.g. FGF8b, FGF8f and/or FGF17) is that that these factors have the ability to increase brown adipose tissue in white adipose tissue depots, and thus, can increase weight loss induced through the action of the brown adipose tissue.

The functionality of "brown adipose tissue" is commonly known in the art and described in detail, e.g., in Klingenspor and Fromme (2012) M. E. Symonds (ed.), Adipose Tissue Biology, Chapter 3, p. 39-69. In particular, in mammals, a constant body temperature can only be maintained when the rate of heat dissipation equals the rate of heat loss. Thermoregulatory heat production mechanisms compensating heat loss are classically categorized as shivering and non-shivering thermogenesis. Non-shivering thermogenesis occurs in brown adipose tissue which represents a unique heater organ.

Brown adipocytes are characterized by an abundance of small lipid droplets (multilocular) in contrast to white adipocytes which typically feature a single large lipid droplet (unilocular). They furthermore contain an unusually high amount of mitochondria which confer the eponymous brown color to the tissue. In mitochondria of brown adipose tissue the proton motive force (PMF) across the inner membrane is dissipated as heat rather than converted to ATP (Klingenspor and Fromme, M. E. Symonds (ed.), Adipose Tissue Biology, Chapter 3, p. 39-69). This tightly regulated process is catalyzed by the uncoupling protein 1 (Ucp1). Non-shivering thermogenesis is elicited by the sympathetic innervation from hypothalamic and brain stem control regions which are activated, e.g., by cold sensation. In a cold environment, up to half of the metabolic rate of rodents can be attributed to non-shivering thermogenesis in brown adipose tissue (Klingenspor and Fromme, M. E. Symonds (ed.), Adipose Tissue Biology, Chapter 3, p. 39-69). Accordingly, brown adipose tissue is significantly involved in the prevention of sustained and life threatening hypothermia in the cold.

Notably, the high thermogenic capacity of brown adipose tissue recruited in the defense of normothermia may also play a role in the regulation of energy balance in the face of hypercaloric nutrition (Klingenspor and Fromme, M. E. Symonds (ed.), Adipose Tissue Biology, Chapter 3, p. 39-69).

The terms "visceral" and "subcutaneous" adipose tissue are commonly known in the art and described, e.g., in Ibrahim, Obesity Reviews 11 (2009) 11-18. In particular, there are differences between adipose tissue present in subcutaneous areas and visceral adipose tissue present in the abdominal cavity. These include anatomical, cellular, molecular, physiological, clinical and prognostic differences. Anatomically, visceral adipose tissue is present mainly in the mesentery and omentum, and drains directly through the portal circulation to the liver. Visceral compared with subcutaneous adipose tissue contains a larger number of inflammatory and immune cells, lesser preadipocyte differentiating capacity and a greater percentage of large adipocytes. There are more glucocorticoid and androgen receptors in visceral adipose tissue than in subcutaneous adipose tissue. In addition, visceral adipose tissue has a greater capacity to generate free fatty acids and to uptake glucose than subcutaneous adipose tissue and is more sensitive to adrenergic stimulation, while subcutaneous adipose tissue is more avid in absorption of circulating free fatty acids and triglycerides. Importantly, preferential fat storage in visceral adipose tissue is associated with an increased mortality.

Fat present around abdominal viscera in mesentery and omentum, known as visceral fat, is different from that present in subcutaneous areas (subcutaneous fat). The type of fat cells (adipocytes), their endocrine function, lipolytic activity, response to insulin and other hormones differ between subcutaneous adipose tissue (SCAT) and visceral adipose tissue (VAT). Subcutaneous fat accumulation represents the normal physiological buffer for excess energy intake (high caloric diet) with limited energy expenditure (physical inactivity). It acts as a metabolic sink where excess free fatty acids (FFAs) and glycerol are stored as triglycerides (TGs) in adipocytes (Freedland, Nutr. Metab. 1 (2004) 12). When the storage capacity of subcutaneous adipose tissue is exceeded or its ability to generate new adipocytes is impaired because of either genetic predisposition or stresses (physiological and mental stress), fat begins to accumulate in areas outside the subcutaneous tissue (the natural store house for energy) and visceral adipose depots develop (Ibrahim, Obesity Reviews 11 (2009) 11-18). Individuals with upper abdominal, central or android obesity are at a greater risk than those with gluteofemoral, peripheral or gynoid obesity for developing several secondary diseases of obesity such as dyslipidemia, diabetes, insulin resistance, hyperglycemia, metabolic syndrome and premature death. In the following, we will use the terms central and peripheral to distinguish between these fat distribution patterns.

More specifically, central obesity carries have a greater risk of developing diabetes and future cardiovascular events than peripheral obese individuals (Ibrahim, Obesity Reviews 11 (2009) 11-18). In addition, central fat accumulation is associated with tendency to hyperglycaemia, hyperinsulinemia, hypertriglyceridemia, impaired glucose tolerance and increased apolipoproteins B-rich lipoproteins, which are features of the insulin resistance syndrome (Ibrahim, Obesity Reviews 11 (2009) 11-18). In addition, increased risk of developing diabetes is also greater in individuals with excess visceral adipose tissue (Bjorntorp, Diabetes Metab. 26, Suppl. 3 (2000) 10-12; Lemieux, Diabetes Metab. 20 (1994); Dobbelsteyn, Int. J. Obs. Relat. Metab. Disord. 25 (2001) 652). Furthermore, individuals with high levels of visceral adipose tissue area have higher mean plasma cholesterol and triglyceride levels and lower high-density lipoprotein cholesterol values as compared to peripheral obese individuals (Despres, Metabolism 34 (1985)967-973).

Moreover, an increased body waist circumference is considered to be a prerequisite of the metabolic syndrome. Visceral obesity, like hyperinsulinemia and insulin resistance, not only accompanies but antedates the components of the metabolic syndrome (Lemieux, Diabetes Metab. 20 (1994) 375-393; Bergstrom, Diabetes 39 (1990) 104-111). In addition, elevated arterial blood pressure that is one of the components of the metabolic syndrome was explained by insulin resistance and compensating hyperinsulinemia in central obese individuals (Rocchini, Am. J. Hypertens. 15 (2002) 505-525; Sharma, Curr. Hypertens. Rep. 3 (2001) 152-156; Mc Farlane, J. Clin. Endocrinol. Metabol. 86 (2001) 713-718). Furthermore, central obesity can induce the development of hypertension through increased activity of adipose tissue renin-angiotensin-aldosterone system, sympathetic activation and other mechanisms closely connected with insulin resistance (Ibrahim, Obesity Reviews 11 (2009) 11-18).

Visceral fat quantified as waist size has been identified as an independent risk factor for cardiovascular disease, hypertension and stroke (Dobbelsteyn, Int. J. Obs. Relat. Metab. Disord. 25 (2001) 652; Despres, Int. Congr. Ser. 23 (2003) 27-34). In addition, excess visceral adipose tissue has the potential to cause hypercoagulability because of increased secretion of PAI-1. Importantly, increased waist circumference when accompanied by increased triglycerides leads to increased risk of coronary heart disease (Tanko, Circulation 111 (2005) 1883-1890; Lemieux, Circulation 102 (2000) 179-184).

Central obesity correlates closely with other measures of atherosclerosis such as intima-media thickness (Harris, Obes. Res. 8 (2000) 516-524). Peripheral arterial disease also has been correlated to visceral adipose tissue, but not to total body fat in elderly subjects (Planas, Int. J. Obes. Relat. Metab. Disord. 25 (2001) 1068-1070). In addition, subjects with abdominal obesity were reported to have greater risk of having an abnormal albumin excretion rate (Mulyadi, Ann. Nutr. Metab. 45 (2000) 6-71) and microalbuminuria signifies enhanced cardiovascular risk. Moreover, hyperinsulinemia, associated with visceral (i.e. central) obesity, is a predictor of coronary artery disease (Fontbonne, Diabetologica 34 (1991) 356-361).

In addition, increase in circulating free fatty acids in abdominal obesity is associated with increase in cardiovascular risk. In addition, elevations in free fatty acid levels have been demonstrated to promote endothelial dysfunction (Sharma, 3 Curr. Hypertens. Rep. 3 (2001) 152-156).

Accordingly, assessment of cardiovascular risk in obese patients from the measurement of body weight may be misleading (Kissebah, Diabet. Rev. 5 (1997) 8-20). Only obese individuals characterized by increased visceral adipose tissue show the complications predictive of type 2 diabetes and cardiovascular disease (Mc Farlane, J. Clin. Endocrinol. Metabol. 86 (2001) 713-718). Women generally display a more favorable risk profile than men, and generally lower level of visceral adipose tissue than men. Interestingly, adjustments for differences in visceral fat between men and women eliminated most of the sex differences in cardiovascular risk factors (Lemieax, Diabetologica 37 (1994) 757-764). Peripheral or gluteofemoral fat distribution seems to be even protective against atherosclerosis (Tanko, Eur. Heart. J. 24 (2003) 1531-1537; Tanko, Circulation 107 (2003) 1626-1631; Lassner, Obes. Res. 9 (2001) 644-646).

It is known that obesity is associated with increased cardiovascular disease mortality (Dagenais, Am. Heart. J. 149 (2005) 54-60; Allison, JAMA 282 (1999) 1530-1538). Cardiovascular disease death rates are directly related to body mass index in both men and women and obesity in adulthood is associated with a striking reduction in life expectancy (Lee, J. Gerontol. A. Biol. Sci. Med. Sci. 56 (2001) 7-19). In addition, in particular abdominal adiposity as measured by waist circumference is a significant predictor of mortality independently of body mass index (Zhang, Arch. Intern. Med. 167 (2007) 886-892).

Advantageously, the herein provided paracrine FGFs (e.g. FGF8b, FGF8f and/or FGF17) specifically and effectively target visceral fat which is associated with several severe diseases (such as type 2 diabetes, insulin resistance syndrome, metabolic syndrome, cardiovascular disease, coronary heart disease, hypertension and stroke) and is a strong, independent predictor of all-cause mortality in men (Kuk, Obesity 14 (2006) 336-341).

The anatomical and physiological differences between visceral adipose tissue and subcutaneous adipose tissue help explain the increased metabolic and cardiovascular risks associated with abdominal (i.e. central) obesity.

Anatomical differences between visceral adipose tissue and subcutaneous adipose tissue are known in the art and described, e.g., in Ibrahim, Obesity Reviews 11 (2009) 11-18. In particular, the main areas for subcutaneous fat deposition are the femerogluteal regions. About 80% of all body fat is in the subcutaneous area (Wajchenberg, Endocr. Rev. 21 (2000) 679-738; Arner, J. Endocrinol. 155 (1997) 191-192). Intra-abdominal fat is visceral fat which accounts for up to 10-20% of total fat in men and 5-8% in women (Wajchenberg, Endocr. Rev. 21 (2000) 679-738). The amount of visceral fat increases with age in both genders.

Because of its anatomical position, visceral fat venous blood is drained directly to the liver through the portal vein (Ibrahim, Obesity Reviews 11 (2009) 11-18). This contrasts with subcutaneous fat where venous drainage is through systemic veins. The portal drainage of visceral fat provides direct hepatic access to free fatty acids and adipokines secreted by visceral adipocytes. Adipokines activate hepatic immune mechanisms with production of inflammatory mediators such as C-reactive protein (CRP) (Heinrich, Biochem. J. 265 (1990) 621-636; Mårin, Metabolism 41 (1992) 1241-1248).

There are several physiological and metabolic differences between subcutaneous and visceral adipose tissue (Ibrahim, Obesity Reviews 11 (2009) 11-18). For example, in the obesity state, adipocytes from visceral adipose tissue are more insulin-resistant than subcutaneous adipose tissue adipocytes (Abate, J. Clin. Invest. 96 (1995) 88-98; Frayn, Br. J. Nutr. 83, Suppl. 1 (2000) S71-S77). It is noted that smaller adipocytes tend to be more insulin-sensitive whereas large adipocytes become insulin-resistant (Salans, J. Clin. Invest. 52 (1973) 929-941; Bjorntorp, Diabetes Metab. 26, Suppl. 3 (2000) 10-12). In addition, it has been found that the amount of visceral fat represents an important factor associated with variations in insulin sensitivity (Mårin, Metabolism 41 (1992) 1241-1248; Hisra, Nutrition 19 (2003) 457-466; Kadswaki, Exp. Biol. Med. 228 (2003) 1111-1117).

Insulin resistance prevents glucose and more fat from entering the cell and becoming preferentially oxidized. Subjects with visceral abdominal obesity, when compared with those with peripheral obesity, had lower glucose disposal, glucose oxidation and greater lipid oxidation (Ibrahim, Obesity Reviews 11 (2009) 11-18). Insulin resistance may be one of the most important factors linking abdominal visceral adiposity to cardiovascular risk.

Free fatty acids are known to induce insulin resistance (Ibrahim, Obesity Reviews 11 (2009) 11-18). In the liver, insulin inhibits gluconeogenesis and glycogenolysis and stimulates glycogen formation. It has been shown that the degree of free fatty acid suppression following meal ingestion differs between abdominally and peripherally obese persons. In particular, the release of free fatty acids is greater in the abdominally obese individuals (Freedland, Nutr. Metab. 1 (2004) 12).

In addition, in the healthy state, visceral adipose tissue has higher rate of insulin-stimulated glucose uptake compared with subcutaneous adipose tissue adipocytes. Small adipocytes in subcutaneous adipose tissue have a high avidity for free fatty acid and triglyceride uptake. The new, small, more insulin-sensitive adipocytes act as a sink or powerful 'buffers', avidly absorbing circulating free fatty acids and triglycerides in the postprandial period (Freedland, Nutr. Metab. 1 (2004) 12; Arner, J. Endocrinol. 155 (1997) 191-192). Accordingly, subcutaneous adipose tissue cells may act as a buffer or sink for circulating free fatty acids and triglycerides, but once they reach their capacity they lose their protective benefit and fat begins to accumulate in tissues not suited for lipid storage (Freedland, Nutr. Metab. 1 (2004) 12). Notably, subcutaneous adipose tissue in abdominal wall has higher uptake of triglycerides and larger free fatty acid release per kilograms than femoral fat (Mårin, Metabolism 41 (1992) 1241-1248; Kadswaki, Exp. Biol. Med. 228 (2003) 1111-1117).

Accordingly, visceral and subcutaneous fat are tissues with anatomical, cellular, molecular and physiological differences. Obviously, these considerable differences are the reason for the fact that especially visceral adipose tissue amount correlates with the risk for several diseases such as dyslipidemia, diabetes, insulin resistance, hyperglycemia and metabolic syndrome.

As indicated above, the present invention relates to a pharmaceutical composition comprising the herein provided paracrine FGFs (e.g. FGF8b, FGF8f and/or FGF17) for use in treating (and/or preventing) a disease or disorder of energy homeostasis (e.g. obesity), further comprising a pharmaceutically acceptable carrier and/or diluent. In context of the present invention, said "pharmaceutical composition(s)" are medicaments. Such pharmaceutical compositions may be administered to a subject in need of medical intervention of a disease or disorder of energy homeostasis (e.g. obesity [such as central obesity], dyslipidemia, diabetes, insulin resistance, hyperglycemia or metabolic syndrome). Thus, the invention also relates to a method of treating a disease or disorder of energy homeostasis by administering an effective dose of the herein provided paracrine FGFs (e.g. FGF8b, FGF8f and/or FGF17), to a subject in need of such treatment. In context of the present invention, a subject is a mammal, e.g., a mouse, rat, hamster, rabbit, guinea pig, ferret, cat, dog, chicken, sheep, bovine species, horse, camel, primate or a human being. It is prioritized that the subject is a pet animal (e.g. a dog, a cat, a rabbit, a hamster, a bird, a horse, a monkey or a camel. It is even more prioritized that the subject is a human being.

The pharmaceutical compositions as described herein may be administered to a subject in need of medical intervention of a disease or disorder of energy homeostasis in an amount of about 1 ng/kg body weight per day to about 100 mg/kg body weight per day. For example, the pharmaceutical composition for use in treating a disease or disorder of energy homeostasis may be administered to the subject in an amount of about 0.01 µg/kg body weight per day to about 50 mg/kg body weight per day, or about 0.05 µg/kg body weight per day to about 50 µg/kg body weight per day, or about 0.1 µg/kg body weight per day to about 10 µg/kg body weight per day, or about 1 µg/kg body weight per day to about 5 µg/kg body weight per day, or about 2 µg/kg body weight per day to about 3 µg/kg body weight per day. For example, the pharmaceutical composition or the polypeptide of the invention may be administered in an amount of 5 μg/kg body weight per day or in an amount of 2.5 μg/kg body weight per day.

It is envisaged in context of the invention, that an implantable drug depot (e.g. a "pellet" [Innovative Research of America, Sarasota, Fla., USA or a minipump) which locally releases the herein provided pharmaceutical composition, polypeptide and/or polynucleotide, is implanted into the subject in need of such treatment. Said pellet or minipump may locally release the above listed amounts of the herein described pharmaceutical composition, polypeptide and/or polynucleotide. For example, said pellet or minipump may locally release 0.2 μg/kg body weight per day to about 1 μg/kg body weight per day. For example, said pellet or minipump may locally release 0.25 μg/kg body weight per day or 0.5 μg/kg body weight per day. The pharmaceutical composition as disclosed herein as well as releasing quantities for local release from a drug depot will be formulated, dosed and provided in a fashion consistent with good medical practice, taking into account the clinical condition of the individual patient, the site of delivery of the pharmaceutical composition, the method of administration, the scheduling of administration, and other factors known to practitioners/physicians. The "effective amount" of the pharmaceutical composition and/or the releasing quantities for purposes herein described is thus determined by such considerations.

Accordingly, also doses below or above the exemplary ranges described hereinabove are envisioned. The skilled person knows that the effective amount of pharmaceutical compositions administered to an individual will, inter alia, depend on the nature of the compound. For example, the dose may be further decreased or increased as subject to therapeutic discretion, in particular if concomitantly certain lipids are applied or if the administered polypeptide is subject to certain chemical modifications. The particular amounts may be determined by conventional tests which are well known to the person skilled in the art. The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently.

The polypeptides of the present invention may also be used in combinations of two or more polypeptides provided herein. For example, in context of the present invention, the polypeptides FGF8b, FGF8f and/or FGF17 may be administered in combination (simultaneously, sequentially or separate). Accordingly, the pharmaceutical compositions of the present invention may comprise two or more polypeptides provided herein, optionally also in combination with other compounds described and provided herein. Said other compounds may be compounds which activate brown adipose tissue, such as beta-adrenergic agonists (e.g. beta3-adrenergic agonists such as CL 316243), noradrenalin, ephedrine, isoproterenol, methylphenidate, BRL 35135, ICI D7114, CGP-12177A or atrial natriuretic peptide (ANP)).

It is envisaged in context of the present invention that the herein provided pharmaceutical composition, polypeptide or polynucleotide is administered locally. Accordingly, administration of the pharmaceutical compositions, polypeptides or polynucleotides provided herein may be effected by different ways, e.g., parenterally (e.g. intraviscerally, subcutaneous, transdermally, intramuscularly or intraperitoneally) or as an implantable drug depot (e.g. as an erodible implant made of biodegradable polymers, such as cellulose, polylactate or polyglycolate).

Thus, the pharmaceutical composition described and provided herein may be also administered by sustained-release systems. Further suitable examples of sustained-release compositions include semi-permeable polymer matrices in the form of shaped articles, e.g., films, or microcapsules. Sustained-release matrices include polylactides (U.S. Pat. No. 3,773,919, EP-A1 58481), copolymers of L-glutamic acid and gamma-ethyl-L-glutamate (Biopolymers, 1983, 22: 547-556), poly (2-hydroxyethyl methacrylate) (J Biomed Mater Res, 1981, 15: 167-277; Langer, Chem Tech, 1982, 12: 98-105), ethylene vinyl acetate (Langer, loc. cit.) or poly-D-(−)-3-hydroxybutyric acid (EP-A1 133988). Sustained release of pharmaceutical compositions may also include liposomally entrapped compounds. Liposomes containing the pharmaceutical composition may be prepared by methods known in the art, such as described in DE 3218121; Proc Natl Acad Sci USA, 1985, 82: 3688-3692; Proc Natl Acad Sci USA 77: 4030-4034, 1980; EP-A1 52322; EP-A1 36676; EP-A1 88046; EP-A1 143949; EP-A1 142641; Japanese Pat. Appl. 83-118008; U.S. Pat. Nos. 4,485,045 and 4,544,545; and EP-A1 102324.

In certain circumstances the herein provided pharmaceutical compositions, polypeptides or polynucleotides may be administered intravenously, intraperitoneal, intramuscular, via inhalation (e.g., intrabronchially) or enterally (e.g. a pill, tablet, [e.g. buccal, sublingual, orally or disintegrating], capsule, thin film, liquid solution suspension, powder, solid crystals or liquid), rectally (e.g., suppository, enema), topically, vaginally, epicutaneously or intranasally. However, it is prioritized in context of the invention that the herein provided pharmaceutical compositions, polypeptides or polynucleotides are administered locally (e.g. locally into the visceral adipose tissue). Thus, the herein provided pharmaceutical compositions, polynucleotides or polypeptides may be administered directly to the target site, e.g., by implantation of an implantable drug depot, biolistic delivery to the target site or by catheter.

As mentioned above, the inventive pharmaceutical compositions comprise a pharmaceutically acceptable carrier and/or diluents. Pharmaceutically acceptable carriers are well known in the art and include, e.g., non-aqueous carriers such as propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral carriers include sodium chloride solution, Ringer's dextrose, dextrose and sodium chloride, lactated Ringer's, or fixed oils. Intravenous carriers include fluid and nutrient replenishers, electrolyte replenishers (such as those based on Ringer's dextrose), and the like. Preservatives and other additives may also be present such as, for example, antimicrobials, anti-oxidants, chelating agents, inert gases and the like. Diluents which are used in pharmaceuticals are inactive ingredients that are added to medicaments in addition to the active drug. Diluents may be used as binders, disintegrants (help the tablet break apart in the digestive system), or flavor enhancers. Some very common diluents include starch, cellulose, cellulose derivatives, lactose and magnesium stearate (a lubricant).

As used herein, the terms "treatment", "treating" and the like also means "preventing" and "ameliorating" of a disease such as a disease or disorder of energy homeostasis (e.g. obesity). These terms are used herein to generally mean obtaining a desired pharmacological and/or physiological effect. The effect may be prophylactic in terms of completely or partially preventing a disease or symptom thereof and/or may be therapeutic in terms of partially or completely curing a disease and/or adverse effect attributed to the disease. The term "treatment/treating" as used herein covers any treatment of a disease in a subject and includes: (a) preventing and ameliorating a disease or disorder of energy homeostasis from occurring in a subject which may be predisposed to the disease; (b) inhibiting a disease or disorder of energy homeostasis, e.g. arresting its development; or (c) relieving a disease or disorder of energy homeostasis, e.g. causing regression of a disease or disorder of energy homeostasis. In accordance with the present invention, the term "prevention" or "preventing" of an disease means the disease per se can be hindered of developing or to develop into an even worse situation. Accordingly, it is one aspect of the present invention that the herein described polypeptides can be employed in avoidance of a disease or disorder of energy homeostasis. In accordance with the present invention, the peptides as described herein may be employed before a disease or disorder of energy homeostasis develops.

As described herein, the polypeptides for use in treating a disease or disorder of energy homeostasis as described herein may also be employed in the amelioration and/or treatment of disorders wherein the diseased status has already developed, i.e. in the treatment of an existing disease or disorder of energy homeostasis. Accordingly, the term "treatment/treating" as used herein also relates to medical intervention of an already manifested disorder, like the treatment of an already defined and manifested disease or disorder of energy homeostasis. Thus, the present invention relates to the treatment or prevention of a disease or disorder of energy homeostasis by using the polypeptides as described herein, the polynucleotides as described herein or the pharmaceutical compositions as defined herein.

The terms "paracrine FGF(s) of the (present) invention" "paracrine FGF(s) provided herein", "herein provided paracrine FGF(s)", "inventive paracrine FGF(s)", "paracrine FGF(s) described and provided herein", "herein described and provided paracrine FGF(s)", "paracrine FGF(s) for use in treating a disease or disorder of energy homeostasis" and the like are used interchangeably herein and relate to a polypeptide for use in treating a disease or disorder of energy homeostasis, wherein the polypeptide is selected from the group consisting of:

(a) a polypeptide comprising an amino acid sequence encoded by a nucleic acid molecule having the nucleic acid sequence as depicted in SEQ ID NO:2 or the nucleic acid sequence comprising nucleic acid residues 67-648 in SEQ ID NO:2;

(b) a polypeptide comprising an amino acid sequence as depicted in SEQ ID NO:16 or an amino acid sequence comprising amino acids 23-215 in SEQ ID NO:16, (c) a polypeptide encoded by a nucleic acid molecule encoding a polypeptide comprising an amino acid sequence having amino acids 23-215 in SEQ ID NO:16 or having an amino acid sequence as depicted in SEQ ID NO:16;

(d) a polypeptide comprising an amino acid sequence encoded by a nucleic acid molecule hybridizing under stringent conditions to the complementary strand of a nucleic acid molecule as defined in (a) or (c) and encoding a functional polypeptide, wherein the function comprises the ability to induce differentiation or conversion of white adipocytes and/or preadipocytes to brown adipocytes;

(e) a polypeptide having at least 40% identity to the polypeptide of any one of (a) to (d), whereby said polypeptide is functional, wherein the function comprises the ability to induce differentiation or conversion of white adipocytes and/or preadipocytes to brown adipocytes; and (f) a polypeptide comprising an amino acid sequence encoded by a nucleic acid molecule being degenerate as a result of the genetic code to the nucleotide sequence of a nucleic acid molecule as defined in (a), (c) and (d).

As mentioned, the function of the above described polypeptide of the invention is ability to induce differentiation or conversion of white adipocytes and/or preadipocytes (in particular white visceral adipocytes and/or white visceral preadipocytes) to brown adipocytes.

In accordance with the present invention, the polypeptide of item (e) above may have at least 45%, at least 50%, at least 55%, at least 60%, at least 65%, at least 70%, at least 75%, at least 80%, at least 85%, at least 90%, at least 95% or at least 99% identity to the polypeptide of any one of (a) to (d), whereby said polypeptide is functional, wherein the function comprises the ability to induce differentiation or conversion of white adipocytes and/or preadipocytes (e.g. white visceral adipocytes and/or white visceral preadipocytes) to brown adipocytes. Herein, the above defined polypeptide is also termed "polypeptide(s) of the invention" or "polypeptide(s) of the present invention".

In addition, the terms "paracrine FGF(s) of the (present) invention" "paracrine FGF(s) provided herein", "herein provided paracrine FGF(s)", "inventive paracrine FGF(s)", "paracrine FGF(s) described and provided herein", "herein described and provided paracrine FGF(s)", "paracrine FGF(s) as provided herein", "paracrine FGF(s) for use in treating a disease or disorder of energy homeostasis" and the like also relate to the polynucleotide for use in treating a disease or disorder of energy homeostasis, wherein the polynucleotide encodes the polypeptide described above. Herein, this polynucleotide is also termed "polynucleotide(s) of the (present) invention".

The terms "polypeptide(s) of the (present) invention" or "polynucleotide(s) of the (present) invention" relate to paracrine FGFs, in particular FGF8b, FGF8f and/or FGF17, for use in treating a disease or disorder of energy homeostasis (such as obesity). The term "polypeptide(s) of the (present) invention" or "polynucleotide(s) of the (present) invention" also includes (a) functional fragment(s) of the herein described paracrine FGFs (such as functional fragments of FGF8b, FGF8f or FGF17).

As mentioned above, the invention provides for a polypeptide for use in accordance with the present invention, particularly for use in treating diseases or disorders of energy homeostasis (e.g. obesity). This polypeptide may have a length of 10-1000 amino acids, preferably of 30-800 amino acids, 50-700 amino acids or 70-500 amino acids; more preferably, of 90-300 amino acids, 110-280 amino acids, 150-200 amino acids or 170-270 amino acids; or, most preferably, of 200-230 amino acids. The term "polypeptide" also encompasses fragments and variants of the specific polypeptides provided herein that have the biological function/activity of the herein described polypeptides. Also the use of short peptides consisting of about 11 or less amino acids is envisaged. These peptides can consist of 10, 9, 8, 7, 6, 5 or 4 amino acids. Also these peptides are polypeptides for use in accordance with the present invention. In one particular aspect of the invention, the polypeptide of the invention has a length of 215 amino acids.

It is preferred that the polypeptides for use in accordance with the present invention, particularly for use in treating diseases or disorders of energy homeostasis (e.g. obesity) comprise the amino acid sequence VTVQSSPNFTQ (SEQ ID NO:103) or related sequences like QVTVQSSPNFTQ (SEQ ID NO:105) or QVTVQSSPNFT (SEQ ID NO:106), preferably of from position 26 to position 37 of the respective amino acid sequence, or fragments thereof that contribute to mediating the biological effect of the polypeptide.

It is preferred that the polypeptides to be used herein comprise the amino acid sequence SPNF, preferably of from position 29 to position 32 of the respective amino acid sequence of FGF8b (exemplary amino acid sequence of FGF8b is shown in SEQ ID NO:16) or of from position 30 to position 33 of the respective amino acid sequence of FGF17 (exemplary amino acid sequence of FGF8b is shown in SEQ ID NO:18). And both FGF8b and FGF17 share the amino acid residue Q at position 34 of the respective amino acid sequence of FGF8b (exemplary amino acid sequence of FGF8b is shown in SEQ ID NO:16) or at position 35 of the respective amino acid sequence of FGF17 (exemplary amino acid sequence of FGF8b is shown in SEQ ID NO:18). Thus, they share the motif "SPNFXQ" (SEQ ID NO:108). Therefore, it is preferred that the polypeptides to be used herein comprise the amino acid sequence SPNFXQ (SEQ ID NO:108), preferably of from position 29 to position 34 of the respective amino acid sequence of FGF8b (exemplary amino acid sequence of FGF8b is shown in SEQ ID NO:16) or of from position 30 to position 35 of the respective amino acid sequence of FGF17 (exemplary amino acid sequence of FGF8b is shown in SEQ ID NO:18). X may be T or N.

The illustrative appended examples demonstrate that the paracrine FGFs of the invention have the ability to induce differentiation (or conversion) of white (visceral) adipocytes (and/or preadipocytes) to brown adipocytes also without their signal sequence. Such a protein is, e.g., a polypeptide having the amino acid sequence consisting of the amino acid residues 23-215 of SEQ ID NO:16. Thus, a functional fragment of the herein provided paracrine FGF(s) include the respective FGF without its signal sequence. However, also other functional fragments of the herein provided paracrine FGF(s) are encompassed by the present invention.

Thus, the invention relates to a polypeptide for use in treating a disease or disorder of energy homeostasis, wherein the polypeptide is selected from the group consisting of:
(a) a polypeptide comprising an amino acid sequence encoded by a nucleic acid molecule having the nucleic acid sequence as depicted in SEQ ID NO:2 or the nucleic acid sequence comprising nucleic acid residues 67-648 in SEQ ID NO:2;
(b) a polypeptide comprising an amino acid sequence as depicted in SEQ ID NO:16 or an amino acid sequence comprising amino acids 23-215 in SEQ ID NO:16,
(c) a polypeptide encoded by a nucleic acid molecule encoding a polypeptide comprising an amino acid sequence having amino acids 23-215 in SEQ ID NO:16 or having an amino acid sequence as depicted in SEQ ID NO:16, or a functional fragment thereof, wherein the function comprises the ability to induce differentiation or conversion of white adipocytes and/or preadipocytes to brown adipocytes;
(d) a polypeptide comprising an amino acid sequence encoded by a nucleic acid molecule hybridizing under stringent conditions to the complementary strand of a nucleic acid molecule as defined in (a) or (c) and encoding a functional polypeptide, or a functional fragment thereof; wherein the function comprises the ability to induce differentiation or conversion of white adipocytes and/or preadipocytes to brown adipocytes,
(e) a polypeptide having at least 40%, at least 45%, at least 50%, at least 55%, at least 60%, at least 65%, at least 70%, at least 75%, at least 80%, at least 85%, at least 90%, at least 95% or at least 99% identity to the polypeptide of any one of (a) to (d), whereby said polypeptide is functional, or a functional fragment thereof; wherein the function comprises the ability to induce differentiation or conversion of white adipocytes and/or preadipocytes to brown adipocytes; and
(f) a polypeptide comprising an amino acid sequence encoded by a nucleic acid molecule being degenerate as a result of the genetic code to the nucleotide sequence of a nucleic acid molecule as defined in (a), (c) and (d).

As mentioned, the function of the above described polypeptide of the invention is ability to induce differentiation or conversion of white adipocytes and/or preadipocytes (in particular white visceral adipocytes and/or white visceral preadipocytes) to brown adipocytes.

The illustrative appended examples show that the paracrine FGFs of the present invention are active in browning visceral adipose tissue. Moreover, the appended examples show that of 13 fibroblast growth factors, FGF8 strongest induced expression of (the brown adipocyte specific gene) Ucp1 in white adipose cell lines. In these experiments FGF8b was shown to have browning potential in both visceral and subcutaneous adipose tissue. In contrast, FGF8f specifically induces browning of visceral adipose tissue. Therefore, one aspect of the invention relates to FGF8f for use in treating diseases or disorders of energy homeostasis such as (central) obesity.

Thus, one aspect of the invention relates to a polypeptide for use in treating a disease or disorder of energy homeostasis, wherein the polypeptide is selected from the group consisting of:
(a) a polypeptide comprising an amino acid sequence encoded by a nucleic acid molecule having the nucleic acid sequence as depicted in SEQ ID NO:4 or the nucleic acid sequence comprising nucleic acid residues 67-735 in SEQ ID NO:4;
(b) a polypeptide comprising an amino acid sequence as depicted in SEQ ID NO:18 or an amino acid sequence comprising amino acids 23-244 in SEQ ID NO:18;
(c) a polypeptide encoded by a nucleic acid molecule encoding a polypeptide comprising an amino acid sequence having amino acids 23-244 in SEQ ID NO:18 or having an amino acid sequence as depicted in SEQ ID NO:18;
(d) a polypeptide comprising an amino acid sequence encoded by a nucleic acid molecule hybridizing under stringent conditions to the complementary strand of a nucleic acid molecule as defined in (a) or (c) and encoding a functional polypeptide, wherein the function comprises the ability to induce differentiation or conversion of white adipocytes and/or preadipocytes to brown adipocytes;
(e) a polypeptide having at least 40%, at least 45%, at least 50%, at least 55%, at least 60%, at least 65%, at least 70%, at least 75%, at least 80%, at least 85%, at least 90%, at least 95% or at least 99% identity to the polypeptide of any one of (a) to (d), whereby said polypeptide is functional, wherein the function comprises the ability to induce differentiation or conversion of white adipocytes and/or preadipocytes to brown adipocytes; and
(f) a polypeptide comprising an amino acid sequence encoded by a nucleic acid molecule being degenerate as a result of the genetic code to the nucleotide sequence of a nucleic acid molecule as defined in (a), (c) and (d).

The illustrative appended examples also demonstrate that FGF17 is active in browning visceral adipose tissue.

Accordingly, the invention also relates to FGF17 for use in treating a disease or disorder of energy homeostasis.

Thus, one aspect of the invention relates to a polypeptide for use in treating a disease or disorder of energy homeostasis, wherein the polypeptide is selected from the group consisting of:
(a) a polypeptide comprising an amino acid sequence encoded by a nucleic acid molecule having the nucleic acid sequence as depicted in SEQ ID NO:9 or the nucleic acid sequence comprising nucleic acid residues 67-651 in SEQ ID NO:9;
(b) a polypeptide comprising an amino acid sequence as depicted in SEQ ID NO:23 or an amino acid sequence comprising amino acids 23-216 in SEQ ID NO:23;
(c) a polypeptide encoded by a nucleic acid molecule encoding a polypeptide comprising an amino acid sequence having amino acids 23-216 in SEQ ID NO:23 or having an amino acid sequence as depicted in SEQ ID NO:23;
(d) a polypeptide comprising an amino acid sequence encoded by a nucleic acid molecule hybridizing under stringent conditions to the complementary strand of a nucleic acid molecule as defined in (a) or (c) and encoding a functional polypeptide, wherein the function comprises the ability to induce differentiation or conversion of white adipocytes and/or preadipocytes to brown adipocytes;
(e) a polypeptide having at least 40%, at least 45%, at least 50%, at least 55%, at least 60%, at least 65%, at least 70%, at least 75%, at least 80%, at least 85%, at least 90%, at least 95% or at least 99% identity to the polypeptide of any one of (a) to (d), whereby said polypeptide is functional, wherein the function comprises the ability to induce differentiation or conversion of white adipocytes and/or preadipocytes to brown adipocytes; and
(f) a polypeptide comprising an amino acid sequence encoded by a nucleic acid molecule being degenerate as a result of the genetic code to the nucleotide sequence of a nucleic acid molecule as defined in (a), (c) and (d).

As indicated above, the function of the above described polypeptide of the invention is ability to induce differentiation or conversion of white adipocytes and/or preadipocytes (in particular white visceral adipocytes and/or white visceral preadipocytes) to brown adipocytes.

Thus, the polypeptide of the invention may be FGF8b, FGF8f or FGF17. Preferably, polypeptide of the invention is FGF8b or FGF8f. More preferably, the polypeptide of the invention is FGF8b.

As used herein, a "functional fragment" of a protein which displays a specific biological activity relates to a fragment of said protein having a sufficient length to display said activity. Accordingly, a functional fragment of a protein showing a specific (e.g. signalling) activity may relate to a polypeptide which corresponds to a fragment of said protein which is still capable of showing said (signalling) activity. For example, a functional fragment of a paracrine FGF as provided herein (e.g. FGF8b) may correspond to the fragment of the paracrine FGF (e.g. of FGF8b) which has the same signalling activity as the paracrine FGF (e.g. as FGF8b). Methods for determining whether a certain fragment of a protein is a functional fragment are known in the art. For example, a test for determining whether a fragment of a paracrine FGF as provided herein (e.g. FGF8b) is functional, (i.e., is still capable of inducing differentiation or conversion of white visceral adipocytes and/or preadipocytes to brown adipocytes), is for example, treating cultured white adipocytes or preadipocytes with the fragment to be tested and measuring the expression of marker genes of brown adipose tissues (e.g. Ucp1) after differentiation. This method is used herein in the appended examples. Preferably, a functional fragment of a paracrine FGF of the present invention has substantially the same biological activity as the paracrine FGF of the present invention itself. Preferably, the functional fragment is at least 50% more preferably at least 60%, 70%, 80%, 85%, 90%, 95% or 99% of the amino acid sequence of the full length sequences of the paracrine FGF of the invention (e.g. FGF8b).

Without deferring from the gist of the present invention also (a) functional fragment(s) or (a) functional derivative(s) of the herein provided polypeptides or proteins can be used, for example, (functional) fragment(s) or (functional) derivative(s) of the polypeptides as shown in SEQ ID NO:16, 18 or 23.

Thus, a functional fragment of the above polypeptide(s)/protein(s) provided herein and to be used in accordance with the present invention can be any of the above specific polypeptides as shown in any one of SEQ ID NO:16, 18 or 23, respectively, wherein one or more amino acids are deleted.

A (functional) derivative(s) of the above polypeptide(s)/protein(s) provided herein and to be used in accordance with the present invention can be any of the above specific polypeptides as shown in SEQ ID NO:16, 18 or 23, respectively, wherein one or more amino acids are inserted, added or substituted.

1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 amino acids can, for example, be deleted, inserted, added or substituted within the amino acid sequence of the polypeptides as shown SEQ ID NO:16, 18 or 23.

The term "one or more amino acids deleted" relates to functional fragments of the specific paracrine FGF polypeptides provided herein.

A preferred (functional) fragment of the above mentioned polypeptides provided herein and to be used in accordance with the present invention consists of from 4 to 15 contiguous amino acids. Accordingly, a (functional) fragment of the above mentioned polypeptides provided herein and to be used in accordance with the present invention preferably consists of 4, 5, 6, 7, 8, 9, 10, 11, 12, 13, 14, or 15, contiguous amino acids.

A (functional) fragment of the above mentioned polypeptides provided herein and to be used in accordance with the present invention preferably consists of from 15 to 25 contiguous amino acids of the amino acid sequence shown in of the polypeptides as shown SEQ ID NO:16, 18 or 23.

The fragment or derivative preferably has the same (or essentially the same) biological activity as the full length polypeptide from which it is derived, the full length polypeptide having the amino acid sequence as shown in SEQ ID NO:16, 18 or 23. In this sense, the fragment or derivative is a "functional" fragment or derivative to be used herein.

The herein provided polypeptide (as shown, for example, in SEQ ID NO:16, 18 or 23, respectively) may have one or more amino acids deleted, inserted, added and/or substituted provided that the polypeptide maintains essentially the biological activity which is characteristic of the polypeptides from which it is derived.

Preferably, any such deletions, insertions, additions and/or substitutions (in this context particularly substitutions) are conservative, i.e. amino acids are substituted by amino acids having the same or similar characteristics. For example, a hydrophobic amino acid will preferably be substituted by another hydrophobic amino acid and so on.

Preferred fragments to be used herein are QVTVQSSP-NFT (SEQ ID NO:106), QVTVQSSPNFTQ (SEQ ID NO:105), VTVQSSPNFTQ (SEQ ID NO:103), SPNF (SEQ ID NO:107), SPNFXQ (SEQ ID NO:108) (wherein X may be T or N), or functional fragments thereof.

In certain aspects, the present invention relates to the following items:

1. A paracrine fibroblast growth factor (FGF) for use in treating a disease or disorder of energy homeostasis.
2. The paracrine fibroblast growth factor (FGF) for use in treating a disease or disorder of energy homeostasis according to item 1, wherein the paracrine fibroblast growth factor (FGF) is FGF8b.
3. The paracrine fibroblast growth factor (FGF) for use in treating a disease or disorder of energy homeostasis according to item 1 or 2, wherein the paracrine fibroblast growth factor (FGF) is human FGF8b.
4. The paracrine fibroblast growth factor (FGF) for use in treating a disease or disorder of energy homeostasis according to any one of items 1 to 3, wherein the paracrine fibroblast growth factor (FGF) is a polypeptide, wherein the polypeptide is selected from the group consisting of:
    (a) a polypeptide comprising an amino acid sequence encoded by a nucleic acid molecule having the nucleic acid sequence as depicted in SEQ ID NO:2 or the nucleic acid sequence comprising nucleic acid residues 67-648 in SEQ ID NO:2;
    (b) a polypeptide comprising an amino acid sequence as depicted in SEQ ID NO:16 or an amino acid sequence comprising amino acids 23-215 in SEQ ID NO:16;
    (c) a polypeptide encoded by a nucleic acid molecule encoding a polypeptide comprising an amino acid sequence having amino acids 23-215 in SEQ ID NO:16 or having an amino acid sequence as depicted in SEQ ID NO:16;
    (d) a polypeptide comprising an amino acid sequence encoded by a nucleic acid molecule hybridizing under stringent conditions to the complementary strand of a nucleic acid molecule as defined in (a) or (c);
    (e) a polypeptide having at least 40% identity to the polypeptide of any one of (a) to (d);
    (f) a protein as defined in any one of (a) to (e) wherein one or more amino acids are deleted, inserted, added or substituted; and
    (g) a polypeptide comprising an amino acid sequence encoded by a nucleic acid molecule being degenerate as a result of the genetic code to the nucleotide sequence of a nucleic acid molecule as defined in (a), (c) and (d).
5. The paracrine fibroblast growth factor (FGF) for use in treating a disease or disorder of energy homeostasis according to item 1, wherein the paracrine fibroblast growth factor (FGF) is FGF8f.
6. The paracrine fibroblast growth factor (FGF) for use in treating a disease or disorder of energy homeostasis according to item 1 or 5, wherein the paracrine fibroblast growth factor (FGF) is human FGF8f.
7. The paracrine fibroblast growth factor (FGF) for use in treating a disease or disorder of energy homeostasis according to any one of items 1, 5 and 6, wherein the paracrine fibroblast growth factor (FGF) is a polypeptide, wherein the polypeptide is selected from the group consisting of:
    (a) a polypeptide comprising an amino acid sequence encoded by a nucleic acid molecule having the nucleic acid sequence as depicted in SEQ ID NO:4 or the nucleic acid sequence comprising nucleic acid residues 67-735 in SEQ ID NO:4;
    (b) a polypeptide comprising an amino acid sequence as depicted in SEQ ID NO:18 or an amino acid sequence comprising amino acids 23-244 in SEQ ID NO:18;
    (c) a polypeptide encoded by a nucleic acid molecule encoding a polypeptide comprising an amino acid sequence having amino acids 23-244 in SEQ ID NO:18 or having an amino acid sequence as depicted in SEQ ID NO:18;
    (d) a polypeptide comprising an amino acid sequence encoded by a nucleic acid molecule hybridizing under stringent conditions to the complementary strand of a nucleic acid molecule as defined in (a) or (c);
    (e) a polypeptide having at least 40% identity to the polypeptide of any one of (a) to (d);
    (f) a protein as defined in any one of (a) to (e) wherein one or more amino acids are deleted, inserted, added or substituted; and
    (g) a polypeptide comprising an amino acid sequence encoded by a nucleic acid molecule being degenerate as a result of the genetic code to the nucleotide sequence of a nucleic acid molecule as defined in (a), (c) and (d).
8. The paracrine fibroblast growth factor (FGF) for use in treating a disease or disorder of energy homeostasis according to item 1, wherein the paracrine fibroblast growth factor (FGF) is FGF17.
9. The paracrine fibroblast growth factor (FGF) for use in treating a disease or disorder of energy homeostasis according to item 1 or 8, wherein the paracrine fibroblast growth factor (FGF) is human FGF17.
10. The paracrine fibroblast growth factor (FGF) for use in treating a disease or disorder of energy homeostasis according to any one of items 1, 8 and 9, wherein the paracrine fibroblast growth factor (FGF) is a polypeptide, wherein the polypeptide is selected from the group consisting of:
    (a) a polypeptide comprising an amino acid sequence encoded by a nucleic acid molecule having the nucleic acid sequence as depicted in SEQ ID NO:9 or the nucleic acid sequence comprising nucleic acid residues 67-651 in SEQ ID NO:9;
    (b) a polypeptide comprising an amino acid sequence as depicted in SEQ ID NO:23 or an amino acid sequence comprising amino acids 23-216 in SEQ ID NO:23;
    (c) a polypeptide encoded by a nucleic acid molecule encoding a polypeptide comprising an amino acid sequence having amino acids 23-216 in SEQ ID NO:23 or having an amino acid sequence as depicted in SEQ ID NO:23;
    (d) a polypeptide comprising an amino acid sequence encoded by a nucleic acid molecule hybridizing under stringent conditions to the complementary strand of a nucleic acid molecule as defined in (a) or (c);
    (e) a polypeptide having at least 40% identity to the polypeptide of any one of (a) to (d);
    (f) a protein as defined in any one of (a) to (e) wherein one or more amino acids are deleted, inserted, added or substituted; and
    (g) a polypeptide comprising an amino acid sequence encoded by a nucleic acid molecule being degenerate as a result of the genetic code to the nucleotide sequence of a nucleic acid molecule as defined in (a), (c) and (d).
11. The paracrine fibroblast growth factor (FGF) for use in treating a disease or disorder of energy homeostasis according to any one of items 4, 7 and 10, wherein the polypeptide is a polypeptide having at least 45%, at least 50%, at least 55%, at least 60%, at least 65%, at least 70%, at least 75%, at least 80%, at least 85%, at least 90%, at least 95% or at least 99% identity to the polypeptide of any one of (a) to (d).

12. The paracrine fibroblast growth factor (FGF) for use in treating a disease or disorder of energy homeostasis according to any one of items 4, 7 and 10, wherein the polypeptide is a polypeptide having at least 90% identity to the polypeptide of any one of (a) to (d).

13. The paracrine fibroblast growth factor (FGF) for use in treating a disease or disorder of energy homeostasis according to any one of items 4, 7 and 10, wherein the polypeptide is a polypeptide having at least 95% identity to the polypeptide of any one of (a) to (d).

14. The paracrine fibroblast growth factor (FGF) for use in treating a disease or disorder of energy homeostasis according to any one of items 4, 7 and 10, wherein the polypeptide is a polypeptide having at least 99% identity to the polypeptide of any one of (a) to (d).

15. The paracrine fibroblast growth factor (FGF) for use in treating a disease or disorder of energy homeostasis according to any one of items 1 to 14, wherein the paracrine fibroblast growth factor (FGF) is a polypeptide that is able to induce differentiation or conversion of white adipocytes and/or white preadipocytes to brown adipocytes.

16. The paracrine fibroblast growth factor (FGF) for use in treating a disease or disorder of energy homeostasis according to any one of items 1 to 14, wherein the paracrine fibroblast growth factor (FGF) is a polypeptide that is able to induce differentiation or conversion of white visceral adipocytes and/or white visceral preadipocytes to brown adipocytes.

17. The paracrine fibroblast growth factor (FGF) for use in treating a disease or disorder of energy homeostasis according to any one of items 1 to 7 and 11 to 16, wherein the paracrine fibroblast growth factor (FGF) is a polypeptide comprising or consisting of the amino acid sequence VTVQSSPNFTQ (SEQ ID NO:103) or a fragment thereof.

18. The paracrine fibroblast growth factor (FGF) for use in treating a disease or disorder of energy homeostasis according to any one of items 1 to 4 and 11 to 16, wherein the paracrine fibroblast growth factor (FGF) is a polypeptide comprising the amino acid sequence VTVQSSPNFTQ (SEQ ID NO:103) from position 24 to position 34 of the amino acid sequence of the polypeptide.

19. The paracrine fibroblast growth factor (FGF) for use in treating a disease or disorder of energy homeostasis according to item 18, wherein the amino acid sequence of the polypeptide is shown in SEQ ID NO:16 (FGF8b).

20. The paracrine fibroblast growth factor (FGF) for use in treating a disease or disorder of energy homeostasis according to any one of items 1, 5 to 7 and 11 to 16, wherein the paracrine fibroblast growth factor (FGF) is a polypeptide comprising the amino acid sequence VTVQSSPNFTQ (SEQ ID NO:103) from position 53 to position 63 of the amino acid sequence of the polypeptide.

21. The paracrine fibroblast growth factor (FGF) for use in treating a disease or disorder of energy homeostasis according to item 20, wherein the amino acid sequence of the polypeptide is shown in SEQ ID NO:18 (FGF8f).

22. The paracrine fibroblast growth factor (FGF) for use in treating a disease or disorder of energy homeostasis according to any one of items 1 to 7 and 11 to 16, wherein the paracrine fibroblast growth factor (FGF) is a polypeptide comprising or consisting of the amino acid sequence QVTVQSSPNFTQ (SEQ ID NO:105) or a fragment thereof.

23. The paracrine fibroblast growth factor (FGF) for use in treating a disease or disorder of energy homeostasis according to any one of items 1 to 4 and 11 to 16, wherein the paracrine fibroblast growth factor (FGF) is a polypeptide comprising the amino acid sequence QVTVQSSPNFTQ (SEQ ID NO:105) from position 23 to position 34 of the amino acid sequence of the polypeptide.

24. The paracrine fibroblast growth factor (FGF) for use in treating a disease or disorder of energy homeostasis according to item 23, wherein the amino acid sequence of the polypeptide is shown in SEQ ID NO:16 (FGF8b).

25. The paracrine fibroblast growth factor (FGF) for use in treating a disease or disorder of energy homeostasis according to any one of items 1, 5 to 7 and 11 to 16, wherein the paracrine fibroblast growth factor (FGF) is a polypeptide comprising the amino acid sequence QVTVQSSPNFTQ (SEQ ID NO:105) from position 52 to position 63 of the amino acid sequence of the polypeptide.

26. The paracrine fibroblast growth factor (FGF) for use in treating a disease or disorder of energy homeostasis according to item 25, wherein the amino acid sequence of the polypeptide is shown in SEQ ID NO:18 (FGF8f).

27. The paracrine fibroblast growth factor (FGF) for use in treating a disease or disorder of energy homeostasis according to any one of items 1 to 7 and 11 to 16, wherein the paracrine fibroblast growth factor (FGF) is a polypeptide comprising or consisting of the amino acid sequence QVTVQSSPNFT (SEQ ID NO:106) or a fragment thereof.

28. The paracrine fibroblast growth factor (FGF) for use in treating a disease or disorder of energy homeostasis according to any one of items 1 to 4 and 11 to 16, wherein the paracrine fibroblast growth factor (FGF) is a polypeptide comprising the amino acid sequence QVTVQSSPNFT (SEQ ID NO:106) from position 23 to position 33 of the amino acid sequence of the polypeptide.

29. The paracrine fibroblast growth factor (FGF) for use in treating a disease or disorder of energy homeostasis according to item 28, wherein the amino acid sequence of the polypeptide is shown in SEQ ID NO:16 (FGF8b).

30. The paracrine fibroblast growth factor (FGF) for use in treating a disease or disorder of energy homeostasis according to any one of items 1, 5 to 7 and 11 to 16, wherein the paracrine fibroblast growth factor (FGF) is a polypeptide comprising the amino acid sequence QVTVQSSPNFT (SEQ ID NO:106) from position 52 to position 62 of the amino acid sequence of the polypeptide.

31. The paracrine fibroblast growth factor (FGF) for use in treating a disease or disorder of energy homeostasis according to item 30, wherein the amino acid sequence of the polypeptide is shown in SEQ ID NO:18 (FGF8f).

32. The paracrine fibroblast growth factor (FGF) for use in treating a disease or disorder of energy homeostasis according to any one of items 1 to 16, wherein the paracrine fibroblast growth factor (FGF) is a polypeptide comprising or consisting of the amino acid sequence SPNFXQ (SEQ ID NO:108) or a fragment thereof.

33. The paracrine fibroblast growth factor (FGF) for use in treating a disease or disorder of energy homeostasis according to any one of items 1 to 4 and 11 to 16, wherein the paracrine fibroblast growth factor (FGF) is a polypeptide comprising the amino acid sequence SPNFXQ (SEQ ID NO:108) from position 29 to position 34 of the amino acid sequence of the polypeptide.

34. The paracrine fibroblast growth factor (FGF) for use in treating a disease or disorder of energy homeostasis according to item 33, wherein the amino acid sequence of the polypeptide is shown in SEQ ID NO:16 (FGF8b).
35. The paracrine fibroblast growth factor (FGF) for use in treating a disease or disorder of energy homeostasis according to any one of items 1, 5 to 7 and 11 to 16, wherein the paracrine fibroblast growth factor (FGF) is a polypeptide comprising the amino acid sequence SPN-FXQ (SEQ ID NO:108) from position 58 to position 63 of the amino acid sequence of the polypeptide.
36. The paracrine fibroblast growth factor (FGF) for use in treating a disease or disorder of energy homeostasis according to item 35, wherein the amino acid sequence of the polypeptide is shown in SEQ ID NO:18 (FGF8f).
37. The paracrine fibroblast growth factor (FGF) for use in treating a disease or disorder of energy homeostasis according to any one of items 1 and 8 to 16, wherein the paracrine fibroblast growth factor (FGF) is a polypeptide comprising the amino acid sequence SPNFXQ (SEQ ID NO:108) from position 30 to position 35 of the amino acid sequence of the polypeptide.
38. The paracrine fibroblast growth factor (FGF) for use in treating a disease or disorder of energy homeostasis according to item 37, wherein the amino acid sequence of the polypeptide is shown in SEQ ID NO:23 (FGF17).
39. The paracrine fibroblast growth factor (FGF) for use in treating a disease or disorder of energy homeostasis according to any one of items 32 to 38, wherein residue X in the amino acid sequence SPNFXQ (SEQ ID NO:108) is T or N.
40. The paracrine fibroblast growth factor (FGF) for use in treating a disease or disorder of energy homeostasis according to any one of items 1 to 16, wherein the paracrine fibroblast growth factor (FGF) is a polypeptide comprising or consisting of the amino acid sequence SPNF (SEQ ID NO:107) or a fragment thereof.
41. The paracrine fibroblast growth factor (FGF) for use in treating a disease or disorder of energy homeostasis according to any one of items 1 to 4 and 11 to 16, wherein the paracrine fibroblast growth factor (FGF) is a polypeptide comprising the amino acid sequence SPNF (SEQ ID NO:107) from position 29 to position 32 of the amino acid sequence of the polypeptide.
42. The paracrine fibroblast growth factor (FGF) for use in treating a disease or disorder of energy homeostasis according to item 41, wherein the amino acid sequence of the polypeptide is shown in SEQ ID NO:16 (FGF8b).
43. The paracrine fibroblast growth factor (FGF) for use in treating a disease or disorder of energy homeostasis according to any one of items 1, 5 to 7 and 11 to 16, wherein the paracrine fibroblast growth factor (FGF) is a polypeptide comprising the amino acid sequence SPNF (SEQ ID NO:107) from position 58 to position 61 of the amino acid sequence of the polypeptide.
44. The paracrine fibroblast growth factor (FGF) for use in treating a disease or disorder of energy homeostasis according to item 43, wherein the amino acid sequence of the polypeptide is shown in SEQ ID NO:18 (FGF8f).
45. The paracrine fibroblast growth factor (FGF) for use in treating a disease or disorder of energy homeostasis according to any one of items 1 and 8 to 16, wherein the paracrine fibroblast growth factor (FGF) is a polypeptide comprising the amino acid sequence SPNF (SEQ ID NO:107) from position 30 to position 33 of the amino acid sequence of the polypeptide.
46. The paracrine fibroblast growth factor (FGF) for use in treating a disease or disorder of energy homeostasis according to item 45, wherein the amino acid sequence of the polypeptide is shown in SEQ ID NO:23 (FGF17).
47. A polynucleotide for use in treating a disease or disorder of energy homeostasis, wherein the polynucleotide encodes the paracrine fibroblast growth factor (FGF) of any one of items 1 to 46.
48. A pharmaceutical composition comprising the paracrine fibroblast growth factor (FGF) of any one of items 1 to 46 and/or the polynucleotide of item 47 for use in treating a disease or disorder of energy homeostasis, further comprising a pharmaceutically acceptable carrier and/or diluent.
49. A method of treating a disease or disorder of energy homeostasis by administering an effective dose of the paracrine fibroblast growth factor (FGF) of any one of items 1 to 46, the polynucleotide of item 47, or the pharmaceutical composition of item 48, to a subject in need of such treatment.
50. The method of item 49, wherein the subject is a human patient.
51. The paracrine fibroblast growth factor (FGF) of any one of items 1 to 46, the polynucleotide of item 47, or the pharmaceutical composition of item 48, wherein a human patient suffering from a disease or disorder of energy homeostasis or being prone to suffering from a disease or disorder of energy homeostasis is to be treated.
52. The paracrine fibroblast growth factor (FGF) of any one of items 1 to 46 and 51, the polynucleotide of item 47 or 51, the pharmaceutical composition of item 48 or 51, or the method of item 49 or 50, wherein said paracrine fibroblast growth factor (FGF) binds to an FGF receptor or is capable of binding to an FGF receptor.
53. The paracrine fibroblast growth factor (FGF) of item 52, the polynucleotide of item 52, the pharmaceutical composition of item 52, or the method of item 52, wherein said FGF receptor is at least one FGF receptor selected from the group consisting of FGF receptor 4, FGF receptor 1, FGF receptor 2 and FGF receptor 3.
54. The paracrine fibroblast growth factor (FGF) of any one of items 1 to 46 and 51 to 53, the polynucleotide of any one of items 47 and 51 to 53, the pharmaceutical composition of any one of items 48 and 51 to 53, or the method of any one of item 49 to 53, wherein said paracrine fibroblast growth factor (FGF), polynucleotide or pharmaceutical composition is to be administrated locally.
55. The paracrine fibroblast growth factor (FGF) of item 54, the polynucleotide of item 54, the pharmaceutical composition of item 54, or the method of item 54, wherein said paracrine fibroblast growth factor (FGF), polynucleotide or pharmaceutical composition is to be administrated locally into the visceral adipose tissue.
56. The paracrine fibroblast growth factor (FGF) of any one of items 1 to 46 and 51 to 55, the polynucleotide of any one of items 47 and 51 to 55, the pharmaceutical composition of any one of items 48 and 51 to 55, or the method of any one of items 49 to 55, wherein said paracrine fibroblast growth factor (FGF), polynucleotide or pharmaceutical composition is to be administered into the visceral adipose tissue.
57. The paracrine fibroblast growth factor (FGF) of any one of items 1 to 46 and 51 to 56, the polynucleotide of any one of items 47 and 51 to 56, the pharmaceutical composition of any one of items 48 and 51 to 56, or the method of any one of items 49 to 56, wherein said paracrine fibroblast growth factor (FGF), polynucleotide or pharmaceutical composition is in the form of an erodible implant, an implantable drug release device, a gel for injection or a solution for injection. 58. The paracrine fibroblast growth factor (FGF) of any one of items 1 to 46 and 51 to 57, the polynucleotide of any one of items 48 and 51 to 57, the pharmaceutical composition of any one of items 48 and 51 to 57, or the method of any one of items 49 to 57, wherein said paracrine fibroblast growth factor (FGF), polynucleotide or pharmaceutical composition is to be administered via a minipump.
59. The paracrine fibroblast growth factor (FGF) of any one of items 1 to 46 and 51 to 58, the polynucleotide of any one of items 48 and 51 to 58, the pharmaceutical composition of any one of items 49 and 51 to 58, or the method of any one items 49 to 58, wherein said disease or disorder of energy homeostasis is at least one disease or disorder selected from the group consisting of obesity, dyslipidemia, diabetes, insulin resistance, hyperglycemia and metabolic syndrome.
60. The paracrine fibroblast growth factor (FGF) of any one of items 1 to 46 and 51 to 58, the polynucleotide of any one of items 48 and 51 to 58, the pharmaceutical composition of any one of items 49 and 51 to 58, or the method of any one items 49 to 58, wherein said disease or disorder of energy homeostasis is obesity.
61. The paracrine fibroblast growth factor (FGF) of item 60, the polynucleotide of item 60, the pharmaceutical composition of item 60, or the method of item 60, wherein said obesity is central obesity.
62. The paracrine fibroblast growth factor (FGF) of any one of items 1 to 46 and 51 to 58, the polynucleotide of any one of items 48 and 51 to 58, the pharmaceutical composition of any one of items 49 and 51 to 58, or the method of any one items 49 to 58, wherein said disease or disorder of energy homeostasis is dyslipidemia.
63. The paracrine fibroblast growth factor (FGF) of any one of items 1 to 46 and 51 to 58, the polynucleotide of any one of items 48 and 51 to 58, the pharmaceutical composition of any one of items 49 and 51 to 58, or the method of any one items 49 to 58, wherein said disease or disorder of energy homeostasis is diabetes.
64. The paracrine fibroblast growth factor (FGF) of any one of items 1 to 46 and 51 to 58, the polynucleotide of any one of items 48 and 51 to 58, the pharmaceutical composition of any one of items 49 and 51 to 58, or the method of any one items 49 to 58, wherein said disease or disorder of energy homeostasis is insulin resistance.
65. The paracrine fibroblast growth factor (FGF) of any one of items 1 to 46 and 51 to 58, the polynucleotide of any one of items 48 and 51 to 58, the pharmaceutical composition of any one of items 49 and 51 to 58, or the method of any one items 49 to 58, wherein said disease or disorder of energy homeostasis is hyperglycemia.
66. The paracrine fibroblast growth factor (FGF) of any one of items 1 to 46 and 51 to 58, the polynucleotide of any one of items 48 and 51 to 58, the pharmaceutical composition of any one of items 49 and 51 to 58, or the method of any one items 49 to 58, wherein said disease or disorder of energy homeostasis is metabolic syndrome.
67. The paracrine fibroblast growth factor (FGF) of any one of items 1 to 46 and 51 to 66, the polynucleotide of any one of items 47 and 51 to 66, the pharmaceutical composition of any one of items 48 and 51 to 66, or the method of any one of items 49 to 66, wherein said paracrine fibroblast growth factor (FGF), polynucleotide or pharmaceutical composition is co-administered with at least one other active agent.
68. The paracrine fibroblast growth factor (FGF) of item 67, the polynucleotide of item 67, the pharmaceutical composition of item 67, or the method of item 67, wherein said other active agent is at least one active agent selected from the group consisting of beta-adrenergic agonists (e.g. noradrenalin, isoproterenol, BRL 35135, ICI D7114, CGP-12177A, CL 316243), indirect sympathomimetics (e.g. ephedrine, methylphenidate), atrial natriuretic peptide (e.g. ANP, BNP) and ANP/BNP receptor agonists (e.g. AP-811).
69. The paracrine fibroblast growth factor (FGF) of item 68, the polynucleotide of item 68, the pharmaceutical composition of item 68, or the method of item 68, wherein said beta-adrenergic agonist is a beta3-adrenergic agonist.
70. The paracrine fibroblast growth factor (FGF) of item 69, the polynucleotide of item 69, the pharmaceutical composition of item 69, or the method of item 69, wherein said beta3-adrenergic agonist is CL 316243.
71. A method for the preparation of a pharmaceutical composition for use in treating a disease or disorder of energy homeostasis, wherein the method comprises the following steps:
    (a) contacting the paracrine fibroblast growth factor (FGF) of any one of items 1 to 46 and/or the polynucleotide of item 47 with a liquid carrier or a solid carrier;
    (b) optionally, adjusting the pH and/or the osmolarity of the product obtained in step (a);
    (c) optionally, sterilizing the product obtained in step (a) or (b); and (d) formulating and/or packaging the product obtained in step (a), (b) or (c) as a finished medical product.
72. The method of item 71, wherein said carrier is at least one carrier selected from the group consisting of cellulose, lactose, water, saline, Ringer's solution, dextrose solution, a fixed oil, ethyl oleate and liposomes.

In the present invention and in the appended examples, a link between paracrine FGFs (including FGF8b, FGF8f and/or FGF17, preferably FGF8b) and brown adipose tissue (BAT) has been established. Because the art acknowledges the link between BAT and the treatment of diseases of energy homeostasis (including obesity, diabetes etc.), it is credible and plausible that paracrine FGFs (including FGF8b, FGF8f and/or FGF17, preferably FGF8b) can be used in the therapy of these diseases or disorders. In the same vein, it is evident that the activation of paracrine FGFs will have the same beneficial therapeutic effect in the therapy of these diseases or disorders in subjects in need of such a therapy or treatment. Said subject may be a human subject.

Several mechanisms and pathways exist that can be used to activate paracrine FGFs (including FGF8b, FGF8f and/or FGF17, preferably FGF8b) in accordance with the present invention. In the following exemplary activators of paracrine FGFs are described which can be used in accordance with the invention.

The following table shows activators of FGF signalling:

| Pathway | Activators |
| --- | --- |
| FGF receptors | Strontium ranelate (Caverzasio & Thouverey) |
| MAPK | Anisomycin (p38 MAP and JNK), PAR C-16 (MEK), t-butylhydroquinone (Erk2) |

-continued

| Pathway | Activators |
|---------|-----------|
| IP3 | Phorbol 12-myristate 13-acetate (PKC), Cell permeant caged IP3 |
| PI3K | 740 Y-P (IP3R), sc-3036 (IP3R) |

Further activators of paracrine FGFs are shown in the following table:

| | substance | IUPAC International Chemical Identifier (InChI), reference or chemical nomenclature/trivial name |
|---|---|---|
| Mechanism: Influencing FGF-heparin-binding | | |
| Activators | Sucrose octasulfate | WEPNHBQBLCNOBB-FZJVNAOYSA-N |
| | Inositol hexasulfate | NBTMNFYXJYCQHQ-UHFFFAOYSA-N |
| Mechanism: Supply of heparin for activating the FGFR-FGF-Heparin-complex | | |
| activating | administration of heparin (or of a heparin derivative) | Classical heparin; further heparin derivavites, such as certoparin, dalteparin, enoxaparin, nadroparin, danaparoid |
| Mechanism: Influencing stability of protein conformation | | |
| Stabilizing agent | Alpha-Cyclodextrin and other Cyclodextrinderivatives | HFHDHCJBZVLPGP-RWMJIURBSA-N |
| Mechanism: Influencing heparanase-mediated degradation of heparan-sulfate proteoglycan (HSPG) of the extracellular matrix | | |
| Heparanase (endo-beta-D-glucuronidase heparanase) inhibitor | PI-88 is a mixture of highly sulfated, monophosphorylated mannose oligosaccharides; Name: MUPARFOSTAT | |
| Heparanase inhibitor | OGT 2115 | 2-[4-[[3-(4-Bromophenyl)-1-oxo-2-propenyl]amino]-3-fluorophenyl]-5-benzoxazoleacetic acid |
| Mechanism: Influencing FGFR activity | | |
| FGFR1 | | |
| Activator: | SUN11602 | 4-[[4-[[2-[(4-Amino-2,3,5,6-tetramethylphenyl)amino]acetyl]methylamino]-1-piperidinyl]methylibenzamide |
| FGFR3 | | |
| Activator: | Botulinum neurotoxin serotype A (BoNT/A) | |
| FGFR4 | | |
| Activator: | Monoclonal Antibody: 4FA6D3C10 | US 2009/0123462 A1 |

Also heparin sulfate can be used as activator.

In one aspect, the present invention relates to an activator of a paracrine FGF including FGF8b, FGF8f or FGF17 as defined herein for use in treating a disease or disorder of energy homeostasis, particularly wherein said disease or disorder is obesity, dyslipidemia, diabetes, insulin resistance, hyperglycemia or metabolic syndrome. In a preferred aspect, the present invention relates to an activator of FGF8b as defined herein for use in treating a disease or disorder of energy homeostasis, particularly wherein said disease or disorder is obesity, dyslipidemia, diabetes, insulin resistance, hyperglycemia or metabolic syndrome.

The term "FGF8b" as used herein can refer to a polypeptide, wherein the polypeptide is selected from the group consisting of:

(a) a polypeptide comprising an amino acid sequence encoded by a nucleic acid molecule having the nucleic acid sequence as depicted in SEQ ID NO:2 or the nucleic acid sequence comprising nucleic acid residues 67-648 in SEQ ID NO:2;

(b) a polypeptide comprising an amino acid sequence as depicted in SEQ ID NO:16 or an amino acid sequence comprising amino acids 23-215 in SEQ ID NO:16, (c) a polypeptide comprising an amino acid sequence encoded by a nucleic acid molecule hybridizing under stringent conditions to the complementary strand of a nucleic acid molecule as defined in (a) and encoding a functional polypeptide, wherein the function comprises the ability to induce differentiation or conversion of white adipocytes and/or preadipocytes to brown adipocytes;

(d) a polypeptide having at least 40% identity to the polypeptide of any one of (a) to (c), whereby said polypeptide is functional, wherein the function comprises the ability to induce differentiation or conversion of white visceral adipocytes and/or preadipocytes to brown adipocytes; and
(e) a polypeptide comprising an amino acid sequence encoded by a nucleic acid molecule being degenerate as a result of the genetic code to the nucleotide sequence of a nucleic acid molecule as defined in (a), and (c).

The term "FGF8b" also refers to fragments of the polypeptide.

The term "agonist of a paracrine FGF" or "activator of a paracrine FGF" or "enhancer of a paracrine FGF" means in context of the present invention a compound capable of fully or partially stimulating or increasing the physiologic activity and/or expression level of (a) a paracrine FGF. The terms "activator" or "enhancer" are used interchangeably herein.

The term "agonist" can refer to a chemical compound/substance that binds to a receptor and activates the receptor to produce a biological response. Thus, an "agonist of a paracrine FGF" can be a chemical compound/substance that binds to a receptor of paracrine FGF (like FGFR1, FGFR2, FGFR3 or FGFR4) and induces the same or essential the same biological activity as the the paracrine FGF. The term "activator of a paracrine FGF" can encompass "agonist(s) of a paracrine FGF".

In one aspect, the present invention relates to an agonist of a paracrine FGF including FGF8b, FGF8f or FGF17 as defined herein for use in treating a disease or disorder of energy homeostasis, particularly wherein said disease or disorder is obesity, dyslipidemia, diabetes, insulin resistance, hyperglycemia or metabolic syndrome. In a preferred aspect, the present invention relates to an agonist of FGF8b as defined herein for use in treating a disease or disorder of energy homeostasis, particularly wherein said disease or disorder is obesity, dyslipidemia, diabetes, insulin resistance, hyperglycemia or metabolic syndrome.

The activator/agonist of paracrine FGF can be administered, for example, locally or or orally. Local administration encompasses injection or implantation e.g. by using an implantable drug depot. As used herein, the term "agonist" or "activator" also encompasses partial agonists or co-agonists/co-activators. In addition thereto, an "activator" of paracrine FGF in the context of the present invention may also be capable of stimulating the function of the paracrine FGF by inducing/enhancing the expression of the nucleic acid molecule encoding for said paracrine FGF. Thus, an activator of a paracrine FGF may lead to an increased expression level of the paracrine FGF (e.g. increased level of paracrine FGF mRNA, paracrine FGF protein); this may be reflected in an increased paracrine FGF activity. In addition thereto, an "activator" of paracrine FGF in the context of the present invention may also be an inhibitor of proteolysis of the paracrine FGF and thus enhancing paracrine FGF function by increasing amounts of effective material. Furthermore, "activators" of paracrine FGF in the context of the invention may be capable of stabilizing paracrine FGF e.g. capable of preventing degradation of paracrine FGF. This increased activity can be measured/detected by the herein described methods.

An activator of the paracrine FGF in the context of the present invention may also encompass transcriptional activators of paracrine FGF expression that are capable of enhancing paracrine FGF function. The term "activator" comprises partial activators. As partial activator the art defines candidate molecules that behave like activator, but that, even at high concentrations, cannot activate a paracrine FGF to the same extent as a full activator. Furthermore, the activator of a paracrine FGF may have an effect on interactions of the paracrine FGF protein(s) with other proteins (thus, for example, having an effect on the activity of complexes involving paracrine FGF protein(s)) or, in general, with its synthesis, e.g. by having an effect on upstream steps of paracrine FGF expression or with signalling pathways in which the paracrine FGF is involved. Depending on the mode of action, such activator may, for example, be denoted "sequestering activator" or "signalling activator".

Hence, the use of potent activators of a paracrine FGF will lead to an increase of paracrine FGF expression level and/or activity, and thereby increase differentiation or conversion of white adipocytes and/or preadipocytes (in particular white visceral adipocytes and/or white visceral preadipocytes) to brown adipocytes. In accordance with the above definition of "activator" also a paracrine FGF itself can be considered as its own activator. For example, overexpression of a paracrine FGF may lead to enhanced paracrine FGF activity, thus increasing paracrine FGF function. Accordingly, it is preferred that a paracrine FGF as defined herein can be used for the treatment of a disease or disorder of energy homeostasis, particularly wherein said disease or disorder is obesity, dyslipidemia, diabetes, insulin resistance, hyperglycemia or metabolic syndrome.

It is envisaged and preferred herein that the activator of a paracrine FGF targets, preferably specifically targets, the paracrine FGF polypeptide (or the nucleic acid encoding same) itself, particularly the biologically active region thereof. The term "targeting" refers in this context to the binding to paracrine FGF polypeptide (and here in particular to the biologically active region thereof) and/or increasing the activity of paracrine FGF, in particular the increase in its capacity/ability to induce differentiation or conversion of white adipocytes and/or preadipocytes (in particular white visceral adipocytes and/or white visceral preadipocytes) to brown adipocytes. The increase of the activity of paracrine FGF can also refer, for example, to the interference with/activation of the activity of paracrine FGF to act as a scaffold or as a recruiting platform for interaction partners, in particular forming a complex with its FGFR receptor and/or heparansulfate. The latter member of this FGFR signaling activator complex belongs to the group of the heparine molecules.

As explained above, 11 amino acids on exon 1D of paracrine FGFs to be used in accordance with the present invention are likely sufficient to mediate a biological effect. Therefore, a preferred biologically active region of the polypeptides for use in accordance with the present invention comprises the amino acid sequence VTVQSSPNFTQ (SEQ ID NO:103) or related sequences like QVTVQSSP-NFTQ (SEQ ID NO:105) or QVTVQSSPNFT (SEQ ID NO:106) or fragments thereof that contribute to mediating the biological effect of the polypeptide. This biologically active region can be targeted by activators of paracrine FGF.

We have explained above that the phenylalanine residue 32 (F32) of this short amino acid peptide has been shown to interact with the hydrophobic groove within the Ig domain III, i.e. the "c" variants of the FGF receptors (Olsen et al. 2013). The "c" spliceforms comprise FGFR1c, FGFR2c, FGFR3c, and FGFR4. Strikingly, FGF17, an endocrine FGF, is also active to induce UCP1 mRNA gene expression (FIG. 1A) and also shares F32. Thus, it is preferred that the biologically active region that can be targeted by activators of paracrine FGF comprising the amino acid sequence SPNF, preferably of from position 29 to position 32 of the respective amino acid sequence of FGF8b (exemplary amino acid sequence of FGF8b is shown in SEQ ID NO:16) or of from position 30 to position 33 of the respective amino acid sequence of FGF17 (exemplary amino acid sequence of FGF8b is shown in SEQ ID NO:18). And both FGF8b and FGF17 share the amino acid residue Q at position 34 of the respective amino acid sequence of FGF8b (exemplary amino acid sequence of FGF8b is shown in SEQ ID NO:16) or at position 35 of the respective amino acid sequence of FGF17 (exemplary amino acid sequence of FGF8b is shown in SEQ ID NO:18) Thus, they share the motif "SPNFXQ" (SEQ ID NO:108). Therefore, it is preferred that the biologically active region that can be targeted by activators of paracrine FGF comprises the amino acid sequence SPNFXQ (SEQ ID NO:108), preferably of from position 29 to position 34 of the respective amino acid sequence of FGF8b (exemplary amino acid sequence of FGF8b is shown in SEQ ID NO:16) or of from position 30 to position 35 of the respective amino acid sequence of FGF17 (exemplary amino acid sequence of FGF8b is shown in SEQ ID NO:18). X may be T or N.

Further, the biologically active region that can be targeted by activators of paracrine FGF can comprise the heparin binding domains of the FGF8 subfamily. The heparin binding domains are of importance because FGF8-subfamily members bind to heparin molecules and are therefore with regard to the extracellular space tightly bound to heparan-sulfate proteoglycans, and subsequently, trapped in the extracellular matrix. This aspect is advantageous in context of the present invention, because this local entrapment of active peptides prevents potential side effects to have systemic consequences.

More than 100 heparin binding proteins have been identified, and the ability to bind heparin itself has, up to now, not been attributed to a specific sequence. Fromm et al. have reported that heparin binding sites frequently contain clusters of basic amino acids, like XBX, XBBX (SEQ ID NO:111), XBBBX (SEQ ID NO:112) (Fromm Arch Biochem Biophys 1997).

Moreover, activators/agonists of paracrine FGF to be used herein can target FGF receptors. As shown in FIG. 8C FGF8b-mediated responsiveness correlated with Fgf receptor 4 mRNA abundance in immortalized inguinal as well as epididymal adipocytes. Data as provided herein show a similar correlation between the FGF8b-mediated responsiveness and other "c" variants of the FGF receptors. Ig domain III "c" variants of the FGF receptor comprise exon 7, 9, and the transmembrane domain of the FGF receptors (FIG. 9). It is contemplated herein that the observed effect of FGF8b-mediated browning of white adipocytes is a FGF8-subfamily group effect based on interaction of FGF8-subfamily members with the "c" splice variants of the FGFR 1-4. Thus, strengthening this interaction by activators/agonists of paracrine FGF is contemplated herein.

The agonist(s)/activator may be (a) small molecule drug(s), (a) (small) binding molecule, a peptidomemetic, and/or a poly-/monoclonal antibody.

Agonists/activators to be used herein can be (a) small molecule drug(s). The terms "small molecule drug" and "small molecule compound" are used interchangeably herein. (A) small molecule drug(s) to be used herein as agonist/activators of paracrine FGF can refer to an (organic) low molecular weight (<900 Daltons) compound. Small molecules can help to regulate a biological process and have usually a size in the order of $10^{-9}$ m. Agonists/activators to be used herein, like small molecules (drugs), can, for example, be identified by screening compound libraries, for example Enamine, Chembridge or Prestwick chemical libraries. Exemplary small molecule drugs to be used herein are provide in the Tables above.

For example, an agonist/activator of paracrine FGF can be a binding molecule(s), such as be (an) aptamer(s) and/or (an) intramer(s).

It is also envisaged in the present invention that peptides, particularly cyclic peptides can be used as agonists/activators of paracrine FGF. Cyclic peptides are polypeptide chains, wherein the amino termini and carboxyl termini, amino termini and side chain, carboxyl termini and side chain, or side chain and side chain are linked with a covalent bond that generates the ring. It is also envisaged herein that biological selection technology, such as phage display is used in order to select peptide ligands tethered to synthetic molecular structures. These peptide ligands show specificity to target paracrine FGF. In certain aspects of the invention, monomeric monocyclic peptide agonists/activators and dimeric bicyclic peptide agonists/activators of paracrine FGF are used.

The agonist/activators is preferably a selective agonist of paracrine FGF.

Selectivity expresses the biologic fact that at a given compound concentration enzymes (or proteins) are affected to different degrees. In the case of enzymes selective activation can be defined as preferred activation by a compound at a given concentration. Or in other words, an enzyme (or protein) is selectively activated over another enzyme (or protein) when there is a concentration, which results in activation of the first enzyme (or protein) whereas the second enzyme (or protein) is not, or not substantially, affected. To compare compound effects on different enzymes it is crucial to employ similar assay formats, such as the FRET assay, Plus assay, HMT assays, thermoshift assays, biological readouts (of reporter proteins/enzymes, such as Cxcl1/CXCL8), or chemical proteomics. For example, commercially available test kits, like the commercial ELISA kit can be employed (Mouse CXCL1/KC Quantikine ELISA Kit (MKC00B) from R&D Systems.

The agonists/activators to be used herein are preferably specific for paracrine FGF, i.e. the compounds specifically activate paracrine FGF. In other words, the paracrine FGF agonists/activators are preferably selective paracrine FGF agonists/activators.

The term "selective paracrine FGF activator(s)" as used herein refers to (a) paracrine FGF activator(s) as defined herein (in particular (a) small molecule drug(s)) that activates or display(s) increased activity towards paracrine FGF without displaying substantial activity towards another protein or enzyme, in particular another FGF (like FGF1, FGF2, FGF3, FGF4, FGF5, FGF6, FGF7, FGF8a, FGF8d, FGF9, FGF10, FGF11, FGF12, FGF 13, FGF 14, FGF15, FGF16 or FGF18, FGF19, or FGF21) as defined herein above.

Accordingly, a paracrine FGF activator that is selective for a paracrine FGF exhibits a paracrine FGF selectivity of greater than about 2-fold, 3-fold, 4-fold, 5-fold, 6-fold, 7-fold, 8-fold, 9-fold, 10-fold, 20-fold, 50-fold or greater than about 100-fold with respect to activation of another protein or enzyme (in particular another FGF as defined above).

For example, pan-FGF activators (i.e. compounds that broadly activate substantially any FGF) are not considered herein as selective paracrine FGF activators.

Binding molecules are also envisaged herein as agonists/activators of paracrine FGF. It is envisaged herein that the binding molecule activating paracrine FGF specifically binds to paracrine FGF as defined herein. It is envisaged herein that the aptamers/intramers can specifically target/bind to (functional) fragments or (functional) derivatives of the paracrine FGF proteins as defined herein, for example also to polypeptides having at least 40% or more identity to herein provided paracrine FGF protein(s). Accordingly, the present invention relates to the use of these aptamers/intramers in particular in the therapeutic methods of the present invention.

Activators for use in accordance with the present invention are described and provided herein. Also the use of agonists/activators yet to be generated or known compounds to be tested for their agonizing/activating activity is envisaged in context of the present invention.

Therefore, the present invention provides a method for assessing the activity of a candidate molecule suspected of being an activator of a paracrine FGF as defined and provided herein comprising the steps of:
a) contacting a cell, tissue or a non-human animal comprising a paracrine FGF with said candidate molecule;
b) detecting an increase in activity of said paracrine FGF; and
c) selecting a candidate molecule that increases activity of said paracrine FGF.

An increase of the paracrine FGF receptor activity can indicate the capacity of the selected molecule to activate paracrine FGF.

In a certain aspect, the present invention provides a method for assessing the activity of a candidate molecule suspected of being an agonist of a paracrine FGF as defined and provided herein comprising the steps of:
a) contacting a cell, tissue or a non-human animal comprising a paracrine FGF receptor with said candidate molecule;
b) detecting an increase in activity of said paracrine FGF receptor; and
c) selecting a candidate molecule that increases activity of said paracrine FGF receptor.

An increase of the paracrine FGF receptor activity can indicate the capacity of the selected molecule to agonize a paracrine FGF.

The activity of paracrine FGF can, in particular, be reflected in the increase in the capacity/ability of paracrine FGF to induce differentiation or conversion of white adipocytes and/or preadipocytes (in particular white visceral adipocytes and/or white visceral preadipocytes) to brown adipocytes. The activity of paracrine FGF can also refer, for example, to the interference with/activation of the activity of paracrine FGF to act as a scaffold or as a recruiting platform for interaction partners, in particular forming a complex with its FGFR receptor and/or heparine.

Such assays are provided herein and described in more detail further below.

Also an increase in the (expression) level can indicate useful agonists of a paracrine FGF. Accordingly, the term "activity" above can comprise and relate to the "expression level" and vice versa.

The present invention relates to a method for assessing the (expression) level of a candidate molecule suspected of being an agonist of a paracrine FGF as defined and provided herein comprising the steps of:
a) contacting a cell, tissue or a non-human animal comprising a paracrine FGF with said candidate molecule;
b) detecting an increase in the (expression) level of said paracrine FGF; and
c) selecting a candidate molecule that increases the (expression) level of said paracrine FGF.

An increase of the paracrine FGF (expression) level can indicate the capacity of the selected molecule to activate paracrine FGF.

It is understood that the detected activity or expression level of a paracrine FGF is compared to a standard or reference value of a paracrine FGF activity. The standard/reference value may be detected in a cell, tissue, or non-human animal as defined herein, which has not been contacted with a potential paracrine FGF agonist/activator or prior to the above contacting step. The increase in the activity or expression level of the paracrine FGF upon contacting with (a) candidate molecule(s) may also be compared to the increase in paracrine FGF activity induced by (a) routinely used reference compound(s). A skilled person is easily in the position to determine/assess whether the activity and/or expression of a paracrine FGF is increased.

In accordance with this invention, in particular the screening or identifying methods described herein, a cell, tissue or non-human animal to be contacted with a candidate molecule comprises paracrine FGF as defined herein. For example said cell, tissue or non-human animal may express a paracrine FGF gene, in particular also (an) additional (copy) copies of a paracrine FGF gene, (a) paracrine FGF mutated gene(s), a recombinant paracrine FGF gene construct and the like. As explained herein, the capability of a candidate molecule to activate/agonize paracrine FGF may, accordingly, be detected by measuring the expression level of such gene products of paracrine FGF or of corresponding gene constructs (e.g. mRNA or protein), wherein a high expression level (compared to a standard or reference value) is indicative for the capability of the candidate molecule to act as activator/agonist.

The term "comprising paracrine FGF" may, for example, relate to to the paracrine FGF gene(s) or proteins known in the art and described herein, but also to a reporter construct which comprises the paracrine FGF (or a functional fragment thereof) and a "reporter". Exemplary reporters (reporter gene products), which can be used in the screening methods of the invention are luciferase, (green/red) fluorescent protein and variants thereof, EGFP (enhanced green fluorescent protein), RFP (red fluorescent protein, like DsRed or DsRed2), CFP (cyan fluorescent protein), BFP (blue green fluorescent protein), YFP (yellow fluorescent protein), β-galactosidase or chloramphenicol acetyltransferase. The skilled person is readily in the position to generate and use also other reporters/reporter constructs, which can be employed in accordance with the present invention. The use of fusion proteins containing a paracrine FGF protein (or a functional fragment thereof) and a reporter gene product is also envisaged in the methods of the present invention.

All definitions and explanations provided herein above, inter alia, in relation to "paracrine FGF" (and related compounds), "agonist", "activity" and the like, apply mutatis mutandis in the context of these methods for assessing the activity (or (expression) level) of a candidate molecule suspected of being an activator/agonist of a paracrine FGF.

The following exemplary assays can be used in the determination that a candidate molecule is indeed an agonist/activator of a paracrine FGF to be used in accordance with the present invention:

A candidate molecule can be applied into a culture of proliferating or differentiating white preadipocytes, e.g. immortalized murine white preadipocytes. After full differentiation a quantification of UCP1 mRNA, e.g. by qPCR, is able to demonstrate, whether the candidate molecule led to a recruitment of brown adipocytes, as FGF8b does in the experiments we describe herein.

Furthermore, a candidate molecule can be tested in vivo by introducing it into a white adipose tissue depot, e.g. the epididymal adipose tissue depot, of mice. The candidate molecule may be applied directly or embedded in a releasing matrix or device. After several days or weeks mice are sacrificed, the tissue surrounding the site of application excised and analyzed for expression of UCP1 mRNA, e.g. by qPCR, and/or analyzed histologically for the presence of multilocular cells. These parameters will demonstrate, whether a candidate molecule led to recruitment of brown adipocytes in a similar fashion as FGF8b does in the experiments we describe herein.

Exemplary methods are described in detail in the appended examples.

Antibodies, in particular monoclonal antibodies, that specifically bind to paracrine FGF as defined herein can be used in the herein provided screening assays in order to detect the expression level of a paracrine. For example, such antibodies can be used in techniques like global ChIP-seq, imaging/co-localisations, immunoprecipitation to find new interaction partners by mass-spec, and the like. Such antibodies are valuable research tools.

In certain aspects, the present invention relates to the following items:

1. An activator of paracrine fibroblast growth factor (FGF) for use in treating a disease or disorder of energy homeostasis.
2. The activator of paracrine fibroblast growth factor (FGF) for use in treating a disease or disorder of energy homeostasis according to item 1, wherein the paracrine fibroblast growth factor (FGF) is FGF8b.
3. The activator of paracrine fibroblast growth factor (FGF) for use in treating a disease or disorder of energy homeostasis according to item 1 or 2, wherein the paracrine fibroblast growth factor (FGF) is human FGF8b.
4. The activator of paracrine fibroblast growth factor (FGF) for use in treating a disease or disorder of energy homeostasis according to any one of items 1 to 3, wherein the paracrine fibroblast growth factor (FGF) is a polypeptide, wherein the polypeptide is selected from the group consisting of:
   (a) a polypeptide comprising an amino acid sequence encoded by a nucleic acid molecule having the nucleic acid sequence as depicted in SEQ ID NO:2 or the nucleic acid sequence comprising nucleic acid residues 67-648 in SEQ ID NO:2;
   (b) a polypeptide comprising an amino acid sequence as depicted in SEQ ID NO:16 or an amino acid sequence comprising amino acids 23-215 in SEQ ID NO:16;
   (c) a polypeptide encoded by a nucleic acid molecule encoding a polypeptide comprising an amino acid sequence having amino acids 23-215 in SEQ ID NO:16 or having an amino acid sequence as depicted in SEQ ID NO:16;
   (d) a polypeptide comprising an amino acid sequence encoded by a nucleic acid molecule hybridizing under stringent conditions to the complementary strand of a nucleic acid molecule as defined in (a) or (c);
   (e) a polypeptide having at least 40% identity to the polypeptide of any one of (a) to (d);
   (f) a protein as defined in any one of (a) to (e) wherein one or more amino acids are deleted, inserted, added or substituted; and
   (g) a polypeptide comprising an amino acid sequence encoded by a nucleic acid molecule being degenerate as a result of the genetic code to the nucleotide sequence of a nucleic acid molecule as defined in (a), (c) and (d).
5. The activator of paracrine fibroblast growth factor (FGF) for use in treating a disease or disorder of energy homeostasis according to item 1, wherein the paracrine fibroblast growth factor (FGF) is FGF8f.
6. The activator of paracrine fibroblast growth factor (FGF) for use in treating a disease or disorder of energy homeostasis according to item 1 or 5, wherein the paracrine fibroblast growth factor (FGF) is human FGF8f.
7. The activator of paracrine fibroblast growth factor (FGF) for use in treating a disease or disorder of energy homeostasis according to any one of items 1, 5 and 6, wherein the paracrine fibroblast growth factor (FGF) is a polypeptide, wherein the polypeptide is selected from the group consisting of:
   (a) a polypeptide comprising an amino acid sequence encoded by a nucleic acid molecule having the nucleic acid sequence as depicted in SEQ ID NO:4 or the nucleic acid sequence comprising nucleic acid residues 67-735 in SEQ ID NO:4;
   (b) a polypeptide comprising an amino acid sequence as depicted in SEQ ID NO:18 or an amino acid sequence comprising amino acids 23-244 in SEQ ID NO:18;
   (c) a polypeptide encoded by a nucleic acid molecule encoding a polypeptide comprising an amino acid sequence having amino acids 23-244 in SEQ ID NO:18 or having an amino acid sequence as depicted in SEQ ID NO:18;
   (d) a polypeptide comprising an amino acid sequence encoded by a nucleic acid molecule hybridizing under stringent conditions to the complementary strand of a nucleic acid molecule as defined in (a) or (c);
   (e) a polypeptide having at least 40% identity to the polypeptide of any one of (a) to (d);
   (f) a protein as defined in any one of (a) to (e) wherein one or more amino acids are deleted, inserted, added or substituted; and
   (g) a polypeptide comprising an amino acid sequence encoded by a nucleic acid molecule being degenerate as a result of the genetic code to the nucleotide sequence of a nucleic acid molecule as defined in (a), (c) and (d).
8. The activator of paracrine fibroblast growth factor (FGF) for use in treating a disease or disorder of energy homeostasis according to item 1, wherein the paracrine fibroblast growth factor (FGF) is FGF17.
9. The activator of paracrine fibroblast growth factor (FGF) for use in treating a disease or disorder of energy homeostasis according to item 1 or 8, wherein the paracrine fibroblast growth factor (FGF) is human FGF17.
10. The activator of paracrine fibroblast growth factor (FGF) for use in treating a disease or disorder of energy homeostasis according to any one of items 1, 8 and 9, wherein the paracrine fibroblast growth factor (FGF) is a polypeptide, wherein the polypeptide is selected from the group consisting of:
    (a) a polypeptide comprising an amino acid sequence encoded by a nucleic acid molecule having the nucleic acid sequence as depicted in SEQ ID NO:9 or the nucleic acid sequence comprising nucleic acid residues 67-651 in SEQ ID NO:9;
    (b) a polypeptide comprising an amino acid sequence as depicted in SEQ ID NO:23 or an amino acid sequence comprising amino acids 23-216 in SEQ ID NO:23;
    (c) a polypeptide encoded by a nucleic acid molecule encoding a polypeptide comprising an amino acid sequence having amino acids 23-216 in SEQ ID NO:23 or having an amino acid sequence as depicted in SEQ ID NO:23;

(d) a polypeptide comprising an amino acid sequence encoded by a nucleic acid molecule hybridizing under stringent conditions to the complementary strand of a nucleic acid molecule as defined in (a) or (c);

(e) a polypeptide having at least 40% identity to the polypeptide of any one of (a) to (d);

(f) a protein as defined in any one of (a) to (e) wherein one or more amino acids are deleted, inserted, added or substituted; and (g) a polypeptide comprising an amino acid sequence encoded by a nucleic acid molecule being degenerate as a result of the genetic code to the nucleotide sequence of a nucleic acid molecule as defined in (a), (c) and (d).

11. The activator of paracrine fibroblast growth factor (FGF) for use in treating a disease or disorder of energy homeostasis according to any one of items 4, 7 and 10, wherein the polypeptide is a polypeptide having at least 45%, at least 50%, at least 55%, at least 60%, at least 65%, at least 70%, at least 75%, at least 80%, at least 85%, at least 90%, at least 95% or at least 99% identity to the polypeptide of any one of (a) to (d).

12. The activator of paracrine fibroblast growth factor (FGF) for use in treating a disease or disorder of energy homeostasis according to any one of items 4, 7 and 10, wherein the polypeptide is a polypeptide having at least 90% identity to the polypeptide of any one of (a) to (d).

13. The activator of paracrine fibroblast growth factor (FGF) for use in treating a disease or disorder of energy homeostasis according to any one of items 4, 7 and 10, wherein the polypeptide is a polypeptide having at least 95% identity to the polypeptide of any one of (a) to (d).

14. The activator of paracrine fibroblast growth factor (FGF) for use in treating a disease or disorder of energy homeostasis according to any one of items 4, 7 and 10, wherein the polypeptide is a polypeptide having at least 99% identity to the polypeptide of any one of (a) to (d).

15. The activator of paracrine fibroblast growth factor (FGF) for use in treating a disease or disorder of energy homeostasis according to any one of items 1 to 14, wherein the paracrine fibroblast growth factor (FGF) is a polypeptide that is able to induce differentiation or conversion of white adipocytes and/or white preadipocytes to brown adipocytes.

16. The activator of paracrine fibroblast growth factor (FGF) for use in treating a disease or disorder of energy homeostasis according to any one of items 1 to 14, wherein the paracrine fibroblast growth factor (FGF) is a polypeptide that is able to induce differentiation or conversion of white visceral adipocytes and/or white visceral preadipocytes to brown adipocytes.

17. The activator of paracrine fibroblast growth factor (FGF) for use in treating a disease or disorder of energy homeostasis according to any one of items 1 to 7 and 11 to 16, wherein the paracrine fibroblast growth factor (FGF) is a polypeptide comprising or consisting of the amino acid sequence VTVQSSPNFTQ (SEQ ID NO:103) or a fragment thereof.

18. The activator of paracrine fibroblast growth factor (FGF) for use in treating a disease or disorder of energy homeostasis according to any one of items 1 to 4 and 11 to 16, wherein the paracrine fibroblast growth factor (FGF) is a polypeptide comprising the amino acid sequence VTVQSSPNFTQ (SEQ ID NO:103) from position 24 to position 34 of the amino acid sequence of the polypeptide.

19. The activator of paracrine fibroblast growth factor (FGF) for use in treating a disease or disorder of energy homeostasis according to item 18, wherein the amino acid sequence of the polypeptide is shown in SEQ ID NO:16 (FGF8b).

20. The activator of paracrine fibroblast growth factor (FGF) for use in treating a disease or disorder of energy homeostasis according to any one of items 1, 5 to 7 and 11 to 16, wherein the paracrine fibroblast growth factor (FGF) is a polypeptide comprising the amino acid sequence VTVQSSPNFTQ (SEQ ID NO:103) from position 53 to position 63 of the amino acid sequence of the polypeptide.

21. The activator of paracrine fibroblast growth factor (FGF) for use in treating a disease or disorder of energy homeostasis according to item 20, wherein the amino acid sequence of the polypeptide is shown in SEQ ID NO:18 (FGF8f).

22. The activator of paracrine fibroblast growth factor (FGF) for use in treating a disease or disorder of energy homeostasis according to any one of items 1 to 7 and 11 to 16, wherein the paracrine fibroblast growth factor (FGF) is a polypeptide comprising or consisting of the amino acid sequence QVTVQSSPNFTQ (SEQ ID NO:105) or a fragment thereof.

23. The activator of paracrine fibroblast growth factor (FGF) for use in treating a disease or disorder of energy homeostasis according to any one of items 1 to 4 and 11 to 16, wherein the paracrine fibroblast growth factor (FGF) is a polypeptide comprising the amino acid sequence QVTVQSSPNFTQ (SEQ ID NO:105) from position 23 to position 34 of the amino acid sequence of the polypeptide.

24. The activator of paracrine fibroblast growth factor (FGF) for use in treating a disease or disorder of energy homeostasis according to item 23, wherein the amino acid sequence of the polypeptide is shown in SEQ ID NO:16 (FGF8b).

25. The activator of paracrine fibroblast growth factor (FGF) for use in treating a disease or disorder of energy homeostasis according to any one of items 1, 5 to 7 and 11 to 16, wherein the paracrine fibroblast growth factor (FGF) is a polypeptide comprising the amino acid sequence QVTVQSSPNFTQ (SEQ ID NO:105) from position 52 to position 63 of the amino acid sequence of the polypeptide.

26. The activator of paracrine fibroblast growth factor (FGF) for use in treating a disease or disorder of energy homeostasis according to item 25, wherein the amino acid sequence of the polypeptide is shown in SEQ ID NO:18 (FGF8f).

27. The activator of paracrine fibroblast growth factor (FGF) for use in treating a disease or disorder of energy homeostasis according to any one of items 1 to 7 and 11 to 16, wherein the paracrine fibroblast growth factor (FGF) is a polypeptide comprising or consisting of the amino acid sequence QVTVQSSPNFT (SEQ ID NO:106) or a fragment thereof.

28. The activator of paracrine fibroblast growth factor (FGF) for use in treating a disease or disorder of energy homeostasis according to any one of items 1 to 4 and 11 to 16, wherein the paracrine fibroblast growth factor (FGF) is a polypeptide comprising the amino acid sequence QVTVQSSPNFT (SEQ ID NO:106) from position 23 to position 33 of the amino acid sequence of the polypeptide.

29. The activator of paracrine fibroblast growth factor (FGF) for use in treating a disease or disorder of energy homeostasis according to item 28, wherein the amino acid sequence of the polypeptide is shown in SEQ ID NO:16 (FGF8b).

30. The activator of paracrine fibroblast growth factor (FGF) for use in treating a disease or disorder of energy homeostasis according to any one of items 1, 5 to 7 and 11 to 16, wherein the paracrine fibroblast growth factor (FGF) is a polypeptide comprising the amino acid sequence QVTVQSSPNFT (SEQ ID NO:106) from position 52 to position 62 of the amino acid sequence of the polypeptide.

31. The activator of paracrine fibroblast growth factor (FGF) for use in treating a disease or disorder of energy homeostasis according to item 30, wherein the amino acid sequence of the polypeptide is shown in SEQ ID NO:18 (FGF8f).

32. The activator of paracrine fibroblast growth factor (FGF) for use in treating a disease or disorder of energy homeostasis according to any one of items 1 to 16, wherein the paracrine fibroblast growth factor (FGF) is a polypeptide comprising or consisting of the amino acid sequence SPNFXQ (SEQ ID NO:108) or a fragment thereof.

33. The activator of paracrine fibroblast growth factor (FGF) for use in treating a disease or disorder of energy homeostasis according to any one of items 1 to 4 and 11 to 16, wherein the paracrine fibroblast growth factor (FGF) is a polypeptide comprising the amino acid sequence SPNFXQ (SEQ ID NO:108) from position 29 to position 34 of the amino acid sequence of the polypeptide.

34. The activator of paracrine fibroblast growth factor (FGF) for use in treating a disease or disorder of energy homeostasis according to item 33, wherein the amino acid sequence of the polypeptide is shown in SEQ ID NO:16 (FGF8b).

35. The activator of paracrine fibroblast growth factor (FGF) for use in treating a disease or disorder of energy homeostasis according to any one of items 1, 5 to 7 and 11 to 16, wherein the paracrine fibroblast growth factor (FGF) is a polypeptide comprising the amino acid sequence SPNFXQ (SEQ ID NO:108) from position 58 to position 63 of the amino acid sequence of the polypeptide.

36. The activator of paracrine fibroblast growth factor (FGF) for use in treating a disease or disorder of energy homeostasis according to item 35, wherein the amino acid sequence of the polypeptide is shown in SEQ ID NO:18 (FGF8f).

37. The activator of paracrine fibroblast growth factor (FGF) for use in treating a disease or disorder of energy homeostasis according to any one of items 1 and 8 to 16, wherein the paracrine fibroblast growth factor (FGF) is a polypeptide comprising the amino acid sequence SPNFXQ (SEQ ID NO:108) from position 30 to position 35 of the amino acid sequence of the polypeptide.

38. The activator of paracrine fibroblast growth factor (FGF) for use in treating a disease or disorder of energy homeostasis according to item 37, wherein the amino acid sequence of the polypeptide is shown in SEQ ID NO:23 (FGF17).

39. The activator of paracrine fibroblast growth factor (FGF) for use in treating a disease or disorder of energy homeostasis according to any one of items 32 to 38, wherein residue X in the amino acid sequence SPNFXQ (SEQ ID NO:108) is T or N.

40. The activator of paracrine fibroblast growth factor (FGF) for use in treating a disease or disorder of energy homeostasis according to any one of items 1 to 16, wherein the paracrine fibroblast growth factor (FGF) is a polypeptide comprising or consisting of the amino acid sequence SPNF (SEQ ID NO:107) or a fragment thereof.

41. The activator of paracrine fibroblast growth factor (FGF) for use in treating a disease or disorder of energy homeostasis according to any one of items 1 to 4 and 11 to 16, wherein the paracrine fibroblast growth factor (FGF) is a polypeptide comprising the amino acid sequence SPNF (SEQ ID NO:107) from position 29 to position 32 of the amino acid sequence of the polypeptide.

42. The activator of paracrine fibroblast growth factor (FGF) for use in treating a disease or disorder of energy homeostasis according to item 41, wherein the amino acid sequence of the polypeptide is shown in SEQ ID NO:16 (FGF8b).

43. The activator of paracrine fibroblast growth factor (FGF) for use in treating a disease or disorder of energy homeostasis according to any one of items 1, 5 to 7 and 11 to 16, wherein the paracrine fibroblast growth factor (FGF) is a polypeptide comprising the amino acid sequence SPNF (SEQ ID NO:107) from position 58 to position 61 of the amino acid sequence of the polypeptide.

44. The activator of paracrine fibroblast growth factor (FGF) for use in treating a disease or disorder of energy homeostasis according to item 43, wherein the amino acid sequence of the polypeptide is shown in SEQ ID NO:18 (FGF8f).

45. The activator of paracrine fibroblast growth factor (FGF) for use in treating a disease or disorder of energy homeostasis according to any one of items 1 and 8 to 16, wherein the paracrine fibroblast growth factor (FGF) is a polypeptide comprising the amino acid sequence SPNF (SEQ ID NO:107) from position 30 to position 33 of the amino acid sequence of the polypeptide.

46. The activator of paracrine fibroblast growth factor (FGF) for use in treating a disease or disorder of energy homeostasis according to item 45, wherein the amino acid sequence of the polypeptide is shown in SEQ ID NO:23 (FGF17).

47. A pharmaceutical composition comprising the activator of paracrine fibroblast growth factor (FGF) of any one of items 1 to 46 for use in treating a disease or disorder of energy homeostasis, further comprising a pharmaceutically acceptable carrier and/or diluent.

48. A method of treating a disease or disorder of energy homeostasis by administering an effective dose of the activator of paracrine fibroblast growth factor (FGF) of any one of items 1 to 46, or the pharmaceutical composition of item 47, to a subject in need of such treatment.

49. The method of item 48, wherein the subject is a human patient.

50. The activator of paracrine fibroblast growth factor (FGF) of any one of items 1 to 46, or the pharmaceutical composition of item 47, wherein a human patient suffering from a disease or disorder of energy homeostasis or being prone to suffering from a a disease or disorder of energy homeostasis is to be treated.

51. The activator of paracrine fibroblast growth factor (FGF) of any one of items 1 to 46 and 50, the pharmaceutical composition of item 47 or 50, or the method of item 48 or 49, wherein said paracrine fibroblast growth factor (FGF) binds to an FGF receptor or is capable of binding to an FGF receptor.

52. The activator of paracrine fibroblast growth factor (FGF) of item 51, the pharmaceutical composition of item 51, or the method of item 51, wherein said FGF receptor is at least one FGF receptor selected from the group consisting of FGF receptor 4, FGF receptor 1, FGF receptor 2 and FGF receptor 3.

53. The activator of paracrine fibroblast growth factor (FGF) of any one of items 1 to 46 and 50 to 52, the pharmaceutical composition of any one of items 47 and 50 to 52, or the method of any one of item 48 to 52, wherein said activator of paracrine fibroblast growth factor (FGF) or said pharmaceutical composition is to be administrated orally or locally.
54. The activator of paracrine fibroblast growth factor (FGF) of item 43, the pharmaceutical composition of item 53, or the method of item 53, wherein said activator of paracrine fibroblast growth factor (FGF), or said pharmaceutical composition is to be administrated locally into the visceral adipose tissue.
55. The activator of paracrine fibroblast growth factor (FGF) of any one of items 1 to 46 and 50 to 54, the pharmaceutical composition of any one of items 47 and 50 to 54, or the method of any one of items 48 to 54, wherein said activator of paracrine fibroblast growth factor (FGF), or said pharmaceutical composition is to be administered into the visceral adipose tissue.
56. The activator of paracrine fibroblast growth factor (FGF) of any one of items 1 to 46 and 50 to 55, the pharmaceutical composition of any one of items 47 and 50 to 55, or the method of any one of items 48 to 55, wherein said activator of paracrine fibroblast growth factor (FGF), or pharmaceutical composition is in the form of an erodible implant, an implantable drug release device, a gel for injection or a solution for injection.
57. The activator of paracrine fibroblast growth factor (FGF) of any one of items 1 to 46 and 50 to 56, the pharmaceutical composition of any one of items 47 and 50 to 56, or the method of any one of items 48 to 56, wherein said activator of paracrine fibroblast growth factor (FGF) or said pharmaceutical composition is to be administered via a minipump.
58. The activator of paracrine fibroblast growth factor (FGF) of any one of items 1 to 46 and 50 to 57, the pharmaceutical composition of any one of items 48 and 50 to 57, or the method of any one items 48 to 57, wherein said disease or disorder of energy homeostasis is at least one disease or disorder selected from the group consisting of obesity, dyslipidemia, diabetes, insulin resistance, hyperglycemia and metabolic syndrome.
59. The activator of paracrine fibroblast growth factor (FGF) of any one of items 1 to 46 and 50 to 57, the pharmaceutical composition of any one of items 48 and 50 to 57, or the method of any one items 48 to 57, wherein said disease or disorder of energy homeostasis is obesity.
60. The activator of paracrine fibroblast growth factor (FGF) of item 59, the pharmaceutical composition of item 59, or the method of item 59, wherein said obesity is central obesity.
61. The activator of paracrine fibroblast growth factor (FGF) of any one of items 1 to 46 and 50 to 57, the pharmaceutical composition of any one of items 48 and 50 to 57, or the method of any one items 48 to 57, wherein said disease or disorder of energy homeostasis is dyslipidemia.
62. The activator of paracrine fibroblast growth factor (FGF) of any one of items 1 to 46 and 50 to 57, the pharmaceutical composition of any one of items 48 and 50 to 57, or the method of any one items 48 to 57, wherein said disease or disorder of energy homeostasis is diabetes.
63. The activator of paracrine fibroblast growth factor (FGF) of any one of items 1 to 46 and 50 to 57, the pharmaceutical composition of any one of items 48 and 50 to 57, or the method of any one items 48 to 57, wherein said disease or disorder of energy homeostasis is insulin resistance.
64. The activator of paracrine fibroblast growth factor (FGF) of any one of items 1 to 46 and 50 to 57, the pharmaceutical composition of any one of items 48 and 50 to 57, or the method of any one items 48 to 57, wherein said disease or disorder of energy homeostasis is hyperglycemia.
65. The activator of paracrine fibroblast growth factor (FGF) of any one of items 1 to 46 and 50 to 57, the pharmaceutical composition of any one of items 48 and 50 to 57, or the method of any one items 48 to 57, wherein said disease or disorder of energy homeostasis is metabolic syndrome.
66. The activator of paracrine fibroblast growth factor (FGF) of any one of items 1 to 46 and 50 to 65, the pharmaceutical composition of any one of items 47 and 50 to 65, or the method of any one of items 48 and 50 to 65, wherein said activator of paracrine fibroblast growth factor (FGF), pharmaceutical composition is co-administered with at least one other active agent.
67. The activator of paracrine fibroblast growth factor (FGF) of item 66, the pharmaceutical composition of item 66, or the method of item 66, wherein said other active agent is at least one active agent selected from the group consisting of beta-adrenergic agonists (e.g. noradrenalin, isoproterenol, BRL 35135, ICI D7114, CGP-12177A, CL 316243), indirect sympathomimetics (e.g. ephedrine, methylphenidate), atrial natriuretic peptide (e.g. ANP, BNP) and ANP/BNP receptor agonists (e.g. AP-811).
68. The activator of paracrine fibroblast growth factor (FGF) of item 67, the pharmaceutical composition of item 67, or the method of item 68, wherein said beta-adrenergic agonist is a beta3-adrenergic agonist.
69. The activator of paracrine fibroblast growth factor (FGF) of item 68, the pharmaceutical composition of item 68, or the method of item 68, wherein said beta3-adrenergic agonist is CL 316243.
70. The activator of paracrine fibroblast growth factor (FGF) of any one of items 1 to 46 and 50 to 69, the pharmaceutical composition of any one of items 47 and 50 to 69, or the method of any one of items 48 and 50 to 69, wherein said activator of paracrine fibroblast growth factor (FGF) is capable of influencing FGF-heparin-binding or influences FGF-heparin-binding.
71. The activator of paracrine fibroblast growth factor (FGF) of item 70, the pharmaceutical composition of item 70, or the method of item 70, wherein said activator of paracrine fibroblast growth factor (FGF) is sucrose octasulfate or inositol hexasulfate.
72. The activator of paracrine fibroblast growth factor (FGF) of any one of items 1 to 46 and 50 to 69, the pharmaceutical composition of any one of items 47 and 50 to 69, or the method of any one of items 48 and 50 to 69, wherein said activator of paracrine fibroblast growth factor (FGF) is capable of activating the FGFR-FGF-Heparin-complex or activates the FGFR-FGF-Heparin-complex.
73. The activator of paracrine fibroblast growth factor (FGF) of item 72, the pharmaceutical composition of item 72, or the method of item 72, wherein said activator of paracrine fibroblast growth factor (FGF) is heparin or a heparin derivative, such as certoparin, dalteparin, enoxaparin, nadroparin or danaparoid.
74. The activator of paracrine fibroblast growth factor (FGF) of any one of items 1 to 46 and 50 to 69, the pharmaceutical composition of any one of items 47 and 50 to 69, or the method of any one of items 48 and 50 to 69, wherein said activator of paracrine fibroblast growth factor (FGF) is capable of influencing stability of protein conformation or influences stability of protein conformation.

75. The activator of paracrine fibroblast growth factor (FGF) of item 74, the pharmaceutical composition of item 74, or the method of item 74, wherein said activator of paracrine fibroblast growth factor (FGF) is Alpha-Cyclodextrin or a Cyclodextrin-derivative.

76. The activator of paracrine fibroblast growth factor (FGF) of any one of items 1 to 46 and 50 to 69, the pharmaceutical composition of any one of items 47 and 50 to 69, or the method of any one of items 48 and 50 to 69, wherein said activator of paracrine fibroblast growth factor (FGF) is capable of influencing heparanase-mediated degradation of heparan-sulfate proteoglycan (HSPG) of the extracellular matrix or influences heparanase-mediated degradation of heparan-sulfate proteoglycan (HSPG) of the extracellular matrix.

77. The activator of paracrine fibroblast growth factor (FGF) of item 76, the pharmaceutical composition of item 76, or the method of item 76, wherein said activator of paracrine fibroblast growth factor (FGF) is PI-88 (a mixture of highly sulfated, monophosphorylated mannose oligosaccharides) or OGT 2115.

78. The activator of paracrine fibroblast growth factor (FGF) of any one of items 1 to 46 and 50 to 69, the pharmaceutical composition of any one of items 47 and 50 to 69, or the method of any one of items 48 and 50 to 69, wherein said activator of paracrine fibroblast growth factor (FGF) is capable of influencing FGFR activity or influences FGFR activity.

79. The activator of paracrine fibroblast growth factor (FGF) of item 78, the pharmaceutical composition of item 78, or the method of item 78, wherein said FGFR is FGFR1.

80. The activator of paracrine fibroblast growth factor (FGF) of item 79, the pharmaceutical composition of item 79, or the method of item 79, wherein said activator of paracrine fibroblast growth factor (FGF) is SUN11602.

81. The activator of paracrine fibroblast growth factor (FGF) of item 78, the pharmaceutical composition of item 78, or the method of item 78, wherein said FGFR is FGFR3.

82. The activator of paracrine fibroblast growth factor (FGF) of item 81, the pharmaceutical composition of item 81, or the method of item 81, wherein said activator of paracrine fibroblast growth factor (FGF) is Botulinum neurotoxin serotype A (BoNT/A).

83. The activator of paracrine fibroblast growth factor (FGF) of item 78, the pharmaceutical composition of item 78, or the method of item 78, wherein said FGFR is FGFR4.

84. The activator of paracrine fibroblast growth factor (FGF) of item 83, the pharmaceutical composition of item 83, or the method of item 83, wherein said activator of paracrine fibroblast growth factor (FGF) is monoclonal Antibody: 4FA6D3C10.

85. The activator of paracrine fibroblast growth factor (FGF) of any one of items 1 to 46 and 50 to 69, the pharmaceutical composition of any one of items 47 and 50 to 69, or the method of any one of items 48 and 50 to 69, wherein said activator of paracrine fibroblast growth factor (FGF) is strontium ranelate, anisomycin, PAF C-16, t-butylhydroquinone, phorbol 12-myristate 13-acetate, cell permeant caged IP3, 740 Y-P, or sc-3036.

86. A method for the preparation of a pharmaceutical composition for use in treating a disease or disorder of energy homeostasis, wherein the method comprises the following steps:
(a) contacting the activator of paracrine fibroblast growth factor (FGF) of any one of items 1 to 85 with a liquid carrier or a solid carrier;
(b) optionally, adjusting the pH and/or the osmolarity of the product obtained in step (a);
(c) optionally, sterilizing the product obtained in step (a) or (b); and
(d) formulating and/or packaging the product obtained in step (a), (b) or (c) as a finished medical product.

87. The method of item 86, wherein said carrier is at least one carrier selected from the group consisting of cellulose, lactose, water, saline, Ringer's solution, dextrose solution, a fixed oil, ethyl oleate and liposomes.

The herein provided paracrine FGFs are able to specifically target visceral fat (i.e. visceral adipose tissue). Visceral fat, also known as organ fat, intra-abdominal fat or belly fat, is located inside the peritoneal cavity and packed in between internal organs and torso. The aesthetic problem arising from an excess of visceral fat is called "pot belly" or "beer belly", in which the abdomen protrudes to an unaesthetic extent. Thus, an excess of visceral fat negatively influences the bodily appearance. Furthermore, a waist to hip ratio (WHR) of 0.7 for women and 0.9 for men has been shown to correlate strongly with fertility and a WHR of less than 0.7 is a significant measure of female attractiveness in Caucasian cultures. Accordingly, the present invention relates to a non-therapeutic cosmetic product comprising the herein provided paracrine FGF (e.g. FGF8b, FGF8f and/or FGF17).

Thus, one embodiment of the present invention relates to a cosmetic product comprising a polypeptide, wherein said polypeptide is selected from the group consisting of:
(a) a polypeptide comprising an amino acid sequence encoded by a nucleic acid molecule having the nucleic acid sequence as depicted in SEQ ID NO:2 or the nucleic acid sequence comprising nucleic acid residues 67-648 in SEQ ID NO:2;
(b) a polypeptide comprising an amino acid sequence as depicted in SEQ ID NO:16 or an amino acid sequence comprising amino acids 23-215 in SEQ ID NO:16,
(c) a polypeptide encoded by a nucleic acid molecule encoding a polypeptide comprising an amino acid sequence having amino acids 23-215 in SEQ ID NO:16 or having an amino acid sequence as depicted in SEQ ID NO:16;
(d) a polypeptide comprising an amino acid sequence encoded by a nucleic acid molecule hybridizing under stringent conditions to the complementary strand of a nucleic acid molecule as defined in (a) or (c) and encoding a functional polypeptide, wherein the function comprises the ability to induce differentiation or conversion of white adipocytes and/or preadipocytes to brown adipocytes;
(e) a polypeptide having at least 40% to the polypeptide of any one of (a) to (d), whereby said polypeptide is functional, wherein the function comprises the ability to induce differentiation or conversion of white adipocytes and/or preadipocytes to brown adipocytes; and
(f) a polypeptide comprising an amino acid sequence encoded by a nucleic acid molecule being degenerate as a result of the genetic code to the nucleotide sequence of a nucleic acid molecule as defined in (a), (c) and (d).

As mentioned, the function of the above described polypeptide of the invention is ability to induce differentiation or conversion of white adipocytes and/or preadipocytes (in particular white visceral adipocytes and/or white visceral preadipocytes) to brown adipocytes.

The polypeptide of item (e) above may have at least 45%, at least 50%, at least 55%, at least 60%, at least 65%, at least 70%, at least 75%, at least 80%, at least 85%, at least 90%, at least 95% or at least 99% identity to the polypeptide of any one of (a) to (d), whereby said polypeptide is functional, wherein the function comprises the ability to induce differentiation or conversion of visceral adipocytes and/or preadipocytes (e.g. white visceral adipocytes and/or white visceral preadipocytes) to brown adipocytes.

The illustrative appended examples show that FGF8 is active in browning visceral adipose tissue. Whereas FGF8b was shown to have browning potential in both visceral and subcutaneous adipose tissue, FGF8f specifically induces browning of visceral adipose tissue. Therefore, one aspect of the invention relates to a non-therapeutic cosmetic product comprising FGF8f.

Thus, one aspect of the invention relates to a cosmetic product comprising a polypeptide, wherein said polypeptide is selected from the group consisting of:
(a) a polypeptide comprising an amino acid sequence encoded by a nucleic acid molecule having the nucleic acid sequence as depicted in SEQ ID NO:4 or the nucleic acid sequence comprising nucleic acid residues 67-735 in SEQ ID NO:4;
(b) a polypeptide comprising an amino acid sequence as depicted in SEQ ID NO:18 or an amino acid sequence comprising amino acids 23-244 in SEQ ID NO:18;
(c) a polypeptide encoded by a nucleic acid molecule encoding a polypeptide comprising an amino acid sequence having amino acids 23-244 in SEQ ID NO:18 or having an amino acid sequence as depicted in SEQ ID NO:18;
(d) a polypeptide comprising an amino acid sequence encoded by a nucleic acid molecule hybridizing under stringent conditions to the complementary strand of a nucleic acid molecule as defined in (a) or (c) and encoding a functional polypeptide, wherein the function comprises the ability to induce differentiation or conversion of white adipocytes and/or preadipocytes to brown adipocytes;
(e) a polypeptide having at least 40% identity to the polypeptide of any one of (a) to (d), whereby said polypeptide is functional, wherein the function comprises the ability to induce differentiation or conversion of white adipocytes and/or preadipocytes to brown adipocytes; and
(f) a polypeptide comprising an amino acid sequence encoded by a nucleic acid molecule being degenerate as a result of the genetic code to the nucleotide sequence of a nucleic acid molecule as defined in (a), (c) and (d).

As mentioned, the function of the above described polypeptide of the invention is ability to induce differentiation or conversion of white adipocytes and/or preadipocytes (in particular white visceral adipocytes and/or white visceral preadipocytes) to brown adipocytes.

The polypeptide of item (e) above may have at least 45%, at least 50%, at least 55%, at least 60%, at least 65%, at least 70%, at least 75%, at least 80%, at least 85%, at least 90%, at least 95% or at least 99% identity to the polypeptide of any one of (a) to (d), whereby said polypeptide is functional, wherein the function comprises the ability to induce differentiation or conversion of white adipocytes and/or preadipocytes (e.g. white visceral adipocytes and/or white visceral preadipocytes) to brown adipocytes.

The illustrative appended examples demonstrate that FGF17 is active in browning visceral adipose tissue. Therefore, one aspect of the invention relates to a non-therapeutic cosmetic product comprising FGF17.

Thus, one aspect of the invention relates to a cosmetic product comprising a polypeptide, wherein said polypeptide is selected from the group consisting of:
(a) a polypeptide comprising an amino acid sequence encoded by a nucleic acid molecule having the nucleic acid sequence as depicted in SEQ ID NO:9 or the nucleic acid sequence comprising nucleic acid residues 67-651 in SEQ ID NO:9;
(b) a polypeptide comprising an amino acid sequence as depicted in SEQ ID NO:23 or an amino acid sequence comprising amino acids 23-216 in SEQ ID NO:23;
(c) a polypeptide encoded by a nucleic acid molecule encoding a polypeptide comprising an amino acid sequence having amino acids 23-216 in SEQ ID NO:23 or having an amino acid sequence as depicted in SEQ ID NO:23;
(d) a polypeptide comprising an amino acid sequence encoded by a nucleic acid molecule hybridizing under stringent conditions to the complementary strand of a nucleic acid molecule as defined in (a) or (c) and encoding a functional polypeptide, wherein the function comprises the ability to induce differentiation or conversion of white adipocytes and/or preadipocytes to brown adipocytes;
(e) a polypeptide having at least 40% identity to the polypeptide of any one of (a) to (d), whereby said polypeptide is functional, wherein the function comprises the ability to induce differentiation or conversion of white adipocytes and/or preadipocytes to brown adipocytes; and
(f) a polypeptide comprising an amino acid sequence encoded by a nucleic acid molecule being degenerate as a result of the genetic code to the nucleotide sequence of a nucleic acid molecule as defined in (a), (c) and (d).

As mentioned, the function of the above described polypeptide of the invention is ability to induce differentiation or conversion of white adipocytes and/or preadipocytes (in particular white visceral adipocytes and/or white visceral preadipocytes) to brown adipocytes.

The polypeptide of item (e) above may have at least 45%, at least 50%, at least 55%, at least 60%, at least 65%, at least 70%, at least 75%, at least 80%, at least 85%, at least 90%, at least 95% or at least 99% identity to the polypeptide of any one of (a) to (d), whereby said polypeptide is functional, wherein the function comprises the ability to induce differentiation or conversion of white adipocytes and/or preadipocytes (e.g. white visceral adipocytes and/or white visceral preadipocytes) to brown adipocytes.

The herein provided non-therapeutic cosmetic product can be used to reduce body weight. Thus, one aspect of the invention relates to the use of the cosmetic product of the invention for reducing body weight. Accordingly, the invention provides a method for improving the bodily appearance of a mammal (e.g. a human being) which comprises administering to said mammal the paracrine FGF of the invention (e.g. FGF8b, FGF8f and/or FGF17) in a dose and for a period of time to effectively reduce visceral adipose tissue, and repeating said administration until a cosmetically beneficial loss of body weight has occurred.

In one aspect, the invention relates to the herein provided cosmetic product, or the use of said cosmetic product, wherein said polypeptide binds to a FGF receptor. Said FGF receptor may be at least one FGF receptor selected from the group consisting of FGF receptor 4, FGF receptor 1, FGF receptor 2 and FGF receptor 3. It is preferred that the FGF receptor is FGF receptor 4 (FGFR4) or the FGF receptor c spliceform of FGF receptor 1, 2, and 3.

As mentioned, the cosmetic product provided herein effectively reduces visceral adipose tissue which is visible as "belly fat" or "abdominal fat". Thus, the invention also relates to the cosmetic product of the invention, or the use of said cosmetic product, wherein said cosmetic product reduces abdominal adipose tissue.

The herein provided cosmetic product may be in the form for oral administration. Thus, the cosmetic product may be in the form of a liquid solution, a pill, a tablet, a capsule or a powder for oral administration. In one example of the invention, the cosmetic product is in the form of a healthy food, e.g. a diet drink. In another aspect of the invention, the cosmetic product is in the form of a cream, salve or gel. In this embodiment the herein provided cosmetic product can be administered on the skin and penetrate the skin in order to effectively target the adipose tissue. Thus, the cosmetic product(s) provided herein may further comprise a chemical penetration enhancer. Chemical penetration enhancers (i.e. skin penetration enhancers) are commonly known to deliver drugs and cosmetics through the skin (see, e.g., Lane, International Journal of Pharmaceutics 447 (2013) 12-21). In accordance with the invention, said chemical penetration enhancer may be at least one chemical penetration enhancer selected from the group consisting of ethanol, isopropyl alcohol, decanol, hexanol, lauryl alcohol, myristyl alcohol, octanol, octyl dodecanol, oleyl alcohol, azone, ethyl acetate, octyl salicylate, 2-ethylhexyl 4-(dimethylamino)benzoate, ethyl oleate, glyceryl monoleate, glyceryl monocaprate, glyceryl tricaprylate, isopropyl myristate, isopropyl palmitate, propylene glycol monolaurate, propylene glycol mono-caprylate, 2-(2-ethoxyethoxy)ethanol, lauric acid, linoleic acid, linolenic acid, myristic acid, oleic acid, palmitic acid, stearic acid, isostearic acid, dipropylene glycol, propylene glycol, 1,2-butylene glycol, 1,3-butylene glycol, N-methyl-2-pyrrolidone, 2-pyrrolidone, decylmethyl sulphoxide, dimethyl sulfoxide, sodium lauryl sulphate, alkyl dimethylbenzyl ammonium halides, alkyl trimethyl ammonium halides, alkyl pyridinium halides, 2-(dodecyloxy)ethanol, polyoxyethylen(20)-sorbitan-monooleat, eugenol, d-limonene, menthol, menthone, farnesol and neridol.

In certain aspects, the present invention relates to the following items:

1. A cosmetic product comprising a paracrine fibroblast growth factor (FGF).
2. The cosmetic product according to item 1, wherein the paracrine fibroblast growth factor (FGF) is FGF8b.
3. The cosmetic product according to item 1 or 2, wherein the paracrine fibroblast growth factor (FGF) is human FGF8b.
4. The cosmetic product according to any one of items 1 to 3, wherein the paracrine fibroblast growth factor (FGF) is a polypeptide, wherein the polypeptide is selected from the group consisting of:
   (a) a polypeptide comprising an amino acid sequence encoded by a nucleic acid molecule having the nucleic acid sequence as depicted in SEQ ID NO:2 or the nucleic acid sequence comprising nucleic acid residues 67-648 in SEQ ID NO:2;
   (b) a polypeptide comprising an amino acid sequence as depicted in SEQ ID NO:16 or an amino acid sequence comprising amino acids 23-215 in SEQ ID NO:16;
   (c) a polypeptide encoded by a nucleic acid molecule encoding a polypeptide comprising an amino acid sequence having amino acids 23-215 in SEQ ID NO:16 or having an amino acid sequence as depicted in SEQ ID NO:16;
   (d) a polypeptide comprising an amino acid sequence encoded by a nucleic acid molecule hybridizing under stringent conditions to the complementary strand of a nucleic acid molecule as defined in (a) or (c);
   (e) a polypeptide having at least 40% identity to the polypeptide of any one of (a) to (d);
   (f) a protein as defined in any one of (a) to (e) wherein one or more amino acids are deleted, inserted, added or substituted; and
   (g) a polypeptide comprising an amino acid sequence encoded by a nucleic acid molecule being degenerate as a result of the genetic code to the nucleotide sequence of a nucleic acid molecule as defined in (a), (c) and (d).
5. The cosmetic product according to item 1, wherein the paracrine fibroblast growth factor (FGF) is FGF8f.
6. The cosmetic product according to item 1 or 5, wherein the paracrine fibroblast growth factor (FGF) is human FGF8f.
7. The cosmetic product according to any one of items 1, 5 and 6, wherein the paracrine fibroblast growth factor (FGF) is a polypeptide, wherein the polypeptide is selected from the group consisting of:
   (a) a polypeptide comprising an amino acid sequence encoded by a nucleic acid molecule having the nucleic acid sequence as depicted in SEQ ID NO:4 or the nucleic acid sequence comprising nucleic acid residues 67-735 in SEQ ID NO:4;
   (b) a polypeptide comprising an amino acid sequence as depicted in SEQ ID NO:18 or an amino acid sequence comprising amino acids 23-244 in SEQ ID NO:18;
   (c) a polypeptide encoded by a nucleic acid molecule encoding a polypeptide comprising an amino acid sequence having amino acids 23-244 in SEQ ID NO:18 or having an amino acid sequence as depicted in SEQ ID NO:18;
   (d) a polypeptide comprising an amino acid sequence encoded by a nucleic acid molecule hybridizing under stringent conditions to the complementary strand of a nucleic acid molecule as defined in (a) or (c);
   (e) a polypeptide having at least 40% identity to the polypeptide of any one of (a) to (d);
   (f) a protein as defined in any one of (a) to (e) wherein one or more amino acids are deleted, inserted, added or substituted; and
   (g) a polypeptide comprising an amino acid sequence encoded by a nucleic acid molecule being degenerate as a result of the genetic code to the nucleotide sequence of a nucleic acid molecule as defined in (a), (c) and (d).
8. The cosmetic product according to item 1, wherein the paracrine fibroblast growth factor (FGF) is FGF17.
9. The cosmetic product according to item 1 or 8, wherein the paracrine fibroblast growth factor (FGF) is human FGF17.
10. The cosmetic product according to any one of items 1, 8 and 9, wherein the paracrine fibroblast growth factor (FGF) is a polypeptide, wherein the polypeptide is selected from the group consisting of:
    (a) a polypeptide comprising an amino acid sequence encoded by a nucleic acid molecule having the nucleic acid sequence as depicted in SEQ ID NO:9 or the nucleic acid sequence comprising nucleic acid residues 67-651 in SEQ ID NO:9;
    (b) a polypeptide comprising an amino acid sequence as depicted in SEQ ID NO:23 or an amino acid sequence comprising amino acids 23-216 in SEQ ID NO:23;
    (c) a polypeptide encoded by a nucleic acid molecule encoding a polypeptide comprising an amino acid sequence having amino acids 23-216 in SEQ ID NO:23 or having an amino acid sequence as depicted in SEQ ID NO:23;
    (d) a polypeptide comprising an amino acid sequence encoded by a nucleic acid molecule hybridizing under stringent conditions to the complementary strand of a nucleic acid molecule as defined in (a) or (c);
(e) a polypeptide having at least 40% identity to the polypeptide of any one of (a) to (d);
(f) a protein as defined in any one of (a) to (e) wherein one or more amino acids are deleted, inserted, added or substituted; and
(g) a polypeptide comprising an amino acid sequence encoded by a nucleic acid molecule being degenerate as a result of the genetic code to the nucleotide sequence of a nucleic acid molecule as defined in (a), (c) and (d).

11. The cosmetic product according to any one of items 4, 7 and 10, wherein the polypeptide is a polypeptide having at least 45%, at least 50%, at least 55%, at least 60%, at least 65%, at least 70%, at least 75%, at least 80%, at least 85%, at least 90%, at least 95% or at least 99% identity to the polypeptide of any one of (a) to (d).

12. The cosmetic product according to any one of items 4, 7 and 10, wherein the polypeptide is a polypeptide having at least 90% identity to the polypeptide of any one of (a) to (d).

13. The cosmetic product according to any one of items 4, 7 and 10, wherein the polypeptide is a polypeptide having at least 95% identity to the polypeptide of any one of (a) to (d).

14. The cosmetic product according to any one of items 4, 7 and 10, wherein the polypeptide is a polypeptide having at least 99% identity to the polypeptide of any one of (a) to (d).

15. The cosmetic product according to any one of items 1 to 14, wherein the paracrine fibroblast growth factor (FGF) is a polypeptide that is able to induce differentiation or conversion of white adipocytes and/or white preadipocytes to brown adipocytes.

16. The cosmetic product according to any one of items 1 to 14, wherein the paracrine fibroblast growth factor (FGF) is a polypeptide that is able to induce differentiation or conversion of white visceral adipocytes and/or white visceral preadipocytes to brown adipocytes.

17. The cosmetic product according to any one of items 1 to 7 and 11 to 16, wherein the paracrine fibroblast growth factor (FGF) is a polypeptide comprising or consisting of the amino acid sequence VTVQSSPNFTQ (SEQ ID NO.103) or a fragment thereof.

18. The cosmetic product according to any one of items 1 to 4 and 11 to 16, wherein the paracrine fibroblast growth factor (FGF) is a polypeptide comprising the amino acid sequence VTVQSSPNFTQ (SEQ ID NO:103) from position 24 to position 34 of the amino acid sequence of the polypeptide.

19. The cosmetic product according to item 18, wherein the amino acid sequence of the polypeptide is shown in SEQ ID NO:16 (FGF8b).

20. The cosmetic product according to any one of items 1, 5 to 7 and 11 to 16, wherein the paracrine fibroblast growth factor (FGF) is a polypeptide comprising the amino acid sequence VTVQSSPNFTQ (SEQ ID NO:103) from position 53 to position 63 of the amino acid sequence of the polypeptide.

21. The cosmetic product according to item 20, wherein the amino acid sequence of the polypeptide is shown in SEQ ID NO:18 (FGF8f).

22. The cosmetic product according to any one of items 1 to 7 and 11 to 16, wherein the paracrine fibroblast growth factor (FGF) is a polypeptide comprising or consisting of the amino acid sequence QVTVQSSPNFTQ (SEQ ID NO:105) or a fragment thereof.

23. The cosmetic product according to any one of items 1 to 4 and 11 to 16, wherein the paracrine fibroblast growth factor (FGF) is a polypeptide comprising the amino acid sequence QVTVQSSPNFTQ (SEQ ID NO:105) from position 23 to position 34 of the amino acid sequence of the polypeptide.

24. The cosmetic product according to item 23, wherein the amino acid sequence of the polypeptide is shown in SEQ ID NO:16 (FGF8b).

25. The cosmetic product according to any one of items 1, 5 to 7 and 11 to 16, wherein the paracrine fibroblast growth factor (FGF) is a polypeptide comprising the amino acid sequence QVTVQSSPNFTQ (SEQ ID NO:105) from position 52 to position 63 of the amino acid sequence of the polypeptide.

26. The cosmetic product homeostasis according to item 25, wherein the amino acid sequence of the polypeptide is shown in SEQ ID NO:18 (FGF8f).

27. The cosmetic product according to any one of items 1 to 7 and 11 to 16, wherein the paracrine fibroblast growth factor (FGF) is a polypeptide comprising or consisting of the amino acid sequence QVTVQSSPNFT (SEQ ID NO:106) or a fragment thereof.

28. The cosmetic product according to any one of items 1 to 4 and 11 to 16, wherein the paracrine fibroblast growth factor (FGF) is a polypeptide comprising the amino acid sequence QVTVQSSPNFT (SEQ ID NO:106) from position 23 to position 33 of the amino acid sequence of the polypeptide.

29. The cosmetic product according to item 28, wherein the amino acid sequence of the polypeptide is shown in SEQ ID NO:16 (FGF8b).

30. The cosmetic product according to any one of items 1, 5 to 7 and 11 to 16, wherein the paracrine fibroblast growth factor (FGF) is a polypeptide comprising the amino acid sequence QVTVQSSPNFT (SEQ ID NO:106) from position 52 to position 62 of the amino acid sequence of the polypeptide.

31. The cosmetic product according to item 30, wherein the amino acid sequence of the polypeptide is shown in SEQ ID NO:18 (FGF8f).

32. The cosmetic product according to any one of items 1 to 16, wherein the paracrine fibroblast growth factor (FGF) is a polypeptide comprising or consisting of the amino acid sequence SPNFXQ (SEQ ID NO:108) or a fragment thereof.

33. The cosmetic product according to any one of items 1 to 4 and 11 to 16, wherein the paracrine fibroblast growth factor (FGF) is a polypeptide comprising the amino acid sequence SPNFXQ (SEQ ID NO:108) from position 29 to position 34 of the amino acid sequence of the polypeptide.

34. The cosmetic product according to item 33, wherein the amino acid sequence of the polypeptide is shown in SEQ ID NO:16 (FGF8b).

35. The cosmetic product according to any one of items 1, 5 to 7 and 11 to 16, wherein the paracrine fibroblast growth factor (FGF) is a polypeptide comprising the amino acid sequence SPNFXQ (SEQ ID NO:108) from position 58 to position 63 of the amino acid sequence of the polypeptide.

36. The cosmetic product according to item 35, wherein the amino acid sequence of the polypeptide is shown in SEQ ID NO:18 (FGF8f).

37. The cosmetic product according to any one of items 1 and 8 to 16, wherein the paracrine fibroblast growth factor (FGF) is a polypeptide comprising the amino acid sequence SPNFXQ (SEQ ID NO:108) from position 30 to position 35 of the amino acid sequence of the polypeptide.
38. The cosmetic product according to item 37, wherein the amino acid sequence of the polypeptide is shown in SEQ ID NO:23 (FGF17).
39. The cosmetic product according to any one of items 32 to 38, wherein residue X in the amino acid sequence SPNFXQ (SEQ ID NO:108) is T or N.
40. The cosmetic product according to any one of items 1 to 16, wherein the paracrine fibroblast growth factor (FGF) is a polypeptide comprising or consisting of the amino acid sequence SPNF (SEQ ID NO:107) or a fragment thereof.
41. The cosmetic product according to any one of items 1 to 4 and 11 to 16, wherein the paracrine fibroblast growth factor (FGF) is a polypeptide comprising the amino acid sequence SPNF (SEQ ID NO:107) from position 29 to position 32 of the amino acid sequence of the polypeptide.
42. The cosmetic product according to item 41, wherein the amino acid sequence of the polypeptide is shown in SEQ ID NO:16 (FGF8b).
43. The cosmetic product according to any one of items 1, 5 to 7 and 11 to 16, wherein the paracrine fibroblast growth factor (FGF) is a polypeptide comprising the amino acid sequence SPNF (SEQ ID NO:107) from position 58 to position 61 of the amino acid sequence of the polypeptide.
44. The cosmetic product according to item 43, wherein the amino acid sequence of the polypeptide is shown in SEQ ID NO:18 (FGF8f).
45. The cosmetic product according to any one of items 1 and 8 to 16, wherein the paracrine fibroblast growth factor (FGF) is a polypeptide comprising the amino acid sequence SPNF (SEQ ID NO:107) from position 30 to position 33 of the amino acid sequence of the polypeptide.
46. The cosmetic product according to item 45, wherein the amino acid sequence of the polypeptide is shown in SEQ ID NO:23 (FGF17).
47. Use of the cosmetic product of any one of items 1 to 46 for reducing body weight preferably in a healthy patient, more preferably in a healthy human patient.
48. The cosmetic product of any one of items 1 to 46, or the use of item 47, wherein said paracrine fibroblast growth factor (FGF) binds to a FGF receptor or is capable of binding to an FGF receptor.
49. The cosmetic product of item 48, or the use of item 48, wherein said FGF receptor is at least one FGF receptor selected from the group consisting of FGF receptor 4, FGF receptor 1c, FGF receptor 2c and FGF receptor 3c.
50. The cosmetic product of any one of items 1 to 46, 48 and 49, or the use of any one of items 47 to 49, wherein said cosmetic product reduces abdominal adipose tissue.
51. The cosmetic product of any one of items 1 to 46, and 48 to 50, or the use of any one of items 47 to 50, wherein said cosmetic product is in the form of a cream, salve or gel.
52. The cosmetic product of any one of items 1 to 46, and 48 to 551, or the use of any one of items 47 to 51, wherein said cosmetic product further comprises a chemical penetration enhancer.
52. The cosmetic product of item 52, or the use of item 52, wherein said chemical penetration enhancer is at least one chemical penetration enhancer selected from the group consisting of ethanol, isopropyl alcohol, decanol, hexanol, lauryl alcohol, myristyl alcohol, octanol, octyl dodecanol, oleyl alcohol, azone, ethyl acetate, octyl salicylate, 2-ethylhexyl 4-(dimethylamino)benzoate, ethyl oleate, glyceryl monoleate, glyceryl monocaprate, glyceryl tricaprylate, isopropyl myristate, isopropyl palmitate, propylene glycol monolaurate, propylene glycol monocaprylate, 2-(2-ethoxyethoxy)ethanol, lauric acid, linoleic acid, linolenic acid, myristic acid, oleic acid, palmitic acid, stearic acid, isostearic acid, dipropylene glycol, propylene glycol, 1,2-butylene glycol, 1,3-butylene glycol, N-methyl-2-pyrrolidone, 2-pyrrolidone, decylmethyl sulphoxide, dimethyl sulfoxide, sodium lauryl sulphate, alkyl dimethylbenzyl ammonium halides, alkyl trimethyl ammonium halides, alkyl pyridinium halides, 2-(dodecyloxy)ethanol, polyoxyethylen(20)-sorbitan-monooleat, eugenol, d-limonene, menthol, menthone, farnesol and neridol.

In context of the present invention, "homologous" or "percent homology" means that amino acid or nucleotide sequences have identities of at least 40%, at least 45%, at least 50%, at least 55%, at least 60%, at least 65%, at least 70%, at least 75%, at least 80%, at least 85%, at least 90%, at least 95% or at least 99% to the sequences shown herein, e.g. those of human FGF8b, FGF8f or FGF17, wherein the higher identity values are preferred upon the lower ones.

In accordance with the present invention, the term "identity/identities" or "percent identity/identities" in the context of two or more nucleic acid or amino acid sequences, refers to two or more sequences or subsequences that are the same, or that have a specified percentage of amino acid residues or nucleotides that are the same (e.g., 40% or 45% identity, preferably, 70-95% identity, more preferably at least 99% identity with the nucleic acid sequences of, e.g., SEQ ID NO:2, 4 or 9, or with the amino acid sequences of, e.g., SEQ ID NO:16, 18 or 23, and being functional, wherein the function comprises ability to induce differentiation or conversion of white (e.g. visceral) adipocytes and/or preadipocytes to brown adipocytes), when compared and aligned for maximum correspondence over a window of comparison, or over a designated region as measured using a sequence comparison algorithm as known in the art, or by manual alignment and visual inspection.

Those having skill in the art will know how to determine percent identity between/among sequences using, for example, algorithms such as those based on CLUSTALW computer program (Thompson; 1994; Nucl Acids Res; 2; 4673-4680) or FASTDB (Brutlag; 1990; Comp App Biosci; 6; 237-245), as known in the art.

Also available to those having skill in this art are the BLAST and BLAST 2.0 algorithms (Altschul; 1997; Nucl Acids Res 25; 3389-3402, Altschul; 1993; J Mol Evol; 36; 290-300, Altschul; 1990; J Mol Biol 215; 403-410). The BLASTN program for nucleic acid sequences uses as defaults a word length (W) of 11, an expectation (E) of 10, M=5, N=4, and a comparison of both strands. For amino acid sequences, the BLASTP program uses as defaults a word length (W) of 3, and an expectation (E) of 10. The BLOSUM62 scoring matrix (Henikoff; 1989; PNAS; 89; 10915) uses alignments (B) of 50, expectation (E) of 10, M=5, N=4, and a comparison of both strands.

In addition, the present invention relates to a polypeptide comprising an amino acid sequence encoded by a nucleic acid molecule being degenerate as a result of the genetic code. When used in accordance with the present invention, the term "being degenerate as a result of the genetic code" means that due to the redundancy of the genetic code different nucleotide sequences code for the same amino acid.

In order to determine whether an amino acid residue or nucleotide residue in an amino acid or nucleic acid sequence corresponds to a certain position in the amino acid sequence of, e.g., SEQ ID NO:16, 18 or 23, or nucleotide sequence of e.g. SEQ ID NO:2, 4 or 9, the skilled person can use means and methods well-known in the art, e.g., alignments, either manually or by using computer programs.

In accordance with the present invention, the terms "homology" or "percent homology" or "identical" or "percent identity" or "percentage identity" or "sequence identity" in the context of two or more nucleic acid sequences refers to two or more sequences or subsequences that are the same, or that have a specified percentage of nucleotides that are the same (at least 40%, 50%, 60%, 70%, 75%, 80%, 85%, most preferably at least 90%, 91%, 92%, 93%, 94%, 95%, 96%, 97% or 98% identity, most preferably at least 99% identity), when compared and aligned for maximum correspondence over a window of comparison (preferably over the full length), or over a designated region as measured using a sequence comparison algorithm as known in the art, or by manual alignment and visual inspection. Sequences having, for example, 75% to 90% or greater sequence identity may be considered to be substantially identical. Such a definition also applies to the complement of a test sequence. Preferably the described identity exists over a region that is at least about 15 to 25 nucleotides in length, more preferably, over a region that is at least about 50 to 100 nucleotides in length and most preferably over the full length. Those having skill in the art will know how to determine percent identity between/among sequences using, for example, algorithms such as those based on CLUSTALW computer program (Thompson Nucl. Acids Res. 2 (1994), 4673-4680) or FASTDB (Brutlag Comp. App. Biosci. 6 (1990), 237-245), as known in the art.

Although the FASTDB algorithm typically does not consider internal non-matching deletions or additions in sequences, i.e., gaps, in its calculation, this can be corrected manually to avoid an overestimation of the % identity. CLUSTALW, however, does take sequence gaps into account in its identity calculations. Also available to those having skill in this art are the BLAST and BLAST 2.0 algorithms (Altschul, (1997) Nucl. Acids Res. 25:3389-3402; Altschul (1993) J. Mol. Evol. 36:290-300; Altschul (1990) J. Mol. Biol. 215:403-410). The BLASTN program for nucleic acid sequences uses as defaults a word length (W) of 11, an expectation (E) of 10, M=5, N=4, and a comparison of both strands. The BLOSUM62 scoring matrix (Henikoff (1989) PNAS 89:10915) uses alignments (B) of 50, expectation (E) of 10, M=5, N=4, and a comparison of both strands.

For example, BLAST 2.0, which stands for Basic Local Alignment Search Tool BLAST (Altschul; 1997; loc. cit., Altschul; 1993; loc. cit.; Altschul; 1990; loc. cit.), can be used to search for local sequence alignments. BLAST, as discussed above, produces alignments of both nucleotide and amino acid sequences to determine sequence similarity. Because of the local nature of the alignments, BLAST is especially useful in determining exact matches or in identifying similar sequences. The fundamental unit of BLAST algorithm output is the High-scoring Segment Pair (HSP). An HSP consists of two sequence fragments of arbitrary but equal lengths whose alignment is locally maximal and for which the alignment score meets or exceeds a threshold or cut-off score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

Analogous computer techniques using BLAST (Altschul; 1997; loc. cit., Altschul; 1993; loc. cit., Altschul; 1990; loc. cit.) are used to search for identical or related molecules in nucleotide databases such as GenBank or EMBL. This analysis is much faster than multiple membrane-based hybridizations. In addition, the sensitivity of the computer search can be modified to determine whether any particular match is categorized as exact or similar. The basis of the search is the product score which is defined as:

$$\frac{\% \text{ sequence identity} \times \% \text{ maximum BLAST score}}{100}$$

and it takes into account both the degree of similarity between two sequences and the length of the sequence match. For example, with a product score of 40, the match will be exact within a 1-2% error; and at 70, the match will be exact. Similar molecules are usually identified by selecting those which show product scores between 15 and 40, although lower scores may identify related molecules. Another example for a program capable of generating sequence alignments is the CLUSTALW computer program (Thompson; 1994; Nucl Acids Res; 2; 4673-4680) or FASTDB (Brutlag; 1990; Comp App Biosci 6; 237-245), as known in the art.

The terms "hybridization", "hybridizes" or "hybridizing" as used herein relate to complementary (antisense) molecules, which specifically interact with/hybridizes to one or more nucleic acid molecules encoding the herein defined paracrine FGFs (e.g. FGF8b, FGF8f and/or FGF17). Highly mutated complementary constructs, which are not capable of hybridizing to a nucleic acid molecule encoding the paracrine FGF of the invention are not to be employed in the context of the present invention. The person skilled in the art can easily deduce whether a complementary construct specifically hybridizes to sequences encoding the paracrine FGF of the present invention (e.g. FGF8b, FGF8f and/or FGF17). These tests comprise, but are not limited to hybridization assays, RNAse protection assays, Northern Blots, North-western blots, nuclear magnetic resonance and fluorescence binding assays, dot blots, micro- and macroarrays and quantitative PCR. In addition, such a screening may not be restricted to mRNA molecules, but may also include mRNA/protein (RNP) complexes (Hermann; 2000; Angew Chem Int Ed Engl; 39; 1890-1904, DeJong; 2002; Curr Trop Med Chem, 2; 289-302). Furthermore, functional tests including Western blots, immunohistochemistry, immunoprecipitation assays, and bioassays based on responsive promoters are envisaged for testing whether a particular complementary construct is capable of specifically interacting with/hybridizing to the nucleic acid molecule encoding the paracrine FGF of the present invention.

In addition, the terms "hybridization", "hybridizes" or "hybridizing" as used herein further relate to hybridizations under stringent or non-stringent conditions. Said hybridization conditions may be established according to conventional protocols, described, e.g., in Sambrook, Russell "Molecular Cloning, A Laboratory Manual", Cold Spring Harbor Laboratory, N.Y. (2001), Ausubel, "Current Protocols in Molecular Biology", Green Publishing Associates and Wiley Interscience, N.Y. (1989), or Higgins and Hames (Eds.) "Nucleic acid hybridization, a practical approach" IRL Press Oxford, Washington D.C., (1985). The setting of conditions is well within the skill of the artisan and can be determined according to protocols described in the art. Thus, the detection of only specifically hybridizing sequences will usually require stringent hybridization and washing conditions such as 0.1×SSC, 0.1% SDS at 65° C. Non-stringent hybridization conditions for the detection of homologous or not exactly complementary sequences may be set at 6×SSC, 1% SDS at 65° C. As is well known, the length of the probe and the composition of the nucleic acid to be determined constitute further parameters of the hybridization conditions. Note that variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

Hybridizing nucleic acid molecules also comprise fragments of the above described molecules. Such fragments may comprise complementary nucleic acid sequences of the nucleic acid molecules which code for the paracrine FGF(s) of the present invention (e.g. FGF8b) or functional fragments thereof. Furthermore, also the complementary nucleic acid molecule, the complementary fragments and (allelic) variants of the nucleic acid molecules which hybridize with any of the aforementioned nucleic acid molecules are included in the present invention.

Additionally, a hybridization complex refers to a complex between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an anti-parallel configuration. A hybridization complex may be formed in solution (e.g., Cot or Rot analysis) or between one nucleic acid sequence present in solution and another nucleic acid sequence immobilized on a solid support (e.g., membranes, filters, chips, pins or glass slides to which, e.g., cells have been fixed). In context of the present invention, the terms "complementary" or "complementarity" refers to the natural binding of polynucleotides under permissive salt and temperature conditions by base-pairing. A complementary polynucleotide of a specified nucleotide sequence is an antisense polynucleotide of said specified nucleotide sequence. For example, the sequence "A-G-T" binds to the complementary sequence "T-C-A". Complementarity between two single-stranded molecules may be "partial", in which only some of the nucleic acids bind, or it may be complete when total complementarity exists between single-stranded molecules. The degree of complementarity between nucleic acid strands has significant effects on the efficiency and strength of hybridization between nucleic acid strands. This is of particular importance in amplification reactions, which depend upon binding between nucleic acids strands.

The term "hybridizing (sequences)" preferably refers to the sequences which display a sequence identity of at least 60%, preferably at least 70%, more preferably at least 80%, even more preferably at least 90%, particularly preferred at least 95%, more particularly preferred at least 96%, even more particularly preferred at least 97% and most preferably at least 98% or up to 100% identity with a complementary nucleic acid sequence of the nucleic acid sequence encoding the paracrine FGF of the invention (e.g. FGF8b, FGF8f and/or FGF17) or a functional fragment thereof and being a functional polypeptide, wherein the function comprises the ability to induce differentiation or conversion of white adipocytes and/or preadipocytes (e.g. white visceral adipocytes and/or white visceral preadipocytes) to brown adipocytes as described herein. Moreover, the term "hybridizing (sequences)" preferably refers to complementary nucleic acid sequences of the nucleic acid sequences encoding amino acid molecules having a sequence identity of at least 60%, preferably at least 70%, more preferably at least 80%, even more preferably at least 90%, particularly preferred at least 95%, more particularly preferred at least 96%, even more particularly preferred at least 97% and most preferably at least 98% or up to 100% identity with an amino acid sequence of the paracrine FGF of the invention (e.g. SEQ ID NO:16, 18 or 23) or a functional fragment thereof and being a functional polypeptide, wherein the function comprises the ability to induce differentiation or conversion of white adipocytes and/or preadipocytes (e.g. white visceral adipocytes and/or white visceral preadipocytes) to brown adipocytes.

The explanations and definitions given herein above in respect of "homology/identity of nucleic acid sequences" apply, mutatis mutandis, to "amino acid sequences" of the herein provided amino acid sequence of the paracrine FGF of the invention (e.g. SEQ ID NO:16, 18 or 23).

The polypeptide to be used in accordance with the present invention may have at least 40, 50, 60 or 70% identity/similarity to the proteins having the amino acid sequence as, for example, depicted in SEQ ID NO:16, 18 or 23, respectively. More preferably, the polypeptide has at least 90%, 91%, 92%, 93%, 94%, 95%, 96%, 97% or 98% identity/similarity to the proteins depicted in SEQ ID NO:16, 18 or 23, respectively, wherein the higher values are preferred. Most preferably, the polypeptide has at least 99% homology to the protein as depicted in SEQ ID NO:16, 18 or 23.

As used herein, the terms "comprising" and "including" or grammatical variants thereof are to be taken as specifying the stated features, integers, steps or components but do not preclude the addition of one or more additional features, integers, steps, components or groups thereof. This term encompasses the terms "consisting of" and "consisting essentially of." Thus, the terms "comprising"/"including"/ "having" mean that any further component (or likewise features, integers, steps and the like) can/may be present.

The term "consisting of" means that no further component (or likewise features, integers, steps and the like) is present.

The term "consisting essentially of" or grammatical variants thereof when used herein are to be taken as specifying the stated features, integers, steps or components but do not preclude the addition of one or more additional features, integers, steps, components or groups thereof but only if the additional features, integers, steps, components or groups thereof do not materially alter the basic and novel characteristics of the claimed composition, device or method.

Thus, the term "consisting essentially of" means that specific further components (or likewise features, integers, steps and the like) can be present, namely those not materially affecting the essential characteristics of the composition, device or method. In other words, the term "consisting essentially of" (which can be interchangeably used herein with the term "comprising substantially"), allows the presence of other components in the composition, device or method in addition to the mandatory components (or likewise features, integers, steps and the like), provided that the essential characteristics of the device or method are not materially affected by the presence of other components.

It is preferred herein that the polypeptides to be used in accordance with the present invention consist essentially of, more preferably consist of, the amino acid sequences as defined herein.

The present invention is further described by reference to the following non-limiting figures and example.

The Figures show:

FIGS. 1A-C.

Screening paracrine FGFs for a browning potential. A, B—Screening of all paracrine FGFs in immortalized white adipocytes. Subcutaneous, inguinal and visceral, epididymal white adipocytes were grown to confluence in Dulbecco's modified Eagle's medium with 4.5 g/l glucose, supplemented with 20 nmol/l insulin, 1 nmol/l triiodothyronine, 20% fetal bovine serum, and penicillin/streptomycin. Upon reaching confluence, differentiation was induced with 500 mmol/l isobutylmethylxanthine, 250 mmol/l indomethacine, and 2 mg/ml dexamethasone for 24 hours. Subsequently, members of the paracrine FGF protein family were added to the medium for the following six days. The medium and the FGF indicated were changed every 48 hours. Untreated cells served as a negative control. At the end of the differentiation process total RNA was isolated using TRIzol reagents, RNA quality and concentration was measured by photometric analysis, and 5 µg of total RNA was reverse-transcribed to cDNA. Finally, quantitative analysis of UCP-1 mRNA expression was performed. A bar graph analysis including the SEM of 3 to 6 independent experiments is shown. A: FGF8b and FGF17 lead to increased expression of Ucp1 mRNA expression in epididymal adipocytes as measured by quantitative PCR. B—Four different splicing forms of the Fgf8 gene were compared by quantifying Ucp1 mRNA expression in fully differentiated white adipocytes. UCP-1 mRNA abundance is shown in percent of the FGF8b value. Fgf8b and Fgf8f were able to increase expression in epididymal adipocytes. C—Illustration depicting the different exon usage that characterizes the FGF8 spliceforms a, b, e, and f.

FIGS. 2A-B.

Dose dependency of Ffg8b action. A, B—Subcutaneous, inguinal and visceral, epididymal white adipocytes were grown to confluence in Dulbecco's modified Eagle's medium with 4.5 g/l glucose, supplemented with 20 nmol/l insulin, 1 nmol/l triiodothyronine, 20% fetal bovine serum, and penicillin/streptomycin. Upon reaching confluence, differentiation was induced with 500 mmol/l isobutylmethylxanthine, 250 mmol/l indomethacine, and 2 mg/ml dexamethasone for 24 hours. Subsequently, FGF8b in five indicated concentrations were added to the medium for the following six days. The medium and the FGF8b were changed every 48 hours. Untreated cells served as a negative control. At the end of the differentiation process total RNA was isolated using TRIzol reagents, RNA quality and concentration was measured by photometric analysis, and 5 µg of total RNA was reverse-transcribed to cDNA. Finally, quantitative analysis of UCP-1 mRNA expression was performed. FGF8b induces Ucp1 mRNA abundance in inguinal and epididymal adipocytes. Epididymal fat cells were more dose dependently responsive to Fgf8b treatment as compared to inguinal cells. The latter were responsive to FGF8b treatment above the threshold indicated. B—The absolute increase of several genes typical for brown fat cells. Both Ucp1 and Cidea mRNA were strongly increased by Fgf8b, while Cox7a1 and elovl3 were not significantly altered. In fully differentiated cells, Pgc1a mRNA was found to be lower expresse than in untreated cells.

FIGS. 3A-B.

Treatment timecourse experiment. A, B—Subcutaneous, inguinal and visceral, epididymal white adipocytes were grown to confluence (prolif. denotes proliferation period) in Dulbecco's modified Eagle's medium with 4.5 g/l glucose, supplemented with 20 nmol/l insulin, 1 nmol/l triiodothyronine, 20% fetal bovine serum, and penicillin/streptomycin. Upon reaching confluence, differentiation was induced with 500 mmol/l isobutylmethylxanthine, 250 mmol/l indomethacine, and 2 mg/ml dexamethasone for 24 hours (induction). Subsequently, the cells were cultured for another six days (differentiation). At the end of the differentiation process total RNA was isolated using TRIzol reagents, RNA quality and concentration was measured by photometric analysis, and 5 µg of total RNA was reverse-transcribed to cDNA. Finally, quantitative analysis of UCP-1 mRNA expression was performed. Untreated cells served as a negative control. A bar graph analysis including the SEM of 5 independent experiments is shown. A—Epididymal fat cells were treated with FGF8b during different time windows as given by black squares indicating one day of treatment each. Treatment during the entire differentiation period led to strongest Ucp1 induction. This effect could be mimicked by only treating the cells during the second day or last day of differentiation indicting sensitive time windows. Treatment during the induction period inhibited Ucp1 induction. B—Inguinal fat cells were treated with FGF8b during different time windows as given by black squares indicating one day of treatment each. Treatment during the last day of differentiation led to the highest increase in Ucp1 mRNA abundance. n.d. denotes not detectable.

FIGS. 4A-H.

Timecourse of brown adipose tissue (BAT) marker gene expression following a short period of Fgf8b treatment. Visceral, epididymal white adipocytes were grown to confluence in Dulbecco's modified Eagle's medium with 4.5 g/l glucose, supplemented with 20 nmol/l insulin, 1 nmol/l triiodothyronine, 20% fetal bovine serum, and penicillin/ streptomycin within 96 hours. During this proliferation period cells were treated with FGF8b for 48 hours during the second half of proliferation. Upon reaching confluence, differentiation was induced with 500 mmol/l isobutylmethylxanthine, 250 mmol/l indomethacine, and 2 mg/ml dexamethasone for 24 hours (induction). Subsequently, the cells were cultured for another six days (differentiation). A subset of culture plates were harvested (1, acute) right after FGF8b treatment, (2, d1 p.i. denotes day one post induction) right after the induction period, (3, d2 p.i. denotes day two post induction) after two days of differentiation, (4, d4 p.i. denotes day four post induction) after four days of differentiation, and (5, d6 p.i. denotes day six post induction) after six days, id est the end of the differentiation period. At these indicated times total RNA was isolated using TRIzol reagents, RNA quality and concentration was measured by photometric analysis, and 5 µg of total RNA was reverse-transcribed to cDNA. Finally, quantitative analysis of UCP-1 mRNA expression was performed. Untreated cells served to normalize the data to the natural course of BAT marker values during differentiation. A graph analysis including the SEM of 5 independent experiments is shown. Ucp1 mRNA abundance increased 6 days after induction for the first time. A similar pattern was observed for the brown fat marker genes Cidea and Cox7a1 increasing at day 4 or 6 after induction. Pgc1a was acutely downregulated by Fgf8b treatment and increased expression above control levels at day 6 after induction. Known or suspected regulators of brown adipocyte differentiation Prdm16, Foxc2 and Prb displayed characteristic patterns of transient increases during the differentiation process.

FIGS. 5A-F.

Expression of Fgf receptors Fgfr1, Fgfr2, Fgfr3 and Fgfr4 and cofactors alpha and beta klotho in differentiating epididymal and inguinal adipocytes. Subcutaneous, inguinal and visceral, epididymal white adipocytes were grown to confluence in Dulbecco's modified Eagle's medium with 4.5 g/l glucose, supplemented with 20 nmol/l insulin, 1 nmol/l triiodothyronine, 20% fetal bovine serum, and penicillin/streptomycin within 96 hours. Upon reaching confluence, differentiation was induced with 500 mmol/l isobutylmethylxanthine, 250 mmol/l indomethacine, and 2 mg/ml dexamethasone for 24 hours (induction). Subsequently, the cells were cultured for another six days (differentiation). A subset of culture plates were harvested every 24 hours starting after 48 hours in the proliferation phase. Total RNA was isolated using TRIzol reagents, RNA quality and concentration was measured by photometric analysis, and 5 μg of total RNA was reverse-transcribed to cDNA. Finally, quantitative analysis of Fgfr1-4 expression was performed. Analysis of 5 independent experiments is shown. Fgfr1-3 are constantly present during all stages of differentiation in both cell lines. Fgfr4 is only little expressed in proliferating cells and induced during the induction phase at day 2 and peaks soon after the change to differentiation medium at day 3. Alpha Klotho is expressed in negligible amounts at all times while beta Klotho continuously increased with ongoing differentiation.

FIGS. 6A-C.

Implantation of Ffg8b releasing pellets into the visceral, epididymal white adipose tissue depot leads to recruitment of brown adipocytes. A—Representative photographs centered on the implantation site of three control pellets (upper panels) and three Fgf8b pellets (lower panels). The epididymal fat depot is discernible in light gray shades surrounded by darker non-adipose tissues. The area of visible browning is marked by a dotted line. B—To highlight "visual browning" in this gray-scale images we digitally removed all pixels with a colour saturation of more than 162 (on a scale of 0-255). Here, white areas correspond to brown colour on a background of whitish adipose tissue. C—The mRNA abundance of several brown adipocyte marker genes in the entire depot. Ucp1 and Cox7a1 mRNA are increased by Fgf8b treatment but not by the placebo pellet.

FIGS. 7A-F.

Physiological data of animals implanted with drug release pellets. A—The absolute body mass of mice was not altered by Fgf8b. B—Both placebo and Fgf8b implanted mice lost a comparable small amount of body mass during the three weeks of the experimental procedure. C—The masses of the implanted epididymal fat depot and the contralateral non-implanted depot were not different. Interscapular brown adipose tissue was not different in placebo and Fgf8b treated animals. D—The implanted adipose tissue depot did not differ in body mass specific mass between Fgf8b and placebo treated mice. E—Plasma metabolites of carbohydrate and lipid metabolisms were not affected by Fgf8b treatment (GLU—glucose, CHOL—total cholesterol, nHDLc—non-HDL cholesterol, HDL—high density lipoproteins, LDL—low density lipoproteins, VLDL—very low density lipoproteins, TRIG—triglycerides). F—Liver enzymes in the plasma were not altered by Fgf8b treatment.

FIGS. 8A-D.

Fgfr4 expression correlates with Fgf8b sensitivity. A—Fgfr4 and alpha klotho are present in the epididymal adipose tissue depot but not in the inguinal depot. B—All analyzes receptors/cofactors were present in epididymal adipose tissue, while the amounts of Fgfr4 in inguinal fat is neglecable. C—Comparison of Fgf8b sensitivity and Fgfr4 expression in cultured adipocytes. Filled squares denote the Fgfr4 mRNA abundance at different days of differentiation. Empty squares give the Ucp1 mRNA abundance of fully differentiated adipocytes after Fgf8b treatment at the respective day of differentiation. Both Fgfr4 expression and Fgf8b sensitivity correlate. D—FGFR3 splice variant c mRNA expression in fold of day 1 at the respective day of differentiation.

FIG. 9.

The primary structure of the FGF receptors (FGFR). FGFRs each contain three immunoglobulin-like domains (Ig I-III), a single transmembrane domain (TM), and two tyrosine kinase domains (KD1-2). The Ig domains are disulfide-linked and therefore stabilized. Within the Ig III domain are three different exons (exon 7=A, exon 8=B, and exon 9=C) which encode possible splice alternatives at the N-terminal end of the receptor (Ig III C—exon 7, 9, and 10; Ig III B—exon 7, 8, and 10). The short form of the FGFRs lacks the Ig I domain. There is evidence in the literature that the Ig III C spliceform is epithelial tissue-specific and the Ig III B form is mesenchymal tissue-specific. sp represents the signal peptide; sc represents an acid box. The heparin-binding site (HBS) is marked by a circle in Ig II domain.

Figure 10:
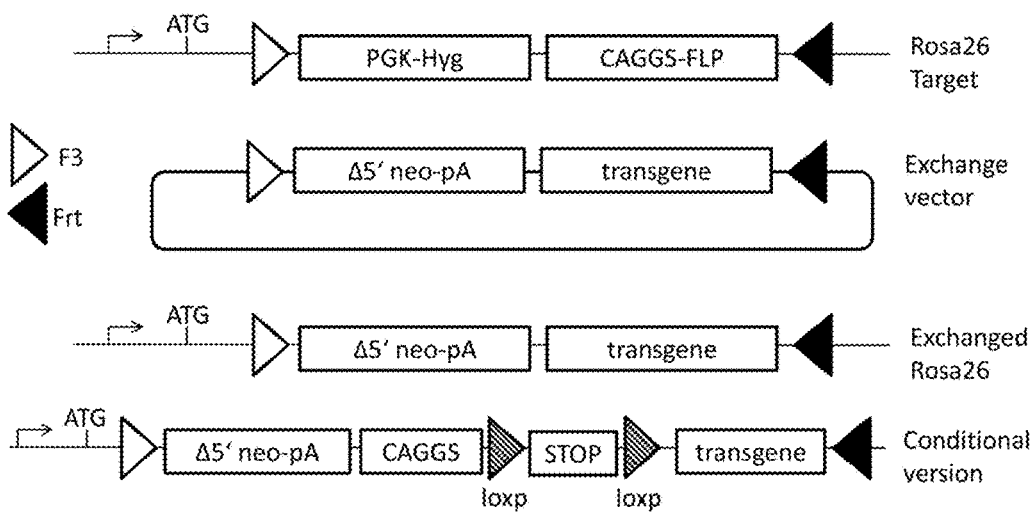

FIG. 10. Strategy to generate a mouse model with adipocyte specific, inducible expression of FGF8b.

On the exchange vector, a loxP (lox) flanked stop cassette interferes with FGF8b coding sequence ("transgene") expression. It also carries a neomycin (neo) resistance gene. Both cds carry polyadenylation signals. The vector construct is recombined into the Rosa26 target mouse line. The resulting mouseline is crossed with an existing one expressing CreERT2 driven by the adiponectin (adipoq) promotor. Activation of CreERT2 by OHT treatment leads to removal of the stop cassette and FGF8b expression.

Figure 11:
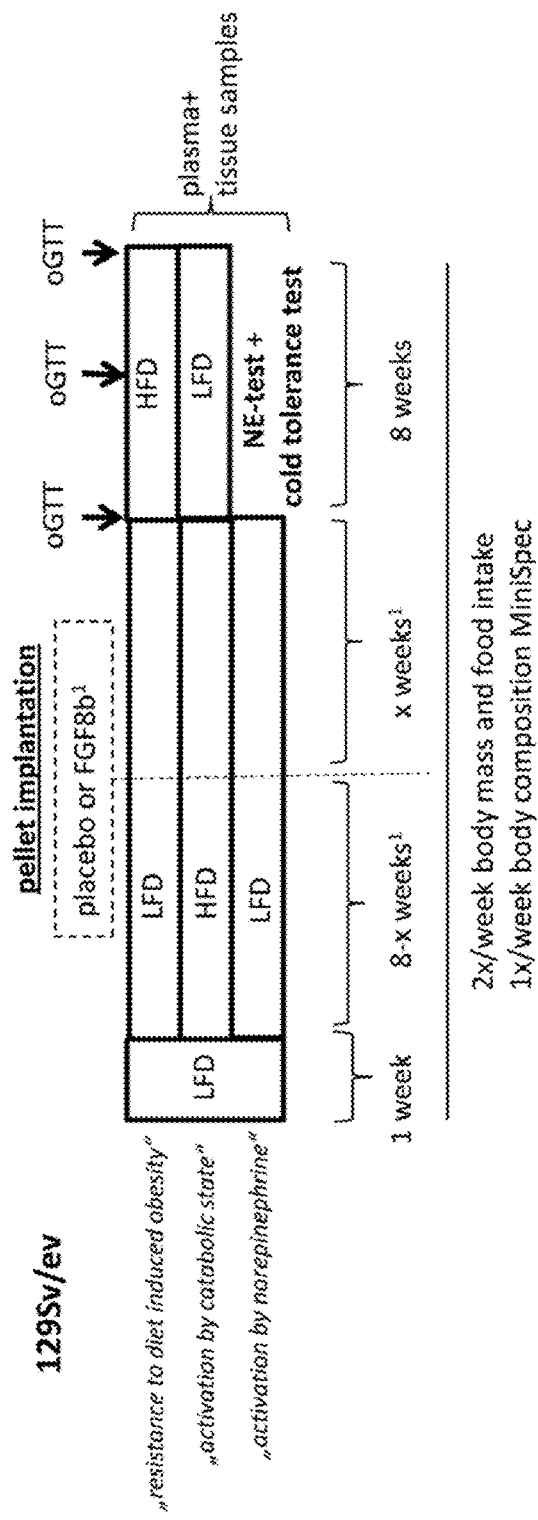

FIG. 11: Experimental setup for pellet implanted mice.

Mice are fed with purified diets, either low fat control diet (LFD) or a high fat diet (HFD) for 8 weeks in total. Depending on the optimal treatment time "x", the timepoint is chosen to implant pellets releasing FGF8b. After several weeks of treatment oral glucose tolerance tests (oGTT), norepinephrine tests (NE-test), cold tolerance tests are performed and plasma and tissue samples are collected. Body mass, body composition and food intake is determined on a regular basis.

Figure 12:
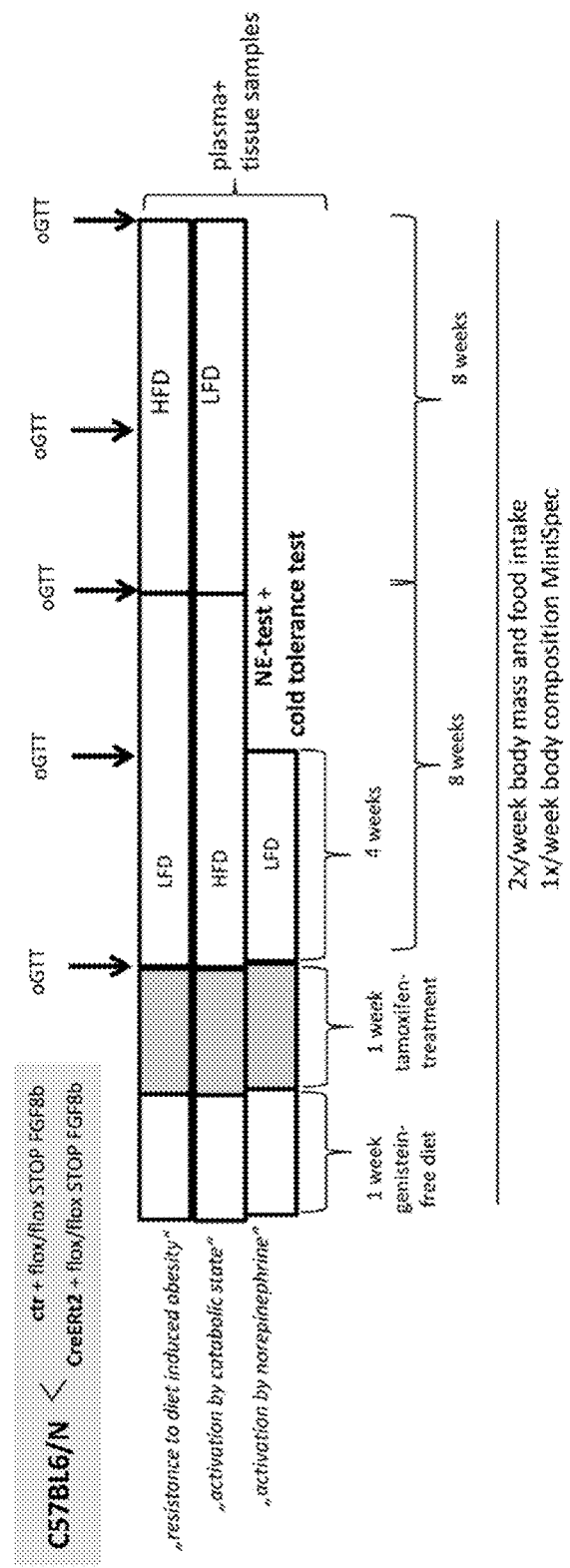

FIG. 12: Experimental setup for transgenic mice.

Mice of the C57BL6/N strain are fed with a diet free of genistein followed by a week of OHT treatment to induce FGF8b expression in white adipose tissue. Afterwards, mice are fed purified diets, either low fat control diet (LFD) or a high fat diet (HFD). Regularly, oral glucose tolerance tests (oGTT) are performed and body mass, body composition and food intake is determined. In one group a norepinephrine tests (NE-test) and a cold tolerance test is performed. In all groups plasma and tissue samples are collected.

Figure 13:
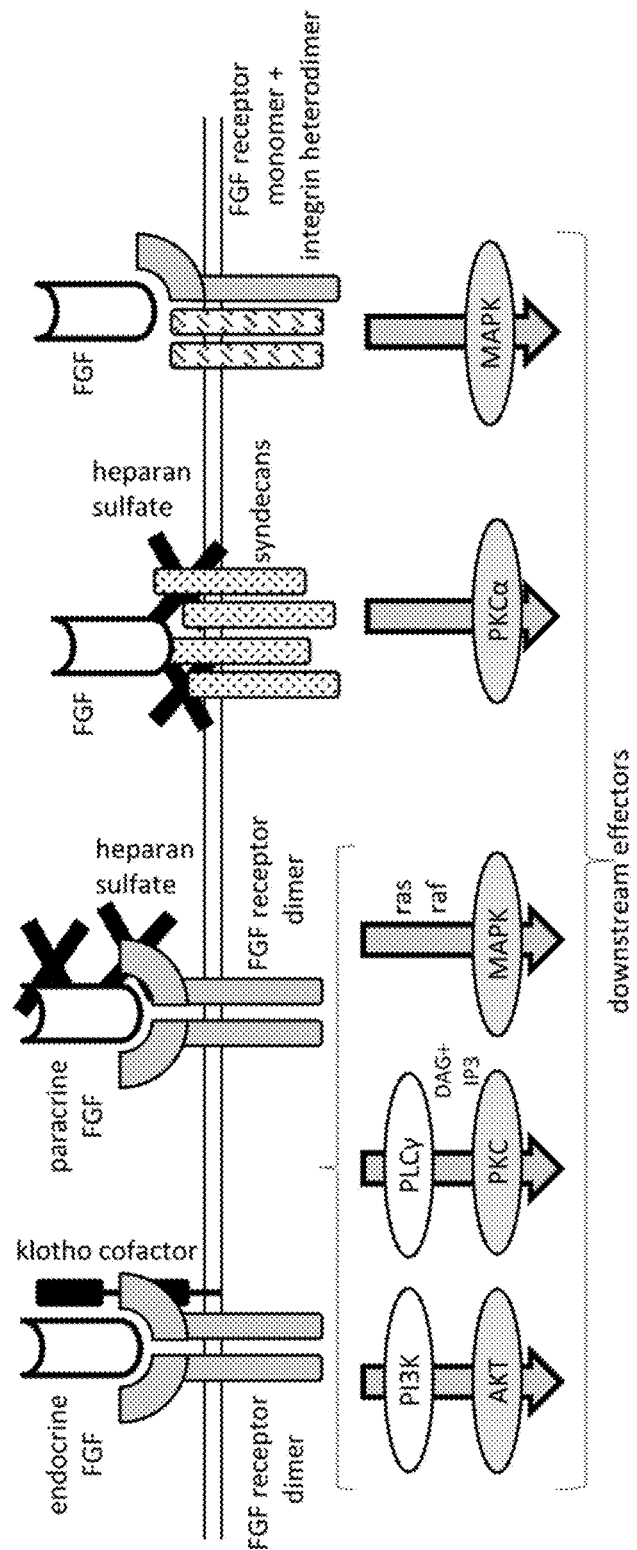

FIG. 13: FGF signaling.

Canonical FGF signaling involves dimerization of a FGF receptor. Binding of the ligand FGF to the dimer is stabilized either by a klotho cofactor (endocrine FGFs) or by heparan sulfate (paracrine FGFs). FGF receptors trigger three intracellular signaling cascades: the PI3K/AKT, PLC/PKC and MAPK. Non-canonical FGF signaling is mediated by syndecans interacting with heparan sulfate and an FGF to aktivate intracellular PKCa or, alternatively, by an integrin heterodimer interacting with an FGF receptor to activate the intracellular MAPK cascade.

The Example illustrates the invention.

EXAMPLE 1: Paracrine FGFs induce a brown adipose tissue (BAT) phenotype in white adipose tissue and are therefore useful in therapy of disorders and diseases of energy homeostasis (including obesity, diabetes, dyslipidemia, insulin resistance, hyperglycemia or metabolic syndrome)

Material & Methods

Fibroblast Growth Factors

We obtained fibroblast growth factors (FGFs) 1, 2 and 9 of murine origin and human FGFs 5 and 16-21 from PeproTech (Hamburg, Germany). The murine FGFs 4, 6, 7, 8b, 10, and 23 and human FGFs 3, 8a, 8e, 8f and 22 were purchased from R&D Systems (Minneapolis, Minn., United States of America). If not stated otherwise, the concentration used for screening purposes in cell culture were as follows (ng/ml): FGF1 2.5, FGF2 5.0, FGF3 25.0, FGF4 5.0, FGF5 2.5, FGF6 5.0, FGF7 25.0, FGF8a, b, e, and f 25.0, FGF9 1.0, FGF10 50.0, FGF16 2.5, FGF17 10.0, FGF18 5.0, FGF19 100.0, FGF21 10.0, FGF22 125.0 and FGF23 50.0.

Cell Culture

Preadipocytes were isolated from the stromal vascular fraction of subcutaneous inguinal or visceral epididymal white adipose tissue of newborn wild-type mice. Cells were immortalized by infection with a puromycin resistance-conferring retroviral vector encoding the Simian Vacuolating Virus 40 large T antigen (SV40 T-antigen) and selected with puromycin as published previously (J. Klein 2002). Cells were grown to confluence in Dulbecco's modified Eagle medium (4.5 g/l glucose, GE Healthcare Bio-Sciences Corp, Piscataway, N.J., USA) supplemented with 20% fetal bovine serum (Life Technologies, Carlsbad, Calif., USA), 20 nM insulin and 1 nM T3. Adipocyte differentiation was induced by complementing this medium with 250 µM indomethacin, 500 µM isobutylmethylxanthine and 2 µg/ml dexamethasone for 24 h after confluence. Cell culture was continued for up to six more days. Differentiated adipocytes were used between passages 10 and 30.

Quantitative PCR

Total RNA was isolated using the Qiazol reagent (Qiagen, Hilden, Germany). Quality of RNA was tested by photometric analysis and agarose gel electrophoresis. 5 µg of total RNA were reverse transcribed using the iScript cDNA Synthesis Kit (Biorad, Hercules, Calif., USA) in a 20 µl reaction. Target mRNAs were amplified in a total volume of 25 µl containing iQ SYBR Green Supermix (Biorad, Hercules, Calif., USA) and 10 pmol of each primer using the Mastercycler realplex 2 detection system (Eppendorf, Hamburg, Germany). The mRNA abundance was normalized to the expression of either beta-actin or Hsp90 as housekeeping genes. The following primers were used:

Actb AGAGGGAAATCGTGCGTGAC (SEQ ID NO:51) and CAATAGTGATGACCTGGCCGT (SEQ ID NO:52), Cidea TGCTCTTCTGTATCGCCCAGT (SEQ ID NO:53) and GCCGTGTTAAGGAATCTGCTG (SEQ ID NO:54), Cox7a1 CCGACAATGACCTCCCAGTA (SEQ ID NO:55) and TGTTTGTCCAAGTCCTCCAA (SEQ ID NO:56), Elovl3 TCCGCGTTCTCATGTAGGTCT (SEQ ID NO:57) and GGACCTGATGCAACCCTATGA (SEQ ID NO:58), Foxc2 ACGAGTGCGGATTTGTAACC (SEQ ID NO:59) and CAGTTTGGGGAGGGACCTAT (SEQ ID NO:60), Hsp90 AGGAGGGTCAAGGAAGTGGT (SEQ ID NO:61) and TTTTTCTTGTCTTTGCCGCT (SEQ ID NO:62), Otop1 GGACCTGATGCAACCCTATGA (SEQ ID NO:63) and ACCATGCTCTACGTGCTGTG (SEQ ID NO:64), Ppargc1a GGACGGAAGCAATTTTTCAA (SEQ ID NO:65) and GAGTCTTGGGAAAGGACACG (SEQ ID NO:66), Prb TAAACATCTCCCAGCGGAGT (SEQ ID NO:67) and ACAACCATGAGCCAGGAGTC (SEQ ID NO:68), Prdm16 CTGTTAGCTTTGGAGCCGAC (SEQ ID NO:69) and GACGAGGGTCCTGTGATGTT (SEQ ID NO:70), Ucp1 TCTCTGCCAGGACAGTACCC (SEQ ID NO:71) and AGAAGCCCAATGATGTTCAG (SEQ ID NO:72), Fgfr1 CCGGATCTACACACACCAGA (SEQ ID NO:73) and CCACCAACTGCTTGAACGTA (SEQ ID NO:74), Fgfr2 AGGGACACAGGATGGACAAG (SEQ ID NO:75) and AAACACAGAATCGTCCCCTG (SEQ ID NO:76), Fgfr3 ACCGAGTCTACACCCACCAG (SEQ ID NO:77) and TGAGGATGCGGTCTAAATCC (SEQ ID NO:78), Fgfr4 TGGAAGCTCTGGACAAGGTC (SEQ ID NO:79) and ATACAACATTGCTGCTCCCC (SEQ ID NO:80), aklotho GGCTCAACTCTCCCAGTCAG (SEQ ID NO:81) and CGCAAACTAGCCACAAAGGT (SEQ ID NO:82), bklotho ATGTCCAGGAGGCTCTGAAA (SEQ ID NO:83) and AGCAAATGGTGCAGTCTGTG (SEQ ID NO:84), Fgfr3c CTCCTTGTCGGTGGT (SEQ ID NO:101) and ACGGCACGCCCTACG ((SEQ ID NO:102).

Animal Experimentation

Pellets 1.5 mm in diameter were fabricated from a biodegradable matrix to locally release 100 ng FGF8b per day for 21 days (Innovative Research of America, Sarasota, Fla., USA). Matching placebo pellets did not contain FGFs. To implant a pellet into the subcutaneous adipose tissue, a mouse of the 129Sv/ev strain was anesthetized, abdominal fur removed and the pellet pushed into the depot through a short cut in the skin. To target the visceral adipose tissue, the pellet was introduced through a small cut each into skin and abdominal wall and placed between lobes of epididymal adipose tissue.

Mice were kept in a specific pathogen free barrier facility at room temperature in a 12:12 hour light:dark cycle with free access to food and water. Three weeks after implantation mice were killed by carbon dioxide exposure and dissected. Blood parameters were analyzed with an automated clinical chemistry analyzer (Piccolo xpress system, Abaxis, Darmstadt, Germany). All animal experiments were performed according to the German animal welfare law (permission no. 55.2-1-54-2532-174-11).

Introduction

Brown adipose tissue (BAT) is an organ equipping mammals with a means of non-shivering thermogenesis. In brown adipocyte mitochondria, uncoupling protein 1 (Ucp1) allows re-entry of protons from the intermembrane space into the matrix bypassing ATP synthase and thus uncoupling oxygen consumption from ATP production. By this mechanism, the energy stored in the form of proton motive force is released as heat (reviewed in (Klingenspor, 2012)).

BAT and its ability to combust nutrient energy into heat has recently gained increased attention after the repeated and convincing demonstration that adult healthy humans possess appreciable amounts of metabolically active BAT (Cypess et al., 2009; van Marken Lichtenbelt et al., 2009; Virtanen et al., 2009). Physiological or pharmacological activation of BAT thermogenesis may prove effective in treating some of the most widespread diseases of our time including obesity, diabetes and dyslipidemia. The amount of human BAT, however, is limited and estimated to account for approximately 0.05-0.1% of body mass as compared to a far more than 10-fold higher amount in mice (Virtanen et al., 2009). Thus, to therapeutically employ the unique capabilities of BAT, not only acute activators are required, but also agents that recruit a greater number of brown adipocytes.

The term "brown adipocytes" refers to all types of thermogenic, UCP1 expressing and/or multilocular cells. These are sometimes categorized into "classical brown" versus "beige" or "brite" and others. The term "brown adipocytes" is intended to encompass all of this, e.g. "brown adipocytes in white adipose tissue" is synonym to both "beige" and "brite".

Brown adipocytes are not restricted to uniform, classical BAT depots but are often found interspersed in white adipose tissue (WAT) depots. This second type of brown adipocyte has been termed beige or brite (brown in white) and seems to emerge from a different progenitor cell than classical brown fat cells (reviewed in (Pfeifer & Hoffmann, 2014)). To convert WAT into BAT by means of recruiting brite cells offers a possibility to massively increase the BAT amount accessible to therapeutic activation and at the same time decreases the amount of WAT, thereby replacing an energy-storing organ with an energy-dissipating one. This browning of white fat has been subject to intense research during the last years and several systemic interventions have been identified increasing the number of brite cells in mice, including cold exposure and treatment with β-adrenergic agonists or cardiac natriuretic peptides (Bordicchia et al., 2012; Fisher et al., 2012; Guerra, Koza, Yamashita, Walsh, & Kozak, 1998; Young, Arch, & Ashwell, 1984).

FGFs can be grouped by their mechanism of action into intracellular, paracrine and endocrine peptides (reviewed in (Itoh & Ornitz, 2008)). FGF21 belongs to the small group of endocrine FGFs and is therefore able to exhibit systemic effect on multiple target tissues. The largest group is formed by the paracrine FGFs which feature a protein domain binding to extracellular matrix components and are thereby less mobile and not found in circulation. Their matrix anchor also serves to stabilize interaction with FGF receptors, while endocrine FGFs require an additional cofactor of the klotho family for that purpose. Paracrine FGFs can be expected to act locally on the target tissue they are released into.

Results

It is shown herein that paracrine fibroblast growth factors FGF8 and FGF17 are active in browning visceral adipose tissue.

Screening of Paracrine Fibroblast Growth Factors in Immortalized White Adipocytes Paracrine fibroblast growth factors are encoded by a gene family of 13 members designated Fgf1-10 and Fgf16-18. We obtained the respective peptides of recombinant murine or human origin to screen their potential to induce the expression of the brown adipocyte specific gene uncoupling protein 1 (Ucp1) in white adipocyte cell lines. We chose two immortalized white adipocyte lines established from primary stromal-vascular cells isolated from the murine inguinal and epididymal adipose tissue depot. Treatment of the cells was started after induction and continued for the entire differentiation period of 6 days. The concentration chosen for each factors was based on the biological 1050 value determined in fibroblast proliferation assays by the supplier and ranged between 1 and 50 ng/ml. Of 13 fibroblast growth factors tested, Fgf8 strongest induced Ucp1 mRNA abundance of both fully differentiated adipocyte cell lines (epididymal: 27.4-fold, inguinal 2.1-fold) (FIG. 1A). The murine FGF8 gene gives rise to 8 differently spliced transcripts leading to 8 different peptide factors Fgfa-f of which we initially tested the major spliceform Fgf8b (FIG. 1C). We compared the ability of those 4 murine isoforms that are also present in humans (Fgf8a, b, e, and f) to induce Ucp1 mRNA abundance (FIG. 1B). In adipocytes of inguinal origin, Fgf8b was the only isoform with browning potential, while in epididymal adipocytes Fgf8b and Fgf8f were both effective. For further experiments we chose the most potent spliceform Fgf8b which is the dominant spliceform in mice and humans with a completely identical amino acid sequence in both species.

FGF8b Dose Dependently Induces a Brown Adipocyte Phenotype in White Adipocytes

We treated inguinal and epididymal adipocytes with different concentrations of Fgf8b during the entire differentiation phase of 6 days. In both cell lines, the highest concentration of 125 ng/ml proved most effective (FIG. 2A). In epididymal cells, Fgf8b induced Ucp1 mRNA abundance in a dose dependent manner, while in inguinal cells only the highest dose increased Ucp1 expression in an above threshold manner.

Abundance of the brown adipocyte marker cell death-inducing DNA fragmentation factor alpha like effector A (Cidea) mRNA was increased by Fgf8b treatment similarly to Ucp1 with a greater effect size in epididymal as compared to inguinal adipocytes. Subunit of complex IV 7a1 (Cox7a1) and elongase of very long chain fatty acids 3 (Elovl3) mRNA was not or only slightly increased by Fgf8b treatment. The master regulator of mitochondrial biogenesis, PPAR gamma coactivator 1a (Pgc1a), was strongly down-regulated in fully differentiated adipocytes treated with Fgf8b.

FGF8b Reprograms both Proliferating and Differentiating Preadipocytes

During differentiation in culture, immortalized (pre-)adipocytes undergo drastic changes in morphology, gene expression signature and function. The sensitivity towards an external stimulus can thus vary between different stages of differentiation. In particular the browning of white adipose tissue has been proposed to either include the trans-differentiation of mature white adipocytes or to be caused by the differentiation of a certain pool of precursor cells. To assess the sensitive time window for FGF8b induced browning, we treated inguinal and epididymal white adipocytes during different days of proliferation, induction and/or differentiation and measured the final Ucp1 mRNA abundance after full differentiation.

Figure 3A:
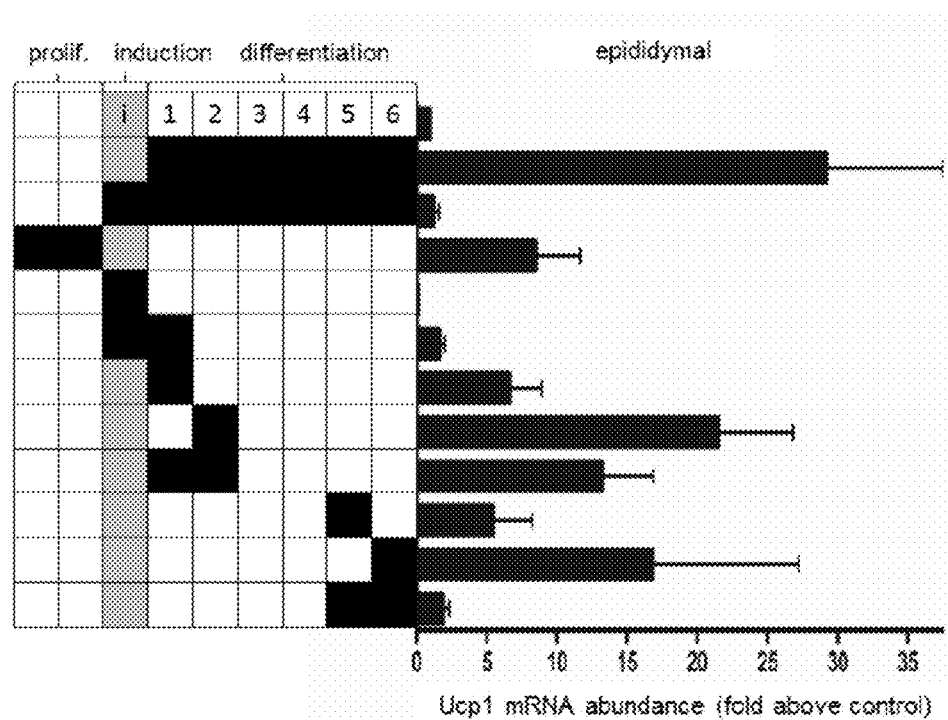
Figure 3B:
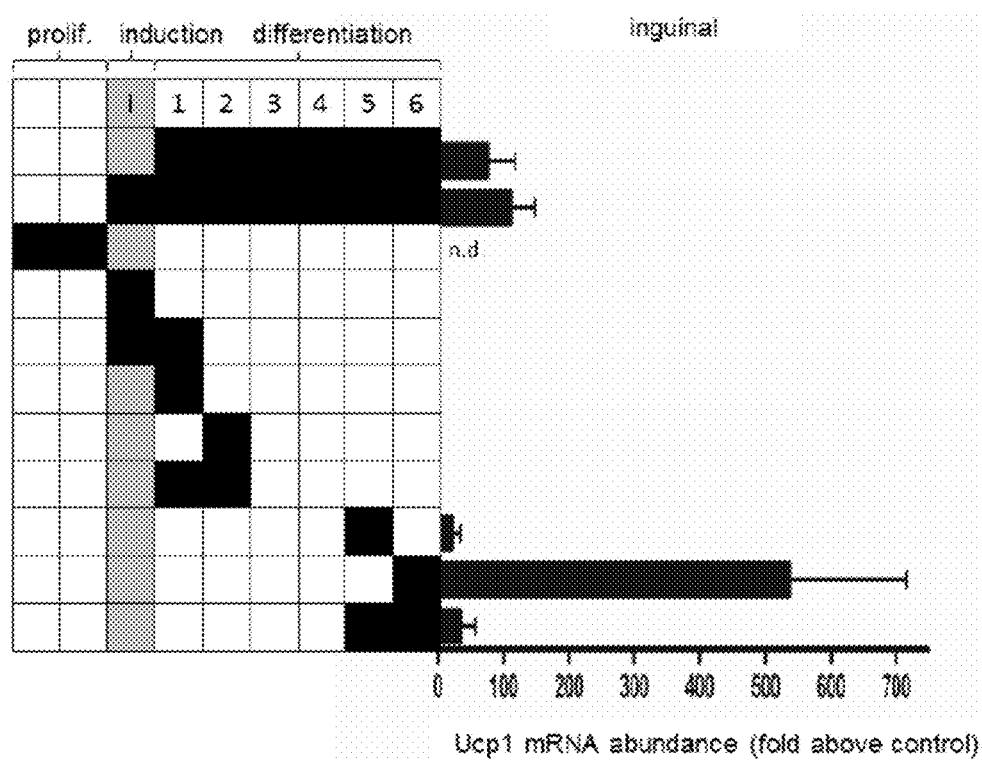

Adipocytes of inguinal origin were only responsive to FGF8b treatment in their fully differentiated state (FIG. 3B). Thus, the effect of prolonged treatment during the entire differentiation phase can be attributed to this late, sensitive period. While epididymal cells also respond to a comparably late treatment, they display a second even more sensitive time window during early differentiation directly following induction (FIG. 3A) and a third during proliferation. Interestingly, treatment during the induction phase is not only ineffective. Including the induction day furthermore abrogates the browning effect of otherwise sensitive treatment regimes.

The sensitivity of proliferating epididymal adipocytes towards FGF8b allowed us to follow the expression of brown adipocyte characteristic transcripts in a timecourse experiment covering the entire differentiation phase. We treated cells for 48 hours prior to induction and took samples immediately afterwards, on day 1 post induction (p.i.), day 2 p.i., day 4 p.i. and after full differentiation at day 6 p.i. The mRNA abundance of four brown adipocyte marker genes (Ucp1, Cidea, Cox7a1 and Elovl3) was increased in mature adipocytes treated with FGF8b during proliferation with Cidea and Elovl3 already increasing on day 4 p.i. and Ucp1 and Cidea following on day 6 p.i. (FIG. 4). Interestingly, Pgc1a was acutely downregulated by FGF8b treatment in line with our previous data of epididymal cells continuously treated during differentiation (FIG. 2B). However, early treatment during proliferation still led to increased Pgc1a mRNA abundance after complete differentiation. The transcription factor Prdm16, presumably implicated in brown adipocyte differentiation, displays a transient increase in abundance directly following induction. The transcription factors Foxc2 and pRb do not acutely respond to FGF8b treatment.

Fgf Receptor Expression in Immortalized Adipocytes

The cellular response to FGFs is mediated by FGF receptors (FGFR). A variety of FGFRs is produced from four different genes by differential splicing (FGFR1-4). We quantified mRNA abundance of transcripts of all four genes with primers that do not differentiate between individual spliceforms during every day of adipocyte differentiation in cell culture (FIG. 5). Transcripts of all four genes were present in both cell lines at every timepoint. While FGFR1-3 transcripts did not display marked expression changes during differentiation, FGFR4 was clearly less abundant in proliferating cells and strongly upregulated upon induction and early differentiation. The binding of endocrine FGFs further requires the presence of one of the klotho cofactors, alpha-klotho or beta-klotho. Paracrine FGFs are not considered to require a cofactor for FGFR binding because their affinity for extracellular matrix components stabilizes ligand-receptor interaction. We nevertheless determined transcript abundance of the klotho genes to not overlook a possible, previously non-appreciated role in FGF8b signaling. Alpha-klotho was hardly detectable at all in any sample and accordingly displayed a very high variability. Beta-klotho strongly increased in abundance during differentiation from very low levels in proliferating cells to strong expression in mature adipocytes.

Figure 7F:
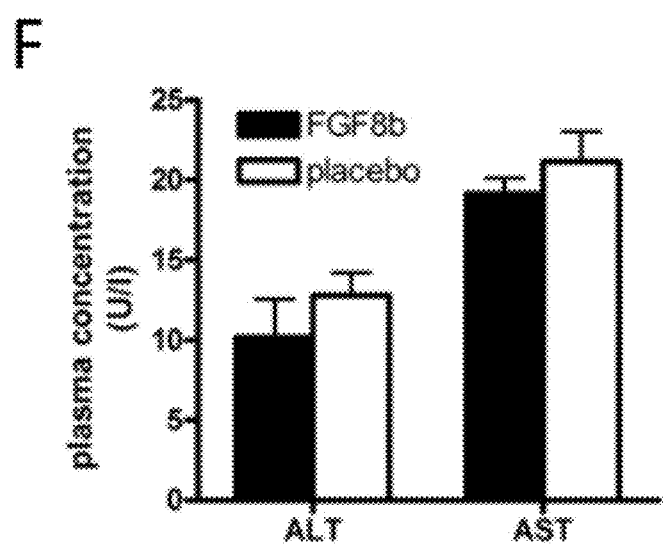

FGF8b Transforms Epididymal White Adipose Tissue into Brown Adipose Tissue In Vivo To investigate the ability of FGF8b to transform white adipose tissue into brown adipose tissue in vivo, we obtained pellets that release 100 ng FGF8b per day and placebo pellets. One pellet each was implanted into the epididymal white adipose tissue of adult male 129Sv/ev mice. After three weeks mice were sacrificed and the tissue analyzed. Final body weight was comparable between the FGF8b and the placebo group as well as the change in body weight during the 3 weeks of treatment (FIG. 7). The depot mass of implanted and non-implanted epididymal fat and of interscapular brown adipose tissue was not different between groups. Accordingly, the relationship between depot mass and body mass was not influenced by FGF8b treatment (FIG. 7D). A panel of blood parameters including glucose, plasma lipids and liver enzymes did not differ between FGF8b and placebo treated animals. In summary, we found no evidence of any gross metabolic difference between treatment groups.

By visual inspection, the implantation site of FGF8b pellets and the surrounding adipose tissue was of a brown colour, while both the non-implanted contralateral depot and the implantation site of placebo pellets remained characteristically white (FIG. 6A). The browned area extended approximately 3 mm away from the implanted pellet in line with the effect of an infused paracrine factor. The individual effect size varied considerably with the final position of the pellet within the depot. Implantation of FGF8b pellets into inguinal adipose tissue did not lead to visual browning or increased expression of brown adipocyte marker genes.

We measured mRNA abundance of brown fat marker genes. Ucp1 and Cox7a1 were increased when measuring in a RNA preparation of the complete unilateral depot (FIG. 6).

FGF Receptor 4 Expression Correlates with FGF8b Sensitivity

The different response of epididymal and inguinal adipose tissue to FGF8b treatment might be explained by a different expression of according receptors. We thus measured mRNA abundance of all FGF receptors and klotho co-receptors in the two depots of untreated male mice. The three receptors Fgf receptor 1-3 and beta-klotho were well detectable in both depots and of comparable abundance (FIG. 8A-B). Appreciable amounts of Fgfr4 and alpha-klotho were only found in epididymal adipose tissue, while only traces were present in inguinal fat.

Since Fgf receptor 4 displayed an expression pattern that may account for the different responsiveness of inguinal and epididymal adipose tissue to FGF8b, we also compared responsiveness of immortalized cultures adipocytes with Fgf4 receptor mRNA abundance. In both inguinal and epididymal cells receptor expression and responsiveness displayed a similar pattern. In inguinal adipocytes the common peak is detected in fully differentiated, mature adipocytes. In epididymal adipocytes both parameters display a maximum during early differentiation.

Discussion

The fibroblast growth factors (FGF) gene family comprises 22 members that are considered key players in proliferation and differentiation of a wide variety of cells and tissues. Most FGFs mediate their biological effects as secreted, extracellular proteins by binding to and activating cell surface tyrosine kinase FGF receptors. The FGF protein family as well as the FGF receptors are highly conserved across species. Three distinct subgroups of FGFs can be defined: endocrine FGFs (19-23), paracrine FGFs (1-12 & 16-18) and intracellular FGFs (11-14).

Members of the endocrine FGFs, especially FGF19 and FGF21, are implicated in energy homeostasis and reported to be activators of brown adipose tissue. In addition, FGF21 has been reported to induce browning in white adipose tissue. In principal, endocrine and paracrine FGFs share the same set of receptors FGFR1-4. Thus, we screened all paracrine FGF proteins for their potential to induce Ucp1 gene expression in white adipocytes.

Interestingly, we identified FGF8 and FGF17 of the paracrine FGF8-like subfamily to be able to strongly induce Ucp1 mRNA expression in subcutaneous, inguinal and visceral, epididymal adipocytes. Of four different FGF8 spliceforms, FGF8b most potently led to UCP1 expression in inguinal and epididymal adipocytes. Thus, further studies were carried out with this paracrine peptide.

FGF8b increased the mRNA expression of Ucp1 and further brown adipocyte marker genes in epididymal adipocytes. A timecourse treatment during differentiation identified two separate sensitive time windows: epididymal adipocytes responded to FGF8b during two days following induction of differentiation, while both inguinal and epididymal adipocytes reacted to acute FGF8b treatment once fully differentiated. After treatment of epididymal cells during the first day of differentation, several marker genes of mature brown adipocytes were first upregulated during day 4 (Cidea, Elovl3) or day 6 (Ucp1, Cox7a1) of differentiation. The timespan of several days between treatment of early preadipocytes and first marker gene expression in fully differentiated cells clearly indicates a reprogramming of the differentation process and not a direct, acute effect on marker gene transcription. The well-known regulator of early brown adipocyte differentiation, PRDM16, however, was immediately and transiently upregulated upon FGF8b treatment. Possibly, the FGF8b effect is intracellularly mediated by the PRDM16 signaling axis.

We determined mRNA abundance of FGF receptors during differentiation of adipocytes to identify candidate receptors transducing the FGF8b effect. FGFR1-3 were constantly present during all stages in large amounts. FGFR4 was drastically upregulated directly following induction and thus displayed a similar pattern as FGF8b sensitivity of these cells. In murine tissue samples, FGFR4 was clearly present in epididymal adipose tissue while only much lower trace amounts were determined in the inguinal fat depot. Taken together, FGFR4 is a candidate receptor to transduce browning induced by FGF8b.

The efficacy of FGF8b to convert white into brown adipose tissue was determined in vivo. Drug release pellets were designed to locally release 100 nmol FGF8b per day and implanted into the epididymal adipose tissue depot. After three weeks, the adipose tissue surrounding the implanted FGF8b pellet turned visibly brown, while placebo pellets did not display a similar phenomenon. The expression of brown fat marker genes increased in FGF8b treated depots. The small effect size is probably due to a dilution effect of the large amounts of unconverted, white adipose tissue surrounding the affected region. Indeed, the entire depot was used to prepare the RNA sample for gene expressin analysis.

Neither body mass, nor fat mass was affected by pellet implantation. Typical metabolic blood parameters (including glucose, triglyceride and liver enzymes) did not change upon FGF8b pellet implantation. Taken together we find no evidence for any systemic adverse reaction to FGF8b.

In summary, FGF8b is able to locally turn visceral, epididymal white adipocytes into a cell type resembling brown adipocytes in cell culture and in vivo without evidence for a systemic effect.

The herein provided experiments follow a sequence of the following rationale: First, peptides were identified that reprogram white adipocytes to display brown adipocyte characteristics in a cell culture screen. Second, mechanistic details were characterized in a cell culture model. Third, the principal transferability of the cell culture data was confirmed in an animal model. The efficacy of recruiting brown fat cells within white adipose tissue to treat a number of metabolic diseases including obesity, diabetes and dyslipidemia can be confirmed in animal experiments and clinical studies.

Specifically, the lack of changes in parameters of blood chemistry and body composition in the mouse experiments does not argue against a possible therapeutic benefit of such treatment. These experiments were specifically designed and intended to demonstrate that FGF8b is able to recruit brown fat in vivo. The miniscule amount of recruited brown fat by implantation of a single pellet of the employed low dose was not expected to affect metabolic parameters. Conversely, the absence of such alterations even proves the lack of any dramatic side effects.

The in vivo experiments were conducted in lean, healthy mice, not in disease models. Amelioration of disease parameters can thus not be the expected outcome of the experiment (as these were absent to start with).

The amount of brown adipose tissue in a mouse, which has been therapeutically activated to help against metabolic disease in the literature, is in the range of 1% of body mass. To generate additional brown adipose tissue by FGF8b in an amount to notably increase this background, the dose, treatment time and/or pellet number can be increased. In addition, a transgenic mouse model expressing FGF8b in white adipose tissue can be characterized.

The therapeutic benefit of brown adipose tissue is a function of tissue mass and sympathetic tone (sympathetic catecholamines are activators of brown fat activity). The more brown fat is recruited in white adipose tissue with its specific, given sympathetic tone, the more therapeutic activity must be expected. In addition to brown fat recruitment by a paracrine FGF, the sympathetic tone can be increased (i.e. by fasting) or mimicked by co-administration of sympathomimetic drugs.

In summary, it was not the goal of the mouse experiments provided the above to prove the applicability of brown fat recruitment for the treatment of obesity, diabetes and dyslipidemia The in vivo experiment aimed at confirming brown fat recruitment by FGF8b and successfully did so. In view of this demonstrated effect it is credible that paracrine FGFs like FGF8b can be used in the therapy of metabolic diseases, because the art recognizes the link between brown fat recruitment and therapy of metabolic diseases.

The above results can be validated in appropriate animal experiments as follows.

Animal models can be used to determine the physiological consequences of FGF8b generated brown adipose tissue.

For example, pellet treatment can be optimized. In the experiments provided above, pellets were implanted releasing FGF8b into the visceral white adipose tissue of mice. The pellet design in relation to the parameters peptide amount, release rate and treatment duration can be optimized.

In addition to the pharmacological application of the active agent a mouse model of inducible, white fat specific FGF8b expression can be generated. This model allows a uniform treatment of the entire white adipose tissue for an indefinite time period and will be highly versatile to study the mechanisms underlying brown adipocyte recruitment.

Furthermore, physiological consequences of FGF8b induced brown adipocyte recruitment can be determined. Upon activation, brown adipocytes release chemical energy into heat by oxidizing lipids and glucose, making them an attractive target cell type for the treatment of diseases and disorders of energy homeostasis, including diabetes, obesity and dyslipidemia.

To validate the functionality of FGF8b recruited brown fat cells in vivo, the above mouse models can be assessed in respect to their thermogenic capacity, glucose tolerance and resistance towards diet induced obesity. The activity of FGF8b can be increased, for example by different manipulations to stimulate thermogenic activity including treatment with sympathomimetics and activation of the sympathetic nervous system by cold and fasting.

Brown adipocytes recruited by FGF8b need to be activated. The therapeutic benefit of brown adipose tissue is a function of tissue mass and sympathetic tone (sympathetic catecholamines are activators of brown fat activity). The more brown fat is recruited in white adipose tissue with its specific, given sympathetic tone, the more therapeutic activity must be expected. In addition to brown fat recruitment by a paracrine FGF, the sympathetic tone can be increased (e.g. by fasting) or mimicked by co-administration of sympathomimetic drugs.

As a first step, two in vivo model systems will be established. The local release of a paracrine peptide by implanted pellets serves as an ideal model for an therapeutic application in human medicine, while a transgenic mouse model of inducible, white fat specific FGF8b expression will be highly versatile to further study the mechanisms underlying brown adipocyte recruitment.

Model Establishment: Optimization of Pellet Treatment

FGF8b action is limited to paracrine targets due to an anchor sequence interacting with extracellular matrix components. It can thus be applied locally to a target tissue without affecting other tissues via distribution in the bloodstream. For this purpose, drug release pellets, 3 mm in diameter, were implanted into white fat in the above provided experiments. These pellets (Innovative Research of America, www.innovrsrch.com) were produced from a biodegradable carrier matrix and recombinant FGF8b (R&D Systems) to release 100 ng peptide per day for 3 weeks. The experiments were performed in a specific pathogen free (SPF) mouse research unit at the TUM.

For further experiments, the required amounts of FGF8b (~1 mg) are obtained from the same supplier (R&D Systems) and pellets are produced commercially as outlined below (Innovative Research of America, www.innovrsrch.com).

In this first part, it is aimed to optimize pellet design with respect to dose and treatment duration. Pellets of the known, effective dose (100 ng/d) are implanted into the epididymal white adipose tissue of male mice and three different treatment durations of continuous release (1 week, 3 weeks, 6 weeks) are compared. Once the optimal duration is validated, the release rate (10 ng/d, 100 ng/d and 1 µg/d) is varied. Pellets with a respective release rate and depot size of FGF8b can technically be produced according to the manufacturer. All pellet treatments are evaluated in comparison to appropriate placebo pellets.

In the above experiments, mice of the 129Sv/ev-S6 strain were employed. The 129Sv/ev-S6 strain is known for its high number of brown adipocytes in white fat. On the one hand, that may indicate a high sensitivity to browning stimuli like FGF8b. On the other hand, it may decrease the maximal effect size possible. Therefore, in parallel mice of the C57BL6/N mice are used. The extensive phenotyping described herein is limited to the strain proving more susceptible to FGF8b-induced browning.

Color and macroscopic appearance of the implantation sites is documented photographically. To quantify effectiveness of a treatment mRNA abundance of brown adipocyte marker genes (Ucp1, Cidea, Cox7a1, etc.) is determined by quantitative PCR (qPCR) and histological sections are generated.

All RNA and tissue samples generated during this work block are archived for further investigation as outlined below.

Model Establishment: Generation of a Transgenic Mouse Model

Release of FGF8b into the visceral, white adipose tissue led to recruitment of brown adipocytes in the experiments provided above. As a complement to local application in the form of pellets (see above), it is aimed to generate a mouse model that intrinsically produces FGF8b in white adipocytes. By this method, the entire white fat can be treated in a uniform manner and for any duration desired. While pharmacological treatment is an ideal model system for a possible therapeutic application, this transgenic mouse line with its envisioned greater effect size is optimal to study the molecular mechanisms behind brown adipocyte recruitment and its metabolic consequences.

A mouse line already established is used, which expresses CreERT2 recombinase under the control of the white fat specific adiponectin promotor. The CreERT2 fusion protein consists of a Cre recombinase and a variant estrogen receptor insensitive to estradiol, but binding to 4-hydroxytamoxifen (OHT). Upon treatment with OHT the fusion protein relocates from the cytosol into the nucleus and allows Cre-mediated recombination. This mouse line is of the C57BL6/N strain.

A further required mouse line of the same strain is generated by a commercial service provider (such as TaconicArtemis). The required mouse line is intended to comprise an expression construct inserted into a defined locus driving FGF8b expression from a ubiquitously active promotor (FIG. 10). This construct is silenced by a stop-cassette flanked by loxF-sites. The stop cassette can be removed by the action of Cre recombinase which will lead to expression of the otherwise silent gene. By interbreeding this FGF8b mouse with the CreERT2 mouse line a mouse model with white adipocyte specific (adiponectin promotor), inducible (OHT inducible CreER2t) expression of FGF8b is generated.

Activation of CreERT2 is possible by feeding a diet containing OHT (400 mg/kg). After a washout phase with a diet devoid of soy genistein for one week, OHT-containing diet is fed ad libitum for a further week. This regime leads to an approximate uptake of 3 mg OHT per mouse and day which is effective and well tolerable.

The resulting mouse model is extensively phenotyped.

Molecular Characteristics of In Vivo Recruited Brown Adipocytes

Both animal models described above (pellet implanted & transgenic) are expected to display FGF8b induced emergence of brown adipocytes in white adipose tissue. The measurements outlined here aim to characterize these cells on the cellular and the molecular level. FGF8b-treated white adipose tissue is compared with other adipose tissue depots: interscapular brown fat exclusively consists of classical brown adipocytes, inguinal white fat contains brite adipocytes and untreated epididymal white fat is considered nearly purely white. This comparison will elucidate whether FGF8b recruited brown adipocytes are rather similar to brown or brite adipocytes or even constitute a different, novel class of adipocyte.

Functional Characterization

A remarkable feature of brown as compared to white adipocytes is the excessive respiratory capacity conferred by a large number of mitochondria with dense christae. A change in mitochondrial amount on the level of mitochondrial enzyme activity, specifically citrate synthase of the TCA cycle and complex IV of the respiratory chain is detected. The maximal activity of both solubilized enzymes can be measured under conditions of substrate excess and constitute a surrogate measure for mitochondrial abundance and respiratory capacity. The respective assays are routinely applied.

Furthermore, brown and white adipocyte mitochondria differ in their substrate preference. Glycerol-3-phosphate (G3P) is oxidized preferentially by brown fat mitochondria due to more abundant mitochondrial G3P dehydrogenase (Chaffee, Allen, Cassuto, & Smith, 1964; Gong, Bi, Weintraub, & Reitman, 1998). Sufficient amounts of mitochondria might not be isolated from the small adipose tissue explants. Therefore floating cells from collagen-dissociated tissue can be analyzed. Oxygen consumption of such homogenates are measured in a respirometer (Oroboros O2k Oxygraph) in the absence/presence of different substrates to detect a possible shift in preference between placebo and FGF8b implanted mice.

Transcriptome Analysis

Biopsies are subjected to a transcriptome analysis by next generation sequencing (NGS). By comparison of expression patterns to classical brown, white and brite adipocyte insight into the cellular identity of FGF8b generated brown adipocytes is gained. Furthermore, candidate signal transduction pathways activated by FGF8b treatment are identified and tested experimentally.

Importantly, transcriptome analysis will allow identification of both signal transduction and effector genes in an unbiased fashion, i.e. in addition to the current knowledge on downstream FGF receptor signaling (FIG. 13). Candidate transcripts are validated by qPCR in independent biological samples. These will include tissue samples of both animal models as well as cultured cells.

For the validation of identified pathways cell culture experiments are performed, in which the respective pathway is activated/inhibited/challenged. The exact experimental design strongly depends on the identified target pathways, but may include pharmacological and biochemical compounds and/or physiological stimuli (starvation etc.). Primary outcome will be Ucp1 mRNA expression in fully differentiated cells.

Metabolic Consequences of FGF8b-Induced Recruitment of Brown Adipocytes

Both animal models described above (pellet implanted & transgenic) are expected to display FGF8b induced emergence of brown adipocytes in white adipose tissue. The physiological function of brown adipocytes is to release chemical energy from nutrient macromolecules into heat. Increasing the number and/or activity of this cell type can thus be expected to lead to the metabolic consequences listed below.

Maximal non-shivering thermogenic capacity: Brown adipocyte non-shivering thermogenesis is under the control of sympathetic catecholamines. An injection of norepinephrine activates the tissue and maximal thermogenic capacity can be assessed by indirect calorimetry (Meyer et al., 2010). Should the FGF8b recruited brown adipocytes be thermogenic, they will contribute to total capacity.

Glucose homeostasis: Active brown adipocytes take up large amounts of glucose and are therefore discussed as a treatment target for type 2 diabetes (T2D). In several mouse models with an increased number of brite adipocytes in white adipose tissue, an improved glucose tolerance has been described (Armani et al., 2014; Bi et al., 2014). Glucose tolerance tests are performed in both mouse models to assess the plausibility of FGF8b as a candidate T2D treatment option. The technique is established (Bolze et al., 2013).

Blood chemistry: Despite a large glucose uptake, this substrate only amounts to 10% of total energy expenditure in active brown adipocytes while the rest reflects lipid oxidation (Virtanen et al., 2009). Lipids are mobilized from intracellular stores or imported from the blood. This import can lead to massive alterations in the plasma lipoprotein pattern possibly beneficial in dyslipidemic patients (Bartelt et al., 2011). Blood chemical and lipoprotein parameters are determined in the mouse models by an automated clinical chemistry analyzer (Abaxis Piccolo Xpress).

Body mass and composition: Non-shivering thermogenesis causes increased energy expenditure. An altered number or activity of brown adipocytes can thus lead to a shift in energy balance and confer resistance to and/or relieve from diet induced obesity. These properties are assessed in feeding trials with both mouse models (see experimental setup below). Body composition will be analyzed by nuclear magnetic resonance spectroscopy (Bruker MiniSpec).

Activation of brown adipocytes: The activity of brown adipose tissue is controlled by the sympathetic innervation that releases norepinephrine to activate non-shivering thermogenesis. Brown adipocytes residing ectopically in white adipose tissue depots must be expected to be subject to the sympathetic tone in their respective depot. In white adipose tissue, lipolysis and lipid provision is increased in response to a catabolic state of the organism. Possibly, ectopically recruited brown adipocytes can be stimulated by this route and support fat loss during fasting.

The described metabolic consequences of FGF8b recruited brown adipocytes can be assessed in the following experimental setup (FIGS. 11 and 12):

Group 1: Resistance to Diet Induced Obesity

The comparison of control versus treated mice will reveal a possible contribution of FGF8b-recruited brown adipocytes to resistance to diet induced obesity and/or improved glucose homeostasis both in lean and in progressively obese, glucose intolerant mice.

In the pellet implantation mouse model (FIG. 11), mice are continuously fed a low fat diet and implanted with either placebo or FGF8b releasing pellets into the epididymal white adipose tissue following an optimized treatment regime as determined earlier. After maximal expected recruitment of brown adipocytes, mice are switched onto a high fat diet for 8 weeks to induce diet induced obesity. Body mass, body composition, food intake and glucose tolerance is monitored.

In the transgenic mouse model (FIG. 12), after activation of white fat FGF8b expression, the development of body mass, fat mass, food intake and glucose tolerance is monitored for 8 weeks feeding a control low fat diet. Subsequently, mice are fed a high fat diet to induce diet induced obesity.

Both the 129Sv/ev-S6 and the C57BL6/N mouse strain are susceptible to diet-induced obesity under these conditions.

Group 2: Activation by Catabolic State

During energy restriction, white adipose tissue lipolysis is activated by norepinephrine released from sympathetic nerve fibers. It is observed whether the increased sympathetic tone in epididymal white fat activates FGF8b-recruited brown adipocytes. In that case, the loss of body mass and fat mass as well as the improvement in glucose tolerance would be increased in FGF8b treated animals.

In the pellet implantation mouse model (FIG. 11), mice are fed a high fat diet ad libitum for 8 weeks to induce obesity. During this phase, pellets (placebo or FGF8b) are implanted into the epididymal white adipose tissue at such a timepoint that maximal recruitment of brown adipocytes can be expected to occur in mice with established obesity. A diet change to low fat diet leads to a catabolic state characterized by a loss in body mass and fat mass.

In the transgenic mouse model (FIG. 12), after activation of white fat FGF8b expression, the development of body mass, fat mass, food intake and glucose tolerance for 8 weeks feeding a high fat diet is monitored. Subsequently, mice are fed a control low fat diet to induce a catabolic state.

Group 3:—Activation by Norepinephrine.

Injection of the endogenous activator norepinephrine leads to maximal non-shivering thermogenesis in brown adipocytes. Alternatively, mice can be exposed to a series of decreasing ambient temperatures. In both cases, indirect calorimetry can used to determine maximal cold induced thermogenic capacity (norepinephrine) and cold limit (cold), respectively (Meyer et al., 2010; Nau et al., 2008). The measurement with these parameters will reveal a thermogenic contribution of FGF8b-recruited brown adipocytes.

In the pellet implantation mouse model (FIG. 11), mice are implanted with either placebo or FGF8b releasing pellets into the epididymal white adipose tissue following an optimized treatment regime as determined earlier. After maximal expected recruitment of brown adipocytes, thermogenic capacity is determined by indirect calorimetry following injection of norepinephrine. After a recovery period of several days, mice are subjected to a series of decreasing ambient temperatures to determine the cold limit.

In the transgenic mouse model (FIG. 12), four weeks after activation of white fat FGF8b expression, thermogenic capacity by norepinephrine injection is assessed. After a recovery period of several days, mice are subjected to a series of decreasing ambient temperatures to determine the cold limit.

In all completed study groups, tissue and plasma samples are collected for further analysis, e.g. to determine expression levels of brown adipocyte marker genes and to determine plasma glucose and lipids. Furthermore, tissue samples will be bioenergetically characterized as outlined above, i.e. citrate synthase activity, complex IV activity and comprehensive respirometry. This sample set allows investigating the persistence of recruited brown adipocytes 8 weeks after maximal recruitment.

Further, the used cell culture model can be refined in order to better characterize the signal transduction cascades responsible.

Immortalized white adipocytes were treated during the entire differentiation phase. To refine this model, it is aimed to shorten treatment to 48 hour time windows during different phases of cell differentiation (i.e. during proliferation, during induction, during different days of differentiation) and determine the most effective treatment scheme. Fresh (non-immortalized) primary white adipocytes from several murine adipose tissue depots are prepared to employ in the following experiment characterizing the responsible signal transduction cascade.

FGF8b exerts its effect by binding to a FGF receptor. Candidate receptors are described herein. They can be validated by analysis of responsive cells and tissues and test their relevance by RNA interference.

FGF receptors are known to couple to a number of different intracellular signal transduction cascades. By pharmacological inhibition the cascade necessary for brown adipocyte recruitment is pinpointed. The known target genes of such a cascade are searched for possible effector gene products.

When receptor and signal transduction cascade are characterized, possible alternative routes of activation are investigated, e.g. shortened FGF8b versions and small molecules interacting with signaling components.

Fibroblast growth factors and their receptors are highly conserved across mammals and beyond. Metabolically active brown adipocytes are found in both mice and man. Thus, a transferability of the results provided herein to the human system is possible.

This can be validated in cell cultures of primary, human adipocytes of subcutaneous and visceral origin. The cells are treated with FGF8b and further effectors as described herein and identified in accordance with the herein provided teaching. Recruitment of brown adipocytes is measured by the expression of brown fat marker genes.

Respirometric Assessment of Ucp1 Activity in Recruited Brown Adipocytes

In the experiments provided herein, immortalized epididymal white adipocytes with FGF8b were treated. This treatment led to expression of several brown adipocyte marker genes. The mRNA expression of marker genes alone indicates the presence of functional brown adipocytes. However, the functionality of recruited brown adipocytes can be validated and evaluated by respirometry in an extracellular flux analyzer (XFe96, Seahorse Bioscience).

A measurement protocol for the specific detection of functional uncoupling protein 1 (Ucp1) has been developed by Li, Fromme, Schweizer, Schottl, & Klingenspor, 2014). Briefly, oxygen consumption of fully differentiated adipocytes is determined in the presence of bovine serum albumine to buffer free fatty acids. The fraction of respiration attributable to proton leak is determined by addition of the complex V inhibitor oligomycin. Maximal Ucp1 mediated uncoupling is invoked by adrenergic stimulation with isoproterenol and maximal uncoupled respiration by the chemical uncoupler FCCP. Finally, non-mitochondrial respiration is detected by addition of the complex Ill inhibitor antimycin A. From these values, specific Ucp1 activity can be detected and quantified. Data from FGF8b recruited brown adipocytes is compared with both untreated white and brown adipocytes.

Characterization of the Signal Transduction Cascade

Identification of the FGF8b Receptor

Fibroblast growth factors (FGFs) exert their biological activity by interacting with FGF receptors. While endocrine FGFs require the presence of the cofactor α- or β-klotho, binding of paracrine FGFs is sufficiently stabilized by interaction with heparan sulfate. FGF receptors are tyrosine kinases coded on four different genes FGFR1-4 giving rise to at least seven different transcripts by differential splicing. The specificity of ligand receptor interaction is not fully resolved and FGF8b can bind to at least four different FGF receptor variants.

Alternatively, FGFs can bind to non-canonical target structures that also transmit information into the cell, either alone or in cooperation with classical FGF receptors. These include abundant cell surface proteins of the syndecan family (4 members) and integrin heterodimers (at least 18α and 8β subunits=144) (Murakami, Elfenbein, & Simons, 2008) (FIG. 13).

The receptor(s) that mediate FGF8b signaling implicated in brown adipocyte recruitment are validated and assessed as follows. As a first step, a correlation between receptor expression and responsivity of cells and tissues to FGF8b is assessed.

Correlative Approach: Time Frame Experiment

Immortalized, primary white adipocytes isolated from murine epididymal adipose tissue were utilized above to identify FGF8b as a potent activator of BAT. In the setup, cells were treated continuously during the entire phase of differentiation. The time window most sensitive to the browning stimulus is, however, very different for several known causative agents. BMP7, for instance, exerts a maximal effect when applied during proliferation, while rosiglitazone is effective during differentiation (Li, Bolze, Fromme, & Klingenspor, 2014; Tseng et al., 2008).

In a time frame experiment, cells are treated for 2 consecutive days during proliferation, induction phase and differentiation phase. All cells are fully differentiated and RNA prepared. Brown adipocyte marker gene and FGF receptor, syndecan and integrin transcript abundance will be measured by qPCR.

Both immortalized and freshly isolated primary cells of different adipose tissue depots are included. This experiment not only shows, which receptor is expressed in a sensitive timeframe and cell type, but also provides insight into the mechanism of brown adipocyte recruitment: sensitivity of proliferating cells would argue for an early determination process while a late sensitivity would argue for transdifferentiation of already differentiated or committed cells.

Correlative Approach: Expression Panel

Implanting pellets into epididymal adipose tissue led to recruitment of brown adipocytes, while it did not in inguinal adipose tissue. The expression of FGF receptors, syndecans and integrins in both adipose tissue depots and in the respective immortalized primary cell lines is determined to narrow down the range of FGF receptors conferring this effect.

Candidate Validation: RNA Interference

A knockdown strategy targeting all seven major FGF receptors and identified candidate syndecans/integrins by RNA interference is developed. Established procedures are used based on the viral transfection of vectors encoding a siRNA expression cassette into preadipocytes or alternatively, chemical transfection of pre-made, commercial siRNAs (Hoffmann et al., 2013).

The available knockdown methods are tested to find optimal strategies for the receptors. The crucial validation test will be whether knockdown of a receptor leads to loss in sensitivity to FGF8b mediated brown adipocyte recruitment as measured by marker gene expression. The receptor(s) directly responsible are pinpointed, thereby providing a target for alternative activation. Furthermore, validation of the receptor will provide candidate intracellular signaling pathways to test in the following experiment.

Elucidation of Intracellular Signaling Cascades

Canonical FGF receptor signaling is triggered by FGF binding and subsequent dimerization of the receptor (FIG. 13). Several residues of the dimer are autophosphorylated by its tyrosine kinase activity. These sites form docking domains for interacting proteins that in turn activate downstream signaling cascades. Some of the best studied signal transduction pathways emerge from here: the MAPK pathway (Erk1/2, p38, JNK), the IP3 pathway (PLCγ, IP3/DAG, PKCs) and the PI3K pathway (PI3K, AKT). The less studied non-canonical FGF signaling via syndecans and integrin also includes activation of a MAPK cascade (Murakami et al., 2008).

The signaling pathway essential for the recruitment of brown adipocytes by FGF8b by pharmacological inhibition is validated. All three major pathways can be specifically inhibited at multiple sites by commercially available small molecules (Table 1). Such inhibitors are utilized in cultures of immortalized white adipocytes treated with FGF8b and the mRNA abundance of brown adipocyte marker genes (Ucp1, Cidea, etc.) is measured by qPCR. Conversely, activators of candidate signaling cascades to mimic FGF8b action are employed.

To not overlook a possible unknown route of signal transduction, a pathway analysis with the transcriptome data generated above is conducted. Signaling cascades or groups of target genes coordinately regulated by FGF8b treatment are included into the experiment and targeted with small molecule inhibitors/activators.

The following exemplary compounds may be used.

TABLE 1

Activators and inhibitors of FGF signaling

| Pathway | Inhibitors | Activators |
|---|---|---|
| FGF receptors | None strictly isoform specific known SU11248 (pan-Receptor-Tyrosine-kinase) | Strontium ranelate (Caverzasio & Thouverey) |
| MAPK | Sorafenib (Raf), SB203580 (pan-p38), SP600125 (pan-JNK), Trametinib (MEK1/2), PD98059 (MEK1), SCH772984 (ERK1/2) | Anisomycin (p38 MAP and JNK), PAR C-16 (MEK), t-butylhydroquinone (Erk2) |
| IP3 | Sotrastaurin (pan-PKC), Bisindolylmaleimide 1 (pan-PKC), Gö6983 (pan-PKC), U-73122 (PLCg) | Phorbol 12-myristate 13-acetate (PKC), Cell permeant caged IP3 |
| PI3K | Wortmannin (PI3K), LY294002 (PI3K) | 740 Y-P (IP3R), sc-3036 (IP3R) |

TABLE 2

Activators and inhibitors of paracrine FGFs

| substance | IUPAC International Chemical Identifier (InChI), reference or chemical nomenclature/trivial name |
|---|---|
| Mechanism: Influencing FGF-heparin-binding | |

| | substance | IUPAC International Chemical Identifier (InChI), reference or chemical nomenclature/trivial name |
|---|---|---|
| Inhibitors | naphthalene-1,3,6-trisulfonate | ZPBSAMLXSQCSOX-UHFFFAOYSA-K |
| | 2-O-Bn sucrose heptasulfate | WO 03/038054A2 |
| | 1'-O-Bn sucrose heptasulfate | WO 03/038054A2 |
| | 1',2-di-O-Bn sucrose hexasulfate | WO 03/038054A2 |

TABLE 2-continued

Activators and inhibitors of paracrine FGFs

| substance | | IUPAC International Chemical Identifier (InChI), reference or chemical nomenclature/trivial name |
|---|---|---|
| Activators | 6'-O-hexadecanoyl sucrose hexasulfate | WO 03/038054A2 |
| | 2-O-dodecanoylhexasulfate | WO 03/038054A2 |
| | 6'-O-hexadecanoyl sucrose hexasulfate | WO 03/038054A2 |
| | 4,6-O-isopropylidene sucrose hexasulfate | WO 03/038054A2 |
| | Sucrose octasulfate | WEPNHBQBLCNOBB-FZJVNAOYSA-N |
| | Inositol hexasulfate | NBTMNFYXJYCQHQ-UHFFFAOYSA-N |

Mechanism: Supply of heparin for activating the FGFR-FGF-Heparin-complex

| activating | administration of heparin (or of a heparin derivative) | Classical heparin; further heparin derivatives, such as Certoparin, Dalteparin, Enoxaparin, Nadroparin, Danaparoid |
|---|---|---|

Mechanism: Influencing stability of protein conformation

| Stabilizing agent | Alpha-Cyclodextrin and other Cyclodextrinderivatives | HFHDHCJBZVLPGP-RWMJIURBSA-N |
|---|---|---|

Mechanism: Influencing heparanase-mediated degradation of heparan-sulfate proteoglycan (HSPG) oft eh extracellular matrix

| Heparanase (endo-beta-D-glucuronidase heparanase) inhibitor | PI-88 is a mixture of highly sulfated, monophosphorylated mannose oligosaccharides; Name: MUPARFOSTAT | |
|---|---|---|
| Heparanase inhibitor | OGT 2115 | 2-[4-[[3-(4-Bromophenyl)-1-oxo-2-propenyl]amino]-3-fluorophenyl]-5-benzoxazoleacetic acid |

Mechanism: Influencing FGFR activity

FGFR1

| Activator: | SUN11602 | 4-[[4-[[2-[(4-Amino-2,3,5,6-tetramethylphenyl)amino]acetyl]methylamino]-1-piperidinyl]methyl]penzamide |
|---|---|---|
| Inhibitor: | PD166866 | 1-[2-Amino-6-(3,5-dimethoxyphenyl)-pyrido[2,3-d]pyrimidin-7-yl]-3-tert-butyl urea |
| | PD 173074 | N-[2-[[4-(Diethylamino)butyl]amino-6-(3,5-dimethoxyphenyl)pyrido[2,3-d]pyrimidin-7-yl]-N'-(1,1-dimethylethyl)urea |

FGFR2

| Activator: | none described | |
|---|---|---|
| Inhibitor: | Ki23057 | 2-((2-((4-(4-((4-(tert-butyl)phenyl)amino)phenoxy)-6-methoxyquinolin-7-yl)oxy)ethyl)amino)ethanol |

FGFR3

| Activator: | Botulinum neurotoxin serotype A (BoN

TABLE 2-continued

Activators and inhibitors of paracrine FGFs

| | substance | IUPAC International Chemical Identifier (InChI), reference or chemical nomenclature/trivial name |
|---|---|---|
| FGFR (unspecific) | | |
| Activator: | — | |
| Inhibitor: | FIIN 1 hydrochloride | N-(3-((3-(2,6-dichloro-3,5-dimethoxyphenyl)-7-(4-(diethylamino)butylamino)-2-oxo-3,4-dihydropyrimido[4,5-d]pyrimidin-1(2H)-yl)methyl)phenyl)acrylamide |
| | PD 161570 | N-[6-(2,6-Dichlorophenyl)-2-[[4-(diethylamino)butyl]amino]pyrido[2,3-d]pyrimidin-7-yl]-N'-(1,1-dimethylethyl)urea |
| | SU 5402 | 2-[(1,2-Dihydro-2-oxo-3H-indol-3-ylidene)methyl]-4-methyl-1H-pyrrole-3-propanoic acid |
| | SU 6668 | 5-[1,2-Dihydro-2-oxo-3H-indol-3-ylidene)methyl]-2,4-dimethyl-1H-pyrrole-3-propanoic acid |
| Inhibitor FGFR1-3 | CH-5183284 | CAS#: 1265229-25-1 |
| FGFR downstream (FGFR Kinase) modulation) | | |
| Activator: | | |
| Inhibitor: | AP24534 | 3-(2-Imidazo[1,2-b]pyridazin-3-ylethynyl)-4-methyl-N-[4-[(4-methyl-1-piperazinyl)methyl]-3-(trifluoromethyl)phenyl]-benzamide |
| | BGJ398 | 3-(2,6-dichloro-3,5-dimethoxyphenyl)-1-(6-((4-(4-ethylpiperazin-1-yl)phenyl)amino)pyrimidin-4-yl)-1-methylurea. |

Receptor Activation by Alternative Ligands

FGFs have been successfully modified to peptides as short as 10 amino acids retaining biological activity (Ray, Baird, & Gage, 1997). Shorter variants offer the chance to identify FGF8b-based peptides with increased stability, altered tissue penetration and lower production cost.

The human FGF8 gene gives rise to at least 8 different transcripts, 4 of which are present in the mouse (Fgf8a, b, e and f) (Sunmonu, Li, & Li, 2011). These 4 isoforms were compared in terms of their potency to induce browning in immortalized white adipocytes to narrow down essential regions of the peptide (FIG. 1AB). FGF8b and FGF8f treatment is effective in immortalized white adipocytes of epididymal origin, while FGF8b is effective in epididymal as well as inguinal white adipocytes. The only difference between the ineffective FGF8a isoform and FGF8b is the presence of an additional 11 amino acids near the N terminus of FGF8b. Crucial amino acids of a FGF receptor interaction domain are located in precisely this region (Olsen et al. 2013). Therefore, it seems possible that the 11 amino acids on exon 1D might be sufficient to mediate a biological effect. But it remains possible that other parts of the protein might be useful and/or necessary.

This peptide is synthesized commercially and its biological potency to induce Ucp1 mRNA gene expression is tested. Further, the heparan sulfate anchor region is added to preserve paracrine tissue effectiveness in vivo. Conversely, the heparan sulfate anchor region is replaced with the klotho-interacting domain of endocrine FGFs to test potential adverse effects of FGF8 treatment in vivo. This "endocrinization" of a paracrine FGF has been successfully applied before (Goetz et al., 2012; Suh et al., 2014). Recombinant FGF8b variants are tested in cell cultures of murine epididymal white adipocytes for their potential to recruit brown adipocytes.

FGF8b Action on Human Cells

Both brown adipocytes and the fibroblast growth factor signaling system are conserved in mice and men. The mouse data are transferred to a human system to provide for applied studies employing FGF signaling as a therapeutic means to recruit brown adipocytes in humans.

Primary white adipocytes isolated freshly from surgical biopsies are used. The cells will be subjected to the most effective FGF8b treatment as identified above and mRNA abundance of brown adipocyte marker genes (Ucp1, Cidea etc.) is quantified by qPCR.

Following brown adipocyte recruitment in a human model system, brown adipocyte are characterized and the respective inhibitors and activators identified herein are tested. By this approach it can be confirmed that the same signaling pathways are utilized in both human and mouse cells to induce brown adipocyte recruitment.

Human Biopsies

To test the effect of FGF8b on human primary adipocytes clinical material from routine human visceral, trauma or general surgery are gathered; e.g. cholecystomie, hemicolectomy. Written informed consent after intensive counseling is obtained from every participating human being. Relevant individual data will be anonymized and pseudonymized to exclude drawing conclusions back to the involved patient. Patients, from whom significant impact of individual pathology or concomitant disease on study results cannot be excluded, will not be included in this project. Surgery indication is independent from the purpose of this study and no additional material is obtained during these routine operations, an additional risk for patients can be excluded.

Animal Experimentation

All animal experimentation as outlined herein is conducted in specific pathogen free (SPF) breeding facilities according to the German Animal Welfare law. Proposals for ethical approvals will be submitted to the Government The present invention refers to the following nucleotide and amino acid sequences:

The following sequence information is based on the Ensembl.org database using the following accession numbers:

Spliceforms of the Human FGF8 Gene

| Isoform | ENSEMBL transcript no. | ENSEMBL transcript ID |
|---|---|---|
| FGF8a | FGF8-003 | ENST00000346714 |
| FGF8b | FGF8-001 | ENS100000347978 |
| FGF8e | FGF8-004 | ENST00000344255 |
| FGF8f | FGF8-002 | ENST00000320185 |

Spliceforms of the Murine FGF8 Gene

| Isoform | ENSEMBL transcript no. | ENSEMBL transcript ID |
|---|---|---|
| FGF8a | FGF8-003 | ENSMUST00000111927 |
| FGF8b | FGF8-002 | ENSMUST00000111928 |
| FGF8e | FGF8-006 | ENSMUST00000111925 |
| FGF8f | FGF8-001 | ENSMUST00000026240 |

FGF17 Gene

| Species | ENSEMBL transcript no. | ENSEMBL transcript ID |
|---|---|---|
| human | FGF17-001 | ENST00000359441 |
| murine | Fgf17-201 | ENSMUST00000022697 |

FGF15/19 Gene (the Murine Ortholog of Human FGF19 is Called FGF15.)

| Species | ENSEMBL transcript no. | ENSEMBL transcript ID |
|---|---|---|
| human | FGF19-001 | ENST00000294312 |
| murine | Fgf15-201 | ENSMUST00000033389 |

FGF21 Gene

| Species | ENSEMBL transcript no. | ENSEMBL transcript ID |
|---|---|---|
| human | FGF21-201 | ENST00000222157 |
| murine | Fgf21-201 | ENSMUST00000033099 |

For the following FGFR1, 2, 3, and 4 sequences please note: Given are examples for a protein coding main transcript—other transcripts or transcript variants to be employed in accordance with this invention are deposited in the Ensembl.org database. Principles of alternative slicing of FGFR1, 2, and 3 are explained in FIG. 9 and are also known in the art.

FGFR1 Gene

| Species | ENDEMBL transcript no. | ENSEMBL transcript ID |
|---|---|---|
| human | FGFR1-001 | ENST00000397091 |
| murine | Fgfr1-001 | ENSMUST00000084027 |

FGFR2 Gene

| Species | ENDEMBL transcript no. | ENSEMBL transcript ID |
|---|---|---|
| human | FGFR2-001 | ENS100000358487 |
| murine | Fgfr2-004 | ENSMUST00000122054 |

FGFR3 Gene

| Species | ENDEMBL transcript no. | ENSEMBL transcript ID |
|---|---|---|
| Human | FGFR3-001 | EN5T00000260795 |
| murine | Fgfr3-002 | ENSMUST00000087820 |

FGFR3 Gene Transcript Variant c

| Species | ENDEMBL transcript no. | ENSEMBL transcript ID |
|---|---|---|
| Human | FGFR3-203 | ENST00000440486 |
| murine | Fgfr3-202 | ENSMUST00000169212 |

FGFR4 Gene

| Species | ENDEMBL transcript no. | ENSEMBL transcript ID |
|---|---|---|
| Human | FGFR4-001 | ENST00000292408 |
| murine | Fgfr4-001 | ENSMUST00000005452 | cDNA Sequences Sorted by Gene/Transcript

Code: non-underlined/underlined denoted alternating exons

SEQ ID NO: 1. human FGF8a
ATGGGCAGCCCCGCTCCGCGCTGAGCTGCCTGCTGTTGCACTTGCTGGTCCTCTGCCTCCAAGCCCAGCATGTG

AGGGAGCAGAGCCTGGTGACGGATCAGCTCAGCCGCCGCCTCATCCGGACCTACCAACTCTACAGCCGCACCAGC

GGGAAGCACGTGCAGGTCCTGGCCAACAAGCGCATCAACGCCATGGCAGAGGACGGCGACCCCTTCGCAAAGCTC

ATCGTGGAGACGGACACCTTTGGAAGCAGAGTTCGAGTCCGAGGAGCCGAGACGGGCCTCTACATCTGCATGAAC

AAGAAGGGGAAGCTGATCGCCAAGAGCAACGGCAAAGGCAAGGACTGCGTCTTCACGGAGATTGTGCTGGAGAAC

```
                    AACTACACAGCGCTGCAGAATGCCAAGTACGAGGGCTGGTACATGGCCTTCACCCGCAAGGGCCGGCCCCGCAAG

GGCTCCAAGACGCGGCAGCACCAGCGTGAGGTCCACTTCATGAAGCGGCTGCCCCGGGGCCACCACACCACCGAG

CAGAGCCTGCGCTTCGAGTTCCTCAACTACCCGCCCTTCACGCGCAGCCTGCGCGGCAGCCAGAGGACTTGGGCC

CCCGAGCCCCGATAG

SEQ ID NO: 2. human FGF8b
ATGGGCAGCCCCCGCTCCGCGCTGAGCTGCCTGCTGTTGCACTTGCTGGTCCTCTGCCTCCAAGCCCAGGTAACT

GTTCAGTCCTCACCTAATTTTACACAGCATGTGAGGGAGCAGAGCCTGGTGACGGATCAGCTCAGCCGCCGCCTC

ATCCGGACCTACCAACTCTACAGCCGCACCAGCGGGAAGCACGTGCAGGTCCTGGCCAACAAGCGCATCAACGCC

ATGGCAGAGGACGGCGACCCCTTCGCAAAGCTCATCGTGGAGACGGACACCTTTGGAAGCAGAGTTCGAGTCCGA

GGAGCCGAGACGGGCCTCTACATCTGCATGAACAAGAAGGGGAAGCTGATCGCCAAGAGCAACGGCAAAGGCAAG

GACTGCGTCTTCACGGAGATTGTGCTGGAGAACAACTACACAGCGCTGCAGAATGCCAAGTACGAGGGCTGGTAC

ATGGCCTTCACCCGCAAGGGCCGGCCCCGCAAGGGCTCCAAGACGCGGCAGCACCAGCGTGAGGTCCACTTCATG

AAGCGGCTGCCCCGGGGCCACCACACCACCGAGCAGAGCCTGCGCTTCGAGTTCCTCAACTACCCGCCCTTCACG

CGCAGCCTGCGCGGCAGCCAGAGGACTTGGGCCCCCGAGCCCCGATAG

SEQ ID NO: 3. human FGF8e
ATGGGCAGCCCCCGCTCCGCGCTGAGCTGCCTGCTGTTGCACTTGCTGGTCCTCTGCCTCCAAGCCCAGGAAGGC

CCGGGCAGGGGCCCTGCGCTGGGCAGGGAGCTCGCTTCCCTGTTCCGGGCTGGCCGGGAGCCCCAGGGTGTCTCC

CAACAGCATGTGAGGGAGCAGAGCCTGGTGACGGATCAGCTCAGCCGCCGCCTCATCCGGACCTACCAACTCTAC

AGCCGCACCAGCGGGAAGCACGTGCAGGTCCTGGCCAACAAGCGCATCAACGCCATGGCAGAGGACGGCGACCCC

TTCGCAAAGCTCATCGTGGAGACGGACACCTTTGGAAGCAGAGTTCGAGTCCGAGGAGCCGAGACGGGCCTCTAC

ATCTGCATGAACAAGAAGGGGAAGCTGATCGCCAAGAGCAACGGCAAAGGCAAGGACTGCGTCTTCACGGAGATT

GTGCTGGAGAACAACTACACAGCGCTGCAGAATGCCAAGTACGAGGGCTGGTACATGGCCTTCACCCGCAAGGGC

CGGCCCCGCAAGGGCTCCAAGACGCGGCAGCACCAGCGTGAGGTCCACTTCATGAAGCGGCTGCCCCGGGGCCAC

CACACCACCGAGCAGAGCCTGCGCTTCGAGTTCCTCAACTACCCGCCCTTCACGCGCAGCCTGCGCGGCAGCCAG

AGGACTTGGGCCCCCGAGCCCCGATAG

SEQ ID NO: 4. human FGF8f
ATGGGCAGCCCCCGCTCCGCGCTGAGCTGCCTGCTGTTGCACTTGCTGGTCCTCTGCCTCCAAGCCCAGGAAGGC

CCGGGCAGGGGCCCTGCGCTGGGCAGGGAGCTCGCTTCCCTGTTCCGGGCTGGCCGGGAGCCCCAGGGTGTCTCC

CAACAGGTAACTGTTCAGTCCTCACCTAATTTTACACAGCATGTGAGGGAGCAGAGCCTGGTGACGGATCAGCTC

AGCCGCCGCCTCATCCGGACCTACCAACTCTACAGCCGCACCAGCGGGAAGCACGTGCAGGTCCTGGCCAACAAG

CGCATCAACGCCATGGCAGAGGACGGCGACCCCTTCGCAAAGCTCATCGTGGAGACGGACACCTTTGGAAGCAGA

GTTCGAGTCCGAGGAGCCGAGACGGGCCTCTACATCTGCATGAACAAGAAGGGGAAGCTGATCGCCAAGAGCAAC

GGCAAAGGCAAGGACTGCGTCTTCACGGAGATTGTGCTGGAGAACAACTACACAGCGCTGCAGAATGCCAAGTAC

GAGGGCTGGTACATGGCCTTCACCCGCAAGGGCCGGCCCCGCAAGGGCTCCAAGACGCGGCAGCACCAGCGTGAG

GTCCACTTCATGAAGCGGCTGCCCCGGGGCCACCACACCACCGAGCAGAGCCTGCGCTTCGAGTTCCTCAACTAC

CCGCCCTTCACGCGCAGCCTGCGCGGCAGCCAGAGGACTTGGGCCCCCGAGCCCCGATAG

SEQ ID NO: 5. murine FGF8a
ATGGGCAGCCCCCGCTCCGCGCTGAGCTGCCTGCTGTTGCACTTGCTGGTTCTCTGCCTCCAAGCCCAGCATGTG

AGGGAGCAGAGCCTGGTGACGGATCAGCTCAGCCGCCGCCTCATCCGGACCTACCAGCTCTACAGCCGCACCAGC

GGGAAGCACGTGCAGGTCCTGGCCAACAAGCGCATCAACGCCATGGCAGAAGACGGAGACCCCTTCGCGAAGCTC

ATTGTGGAGACCGATACTTTTGGAAGCAGAGTCCGAGTTCGCGGCGCAGAGACAGGTCTCTACATCTGCATGAAC

AAGAAGGGGAAGCTAATTGCCAAGAGCAACGGCAAAGGCAAGGACTGCGTATTCACAGAGATCGTGCTGGAGAAC

AACTACACGGCGCTGCAGAACGCCAAGTACGAGGGCTGGTACATGGCCTTTACCCGCAAGGGCCGGCCCCGCAAG
```

```
GGCTCCAAGACGCGCCAGCATCAGCGCGAGGTGCACTTCATGAAGCGCCTGCCGCGGGGCCACCACACCACCGAG

CAGAGCCTGCGCTTCGAGTTCCTCAACTACCCGCCCTTCACGCGCAGCCTGCGCGGCAGCCAGAGGACTTGGGCC

CCGGAGCCCCGATAG

SEQ ID NO: 6. murine FGF8b
ATGGGCAGCCCCGCTCCGCGCTGAGCTGCCTGCTGTTGCACTTGCTGGTTCTCTGCCTCCAAGCCCAGGTAACT

GTTCAGTCCTCACCTAATTTTACACAGCATGTGAGGGAGCAGAGCCTGGTGACGGATCAGCTCAGCCGCCGCCTC

ATCCGGACCTACCAGCTCTACAGCCGCACCAGCGGGAAGCACGTGCAGGTCCTGGCCAACAAGCGCATCAACGCC

ATGGCAGAAGACGGAGACCCCTTCGCGAAGCTCATTGTGGAGACCGATACTTTTGGAAGCAGAGTCCGAGTTCGC

GGCGCAGAGACAGGTCTCTACATCTGCATGAACAAGAAGGGGAAGCTAATTGCCAAGAGCAACGGCAAAGGCAAG

GACTGCGTATTCACAGAGATCGTGCTGGAGAACAACTACACGGCGCTGCAGAACGCCAAGTACGAGGCCTGGTAC

ATGGCCTTTACCCGCAAGGGCCGGCCCCGCAAGGGCTCCAAGACGCGCCAGCATCAGCGCGAGGTGCACTTCATG

AAGCGCCTGCCGCGGGGCCACCACACCACCGAGCAGAGCCTGCGCTTCGAGTTCCTCAACTACCCGCCCTTCACG

CGCAGCCTGCGCGGCAGCCAGAGGACTTGGGCCCCGGAGCCCCGATAG

SEQ ID NO: 7. murine FGF8e
ATGGGCAGCCCCGCTCCGCGCTGAGCTGCCTGCTGTTGCACTTGCTGGTTCTCTGCCTCCAAGCCCAGGAAGGC

CCGGGCGGGGGGCCTGCGCTGGGCAGGGAGCCCACTTCCCTGCTCCGAGCTGGCCGGGAGCCCCAGGGTGTTTCC

CAACAGCATGTGAGGGAGCAGAGCCTGGTGACGGATCAGCTCAGCCGCCGCCTCATCCGGACCTACCAGCTCTAC

AGCCGCACCAGCGGGAAGCACGTGCAGGTCCTGGCCAACAAGCGCATCAACGCCATGGCAGAAGACGGAGACCCC

TTCGCGAAGCTCATTGTGGAGACCGATACTTTTGGAAGCAGAGTCCGAGTTCGCGGCGCAGAGACAGGTCTCTAC

ATCTGCATGAACAAGAAGGGGAAGCTAATTGCCAAGAGCAACGGCAAAGGCAAGGACTGCGTATTCACAGAGATC

GTGCTGGAGAACAACTACACGGCGCTGCAGAACGCCAAGTACGAGGGCTGGTACATGGCCTTTACCCGCAAGGGC

CGGCCCCGCAAGGGCTCCAAGACGCGCCAGCATCAGCGCGAGGTGCACTTCATGAAGCGCCTGCCGCGGGGCCAC

CACACCACCGAGCAGAGCCTGCGCTTCGAGTTCCTCAACTACCCGCCCTTCACGCGCAGCCTGCGCGGCAGCCAG

AGGACTTGGGCCCCGGAGCCCCGATAG

SEQ ID NO: 8. murine FGF8f
ATGGGCAGCCCCGCTCCGCGCTGAGCTGCCTGCTGTTGCACTTGCTGGTTCTCTGCCTCCAAGCCCAG GAAGGC

CCGGGCGGGGGGCCTGCGCTGGGCAGGGAGCCCACTTCCCTGCTCCGAGCTGGCCGGGAGCCCCAGGGTGTTTCC

CAACAGGTAACTGTTCAGTCCTCACCTAATTTTACACAGCATGTGAGGGAGCAGAGCCTGGTGACGGATCAGCTC

AGCCGCCGCCTCATCCGGACCTACCAGCTCTACAGCCGCACCAGCGGGAAGCACGTGCAGGTCCTGGCCAACAAG

CGCATCAACGCCATGGCAGAAGACGGAGACCCCTTCGCGAAGCTCATTGTGGAGACCGATACTTTTGGAAGCAGA

GTCCGAGTTCGCGGCGCAGAGACAGGTCTCTACATCTGCATGAACAAGAAGGGGAAGCTAATTGCCAAGAGCAAC

GGCAAAGGCAAGGACTGCGTATTCACAGAGATCGTGCTGGAGAACAACTACACGGCGCTGCAGAACGCCAAGTAC

GAGGGCTGGTACATGGCCTTTACCCGCAAGGGCCGGCCCCGCAAGGGCTCCAAGACGCGCCAGCATCAGCGCGAG

GTGCACTTCATGAAGCGCCTGCCGCGGGGCCACCACACCACCGAGCAGAGCCTGCGCTTCGAGTTCCTCAACTAC

CCGCCCTTCACGCGCAGCCTGCGCGGCAGCCAGAGGACTTGGGCCCCGGAGCCCCGATAG

SEQ ID NO: 9. human FGF17
ATGGGAGCCGCCCGCCTGCTGCCCAACCTCACTCTGTGCTTACAGCTGCTGATTCTCTGCTGTCAAACTCAGGGG

GAGAATCACCCGTCTCCTAATTTTAACCAGTACGTGAGGGACCAGGGCGCCATGACCGACCAGCTGAGCAGGCGG

CAGATCCGCGAGTACCAACTCTACAGCAGGACCAGTGGCAAGCACGTGCAGGTCACCGGGCGTCGCATCTCCGCC

ACCGCCGAGGACGGCAACAAGTTTGCCAAGCTCATAGTGGAGACGGACACGTTTGGCAGCCGGGTTCGCATCAAA

GGGGCTGAGAGTGAGAAGTACATCTGTATGAACAAGAGGGGCAAGCTCATCGGGAAGCCCAGCGGGAAGAGCAAA

GACTGCGTGTTCACGGAGATCGTGCTGGAGAACAACTATACGGCCTTCCAGAACGCCCGGCACGAGGGCTGGTTC
```

```
                      -continued
ATGGCCTTCACGCGGCAGGGGCGGCCCCGCCAGGCTTCCCGCAGCCGCCAGAACCAGCGCGAGGCCCACTTCATC

AAGCGCCTCTACCAAGGCCAGCTGCCCTTCCCCAACCACGCCGAGAAGCAGAAGCAGTTCGAGTTTGTGGGCTCC

GCCCCCACCCGCCGGACCAAGCGCACACGGCGGCCCCAGCCCCTCACGTAG

SEQ ID NO: 10. murine FGF17
ATGGGAGCCGCCCGCCTGCTGCCTAACCTTACCCTGTGCTTGCAGCTATTGATTCTCTGCTGTCAAACACAGGGG

GAGAATCACCCGTCTCCTAATTTTAACCAGTACGTGAGGGACCAGGGCGCTATGACCGACCAGCTGAGCAGGCGG

CAAATCCGTGAATACCAGCTCTACAGCCGGACCAGTGGCAAGCACGTGCAGGTCACCGGACGTCGCATCTCTGCC

ACCGCAGAGGATGGCAACAAGTTCGCCAAGCTCATCGTGGAGACAGATACATTCGGCAGCAGAGTCCGCATCAAG

GGGGCAGAGAGCGAGAAGTACATCTGTATGAACAAGAGGGGCAAGCTGATTGGGAAGCCGAGCGGGAAGAGCAAA

GACTGCGTGTTCACCGAGATCGTACTGGAGAACAACTACACGGCCTTCCAGAACGCCCGGCACGAGGGCTGGTTC

ATGGCTTTCACTCGGCAGGGCCGGCCACGCCAGGCCTCCCGGAGCCGCCAGAACCAGCGAGAGGCCCACTTCATC

AAGCGCCTCTACCAAGGCCAGCTGCCTTTTCCCAACCACGCTGAAAGGCAGAAGCAGTTCGAATTTGTGGGCTCC

GCCCCCACTCGCAGGACCAAGCGCACTCGGAGGCCCCAGTCCCAAACGTAG

SEQ ID NO: 11. human FGF19
ATGCGGAGCGGGTGTGTGGTGGTCCACGTATGGATCCTGGCCGGCCTCTGGCTGGCCGTGGCCGGGCGCCCCCTC

GCCTTCTCGGACGCGGGGCCCCACGTGCACTACGGCTGGGGCGACCCCATCCGCCTGCGGCACCTGTACACCTCC

GGCCCCCACGGGCTCTCCAGCTGCTTCCTGCGCATCCGTGCCGACGGCGTCGTGGACTGCGCGCGGGGCCAGAGC

GCGCACAGTTTGCTGGAGATCAAGGCAGTCGCTCTGCGGACCGTGGCCATCAAGGGCGTGCACAGCGTGCGGTAC

CTCTGCATGGGCGCCGACGGCAAGATGCAGGGGCTGCTTCAGTACTCGGAGGAAGACTGTGCTTTCGAGGAGGAG

ATCCGCCCAGATGGCTACAATGTGTACCGATCCGAGAAGCACCGCCTCCCGGTCTCCCTGAGCAGTGCCAAACAG

CGGCAGCTGTACAAGAACAGAGGCTTTCTTCCACTCTCTCATTTCCTGCCCATGCTGCCCATGGTCCCAGAGGAG

CCTGAGGACCTCAGGGGCCACTTGGAATCTGACATGTTCTCTTCGCCCCTGGAGACCGACAGCATGGACCCATTT

GGGCTTGTCACCGGACTGGAGGCCGTGAGGAGTCCCAGCTTTGAGAAGTAA

SEQ ID NO: 12. murine FGF15
ATGGCGAGAAAGTGGAACGGGCGTGCGGTGGCCCGAGCCCTGGTCCTGGCCACTCTGTGGCTGGCTGTGTCTGGG

CGTCCCCTGGCTCAGCAATCCCAGTCTGTGTCAGATGAAGATCCACTCTTTCTCTACGGCTGGGGCAAGATTACC

CGCCTGCAGTACCTGTACTCCGCTGGTCCCTATGTCTCCAACTGCTTCCTCCGAATCCGGAGCGACGGCTCTGTG

GACTGCGAGGAGGACCAAAACGAACGAAATTTGTTGGAATTCCGCGCGGTCGCTCTGAAGACGATTGCCATCAAG

GACGTCAGCAGCGTGCGGTACCTCTGCATGAGCGCGGACGGCAAGATATACGGGCTGATTCGCTACTCGGAGGAA

GACTGTACCTTCAGGGAGGAAATGGACTGTTTAGGCTACAACCAGTACAGATCCATGAAGCACCATCTCCATATC

ATCTTCATCCAGGCCAAGCCCAGAGAACAGCTCCAGGACCAGAAACCCTCAAACTTTATCCCCGTGTTTCACCGC

TCCTTCTTTGAAACCGGGGACCAGCTGAGGTCTAAAATGTTCTCCCTGCCCCTGGAGAGTGACAGCATGGATCCG

TTCAGGATGGTGGAGGATGTAGACCACCTAGTGAAGAGTCCCAGCTTCCAGAAATGA

SEQ ID NO: 13. human FGF21
ATGGACTCGGACGAGACCGGGTTCGAGCACTCAGGACTGTGGGTTTCTGTGCTGGCTGGTCTTCTGCTGGGAGCC

TGCCAGGCACACCCCATCCCTGACTCCAGTCCTCTCCTGCAATTCGGGGGCCAAGTCCGGCAGCGGTACCTCTAC

ACAGATGATGCCCAGCAGACAGAAGCCCACCTGGAGATCAGGGAGGATGGGACGGTGGGGGGCGCTGCTGACCAG

AGCCCCGAAAGTCTCCTGCAGCTGAAAGCCTTGAAGCCGGGAGTTATTCAAATCTTGGGAGTCAAGACATCCAGG

TTCCTGTGCCAGCGGCCAGATGGGGCCCTGTATGGATCGCTCCACTTTGACCCTGAGGCCTGCAGCTTCCGGGAG

CTGCTTCTTGAGGACGGATACAATGTTTACCAGTCCGAAGCCCACGGCCTCCCGCTGCACCTGCCAGGGAACAAG

TCCCCACACCGGGACCCTGCACCCCGAGGACCAGCTCGCTTCCTGCCACTACCAGGCCTGCCCCCGCACTCCCG

GAGCCACCCGGAATCCTGGCCCCCCAGCCCCCGATGTGGGCTCCTCGGACCCTCTGAGCATGGTGGGACCTTCC

CAGGGCCGAAGCCCCAGCTACGCTTCCTGA
```

SEQ ID NO: 14. murine FGF21
ATGGAATGGATGAGATCTAGAGTTGGGACCCTGGGACTGTGGGTCCGACTGCTGCTGGCTGTCTTCCTGCTGGGG

GTCTACCAAGCATACCCCATCCCTGACTCCAGCCCCTCCTCCAGTTTGGGGGTCAAGTCCGGCAGAGGTACCTC

TACACAGATGACGACCAAGACACTGAAGCCCACCTGGAGATCAGGGAGGATGGAACAGTGGTAGGCGCAGCACAC

CGCAGTCCAGAAA<u>GTCTCCTGGAGCTCAAAGCCTTGAAGCCAGGGGTCATTCAAATCCTGGGTGTCAAAGCCTCT</u>

<u>AGGTTTCTTTGCCAACAGCCAGATGGAGCTCTCTATGGATC</u>GCCTCACTTTGATCCTGAGGCCTGCAGCTTCAGA

GAACTGCTGCTGGAGGACGGTTACAATGTGTACCAGTCTGAAGCCCATGGCCTGCCCCTGCGTCTGCCTCAGAAG

GACTCCCCAAACCAGGATGCAACATCCTGGGGACCTGTGCGCTTCCTGCCCATGCCAGGCCTGCTCCACGAGCCC

CAAGACCAAGCAGGATTCCTGCCCCCAGAGCCCCCAGATGTGGGCTCCTCTGACCCCCTGAGCATGGTAGAGCCT

TTACAGGGCCGAAGCCCCAGCTATGCGTCCTGA

SEQ ID NO: 29. human FGFR1
<u>ATGTGGAGCTGGAAGTGCCTCCTCTTCTGGGCTGTGCTGGTCACAGCCACACTCTGCACCGCTAGGCCGTCCCCG</u>

<u>ACCTTGCCTGAACAAG</u>CCCAGCCCTGGGGAGCCCCTGTGGAAGTGGAGTCCTTCCTGGTCCACCCCGGTGACCTG

CTGCAGCTTCGCTGTCGGCTGCGGGACGATGTGCAGAGCATCAACTGGCTGCGGGACGGGGTGCAGCTGGCGGAA

AGCAACCGCACCCGCATCACAGGGGAGGAGGTGGAGGTGCAGGACTCCGTGCCCGCAGACTCCGGCCTCTATGCT

TGCGTAACCAGCAGCCCCTCGGGCAGTGACACCACCTACTTCTCCGTCAATGTTTCAG<u>ATGCTCTCCCCTCCTCG</u>

<u>GAGGATGATGATGATGATGATGACTCCTCTTCAGAGGAGAAAGAAACAGATAACACCAAACCAAACCCCGTAGCT</u>

CCATATTGGACATCCCCAGAAAAGATGGAAAAGAAATTGCATGCAGTGCCGGCTGCCAAGACAGTGAAGTTCAAA

TGCCCTTCCAGTGGGACCCCAAACCCCACACTGCGCTGGTTGAAAAATGGCAAAGAATTCAAACCTGACCACAGA

ATTGGAGGCTACAAG<u>GTCCGTTATGCCACCTGGAGCATCATAATGGACTCTGTGGTGCCCTCTGACAAGGGCAAC</u>

<u>TACACCTGCATTGTGGAGAATGAGTACGGCAGCATCAACCACACATACCAGCTGGATGTCGTGGAGCGGTCCCCT</u>

CACCGGCCCATCCTGCAAGCAGGGTTGCCCGCCAACAAAACAGTGGCCCTGGGTAGCAACGTGGAGTTCATGTGT

AAGGTGTACAGTGACCCGCAGCCGCACATCCAGTGGCTAAAGCACATCGAGGTGAATGGGAGCAAGATTGGCCCA

GACAACCTGCCTTATGTCCAGATCTTGAAG<u>ACTGCTGGAGTTAATACCACCGACAAAGAGATGGAGGTGCTTCAC</u>

<u>TTAAGAAATGTCTCCTTTGAGGACGCAGGGGAGTATACGTGCTTGGCGGGTAACTCTATCGGACTCTCCCATCAC</u>

<u>TCTGCATGGTTGACCGTTCTGGAAG</u>CCCTGGAAGAGAGGCCGGCAGTGATGACCTCGCCCCTGTACCTGGAGATC

ATCATCTATTGCACAGGGGCCTTCCTCATCTCCTGCATGGTGGGGTCGGTCATCGTCTACAAGATGAAGAGTGGT

ACCAAGAAGAGTGACTTCCACAGCCAGATGGCTGTGCACAAGCTGGCCAAGAGCATCCCTCTGCGCAGACAGGTA

ACAGTGTCTGCTGACTCCAGTGCATCCATGAACTCTGGGGTTCTTCTGGTTCGGCCATCACGGCTCTCCTCCAGT

GGGACTCCCATGCTAGCAGGGGTCTCTGAGTATGAGCTTCCCGAAGACCCTCGCTGGGAGCTGCCTCGGGACAGA

CTGGTCTTAGGCAAACCCCTGGGAGAGGGCTGCTTTGGGCAGGTGGTGTTGGCAGAGGCTATCGGGCTGGACAAG

GACAAACCCAACCGTGTGACCAAAGTGGCTGTGAAGATGTTGAAG<u>TCGGACGCAACAGAGAAAGACTTGTCAGAC</u>

<u>CTGATCTCAGAAATGGAGATGATGAAGATGATCGGGAAGCATAAGAATATCATCAACCTGCTGGGGGCCTGCACG</u>

<u>CAGGAT</u>GGTCCCTTGTATGTCATCGTGGAGTATGCCTCCAAGGGCAACCTGCGGGAGTACCTGCAGGCCCGGAGG

CCCCCAGGGCTGGAATACTGCTACAACCCCAGCCACAACCCAGAGGAGCAGCTCTCCTCCAAGGACCTGGTGTCC

TGCGCCTACCAGGTGGCCCGAGGCATGGAGTATCTGGCCTCCAAGAAG<u>TGCATACACCGAGACCTGGCAGCCAGG</u>

<u>AATGTCCTGGTGACAGAGGACAATGTGATGAAGATAGCAGACTTTGGCCTCGCACGGGACATTCACCACATCGAC</u>

<u>TACTATAAAAAGACAACCAACGGCCGACTGCCTGTGAAGTGGATGGCACCCGAGGCATTATTTGACCGGATCTAC</u>

ACCCACCAGAGTGATGT<u>GTGGTCTTTCGGGGTGCTCCTGTGGGAGATCTTCACTCTGGGCGGCTCCCCATACCCC</u>

<u>GGTGTGCCTGTGGAGGAACTTTTCAAGCTGCTGAAGGAGGGTCACCGCATGGACAAGCCCAGTAACTGCACCAAC</u>

<u>GAGCTG</u>TACATGATGATGCGGGACTGCTGGCATGCAGTGCCCTCACAGAGACCCACCTTCAAGCAGCTGGTGGAA

-continued

GACCTGGACCGCATCGTGGCCTTGACCTCCAACCAG<u>GAGTACCTGGACCTGTCCATGCCCCTGGACCAGTACTCC</u>
<u>CCCAGCTTTCCCGACACCCGGAGCTCTACGTGCTCCTCAGGGGAGGATTCCGTCTTCTCTCATGAGCCGCTGCCC</u>
<u>GAGGAGCCCTGCCTGCCCCGACACCCAGCCCAGCTTGCCAATGGCGGACTCAAACGCCGCTGA</u>

SEQ ID NO: 30. murine FGFR1
ATGTGGGGCTGGAAGTGCCTCCTCTTCTGGGCTGTGCTGGTCACAGCCACTCTCTGCACTGCCAGGCCAGCCCCA
ACCTTGCCTGAACAAG<u>CTCAGCCCTGGGGAGTCCCTGTGGAAGTGGAGTCTCTCCTGGTCCACCCTGGCGACCTG</u>
<u>CTACAGCTTCGCTGTCGGCTTCGCGATGATGTGCAGAGCATCAACTGGCTGCGGGATGGGGTGCAGCTGGTGGAG</u>
<u>AGCAACCGTACCCGCATCACAGGGGAGGAGGTGGAGGTGCGGGACTCCATCCCCGCTGACTCTGGCCTCTACGCT</u>
<u>TGCGTGACCAGCAGCCCCTCTGGCAGCGATACCACCTACTTCTCCGTCAATGTCTCAGATGCACTCCCATCCTCG</u>
GAAGATGATGACGACGACGATGACTCCTCCTCGGAGGAGAAAGAGACGGACAACACCAAACCAAACCGTAGG<u>CT</u>
<u>GTAGCTCCCTACTGGACATCCCCAGAGAAAATGGAGAAGAAACTGCATGCGGTGCCCGCTGCCAAGACGGTGAAG</u>
<u>TTCAAGTGCCCGTCGAGTGGGACACCCAACCCCACTCTGCGCTGGTTGAAAAATGGCAAAGAGTTTAAGCCTGAC</u>
<u>CACCGAATTGGAGGCTACAAGGTTCGCTATGCCACCTGGAGCATCATAATGGATTCTGTGGTGCCTTCTGACAAG</u>
GGCAACTACACCTGCATCGTGGAGAATGAGTATGGGAGCATCAACCACACCTACCAGCTTGACGTCGTGG<u>AACGA</u>
<u>TCTCCGCACCGACCCATCCTTCAGGCAGGGCTGCCTGCCAACAAGACAGTGGCCCTGGGCAGCAATGTGGAGTTC</u>
<u>ATGTGTAAGGTGTACAGCGATCCGCAGCCTCACATTCAGTGGCTGAAGCACATCGAGGTGAACGGGAGTAAGATC</u>
<u>GGGCCAGACAACTTGCCGTATGTCCAGATCCTGAAG</u>ACTGCTGGAGTTAATACCACCGACAAGGAAATGGAGGTG
CTTCATCTACGGAATGTCTCCTTTGAGGATGCGGGGGAGTATACGTGCTTGGCGGGTAACTCTATCGGACTCTCC
CATCACTCTGCATGGTTGACCGTTCTGGAAG<u>CCCTGGAAGAGAGACCAGCTGTGATGACCTCACCGCTCTACCTG</u>
<u>GAGATCATTATCTACTGCACCGGGGCCTTCCTGATCTCCTGCATGTTGGGCTCTGTCATCATCTATAAGATGAAG</u>
<u>AGCGGCACCAAGAAGAGCGACTTCCATAGCCAGATGGCTGTGCACAAGCTGGCCAAGAGCATCCCTCTGCGCAGA</u>
<u>CAGGTAAC</u>AGTGTCAGCTGACTCCAGTGCATCCATGAACTCTGGGGTTCTCCTGGTTCGGCCCTCACGGCTCTCC
TCCAGCGGGACCCCCATGCTGGCTGGAGTCTCCGAATATGAGCTCCCTGAGGATCCCCGCTGGGAGCTGCCACGA
GACAG<u>ACTGGTCTTAGGCAAACCACTTGGCGAGGGCTGCTTCGGGCAGGTGGTGTTGGCTGAGGCCATCGGGCTG</u>
<u>GATAAGGACAAACCCAACCGTGTGACCAAAGTGGCCGTGAAGATGTTGAAGTCCGACGCAACGGAGAAGGACCTG</u>
TCGGATCTGATCTCGGAGATGGAGATGATGAAAATGATTGGGAAGCACAAGAATATCATCAACCTTCTGGGAGCG
TGCACACAGGATGGTCCTCTTTATGTCATTGTGGAGTACGCCTCCAAAGGCAATCTCCGGGAGTATCTACAGGCC
CGGAGGCCTCCTGGGCTGGAGTACTGCTATAACCCCAGCCACAACCCCGAGGAACAGCTGTCTTCCAAAGATCTG
GTATCCTGTGCCTATCAGGTGGCTCGGGGCATGGAGTATCTTGCCTCTAAGAAGTGTATACACCGAGACCTGGCT
GCTAGGAACGTCCTGGTGACCGAGGATAACGTAATGAAGATCGCAGACTTTGGCTTAGCTCGAGACATTCATCAT
ATCGACTACTACAAGAAAACCACCAACGGCCGGCTGCCTGTGAAGTGGATGGCCCCTGAGGCGTTGTTTGACCGG
ATCTACACACACCAGAGCGATGTGTGGTCTTTTGGAGTGCTCTTGTGGGAGATCTTCACTCTGGGTGGCTCCCCA
TACCCCGGTGTGCCTGTGGAGGAACTTTTCAAGCTGCTGAAGGAGGGTCATCGAATGGACAAGCCCAGTAACTGT
ACCAATGAGCT<u>GTACATGATGATGCGGGACTGCTGGCATGCAGTGCCCTCTCAGAGACCTACGTTCAAGCAGTTG</u>
<u>GTGGAAGACCTGGACCGCATTGTGGCCTTGACCTCCAACCAGGAGTATCTGGACCTGTCCATACCGCTGGACCAG</u>
TACTCACCCAGCTTTCCCGACACACGGAGCTCCACCTGCTCCTCAGGGGAGGACTCTGTCTTCTCTCATGAGCCG
TTACCTGAGGAGCCCTGTCTGCCTCGACACCCCACCCAGCTTGCCAACAGTGGACTCAAACGGCGCTGA SEQ ID NO: 31. human FGFR2
ATGGTCAGCTGGGGTCGTTTCATCTGCCTGGTCGTGGTCACCATGGCAACCTTGTCCCTGGCCCGGCCCTCCTTC
AGTTTAGTTGAGGATACCACATTAGAGCCAGAAG<u>AGCCACCAACCAAATACCAAATCTCTCAACCAGAAGTGTAC</u>
<u>GTGGCTGCGCCAGGGGAGTCGCTAGAGGTGCGCTGCCTGTTGAAAGATGCCGCCGTGATCAGTTGGACTAAGGAT</u>
<u>GGGGTGCACTTGGGGCCCAACAATAGGACAGTGCTTATTGGGGAGTACTTGCAGATAAAGGGCGCCACGCCTAGA</u>

GACTCCGGCCTCTATGCTTGTACTGCCAGTAGGACTGTAGACAGTGAAACTTGGTACTTCATGGTGAATGTCACA
GATGCCATCTCATCCGGAGATGATGAGGATGACACCGATGGTGCGGAAGATTTTGTCAGTGAGAACAGTAACAAC
AAGAGAGCACCATACTGGACCAACACAGAAAAGATGGAAAAGCGGCTCCATGCTGTGCCTGCGGCCAACACTGTC
AAGTTTCGCTGCCCAGCCGGGGGGAACCCAATGCCAACCATGCGGTGGCTGAAAAACGGGAAGGAGTTTAAGCAG
GAGCATCGCATTGGAGGCTACAAGGTACGAAACCAGCACTGGAGCCTCATTATGGAAAGTGTGGTCCCATCTGAC
AAGGGAAATTATACCTGTGTAGTGGAGAATGAATACGGGTCCATCAATCACACGTACCACCTGGATGTTGTGGAG
CGATCGCCTCACCGGCCCATCCTCCAAGCCGGACTGCCGGCAAATGCCTCCACAGTGGTCGGAGGAGACGTAGAG
TTTGTCTGCAAGGTTTACAGTGATGCCCAGCCCCACATCCAGTGGATCAAGCACGTGGAAAAGAACGGCAGTAAA
TACGGGCCCGACGGGCTGCCCTACCTCAAGGTTCTCAAGGCCGCCGGTGTTAACACCACGGACAAAGAGATTGAG
GTTCTCTATATTCGGAATGTAACTTTTGAGGACGCTGGGGAATATACGTGCTTGGCGGGTAATTCTATTGGGATA
TCCTTTCACTCTGCATGGTTGACAGTTCTGCCAGCGCCTGGAAGAGAAAAGGAGATTACAGCTTCCCCAGACTAC
CTGGAGATAGCCATTTACTGCATAGGGGTCTTCTTAATCGCCTGTATGGTGGTAACAGTCATCCTGTGCCGAATG
AAGAACACGACCAAGAAGCCAGACTTCAGCAGCCAGCCGGCTGTGCACAAGCTGACCAAACGTATCCCCCTGCGG
AGACAGGTAACAGTTTCGGCTGAGTCCAGCTCCTCCATGAACTCCAACACCCCGCTGGTGAGGATAACAACACGC
CTCTCTTCAACGGCAGACACCCCCATGCTGGCAGGGGTCTCCGAGTATGAACTTCCAGAGGACCCAAAATGGGAG
TTTCCAAGAGATAAGCTGACACTGGGCAAGCCCCTGGGAGAAGGTTGCTTTGGGCAAGTGGTCATGGCGGAAGCA
GTGGGAATTGACAAAGACAAGCCCAAGGAGGCGGTCACCGTGGCCGTGAAGATGTTGAAAGATGATGCCACAGAG
AAAGACCTTTCTGATCTGGTGTCAGAGATGGAGATGATGAAGATGATTGGGAAACACAAGAATATCATAAATCTT
CTTGGAGCCTGCACACAGGATGGGCCTCTCTATGTCATAGTTGAGTATGCCTCTAAAGGCAACCTCCGAGAATAC
CTCCGAGCCCGGAGGCCACCCGGGATGGAGTACTCCTATGACATTAACCGTGTTCCTGAGGAGCAGATGACCTTC
AAGGACTTGGTGTCATGCACCTACCAGCTGGCCAGAGGCATGGAGTACTTGGCTTCCCAAAAATGTATTCATCGA
GATTTAGCAGCCAGAAATGTTTTGGTAACAGAAAACAATGTGATGAAAATAGCAGACTTTGGACTCGCCAGAGAT
ATCAACAATATAGACTATTACAAAAAGACCACCAATGGGCGGCTTCCAGTCAAGTGGATGGCTCCAGAAGCCCTG
TTTGATAGAGTATACACTCATCAGAGTGATGTCTGGTCCTTCGGGGTGTTAATGTGGGAGATCTTCACTTTAGGG
GGCTCGCCCTACCCAGGGATTCCCGTGGAGGAACTTTTTAAGCTGCTGAAGGAAGGACACAGAATGGATAAGCCA
GCCAACTGCACCAACGAACTGTACATGATGATGAGGGACTGTTGGCATGCAGTGCCCTCCCAGAGACCAACGTTC
AAGCAGTTGGTAGAAGACTTGGATCGAATTCTCACTCTCACAACCAATGAGGAATACTTGGACCTCAGCCAACCT
CTCGAACAGTATTCACCTAGTTACCCTGACACAAGAAGTTCTTGTTCTTCAGGAGATGATTCTGTTTTTTCTCCA
GACCCCATGCCTTACGAACCATGCCTTCCTCAGTATCCACACATAAACGGCAGTGTTAAAACATGA
SEQ ID NO: 32. murine FGFR2
ATGGGATTACCGTCCACGTGGAGATATGGAAGAGGACCAGGGATTGGCACTGTGACCATGGTCAGCTGGGGCGC
TTCATCTGCCTGGTCTTGGTCACCATGGCAACCTTGTCCCTGGCCCGGCCCTCCTTCAGTTTAGTTGAGGATACC
ACTTTAGAACCAGAAGAGCCACCAACCAAATACCAAATCTCCCAACCAGAAGCGTACGTGGTTGCCCCCGGGGAA
TCGCTAGAGTTGCAGTGCATGTTGAAAGATGCCGCCGTGATCAGTTGGACTAAGGATGGGGTGCACTTGGGGCCC
AACAATAGGACAGTGCTTATTGGGGAGTATCTCCAGATAAAAGGTGCCACACCTAGAGACTCCGGCCTCTATGCT
TGTACTGCAGCTAGGACGGTAGACAGTGAAACTTGGTACTTCATGGTGAATGTCACAGATGCCATCTCATCTGGA
GATGATGAGGACGACACAGATAGCTCCGAAGACGTTGTCAGTGAGAACAGGAGCAACCAGAGAGCACCGTACTGG
ACCAACACCGAGAAGATGGAGAAGCGGCTCCACGCTGTCCCTGCCGCCAACACTGTGAAGTTCCGCTGTCCGGCT
GGGGGGAATCCAACGCCCACAATGAGGTGGTTAAAAAACGGGAGGAGTTTAAGCAGGAGCATCGCATTGGAGGC
TATAAGGTACGAAACCAGCACTGGAGCCTTATTATGGAAAGTGTGGTCCCGTCAGACAAAGGCAACTACACCTGC
CTGGTGGAGAATGAATACGGGTCCATCAACCACACCTACCACCTCGATGTCGTTGAACGGTCACCACACCGGCCC -continued ATCCTCCAAGCTGGACTGCCTGCAAATGCCTCCACGGTGGTCGGAGGGGATGTGGAGTTTGTCTGCAAGGTTTAC
AGCGATGCCCAGCCCCACATCCAGTGGATCAAGCACGTGGAAAAGAACGGCAGTAAATACGGGCCTGATGGGCTG
CCCTACCTCAAGGTCCTGAAGGCCGCCGGTGTTAACACCACGGACAAAGAGATTGAGGTTCTCTATATTCGGAAT
GTAACTTTTGAGGATGCTGGGGAATATACGTGCTTGGCGGGTAATTCTATCGGGATATCCTTTCACTCTGCATGG
TTGACAGTTCTGCCAGCGCCTGTGAGAGAGAAGGAGATCACGGCTTCCCCAGATTATCTGGAGATAGCTATTTAC
TGCATAGGGGTCTTCTTAATCGCCTGCATGGTGGTGACAGTCATCTTTTGCCGAATGAAGACCACGACCAAGAAG
CCAGACTTCAGCAGCCAGCCAGGTGTGCACAAGCTGACCAAGCGCATCCCCCTGCGGAGACAGGTAACAGTTTCG
GCCGAGTCCAGCTCCTCCATGAACTCCAACACCCCGCTGGTGAGGATAACAACGCGTCTGTCCTCAACAGCGGAC
ACCCCGATGCTAGCAGGGGTCTCCGAGTATGAGTTGCCAGAGGATCCAAAGTGGGAATTCCCCAGAGATAAGCTG
ACGCTGGCCAAACCCCTGGGGGAAGGTTGCTTCGGGCAAGTAGTCATGGCTGAAGCAGTGGGAATCGATAAAGAC
AAACCCAAGGAGGCGGTCACCGTGGCAGTGAAGATGTTGAAAGATGATGCCACAGAGAAGGACCTGTCTGATCTG
GTATCAGAGATGGAGATGATGAAGATGATTGGGAAACATAAGAACATTATCAACCTCCTGGGGGCCTGCACGCAG
GATGGACCTCTCTACGTCATAGTTGAATATGCATCGAAAGGCAACCTCCGGGAATACCTCCGAGCCCGGAGGCCA
CCTGGCATGGAGTACTCCTATGACATTAACCGTGTCCCCGAGGAGCAGATGACCTTCAAGGACTTGGTGTCCTGC
ACCTACCAGCTGGCTAGAGGCATGGAGTACTTGGCTTCCCAAAAATGTATCCATCGAGATTTGGCTGCCAGAAAC
GTGTTGGTAACAGAAAACAATGTGATGAAGATAGCAGACTTTGGCCTGGCCAGGGATATCAACAACATAGACTAC
TATAAAAAGACCACAAATGGGCGACTTCCAGTCAAGTGGATGGCTCCTGAAGCCCTTTTTGATAGAGTTTACACT
CATCAGAGCGATGTCTGGTCCTTCGGGGTGTTAATGTGGGAGATCTTTACTTTAGGGGGCTCACCCTACCCAGGG
ATTCCCGTGGAGGAACTTTTTAAGCTGCTCAAAGAGGGACACAGGATGGACAAGCCCACCAACTGCACCAATGAA
CTGTACATGATGATGAGGGATTGCTGGCATGCTGTACCCTCACAGAGACCCACATTCAAGCAGTTGGTCGAAGAC
TTGGATCGAATTCTGACTCTCACAACCAATGAGGAATACTTGGATCTCACCCAGCCTCTCGAACAGTATTCTCCT
AGTTACCCCGACACAAGGAGCTCTTGTTCTTCAGGGGACGATTCTGTGTTTTCTCCAGACCCCATGCCTTATGAA
CCCTGTCTGCCTCAGTATCCACACATAAACGGCAGTGTTAAAACATGA SEQ ID NO: 33. human FGFR3
ATGGGCGCCCCTGCCTGCGCCCTCGCGCTCTGCGTGGCCGTGGCCATCGTGGCCGGCGCCTCCTCGGAGTCCTTG
GGGACGGAGCAGCGCGTCGTGGGGCGAGCGGCAGAAGTCCCGGGCCCAGAGCCCGGCCAGCAGGAGCAGTTGGTC
TTCGGCAGCGGGGATGCTGTGGAGCTGAGCTGTCCCCCGCCCGGGGGTGGTCCCATGGGGCCCACTGTCTGGGTC
AAGGATGGCACAGGGCTGGTGCCCTCGGAGCGTGTCCTGGTGGGGCCCCAGCGGCTGCAGGTGCTGAATGCCTCC
CACGAGGACTCCGGGGCCTACAGCTGCCGGCAGCGGCTCACGCAGCGCGTACTGTGCCACTTCAGTCTGCGGGTG
ACAGACGCTCCATCCTCGGGAGATGACGAAGACGGGGAGGACGAGGCTGAGGACACAGGTGTGGACACAGGGGCC
CCTTACTGGACACGGCCCGAGCGGATGGACAAGAAGCTGCTGGCCGTGCCGGCCGCCAACACCGTCCGCTTCCGC
TGCCCAGCCGCTGGCAACCCCACTCCCTCCATCTCCTGGCTGAAGAACGGCAGGGAGTTCCGCGGCGAGCACCGC
ATTGGAGGCATCAAGCTGCGGCATCAGCAGTGGAGCCTGGTCATGGAAAGCGTGGTGCCCTCGGACCGCGGCAAC
TACACCTGCGTCGTGGAGAACAAGTTTGGCAGCATCCGGCAGACGTACACGCTGGACGTGCTGGAGCGCTCCCCG
CACCGGCCCATCCTGCAGGCGGGGCTGCCGGCCAACCAGACGGCGGTGCTGGGCAGCGACGTGGAGTTCCACTGC
AAGGTGTACAGTGACGCACAGCCCCACATCCAGTGGCTCAAGCACGTGGAGGTGAATGGCAGCAAGGTGGGCCCG
GACGGCACACCCTACGTTACCGTGCTCAAGACGGCGGGCGCTAACACCACCGACAAGGAGCTAGAGGTTCTCTCC
TTGCACAACGTCACCTTTGAGGACGCCGGGGAGTACACCTGCCTGGCGGGCAATTCTATTGGGTTTTCTCATCAC
TCTGCGTGGCTGGTGGTGCTGCCAGCCGAGGAGGAGCTGGTGGAGGCTGACGAGGCGGGCAGTGTGTATGCAGGC
ATCCTCAGCTACGGGGTGGGCTTCTTCCTGTTCATCCTGGTGGTGGCGGCTGTGACGCTCTGCCGCCTGCGCAGC
CCCCCCAAGAAAGGCCTGGGCTCCCCCACCGTGCACAAGATCTCCCGCTTCCCGCTCAAGCGACAGGTGTCCCTG -continued <u>GAGTCCAACGCGTCCATGAGCTCCAACACACCACTGGTGCGCATCGCAAGGCTGTCCTCAGGGGAGGGCCCCACG</u>
<u>CTGGCCAATGTCTCCGAGCTCGAGCTGCCTGCCGACCCCAAATGGGAGCTGTCTCGGGCCCGGCTGACCCTGGGC</u>
AAGCCCCTTGGGGAGGGCTGCTTCGGCCAGGTGGTCATGGCGGAGGCCATCGGCATTGACAAGGACCGGGCCGCC
AAGCCTGTCACCGTAGCCGTGAAGATGCTGAAAGACGATGCC<u>ACTGACAAGGACCTGTCGGACCTGGTGTCTGAG</u>
<u>ATGGAGATGATGAAGATGATCGGGAAACACAAAAACATCATCAACCTGCTGGGCGCCTGCACGCAGGGCGGGCCC</u>
CTGTACGTGCTGGTGGAGTACGCGGCCAAGGGTAACCTGCGGGAGTTTCTGCGGGCGCGGCGGCCCCGGGCCTG
GACTACTCCTTCGACACCTGCAAGCCGCCCGAGGAGCAGCTCACCTTCAAGGACCTGGTGTCCTGTGCCTACCAG
GTGGCCCGGGGCATGGAGTACTTGGCCTCCCAGAAG<u>TGCATCCACAGGGACCTGGCTGCCCGCAATGTGCTGGTG</u>
<u>ACCGAGGACAACGTGATGAAGATCGCAGACTTCGGGCTGGCCCGGGACGTGCACAACCTCGACTACTACAAGAAG</u>
<u>ACGACCAACGGCCGGCTGCCCGTGAAGTGGATGGCGCCTGAGGCCTTGTTTGACCGAGTCTACACTCACCAGAGT</u>
GACGT<u>CTGGTCCTTTGGGGTCCTGCTCTGGGAGATCTTCACGCTGGGGGGCTCCCCGTACCCCGGCATCCCTGTG</u>
<u>GAGGAGCTCTTCAAGCTGCTGAAGGAGGGCCACCGCATGGACAAGCCCGCCAACTGCACACACGACCTGTACATG</u>
ATCATGCGGGAGTGCTGGCATGCCGCGCCCTCCCAGAGGCCCACCTTCAAGCAGCTGGTGGAGGACCTGGACCGT
GTCCTTACCGTGACGTCCACCGAC<u>GAGTACCTGGACCTGTCGGCGCCTTTCGAGCAGTACTCCCCGGGTGGCCAG</u>
<u>GACACCCCCAGCTCCAGCTCCTCAGGGGACGACTCCGTGTTTGCCCACGACCTGCTGCCCCGGCCCCACCCAGC</u>
<u>AGTGGGGCTCGCGGACGTGA</u>

SEQ ID NO: 34. murine FGFR3
ATGGTAGTCCCGGCCTGCGTGCTAGTGTTCTGCGTGGCGGTCGTGGCTGGAGCTACTTCCGAGCCTCCTGGTCCA
GAGCAGCGAGTTGTGCGGAGAGCGGCAG<u>AGGTTCCAGGGCCTGAACCTAGCCAGCAGGAGCAGGTGGCCTTCGGC</u>
<u>AGTGGGGACACCGTGGAGCTGAGCTGCCATCCTCCTGGAGGTGCCCCCACAGGGCCCACGGTCTGGGCTAAGGAT</u>
<u>GGTACAGGTCTGGTGGCCTCCCACCGCATCCTGCTGGGGCCTCAGAGGCTGCAAGTGCTAAATGCCTCCCACGAA</u>
<u>GATGCAGGGGTCTACAGCTGCCAGCACCGGCTCACTCGGCGTGTGCTGTGCCACTTCAGTGTGCGTGTAACAGGG</u>
GCTCCTTATTGGACTCGCCCGGAGCGAATGGATAAGAAACTGCTGGCTGTGCCAGCCGCAAACACTGTCCGCTTC
CGCTGCCCAGCTGCTGGCAACCCTACCCCCTCCATCTCCTGGCTGAAGAATGGCAAAGAATTCCGAGGGGAGCAT
CGCATTGGGGGCATCAAG<u>CTCCGGCACCAGCAGTGGAGCTTGGTCATGGAAAGTGTGGTACCCTCCGATCGTGGC</u>
<u>AACTATACCTGTGTAGTTGAGAACAAGTTTGGCAGCATCCGGCAGACATACACACTGGATGTGCTGGAGCGCTCC</u>
CCACACCGGCCCATCCTGCAGGCTGGGCTGCCGGCCAACCAGACAGCCATTCTAGGCAGTGACGTGGAGTTCCAC
TGCAAGGTGTACAGCGATGCACAGCCACACATCCAGTGGCTGAAGCACGTGGAAGTGAACGGCAGCAAGGTGGGC
CCTGACGGCACGCCCTACGTCACTGTACTCAAG<u>ACTGCAGGCGCTAACACCACCGACAAGGAGCTAGAGGTTCTG</u>
<u>TCCTTGCACAATGTCACCTTTGAGGACGCGGGGGAGTACACCTGCCTGGCGGGCAATTCTATTGGGTTTTCCCAT</u>
<u>CACTCTGCGTGGCTGGTGGTGCTGCCAGCTGAGGAGGAGCTGATGGAAACTGATGAGGCTGGCAGCGTGTACGCA</u>
GGCGTCCTCAGCTACGGGGTGGTCTTCTTCCTCTTCATCCTGGTGGTGGCAGCTGTGATACTCTGCCGCCTGCGC
AGTCCCCCAAAGAAGGGCTTGGGCTCGCCCACCGTGCACAAGGTCTCTCGCTTCCCGCTTAAGCGACAG<u>GTGTCC</u>
<u>TTGGAATCTAACTCCTCTATGAACTCCAACACACCCCTTGTCCGGATTGCCCGGCTGTCCTCAGGAGAAGGTCCT</u>
<u>GTTCTGGCCAATGTTTCTGAACTTGAGCTGCCTGCTGACCCCAAGTGGGAGCTATCCAGGACCCGGCTGACACTT</u>
GGTAAGCCTCTTGGAGAAGGCTGCTTTGGACAGGTGGTCATGGCAGAAGCTATTGGCATCGACAAGGACCGTACT
GCCAAGCCTGTCACCGTGGCCGTGAAGATGCTGAAAG<u>ATGATGCGACTGACAAGGACCTGTCGGACCTGGTATCT</u>
<u>GAGATGGAGATGATGAAAATGATTGGCAAGCACAAGAACATCATTAACCTGCTGGGGGCGTGCACACAGGGTGGG</u>
CCCCTGTATGTGCTGGTGGAGTACGCAGCCAAGGGCAATCTCCGGGAGTTCCTTCGGGCGCGGCGGCCTCCAGGC
ATGGACTACTCCTTTGATGCCTGCAGGCTGCCAGAGGAACAGCTCACCTGCAAGGATCTAGTGTCCTGTGCCTAC
CAGGTGGCACGGGGCATGGAATACTTGGCTTCTCAGAAG<u>TGTATTCACAGAGACTTGGCTGCCAGAAACGTCCTG</u>

GTGACCGAGGACAATGTGATGAAGATTGCGGACTTTGGCCTGGCTCGAGATGTGCACAACCTGGACTACTACAAG
AAGACCACAAATGGCCGGCTACCTGTGAAGTGGATGGCACCAGAGGCCCTTTTTGACCGAGTCTACACCCACCAG
AGTGATGTTTGGTCTTTTGGTGTCCTCCTCTGGGAGATCTTTACGCTGGGGGGCTCACCGTATCCTGGCATCCCA
GTGGAAGAGCTTTTCAAGCTGTTGAAAGAGGGCCACCGCATGGACAAGCCAGCCAGCTGCACACATGACCTGTAC
ATGATCATGCGGGAATGTTGGCATGCGGTGCCTTCACAGAGGCCCACCTTCAAGCAGTTGGTAGAGGATTTAGAC
CGCATCCTCACTGTGACATCAACCGACGAGTACTTGGACCTCTCCGTGCCGTTTGAGCAGTACTCGCCAGGTGGC
CAGGACACGCCTAGCTCCAGCTCGTCCGGAGATGACTCGGTGTTCACCCATGACCTGCTACCCCAGGTCCACCC
AGTAACGGGGGACCTCGGACGTGA

SEQ ID NO: 35. human FGFR4
ATGCGGCTGCTGCTGGCCCTGTTGGGGGTCCTGCTGAGTGTGCCTGGGCCTCCAGTCTTGTCCCTGGAGGCCTCT
GAGGAAGTGGAGCTTGAGCCCTGCCTGGCTCCCAGCCTGGAGCAGCAAGAGCAGGAGCTGACAGTAGCCCTTGGG
CAGCCTGTGCGTCTGTGCTGTGGGCGGGCTGAGCGTGGTGGCCACTGGTACAAGGAGGGCAGTCGCCTGGCACCT
GCTGGCCGTGTACGGGGCTGGAGGGGCCGCCTAGAGATTGCCAGCTTCCTACCTGAGGATGCTGGCCGCTACCTC
TGCCTGGCACGAGGCTCCATGATCGTCCTGCAGAATCTCACCTTGATTACAGGTGACTCCTTGACCTCCAGCAAC
GATGATGAGGACCCCAAGTCCCATAGGGACCCCTCGAATAGGCACAGTTACCCCCAGCAAGCACCCTACTGGACA
CACCCCCAGCGCATGGAGAAGAAACTGCATGCAGTACCTGCGGGAACACCGTCAAGTTCCGCTGTCCAGCTGCA
GGCAACCCCACGCCCACCATCCGCTGGCTTAAGGATGGACAGGCCTTTCATGGGGAGAACCGCATTGGAGGCATT
CGGCTGCGCCATCAGCACTGGAGTCTCGTGATGGAGAGCGTGGTGCCCTCGGACCGCGGCACATACACCTGCCTG
GTAGAGAACGCTGTGGGCAGCATCCGCTATAACTACCTGCTAGATGTGCTGGAGCGGTCCCCGCACCGGCCCATC
CTGCAGGCCGGGCTCCCGGCCAACACCACAGCCGTGGTGGGCAGCGACGTGGAGCTGCTGTGCAAGGTGTACAGC
GATGCCCAGCCCCACATCCAGTGGCTGAAGCACATCGTCATCAACGGCAGCAGCTTCGGAGCCGACGGTTTCCCC
TATGTGCAAGTCCTAAAGACTGCAGACATCAATAGCTCAGAGGTGGAGGTCCTGTACCTGCGGAACGTGTCAGCC
GAGGACGCAGGCGAGTACACCTGCCTCGCAGGCAATTCCATCGGCCTCTCCTACCAGTCTGCCTGGCTCACGGTG
CTGCCAGAGGAGGACCCCACATGGACCGCAGCAGCGCCCGAGGCCAGGTATACGGACATCATCCTGTACGCGTCG
GGCTCCCTGGCCTTGGCTGTGCTCCTGCTGCTGGCCGGGCTGTATCGAGGGCAGGCGCTCCACGGCCGGCACCCC
CGCCCGCCCGCCACTGTGCAGAAGCTCTCCCGCTTCCCTCTGGCCCGACAGTTCTCCCTGGAGTCAGGCTCTTCC
GGCAAGTCAAGCTCATCCCTGGTACGAGGCGTGCGTCTCTCCTCCAGCGGCCCCGCCTTGCTCGCCGGCCTCGTG
AGTCTAGATCTACCTCTCGACCCACTATGGGAGTTCCCCGGGACAGGCTGGTGCTTGGGAAGCCCCTAGGCGAG
GGCTGCTTTGGCCAGGTAGTACGTGCAGAGGCCTTTGGCATGGACCCTGCCCGGCCTGACCAAGCCAGCACTGTG
GCCGTCAAGATGCTCAAAGACAACGCCTCTGACAAGGACCTGGCCGACCTGGTCTCGGAGATGGAGGTGATGAAG
CTGATCGGCCGACACAAGAACATCATCAACCTGCTTGGTGTCTGCACCCAGGAAGGGCCCCTGTACGTGATCGTG
GAGTGCGCCGCCAAGGGAAACCTGCGGGAGTTCCTGCGGGCCCGGCGCCCCCAGGCCCCGACCTCAGCCCCGAC
GGTCCTCGGAGCAGTGAGGGGCCGCTCTCCTTCCCAGTCCTGGTCTCCTGCGCCTACCAGGTGGCCCGAGGCATG
CAGTATCTGGAGTCCCGGAAGTGTATCCACCGGGACCTGGCTGCCCGCAATGTGCTGGTGACTGAGGACAATGTG
ATGAAGATTGCTGACTTTGGGCTGGCCCGCGGCGTCCACCACATTGACTACTATAAGAAAACCAGCAACGGCCGC
CTGCCTGTGAAGTGGATGGCGCCCGAGGCCTTGTTTGACCGGGTGTACACACACCAGAGTGACGTGTGGTCTTTT
GGGATCCTGCTATGGGAGATCTTCACCCTCGGGGGCTCCCCGTATCCTGGCATCCCGGTGGAGGAGCTGTTCTCG
CTGCTGCGGGAGGGACATCGGATGGACCGACCCCCACACTGCCCCCAGAGCTGTACGGGCTGATGCGTGAGTGC
TGGCACGCAGCGCCCTCCCAGAGGCCTACCTTCAAGCAGCTGGTGGAGGCGCTGGACAAGGTCCTGCTGGCCGTC -continued TCTGAGGAGTACCTCGACCTCCGCCTGACCTTCGGACCCTATTCCCCCTCTGGTGGGGACGCCAGCAGCACCTGC
TCCTCCAGCGATTCTGTCTTCAGCCACGACCCCCTGCCATTGGGATCCAGCTCCTTCCCCTTCGGGTCTGGGGTG
CAGACATGA SEQ ID NO: 36. murine FGFR4
ATGTGGCTGCTCTTTGGCCCTGTTGAGCATCTTTCAGGGGACACCAGCTTTGTCCCTTGAGGCCTCTGAGGAAATG
GAGCAGGAGCCCTGCCTAGCCCCAATCCTGGAGCAGCAAGAGCAGGTGTTGACGGTGGCCCTGGGGCAGCCTGTG
AGGCTGTGCTGTGGGCGCACCGAGCGTGGTCGTCACTGGTACAAAGAGGGCAGCCGCCTAGCATCTGCTGGGCGA
GTACGGGGTTGGAGAGGCCGCCTGGAGATCGCCAGCTTCCTTCCTGAGGATGCTGGCCGATACCTCTGCCTGGCC
CGTGGCTCCATGACCGTCGTACACAATCTTACGTTGCTTATGGATGACTCCTTAACCTCCATCAGTAATGATGAA
GACCCCAAGACACTCAGCAGCTCCTCGAGTGGTCATGTCTACCCACAGCAAGCACCCTACTGGACACACCCCCAA
CGCATGGAGAAGAAACTGCATGCAGTGCCTGCCGGGAATACTGTCAAATTCCGCTGTCCAGCTGCAGGGAACCCC
ATGCCTACCATCCACTGGCTCAAGGATGGACAGGCCTTCCACGGGGAGAATCGTATTGGAGGCATTCGGCTGCGC
CACCAACACTGGAGCCTGGTGATGGAAAGTGTGGTACCCTCGGACCGTGGCACATACACATGCCTTGTGGAGAAC
TCTCTGGGTAGCATTCGCTACAGCTATCTCCTGGATGTGCTGGAGCGGTCCCCGCACCGGCCCATCCTGCAGGCG
GGGCTCCCAGCCAACACCACAGCTGTGGTTGGCAGCGATGTGGAGCTACTCTGCAAGGTGTACAGCGACGCCCAG
CCCCACATACAGTGGCTGAAACACGTCGTCATCAACGGCAGCAGCTTCGGCGCCGACGGTTTCCCCTACGTACAA
GTCCTGAAGACAACAGACATCAATAGCTCGGAGGTAGAGGTCTTGTATCTGAGGAACGTGTCCGCTGAGGATGCA
GGAGAGTATACCTGTCTGGCGGGCAACTCCATCGGCCTTTCCTACCAGTCAGCGTGGCTCACGGTGCTGCCAGAG
GAAGACCTCACGTGGACAACAGCAACCCCTGAGGCCAGATACACAGATATCATCCTGTATGTATCAGGCTCACTG
GTTCTGCTTGTGCTCCTGCTGCTGGCCGGGGTGTATCATCGGCAAGTCATCCGTGGCCACTACTCTCGCCAGCCT
GTCACTATACAAAAGCTGTCCCGTTTCCCTTTGGCCCGACAGTTCTCTTTGGAGTCGAGGTCCTCTGGCAAGTCA
AGTTTGTCCCTGGTGCGAGGTGTCCGTCTCTCCTCCAGCGGCCCGCCCTTGCTCACGGGCCTTGTGAATCTAGAC
CTGCCTCTCGATCCGCTTTGGGAATTCCCCCGGGACAGGTTGGTGCTCGGAAAGCCCCTGGGTGAGGGCTGCTTT
GGGCAAGTGGTTCGTGCAGAGGCCTTTGGTATGGATCCCTCCCGGCCCGACCAAACCAGCACCGTGGCTGTGAAG
ATGCTGAAAGACAATGCCTCCGACAAGGATTTGGCAGACCTGGTCTCCGAGATGGAGGTGATGAAGCTAATCGGA
AGACACAAGAACATCATCAACCTGCTGGGTGTCTGCACTCAGGAAGGGCCCCTGTACGTGATTGTGGAATGTGCC
GCCAAGGGAAACCTTCGGGAATTCCTCCGTGCCCGGCGCCCCCCAGGCCCTGATCTCAGCCCTGATGGACCTCGG
AGCAGCGAAGGACCACTCTCCTTCCCGGCCCTAGTCTCCTGTGCCTACCAGGTGGCCCGAGGCATGCAGTATCTG
GAGTCTCGGAAGTGCATCCACCGGGACCTGGCTGCCCGAAATGTGCTGGTGACCGAGGATGATGTGATGAAGATC
GCTGACTTTGGGCTGGCACGTGGTGTCCACCACATTGACTACTATAAGAAAACCAGCAACGGCCGCCTGCCAGTC
AAATGGATGGCTCCAGAGGCATTGTTCGACCGCGTGTACACACACCAGAGTGACGTGTGGTCTTTCGGGATCCTG
CTGTGGGAAATCTTCACCCTCGGGGCTCCCCATACCCTGGCATTCCGGTGGAGGAGCTCTTCTCACTGCTGCGA
GAGGGGCACAGGATGGAGCGGCCCCCAAACTGCCCCTCAGAGCTGTATGGGCTAATGAGGGAGTGCTGGCACGCA
GCCCCATCTCAGAGGCCTACTTTTAAGCAGCTGGTGGAAGCTCTGGACAAGGTCCTGCTGGCTGTCTCTGAAGAG
TACCTTGACCTCCGCCTGACCTTTGGACCCTTTTCTCCCTCCAATGGGGATGCCAGCAGCACCTGCTCCTCCAGT
GACTCGGTTTTCAGCCACGACCCTTTGCCCCTCGAGCCAAGCCCCTTCCCTTTCTCTGACTCGCAGACGACATGA SEQ ID NO: 85 human FGFR3 spliceform c
ATGGGCGCCCCTGCCTGCGCCCTCGCGCTCTGCGTGGCCGTGGCCATCGTGGCCGGCGCCTCCTCGGAGTCCTTG
GGGACGGAGCAGCGCGTCGTGGGGCGAGCGGCAGAAGTCCCGGGCCCAGAGCCCGGCCAGCAGGAGCAGTTGGTC
TTCGGCAGCGGGGATGCTGTGGAGCTGAGCTGTCCCCCGCCCGGGGGTGGTCCCATGGGGCCCACTGTCTGGGTC
AAGGATGGCACAGGGCTGGTGCCCTCGGAGCGTGTCCTGGTGGGGCCCCAGCGGCTGCAGGTGCTGAATGCCTCC

```
CACGAGGACTCCGGGGCCTACAGCTGCCGGCAGCGGCTCACGCAGCGCGTACTGTGCCACTTCAGTGTGCGGGTG
ACAGACGCTCCATCCTCGGGAGATGACGAAGACGGGGAGGACGAGGCTGAGGACACAGGTGTGGACACAGGGGCC
CCTTACTGGACACGGCCCGAGCGGATGGACAAGAAGCTGCTGGCCGTGCCGGCCGCCAACACCGTCCGCTTCCGC
TGCCCAGCCGCTGGCAACCCCACTCCCTCCATCTCCTGGCTGAAGAACGGCAGGGAGTTCCGCGGCGAGCACCGC
ATTGGAGGCATCAAGCTGCGGCATCAGCAGTGGAGCCTGGTCATGGAAAGCGTGGTGCCCTCGGACCGCGGCAAC
TACACCTGCGTCGTGGAGAACAAGTTTGGCAGCATCCGGCAGACGTACACGCTGGACGTGCTGGAGCGCTCCCCG
CACCGGCCCATCCTGCAGGCGGGGCTGCCGGCCAACCAGACGGCCGTGCTGGGCAGCGACGTGGAGTTCCACTGC
AAGGTGTACAGTGACGCACAGCCCCACATCCAGTGGCTCAAGCACGTGGAGGTGAATGGCAGCAAGGTGGGCCCG
GACGGCACACCCTACGTTACCGTGCTCAAGACGGCGGGCGCTAACACCACCGACAAGGAGCTAGAGGTTCTCTCC
TTGCACAACGTCACCTTTGAGGACGCCGGGGAGTACACCTGCCTGGCGGGCAATTCTATTGGGTTTTCTCATCAC
TCTGCGTGGCTGGTGGTGCTGCCAGCCGAGGAGGAGCTGGTGGAGGCTGACGAGGCGGGCAGTGTGTATGCAGGC
ATCCTCAGCTACGGGGTGGGCTTCTTCCTGTTCATCCTGGTGGTGGCGGCTGTGACGCTCTGCCGCCTGCGCAGC
CCCCCCAAGAAAGGCCTGGGCTCCCCCACCGTGCACAAGATCTCCCGCTTCCCGCTCAAGCGACAGGTGTCCCTG
GAGTCCAACGCGTCCATGAGCTCCAACACACCACTGGTGCGCATCGCAAGGCTGTCCTCAGGGGAGGGCCCCACG
CTGGCCAATGTCTCCGAGCTCGAGCTGCCTGCCGACCCCAAATGGGAGCTGTCTCGGGCCCGGCTGACCCTGGGC
AAGCCCCTTGGGGAGGGCTGCTTCGGCCAGGTGGTCATGGCGGAGGCCATCGGCATTGACAAGGACCGGGCCGCC
AAGCCTGTCACCGTAGCCGTGAAGATGCTGAAAGACGATGCCACTGACAAGGACCTGTCGGACCTGGTGTCTGAG
ATGGAGATGATGAAGATGATCGGGAAACACAAAAACATCATCAACCTGCTGGGCGCCTGCACGCAGGGCGGGCCC
CTGTACGTGCTGGTGGAGTACGCGGCCAAGGGTAACCTGCGGGAGTTTCTGCGGGCGCGGCGGCCCCCGGGCCTG
GACTACTCCTTCGACACCTGCAAGCCGCCCGAGGAGCAGCTCACCTTCAAGGACCTGGTGTCCTGTGCCTACCAG
GTGGCCCGGGGCATGGAGTACTTGGCCTCCCAGAAGTGCATCCACAGGGACCTGGCTGCCCGCAATGTGCTGGTG
ACCGAGGACAACGTGATGAAGATCGCAGACTTCGGGCTGGCCCGGGACGTGCACAACCTCGACTACTACAAGAAG
ACGACCAACGGCCGGCTGCCCGTGAAGTGGATGGCGCCTGAGGCCTTGTTTGACCGAGTCTACACTCACCAGAGT
GACGTCTGGTCCTTTGGGGTCCTGCTCTGGGAGATCTTCACGCTGGGGGGCTCCCCGTACCCCGGCATCCCTGTG
GAGGAGCTCTTCAAGCTGCTGAAGGAGGGCCACCGCATGGACAAGCCCGCCAACTGCACACACGACCTGTACATG
ATCATGCGGGAGTGCTGGCATGCCGCGCCCTCCCAGAGGCCCACCTTCAAGCAGCTGGTGGAGGACCTGGACCGT
GTCCTTACCGTGACGTCCACCGACGAGTACCTGGACCTGTCGGCGCCTTTCGAGCAGTACTCCCCGGGTGGCCAG
GACACCCCCAGCTCCAGCTCCTCAGGGGACGACTCCGTGTTTGCCCACGACCTGCTGCCCCCGGCCCCACCCAGC
AGTGGGGCTCGCGGACGTGA
SEQ ID NO: 86 murine FGFR3 spliceform c
ATGGTAGTCCCGGCCTGCGTGCTAGTGTTCTGCGTGGCGGTCGTGGCTGGAGCTACTTCCGAGCCTCCTGGTCCA
GAGCAGCGAGTTGTGCGGAGAGCGGCAGAGGTTCCAGGGCCTGAACCTAGCCAGCAGGAGCAGGTGGCCTTCGGC
AGTGGGGACACCGTGGAGCTGAGCTGCCATCCTCCTGGAGGTGCCCCCACAGGGCCCACGGTCTGGGCTAAGGAT
GGTACAGGTCTGGTGGCCTCCACCGCATCCTGGTGGGGCCTCAGAGGCTGCAAGTGCTAAATGCCTCCCACGAA
GATGCAGGGGTCTACAGCTGCCAGCACCGGCTCACTCGGCGTGTGCTGTGCCACTTCAGTGTGCGTGTAACAGAT
GCTCCATCCTCAGGAGATGACGAAGATGGGGAGGACGTGGCTGAAGCACAGGGGCTCCTTATTGGACTCGCCCG
GAGCGAATGGATAAGAAACTGCTGGCTGTGCCAGCCGCAAACACTGTCCGCTTCCGCTGCCCAGCTGCTGGCAAC
CCTACCCCCTCCATCTCCTGGCTGAAGAATGGCAAAGAATTCCGAGGGGAGCATCGCATTGGGGCATCAAGCTC
CGGCACCAGCAGTGGAGCTTGGTCATGGAAAGTGTGGTACCCTCCGATCGTGGCAACTATACCTGTAGTTGAG
AACAAGTTTGGCAGCATCCGGCAGACATACACACTGGATGTGCTGGAGCGCTCCCCACACCGGCCCATCCTGCAG
GCTGGGCTGCCGGCCAACCAGACAGCCATTCTAGGCAGTGACGTGGAGTTCCACTGCAAGGTGTACAGCGATGCA
```

-continued

CAGCCACACATCCAGTGGCTGAAGCACGTGGAAGTGAACGGCAGCAAGGTGGGCCCTGACGGCACGCCCTACGTC
ACTGTACTCAAGACTGCAGGCGCTAACACCACCGACAAGGAGCTAGAGGTTCTGTCCTTGCACAATGTCACCTTT
GAGGACGCGGGGGAGTACACCTGCCTGGCGGGCAATTCTATTGGGTTTTCCCATCACTCTGCGTGGCTGGTGGTG
CTGCCAGCTGAGGAGGAGCTGATGGAAACTGATGAGGCTGGCAGCGTGTACGCAGGCGTCCTCAGCTACGGGGTG
GTCTTCTTCCTCTTCATCCTGGTGGTGGCAGCTGTGATACTCTGCCGCCTGCGCAGTCCCCCAAAGAAGGGCTTG
GGCTCGCCCACCGTGCACAAGGTCTCTCGCTTCCCGCTTAAGCGACAGGTGTCCTTGGAATCTAACTCCTCTATG
AACTCCAACACACCCCTTGTCCGGATTGCCCGGCTGTCCTCAGGAGAAGGTCCTGTTCTGGCCAATGTTTCTGAA
CTTGAGCTGCCTGCTGACCCCAAGTGGGAGCTATCCAGGACCCGGCTGACACTTGGTAAGCCTCTTGGAGAAGGC
TGCTTTGGACAGGTGGTCATGGCAGAAGCTATTGGCATCGACAAGGACCGTACTGCCAAGCCTGTCACCGTGGCC
GTGAAGATGCTGAAAGATGATGCGACTGACAAGGACCTGTCGGACCTGGTATCTGAGATGGAGATGATGAAAATG
ATTGGCAAGCACAAGAACATCATTAACCTGCTGGGGCGTGCACACAGGGTGGGCCCCTGTATGTGCTGGTGGAG
TACGCAGCCAAGGGCAATCTCCGGGAGTTCCTTCGGGCGCGGCGGCCTCCAGGCATGGACTACTCCTTTGATGCC
TGCAGGCTGCCAGAGGAACAGCTCACCTGCAAGGATCTAGTGTCCTGTGCCTACCAGGTGGCACGGGGCATGGAA
TACTTGGCTTCTCAGAAGTGTATTCACAGAGACTTGGCTGCCAGAAACGTCCTGGTGACCGAGGACAATGTGATG
AAGATTGCGGACTTTGGCCTGGCTCGAGATGTGCACAACCTGGACTACTACAAGAAGACCACAAATGGCCGGCTA
CCTGTGAAGTGGATGGCACCAGAGGCCCTTTTTGACCGAGTCTACACCCACCAGAGTGATGTTTGGTCTTTTGGT
GTCCTCCTCTGGGAGATCTTTACGCTGGGGGGCTCACCGTATCCTGGCATCCCAGTGGAAGAGCTTTTCAAGCTG
TTGAAAGAGGGCCACCGCATGGACAAGCCAGCCAGCTGCACACATGACCTGTACATGATCATGCGGGAATGTTGG
CATGCGGTGCCTTCACAGAGGCCCACCTTCAAGCAGTTGGTAGAGGATTTAGACCGCATCCTCACTGTGACATCA
ACCGACGAGTACTTGGACCTCTCCGTGCCGTTTGAGCAGTACTCGCCAGGTGGCCAGGACACGCCTAGCTCCAGC
TCGTCCGGAGATGACTCGGTGTTCACCCATGACCTGCTACCCCCAGGTCCACCCAGTAACGGGGACCTCGGACG
TGA

Amino Acid Sequence Sorted by Gene/Transcript
Code: non-underlined/underlined denoted alternating exons, bold face are aminoacids with intron-spanning codons SEQ ID NO: 15
human FGF8a
MGSPRSALSCLLLHLLVLCLQAQHVREQSLVTDQLSRRLIRTYQLYSRTSGKHVQVLANKRINAMAEDGDPFAKL
IVETDTFGSRVRVRGAETGLYICMNKKGKLIAKSNGKGKDCVFTEIVLENNYTALQNAKYEGWYMAFTRKGRPRK
GSKTRQHQREVHFMKRLPRGHHTTEQSLRFEFLNYPPFTRSLRGSQRTWAPEPR.

SEQ ID NO: 16
human FGF8b
MGSPRSALSCLLLHLLVLCLQAQVTVQSSPNFTQHVREQSLVTDQLSRRLIRTYQLYSRTSGKHVQVLANKRINA
MAEDGDPFAKLIVETDTFGSRVRVRGAETGLYICMNKKGKLIAKSNGKGKDCVFTEIVLENNYTALQNAKYEGWY
MAFTRKGRPRKGSKTRQHQREVHFMKRLPRGHHTTEQSLRFEFLNYPPFTRSLRGSQRTWAPEPR.

SEQ ID NO: 17
human FGF8e
MRSPRSALSCLLLHLLVLCLQAQEGPGRGPALGRELASLFRAGREPQGVSQQHVREQSLVTDQLSRRLIRTYQLY
SRTSGKEVQVLANKRINAMAEDGDPFAKLIVETDTFGSRVRVRGAETGLYICMNKKGKLIAKSNGKGKDCVFTEI
VLENNYTALQNAKYEGWYMAFTRKGRPRKGSKTRQHQREVHFMKRLPRGHHTTEQSLRFEFLNYPPFTRSLRGSQ
RTWAPEPR.

```
                                                             SEQ ID NO: 18
human FGF8f
MRSPRSALSCLLHLLVLCLQAQEGPGRGPALGRELASLFRAGREPQGVSQQVTVQSSPNFTQHVREQSLVTDQL

SRRLIRTYQLYSRTSGKHVQVLANKRINAMAEDGDPFAKLIVETDTFGSRVRVRGAETGLYICMNKKGKLIAKSN

GKGKDCVFTEIVLENNYTALQNAKYEGWYMAFTRKGRPRKGSKTRQHQREVHFMKRLPRGHHTTEQSLRFEFLNY

PPFTRSLRGSQRTWAPEPR.

SEQ ID NO: 19
murine FGF8a
MGSPRSALSCLLHLLVLCLQAQHVREQSLVTDQLSRRLIRTYQLYSRTSGKHVQVLANKRINAMAEDGDPFAKL

IVETDTFGSRVRVRGAETGLYICMNKKGKLIAKSNGKGKDCVFTEIVLENNYTALQNAKYEGWYMAFTRKGRPRK

GSKTRQHQREVHFMKRLPRGHHTTEQSLRFEFLNYPPFTRSLRGSQRTWAPEPR.

SEQ ID NO: 20
murine FGF8b
MGSPRSALSCLLHLLVLCLQAQVTVQSSPNFTQHVREQSLVTDQLSRRLIRTYQLYSRTSGKHVQVLANKRINA

MAEDGDPFAKLIVETDTFGSRVRVRGAETGLYICMNKKGKLIAKSNGKGKDCVFTEIVLENNYTALQNAKYEGWY

MAFTRKGRPRKGSKTRQHQREVHFMKRLPRGHHTTEQSLRFEFLNYPPFTRSLRGSQRTWAPEPR.

SEQ ID NO: 21
murine FGF8e
MGSPRSALSCLLHLLVLCLQAQEGPGGGPALGREPTSLLRAGREPQGVSQQHVREQSLVTDQLSRRLIRTYQLY

SRTSGKHVQVLANKRINAMAEDGDPFAKLIVETDTFGSRVRVRGAETGLYICMNKKGKLIAKSNGKGKDCVFTEI

VLENNYTALQNAKYEGWYMAFTRKGRPRKGSKTRQHQREVHFMKRLPRGHHTTEQSLRFEFLNYPPFTRSLRGSQ

RTWAPEPR.

SEQ ID NO: 22
murine FGF8f
MGSPRSALSCLLHLLVLCLQAQEGPGGGPALGREPTSLLRAGREPQGVSQQVTVQSSPNFTQHVREQSLVTDQL

SRRLIRTYQLYSRTSGKHVQVLANKRINAMAEDGDPFAKLIVETDTFGSRVRVRGAETGLYICMNKKGKLIAKSN

GKGKDCVFTEIVLENNYTALQNAKYEGWYMAFTRKGRPRKGSKTRQHQREVHFMKRLPRGHHTTEQSLRFEFLNY

PPFTRSLRGSQRTWAPEPR.

SEQ ID NO: 23
human FGF17
MGAARLLPNLTLCLQLLILCCQTQGENHPSPNFNQYVRDQGAMTDQLSRRQIREYQLYSRTSGKHVQVTGRRISA

TAEDGNKFAKLIVETDTFGSRVRIKGAESEKYICMNKRGKLIGKPSGKSKDCVFTEIVLENNYTAFQNARHEGWF

MAFTRQGRPRQASRSRQNQREAHFIKRLYQGQLPFPNHAEKQKQFEFVGSAPTRRTKRTRRPQPLT.

SEQ ID NO: 24
murine FGF17
MGAARLLPNLTLCLQLLILCCQTQGENHPSPNFNQYVRDQGAMTDQLSRRQIREYQLYSRTSGKHVQVTGRRISA

TAEDGNKFAKLIVETDTFGSRVRIKGAESEKYICMNKRGKLIGKPSGKSKDCVFTEIVLENNYTAFQNARHEGWF

MAFTRQGRPRQASRSRQNQREAHFIKRLYQGQLPFPNHAERQKQFEFVGSAPTRRTKRTRRPQSQT.

SEQ ID NO: 25
human FGF19
MRSGCVVVHVWILAGLWLAVAGRPLAFSDAGPHVHYGWGDPIRLRHLYTSGPHGLSSCFLRIRADGVVDCARGQS

AHSLLEIKAVALRTVAIKGVHSVRYLCMGADGKMQGLLQYSEEDCAFEEEIRPDGYNVYRSEKHRLPVSLSSAKQ

RQLYKNRGFLPLSHFLPMLPMVPEEPEDLRGHLESDMFSSPLETDSMDPFGLVTGLEAVRSPSFEK.

SEQ ID NO: 26
murine FGF15
MARKWNGRAVARALVLATLWLAVSGRPLAQQSQSVSDEDPLFLYGWGKITRLQYLYSAGPYVSNCFLRIRSDGSV

DCEEDQNERNLLEFRAVALKTTATKDVSSVRYLCMSADGKIYGLIRYSEEDCTFREEMDCLGYNQYRSMKHHLHI

IFIQAKPREQLQDQKPSNFIPVFHRSFFETGDQLRSKMFSLPLESDSMDPFRMVEDVDHLVKSPSFQK.
```

SEQ ID NO: 27
human FGF21
MDSDETGFEHSGLWVSVLAGLLLGACQAHPIPDSSPLLQFGGQVRQRYLYTDDAQQTEAHLEIREDGTVGGAADQ SPES<u>LLQLKALKPGVIQILGVKTSRFLCQRPDGALYGS</u>LHFDPEACSFRELLLEDGYNVYQSEAHGLPLHLPGNK

SPHRDPAPRGPARFLPLPGLPPALPEPPGILAPQPPDVGSSDPLSMVGPSQGRSPSYAS.

SEQ ID NO: 28
murine FGF21
MEWMRSRVGTLGLWVRLLLAVFLLGVYQAYPIPDSSPLLQFGGQVRQRYLYTDDDQDTEAHLEIREDGTVVGAAH RSPES<u>LLELKALKPGVIQILGVKASRFLCQQPDGALYGS</u>PHFDPEACSFRELLLEDGYNVYQSEAHGLPLRLPQK

DSPNQDATSWGPVRFLPMPGLLHEPQDQAGFLPPEPPDVGSSDPLSMVEPLQGRSPSYAS.

SEQ ID NO: 43
human FGFR1
MWSWKCLLFWAVLVTATLCTARPSPTLPEQA<u>QPWGAPVEVESFLVHPGDLLQLRCRLRDDVQSINWLRDGVQLAE</u>

<u>SNRTRITGEEVEVQDSVPADSGLYACVTSSPSGSDTTYFSVNVS</u>DALPSSEDDDDDDSSSEEKETDNTKPNPV<u>A</u>

<u>PYWTSPEKMEKKLHAVPAAKTVKFKCPSSGTPNPTLRWLKNGKEFKPDHRIGGYK</u>VRYATWSIIMDSVVPSDKGN

YTCIVENEYGSINHTYQLDVV<u>ERSPHRPILQAGLPANKTVALGSNVEFMCKVYSDPQPHIQWLKHIEVNGSKIGP</u>

<u>DNLPYVQILK</u>TAGVNTTDKEMEVLHLRNVSFEDAGEYTCLAGNSIGLSHHSAWLTVLEA<u>LEERPAVMTSPLYLEI</u>

<u>IIYCTGAFLISCMVGSVIVYKMKSGTKKSDFHSQMAVHKLAKSIPLRRQV</u>TVSADSSASMNSGVLLVRPSRLSSS

GTPMLAGVSEYELPEDPRWELPRD<u>RLVLGKPLGEGCFGQVVLAEATGLDKDKPNRVTKVAVKMLK</u>SDATEKDLSD

LISEMEMMKMIGKHKNIINLLGACTQDG<u>PLYVIVEYASKGNLREYLQARRPPGLEYCYNPSHNPEEQLSSKDLVS</u>

<u>CAYQVARGMEYLASKKC</u>IHRDLAARNVLVTEDNVMKIADEGLARDIHHIDYYKKTTNG<u>RLP</u>VKWMAPEALFDRIY

THQSDVWSFGVLLWEIFTLGGSPYPGVPVEELFKLLKEGHRMDKPSNCTNEL<u>YMMMRDCWHAVPSQRPTFKQLVE</u>

<u>DLDRIVALTSNQ</u>EYLDLSMPLDQYSPSFPDTRSSTCSSGEDSVFSHEPLPEEPCLPRHPAQLANGGLKRR.

SEQ ID NO: 44
murine FGFR1
MWGWKCLLFWAVLVTATLCTARPAPTLPEQA<u>QPWGVPVEVESLLVHPGDLLQIRCRLRDDVQSINWLRDGVQLVE</u>

<u>SNRTRITGEEVEVRDSIPADSGLYACVTSSPSGSDTTYFSVNVS</u>DALPSSEDDDDDDSSSEEKETDNTKPNRRP

<u>VAPYWTSPEKMEKKLHAVPAAKTVKFKCPSSGTPNPTLRWLKNGKEFKPDHRIGGYK</u>VRYATWSIIMDSVVPSDK

GNYTCIVENEYGSINHTYQLDVV<u>ERSPHRPILQAGLPANKTVALGSNVEFMCKVYSDPQPHIQWLKHIEVNGSKI</u>

<u>GPDNLPYVQILK</u>TAGVNTTDKEMEVLHLRNVSFEDAGETTCLAGNSIGLSHHSAWLTVLEA<u>LEERPAVMTSPLYL</u>

<u>EIIIYCTGAFLISCMLGSVIIYKMKSGTKKSDFHSQMAVHKLAKSIPLRRQV</u>TVSADSSASMNSGVLLVRPSRLS

SSGTPMLAGVSEYELPEDPRWELPRD<u>RLVLGKPLGEGCFGQVVLAEAIGLDKDKPNRVTKVAVKMLK</u>SDATEKDL

SDLISEMEMMKMIGKHKNIINLLGACTQDG<u>PLYVIVEYASKGNLREYLQARRPPGLEYCYNPSHNPEEQLSSKDL</u>

VSCAYQVARGMEYLASKKCIHRDLAARNVLVTEDNVMKIADFGLARDIHHIDYYKKTTNG<u>RLP</u>VKWMAPEALFDR

IYTH<u>QS</u>DVWSFGVLLWEIFTLGGSPYPGVPVEELFKLLKEGHRMDKPSNCTNEL<u>YMMMRDCWHAVPSQRPTFKQL</u>

<u>VEDLDRIVALTSNQ</u>EYLDLSIPLDQYSPSFPDTRSSTCSSGEDSVFSHEPLPEEPCLPRHPTQLANSGLKRR.

SEQ ID NO: 45
human FGFR2
MVSWGRFICLVVVTMATLSLARPSFSLVEDTTLEPEE<u>PPTKYQISQPEVYVAAPGESLEVRCLLKDAAVISWTKD</u>

<u>GVHLGPNNRTVLIGEYLQIKGATPRDSGLYACTASRTVDSETWYFMVNV</u>TDAISSGDDEDDTDGAEDFVSENSNN

KR<u>APYWTNTEKMEKRLHAVPAANTVKFRCPAGGNPMPTMRWLKNGKEFKQEHRIGGYK</u>VRNQHWSLIMESVVPSD

KGNYTCVVENEYGSINHTYHLDVV<u>ERSPHRPILQAGLPANASTVVGGDVEFVCKVYSDAQPHIQWIKHVEKNGSK</u>

<u>YGPDGLPYLKVLK</u>AAGVNTTDKEIEVLYIRNVTFEDAGEYTCLAGNSIGISFHSAWLTVLPA<u>PGREKEITASPDY</u>

<u>LEIAIYCIGVFLIACMVVTVILCRMKNTTKKPDFSSQPAVHKLTKRIPLRRQV</u>TVSAESSSSMNSNTPLVRITTR

LSSTADTPMLAGVSEYELPEDPKWEFPRD<u>KLTLGKPLGEGCFGQVVMAEAVGIDKDKPKEAVTVAVKMLK</u>DDATE

-continued

KDLSDLVSEMEMMKMIGKHKNIINLLGACTQDGPLYVIVEYASKGNLREYLRARRPPGMEYSYDINRVPEEQMTF

KDLVSCTYQLARGMEYLASQKCIHRDLAARNVLVTENNVMKIADFGLARDINNIDYYKKTTNGRLPVKWMAPEAL

FDRVYTHQSDVWSFGVLMWEIFTLGGSPYPGIPVEELFKLLKEGHRMDKPANCTNELYMMMRDCWHAVPSQRPTF

KQLVEDLDRILTLTTNEEYLDLSQPLEQYSPSYPDTRSSCSSGDDSVFSPDPMPYEPCLPQYPHINGSVKT.

SEQ ID NO: 46
murine FGFR2
MGLPSTWRYGRGPGIGTVTMVSWGRFICLVLVTMATLSLARPSFSLVEDTTLEPEEPPTKYQISQPEAYVVAPGE

SLELQCMLKDAAVISWTKDGVHLGPNNRTVLIGEYLQIKGATPRDSGLYACTAARTVDSETWYFMVNVTDAISSG

DDEDDTDSSEDVVSENRSNQRAPYWTNTEKMEKRLHAVPAANTVKFRCPAGGNPTPTMRWLKNGKEFKQEHRIGG

YKVRNQHWSLIMESVVPSDKGNYTCLVENEYGSINHTYHLDVVERSPHRPILQAGLPANASTVVGGDVEFVCKVY

SDAQPHIQWIKHVEKNGSKYGPDGLPYLKVLKAAGVNTTDKEIEVLYIRNVTFEDAGEYTCLAGNSIGISFHSAW

LTVLPAPVREKEITASPDYLETAIYCIGVFLIACMVVTVIFCRMKTTTKKPDFSSQPAVHKLTKRIPLRRQVTVS

AESSSSMNSNTPLVRITTRLSSTADTPMLAGVSEYELPEDPKWEFPRDKLTLGKPLGEGCFGQVVMAEAVGIDKD

KPKEAVTVAVKMLKDDATEKDLSDLVSEMEMMKMIGKHKNIINLLGACTQDGPLYVIVEYASKGNLREYLRARRP

PGMEYSYDINRVPEEQMTFKDLVSCTTQLARGMEYLASQKCIHRDLAARNVLVTENNVMKIADFGLARDINNIDY

YKKTTNGRLPVKWMAPEALFDRVYTHQSDVWSFGVLMWEIFTLGGSPYPGIPVEELFKLLKEGHRMDKPTNCTNE

LYMMMRDCWHAVPSQRPTFKQLVEDLDRILTLTTNEEYLDLTQPLEQYSPSYPDTRSSCSSGDDSVFSPDPMPYE

PCLPQYPHINGSVKT.

SEQ ID NO: 47
human FGFR3
MGAPACALALCVAVAIVAGASSESLGTEQRVVGRAAEVPGPEPGQQEQLVFGSGDAVELSCPPPGGGPMGPTVWV

KDGTGLVPSERVLVGPQRLQVLNASHEDSGAYSCRQRLTQRVLCHFSVRVTDAPSSGDDEDGEDEAEDTGVDTGA

PYWTRPERMDKKLLAVPAANTVRFRCPAAGNPTPSISWLKNGREFRGEHRIGGIKLRHQQWSLVMESVVPSDRGN

YTCVVENKFGSIRQTYTLDVLERSPHRPILQAGLPANQTAVLGSDVEFHCKVYSDAQPHIQWLKHVEVNGSKVGP

DGTPYVTVLKTAGANTTDKELEVLSLHNVTFEDAGEYTCLAGNSIGFSHHSAWLVVLPAEEELVEADEAGSVYAG

ILSYGVGFFLFILVVAAVTLCRLRSPPKKGLGSPTVHKISRFPLKRQVSLESNASMSSNTPLVRIARLSSGEGPT

LANVSELELPADPKWELSRARLTLGKPLGEGCFGQVVMAEAIGIDKDRAAKPVTVAVKMLKDDATDKDLSDLVSE

MEMMKMIGKHKNIINLLGACTQGGPLYVLVEYAAKGNLREFLRARRPPGLDYSFDTCKPPEEQLTFKDLVSCAYQ

VARGMEYLASQKCIHRDLAARNVLVTEDNVMKIADFGLARDVHNLDYYKKTTNGRLPVKWMAPEALFDRVYTHQS

DVWSFGVLLWEIFTLGGSPYPGIPVEELFKLLKEGHRMDKPANCTHDLYMIMRECWHAAPSQRPTFKQLVEDLDR

VLTVTSTDEYLDLSAPFEQYSPGGQDTPSSSSSGDDSVFAHDLLPPAPPSSGGSRT.

SEQ ID NO: 48
murine FGFR3
MVVPACVLVFCVAVVAGATSEPPGPEQRVVRRAAEVPGPEPSQQEQVAFGSGDTVELSCHPPGGAPTGPTVWAKD

GTGLVASHRILVGPQRLQVLNASHEDAGVYSCQHRLTRRVLCHFSVRVTGAPYWTRPERMDKKLLAVPAANTVRF

RCPAAGNPTPSISWLKNGKEFRGEHRIGGIKLRHQQWSLVMESVVPSDRGNYTCVVENKFGSIRQTYTLDVLERS

PHRPILQAGLPANQTAILGSDVEFHCKVYSDAQPHIQWLKHVEVNGSKVGPDGTPYVTVLKTAGANTTDKELEVL

SLHNVTFEDAGEYTCLAGNSIGFSHHSAWLVVLPAEEELMETDEAGSVYAGVLSYGVVFFLFILVVAAVILCRLR

SPPKKGLGSPTVHKVSRFPLKRQVSLESNSSMNSNTPLVRIARLSSGEGPVLANVSELELPADPKWELSRTRLTL

GKPLGEGCFGQVVMAEAIGIDKDRTAKPVTVAVKMLKDDATDKDLSDLVSEMEMMKMIGKHKNIINLLGACTQGG

PLYVLVEYAAKGNLREFLRARRPPGMDYSFDACRLPEEQLTCKDLVSCAYQVARGMEYLASQKCIHRDLAARNVL

VTEDNVMKIADFGLARDVHNLDYYKKTTNGRLPVKWMAPEALFDRVYTHQSDVWSFGVLLWEIFTLGGSPYPGIP

VEELFKLLKEGHRMDKPASCTHDLYMIMRECWHAVPSQRPTFKQLVEDLDRILTVTSTDEYLDLSVPFEQYSPGG

QDTPSSSSSGDDSVFTHDLLPPGPPSNGGPRT.

SEQ ID NO: 49
human FGFR4
MRLLLALLGVLLSVPGPPVLSLEASEEVELEPCLAPSLEQQEQELTVALGQPVRLCCGRAERGGHWYKEGSRLAP

AGRVRGWRGRLEIASFLPEDAGRYLCLARGSMIVLQNLTLITGDSLTSSNDDEDPKSHRDPSNRHSYPQQAPYWT

HPQRMEKKLHAVPAGNTVKFRCPAAGNPTPTIRWLKDGQAFHGENRIGGIRLRHQHWSLVMESVVPSDRGTYTCL

VENAVGSIRYNYLLDVLERSPHRPILQAGLPANTTAVVGSDVELLCKVYSDAQPHIQWLKHIVINGSSFGADGFP

YVQVLKTADINSSEVEVLYLRNVSAEDAGEYTCLAGNSIGLSYQSAWLTVLPEEDPTWTAAAPEARYTDIILYAS

GSLALAVLLLLAGLYRGQALHGRHPRPPATVQKLSRFPLARQFSLESGSSGKSSSSLVRGVRLSSSGPALLAGLV

SLDLPLDPLWEFPRDRLVLGKPLGEGCFGQVVRAEAFGMDPARPDQASTVAVKMLKDNASDKDLADLVSEMEVMK

LIGRHKNIINLLGVCTQEGPLYVIVECAAKGNLREFLRARRPPGPDLSPDGPRSSEGPLSFPVLVSCAYQVARGM

QYLESRKCIHRDLAARNVLVTEDNVMKIADFGLARGVHHIDYYKKTSNGRLPVKWMAPEALFDRVYTHQSDVWSF

GILLWEIFTLGGSPYPGIPVEELFSLLREGHRMDRPPHCPPELYGLMRECWHAAPSQRPTFKQLVEALDKVLLAV

SEEYLDLRLTFGPYSPSGGDASSTCSSSDSVFSHDPLPLGSSSFPFGSGVQT.

SEQ ID NO: 50
murine FGFR4
MWLLLALLSIFQGTPALSLEASEEMEQEPCLAPILEQQEQVLTVALGQPVRLCCGRTERGRHWYKEGSRLASAGR

VRGWRGRLEIASFLPEDAGRYLCLARGSMTVVHNLTLLMDDSLTSISNDEDPKTLSSSSSGHVYPQQAPYWTHPQ

RMEKKLHAVPAGNTVKFRCPAAGNPMPTIHWLKDGQAFHGENRIGGIRLRHQHWSLVMESVVPSDRGTYTCLVEN

SLGSIRYSYLLDVLERSPHRPILQAGLPANTTAVVGSDVELLCKVYSDAQPHIQWLKHVVINGSSFGADGFPYVQ

VLKTTDINSSEVEVLYLRNVSAEDAGEYTCLAGNSIGLSYQSAWLTVLPEEDLTWTTATPEARYTDIILYVSGSL

VLLVLLLLAGVYHRQVIRGHYSRQPVTIQKLSRFPLARQFSLESRSSGKSSLSLVRGVRLSSSGPPLLTGLVNLD

LPLDPLWEFPRDRLVLGKPLGEGCFGQVVRAEAFGMDPSRPDQTSTVAVKMLKDNASDKDLADLVSEMEVMKLIG

RHKNIINLLGVCTQEGPLYVIVECAAKGNLREFLRARRPPGPDLSPDGPRSSEGPLSFPALVSCAYQVARGMQYL

ESRKCIHRDLAARNVLVTEDDVMKIADFGLARGVHHIDYYKKTSNGRLPVKWMAPEALFDRVYTHQSDVWSFGIL

LWEIFTLGGSPYPGIPVEELFSLLREGHRMERPPNCPSELYGLMRECWHAAPSQRPTFKQLVEALDKVLLAVSEE

YLDLRLTFGPFSPSNGDASSTCSSSDSVFSHDPLPLEPSPFPFSDSQTT.

SEQ ID NO: 87
human FGFR3 spliceform c
MGAPACALALCVAVAIVAGASSESLGTEQRVVGRAAEVPGPEPGQQEQLVFGSGDAVELSCPPPGGGPMGPTVWV

KDGTGLVPSERVLVGPQRLQVLNASHEDSGAYSCRQRLTQRVLCHFSVRVTDAPSSGDDEDGEDEAEDTGVDTGA

PYWTRPERMDKKLLAVPAANTVRFRCPAAGNPTPSISWLKNGREFRGEHRIGGIKLRHQQWSLVMESVVPSDRGN

YTCVVENKFGSIRQTYTLDVLERSPHRPILQAGLPANQTAVLGSDVEFHCKVYSDAQPHIQWLKHVEVNGSKVGP

DGTPYVTVLKTAGANTTDKELEVLSLHNVTFEDAGEYTCLAGNSIGFSHHSAWLVVLPAEEELVEADEAGSVYAG

ILSYGVGFFLFILVVAAVTLCRLRSPPKKGLGSPTVHKISRFPLKRQVSLESNASMSSNTPLVRIARLSSGEGPT

LANVSELELPADPKWELSRARLTLGKPLGEGCFGQVVMAEAIGIDKDRAAKPVTVAVKMLKDDATDKDLSDLVSE

MEMMKMIGKHKNIINLLGACTQGGPLYVLVEYAAKGNLREFLRARRPPGLDYSFDTCKPPEEQLTFKDLVSCAYQ

VARGMEYLASQKCIHRDLAARNVLVTEDNVMKIADFGLARDVHNLDYYKKTTNGRLPVKWMAPEALFDRVYTHQS

DVWSFGVLLWEIFTLGGSPYPGIPVEELFKLLKEGHRMDKPANCTHDLYMIMRECWHAAPSQRPTFKQLVEDLDR

VLTVTSTDEYLDLSAPFEQYSPGGQDTPSSSSSGDDSVFAHDLLPPAPPSSGGSRT

SEQ ID NO: 88
murine FGFR3 spliceform c
MVVPACVLVFCVAVVAGATSEPPGPEQRVVRRAAEVPGPEPSQQEQVAFGSGDTVELSCHPPGGAPTGPTVWAKD

GTGLVASHRILVGPQRLQVLNASHEDAGVYSCQHRLTRRVLCHFSVRVTDAPSSGDDEDGEDVAEDTGAPYWTRP

ERMDKKLLAVPAANTVRFRCPAAGNPTPSISWLKNGKEFRGEHRIGGIKLRHQQWSLVMESVVPSDRGNYTCVVE

-continued

NKFGSIRQTYTLDVLERSPHRPILQAGLPANQTAILGSDVEFHCKVYSDAQPHIQWLKHVEVNGSKVGPDGTPYV
TVLKTAGANTTDKELEVLSLHNVTFEDAGEYTCLAGNSIGFSHHSAWLVVLPAEEELMETDEAGSVYAGVLSYGV
VFFLFILVVAAVILCRLRSPPKKGLGSPTVHKVSRFPLKRQVSLESNSSMNSNTPLVRIARLSSGEGPVLANVSE
LELPADPKWELSRTRLTLGKPLGEGCFGQVVMAEAIGIDKDRTAKPVTVAVKMLKDDATDKDLSDLVSEMEMMKM
IGKHKNIINLLGACTQGGPLYVLVEYAAKGNLREFLRARRPPGMDYSFDACRLPEEQLTCKDLVSCAYQVARGME
YLASQKCIHRDLAARNVLVTEDNVMKIADEGLARDVHNLDYYKKTTNGRLPVKWMAPEALFDRVYTHQSDVWSFG
VLLWEIFTLGGSPYPGIPVEELFKLLKEGHRMDKPASCTHDLYMIMRECWHAVPSQRPTFKQLVEDLDRILTVTS
TDEYLDLSVPFEQYSPGGQDTPSSSSSGDDSVFTHDLLPPGPPSNGGPRT

SEQ ID NO: 89
human FGFR1b based on Transcript FGFR1-020 ENST00000397108
MWSWKCLLFWAVLVTATLCTARPSPTLPEQAQPWGAPVEVESFLVHPGDLLQLRCRLRDDVQSINWLRDGVQLAE
SNRTRITGEEVEVQDSVPADSGLYACVTSSPSGSDTTYFSVNVSDALPSSEDDDDDDSSSEEKETDNTKPNPVA
PYWTSPEKMEKKLHAVPAAKTVKFKCPSSGTPNPTLRWLKNGKEFKPDHRIGGYKVRYATWSIIMDSVVPSDKGN
YTCIVENEYGSINHTYQLDVVERSPHRPILQAGLPANKTVALGSNVEFMCKVYSDPQPHIQWLKHIEVNGSKIGP
DNLPYVQILKTAGVNTTDKEMEVLHLRNVSFEDAGEYTCLAGNSIGLSHHSAWLTVLEALEERPAVMTSPLYLEI
IIYCTGAFLISCMVGSIVIYKMKSGTKKSDFHSQMAVHKLAKSIPLRRQVTSADSSASMNSGVLLVRPSRLSSS
GTPMLAGVSEYELPEDPRWELPRDRLVLGKPLGEGCFGQVVLAEAIGLDKDKPNRVTKVAVKMLKSDATEKDLSD
LISEMEMMKMIGKHKNIINLLGACTQDGPLYVIVEYASKGNLREYLQARRPPGLEYCYNPSHNPEEQLSSKDLVS
CAYQVARGMEYLASKKCIHRDLAARNVLVTEDNVMKIADFGLARDIHHIDYYKKTTNGRLPVKWMAPEALFDRIY
THQSDVWSFGVLLWEIFTLGGSPYPGVPVEELFKLLKEGHRMDKPSNCTNELYMMMRDCWHAVPSQRPTFKQLVE
DLDRIVALTSNQEYLDLSMPLDQYSPSFPDTRSSTCSSGEDSVFSHEPLPEEPCLPRHPAQLANGGLKRR SEQ ID NO: 90
human FGFR1c based on transcript FGFR1-011 ENST00000397103
MWSWKCLLFWAVLVTATLCTARPSPTLPEQDALPSSEDDDDDDSSSEEKETDNTKPNPVAPYWTSPEKMEKKLH
AVPAAKTVKFKCPSSGTPNPTLRWLKNGKEFKPDHRIGGYKVRYATWSIIMDSVVPSDKGNYTCIVENEYGSINH
TYQLDVVERSPHRPILQAGLPANKTVALGSNVEFMCKVYSDPQPHIQWLKHIEVNGSKIGPDNLPYVQILKHSGI
NSSDAEVLTLFNVTEAQSGEYVCKVSNYIGEANQSAWLTVTRPVAKALEERPAVMTSPLYLEIIIYCTGAFLISC
MVGSVIVYKMKSGTKKSDFHSQMAVHKLAKSIPLRRQVTSADSSASMNSGVLLVRPSRLSSSGTPMLAGVSEYE
LPEDPRWELPRDRLVLGKPLGEGCFGQVVLAEAIGLDKDKPNRVTKVAVKMLKSDATEKDLSDLISEMEMMKMIG
KHKNIINLLGACTQDGPLYVIVEYASKGNLREYLQARRPPGLEYCYNPSHNPEEQLSSKDLVSCAYQVARGMEYL
ASKKCIHRDLAARNVLVTEDNVMKIADFGLARDIHHIDYYKKTTNGRLPVKWMAPEALFDRIYTHQSDVWSFGVL
LWEIFTLGGSPYPGVPVEELFKLLKEGHRMDKPSNCTNELYMMMRDCWHAVPSQRPTFKQLVEDLDRIVALTSNQ
EYLDLSMPLDQYSPSFPDTRSSTCSSGEDSVFSHEPLPEEPCLPRHPAQLANGGLKRR SEQ ID NO: 91
human FGFR2b based on transcript FGFR2-201 ENST00000351936
MVSWGRFICLVVVTMATLSLARPSFSLVEDTTLEPEEPPTKYQISQPEVYVAAPGESLEVRCLLKDAAVISWTKD
GVHLGPNNRTVLIGEYLQIKGATPRDSGLYACTASRTVDSETWYFMVNVTDAISSGDDEDDTDGAEDFVSENSNN
KRAPYWTNTEKMEKRLHAVPAANTVKFRCPAGGNPMPTMRWLKNGKEFKQEHRIGGYKVRNQHWSLIMESVVPSD
KGNYTCVVENEYGSINHTYHLDVVERSPHRPILQAGLPANASTVVGGDVEFVCKVYSDAQPHIQWIKHVEKNGSK
YGPDGLPYLKVLKVFAAGVNTTDKEIEVLYIRNVTFEDAGEYTCLAGNSIGISFHSAWLTVLPAPGREKEITASP
DYLETATYCIGVFLIACMVVTVILCRMKNTTKKPDFSSQPAVHKLTKRIPLRRQVSAESSSSMNSNTPLVRITTR
LSSTADTPMLAGVSEYELPEDPKWEFPRDKLTLGKPLGEGCFGQVVMAEAVGIDKDKPKEAVTVAVKMLKDDATE
KDLSDLVSEMEMMKMIGKHKNIINLLGACTQDGPLYVIVEYASKGNLREYLRARRPPGMEYSYDINRVPEEQMTF
KDLVSCTYQLARGMEYLASQKCIHRDLAARNVLVTENNVMKIADFGLARDINNIDYYKKTTNGRLPVKWMAPEAL -continued

FDRVYTHQSDVWSFGVLMWEIFTLGGSPYPGIPVEELFKLLKEGHRMDKPANCTNELYMMRDCWHAVPSQRPTF

KQLVEDLDRILTLTTNEEYLDLSQPLEQYSPSYPDTRSSCSSGDDSVFSPDPMPYEPCLPQYPHINGSVKT

SEQ ID NO: 92
human FGFR2c based on transcript FGFR2-010 ENST00000457416
MVSWGRFICLVVVTMATLSLARPSFSLVEDTTLEPEEPPTKYQISQPEVYVAAPGESLEVRCLLKDAAVISWTKD

GVHLGPNNRTVLIGEYLQIKGATPRDSGLYACTASRTVDSETWYFMVNVTDAISSGDDEDDTDGAEDFVSENSNN

KRAPYWTNTEKMEKRLHAVPAANTVKFRCPAGGNPMPTMRWLKNGKEFKQEHRIGGYKVRNQHWSLIMESVVPSD

KGNYTCVVENEYGSI

NHTYHLDVVERSPHRPILQAGLPANASTVVGGDVEFVCKVYSDAQPHIQWIKHVEKNGSKYGPDGLPYLKVLKHS

GINSSNAEVLALFNVTEADAGEYICKVSNYIGQANQSAWLTVLPKQQAPGREKEITASPDYLEIAIYCIGVFLIA

CMVVTVILCRMKNTTKKPDFSSQPAVHKLTKRIPLRRQVTVSAESSSSMNSNTPLVRITTRLSSTADTPMLAGVS

EYELPEDPEWEPPRD

KLTLGKPLGEGCFGQVVMAEAVGIDKDKPKEAVTVAVKMLKDDATEKDLSDLVSEMEMMKMIGKHKNIINLLGAC

TQDGPLYVIVEYASKGNLREYLRARRPPGMEYSYDINRVPEEQMTFKDLVSCTYQLARGMEYLASQKCIHRDLAA

RNVLVTENNVMKIADFGLARDINNIDYYKKTINGRLPVKWMAPEALFDRVYTHQSDVWSFGVLMWEIFTLGGSPY

PGIPVEELFKLLKEG

HRMDKPANCTNELYMMMRDCWHAVPSQRPTFKQLVEDLDRILTLTTNEEYLDLSQPLEQYSPSYPDTRSSCSSGD

DSVFSPDPMPYEPCLPQYPHINGSVKT

SEQ ID NO: 93
human FGFR3b based on transcript FGFR3-201 ENST00000340107
MGAPACALALCVAVAIVAGASSESLGTEQRVVGRAAEVPGPEPGQQEQLVFGSGDAVELSCPPPGGGPMGPTVWV

KDGTGLVPSERVLVGPQRLQVLNASHEDSGAYSCRQRLTQRVLCHFSVRVTDAPSSGDDEDGEDEAEDTGVDTGA

PYWTRPERMDKKLLAVPAANTVRFRCPAAGNPTPSISWLKNGREFRGEHRIGGIKLRHQQWSLVMESVVPSDRGN

YTCVVENKFGSIRQT

YTLDVLERSPHRPILQAGLPANQTAVLGSDVEFHCKVYSDAQPHIQWLKHVEVNGSKVGPDGTPYVTVLKSWISE

SVEADVRLRLANVSERDGGEYLCPATNFIGVAEKAFWLSVHGPRAAEEELVEADEAGSVYAGILSYGVGFFLFIL

VVAAVTLCRLRSPPKKGLGSPTVHKISRFPLKRQVSLESNASMSSNTPLVRIARLSSGEGPTLANVSELELPADP

KWELSRARLTLGKPL

GEGCFGQVVMAEAIGIDKDRAAKPVTVAVKMLKDDATDKDLSDLVSEMEMMKMIGKHKNIINLLGACTQGGPLYV

LVEYAAKGNLREFLRARRPPGLDYSFDTCKPPEEQLTFKDLVSCAYQVARGMEYLASQKCIHRDLAARNVLVTED

NVMKIADFGLARDVHNLDYYKKTTNGRLPVKWMAPEALFDRVYTHQSDVWSFGVLLWEIFTLGGSPYPGIPVEEL

FKLLKEGHRMDKPAN

CTHDLYMIMRECWHAAPSQRPTFKQLVEDLDRVLTVTSTDEYLDLSAPFEQYSPGGQDTPSSSSSGDDSVFAHDL

LPPAPPSSGGSRT

SEQ ID NO: 94
human FGFR3c based on transcript FGFR3-203: ENST00000440486
MGAPACALALCVAVAIVAGASSESLGTEQRVVGRAAEVPGPEPGQQEQLVFGSGDAVELSCPPPGGGPMGPTVWV

KDGTGLVPSERVLVGPQRLQVLNASHEDSGAYSCRQRLTQRVLCHFSVRVTDAPSSGDDEDGEDEAEDTGVDTGA

PYWTRPERMDKKLLAVPAANTVRFRCPAAGNPTPSISWLKNGREFRGEHRIGGIKLRHQQWSLVMESVVPSDRGN

YTCVVENKFGSIRQT

YTLDVLERSPHRPILQAGLPANQTAVLGSDVEFHCKVYSDAQPHIQWLKHVEVNGSKVGPDGTPYVTVLKTAGAN

TTDKELEVLSLHNVTFEDAGEYTCLAGNSIGFSHHSAWLVVLPAEEELVEADEAGSVYAGILSYGVGFFLFILVV

AAVTLCRLRSPPKKGLGSPTVHKISRFPLKRQVSLESNASMSSNTPLVRIARLSSGEGPTLANVSELELPADPKW

ELSRAR<u>LTLGKPLGE</u>

<u>GCFGQVVMAEAIGIDKDRAAKPVTVAVKMLK</u>DDATDKDLSDLVSEMEMMKMIGKHKNIINLLGACTQGG<u>PLYVLV</u>

<u>EYAAKGNLREFLRARRPPGLDYSFDTCKPPEEQLTFKDLVSCAYQVARGMEYLASQK</u>CIHRDLAARNVLVTEDNV

MKIADFGLARDVHNLDYYKKTTN<u>GRLPVKWMAPEALFDRVYTHQSD</u>VWSFGVLLWEIFTLGGSPYPGIPVEELFK

LLKEGHRMDKPANCT

HDL<u>YMIMRECWHAAPSQRPTFKQLVEDLDRVLTVTSTD</u>EYLDLSAPFEQYSPGGQDTPSSSSSGDDSVFAHDLLP

PAPPSSGGSRT

SEQ ID NO: 95
murine FGFR1b based on transcript FGFR1-201 ENSMUST00000178276
MWGWKCLLFWAVLVTATLCTARPAPTLPEQD<u>ALPSSEDDDDDDDSSSEEKETDNTKPNP</u>VAPYWTSPEKMEKKLH AVPAAKTVKFKCPSSGTPNPTLRWLKNGKEFKPDHRIGGYK<u>VRYATWSIIMDSVVPSDKGNYTCIVENEYGSINH</u>

<u>TYQLDVVERS</u>PHRPILQAGLPANKTVALGSNVEFMCKVYSDPQPHIQWLKHIEVNGSKIGPDNLPYVQILK<u>HSGI</u>

<u>NSSDAEVLTLFNVTE</u>

<u>AQSGEYVCKVSNYIGEANQSAWLTVTRPVAKALEERPAVMTSPLYLEIIIYCTGAFLISCMLGSVIIYKMKSGTK</u>

<u>KSDFHSQMAVHKLAKSIPLRRQVT</u><u>VSADSSASMNSGVLLVRPSRLSSSGTPMLAGVSEYELPEDPRWELPRDRLV</u>

LGKPLGEGCFGQVVLAEAIGLDKDKPNRVTKVAVKMLKS<u>DATEKDLSDLISEMEMMKMIGKHKNI</u>INLLGACTQD

GPLYVIVEYASKGNL

REYLQARRPPGLEYCYNPSHNPEEQLSSKDLVSCAYQVARGMEYLASKK<u>CIHRDLAARNVLVTEDNVMKIADFGL</u>

<u>ARDIHHIDYYKKTTNGRLPVKWMAPEALFDRIYTHQSD</u><u>WSFGVLLWEIFTLGGSPYPGVPVEELFKLLKEGHRM</u>

<u>DKPSNCTNELYMMMRDCWHAVPSQRPTFKQLVEDLDRIVALTSNQ</u><u>EYLDLSIPLDQYSPSFPDTRSSTCSSGEDS</u>

<u>VFSHEPLPEEPCLPR</u>

<u>HPTQLANSGLKRR</u>

SEQ ID NO: 96
murine FGFR1c based on transcript FGFR1-202 ENSMUST00000179592
MWGWKCLLFWAVLVTATLCTARPAPTLPEQV<u>GSSSWPLWVAAAAQPWGVPVEVESLLVHPGDLLQLRCRLRDDVQ</u>

<u>SINWLRDGVQLVESNRTKITGEEVEVRDSIPADSGLYACVTSSPSGSDTTYFSVNV</u>SDALPSSEDDDDDDSSSE

EKETDNTKPNP<u>VAPYWTSPEKMEKKLHAVPAAKTVKFKCPSSGTPNPTLRWLKNGKEFKPDHRIGGYK</u>VRYATWS

IIMDSVVPSDKGNYT

CIVENEYGSINHTYQLDVV<u>ERSPHRPILQAGLPANKTVALGSNVEFMCKVYSDPQPHIQWLKHIEVNGSKIGPDN</u>

<u>LPYVQILK</u>TAGVNTTDKEMEVLHLRNVSFEDAGEYTCLAGNSIGLSHHSAWLTVLE<u>ALEERPAVMTSPLYLEIII</u>

<u>YCTGAFLISCMLGSVIIYKMKSGTKKSDFHSQMAVHKLAKSIPLRRQVT</u>VSADSSASMNSGVLLVRPSRLSSSGT

PMLAGVSEYELPEDP

RWELPRDR<u>LVLGKPLGEGCFGQVVLAEAIGLDKDKPNRVTKVAVKMLK</u>SDATEKDLSDLISEMEMMKMIGKHKNI

INLLGACTQDG<u>PLYVIVEYASKGNLREYLQARRPPGLEYCYNPSHNPEEQLSSKDLVSCAYQVARGMEYLASKKC</u>

IHRDLAARNVLVTEDNVMKIADFGLARDIHHIDYYKKTTN<u>GRLPVKWMAPEALFDRIYTHQSD</u>VWSFGVLLWEIF

TLGGSPYPGVPVEEL

FKLLKEGHRMDKPSNCTNEL<u>YMMMRDCWHAVPSQRPTFKQLVEDLDRIVALTSNQEYLDLSIPLDQYSPSFPDTR</u>

SSTCSSGEDSVFSHEPLPEEPCLRHPTQLANSGLKRR

SEQ ID NO: 97
murine FGFR2b based on transcript FGFR2-011 ENSMUST00000119260
MVSWGRFICLVLVTMATLSLARPSFSLVEDTTLEPEE<u>PPTKYQISQPEAYVVAPGESLELQCMLKDAAVISWTKD</u>

<u>GVHLGPNNRTVLIGEYLQIKGATPRDSGLYACTAARTVDSETWYFMVNV</u>TDAISSGDDEDDTDSSEDVVSENRSN

<u>QRAPYWTNTEKMEKRLHAVPAANTVKFRCPAGGNPTPTMRWLKNGKEFKQEHRIGGYK</u>VRNQHWSLIMESVVPSD

KGNYTCLVENEYGSI

-continued

NHTYHLDVVERSPHRPILQAGLPANASTVVGGDVEFVCKVYSDAQPHIQWIKHVEKNGSKYGPDGLPYLKVLKAA

GVNTTDKEIEVLYIRNVTFEDAGEYTCLAGNSIGISFHSAWLTVLPAPVREKEITASPDYLETATYCIGVFLIAC

MVVTVIFCRMKTTTKKPDFSSQPAVHKLTKRIPLRRQVSAESSSSMNSNTPLVRITTRLSSTADTPMLAGVSEYE

LPEDPKWEFPRDKLT

LGKPLGEGCFGQVVMAEAVGIDKDKPKEAVTVAVKMLKDDATEKDLSDLVSEMEMMKMIGKHKNIINLLGACTQD

GPLYVIVEYASKGNLREYLRARRPPGMEYSYDINRVPEEQMTFKDLVSCTYQLARGMEYLASQKCIHRDLAARNV

LVTENNVMKIADFGLARDINNIDYYKKTTNGRLPVKWMAPEALFDRVYTHQSDVWSFGVLMWEIFTLGGSPYPGI

PVEELFKLLKEGHRM

DKPTNCTNELYMMMRDCWHAVPSQRPTFKQLVEDLDRILTLTTNEEYLDLTQPLEQYSPSYPDTRSSCSSGDDSV

FSPDPMPYEPCLPQYPHINGSVKT

SEQ ID NO: 98
murine FGFR2c based on transcript FGFR2-012 ENSMUST00000117089
MVSWGRFICLVLVTMATLSLARPSFSLVEDTTLEPEEPPTKYQISQPEAYVVAPGESLELQCMLKDAAVISWTKD

GVHLGPNNRTVLIGEYLQIKGATPRDSGLYACTAARTVDSETWYFMVNVTDAISSGDDEDDTSSEDVVSENRSN

QRAPYWTNTEKMEKRLHAVPAANTVKFRCPAGGNPTPTMRWLKNGKEFKQEHRIGGYKVRNQHWSLIMESVVPSD

KGNYTCLVENEYGSI

NHTYHLDVVERSPHRPILQAGLPANASTVVGGDVEFVCKVYSDAQPHIQWIKHVEKNGSKYGPDGLPYLKVLKHS

GINSSNAEVLALFNVTEMDAGEYICKVSNYIGQANQSAWLTVLPKQQAPVREKEITASPDYLELAIYCIGVFLIA

CMVVTVIFCRMKTTTKKPDFSSQPAVHKLTKRIPLRRQVSAESSSSMNSNTPLVRITTRLSSTADTPMLAGVSEY

ELPEDPKWEFPRDKL

TLGKPLGEGCFGQVVMAEAVGIDKDKPKEAVTVAVKMLKDDATEKDLSDLVSEMEMMKMIGKHKNIINLLGACTQ

DGPLYVIVEYASKGNLREYLRARRPPGMEYSYDINRVPEEQMTFKDLVSCTYQLARGMEYLASQKCIHRDLAARN

VLVTENNVMKIADFGLARDINNIDYYKKTTNGRLPVKWMAPEALFDRVYTHQSDVWSFGVLMWEIFTLGGSPYPG

IPVEELFKLLKEGHR

MDKPTNCTNELYMMMRDCWHAVPSQRPTFKQLVEDLDRILTLTTNEEYLDLTQPLEQYSPSYPDTRSSCSSGDDS

VFSPDPMPYEPCLPQYPHINGSVKT

SEQ ID NO: 99
murine FGFR3b based on transcipt FGFR3-201 ENSMUST00000114411
MVVPACVLVFCVAVVAGATSEPPGPEQRVVRRAAEVPGPEPSQQEQVAFGSGDTVELSCHPPGGAPTGPTVWAKD

GTGLVASHRILVGPQRLQVLNASHEDAGVYSCQHRLTRRVLCHFSVRVTDAPSSGDDEDGEDVAEDTGAPYWTRP

ERMDKKLLAVPAANTVRFRCPAAGNPTPSISWLKNGKEFRGEHRIGGIKLRHQQWSLVMESVVPSDRGNYTCVVE

NKFGSIRQTYTLDVL

ERSPHRPILQAGLPANQTAILGSDVEFHCKVYSDAQPHIQWLKHVEVNGSKVGPDGTPYVTVLKSWISENVEADA

RLRLANVSERDGGEYLCRATNFIGVAEKAFWLRVHGPQAAEEELMETDEAGSVYAGVLSYGVVFFLFILVVAAVI

LCRLRSPPKKGLGSPTVHKVSRFPLKRQVSLESNSSMNSNTPLVRIARLSSGEGPVLANVSELELPADPKWELSR

TRLTLGKPLGEGCFG

QVVMAEAIGIDKDRTAKPVTVAVKMLKDDATDKDLSDLVSEMEMMKMIGKHKNIINLLGACTQGGPLYVLVEYAA

KGNLREFLRARRPPGMDYSFDACRLPEEQLTCKDLVSCAYQVARGMEYLASQKCIHRDLAARNVLVTEDNVMKIA

DFGLARDVHNLDYYKKTTNGRLPVKWMAPEALFDRVYTHQSDVWSFGVLLWEIFTLGGSPYPGIPVEELFKLLKE

GHRMDKPASCTHDLY

MIMRECWHAVPSQRPTFKQLVEDLDRILTVTSTDEYLDLSVPFEQYSPGGQDTPSSSSSGDDSVFTHDLLPPGPP

SNGGPRT

SEQ ID NO: 100
murine FGFR3c based on transcript FGFR3-202 ENSMUST00000169212
MVVPACVLVECVAVVAGATSEPPGPEQRVVRRAAEVPGPEPSQQEQVAFGSGDTVELSCHPPGGAPTGPTVWAKD

GTGLVASHRILVGPQRLQVLNASHEDAGVYSCQHRLTRRVLCHFSVRVTDAPSSGDDEDGEDVAEDTGAPYWTRP

ERMDKKLLAVPAANTVRFRCPAAGNPTPSISWLKNGKEFRGEHRIGGIKLRHQQWSLVMESVVPSDRGNYTCVVE

NKFGSIRQTYTLDVL

ERSPHRPILQAGLPANQTAILGSDVEFHCKVYSDAQPHIQWLKHVEVNGSKVGPDGTPYVTVLKTAGANTTDKEL

EVLSLHNVTFEDAGEYTCLAGNSIGFSHHSAWLVVLPAEEELMETDEAGSVYAGVLSYGVVFFLFILVVAAVILC

RLRSPPKKGLGSPTVHKVSRFPLKRQVSLESNSSMNSNTPLVRIARLSSGEGPVLANVSELELPADPKWELSRTR

LTLGKPLGEGCFGQV

VMAEAIGIDKDRTAKPVTVAVKMLKDDATDKDLSDLVSEMEMMKMIGKHKNIINLLGACTQGGPLYVLVEYAAKG

NLREFLRARRPPGMDYSFDACRLPEEQLTCKDLVSCAYQVARGMEYLASQKCIHRDLAARNVLVTEDNVMKIADF

GLARDVHNLDYYKKTTNGRLPVKWMAPEALFDRVYTHQSDVWSFGVLLWEIFTLGGSPYPGIPVEELFKLLKEGH

RMDKPASCTHDLYMI

MRECWHAVPSQRPTFKQLVEDLDRILTVTSTDEYLDLSVPFEQYSPGGQDTPSSSSSGDDSVFTHDLLPPGPPSN

GGPRT

Primer Sequences:

Actb
(SEQ ID NO: 51)
AGAGGGAAATCGTGCGTGAC, (SEQ ID NO: 52)
CAATAGTGATGACCTGGCCGT;

Cidea
(SEQ ID NO: 53)
TGCTCTTCTGTATCGCCCAGT, (SEQ ID NO: 54)
GCCGTGTTAAGGAATCTGCTG;

Cox7a1
(SEQ ID NO: 55)
CCGACAATGACCTCCCAGTA, (SEQ ID NO: 56)
TGTTTGTCCAAGTCCTCCAA;

Elovl3
(SEQ ID NO: 57)
TCCGCGTTCTCATGTAGGTCT, (SEQ ID NO: 58)
GGACCTGATGCAACCCTATGA;

Foxc2
(SEQ ID NO: 59)
ACGAGTGCGGATTTGTAACC, (SEQ ID NO: 60)
CAGTTTGGGGAGGGACCTAT;

Hsp90
(SEQ ID NO: 61)
AGGAGGGTCAAGGAAGTGGT, (SEQ ID NO: 62)
TTTTTCTTGTCTTTGCCGCT;

Otop1
(SEQ ID NO: 63)
GGACCTGATGCAACCCTATGA, (SEQ ID NO: 64)
ACCATGCTCTACGTGCTGTG;

Ppargc1a
(SEQ ID NO: 65)
GGACGGAAGCAATTTTTCAA, (SEQ ID NO: 66)
GAGTCTTGGGAAAGGACACG;

Prb
(SEQ ID NO: 67)
TAAACATCTCCCAGCGGAGT, (SEQ ID NO: 68)
ACAACCATGAGCCAGGAGTC;

Prdm16
(SEQ ID NO: 69)
CTGTTAGCTTTGGAGCCGAC, (SEQ ID NO: 70)
GACGAGGGTCCTGTGATGTT;

Ucp1
(SEQ ID NO: 71)
TCTCTGCCAGGACAGTACCC, (SEQ ID NO: 72)
AGAAGCCCAATGATGTTCAG;

Fgfr1
(SEQ ID NO: 73)
CCGGATCTACACACACCAGA, (SEQ ID NO: 74)
CCACCAACTGCTTGAACGTA;

Fgfr2
(SEQ ID NO: 75)
AGGGACACAGGATGGACAAG, (SEQ ID NO: 76)
AAACACAGAATCGTCCCTG;

-continued

Fgfr3 (SEQ ID NO: 77)
ACCGAGTCTACACCCACCAG, (SEQ ID NO: 78)
TGAGGATGCGGTCTAAATCC;

Fgfr4 (SEQ ID NO: 79)
TGGAAGCTCTGGACAAGGTC, (SEQ ID NO: 80)
ATACAACATTGCTGCTCCCC;

aklotho (SEQ ID NO: 81)
GGCTCAACTCTCCCAGTCAG, (SEQ ID NO: 82)
CGCAAACTAGCCACAAAGGT;

bklotho (SEQ ID NO. 83)
ATGTCCAGGAGGCTCTGAAA, (SEQ ID NO: 84)
AGCAAATGGTGCAGTCTGTG fgfr3c rev (SEQ ID NO: 101)
CTCCTTGTCGGTGGT
and fgfr3c fwd (SEQ ID NO: 102)
ACGGCACGCCCT ACG.

Human and murine FGF8 isoforms have the following level of identity of amino acid sequences: FGF8a 100%, FGF8b 100%, FGF8e 98.28%, FGF8f 98.36%. Human and murine FGF8 isoforms have the following level of identity of nucleic acid level: FGF8a: 94.96%, FGF8b 95.22%, FGF8e 94.59%, FGF8f 94.83%.

| aa-Human vs. Mouse FGF8a | | | |
|---|---|---|---|
| Percent | Identity | Matrix - created by Clustal2.1 | |
| 1: | h8a | 100.00 | 100.00 |
| 2: | m8a | 100.00 | 100.00 |

CLUSTAL O(1.2.1) multiple sequence alignment

```
h8a     MGSPRSALSCLLLHLLVLCLQAQHVREQSLVTDQLSRRLIRTYQLYSRTSGKHVQVLANK
m8a     MGSPRSALSCLLLHLLVLCLQAQHVREQSLVTDQLSRRLIRTYQLYSRTSGKHVQVLANK
        ************************************************************
h8a     RINAMAEDGDPFAKLIVETDTFGSRVRVRGAETGLYICMNKKGKLIAKSNGKGKDCVFTE
m8a     RINAMAEDGDPFAKLIVETDTFGSRVRVRGAETGLYICMNKKGKLIAKSNGKGKDCVFTE
        ************************************************************
h8a     IVLENNYTALQNAKYEGWYMAFTRKGRPRKGSKTRQHQREVHFMKRLPRGHHTTEQSLRF
m8a     IVLENNYTALQNAKYEGWYMAFTRKGRPRKGSKTRQHQREVHFMKRLPRGHHTTEQSLRF
        ************************************************************
h8a     EFLNYPPFTRSLRGSQRTWAPEPR (SEQ ID NO: 15)
m8a     EFLNYPPFTRSLRGSQRTWAPEPR (SEQ ID NO: 19)
        ***********************
```

| aa-Human vs. Mouse FGF8b | | | |
|---|---|---|---|
| Percent | Identity | Matrix - created by Clustal2.1 | |
| 1: | h8b | 100.00 | 100.00 |
| 2: | m8b | 100.00 | 100.00 |

CLUSTAL O(1.2.1) multiple sequence alignment

```
h8b     MGSPRSALSCLLLHLLVLCLQAQVTVQSSPNFTQHVREQSLVTDQLSRRLIRTYQLYSRT
m8b     MGSPRSALSCLLLHLLVLCLQAQVTVQSSPNFTQHVREQSLVTDQLSRRLIRTYQLYSRT
        ************************************************************
h8b     SGKHVQVLANKRINAMAEDGDPFAKLIVETDTFGSRVRVRGAETGLYICMNKKGKLIAKS
m8b     SGKHVQVLANKRINAMAEDGDPFAKLIVETDTFGSRVRVRGAETGLYICMNKKGKLIAKS
        ************************************************************
h8b     NGKGKDCVFTEIVLENNYTALQNAKYEGWYMAFTRKGRPRKGSKTRQHQREVHFMKRLPR
m8b     NGKGKDCVFTEIVLENNYTALQNAKYEGWYMAFTRKGRPRKGSKTRQHQREVHFMKRLPR
        ************************************************************
h8b     GHHTTEQSLRFEFLNYPPFTRSLRGSQRTWAPEPR (SEQ ID NO: 16)
m8b     GHHTTEQSLRFEFLNYPPFTRSLRGSQRTWAPEPR (SEQ ID NO: 20)
        **********************************
```

| aa-Human vs. Mouse FGF8e | | | |
|---|---|---|---|
| Percent | Identity | Matrix - created by Clustal2.1 | |
| 1: | h8e | 100.00 | 98.28 |
| 2: | m8e | 98.28 | 100.00 |

-continued

| CLUSTAL O(1.2.1) multiple sequence alignment |
| --- |

```
h8e    MGSPRSALSCLLLHLLVLCLQAEGPGRGPALGRELASLFRAGREPQGVSQQHVREQSLV
m8e    MGSPRSALSCLLLHLLVLCLQAEGPGGGPALGREPTSLLRAGREPQGVSQQHVREQSLV
       ************************** ****** :**:*********************
h8e    TDQLSRRLIRTYQLYSRTSGKHVQVLANKRINAMAEDGDPFAKLIVETDTFGSRVRVRGA
m8e    TDQLSRRLIRTYQLYSRTSGKHVQVLANKRINAMAEDGDPFAKLIVETDTFGSRVRVRGA
       ************************************************************
h8e    ETGLYICMNKKGKLIAKSNGKGKDCVFTEIVLENNYTALQNAKYEGWYMAFTRKGRPRKG
m8e    ETGLYICMNKKGKLIAKSNGKGKDCVFTEIVLENNYTALQNAKYEGWYMAFTRKGRPRKG
       ************************************************************
h8e    SKTRQHQREVHFMKRLPRGHHTTEQSLRFEFLNYPPFTRSLRGSQRTWAPEPR
       (SEQ ID NO: 17)
m8e    SKTRQHQREVHFMKRLPRGHHTTEQSLRFEFLNYPPFTRSLRGSQRTWAPEPR
       (SEQ ID NO: 21)
       *****************************************************
```

| aa-Human vs. Mouse FGF8f | | | |
| --- | --- | --- | --- |
| Percent | Identity | Matrix - created by Clustal2.1 | |
| 1: | h8f | 100.00 | 98.36 |
| 2: | m8l | 98.36 | 100.00 |

| CLUSTAL O(1.2.1) multiple sequence alignment |
| --- |

```
h8f    MGSPRSALSCLLLHLLVLCLQAEGPGRGPALGRELASLFRAGREPQGVSQQVTVQSSPN
m8f    MGSPRSALSCLLLHLLVLCLQAEGPGGGPALGREPTSLLRAGREPQGVSQQVTVQSSPN
       ************************** ****** :**:*********************
h8f    FTQHVREQSLVTDQLSRRLIRTYQLYSRTSGKHVQVLANKRINAMAEDGDPFAKLIVETD
m8f    FTQHVREQSLVTDQLSRRLIRTYQLYSRTSGKHVQVLANKRINAMAEDGDPFAKLIVETD
       ************************************************************
h8f    TFGSRVRVRGAETGLYICMNKKGKLIAKSNGKGKDCVFTEIVLENNYTALQNAKYEGWYM
m8f    TFGSRVRVRGAETGLYICMNKKGKLIAKSNGKGKDCVFTEIVLENNYTALQNAKYEGWYM
       ************************************************************
h8f    AFTRKGRPRKGSKTRQHQREVHFMKRLPRGHHTTEQSLRFEFLNYPPFTRSLRGSQRTWA
m8f    AFTRKGRPRKGSKTRQHQREVHFMKRLPRGHHTTEQSLRFEFLNYPPFTRSLRGSQRTWA
       ************************************************************
h8f    PEPR (SEQ ID NO: 18)
m8f    PEPR (SEQ ID NO: 22)
       ****
```

| ns-Human vs. Mouse FGF8a | | | |
| --- | --- | --- | --- |
| Percent | Identity | Matrix - created by Clustal2.1 | |
| 1: | h8a | 100.00 | 94.96 |
| 2: | m8a | 94.96 | 100.00 |

| CLUSTAL O(1.2.1) multiple sequence alignment |
| --- |

```
h8a    ATGGGCAGCCCCCGCTCCGCGCTGAGCTGCCTGCTGTTGCACTTGCTGGTCCTCTGCCTC
m8a    ATGGGCAGCCCCCGCTCCGCGCTGAGCTGCCTGCTGTTGCACTTGCTGGTTCTCTGCCTC
       ************************************************* **********
h8a    CAAGCCCAGCATGTGAGGGAGCAGAGCCTGGTGACGGATCAGCTCAGCCGCCGCCTCATC
m8a    CAAGCCCAGCATGTGAGGGAGGAGAGCCTGGTGACGGATCAGCTCAGCCGCCGCCTCATC
       ********************* **************************************
h8a    CGGAGCTACCAACTCTACAGCCGCACCAGCGGGAAGCACGTGCAGGTCCTCGCCAACAAG
m8a    CGGACCTACCAGCTCTACAGCCGCACCAGCGGGAAGCACGTGCAGGTCCTGGCCAACAAG
       ****  ***** *************************************** ********
h8a    CGCATCAACGCCATGGCAGAGGACGGCGACCCCTTCGCAAAGCTCATCGTGGAGACGGAC
m8a    CGCATCAACGCGATGGCAGAAGACGGAGACCCCTTCGCAAGCTCGATTGTGGAGACCGAT
       *********** ******** ***** ************* *** * * ******** **
h8a    ACCTTTGGAAGCAGAGTTCGAGTCCGAGGAGCCGAGACGGGCCTCTACATCTGCATGAAC
m8a    ACTTTTGGAAGCAGAGTCCGAGTTCGCGGCGCAGAGACAGGTCTCTACATCTGCATGAAC
       ** ************** ***** ** ** ** ***** ** ******************
h8a    AAGAAGGGGAAGCTGATCGCCAAGAGCAACGGCAAAGGCAAGGACTGCGTCTTCACGGAG
m8a    AAGAAGGGGAAGCTAATTGCCAAGAGCAACGGCAAAGGCAAGGACTGCGTATTCACAGAG
       ************** ** ******************************** ***** ***
h8a    ATTGTGCTGGAGAACAACTACACAGCGCTGCAGAATGCCAAGTACGAGGGCTGGTACATG
m8a    ATCGTGCTGGAGAACAACTACACGGCGCTGCAGAACGCCAAGTACGAGGGCTGGTACATG
       ** ******************** *********** ************************
h8a    GCCTTCACCCGCAAGGGCCGGCCCCGCAAGGGCTCCAAGACGCGGCAGCACCAGCGTGAG
m8a    GCCTTTACCCGCAAGGGCCGGCCCCGCAAGGGCTCCAAGACGCGCCAGCATCAGCGCGAG
       ***** ************************************** ***** ***** ***
h8a    GTCCACTTCATGAAGCGGCTGCCCCGGGGCCACCACACCACCGAGCAGAGCCTGCGCTTC
m8a    GTGCACTTCATGAAGCGCCTGCCGCGGGGCCACCACACCACCGAGCAGAGCCTGCGCTTC
       ** ************** ***** ****************************************
```

```
h8a    GAGTTCCTCAACTACCCGCCCTTCACGCGCAGCCTGCGCGGCAGCCAGAGGACTTGGGCC
m8a    GAGTTCCTCAACTACCCGCCCTTCACGCGCAGCCTGCGCGGCAGCCAGAGGACTTGGGCC
       ************************************************************
h8a    CCCGAGCCCCGATAG (SEQ ID NO: 1)
m8a    CCGGAGCCCCGATAG (SEQ ID NO: 5)
       ** ************
```

| ns-Human vs. Mouse FGF8b |||
|---|---|---|
| Percent | Identity | Matrix - created by Clustal2.1 |
| 1: | h8b | 100.00 | 95.22 |
| 2: | m8b | 95.22 | 100.00 |

CLUSTAL O(1.2.1) multiple sequence alignment

```
h8b    ATGGGCAGCCCCCGCTCCGCGCTGAGCTGCCTGCTGTTGCACTTGCTGGTCCTCTGCCTC
m8b    ATGGGCAGCCCCCGCTCCGCGCTGAGCTGCCTGCTGTTGCACTTGCTGGTTCTCTGCCTC
       ***************************************************** ******
h8b    CAAGCCCAGGTAACTGTTCAGTCCTCACCTAATTTTACACAGCATGTGAGGGAGCAGAGC
m8b    CAAGCCCAGGTAACTGTTCAGTCCTCACCTAATTTTACACAGCATGTGAGGGAGCAGAGC
       ************************************************************
h8b    CTGGTGACGGATCAGCTCAGCCGCCGCCTCATCCGGACCTACCAACTCTACAGCCGCACC
m8b    CTGGTGACGGATCAGCTCAGCCGCCGCCTCATCCGGACCTACCAGCTCTACAGCCGCACC
       ********************************************* **************
h8b    AGCGGGAAGCACGTGCAGGTCCTGGCCAACAAGCGCATCAACGCCATGGCAGAGGACGGC
m8b    AGCGGGAAGCACGTGCAGGTCCTGGCCAACAAGCGCATCAACGCCATGGCAGAAGACGGA
       ***************************************************** *****
h8b    GACCCCTTCGCAAAGCTCATCGTGGAGACGGACACCTTTGGAAGCAGAGTTCGAGTCCGA
m8b    GACCCCTTCGCGAAGCTCATTGTGGAGACCGATACTTTTGGAAGCAGAGTCCGAGTTCGC
       *********** ******** ********  ** ** *************  ***** *
h8b    GGAGCCGAGACGGGCCTCTACATCTGCATGAACAAGAAGGGGAAGCTGATCGCCAAGAGC
m8b    GGCGCAGAGACAGGTCTCTACATCTGCATGAACAAGAAGGGGAAGCTAATTGCCAAGAGC
       ** ** ***** ** ******************************* ** *********
h8b    AACGGCAAAGGCAAGGACTGCGTCTTCACGGAGATTGTGCTGGAGAACAACTACACAGCG
m8b    AACGGCAAAGGCAAGGACTGCGTATTCACAGAGATCGTGCTGGAGAACAACTACACGGCG
       *********************** ***** ***** ******************* ***
h8b    CTGCAGAATGCCAAGTACGAGGGCTGGTACATGGCCTTCACCCGCAAGGGCCGGCCCCGC
m8b    CTGCAGAACGCCAAGTACGAGGGCTGGTACATGGCCTTTACCCGCAAGGGCCGGCCCCGC
       ******** ***************************** *********************
h8b    AAGGGCTCCAAGACGCGGCAGCACCAGCGTGAGGTCCACTTCATGAAGCGGCTGCCCCGG
m8b    AAGGGCTCCAAGACGCGCCAGCATCAGCGCGAGGTGCACTTCATGAAGCGCCTGCCGCGG
       ***************** ***** ***** *****  ************ ***** ***
h8b    GGCCACCACACCACCGAGCAGAGCCTGCGCTTCGAGTTCCTCAACTACCCGCCCTTCACG
m8b    GGCCACCACACCACCGAGCAGAGCCTGCGCTTCGAGTTCCTCAACTACCCGCCCTTCACG
       ************************************************************
h8b    CGCAGCCTGCGCGGCAGCCAGAGGACTTGGGCCCCCGAGCCCCGATAG
       (SEQ ID NO: 2)
m8b    CGCAGCCTGCGCGGCAGCCAGAGGACTTGGGCCCCGGAGCCCCGATAG
       (SEQ ID NO: 6)
       *********************************** ************
```

| ns-Human vs. Mouse FGF8e |||
|---|---|---|
| Percent | Identity | Matrix - created by Clustal2.1 |
| 1: | h8e | 100.00 | 94.59 |
| 2: | m8e | 94.59 | 100.00 |

CLUSTAL O(1.2.1) multiple sequence alignment

```
h8e    ATGGGCAGCCCCCGCTCCGCGCTGAGCTGCCTGCTGTTGCACTTGCTGGTCCTCTGCCTC
m8e    ATGGGCAGCCCCCGCTCCGCGCTGAGCTGCCTGCTGTTGCACTTGCTGGTTCTCTGCCTC
       ***************************************************** ******
h8e    CAAGCCCAGGAAGGCCCGGGCAGGGGCCCTGCGCTGGGCAGGGAGCTCGCTTCCCTGTTC
m8e    CAAGCCCAGGAAGGCCCGGGCGGGGGGCCTGCGCTGGGCAGGGAGCCCACTTCCCTGCTC
       ********************* ****  ****************** * ******** *
h8e    CGGGCTGGCCGGGAGCCCCAGGGTGTCTCCCAACAGCATGTGAGGGAGCAGAGCCTGGTG
m8e    CGAGCTGGCCGGGAGCCCCAGGGTGTTTCCCAACAGCATGTGAGGGAGCAGAGCCTGGTG
       ** *********************** *********************************
h8e    ACGGATCAGCTCAGCCGCCGCCTCATCCGGACCTACCAACTCTACAGCCGCACCAGCGGG
m8e    ACGGATCAGCTCAGCCGCCGCCTCATCCGGACCTACCAGCTCTACAGCCGCACCAGCGGG
       ************************************** *********************
h8e    AAGCACGTGCAGGTCCTGGCCAACAAGCGCATCAACGCCATGGCAGAGGACGGCGACCCC
m8e    AAGCACGTGCAGGTCCTGGCCAACAAGCGCATCAACGCCATGGCAGAAGACGGAGACCCC
       *********************************************** ***** ******
h8e    TTCGCAAAGCTCATCGTGGAGACGGACACCTTTGGAAGCAGAGTTCGAGTCCGAGGAGCC
m8e    TTCGCGAAGCTCATTGTGGAGACCGATACTTTTGGAAGCAGAGTCCGAGTTCGCGGCGCA
       ***** ******** ********  ** ** *************  ***** ** ** **
```

```
h8e     GAGACGGGCCTCTACATCTGCATGAACAAGAAGGGGAAGCTGATCGCCAAGAGCAACGGC
m8e     GAGACAGGTCTCTACATCTGCATGAACAAGAAGGGGAAGCTAATTGCCAAGAGCAACGGC
        ***  *******************************  ************** h8e     AAAGGCAAGGACTGCGTCTTCACGGAGATTGTGCTGGAGAACAACTACACAGCGCTGCAG
m8e     AAAGGCAAGGACTGCGTATTCACAGAGATCGTGCTGGAGAACAACTACACGGCGCTGCAG
        *************** * * **** ****** ******* h8e     AATGCCAAGTACGAGGGCTGGTACATGGCCTTCACCCGCAAGGGCCGGCCCCGCAAGGGC
m8e     AACGCCAAGTACGAGGGCTGGTACATGGCCTTTACCCGCAAGGGCCGGCCCCGCAAGGGC
         ************************* ************************* h8e     TCCAAGACGCGGCAGCACCAGCGTGAGGTCCACTTCATGAAGCGGCTGCCCCGGGGCCAC
m8e     TCCAAGACGCGCCAGCATCAGCGCGAGGTGCACTTCATGAAGCGCCTGCCGCGGGGCCAC
        ********* * * * ********** * ******* h8e     CACACCACCGAGCAGAGCCTGCGCTTCGAGTTCCTCAACTACCCGCCCTTCACGCGCAGC
m8e     CACACCACCGAGCAGAGCCTGCGCTTCGAGTTCCTCAACTACCCGCCCTTCACGCGCAGC
        ************************************************************ h8e     CTGCGCGGCAGCCAGAGGACTTGGGCCCCCGAGCCCCGATAG (SEQ ID NO: 3)
m8e     CTGCGCGGCAGCCAGAGGACTTGGGCCCCGGAGCCCCGATAG (SEQ ID NO: 7)
        ***************************** ************
``` ns-Human vs. Mouse FGF8f

```
Percent    Identity       Matrix - created by Clustal2.1

1:     h8f          100.00                    94.83
    2:     m8f           94.83                   100.00
```

CLUSTAL O(1.2.1) multiple sequence alignment

```
h8f     ATGGGCAGCCCCCGCTCCGCGCTGAGCTGCCTGCTGTTGCACTTGCTGGTCCTCTGCCTC
m8f     ATGGGCAGCCCCCGCTCCGCGCTGAGCTGCCTGCTGTTGCACTTGCTGGTTCTCTGCCTC
        ************************************************ ******* h8f     CAAGCCCAGGAAGGCCCGGGCAGGGGCCCTGCGCTGGGCAGGGAGCTCGCTTCCCTGTTC
m8f     CAAGCCCAGGAAGGCCCGGGCGGGGGCCTGCGCTGGGCAGGGAGCCCACTTCCCTGCTC
        *******************  **************** * ****** h8f     CGGGCTGGCCGGGAGCCCCAGGGTGTCTCCCAACAGGTAACTGTTCAGTCCTCACCTAAT
m8f     CGAGCTGGCCGGGAGCCCCAGGGTGTTTCCCAACAGGTAACTGTTCAGTCCTCACCTAAT
         ******************* ******************************* h8f     TTTACACAGCATGTGAGGGAGCAGAGCCTGGTGACGGATCAGCTCAGCCGCCGCCTCATC
m8f     TTTACACAGCATGTGAGGGAGCAGAGCCTGGTGACGGATCAGCTCAGCCGCCGCCTCATC
        ************************************************************ h8f     CGGACCTACCAACTCTACAGCCGCACCAGCGGGAAGCACGTGCAGGTCCTGGCCAACAAG
m8f     CGGACCTACCAGCTCTACAGCCGCACCAGCGGGAAGCACGTGCAGGTCCTGGCCAACAAG
        ********* ********************************************** h8f     CGCATCAACGCCATGGCAGAGGACGGCGACCCCTTCGCAAAGCTCATCGTGGAGACGGAC
m8f     CGCATCAACGCCATGGCAGAAGACGGAGACCCCTTCGCGAAGCTCATTGTGGAGACCGAT
        ****************** * ******* **** *** h8f     ACCTTTGGAAGCAGAGTTCGAGTCCGAGGAGCCGAGACGGGCCTCTACATCTGCATGAAC
m8f     ACTTTTGGAAGCAGAGTCCGAGTTCGCGGCGCAGAGACAGGTCTCTACATCTGCATGAAC
         ********** *    ***  ****************** h8f     AAGAAGGGGAAGCTGATCGCCAAGAGCAACGGCAAAGGCAAGGACTGCGTCTTCACGGAG
m8f     AAGAAGGGGAAGCTAATTGCCAAGAGCAACGGCAAAGGCAAGGACTGCGTATTCACAGAG
        ************  ****************************** * * h8f     ATTGTGCTGGAGAACAACTACACAGCGCTGCAGAATGCCAAGTACGAGGGCTGGTACATG
m8f     ATCGTGCTGGAGAACAACTACACGGCGCTGCAGAACGCCAAGTACGAGGGCTGGTACATG
         **************** ******* ********************** h8f     GCCTTCACCCGCAAGGGCCGGCCCCGCAAGGGCTCCAAGACGCGGCAGCACCAGCGTGAG
m8f     GCCTTTACCCGCAAGGGCCGGCCCCGCAAGGGCTCCAAGACGCGCCAGCATCAGCGCGAG
        *** ********************************** * * * h8f     GTCCACTTCATGAAGCGGCTGCCCCGGGGCCACCACACCACCGAGCAGAGCCTGCGCTTC
m8f     GTGCACTTCATGAAGCGCCTGCCGCGGGGCCACCACACCACCGAGCAGAGCCTGCGCTTC
         ********** * ********************************** h8f     GAGTTCCTCAACTACCCGCCCTTCACGCGCAGCCTGCGCGGCAGCCAGAGGACTTGGGCC
m8f     GAGTTCCTCAACTACCCGCCCTTCACGCGCAGCCTGCGCGGCAGCCAGAGGACTTGGGCC
        ************************************************************ h8f     CCCGAGCCCCGATAG (SEQ ID NO: 4)
m8f     CCGGAGCCCCGATAG (SEQ ID NO: 8)
        ** ************
```

REFERENCES CITED HEREIN

Bartelt, A., Bruns, O. T., Reimer, R., Hohenberg, H., Ittrich, H., Peldschus, K., . . . Heeren, J. (2011). Brown adipose tissue activity controls triglyceride clearance. *Nat Med,* 17(2), 200-205. doi: 10.1038/nm.2297

Bartelt, A., & Heeren, J. (2014). Adipose tissue browning and metabolic health. *Nat Rev Endocrinol,* 10(1), 24-36. doi: 10.1038/nrendo.2013.204

Cinti, S. (2006). The role of brown adipose tissue in human obesity. *Nutr Metab Cardiovasc Dis,* 16(8), 569-574. doi: 10.1016/j.numecd.2006.07.009

Gunawardana, S. C. (2014). Benefits of healthy adipose tissue in the treatment of diabetes. *World J Diabetes,* 5(4), 420-430. doi: 10.4239/wjd.v5.i4.420

Gunawardana, S. C., & Piston, D. W. (2012). Reversal of type 1 diabetes in mice by brown adipose tissue transplant. *Diabetes,* 61(3), 674-682. doi: 10.2337/db11-0510

Himms-Hagen, J. (1979). Obesity may be due to a malfunctioning of brown fat. Can Med Assoc J, 121(10), 1361-1364.

Klingenspor, M., Fromme, T. (2012). Brown adipose tissue. In M. E. Symonds (Ed.), Adipose Tissue Biology (Vol. 414). Heidelberg: Springer.

Lidell, M. E., Betz, M. J., & Enerback, S. (2014). Brown adipose tissue and its therapeutic potential. J Intern Med, 276(4), 364-377. doi: 10.1111/joim.12255

Roman, S., Agil, A., Peran, M., Alvaro-Galue, E., Ruiz-Ojeda, F. J., Fernandez-Vazquez, G., & Marchel, J. A. (2014). Brown adipose tissue and novel therapeutic approaches to treat metabolic disorders. Transl Res. doi: 10.1016/j.trsl.2014.11.002

Rothwell, N. J., & Stock, M. J. (1979). A role for brown adipose tissue in diet-induced thermogenesis. Nature, 281(5726), 31-35.

Saito, M., Okamatsu-Ogura, Y., Matsushita, M., Watanabe, K., Yoneshiro, T., Nio-Kobayashi, J., . . . Tsujisaki, M. (2009). High incidence of metabolically active brown adipose tissue in healthy adult humans: effects of cold exposure and adiposity. Diabetes, 58(7), 1526-1531. doi: 10.2337/db09-0530 van Marken Lichtenbelt, W. D., Vanhommerig, J. W., Smulders, N. M., Drossaerts, J. M., Kemerink, G. J., Bouvy, N. D., . . . Teule, G. J. (2009). Cold-activated brown adipose tissue in healthy men. N Engl J Med, 360(15), 1500-1508. doi: 10.1056/NEJMoa0808718

Virtanen, K. A., Lidell, M. E., Orava, J., Heglind, M., Westergren, R., Niemi, T., . . . Nuutila, P. (2009). Functional brown adipose tissue in healthy adults. N Engl J Med, 360(15), 1518-1525. doi: 10.1056/NEJMoa0808949

LIST OF REFERENCES

Armani, A., Cinti, F., Marzolla, V., Morgan, J., Cranston, G. A., Antelmi, A., . . . Caprio, M. (2014). Mineralocorticoid receptor antagonism induces browning of white adipose tissue through impairment of autophagy and prevents adipocyte dysfunction in high-fat-diet-fed mice. FASEB J, 28(8), 3745-3757. doi: 10.1096/fj.13-245415

Bartelt, A., Bruns, O. T., Reimer, R., Hohenberg, H., Ittrich, H., Peldschus, K., . . . Heeren, J. (2011). Brown adipose tissue activity controls triglyceride clearance. Nat Med, 17(2), 200-205. doi: 10.1038/nm.2297

Bi, P., Shan, T., Liu, W., Yue, F., Yang, X., Liang, X. R., . . . Kuang, S. (2014). Inhibition of Notch signaling promotes browning of white adipose tissue and ameliorates obesity. Nat Med, 20(8), 911-918. doi: 10.1038/nm.3615

Bolze, F., Rink, N., Brumm, H., Kuhn, R., Mocek, S., Schwarz, A. E., . . . Klingenspor, M. (2013). Characterization of the melanocortin-4-receptor nonsense mutation W16X in vitro and in vivo. Pharmacogenomics J, 13(1), 80-93. doi: 10.1038/tpj.2011.43

Bordicchia, M., Liu, D., Amri, E. Z., Ailhaud, G., Dessi-Fulgheri, P., Zhang, C., . . . Collins, S. (2012). Cardiac natriuretic peptides act via p38 MAPK to induce the brown fat thermogenic program in mouse and human adipocytes. J Clin Invest, 122(3), 1022-1036. doi: 10.1172/JCI59701

Caverzasio, J., & Thouverey, C. (2011). Activation of FGF receptors is a new mechanism by which strontium ranelate induces osteoblastic cell growth. Cell Physiol Biochem, 27(3-4), 243-250. doi: 10.1159/000327950

Chaffee, R. R., Allen, J. R., Cassuto, Y., & Smith, R. E. (1964). Biochemistry of Brown Fat and Liver of Cold-Acclimated Hamsters. Am J Physiol, 207, 1211-1214.

Cypess, A. M., Lehman, S., Williams, G., Tal, I., Rodman, D., Goldfine, A. B., . . . Kahn, C. R. (2009). Identification and importance of brown adipose tissue in adult humans. N Engl J Med, 360(15), 1509-1517. doi: 10.1056/NEJMoa0810780

Fisher, F. M., Kleiner, S., Douris, N., Fox, E. C., Mepani, R. J., Verdeguer, F., . . . Spiegelman, B. M. (2012). FGF21 regulates PGC-1alpha and browning of white adipose tissues in adaptive thermogenesis. Genes Dev, 26(3), 271-281. doi: 10.1101/gad.177857.111

Goetz, R., Ohnishi, M., Kir, S., Kurosu, H., Wang, L., Pastor, J., . . . Mohammadi, M. (2012). Conversion of a paracrine fibroblast growth factor into an endocrine fibroblast growth factor. J Biol Chem, 287(34), 29134-29146. doi: 10.1074/jbc.M112.342980

Gong, D. W., Bi, S., Weintraub, B. D., & Reitman, M. (1998). Rat mitochondrial glycerol-3-phosphate dehydrogenase gene: multiple promoters, high levels in brown adipose tissue, and tissue-specific regulation by thyroid hormone. DNA Cell Biol, 17(3), 301-309.

Guerra, C., Koza, R. A., Yamashita, H., Walsh, K., & Kozak, L. P. (1998). Emergence of brown adipocytes in white fat in mice is under genetic control. Effects on body weight and adiposity. J Clin Invest, 102(2), 412-420. doi: 10.1172/JCI3155

Hanssen (2014) Diabetologia doi 10.1007/ss0125-014-3465-8

Hoffmann, C., Zimmermann, A., Hinney, A., Volckmar, A. L., Jarrett, H. W., Fromme, T., & Klingenspor, M. (2013). A novel SP1/SP3 dependent intronic enhancer governing transcription of the UCP3 gene in brown adipocytes. PLoS One, 8(12), e83426. doi: 10.1371/journal.pone.0083426

Itoh, N., & Ornitz, D. M. (2008). Functional evolutionary history of the mouse Fgf gene family. Dev Dyn, 237(1), 18-27. doi: 10.1002/dvdy.21388

Klein, J., Westphal, S., Kraus, D., Meier, B., Perwitz, N., Ott, V., . . . Klein, H. H. (2004). Metformin inhibits leptin secretion via a mitogen-activated protein kinase signalling pathway in brown adipocytes. J Endocrinol, 183(2), 299-307. doi: 10.1677/joe.1.05646

Klingenspor, M., Fromme, T. (2012). Brown adipose tissue. In M. E. Symonds (Ed.), Adipose Tissue Biology (Vol. 414). Heidelberg: Springer.

Kuchler, S., Perwitz, N., Schick, R. R., Klein, J., & Westphal, S. (2010). Arginine-vasopressin directly promotes a thermogenic and pro-inflammatory adipokine expression profile in brown adipocytes. Regul Pept, 164(2-3), 126-132. doi: 10.1016/j.regpep.2010.05.016

Li, Y., Bolze, F., Fromme, T., & Klingenspor, M. (2014). Intrinsic differences in BRITE adipogenesis of primary adipocytes from two different mouse strains. Biochim Biophys Acta, 1841(9), 1345-1352. doi: 10.1016/j.bbalip.2014.06.003

Li, Y., Fromme, T., Schweizer, S., Schottl, T., & Klingenspor, M. (2014). Taking control over intracellular fatty acid levels is essential for the analysis of thermogenic function in cultured primary brown and brite/beige adipocytes. EMBO Rep. doi: 10.15252/embr.201438775

Meyer, C. W., Willershauser, M., Jastroch, M., Rourke, B. C., Fromme, T., Oelkrug, R., . . . Klingenspor, M. (2010). Adaptive thermogenesis and thermal conductance in wild-type and UCP1-KO mice. Am J Physiol Regul Integr Comp Physiol, 299(5), R1396-1406. doi: 10.1152/ajpregu.00021.2009

Murakami, M., Elfenbein, A., & Simons, M. (2008). Non-canonical fibroblast growth factor signalling in angiogenesis. Cardiovasc Res, 78(2), 223-231. doi: 10.1093/cvr/cvm 086

Nau, K., Fromme, T., Meyer, C. W., von Praun, C., Heldmaier, G., & Klingenspor, M. (2008). Brown adipose tissue specific lack of uncoupling protein 3 is associated with impaired cold tolerance and reduced transcript levels of metabolic genes. J Comp Physiol B, 178(3), 269-277. doi: 10.1007/s00360-007-0219-7

Pfeifer, A., & Hoffmann, L. S. (2014). Brown, Beige, and White: The New Color Code of Fat and Its Pharmacological Implications. Annu Rev Pharmacol Toxicol. doi: 10.1146/annurev-pharmtox-010814-124346

Ray, J., Baird, A., & Gage, F. H. (1997). A 10-amino acid sequence of fibroblast growth factor 2 is sufficient for its mitogenic activity on neural progenitor cells. Proc Natl Acad Sci USA, 94(13), 7047-7052.

Seyfarth, K., Poschmann, G., Rozman, J., Fromme, T., Rink, N., Hofmann, A., Wurst, W., Stühler, K., Klingenspor, M. (2014). The development of diet-induced obesity and associated metabolic impairments in Dj-1 deficient mice. Journal of Nutritional Biochemistry, in press.

Suh, J. M., Jonker, J. W., Ahmadian, M., Goetz, R., Lackey, D., Osborn, O., . . . Evans, R. M. (2014). Endocrinization of FGF1 produces a neomorphic and potent insulin sensitizer. Nature. doi: 10.1038/nature13540

Sunmonu, N. A., Li, K., & Li, J. Y. (2011). Numerous isoforms of Fgf8 reflect its multiple roles in the developing brain. J Cell Physiol, 226(7), 1722-1726. doi: 10.1002/jcp.22587

Tseng, Y. H., Kokkotou, E., Schulz, T. J., Huang, T. L., Winnay, J. N., Taniguchi, C. M., . . . Kahn, C. R. (2008). New role of bone morphogenetic protein 7 in brown adipogenesis and energy expenditure. Nature, 454(7207), 1000-1004. doi: 10.1038/nature07221 van Marken Lichtenbelt, W. D., Vanhommerig, J. W., Smulders, N. M., Drossaerts, J. M., Kemerink, G. J., Bouvy, N. D., . . . Teule, G. J. (2009). Cold-activated brown adipose tissue in healthy men. N Engl J Med, 360(15), 1500-1508. doi: 10.1056/NEJMoa0808718

Virtanen, K. A., Lidell, M. E., Orava, J., Heglind, M., Westergren, R., Niemi, T., . . . Nuutila, P. (2009). Functional brown adipose tissue in healthy adults. N Engl J Med, 360(15), 1518-1525. doi: 10.1056/NEJMoa0808949

Wagner, I. V., Perwitz, N., Drenckhan, M., Lehnert, H., & Klein, J. (2011). Cannabinoid type 1 receptor mediates depot-specific effects on differentiation, inflammation and oxidative metabolism in inguinal and epididymal white adipocytes. Nutr Diabetes, 1, e16. doi: 10.1038/nutd.2011.12

Westphal, S., Perwitz, N., Iwen, K. A., Kraus, D., Schick, R., Fasshauer, M., & Klein, J. (2008). Expression of ATRAP in adipocytes and negative regulation by beta-adrenergic stimulation of JAK/STAT. Horm Metab Res, 40(3), 165-171. doi: 10.1055/s-2007-1022547

Wree, A., Mayer, A., Westphal, S., Beilfuss, A., Canbay, A., Schick, R. R., . . . Vaupel, P. (2012). Adipokine expression in brown and white adipocytes in response to hypoxia. J Endocrinol Invest, 35(5), 522-527. doi: 10.3275/7964

Young, P., Arch, J. R., & Ashwell, M. (1984). Brown adipose tissue in the parametrial fat pad of the mouse. FEBS Lett, 167(1), 10-14.

All references cited herein are fully incorporated by reference. Having now fully described the invention, it will be understood by a person skilled in the art that the invention may be practiced within a wide and equivalent range of conditions, parameters and the like, without affecting the spirit or scope of the invention or any embodiment thereof.

The invention claimed is:

1. A method for inducing differentiation or conversion of white adipocytes and/or preadipocytes to brown adipocytes in a subject in need thereof, comprising administering an amount of a polypeptide to the subject effective to induce said differentiation or conversion, wherein the polypeptide is an FGF8 polypeptide.

2. The method of claim 1, wherein the polypeptide is comprised in a pharmaceutical composition, said composition further comprising a pharmaceutically acceptable carrier and/or diluent.

3. The method of claim 2, wherein the pharmaceutical composition is administrated locally.

4. The method of claim 2 wherein the pharmaceutical composition is administered into visceral adipose tissue of the subject.

5. The method of claim 2, wherein the pharmaceutical composition is in the form of an erodible implant, an implantable drug release device, a gel for injection or a solution for injection.

6. The method of claim 2, wherein the pharmaceutical composition is administered to the subject by means of a minipump.

7. The method of claim 2, wherein the pharmaceutical composition is administered to the subject with at least one other active agent, wherein said other active agent is selected from the group consisting of a beta-adrenergic agonist; an indirect sympathomimetic; an ANP receptor agonist; and BNP receptor agonist.

8. The method of claim 1, wherein the subject suffers from central obesity.

9. The method of claim 7, wherein said other active agent is a beta-adrenergic agonist selected from the group consisting of noradrenalin; isoproterenol; BRL 35135; ICI D7114; CGP-12177A; and CL 316243.

10. The method of claim 7, wherein the other active agent is an indirect sympathomimetic selected from the group consisting of ephedrine and methylphenidate.

11. The method of claim 7, wherein the other active agent is a natriuretic peptide selected from the group consisting of ANP and BNP.

12. The method of claim 7, wherein the other active agent is the ANP/BNP receptor agonist AP-811.

13. The method of claim 1, wherein the subject has a disease or disorder of energy homeostasis selected from the group consisting of obesity, dyslipidemia, diabetes, insulin resistance, hyperglycemia and metabolic syndrome.

14. The method of claim 1, wherein the FGF8 polypeptide is a mammalian FGF8.

15. The method of claim 14, wherein the FGF8 is human FGF8.

16. The method of claim 14, wherein the FGF8 polypeptide comprises the amino acid sequence of SEQ ID NO: 16 or amino acids 23-215 of SEQ ID NO: 16.

* * * * *

SEQUENCE LISTING

```
<160> NUMBER OF SEQ ID NOS: 112

<210> SEQ ID NO 1
<211> LENGTH: 615
<212> TYPE: DNA
<213> ORGANISM: Homo sapiens
<220> FEATURE:
<223> OTHER INFORMATION: human FGF8a

<400> SEQUENCE: 1
atgggcagcc cccgctccgc gctgagctgc ctgctgttgc acttgctggt cctctgcctc        60
caagcccagc atgtgaggga gcagagcctg gtgacggatc agctcagccg ccgcctcatc       120
cggacctacc aactctacag ccgcaccagc gggaagcacg tgcaggtcct ggccaacaag       180
cgcatcaacg ccatggcaga ggacggcgac cccttcgcaa agctcatcgt ggagacggac       240
acctttggaa gcagagttcg agtccgagga gccgagacgg gcctctacat ctgcatgaac       300
aagaagggga agctgatcgc caagagcaac ggcaaaggca aggactgcgt cttcacggag       360
attgtgctgg agaacaacta cacagcgctg cagaatgcca agtacgaggg ctggtacatg       420
gccttcaccc gcaaggccg gccccgcaag ggctccaaga cgcggcagca ccagcgtgag       480
gtccacttca tgaagcggct gccccggggc caccacacca ccgagcagag cctgcgcttc       540
gagttcctca actaccgcc cttcacgcgc agcctgcgcg gcagccagag gacttgggcc       600
cccgagcccc gatag                                                        615
```

<210> SEQ ID NO 2
<211> LENGTH: 648
<212> TYPE: DNA
<213> ORGANISM: Homo sapiens
<220> FEATURE:
<223> OTHER INFORMATION: human FGF8b

<400> SEQUENCE: 2

| | | | | | |
|---|---|---|---|---|---|
| atgggcagcc | cccgctccgc | gctgagctgc | ctgctgttgc | acttgctggt | cctctgcctc | 60 |
| caagcccagg | taactgttca | gtcctcacct | aattttacac | agcatgtgag | ggagcagagc | 120 |
| ctggtgacgg | atcagctcag | ccgccgcctc | atccggacct | accaactcta | cagccgcacc | 180 |
| agcgggaagc | acgtgcaggt | cctggccaac | aagcgcatca | acgccatggc | agaggacggc | 240 |
| gaccccttcg | caaagctcat | cgtggagacg | gacacctttg | gaagcagagt | tcgagtccga | 300 |
| ggagccgaga | cgggcctcta | catctgcatg | aacaagaagg | ggaagctgat | cgccaagagc | 360 |
| aacggcaaag | gcaaggactg | cgtcttcacg | gagattgtgc | tggagaacaa | ctacacagcg | 420 |
| ctgcagaatg | ccaagtacga | gggctggtac | atggccttca | cccgcaaggg | ccggccccgc | 480 |
| aagggctcca | gacgcggca | gcaccagcgt | gaggtccact | tcatgaagcg | gctgccccgg | 540 |
| ggccaccaca | ccaccgagca | gagcctgcgc | ttcgagttcc | tcaactaccc | gcccttcacg | 600 |
| cgcagcctgc | gcggcagcca | gaggacttgg | gcccccgagc | ccgatag | | 648 |

<210> SEQ ID NO 3
<211> LENGTH: 702
<212> TYPE: DNA
<213> ORGANISM: Homo sapiens
<220> FEATURE:
<223> OTHER INFORMATION: human FGF8e

<400> SEQUENCE: 3

| | | | | | |
|---|---|---|---|---|---|
| atgggcagcc | cccgctccgc | gctgagctgc | ctgctgttgc | acttgctggt | cctctgcctc | 60 |
| caagcccagg | aaggcccggg | caggggccct | gcgctgggca | gggagctcgc | ttccctgttc | 120 |
| cgggctggcc | gggagcccca | gggtgtctcc | aacagcatg | tgagggagca | gagcctggtg | 180 |
| acggatcagc | tcagccgccg | cctcatccgg | acctaccaac | tctacagccg | caccagcggg | 240 |
| aagcacgtgc | aggtcctggc | caacaagcgc | atcaacgcca | tggcagagga | cggcgacccc | 300 |
| ttcgcaaagc | tcatcgtgga | gacggacacc | tttggaagca | gagttcgagt | ccgaggagcc | 360 |
| gagacgggcc | tctacatctg | catgaacaag | aaggggaagc | tgatcgccaa | gagcaacggc | 420 |
| aaaggcaagg | actgcgtctt | cacggagatt | gtgctggaga | caactacac | agcgctgcag | 480 |
| aatgccaagt | acgagggctg | gtacatggcc | ttcacccgca | agggccggcc | ccgcaagggc | 540 |
| tccagacgc | ggcagcacca | gcgtgaggtc | cacttcatga | agcggctgcc | ccggggccac | 600 |
| cacaccaccg | agcagagcct | gcgcttcgag | ttcctcaact | acccgccctt | cacgcgcagc | 660 |
| ctgcgcggca | gccagaggac | ttgggccccc | gagccccgat | ag | | 702 |

<210> SEQ ID NO 4
<211> LENGTH: 735
<212> TYPE: DNA
<213> ORGANISM: Homo sapiens
<220> FEATURE:
<223> OTHER INFORMATION: human FGF8f

<400> SEQUENCE: 4

| | | | | | |
|---|---|---|---|---|---|
| atgggcagcc | cccgctccgc | gctgagctgc | ctgctgttgc | acttgctggt | cctctgcctc | 60 |
| caagcccagg | aaggcccggg | caggggccct | gcgctgggca | gggagctcgc | ttccctgttc | 120 |

-continued

```
cgggctggcc gggagcccca gggtgtctcc aacaggtaa ctgttcagtc ctcacctaat      180
tttacacagc atgtgaggga gcagagcctg gtgacggatc agctcagccg ccgcctcatc      240
cggacctacc aactctacag ccgcaccagc gggaagcacg tgcaggtcct ggccaacaag      300
cgcatcaacg ccatggcaga ggacggcgac cccttcgcaa agctcatcgt ggagacggac      360
acctttggaa gcagagttcg agtccgagga gccgagacgg gcctctacat ctgcatgaac      420
aagaagggga agctgatcgc caagagcaac ggcaaaggca aggactgcgt cttcacggag      480
attgtgctgg agaacaacta cacagcgctg cagaatgcca agtacgaggg ctggtacatg      540
gccttcaccc gcaagggccg gccccgcaag ggctccaaga cgcggcagca ccagcgtgag      600
gtccacttca tgaagcggct gccccggggc caccacacca ccgagcagag cctgcgcttc      660
gagttcctca actacccgcc cttcacgcgc agcctgcgcg cagccagag gacttgggcc      720
cccgagcccc gatag                                                       735

<210> SEQ ID NO 5
<211> LENGTH: 615
<212> TYPE: DNA
<213> ORGANISM: Mus musculus
<220> FEATURE:
<223> OTHER INFORMATION: murine FGF8a

<400> SEQUENCE: 5
atgggcagcc ccgctccgc gctgagctgc ctgctgttgc acttgctggt tctctgcctc       60
caagcccagc atgtgaggga gcagagcctg gtgacggatc agctcagccg ccgcctcatc      120
cggacctacc agctctacag ccgcaccagc gggaagcacg tgcaggtcct ggccaacaag      180
cgcatcaacg ccatggcaga agacggagac cccttcgcga agctcattgt ggagaccgat      240
acttttggaa gcagagtccg agttcgcggc gcagagacag gtctctacat ctgcatgaac      300
aagaagggga agctaattgc caagagcaac ggcaaaggca aggactgcgt attcacagag      360
atcgtgctgg agaacaacta cacggcgctg cagaacgcca agtacgaggg ctggtacatg      420
gcctttaccc gcaagggccg gccccgcaag ggctccaaga cgcgccagca tcagcgcgag      480
gtgcacttca tgaagcgcct gccgcggggc caccacacca ccgagcagag cctgcgcttc      540
gagttcctca actacccgcc cttcacgcgc agcctgcgcg cagccagag gacttgggcc      600
ccggagcccc gatag                                                       615

<210> SEQ ID NO 6
<211> LENGTH: 648
<212> TYPE: DNA
<213> ORGANISM: Mus musculus
<220> FEATURE:
<223> OTHER INFORMATION: murine FGF8b

<400> SEQUENCE: 6
atgggcagcc ccgctccgc gctgagctgc ctgctgttgc acttgctggt tctctgcctc       60
caagcccagg taactgttca gtcctcacct aattttacac agcatgtgag ggagcagagc      120
ctggtgacgg atcagctcag ccgccgcctc atccggacct accagctcta cagccgcacc      180
agcgggaagc acgtgcaggt cctggccaac aagcgcatca acgccatggc agaagacgga      240
gacccccttcg cgaagctcat tgtggagacc gatacttttg gaagcagagt ccgagttcgc      300
ggcgcagaga caggtctcta catctgcatg aacaagaagg ggaagctaat tgccaagagc      360
aacggcaaag gcaaggactg cgtattcaca gagatcgtgc tggagaacaa ctacacggcg      420
```

| | |
|---|---:|
| ctgcagaacg ccaagtacga gggctggtac atggccttta cccgcaaggg ccggccccgc | 480 |
| aagggctcca agacgcgcca gcatcagcgc gaggtgcact tcatgaagcg cctgccgcgg | 540 |
| ggccaccaca ccaccgagca gagcctgcgc ttcgagttcc tcaactaccc gcccttcacg | 600 |
| cgcagcctgc gcggcagcca gaggacttgg gccccggagc ccgatag | 648 |

<210> SEQ ID NO 7
<211> LENGTH: 702
<212> TYPE: DNA
<213> ORGANISM: Mus musculus
<220> FEATURE:
<223> OTHER INFORMATION: murine FGF8e

<400> SEQUENCE: 7

| | |
|---|---:|
| atgggcagcc cccgctccgc gctgagctgc ctgctgttgc acttgctggt tctctgcctc | 60 |
| caagcccagg aaggcccggg cggggggcct gcgctgggca gggagcccac ttccctgctc | 120 |
| cgagctggcc gggagcccca gggtgtttcc aacagcatgt gaggagca gagcctggtg | 180 |
| acggatcagc tcagccgccg cctcatccgg acctaccagc tctacagccg caccagcggg | 240 |
| aagcacgtgc aggtcctggc caacaagcgc atcaacgcca tggcagaaga cggagacccc | 300 |
| ttcgcgaagc tcattgtgga gaccgatact tttggaagca gagtccgagt tcgcggcgca | 360 |
| gagacaggtc tctacatctg catgaacaag aaggggaagc taattgccaa gagcaacggc | 420 |
| aaaggcaagg actgcgtatt cacagagatc gtgctggaga caactacac ggcgctgcag | 480 |
| aacgccaagt acgagggctg gtacatggcc tttacccgca agggccggcc cgcaagggc | 540 |
| tccaagacgc gccagcatca gcgcgaggtg cacttcatga agcgcctgcc gcggggccac | 600 |
| cacaccaccg agcagagcct gcgcttcgag ttcctcaact accgcccctt cacgcgcagc | 660 |
| ctgcgcggca gccagaggac ttgggccccg gagccccgat ag | 702 |

<210> SEQ ID NO 8
<211> LENGTH: 735
<212> TYPE: DNA
<213> ORGANISM: Mus musculus
<220> FEATURE:
<223> OTHER INFORMATION: murine FGF8f

<400> SEQUENCE: 8

| | |
|---|---:|
| atgggcagcc cccgctccgc gctgagctgc ctgctgttgc acttgctggt tctctgcctc | 60 |
| caagcccagg aaggcccggg cggggggcct gcgctgggca gggagcccac ttccctgctc | 120 |
| cgagctggcc gggagcccca gggtgtttcc aacaggtaa ctgttcagtc ctcacctaat | 180 |
| tttacacagc atgtgaggga gcagagcctg gtgacggatc agctcagccg ccgcctcatc | 240 |
| cggacctacc agctctacag ccgcaccagc gggaagcacg tgcaggtcct ggccaacaag | 300 |
| cgcatcaacg ccatggcaga agacggagac cccttcgcga agctcattgt ggagaccgat | 360 |
| acttttggaa gcagagtccg agttcgcggc gcagagacag gtctctacat ctgcatgaac | 420 |
| aagaagggga agctaattgc caagagcaac ggcaaaggca aggactgcgt attcacagag | 480 |
| atcgtgctgg agaacaacta cacggcgctg cagaacgcca agtacgaggg ctggtacatg | 540 |
| gcctttaccc gcaagggccg gccccgcaag ggctccaaga cgcgccagca tcagcgcgag | 600 |
| gtgcacttca tgaagcgcct gccgcggggc caccacacca ccgagcagag cctgcgcttc | 660 |
| gagttcctca actacccgcc cttcacgcgc agcctgcgcg gcagccagag gacttgggcc | 720 |
| ccggagcccc gatag | 735 |

<210> SEQ ID NO 9
<211> LENGTH: 651
<212> TYPE: DNA
<213> ORGANISM: Homo sapiens
<220> FEATURE:
<223> OTHER INFORMATION: human FGF17

<400> SEQUENCE: 9

```
atgggagccg cccgcctgct gcccaacctc actctgtgct acagctgct gattctctgc      60
tgtcaaactc aggggagaa tcacccgtct cctaatttta accagtacgt gagggaccag     120
ggcgccatga ccgaccagct gagcaggcgg cagatccgcg agtaccaact ctacagcagg    180
accagtggca agcacgtgca ggtcaccggg cgtcgcatct ccgccaccgc cgaggacggc    240
aacaagtttg ccaagctcat agtggagacg gacacgtttg gcagccgggt tcgcatcaaa    300
ggggctgaga gtgagaagta catctgtatg aacaagaggg gcaagctcat cgggaagccc    360
agcgggaaga gcaaagactg cgtgttcacg gagatcgtgc tggagaacaa ctatacggcc    420
ttccagaacg cccggcacga gggctggttc atggccttca cgcggcaggg cggccccgc    480
caggcttccc gcagccgcca gaaccagcgc gaggcccact tcatcaagcg cctctaccaa    540
ggccagctgc ccttccccaa ccacgccgag aagcagaagc agttcgagtt tgtgggctcc    600
gcccccaccc gccggaccaa gcgcacacgg cggccccagc ccctcacgta g             651
```

<210> SEQ ID NO 10
<211> LENGTH: 651
<212> TYPE: DNA
<213> ORGANISM: Mus musculus
<220> FEATURE:
<223> OTHER INFORMATION: murine FGF17

<400> SEQUENCE: 10

```
atgggagccg cccgcctgct gcctaacctt accctgtgct tgcagctatt gattctctgc     60
tgtcaaacac aggggagaa tcacccgtct cctaatttta accagtacgt gagggaccag    120
ggcgctatga ccgaccagct gagcaggcgg caaatccgtg aataccagct ctacagccgg   180
accagtggca agcacgtgca ggtcaccgga cgtcgcatct ctgccaccgc agaggatggc   240
aacaagttcg ccaagctcat cgtggagaca gatacattcg gcagcagagt ccgcatcaag   300
ggggcagaga gcgagaagta catctgtatg aacaagaggg gcaagctgat tgggaagccg   360
agcgggaaga gcaaagactg cgtgttcacc gagatcgtac tggagaacaa ctacacggcc   420
ttccagaacg cccggcacga gggctggttc atggctttca ctcggcaggg ccggccacgc   480
caggcctccc ggagccgcca gaaccagcga gaggcccact tcatcaagcg cctctaccaa   540
ggccagctgc cttttcccaa ccacgctgaa aggcagaagc agttcgaatt tgtgggctcc   600
gcccccactc gcaggaccaa gcgcactcgg aggcccagt cccaaacgta g             651
```

<210> SEQ ID NO 11
<211> LENGTH: 651
<212> TYPE: DNA
<213> ORGANISM: Homo sapiens
<220> FEATURE:
<223> OTHER INFORMATION: human FGF19

<400> SEQUENCE: 11

```
atgcggagcg gtgtgtgtgg ggtccacgta tggatcctgg ccggcctctg gctggccgtg     60
gccgggcgcc cctcgccctt ctcggacgcg gggccccacg tgcactacgg ctggggcgac    120
cccatccgcc tgcggcacct gtacacctcc ggccccacg ggctctccag ctgcttcctg    180
```

```
cgcatccgtg ccgacggcgt cgtggactgc gcgcggggcc agagcgcgca cagtttgctg    240
gagatcaagg cagtcgctct gcggaccgtg gccatcaagg gcgtgcacag cgtgcggtac    300
ctctgcatgg gcgccgacgg caagatgcag gggctgcttc agtactcgga ggaagactgt    360
gctttcgagg aggagatccg cccagatggc tacaatgtgt accgatccga gaagcaccgc    420
ctcccggtct ccctgagcag tgccaaacag cggcagctgt acaagaacag aggctttctt    480
ccactctctc atttcctgcc catgctgccc atggtccagg aggagcctga ggacctcagg    540
ggccacttgg aatctgacat gttctcttcg cccctggaga ccgacagcat ggacccattt    600
gggcttgtca ccggactgga ggccgtgagg agtcccagct ttgagaagta a             651
```

```
<210> SEQ ID NO 12
<211> LENGTH: 657
<212> TYPE: DNA
<213> ORGANISM: Mus musculus
<220> FEATURE:
<223> OTHER INFORMATION: murine FGF15

<400> SEQUENCE: 12
atggcgagaa agtggaacgg gcgtgcggtg gcccgagccc tggtcctggc cactctgtgg    60
ctggctgtgt ctgggcgtcc cctggctcag caatcccagt ctgtgtcaga tgaagatcca    120
ctctttctct acggctgggg caagattacc cgcctgcagt acctgtactc cgctggtccc    180
tatgtctcca actgcttcct ccgaatccgg agcgacggct ctgtggactg cgaggaggac    240
caaaacgaac gaaatttgtt ggaattccgc gcggtcgctc tgaagacgat tgccatcaag    300
gacgtcagca gcgtgcggta cctctgcatg agcgcggacg gcaagatata cgggctgatt    360
cgctactcgg aggaagactg taccttcagg gaggaaatgg actgtttagg ctacaaccag    420
tacagatcca tgaagcacca tctccatatc atcttcatcc aggccaagcc cagagaacag    480
ctccaggacc agaaaccctc aaactttatc cccgtgtttc accgctcctt cttgaaacc    540 ggggaccagc tgaggtctaa aatgttctcc ctgcccctgg agagtgacag catggatccg    600
ttcaggatgg tggaggatgt agaccaccta gtgaagagtc ccagcttcca gaaatga      657
```

```
<210> SEQ ID NO 13
<211> LENGTH: 630
<212> TYPE: DNA
<213> ORGANISM: Homo sapiens
<220> FEATURE:
<223> OTHER INFORMATION: human FGF21

<400> SEQUENCE: 13
atggactcgg acgagaccgg gttcgagcac tcaggactgt gggtttctgt gctggctggt    60
cttctgctgg gagcctgcca ggcacacccc atccctgact ccagtcctct cctgcaattc    120
gggggccaag tccggcagcg gtacctctac acagatgatg cccagcagac agaagcccac    180
ctggagatca gggaggatgg gacggtgggg gcgctgctga ccagagcccg aaagtctc    240 ctgcagctga aagccttgaa gccgggagtt attcaaatct gggagtcaa gacatccagg    300 ttcctgtgcc agcggccaga tggggccctg tatggatcgc tcactttga ccctgaggcc    360 tgcagcttcc gggagctgct tcttgaggac ggatacaatg tttaccagtc cgaagcccac    420
ggcctcccgc tgcacctgcc agggaacaag tccccacacc gggaccctgc accccgagga    480
ccagctcgct cctgccact accaggcctg ccccccgcac tcccggagcc acccggaatc    540 ctggccccc agccccccga tgtgggctcc tcggaccctc tgagcatggt gggaccttcc    600
cagggccgaa gccccagcta cgcttcctga                                    630
```

<210> SEQ ID NO 14
<211> LENGTH: 633
<212> TYPE: DNA
<213> ORGANISM: Mus musculus
<220> FEATURE:
<223> OTHER INFORMATION: murine FGF21

<400> SEQUENCE: 14

```
atggaatgga tgagatctag agttgggacc ctgggactgt gggtccgact gctgctggct      60
gtcttcctgc tgggggtcta ccaagcatac cccatccctg actccagccc cctcctccag     120
tttgggggtc aagtccggca gaggtacctc tacacagatg acgaccaaga cactgaagcc     180
cacctggaga tcagggagga tggaacagtg gtaggcgcag cacaccgcag tccagaaagt     240
ctcctggagc tcaaagcctt gaagccaggg gtcattcaaa tcctgggtgt caaagcctct     300
aggtttcttt gccaacagcc agatggagct ctctatggat cgcctcactt tgatcctgag     360
gcctgcagct tcagagaact gctgctggag gacggttaca atgtgtacca gtctgaagcc     420
catggcctgc ccctgcgtct gcctcagaag gactccccaa accaggatgc aacatcctgg     480
ggacctgtgc gcttcctgcc catgccaggc ctgctccacg agcccaagag ccaagcagga     540
ttcctgcccc cagagccccc agatgtgggc tcctctgacc ccctgagcat ggtagagcct     600
ttacagggcc gaagccccag ctatgcgtcc tga                                  633
```

<210> SEQ ID NO 15
<211> LENGTH: 204
<212> TYPE: PRT
<213> ORGANISM: Homo sapiens
<220> FEATURE:
<223> OTHER INFORMATION: human FGF8a

<400> SEQUENCE: 15

```
Met Gly Ser Pro Arg Ser Ala Leu Ser Cys Leu Leu Leu His Leu Leu
1               5                   10                  15

Val Leu Cys Leu Gln Ala Gln His Val Arg Glu Gln Ser Leu Val Thr
            20                  25                  30

Asp Gln Leu Ser Arg Arg Leu Ile Arg Thr Tyr Gln Leu Tyr Ser Arg
        35                  40                  45

Thr Ser Gly Lys His Val Gln Val Leu Ala Asn Lys Arg Ile Asn Ala
    50                  55                  60

Met Ala Glu Asp Gly Asp Pro Phe Ala Lys Leu Ile Val Glu Thr Asp
65                  70                  75                  80

Thr Phe Gly Ser Arg Val Arg Val Arg Gly Ala Glu Thr Gly Leu Tyr
                85                  90                  95

Ile Cys Met Asn Lys Lys Gly Lys Leu Ile Ala Lys Ser Asn Gly Lys
            100                 105                 110

Gly Lys Asp Cys Val Phe Thr Glu Ile Val Leu Glu Asn Asn Tyr Thr
        115                 120                 125

Ala Leu Gln Asn Ala Lys Tyr Glu Gly Trp Tyr Met Ala Phe Thr Arg
    130                 135                 140

Lys Gly Arg Pro Arg Lys Gly Ser Lys Thr Arg Gln His Gln Arg Glu
145                 150                 155                 160

Val His Phe Met Lys Arg Leu Pro Arg Gly His His Thr Thr Glu Gln
                165                 170                 175

Ser Leu Arg Phe Glu Phe Leu Asn Tyr Pro Pro Phe Thr Arg Ser Leu
            180                 185                 190
```

-continued

Arg Gly Ser Gln Arg Thr Trp Ala Pro Glu Pro Arg
            195                 200

<210> SEQ ID NO 16
<211> LENGTH: 215
<212> TYPE: PRT
<213> ORGANISM: Homo sapiens
<220> FEATURE:
<223> OTHER INFORMATION: human FGF8b

<400> SEQUENCE: 16

Met Gly Ser Pro Arg Ser Ala Leu Ser Cys Leu Leu Leu His Leu Leu
1               5                   10                  15

Val Leu Cys Leu Gln Ala Gln Val Thr Val Gln Ser Ser Pro Asn Phe
            20                  25                  30

Thr Gln His Val Arg Glu Gln Ser Leu Val Thr Asp Gln Leu Ser Arg
        35                  40                  45

Arg Leu Ile Arg Thr Tyr Gln Leu Tyr Ser Arg Thr Ser Gly Lys His
    50                  55                  60

Val Gln Val Leu Ala Asn Lys Arg Ile Asn Ala Met Ala Glu Asp Gly
65                  70                  75                  80

Asp Pro Phe Ala Lys Leu Ile Val Glu Thr Asp Thr Phe Gly Ser Arg
                85                  90                  95

Val Arg Val Arg Gly Ala Glu Thr Gly Leu Tyr Ile Cys Met Asn Lys
            100                 105                 110

Lys Gly Lys Leu Ile Ala Lys Ser Asn Gly Lys Gly Lys Asp Cys Val
        115                 120                 125

Phe Thr Glu Ile Val Leu Glu Asn Asn Tyr Thr Ala Leu Gln Asn Ala
    130                 135                 140

Lys Tyr Glu Gly Trp Tyr Met Ala Phe Thr Arg Lys Gly Arg Pro Arg
145                 150                 155                 160

Lys Gly Ser Lys Thr Arg Gln His Gln Arg Glu Val His Phe Met Lys
                165                 170                 175

Arg Leu Pro Arg Gly His His Thr Thr Glu Gln Ser Leu Arg Phe Glu
            180                 185                 190

Phe Leu Asn Tyr Pro Pro Phe Thr Arg Ser Leu Arg Gly Ser Gln Arg
        195                 200                 205

Thr Trp Ala Pro Glu Pro Arg
    210                 215

<210> SEQ ID NO 17
<211> LENGTH: 233
<212> TYPE: PRT
<213> ORGANISM: Homo sapiens
<220> FEATURE:
<223> OTHER INFORMATION: human FGF8e

<400> SEQUENCE: 17

Met Gly Ser Pro Arg Ser Ala Leu Ser Cys Leu Leu Leu His Leu Leu
1               5                   10                  15

Val Leu Cys Leu Gln Ala Gln Glu Gly Pro Gly Arg Gly Pro Ala Leu
            20                  25                  30

Gly Arg Glu Leu Ala Ser Leu Phe Arg Ala Gly Arg Glu Pro Gln Gly
        35                  40                  45

Val Ser Gln Gln His Val Arg Glu Gln Ser Leu Val Thr Asp Gln Leu
    50                  55                  60

Ser Arg Arg Leu Ile Arg Thr Tyr Gln Leu Tyr Ser Arg Thr Ser Gly
65                  70                  75                  80

```
Lys His Val Gln Val Leu Ala Asn Lys Arg Ile Asn Ala Met Ala Glu
            85                  90                  95

Asp Gly Asp Pro Phe Ala Lys Leu Ile Val Glu Thr Asp Thr Phe Gly
        100                 105                 110

Ser Arg Val Arg Val Arg Gly Ala Glu Thr Gly Leu Tyr Ile Cys Met
        115                 120                 125

Asn Lys Lys Gly Lys Leu Ile Ala Lys Ser Asn Gly Lys Gly Lys Asp
130                 135                 140

Cys Val Phe Thr Glu Ile Val Leu Glu Asn Asn Tyr Thr Ala Leu Gln
145                 150                 155                 160

Asn Ala Lys Tyr Glu Gly Trp Tyr Met Ala Phe Thr Arg Lys Gly Arg
                165                 170                 175

Pro Arg Lys Gly Ser Lys Thr Arg Gln His Gln Arg Glu Val His Phe
            180                 185                 190

Met Lys Arg Leu Pro Arg Gly His His Thr Thr Glu Gln Ser Leu Arg
            195                 200                 205

Phe Glu Phe Leu Asn Tyr Pro Pro Phe Thr Arg Ser Leu Arg Gly Ser
    210                 215                 220

Gln Arg Thr Trp Ala Pro Glu Pro Arg
225                 230

<210> SEQ ID NO 18
<211> LENGTH: 244
<212> TYPE: PRT
<213> ORGANISM: Homo sapiens
<220> FEATURE:
<223> OTHER INFORMATION: human FGF8f

<400> SEQUENCE: 18

Met Gly Ser Pro Arg Ser Ala Leu Ser Cys Leu Leu Leu His Leu Leu
1               5                   10                  15

Val Leu Cys Leu Gln Ala Gln Glu Gly Pro Gly Arg Gly Pro Ala Leu
            20                  25                  30

Gly Arg Glu Leu Ala Ser Leu Phe Arg Ala Gly Arg Glu Pro Gln Gly
        35                  40                  45

Val Ser Gln Gln Val Thr Val Gln Ser Ser Pro Asn Phe Thr Gln His
    50                  55                  60

Val Arg Glu Gln Ser Leu Val Thr Asp Gln Leu Ser Arg Arg Leu Ile
65                  70                  75                  80

Arg Thr Tyr Gln Leu Tyr Ser Arg Thr Ser Gly Lys His Val Gln Val
                85                  90                  95

Leu Ala Asn Lys Arg Ile Asn Ala Met Ala Glu Asp Gly Asp Pro Phe
            100                 105                 110

Ala Lys Leu Ile Val Glu Thr Asp Thr Phe Gly Ser Arg Val Arg Val
        115                 120                 125

Arg Gly Ala Glu Thr Gly Leu Tyr Ile Cys Met Asn Lys Lys Gly Lys
    130                 135                 140

Leu Ile Ala Lys Ser Asn Gly Lys Gly Lys Asp Cys Val Phe Thr Glu
145                 150                 155                 160

Ile Val Leu Glu Asn Asn Tyr Thr Ala Leu Gln Asn Ala Lys Tyr Glu
                165                 170                 175

Gly Trp Tyr Met Ala Phe Thr Arg Lys Gly Arg Pro Arg Lys Gly Ser
            180                 185                 190

Lys Thr Arg Gln His Gln Arg Glu Val His Phe Met Lys Arg Leu Pro
        195                 200                 205
```

```
Arg Gly His His Thr Thr Glu Gln Ser Leu Arg Phe Glu Phe Leu Asn
    210                 215                 220
Tyr Pro Pro Phe Thr Arg Ser Leu Arg Gly Ser Gln Arg Thr Trp Ala
225                 230                 235                 240
Pro Glu Pro Arg

<210> SEQ ID NO 19
<211> LENGTH: 204
<212> TYPE: PRT
<213> ORGANISM: Mus musculus
<220> FEATURE:
<223> OTHER INFORMATION: murine FGF8a

<400> SEQUENCE: 19

Met Gly Ser Pro Arg Ser Ala Leu Ser Cys Leu Leu Leu His Leu Leu
1               5                   10                  15
Val Leu Cys Leu Gln Ala Gln His Val Arg Glu Gln Ser Leu Val Thr
            20                  25                  30
Asp Gln Leu Ser Arg Arg Leu Ile Arg Thr Tyr Gln Leu Tyr Ser Arg
        35                  40                  45
Thr Ser Gly Lys His Val Gln Val Leu Ala Asn Lys Arg Ile Asn Ala
    50                  55                  60
Met Ala Glu Asp Gly Asp Pro Phe Ala Lys Leu Ile Val Glu Thr Asp
65                  70                  75                  80
Thr Phe Gly Ser Arg Val Arg Val Arg Gly Ala Glu Thr Gly Leu Tyr
                85                  90                  95
Ile Cys Met Asn Lys Lys Gly Lys Leu Ile Ala Lys Ser Asn Gly Lys
            100                 105                 110
Gly Lys Asp Cys Val Phe Thr Glu Ile Val Leu Glu Asn Asn Tyr Thr
        115                 120                 125
Ala Leu Gln Asn Ala Lys Tyr Glu Gly Trp Tyr Met Ala Phe Thr Arg
    130                 135                 140
Lys Gly Arg Pro Arg Lys Gly Ser Lys Thr Arg Gln His Gln Arg Glu
145                 150                 155                 160
Val His Phe Met Lys Arg Leu Pro Arg Gly His His Thr Thr Glu Gln
                165                 170                 175
Ser Leu Arg Phe Glu Phe Leu Asn Tyr Pro Pro Phe Thr Arg Ser Leu
            180                 185                 190
Arg Gly Ser Gln Arg Thr Trp Ala Pro Glu Pro Arg
        195                 200

<210> SEQ ID NO 20
<211> LENGTH: 215
<212> TYPE: PRT
<213> ORGANISM: Mus musculus
<220> FEATURE:
<223> OTHER INFORMATION: murine FGF8b

<400> SEQUENCE: 20

Met Gly Ser Pro Arg Ser Ala Leu Ser Cys Leu Leu Leu His Leu Leu
1               5                   10                  15
Val Leu Cys Leu Gln Ala Gln Val Thr Val Gln Ser Ser Pro Asn Phe
            20                  25                  30
Thr Gln His Val Arg Glu Gln Ser Leu Val Thr Asp Gln Leu Ser Arg
        35                  40                  45
Arg Leu Ile Arg Thr Tyr Gln Leu Tyr Ser Arg Thr Ser Gly Lys His
    50                  55                  60
```

```
Val Gln Val Leu Ala Asn Lys Arg Ile Asn Ala Met Ala Glu Asp Gly
 65                  70                  75                  80

Asp Pro Phe Ala Lys Leu Ile Val Glu Thr Asp Thr Phe Gly Ser Arg
             85                  90                  95

Val Arg Val Arg Gly Ala Glu Thr Gly Leu Tyr Ile Cys Met Asn Lys
            100                 105                 110

Lys Gly Lys Leu Ile Ala Lys Ser Asn Gly Lys Gly Lys Asp Cys Val
        115                 120                 125

Phe Thr Glu Ile Val Leu Glu Asn Asn Tyr Thr Ala Leu Gln Asn Ala
    130                 135                 140

Lys Tyr Glu Gly Trp Tyr Met Ala Phe Thr Arg Lys Gly Arg Pro Arg
145                 150                 155                 160

Lys Gly Ser Lys Thr Arg Gln His Gln Arg Glu Val His Phe Met Lys
                165                 170                 175

Arg Leu Pro Arg Gly His His Thr Thr Glu Gln Ser Leu Arg Phe Glu
            180                 185                 190

Phe Leu Asn Tyr Pro Pro Phe Thr Arg Ser Leu Arg Gly Ser Gln Arg
        195                 200                 205

Thr Trp Ala Pro Glu Pro Arg
    210                 215

<210> SEQ ID NO 21
<211> LENGTH: 233
<212> TYPE: PRT
<213> ORGANISM: Mus musculus
<220> FEATURE:
<223> OTHER INFORMATION: murine FGF8e

<400> SEQUENCE: 21

Met Gly Ser Pro Arg Ser Ala Leu Ser Cys Leu Leu Leu His Leu Leu
1               5                   10                  15

Val Leu Cys Leu Gln Ala Gln Glu Gly Pro Gly Gly Gly Pro Ala Leu
            20                  25                  30

Gly Arg Glu Pro Thr Ser Leu Leu Arg Ala Gly Arg Glu Pro Gln Gly
        35                  40                  45

Val Ser Gln Gln His Val Arg Glu Gln Ser Leu Val Thr Asp Gln Leu
 50                  55                  60

Ser Arg Arg Leu Ile Arg Thr Tyr Gln Leu Tyr Ser Arg Thr Ser Gly
 65                  70                  75                  80

Lys His Val Gln Val Leu Ala Asn Lys Arg Ile Asn Ala Met Ala Glu
             85                  90                  95

Asp Gly Asp Pro Phe Ala Lys Leu Ile Val Glu Thr Asp Thr Phe Gly
            100                 105                 110

Ser Arg Val Arg Val Arg Gly Ala Glu Thr Gly Leu Tyr Ile Cys Met
        115                 120                 125

Asn Lys Lys Gly Lys Leu Ile Ala Lys Ser Asn Gly Lys Gly Lys Asp
    130                 135                 140

Cys Val Phe Thr Glu Ile Val Leu Glu Asn Asn Tyr Thr Ala Leu Gln
145                 150                 155                 160

Asn Ala Lys Tyr Glu Gly Trp Tyr Met Ala Phe Thr Arg Lys Gly Arg
                165                 170                 175

Pro Arg Lys Gly Ser Lys Thr Arg Gln His Gln Arg Glu Val His Phe
            180                 185                 190

Met Lys Arg Leu Pro Arg Gly His His Thr Thr Glu Gln Ser Leu Arg
        195                 200                 205
```

```
Phe Glu Phe Leu Asn Tyr Pro Pro Phe Thr Arg Ser Leu Arg Gly Ser
    210                 215                 220

Gln Arg Thr Trp Ala Pro Glu Pro Arg
225                 230

<210> SEQ ID NO 22
<211> LENGTH: 244
<212> TYPE: PRT
<213> ORGANISM: Mus musculus
<220> FEATURE:
<223> OTHER INFORMATION: murine FGF8f

<400> SEQUENCE: 22

Met Gly Ser Pro Arg Ser Ala Leu Ser Cys Leu Leu Leu His Leu Leu
1               5                   10                  15

Val Leu Cys Leu Gln Ala Gln Glu Gly Pro Gly Gly Pro Ala Leu
            20                  25                  30

Gly Arg Glu Pro Thr Ser Leu Leu Arg Ala Gly Arg Glu Pro Gln Gly
        35                  40                  45

Val Ser Gln Gln Val Thr Val Gln Ser Ser Pro Asn Phe Thr Gln His
    50                  55                  60

Val Arg Glu Gln Ser Leu Val Thr Asp Gln Leu Ser Arg Arg Leu Ile
65                  70                  75                  80

Arg Thr Tyr Gln Leu Tyr Ser Arg Thr Ser Gly Lys His Val Gln Val
                85                  90                  95

Leu Ala Asn Lys Arg Ile Asn Ala Met Ala Glu Asp Gly Asp Pro Phe
            100                 105                 110

Ala Lys Leu Ile Val Glu Thr Asp Thr Phe Gly Ser Arg Val Arg Val
        115                 120                 125

Arg Gly Ala Glu Thr Gly Leu Tyr Ile Cys Met Asn Lys Lys Gly Lys
    130                 135                 140

Leu Ile Ala Lys Ser Asn Gly Lys Gly Lys Asp Cys Val Phe Thr Glu
145                 150                 155                 160

Ile Val Leu Glu Asn Asn Tyr Thr Ala Leu Gln Asn Ala Lys Tyr Glu
                165                 170                 175

Gly Trp Tyr Met Ala Phe Thr Arg Lys Gly Arg Pro Arg Lys Gly Ser
            180                 185                 190

Lys Thr Arg Gln His Gln Arg Glu Val His Phe Met Lys Arg Leu Pro
        195                 200                 205

Arg Gly His His Thr Thr Glu Gln Ser Leu Arg Phe Glu Phe Leu Asn
    210                 215                 220

Tyr Pro Pro Phe Thr Arg Ser Leu Arg Gly Ser Gln Arg Thr Trp Ala
225                 230                 235                 240

Pro Glu Pro Arg

<210> SEQ ID NO 23
<211> LENGTH: 216
<212> TYPE: PRT
<213> ORGANISM: Homo sapiens
<220> FEATURE:
<223> OTHER INFORMATION: human FGF17

<400> SEQUENCE: 23

Met Gly Ala Ala Arg Leu Leu Pro Asn Leu Thr Leu Cys Leu Gln Leu
1               5                   10                  15

Leu Ile Leu Cys Cys Gln Thr Gln Gly Glu Asn His Pro Ser Pro Asn
            20                  25                  30
```

```
Phe Asn Gln Tyr Val Arg Asp Gln Gly Ala Met Thr Asp Gln Leu Ser
                35                  40                  45

Arg Arg Gln Ile Arg Glu Tyr Gln Leu Tyr Ser Arg Thr Ser Gly Lys
 50                  55                  60

His Val Gln Val Thr Gly Arg Arg Ile Ser Ala Thr Ala Glu Asp Gly
 65                  70                  75                  80

Asn Lys Phe Ala Lys Leu Ile Val Glu Thr Asp Thr Phe Gly Ser Arg
                85                  90                  95

Val Arg Ile Lys Gly Ala Glu Ser Glu Lys Tyr Ile Cys Met Asn Lys
                100                 105                 110

Arg Gly Lys Leu Ile Gly Lys Pro Ser Gly Lys Ser Lys Asp Cys Val
                115                 120                 125

Phe Thr Glu Ile Val Leu Glu Asn Asn Tyr Thr Ala Phe Gln Asn Ala
                130                 135                 140

Arg His Glu Gly Trp Phe Met Ala Phe Thr Arg Gln Gly Arg Pro Arg
145                 150                 155                 160

Gln Ala Ser Arg Ser Arg Gln Asn Gln Arg Glu Ala His Phe Ile Lys
                165                 170                 175

Arg Leu Tyr Gln Gly Gln Leu Pro Phe Pro Asn His Ala Glu Lys Gln
                180                 185                 190

Lys Gln Phe Glu Phe Val Gly Ser Ala Pro Thr Arg Thr Arg Thr Lys Arg
                195                 200                 205

Thr Arg Arg Pro Gln Pro Leu Thr
210                 215

<210> SEQ ID NO 24
<211> LENGTH: 216
<212> TYPE: PRT
<213> ORGANISM: Mus musculus
<220> FEATURE:
<223> OTHER INFORMATION: murine FGF17

<400> SEQUENCE: 24

Met Gly Ala Ala Arg Leu Leu Pro Asn Leu Thr Leu Cys Leu Gln Leu
 1               5                  10                  15

Leu Ile Leu Cys Cys Gln Thr Gln Gly Glu Asn His Pro Ser Pro Asn
                20                  25                  30

Phe Asn Gln Tyr Val Arg Asp Gln Gly Ala Met Thr Asp Gln Leu Ser
                35                  40                  45

Arg Arg Gln Ile Arg Glu Tyr Gln Leu Tyr Ser Arg Thr Ser Gly Lys
 50                  55                  60

His Val Gln Val Thr Gly Arg Arg Ile Ser Ala Thr Ala Glu Asp Gly
 65                  70                  75                  80

Asn Lys Phe Ala Lys Leu Ile Val Glu Thr Asp Thr Phe Gly Ser Arg
                85                  90                  95

Val Arg Ile Lys Gly Ala Glu Ser Glu Lys Tyr Ile Cys Met Asn Lys
                100                 105                 110

Arg Gly Lys Leu Ile Gly Lys Pro Ser Gly Lys Ser Lys Asp Cys Val
                115                 120                 125

Phe Thr Glu Ile Val Leu Glu Asn Asn Tyr Thr Ala Phe Gln Asn Ala
                130                 135                 140

Arg His Glu Gly Trp Phe Met Ala Phe Thr Arg Gln Gly Arg Pro Arg
145                 150                 155                 160

Gln Ala Ser Arg Ser Arg Gln Asn Gln Arg Glu Ala His Phe Ile Lys
                165                 170                 175
```

```
Arg Leu Tyr Gln Gly Gln Leu Pro Phe Pro Asn His Ala Glu Arg Gln
            180                 185                 190

Lys Gln Phe Glu Phe Val Gly Ser Ala Pro Thr Arg Thr Lys Arg
        195                 200                 205

Thr Arg Arg Pro Gln Ser Gln Thr
        210                 215

<210> SEQ ID NO 25
<211> LENGTH: 216
<212> TYPE: PRT
<213> ORGANISM: Homo sapiens
<220> FEATURE:
<223> OTHER INFORMATION: human FGF19

<400> SEQUENCE: 25

Met Arg Ser Gly Cys Val Val Val His Val Trp Ile Leu Ala Gly Leu
1               5                   10                  15

Trp Leu Ala Val Ala Gly Arg Pro Leu Ala Phe Ser Asp Ala Gly Pro
            20                  25                  30

His Val His Tyr Gly Trp Gly Asp Pro Ile Arg Leu Arg His Leu Tyr
        35                  40                  45

Thr Ser Gly Pro His Gly Leu Ser Ser Cys Phe Leu Arg Ile Arg Ala
    50                  55                  60

Asp Gly Val Val Asp Cys Ala Arg Gly Gln Ser Ala His Ser Leu Leu
65                  70                  75                  80

Glu Ile Lys Ala Val Ala Leu Arg Thr Val Ala Ile Lys Gly Val His
                85                  90                  95

Ser Val Arg Tyr Leu Cys Met Gly Ala Asp Gly Lys Met Gln Gly Leu
            100                 105                 110

Leu Gln Tyr Ser Glu Glu Asp Cys Ala Phe Glu Glu Ile Arg Pro
        115                 120                 125

Asp Gly Tyr Asn Val Tyr Arg Ser Glu Lys His Arg Leu Pro Val Ser
    130                 135                 140

Leu Ser Ser Ala Lys Gln Arg Gln Leu Tyr Lys Asn Arg Gly Phe Leu
145                 150                 155                 160

Pro Leu Ser His Phe Leu Pro Met Leu Pro Met Val Pro Glu Glu Pro
                165                 170                 175

Glu Asp Leu Arg Gly His Leu Glu Ser Asp Met Phe Ser Ser Pro Leu
            180                 185                 190

Glu Thr Asp Ser Met Asp Pro Phe Gly Leu Val Thr Gly Leu Glu Ala
        195                 200                 205

Val Arg Ser Pro Ser Phe Glu Lys
    210                 215

<210> SEQ ID NO 26
<211> LENGTH: 218
<212> TYPE: PRT
<213> ORGANISM: Mus musculus
<220> FEATURE:
<223> OTHER INFORMATION: murine FGF15

<400> SEQUENCE: 26

Met Ala Arg Lys Trp Asn Gly Arg Ala Val Ala Arg Ala Leu Val Leu
1               5                   10                  15

Ala Thr Leu Trp Leu Ala Val Ser Gly Arg Pro Leu Ala Gln Gln Ser
            20                  25                  30

Gln Ser Val Ser Asp Glu Asp Pro Leu Phe Leu Tyr Gly Trp Gly Lys
```

```
                35                  40                  45
Ile Thr Arg Leu Gln Tyr Leu Tyr Ser Ala Gly Pro Tyr Val Ser Asn
 50                  55                  60

Cys Phe Leu Arg Ile Arg Ser Asp Gly Ser Val Asp Cys Glu Glu Asp
 65                  70                  75                  80

Gln Asn Glu Arg Asn Leu Leu Glu Phe Arg Ala Val Ala Leu Lys Thr
                 85                  90                  95

Ile Ala Ile Lys Asp Val Ser Ser Val Arg Tyr Leu Cys Met Ser Ala
                100                 105                 110

Asp Gly Lys Ile Tyr Gly Leu Ile Arg Tyr Ser Glu Glu Asp Cys Thr
                115                 120                 125

Phe Arg Glu Glu Met Asp Cys Leu Gly Tyr Asn Gln Tyr Arg Ser Met
130                 135                 140

Lys His His Leu His Ile Ile Phe Ile Gln Ala Lys Pro Arg Glu Gln
145                 150                 155                 160

Leu Gln Asp Gln Lys Pro Ser Asn Phe Ile Pro Val Phe His Arg Ser
                165                 170                 175

Phe Phe Glu Thr Gly Asp Gln Leu Arg Ser Lys Met Phe Ser Leu Pro
                180                 185                 190

Leu Glu Ser Asp Ser Met Asp Pro Phe Arg Met Val Glu Asp Val Asp
                195                 200                 205

His Leu Val Lys Ser Pro Ser Phe Gln Lys
210                 215

<210> SEQ ID NO 27
<211> LENGTH: 209
<212> TYPE: PRT
<213> ORGANISM: Homo sapiens
<220> FEATURE:
<223> OTHER INFORMATION: human FGF21

<400> SEQUENCE: 27

Met Asp Ser Asp Glu Thr Gly Phe Glu His Ser Gly Leu Trp Val Ser
 1               5                  10                  15

Val Leu Ala Gly Leu Leu Leu Gly Ala Cys Gln Ala His Pro Ile Pro
                20                  25                  30

Asp Ser Ser Pro Leu Leu Gln Phe Gly Gly Gln Val Arg Gln Arg Tyr
                35                  40                  45

Leu Tyr Thr Asp Asp Ala Gln Gln Thr Glu Ala His Leu Glu Ile Arg
 50                  55                  60

Glu Asp Gly Thr Val Gly Gly Ala Ala Asp Gln Ser Pro Glu Ser Leu
 65                  70                  75                  80

Leu Gln Leu Lys Ala Leu Lys Pro Gly Val Ile Gln Ile Leu Gly Val
                 85                  90                  95

Lys Thr Ser Arg Phe Leu Cys Gln Arg Pro Asp Gly Ala Leu Tyr Gly
                100                 105                 110

Ser Leu His Phe Asp Pro Glu Ala Cys Ser Phe Arg Glu Leu Leu Leu
                115                 120                 125

Glu Asp Gly Tyr Asn Val Tyr Gln Ser Glu Ala His Gly Leu Pro Leu
130                 135                 140

His Leu Pro Gly Asn Lys Ser Pro His Arg Asp Pro Ala Pro Arg Gly
145                 150                 155                 160

Pro Ala Arg Phe Leu Pro Leu Pro Gly Leu Pro Pro Ala Leu Pro Glu
                165                 170                 175

Pro Pro Gly Ile Leu Ala Pro Gln Pro Pro Asp Val Gly Ser Ser Asp
```

```
                180             185             190
Pro Leu Ser Met Val Gly Pro Ser Gln Gly Arg Ser Pro Ser Tyr Ala
            195                 200                 205
Ser

<210> SEQ ID NO 28
<211> LENGTH: 210
<212> TYPE: PRT
<213> ORGANISM: Mus musculus
<220> FEATURE:
<223> OTHER INFORMATION: murine FGF21

<400> SEQUENCE: 28

Met Glu Trp Met Arg Ser Arg Val Gly Thr Leu Gly Leu Trp Val Arg
1               5                   10                  15

Leu Leu Leu Ala Val Phe Leu Gly Val Tyr Gln Ala Tyr Pro Ile
            20                  25                  30

Pro Asp Ser Ser Pro Leu Leu Gln Phe Gly Gly Gln Val Arg Gln Arg
            35                  40                  45

Tyr Leu Tyr Thr Asp Asp Gln Asp Thr Glu Ala His Leu Glu Ile
    50                  55                  60

Arg Glu Asp Gly Thr Val Val Gly Ala Ala His Arg Ser Pro Glu Ser
65                  70                  75                  80

Leu Leu Glu Leu Lys Ala Leu Lys Pro Gly Val Ile Gln Ile Leu Gly
                85                  90                  95

Val Lys Ala Ser Arg Phe Leu Cys Gln Gln Pro Asp Gly Ala Leu Tyr
            100                 105                 110

Gly Ser Pro His Phe Asp Pro Glu Ala Cys Ser Phe Arg Glu Leu Leu
        115                 120                 125

Leu Glu Asp Gly Tyr Asn Val Tyr Gln Ser Glu Ala His Gly Leu Pro
    130                 135                 140

Leu Arg Leu Pro Gln Lys Asp Ser Pro Asn Gln Asp Ala Thr Ser Trp
145                 150                 155                 160

Gly Pro Val Arg Phe Leu Pro Met Pro Gly Leu Leu His Glu Pro Gln
                165                 170                 175

Asp Gln Ala Gly Phe Leu Pro Pro Glu Pro Asp Val Gly Ser Ser
            180                 185                 190

Asp Pro Leu Ser Met Val Glu Pro Leu Gln Gly Arg Ser Pro Ser Tyr
            195                 200                 205

Ala Ser
    210

<210> SEQ ID NO 29
<211> LENGTH: 2463
<212> TYPE: DNA
<213> ORGANISM: Homo sapiens
<220> FEATURE:
<223> OTHER INFORMATION: human FGFR1

<400> SEQUENCE: 29
atgtggagct ggaagtgcct cctcttctgg gctgtgctgg tcacagccac actctgcacc      60
gctaggccgt ccccgacctt gcctgaacaa gcccagcccc ggggagcccc tgtggaagtg     120
gagtccttcc tggtccaccc cggtgacctg ctgcagcttc gctgtcggct gcgggacgat     180
gtgcagagca tcaactggct gcgggacggg gtgcagctgg cggaaagcaa ccgcaccccg     240
atcacagggg aggaggtgga ggtgcaggac tccgtgcccg cagactccgg cctctatgct     300
```

| | |
|---|---|
| tgcgtaacca gcagccctc gggcagtgac accacctact tctccgtcaa tgtttcagat | 360 |
| gctctcccct cctcggagga tgatgatgat gatgatgact cctcttcaga ggagaaagaa | 420 |
| acagataaca ccaaaccaaa ccccgtagct ccatattgga catccccaga aaagatggaa | 480 |
| aagaaattgc atgcagtgcc ggctgccaag acagtgaagt tcaaatgccc ttccagtggg | 540 |
| accccaaacc ccacactgcg ctggttgaaa aatggcaaag aattcaaacc tgaccacaga | 600 |
| attggaggct acaaggtccg ttatgccacc tggagcatca taatggactc tgtggtgccc | 660 |
| tctgacaagg gcaactacac ctgcattgtg gagaatgagt acggcagcat caaccacaca | 720 |
| taccagctgg atgtcgtgga gcggtcccct caccggccca tcctgcaagc agggttgccc | 780 |
| gccaacaaaa cagtggccct gggtagcaac gtggagttca tgtgtaaggt gtacagtgac | 840 |
| ccgcagccgc acatccagtg gctaaagcac atcgaggtga atgggagcaa gattggccca | 900 |
| gacaacctgc cttatgtcca gatcttgaag actgctggag ttaataccac cgacaaagag | 960 |
| atggaggtgc ttcacttaag aaatgtctcc tttgaggacg caggggagta tacgtgcttg | 1020 |
| gcgggtaact ctatcggact ctcccatcac tctgcatggt tgaccgttct ggaagccctg | 1080 |
| gaagagaggc cggcagtgat gacctcgccc ctgtacctgg agatcatcat ctattgcaca | 1140 |
| ggggccttcc tcatctcctg catggtgggg tcggtcatcg tctacaagat gaagagtggt | 1200 |
| accaagaaga gtgacttcca cagccagatg gctgtgcaca agctggccaa gagcatccct | 1260 |
| ctgcgcagac aggtaacagt gtctgctgac tccagtgcat ccatgaactc tgggggttctt | 1320 |
| ctggttcggc catcacggct ctcctccagt gggactccca tgctagcagg ggtctctgag | 1380 |
| tatgagcttc ccgaagaccc tcgctgggag ctgcctcggg acagactggt cttaggcaaa | 1440 |
| cccctgggag agggctgctt tgggcaggtg gtgttggcag aggctatcgg gctggacaag | 1500 |
| gacaaaccca accgtgtgac caaagtggct gtgaagatgt tgaagtcgga cgcaacagag | 1560 |
| aaagacttgt cagacctgat ctcagaaatg gagatgatga gatgatcgg gaagcataag | 1620 |
| aatatcatca acctgctggg ggcctgcacg caggatggtc ccttgtatgt catcgtggag | 1680 |
| tatgcctcca agggcaacct gcgggagtac ctgcaggccc ggaggccccc agggctggaa | 1740 |
| tactgctaca accccagcca caacccagag gagcagctct cctccaagga cctggtgtcc | 1800 |
| tgcgcctacc aggtggcccg aggcatggag tatctggcct ccaagaagtg catacaccga | 1860 |
| gacctggcag ccaggaatgt cctggtgaca gaggacaatg tgatgaagat agcagacttt | 1920 |
| ggcctcgcac gggacattca ccacatcgac tactataaaa agacaaccaa cggccgactg | 1980 |
| cctgtgaagt ggatggcacc cgaggcatta tttgaccgga tctacaccca ccagagtgat | 2040 |
| gtgtggtctt tcggggtgct cctgtgggag atcttcactc tgggcggctc cccatacccc | 2100 |
| ggtgtgcctg tggaggaact tttcaagctg ctgaaggagg gtcaccgcat ggacaagccc | 2160 |
| agtaactgca ccaacgagct gtacatgatg atgcgggact gctggcatgc agtgccctca | 2220 |
| cagagaccca ccttcaagca gctggtggaa gacctggacc gcatcgtggc cttgacctcc | 2280 |
| aaccaggagt acctggacct gtccatgccc ctggaccagt actcccccag ctttcccgac | 2340 |
| acccggagct ctacgtgctc ctcaggggag gattccgtct tctctcatga gccgctgccc | 2400 |
| gaggagccct gcctgccccg acacccagcc cagcttgcca atggcggact caaacgccgc | 2460 |
| tga | 2463 |

<210> SEQ ID NO 30
<211> LENGTH: 2469
<212> TYPE: DNA
<213> ORGANISM: Mus musculus
<220> FEATURE:
<223> OTHER INFORMATION: murine FGFR1

<400> SEQUENCE: 30

```
atgtggggct ggaagtgcct cctcttctgg gctgtgctgg tcacagccac tctctgcact      60
gccaggccag ccccaacctt gcctgaacaa gctcagccct ggggagtccc tgtggaagtg     120
gagtctctcc tggtccaccc tggcgacctg ctacagcttc gctgtcggct cgcgatgat     180
gtgcagagca tcaactggct gcgggatggg gtgcagctgg tggagagcaa ccgtacccgc     240
atcacagggg aggaggtgga ggtgcgggac tccatccccg ctgactctgg cctctacgct     300
tgcgtgacca gcagcccctc tggcagcgat accacctact tctccgtcaa tgtctcagat     360
gcactcccat cctcggaaga tgatgacgac gacgatgact cctcctcgga ggagaaagag     420
acggacaaca ccaaaccaaa ccgtaggcct gtagctccct actggacatc cccagagaaa     480
atggagaaga aactgcatgc ggtgcccgct gccaagacgg tgaagttcaa gtgccgtcg     540
agtgggacac ccaaccccac tctgcgctgg ttgaaaaatg caaagagtt taagcctgac     600
caccgaattg gaggctacaa ggttcgctat gccacctgga gcatcataat ggattctgtg     660
gtgccttctg acaagggcaa ctacacctgc atcgtggaga tgagtatgg agcatcaac     720
cacacctacc agcttgacgt cgtggaacga tctccgcacc gacccatcct tcaggcaggg     780
ctgcctgcca acaagacagt ggccctgggc agcaatgtgg agttcatgtg taaggtgtac     840
agcgatccgc agcctcacat tcagtggctg aagcacatcg aggtgaacgg gagtaagatc     900
gggccagaca acttgccgta tgtccagatc ctgaagactg ctggagttaa taccaccgac     960
aaggaaatgg aggtgcttca tctacggaat gtctcctttg aggatgcggg ggagtatacg    1020
tgcttggcgg gtaactctat cggactctcc catcactctg catggttgac cgttctggaa    1080
gccctggaag agagaccagc tgtgatgacc tcaccgctct acctggagat cattatctac    1140
tgcaccgggg ccttcctgat ctcctgcatg ttgggctctg tcatcatcta taagatgaag    1200
agcggcacca agaagagcga cttccatagc cagatggctg tgcacaagct ggccaagagc    1260
atccctctgc gcagacaggt aacagtgtca gctgactcca gtgcatccat gaactctggg    1320
gttctcctgg ttcggccctc acggctctcc tccagcggga cccccatgct ggctggagtc    1380
tccgaatatg agctccctga ggatccccgc tgggagctgc acgagacag actggtctta    1440
ggcaaaccac ttggcgaggg ctgcttcggg caggtggtgt ggctgaggc atcgggctg    1500
gataaggaca aacccaaccg tgtgaccaaa gtggccgtga agatgttgaa gtccgacgca    1560
acggagaagg acctgtcgga tctgatctcg gagatggaga tgatgaaaat gattgggaag    1620
cacaagaata tcatcaacct tctgggagcg tgcacacagg atggtcctct ttatgtcatt    1680
gtggagtacg cctccaaagg caatctccgg gagtatctac aggcccggag gcctcctggg    1740
ctggagtact gctataaccc cagccacaac cccgaggaac agctgtcttc caagatctg    1800
gtatcctgtg cctatcaggt ggctcgggc atggagtatc ttgcctctaa gaagtgtata    1860
caccgagacc tggctgctag gaacgtcctg gtgaccgagg ataacgtaat gaagatcgca    1920
gactttggct tagctcgaga cattcatcat atcgactact acaagaaaac caccaacggc    1980
cggctgcctg tgaagtggat ggcccctgag gcgttgtttg accggatcta cacacaccag    2040
agcgatgtgt ggtcttttgg agtgctcttg tgggagatct tcactctggg tggctcccca    2100
tacccggtg tgcctgtgga ggaacttttc aagctgctga aggagggtca tcgaatggac    2160
aagcccagta actgtaccaa tgagctgtac atgatgatgc gggactgctg gcatgcagtg    2220
```

```
ccctctcaga gacctacgtt caagcagttg gtggaagacc tggaccgcat tgtggccttg      2280
acctccaacc aggagtatct ggacctgtcc ataccgctgg accagtactc acccagcttt      2340
cccgacacac ggagctccac ctgctcctca ggggaggact ctgtcttctc tcatgagccg      2400
ttacctgagg agccctgtct gcctcgacac cccacccagc ttgccaacag tggactcaaa      2460
cggcgctga                                                              2469

<210> SEQ ID NO 31
<211> LENGTH: 2466
<212> TYPE: DNA
<213> ORGANISM: Homo sapiens
<220> FEATURE:
<223> OTHER INFORMATION: human FGFR2

<400> SEQUENCE: 31
atggtcagct ggggtcgttt catctgcctg gtcgtggtca ccatggcaac cttgtccctg        60
gcccggccct ccttcagttt agttgaggat accacattag agccagaaga gccaccaacc       120
aaataccaaa tctctcaacc agaagtgtac gtggctgcgc aggggagtc gctagaggtg       180 cgctgcctgt tgaaagatgc cgccgtgatc agttggacta aggatggggt gcacttgggg       240
cccaacaata ggacagtgct tattggggag tacttgcaga taaagggcgc cacgcctaga       300
gactccggcc tctatgcttg tactgccagt aggactgtag acagtgaaac ttggtacttc       360
atggtgaatg tcacagatgc catctcatcc ggagatgatg aggatgacac cgatggtgcg       420
gaagattttg tcagtgagaa cagtaacaac aagagagcac catactggac caacacagaa       480
aagatggaaa agcggctcca tgctgtgcct gcggccaaca ctgtcaagtt cgctgcccca       540
gccgggggga acccaatgcc aaccatgcgg tggctgaaaa acgggaagga gtttaagcag       600
gagcatcgca ttggaggcta caaggtacga aaccagcact ggagcctcat tatggaaagt       660
gtggtcccat ctgacaaggg aaattatacc tgtgtagtgg agaatgaata cgggtccatc       720
aatcacacgt accacctgga tgttgtggag cgatcgcctc accggccccat cctccaagcc       780 ggactgccgg caaatgcctc cacagtggtc ggaggagacg tagagtttgt ctgcaaggtt       840
tacagtgatg cccagcccca catccagtgg atcaagcacg tggaaaagaa cggcagtaaa       900
tacgggcccg acgggctgcc ctacctcaag gttctcaagg ccgccggtgt aacaccacg       960 gacaaagaga ttgaggttct ctatattcgg aatgtaactt ttgaggacgc tggggaatat      1020
acgtgcttgg cgggtaattc tattgggata ccctttcact ctgcatggtt gacagttctg      1080
ccagcgcctg aagagaaaaa ggagattaca gcttccccag actacctgga atagccatt      1140 tactgcatag gggtcttctt aatcgcctgt atggtggtaa cagtcatcct gtgccgaatg      1200
aagaacacga ccaagaagcc agacttcagc agccagccgg ctgtgcacaa gctgaccaaa      1260
cgtatccccc tgcggagaca ggtaacagtt tcggctgagt ccagctcctc catgaactcc      1320 aacacccgc tggtgaggat aacaacacgc tctcttcaa cggcagacac ccccatgctg      1380 gcagggtct ccgagtatga acttccagag acccaaaat gggagtttcc aagagataag      1440
ctgacactgg gcaagccct gggagaaggt tgctttgggc aagtggtcat ggcggaagca      1500
gtgggaattg acaaagacaa gcccaaggag gcggtcaccg tggccgtgaa gatgttgaaa      1560
gatgatgcca cagagaaaga cctttctgat ctggtgtcag agatggagat gatgaagatg      1620
attgggaaac acaagaatat cataaatctt cttggagcct gcacacagga tgggcctctc      1680
tatgtcatag ttgagtatgc ctctaaaggc aacctccgag aatacctccg agcccggagg      1740
ccacccggga tggagtactc ctatgacatt aaccgtgttc ctgaggagca gatgaccttc      1800
```

| | |
|---|---|
| aaggacttgg tgtcatgcac ctaccagctg gccagaggca tggagtactt ggcttcccaa | 1860 |
| aaatgtattc atcgagattt agcagccaga aatgttttgg taacagaaaa caatgtgatg | 1920 |
| aaaatagcag actttggact cgccagagat atcaacaata tagactatta caaaagacc | 1980 |
| accaatgggc ggcttccagt caagtggatg gctccagaag ccctgtttga tagagtatac | 2040 |
| actcatcaga gtgatgtctg gtccttcggg gtgttaatgt gggagatctt cactttaggg | 2100 |
| ggctcgccct acccagggat tcccgtggag gaacttttta gctgctgaa ggaaggacac | 2160 |
| agaatggata agccagccaa ctgcaccaac gaactgtaca tgatgatgag ggactgttgg | 2220 |
| catgcagtgc cctcccagag accaacgttc aagcagttgg tagaagactt ggatcgaatt | 2280 |
| ctcactctca caaccaatga ggaatacttg gacctcagcc aacctctcga acagtattca | 2340 |
| cctagttacc ctgacacaag aagttcttgt tcttcaggag atgattctgt ttttctcca | 2400 |
| gaccccatgc cttacgaacc atgccttcct cagtatccac acataaacgg cagtgttaaa | 2460 |
| acatga | 2466 |

<210> SEQ ID NO 32
<211> LENGTH: 2523
<212> TYPE: DNA
<213> ORGANISM: Mus musculus
<220> FEATURE:
<223> OTHER INFORMATION: murine FGFR2

<400> SEQUENCE: 32

| | |
|---|---|
| atgggattac cgtccacgtg gagatatgga agaggaccag ggattggcac tgtgaccatg | 60 |
| gtcagctggg ggcgcttcat ctgcctggtc ttggtcacca tggcaacctt gtccctggcc | 120 |
| cggccctcct tcagtttagt tgaggatacc actttagaac cagaagagcc accaaccaaa | 180 |
| taccaaatct cccaaccaga agcgtacgtg gttgcccccg gggaatcgct agagttgcag | 240 |
| tgcatgttga aagatgccgc cgtgatcagt tggactaagg atggggtgca cttggggccc | 300 |
| aacaatagga cagtgcttat tgggagtat ctccagataa aggtgccac acctagagac | 360 |
| tccggcctct atgcttgtac tgcagctagg acggtagaca gtgaaacttg gtacttcatg | 420 |
| gtgaatgtca cagatgccat ctcatctgga gatgatgagg acgacacaga tagctccgaa | 480 |
| gacgttgtca gtgagaacag gagcaaccag agagccgt actggaccaa caccgagaag | 540 |
| atggagaagc ggctccacgc tgtccctgcc gccaacactg tgaagttccg ctgtccggct | 600 |
| gggggggaatc caacgcccac aatgaggtgg ttaaaaaacg ggaaggagtt taagcaggag | 660 |
| catcgcattg gaggctataa ggtacgaaac cagcactgga gccttattat ggaaagtgtg | 720 |
| gtcccgtcag acaaaggcaa ctacacctgc ctggtggaga tgaatacgg gtccatcaac | 780 |
| cacacctacc acctcgatgt cgttgaacgg tcaccacacc ggcccatcct caagctggaa | 840 |
| ctgcctgcaa atgcctccac ggtggtcgga ggggatgtgg agtttgtctg caaggtttac | 900 |
| agcgatgccc agccccacat ccagtggatc aagcacgtgg aaaagaacgg cagtaaatac | 960 |
| gggcctgatg gctgccccta cctcaaggtc ctgaaggccg ccggtgttaa caccacggac | 1020 |
| aaagagattg aggttctcta tattcggaat gtaactttg aggatgctgg ggaatatacg | 1080 |
| tgcttggcgg gtaattctat cgggatatcc tttcactctg catggttgac agttctgcca | 1140 |
| gcgcctgtga gagaagga gatcacggct tccccagatt atctggagat agctatttac | 1200 |
| tgcatagggg tcttcttaat cgcctgcatg gtggtgacag tcatcttttg ccgaatgaag | 1260 |
| accacgacca gaagccaga cttcagcagc cagccagctg tgcacaagct gaccaagcgc | 1320 |

```
atcccctgc ggagacaggt aacagtttcg gccgagtcca gctcctccat gaactccaac    1380 acccgctgg tgaggataac aacgcgtctg tcctcaacag cggacacccc gatgctagca    1440
ggggtctccg agtatgagtt gccagaggat ccaaagtggg aattccccag agataagctg    1500
acgctgggca aacccctggg ggaaggttgc ttcgggcaag tagtcatggc tgaagcagtg    1560
ggaatcgata agacaaacc caaggaggcg gtcaccgtgg cagtgaagat gttgaaagat    1620
gatgccacag agaaggacct gtctgatctg tatcagaga tggagatgat gaagatgatt    1680
gggaaacata agaacattat caacctcctg ggggcctgca cgcaggatgg acctctctac    1740
gtcatagttg aatatgcatc gaaaggcaac ctccgggaat acctccgagc ccggaggcca    1800
cctggcatgg agtactccta tgacattaac cgtgtccccg aggagcagat gaccttcaag    1860
gacttggtgt cctgcaccta ccagctggct agaggcatgg agtacttggc ttcccaaaaa    1920
tgtatccatc gagatttggc tgccagaaac gtgttggtaa cagaaaacaa tgtgatgaag    1980
atagcagact ttggcctggc cagggatatc aacaacatag actactataa aaagaccaca    2040
aatgggcgac ttccagtcaa gtggatggct cctgaagccc tttttgatag agtttacact    2100
catcagagcg atgtctggtc cttcggggtg ttaatgtggg agatctttac tttagggggc    2160
tcaccctacc cagggattcc cgtggaggaa cttttaagc tgctcaaaga gggacacagg    2220
atggacaagc ccaccaactg caccaatgaa ctgtacatga tgatgaggga ttgctggcat    2280 gctgtacct cacagagacc cacattcaag cagttggtcg aagacttgga tcgaattctg    2340
actctcacaa ccaatgagga atacttggat ctcacccagc ctctcgaaca gtattctcct    2400
agttaccccg acacaaggag ctcttgttct caggggacg attctgtgtt ttctccagac    2460
cccatgcctt atgaaccctg tctgcctcag tatccacaca taaacggcag tgttaaaaca    2520
tga                                                                 2523
```

<210> SEQ ID NO 33
<211> LENGTH: 2421
<212> TYPE: DNA
<213> ORGANISM: Homo sapiens
<220> FEATURE:
<223> OTHER INFORMATION: human FGFR3

<400> SEQUENCE: 33

```
atgggcgccc ctgcctgcgc cctcgcgctc tgcgtggccg tggccatcgt ggccggcgcc      60
tcctcggagt ccttggggac ggagcagcgc gtcgtggggc gagcggcaga agtcccgggc     120
ccagagcccg ccagcagga gcagttggtc ttcggcagcg ggatgctgt ggagctgagc     180 tgtcccccgc ccgggggtgg tcccatgggg cccactgtct gggtcaagga tggcacaggg     240
ctggtgccct cggagcgtgt cctggtgggg ccccagcggc tgcaggtgct gaatgcctcc     300
cacgaggact ccggggccta cagctgccgg cagcggctca cgcagcgcgt actgtgccac     360
ttcagtgtgc gggtgacaga cgctccatcc tcgggagatg acgaagacgg ggaggacgag     420
gctgaggaca caggtgtgga cacagggcc ccttactgga cacggccga gcggatggac     480 aagaagctgc tggccgtgcc ggccgccaac accgtccgct tccgctgccc agccgctggc     540
aaccccactc cctccatctc ctggctgaag aacggcaggg agttccgcgg cgagcaccgc     600
attggaggca tcaagctgcg gcatcagcag tggagcctgg tcatggaaag cgtggtgccc     660
tcggaccgcg gcaactacac ctgcgtcgtg gagaacaagt ttggcagcat ccggcagacg     720
tacacgctga cgtgctgga cgctcccccg caccggccca tcctgcaggc ggggctgccg     780
gccaaccaga cggcggtgct gggcagcgac gtggagttcc actgcaaggt gtacagtgac     840
```

```
gcacagcccc acatccagtg gctcaagcac gtggaggtga atggcagcaa ggtgggcccg      900
gacggcacac cctacgttac cgtgctcaag acggcgggcg ctaacaccac cgacaaggag      960
ctagaggttc tctccttgca caacgtcacc tttgaggacg ccggggagta cacctgcctg     1020
gcgggcaatt ctattgggtt ttctcatcac tctgcgtggc tggtggtgct gccagccgag     1080
gaggagctgg tggaggctga cgaggcgggc agtgtgtatg caggcatcct cagctacggg     1140
gtgggcttct tcctgttcat cctggtggtg gcggctgtga cgctctgccg cctgcgcagc     1200
cccccccaaga aaggcctggg ctcccccacc gtgcacaaga tctcccgctt cccgctcaag     1260
cgacaggtgt ccctggagtc caacgcgtcc atgagctcca cacaccact ggtgcgcatc      1320
gcaaggctgt cctcagggga gggccccacg ctggccaatg tctccgagct cgagctgcct     1380
gccgacccca atgggagctg tctcgggccc ggctgaccc tgggcaagcc ccttggggag      1440
ggctgcttcg ccaggtggt catggcggag gccatcggca ttgacaagga ccgggccgcc      1500
aagcctgtca ccgtagccgt gaagatgctg aaagacgatg ccactgacaa ggacctgtcg     1560
gacctggtgt ctgagatgga gatgatgaag atgatcggga acacaaaaaa catcatcaac     1620
ctgctgggcg cctgcacgca gggcgggccc ctgtacgtgc tggtggagta cgcggccaag     1680
ggtaacctgc gggagtttct gcgggcgcgg cggccccgg gcctggacta ctccttcgac      1740
acctgcaagc gccccgagga gcagctcacc ttcaaggacc tggtgtcctg tgcctaccag     1800
gtggcccggg gcatggagta cttggcctcc cagaagtgca tccacaggga cctggctgcc     1860
cgcaatgtgc tggtgaccga ggacaacgtg atgaagatcg cagacttcgg gctggcccgg     1920
gacgtgcaca acctcgacta ctacaagaag acgaccaacg gccggctgcc cgtgaagtgg     1980
atggcgcctg aggccttgtt tgaccgagtc tacactcacc agagtgacgt ctggtccttt     2040
ggggtcctgc tctgggagat cttcacgctg gggggctccc cgtaccccgg catccctgtg     2100
gaggagctct tcaagctgct gaaggagggc caccgcatgg acaagcccgc caactgcaca     2160
cacgacctgt acatgatcat gcgggagtgc tggcatgccg cgccctccca gaggcccacc     2220
ttcaagcagc tggtggagga cctggaccgt gtccttaccg tgacgtccac cgacgagtac     2280
ctggacctgt cggcgccttt cgagcagtac tcccgggtg ccaggacac ccccagctcc      2340
agctcctcag gggacgactc cgtgtttgcc cacgacctgc tgcccccggc cccacccagc     2400
agtgggggct cgcggacgtg a                                                2421
```

<210> SEQ ID NO 34
<211> LENGTH: 2349
<212> TYPE: DNA
<213> ORGANISM: Mus musculus
<220> FEATURE:
<223> OTHER INFORMATION: murine FGFR3

<400> SEQUENCE: 34

```
atggtagtcc cggcctgcgt gctagtgttc tgcgtggcgg tcgtggctgg agctacttcc       60
gagcctcctg gtccagagca gcgagttgtg cggagagcgg cagaggttcc agggcctgaa      120
cctagccagc aggagcaggt ggccttcggc agtggggaca ccgtggagct gagctgccat      180
cctcctggag gtgcccccac agggcccacg gtctgggcta aggatggtac aggtctggtg      240
gcctcccacc gcatcctggt ggggcctcag aggctgcaag tgctaaatgc ctcccacgaa      300
gatgcagggg tctacagctg ccagcaccgg ctcactcggc gtgtgctgtg ccacttcagt     360
gtgcgtgtaa caggggctcc ttattggact cgcccggagc gaatggataa gaaactgctg     420
```

| | |
|---|---|
| gctgtgccag ccgcaaacac tgtccgcttc cgctgcccag ctgctggcaa ccctaccccc | 480 |
| tccatctcct ggctgaagaa tggcaaagaa ttccgagggg agcatcgcat tgggggcatc | 540 |
| aagctccggc accagcagtg gagcttggtc atggaaagtg tggtaccctc cgatcgtggc | 600 |
| aactatacct gtgtagttga aacaagttt ggcagcatcc ggcagacata cactctggat | 660 |
| gtgctggagc gctccccaca ccggcccatc ctgcaggctg gctgccggc caaccagaca | 720 |
| gccattctag cagtgacgt ggagttccac tgcaaggtgt acagcgatgc acagccacac | 780 |
| atccagtggc tgaagcacgt ggaagtgaac ggcagcaagg tgggccctga cggcacgccc | 840 |
| tacgtcactg tactcaagac tgcaggcgct aacaccaccg acaaggagct agaggttctg | 900 |
| tccttgcaca atgtcacctt tgaggacgcg ggggagtaca cctgcctggc gggcaattct | 960 |
| attgggtttt cccatcactc tgcgtggctg gtggtgctgc cagctgagga ggagctgatg | 1020 |
| gaaactgatg aggctggcag cgtgtacgca ggcgtcctca gctacgggt ggtcttcttc | 1080 |
| ctcttcatcc tggtggtggc agctgtgata ctctgccgcc tgcgcagtcc cccaaagaag | 1140 |
| ggcttgggct cgcccaccgt gcacaaggtc tctcgcttcc cgcttaagcg acaggtgtcc | 1200 |
| ttggaatcta actcctctat gaactccaac acacccttg tccggattgc ccggctgtcc | 1260 |
| tcaggagaag gtcctgttct ggccaatgtt tctgaacttg agctgcctgc tgaccccaag | 1320 |
| tgggagctat ccaggacccg gctgacactt ggtaagcctc ttggagaagg ctgctttgga | 1380 |
| caggtggtca tggcagaagc tattggcatc gacaaggacc gtactgccaa gcctgtcacc | 1440 |
| gtggccgtga agatgctgaa agatgatgcg actgacaagg acctgtcgga cctggtatct | 1500 |
| gagatggaga tgatgaaaat gattggcaag cacaagaaca tcattaacct gctggggcg | 1560 |
| tgcacacagg gtgggcccct gtatgtgctg gtggagtacg cagccaaggg caatctccgg | 1620 |
| gagttccttc gggcgcggcg gcctccaggc atggactact cctttgatgc ctgcaggctg | 1680 |
| ccagaggaac agctcacctg caaggatcta gtgtcctgtg cctaccaggt ggcacgggc | 1740 |
| atggaatact tggcttctca gaagtgtatt cacagagact ggctgccag aaacgtcctg | 1800 |
| gtgaccgagg acaatgtgat gaagattgcg actttggcc tggctcgaga tgtgcacaac | 1860 |
| ctggactact acaagaagac cacaaatggc cggctacctg tgaagtggat ggcaccagag | 1920 |
| gccctttttg accgagtcta caccaccag agtgatgttt ggtcttttgg tgtcctcctc | 1980 |
| tgggagatct ttacgctggg gggctcaccg tatcctggca tcccagtgga agagcttttc | 2040 |
| aagctgttga aagagggcca ccgcatggac aagccagcca gctgcacaca tgacctgtac | 2100 |
| atgatcatgc gggaatgttg gcatgcggtg ccttcacaga ggcccacctt caagcagttg | 2160 |
| gtagaggatt tagaccgcat cctcactgtg acatcaaccg acgagtactt ggacctctcc | 2220 |
| gtgccgtttg agcagtactc gccaggtggc caggacacgc ctagctccag ctcgtccgga | 2280 |
| gatgactcgg tgttcacccca tgacctgcta cccccaggtc cacccagtaa cggggaccct | 2340 |
| cggacgtga | 2349 |

<210> SEQ ID NO 35
<211> LENGTH: 2409
<212> TYPE: DNA
<213> ORGANISM: Homo sapiens
<220> FEATURE:
<223> OTHER INFORMATION: human FGFR4

<400> SEQUENCE: 35

| | |
|---|---|
| atgcggctgc tgctggccct gttgggggtc ctgctgagtg tgcctggggc tccagtcttg | 60 |
| tccctggagg cctctgagga agtggagctt gagccctgcc tggctcccag cctggagcag | 120 |

```
caagagcagg agctgacagt agcccttggg cagcctgtgc gtctgtgctg tgggcgggct      180
gagcgtggtg gccactggta caaggagggc agtcgcctgg cacctgctgg ccgtgtacgg      240
ggctggaggg gccgcctaga gattgccagc ttcctacctg aggatgctgg ccgctacctc      300
tgcctggcac gaggctccat gatcgtcctg cagaatctca ccttgattac aggtgactcc      360
ttgacctcca gcaacgatga tgaggacccc aagtcccata gggacccctc gaataggcac      420
agttaccccc agcaagcacc ctactggaca caccccagc gcatggagaa gaaactgcat       480
gcagtacctg cggggaacac cgtcaagttc cgctgtccag ctgcaggcaa ccccacgccc      540
accatccgct ggcttaagga tggacaggcc tttcatgggg agaaccgcat tggaggcatt      600
cggctgcgcc atcagcactg gagtctcgtg atggagagcg tggtgccctc ggaccgcggc      660
acatacacct gcctggtaga gaacgctgtg ggcagcatcc gctataacta cctgctagat      720
gtgctggagc ggtccccgca ccggcccatc ctgcaggccg gctcccggc caacaccaca       780 gccgtggtgg gcagcgacgt ggagctgctg tgcaaggtgt acagcgatgc ccagccccac     840
atccagtggc tgaagcacat cgtcatcaac ggcagcagct tcggagccga cggttttcccc    900 tatgtgcaag tcctaaagac tgcagacatc aatagctcag aggtgaggt cctgtacctg      960 cggaacgtgt cagccgagga cgcaggcgag tacacctgcc tcgcaggcaa ttccatcggc     1020
ctctcctacc agtctgcctg gctcacggtg ctgccagagg aggacccac atggaccgca     1080 gcagcgcccg aggccaggta tacggacatc atcctgtacg cgtcgggctc cctggccttg    1140
gctgtgctcc tgctgctggc cgggctgtat cgagggcagg cgctccacgg ccggcacccc    1200
cgcccgcccg ccactgtgca gaagctctcc cgcttccctc tggcccgaca gttctcctg    1260 gagtcaggct cttccggcaa gtcaagctca tccctggtac gaggcgtgcg tctctcctcc    1320
agcggccccg ccttgctcgc cggcctcgtg agtctagatc tacctctcga cccactatgg    1380
gagttccccc gggacaggct ggtgcttggg aagcccctag gcgagggctg ctttggccag    1440
gtagtacgtg cagaggcctt tggcatggac cctgcccggc ctgaccaagc cagcactgtg    1500
gccgtcaaga tgctcaaaga caacgcctct gacaaggacc tggccgacct ggtctcggag    1560
atggaggtga tgaagctgat cggccgacac aagaacatca tcaacctgct tggtgtctgc    1620
acccaggaag ggccctgta cgtgatcgtg gagtgcgccg ccaagggaaa cctgcgggag    1680
ttcctgcggg cccggcgccc cccaggcccc gacctcagcc ccgacggtcc tcggagcagt    1740 gagggggccgc tctccttccc agtcctggtc tcctgcgcct accaggtggc ccgaggcatg    1800
cagtatctga gtcccggaa gtgtatccac cgggacctgg ctgcccgcaa tgtgctggtg    1860
actgaggaca atgtgatgaa gattgctgac tttgggctgg cccgcggcgt ccaccacatt    1920
gactactata agaaaaccag caacggccgc ctgcctgtga gtggatggc gcccgaggcc    1980 ttgtttgacc gggtgtacac acaccagagt gacgtgtggt cttttgggat cctgctatgg    2040
gagatcttca ccctcggggg ctccccgtat cctggcatcc cggtgaagga gctgttctcg    2100
ctgctgcggg agggacatcg gatggaccga ccccacact gcccccaga gctgtacggg      2160 ctgatgcgtg agtgctggca cgcagcgccc tcccagaggc ctaccttcaa gcagctggtg    2220
gaggcgctgg acaaggtcct gctggccgtc tctgaggagt acctcgacct ccgcctgacc    2280
ttcggaccct attccccctc tggtggggac gccagcagca cctgctcctc cagcgattct    2340
gtcttcagcc acgacccct gccattggga tccagctcct ccccttcgg gtctggggtg     2400 cagacatga                                                            2409
```

<210> SEQ ID NO 36
<211> LENGTH: 2400
<212> TYPE: DNA
<213> ORGANISM: Mus musculus
<220> FEATURE:
<223> OTHER INFORMATION: murine FGFR4

<400> SEQUENCE: 36

| | | | | | |
|---|---|---|---|---|---|
| atgtggctgc | tcttggccct | gttgagcatc | tttcagggga | caccagctttt | gtcccttgag | 60 |
| gcctctgagg | aaatggagca | ggagccctgc | ctagccccaa | tcctggagca | gcaagagcag | 120 |
| gtgttgacgg | tggccctggg | gcagcctgtg | aggctgtgct | gtgggcgcac | cgagcgtggt | 180 |
| cgtcactggt | acaaagaggg | cagccgccta | gcatctgctg | ggcgagtacg | gggttggaga | 240 |
| ggccgcctgg | agatcgccag | cttccttcct | gaggatgctg | gccgatacct | ctgcctggcc | 300 |
| cgtggctcca | tgaccgtcgt | acacaatctt | acgttgctta | tggatgactc | cttaacctcc | 360 |
| atcagtaatg | atgaagaccc | caagacactc | agcagctcct | cgagtggtca | tgtctaccca | 420 |
| cagcaagcac | cctactggac | acaccccaa | cgcatggaga | agaaactgca | tgcagtgcct | 480 |
| gccgggaata | ctgtcaaatt | ccgctgtcca | gctgcaggga | ccccatgcc | taccatccac | 540 |
| tggctcaagg | atggacaggc | cttccacggg | agaatcgta | ttggaggcat | tcggctgcgc | 600 |
| caccaacact | ggagcctggt | gatggaaagt | gtggtaccct | cggaccgtgg | cacatacaca | 660 |
| tgccttgtgg | agaactctct | gggtagcatt | cgctacagct | atcctggga | tgtgctggag | 720 |
| cggtccccgc | accggcccat | cctgcaggcg | gggctcccag | ccaacaccac | agctgtggtt | 780 |
| ggcagcgatg | tggagctact | ctgcaaggtg | tacagcgacg | cccagccca | catacagtgg | 840 |
| ctgaaacacg | tcgtcatcaa | cggcagcagc | ttcggcgccg | acggtttccc | ctacgtacaa | 900 |
| gtcctgaaga | acagacacat | caatagctcg | gaggtagagg | tcttgtatct | gaggaacgtg | 960 |
| tccgctgagg | atgcaggaga | gtatacctgt | ctggcgggca | actccatcgg | cctttcctac | 1020 |
| cagtcagcgt | ggctcacggt | gctgccagag | gaagacctca | cgtggacaac | agcaacccct | 1080 |
| gaggccagat | acacagatat | catcctgtat | gtatcaggct | cactggttct | gcttgtgctc | 1140 |
| ctgctgctgg | ccggggtgta | tcatcggcaa | gtcatccgtg | ccactactc | tgccagcct | 1200 |
| gtcactatac | aaaagctgtc | ccgtttccct | ttggcccgac | agttctcttt | ggagtcgagg | 1260 |
| tcctctggca | gtcaagtttt | gtccctggtg | cgaggtgtcc | gtctctcctc | cagcggcccg | 1320 |
| cccttgctca | cgggccttgt | gaatctagac | ctgcctctcg | atccgctttg | ggaattcccc | 1380 |
| cgggacaggt | tggtgctcgg | aaagcccctg | ggtgagggct | gctttgggca | agtggttcgt | 1440 |
| gcagaggcct | ttggtatgga | tccctcccgg | cccgaccaaa | ccagcaccgt | ggctgtgaag | 1500 |
| atgctgaaag | acaatgcctc | cgacaaggat | ttggcagacc | tggtctccga | gatggaggtg | 1560 |
| atgaagctaa | tcggaagaca | caagaacatc | atcaacctgc | tgggtgtctg | cactcaggaa | 1620 |
| gggccctgt | acgtgattgt | ggaatgtgcc | gccaagggaa | accttcggga | attcctccgt | 1680 |
| gccgcgcgcc | cccaggccc | tgatctcagc | cctgatggac | tcggagcag | cgaaggacca | 1740 |
| ctctccttcc | cggccctagt | ctcctgtgcc | taccaggtgg | cccgaggcat | gcagtatctg | 1800 |
| gagtctcgga | agtgcatcca | ccgggacctg | gctgccgaa | atgtgctggt | gaccgaggat | 1860 |
| gatgtgatga | agatcgctga | ctttgggctg | gcacgtggtg | tccaccacat | tgactactat | 1920 |
| aagaaaacca | gcaacggccg | cctgccagtc | aaatggatgg | ctccagaggc | attgttcgac | 1980 |
| cgcgtgtaca | cacaccagag | tgacgtgtgg | tctttcgggg | tcctgctgtg | ggaaatcttc | 2040 |
| accctcgggg | gctccccata | ccctggcatt | ccggtggagg | agctcttctc | actgctgcga | 2100 |

```
gagggggcaca ggatggagcg gccccccaaac tgcccctcag agctgtatgg gctaatgagg    2160
gagtgctggc acgcagcccc atctcagagg cctactttta agcagctggt ggaagctctg    2220
gacaaggtcc tgctggctgt ctctgaagag taccttgacc tccgcctgac ctttggaccc    2280
ttttctccct ccaatgggga tgccagcagc acctgctcct ccagtgactc ggttttcagc    2340
cacgaccctt tgcccctcga gccaagcccc ttcccttttct ctgactcgca gacgacatga    2400
```

<210> SEQ ID NO 37

<400> SEQUENCE: 37

000

<210> SEQ ID NO 38

<400> SEQUENCE: 38

000

<210> SEQ ID NO 39

<400> SEQUENCE: 39

000

<210> SEQ ID NO 40

<400> SEQUENCE: 40

000

<210> SEQ ID NO 41

<400> SEQUENCE: 41

000

<210> SEQ ID NO 42

<400> SEQUENCE: 42

000

<210> SEQ ID NO 43
<211> LENGTH: 820
<212> TYPE: PRT
<213> ORGANISM: Homo sapiens
<220> FEATURE:
<223> OTHER INFORMATION: human FGFR1

<400> SEQUENCE: 43

Met Trp Ser Trp Lys Cys Leu Leu Phe Trp Ala Val Leu Val Thr Ala
1               5                   10                  15

Thr Leu Cys Thr Ala Arg Pro Ser Pro Thr Leu Pro Glu Gln Ala Gln
            20                  25                  30

Pro Trp Gly Ala Pro Val Glu Val Glu Ser Phe Leu Val His Pro Gly
        35                  40                  45

Asp Leu Leu Gln Leu Arg Cys Arg Leu Arg Asp Asp Val Gln Ser Ile
    50                  55                  60

Asn Trp Leu Arg Asp Gly Val Gln Leu Ala Glu Ser Asn Arg Thr Arg
65                  70                  75                  80

Ile Thr Gly Glu Glu Val Glu Val Gln Asp Ser Val Pro Ala Asp Ser

```
                    85                  90                  95
Gly Leu Tyr Ala Cys Val Thr Ser Ser Pro Ser Gly Ser Asp Thr Thr
                100                 105                 110

Tyr Phe Ser Val Asn Val Ser Asp Ala Leu Pro Ser Ser Glu Asp Asp
                115                 120                 125

Asp Asp Asp Asp Asp Ser Ser Ser Glu Glu Lys Glu Thr Asp Asn Thr
130                 135                 140

Lys Pro Asn Pro Val Ala Pro Tyr Trp Thr Ser Pro Glu Lys Met Glu
145                 150                 155                 160

Lys Lys Leu His Ala Val Pro Ala Ala Lys Thr Val Lys Phe Lys Cys
                165                 170                 175

Pro Ser Ser Gly Thr Pro Asn Pro Thr Leu Arg Trp Leu Lys Asn Gly
                180                 185                 190

Lys Glu Phe Lys Pro Asp His Arg Ile Gly Gly Tyr Lys Val Arg Tyr
                195                 200                 205

Ala Thr Trp Ser Ile Ile Met Asp Ser Val Val Pro Ser Asp Lys Gly
                210                 215                 220

Asn Tyr Thr Cys Ile Val Glu Asn Glu Tyr Gly Ser Ile Asn His Thr
225                 230                 235                 240

Tyr Gln Leu Asp Val Val Glu Arg Ser Pro His Arg Pro Ile Leu Gln
                245                 250                 255

Ala Gly Leu Pro Ala Asn Lys Thr Val Ala Leu Gly Ser Asn Val Glu
                260                 265                 270

Phe Met Cys Lys Val Tyr Ser Asp Pro Gln Pro His Ile Gln Trp Leu
                275                 280                 285

Lys His Ile Glu Val Asn Gly Ser Lys Ile Gly Pro Asp Asn Leu Pro
                290                 295                 300

Tyr Val Gln Ile Leu Lys Thr Ala Gly Val Asn Thr Thr Asp Lys Glu
305                 310                 315                 320

Met Glu Val Leu His Leu Arg Asn Val Ser Phe Glu Asp Ala Gly Glu
                325                 330                 335

Tyr Thr Cys Leu Ala Gly Asn Ser Ile Gly Leu Ser His His Ser Ala
                340                 345                 350

Trp Leu Thr Val Leu Glu Ala Leu Glu Glu Arg Pro Ala Val Met Thr
                355                 360                 365

Ser Pro Leu Tyr Leu Glu Ile Ile Ile Tyr Cys Thr Gly Ala Phe Leu
                370                 375                 380

Ile Ser Cys Met Val Gly Ser Val Ile Val Tyr Lys Met Lys Ser Gly
385                 390                 395                 400

Thr Lys Lys Ser Asp Phe His Ser Gln Met Ala Val His Lys Leu Ala
                405                 410                 415

Lys Ser Ile Pro Leu Arg Arg Gln Val Thr Val Ser Ala Asp Ser Ser
                420                 425                 430

Ala Ser Met Asn Ser Gly Val Leu Leu Val Arg Pro Ser Arg Leu Ser
                435                 440                 445

Ser Ser Gly Thr Pro Met Leu Ala Gly Val Ser Glu Tyr Glu Leu Pro
                450                 455                 460

Glu Asp Pro Arg Trp Glu Leu Pro Arg Asp Arg Leu Val Leu Gly Lys
465                 470                 475                 480

Pro Leu Gly Glu Gly Cys Phe Gly Gln Val Val Leu Ala Glu Ala Ile
                485                 490                 495

Gly Leu Asp Lys Asp Lys Pro Asn Arg Val Thr Lys Val Ala Val Lys
                500                 505                 510
```

```
Met Leu Lys Ser Asp Ala Thr Glu Lys Asp Leu Ser Asp Leu Ile Ser
            515                 520                 525

Glu Met Glu Met Met Lys Met Ile Gly Lys His Lys Asn Ile Ile Asn
        530                 535                 540

Leu Leu Gly Ala Cys Thr Gln Asp Gly Pro Leu Tyr Val Ile Val Glu
545                 550                 555                 560

Tyr Ala Ser Lys Gly Asn Leu Arg Glu Tyr Leu Gln Ala Arg Arg Pro
                565                 570                 575

Pro Gly Leu Glu Tyr Cys Tyr Asn Pro Ser His Asn Pro Glu Glu Gln
            580                 585                 590

Leu Ser Ser Lys Asp Leu Val Ser Cys Ala Tyr Gln Val Ala Arg Gly
        595                 600                 605

Met Glu Tyr Leu Ala Ser Lys Lys Cys Ile His Arg Asp Leu Ala Ala
    610                 615                 620

Arg Asn Val Leu Val Thr Glu Asp Asn Val Met Lys Ile Ala Asp Phe
625                 630                 635                 640

Gly Leu Ala Arg Asp Ile His His Ile Asp Tyr Tyr Lys Lys Thr Thr
                645                 650                 655

Asn Gly Arg Leu Pro Val Lys Trp Met Ala Pro Glu Ala Leu Phe Asp
            660                 665                 670

Arg Ile Tyr Thr His Gln Ser Asp Val Trp Ser Phe Gly Val Leu Leu
        675                 680                 685

Trp Glu Ile Phe Thr Leu Gly Gly Ser Pro Tyr Pro Gly Val Pro Val
    690                 695                 700

Glu Glu Leu Phe Lys Leu Leu Lys Glu Gly His Arg Met Asp Lys Pro
705                 710                 715                 720

Ser Asn Cys Thr Asn Glu Leu Tyr Met Met Met Arg Asp Cys Trp His
                725                 730                 735

Ala Val Pro Ser Gln Arg Pro Thr Phe Lys Gln Leu Val Glu Asp Leu
            740                 745                 750

Asp Arg Ile Val Ala Leu Thr Ser Asn Gln Glu Tyr Leu Asp Leu Ser
        755                 760                 765

Met Pro Leu Asp Gln Tyr Ser Pro Ser Phe Pro Asp Thr Arg Ser Ser
    770                 775                 780

Thr Cys Ser Ser Gly Glu Asp Ser Val Phe Ser His Glu Pro Leu Pro
785                 790                 795                 800

Glu Glu Pro Cys Leu Pro Arg His Pro Ala Gln Leu Ala Asn Gly Gly
                805                 810                 815

Leu Lys Arg Arg
            820

<210> SEQ ID NO 44
<211> LENGTH: 822
<212> TYPE: PRT
<213> ORGANISM: Mus musculus
<220> FEATURE:
<223> OTHER INFORMATION: murine FGFR1

<400> SEQUENCE: 44

Met Trp Gly Trp Lys Cys Leu Leu Phe Trp Ala Val Leu Val Thr Ala
1               5                   10                  15

Thr Leu Cys Thr Ala Arg Pro Ala Pro Thr Leu Pro Glu Gln Ala Gln
            20                  25                  30

Pro Trp Gly Val Pro Val Glu Val Glu Ser Leu Leu Val His Pro Gly
        35                  40                  45
```

```
Asp Leu Leu Gln Leu Arg Cys Arg Leu Arg Asp Asp Val Gln Ser Ile
 50                  55                  60

Asn Trp Leu Arg Asp Gly Val Gln Leu Val Glu Ser Asn Arg Thr Arg
 65                      70                  75                  80

Ile Thr Gly Glu Glu Val Glu Val Arg Asp Ser Ile Pro Ala Asp Ser
                 85                  90                  95

Gly Leu Tyr Ala Cys Val Thr Ser Ser Pro Ser Gly Ser Asp Thr Thr
            100                 105                 110

Tyr Phe Ser Val Asn Val Ser Asp Ala Leu Pro Ser Ser Glu Asp Asp
        115                 120                 125

Asp Asp Asp Asp Ser Ser Glu Glu Lys Glu Thr Asp Asn Thr
130                 135                 140

Lys Pro Asn Arg Arg Pro Val Ala Pro Tyr Trp Thr Ser Pro Glu Lys
145                 150                 155                 160

Met Glu Lys Lys Leu His Ala Val Pro Ala Ala Lys Thr Val Lys Phe
                165                 170                 175

Lys Cys Pro Ser Ser Gly Thr Pro Asn Pro Thr Leu Arg Trp Leu Lys
                180                 185                 190

Asn Gly Lys Glu Phe Lys Pro Asp His Arg Ile Gly Gly Tyr Lys Val
                195                 200                 205

Arg Tyr Ala Thr Trp Ser Ile Ile Met Asp Ser Val Val Pro Ser Asp
            210                 215                 220

Lys Gly Asn Tyr Thr Cys Ile Val Glu Asn Glu Tyr Gly Ser Ile Asn
225                 230                 235                 240

His Thr Tyr Gln Leu Asp Val Val Glu Arg Ser Pro His Arg Pro Ile
                245                 250                 255

Leu Gln Ala Gly Leu Pro Ala Asn Lys Thr Val Ala Leu Gly Ser Asn
                260                 265                 270

Val Glu Phe Met Cys Lys Val Tyr Ser Asp Pro Gln Pro His Ile Gln
            275                 280                 285

Trp Leu Lys His Ile Glu Val Asn Gly Ser Lys Ile Gly Pro Asp Asn
            290                 295                 300

Leu Pro Tyr Val Gln Ile Leu Lys Thr Ala Gly Val Asn Thr Thr Asp
305                 310                 315                 320

Lys Glu Met Glu Val Leu His Leu Arg Asn Val Ser Phe Glu Asp Ala
                325                 330                 335

Gly Glu Tyr Thr Cys Leu Ala Gly Asn Ser Ile Gly Leu Ser His His
            340                 345                 350

Ser Ala Trp Leu Thr Val Leu Glu Ala Leu Glu Arg Pro Ala Val
            355                 360                 365

Met Thr Ser Pro Leu Tyr Leu Glu Ile Ile Ile Tyr Cys Thr Gly Ala
            370                 375                 380

Phe Leu Ile Ser Cys Met Leu Gly Ser Val Ile Ile Tyr Lys Met Lys
385                 390                 395                 400

Ser Gly Thr Lys Lys Ser Asp Phe His Ser Gln Met Ala Val His Lys
                405                 410                 415

Leu Ala Lys Ser Ile Pro Leu Arg Arg Gln Val Thr Val Ser Ala Asp
                420                 425                 430

Ser Ser Ala Ser Met Asn Ser Gly Val Leu Leu Val Arg Pro Ser Arg
            435                 440                 445

Leu Ser Ser Gly Thr Pro Met Leu Ala Gly Val Ser Glu Tyr Glu
450                 455                 460
```

Leu Pro Glu Asp Pro Arg Trp Glu Leu Pro Arg Asp Arg Leu Val Leu
465                 470                 475                 480

Gly Lys Pro Leu Gly Glu Gly Cys Phe Gly Gln Val Val Leu Ala Glu
            485                 490                 495

Ala Ile Gly Leu Asp Lys Asp Lys Pro Asn Arg Val Thr Lys Val Ala
        500                 505                 510

Val Lys Met Leu Lys Ser Asp Ala Thr Glu Lys Asp Leu Ser Asp Leu
    515                 520                 525

Ile Ser Glu Met Glu Met Met Lys Met Ile Gly Lys His Lys Asn Ile
530                 535                 540

Ile Asn Leu Leu Gly Ala Cys Thr Gln Asp Gly Pro Leu Tyr Val Ile
545                 550                 555                 560

Val Glu Tyr Ala Ser Lys Gly Asn Leu Arg Glu Tyr Leu Gln Ala Arg
            565                 570                 575

Arg Pro Pro Gly Leu Glu Tyr Cys Tyr Asn Pro Ser His Asn Pro Glu
        580                 585                 590

Glu Gln Leu Ser Ser Lys Asp Leu Val Ser Cys Ala Tyr Gln Val Ala
    595                 600                 605

Arg Gly Met Glu Tyr Leu Ala Ser Lys Lys Cys Ile His Arg Asp Leu
610                 615                 620

Ala Ala Arg Asn Val Leu Val Thr Glu Asp Asn Val Met Lys Ile Ala
625                 630                 635                 640

Asp Phe Gly Leu Ala Arg Asp Ile His His Ile Asp Tyr Tyr Lys Lys
            645                 650                 655

Thr Thr Asn Gly Arg Leu Pro Val Lys Trp Met Ala Pro Glu Ala Leu
        660                 665                 670

Phe Asp Arg Ile Tyr Thr His Gln Ser Asp Val Trp Ser Phe Gly Val
    675                 680                 685

Leu Leu Trp Glu Ile Phe Thr Leu Gly Gly Ser Pro Tyr Pro Gly Val
690                 695                 700

Pro Val Glu Glu Leu Phe Lys Leu Leu Lys Glu Gly His Arg Met Asp
705                 710                 715                 720

Lys Pro Ser Asn Cys Thr Asn Glu Leu Tyr Met Met Met Arg Asp Cys
            725                 730                 735

Trp His Ala Val Pro Ser Gln Arg Pro Thr Phe Lys Gln Leu Val Glu
        740                 745                 750

Asp Leu Asp Arg Ile Val Ala Leu Thr Ser Asn Gln Glu Tyr Leu Asp
    755                 760                 765

Leu Ser Ile Pro Leu Asp Gln Tyr Ser Pro Ser Phe Pro Asp Thr Arg
770                 775                 780

Ser Ser Thr Cys Ser Ser Gly Glu Asp Ser Val Phe Ser His Glu Pro
785                 790                 795                 800

Leu Pro Glu Glu Pro Cys Leu Pro Arg His Pro Thr Gln Leu Ala Asn
            805                 810                 815

Ser Gly Leu Lys Arg Arg
            820

<210> SEQ ID NO 45
<211> LENGTH: 821
<212> TYPE: PRT
<213> ORGANISM: Homo sapiens
<220> FEATURE:
<223> OTHER INFORMATION: human FGFR2

<400> SEQUENCE: 45

```
Met Val Ser Trp Gly Arg Phe Ile Cys Leu Val Val Thr Met Ala
1               5                   10                  15

Thr Leu Ser Leu Ala Arg Pro Ser Phe Ser Leu Val Glu Asp Thr Thr
            20                  25                  30

Leu Glu Pro Glu Glu Pro Pro Thr Lys Tyr Gln Ile Ser Gln Pro Glu
        35                  40                  45

Val Tyr Val Ala Ala Pro Gly Glu Ser Leu Glu Val Arg Cys Leu Leu
    50                  55                  60

Lys Asp Ala Ala Val Ile Ser Trp Thr Lys Asp Gly Val His Leu Gly
65                  70                  75                  80

Pro Asn Asn Arg Thr Val Leu Ile Gly Glu Tyr Leu Gln Ile Lys Gly
                85                  90                  95

Ala Thr Pro Arg Asp Ser Gly Leu Tyr Ala Cys Thr Ala Ser Arg Thr
                100                 105                 110

Val Asp Ser Glu Thr Trp Tyr Phe Met Val Asn Val Thr Asp Ala Ile
                115                 120                 125

Ser Ser Gly Asp Asp Glu Asp Asp Thr Asp Gly Ala Glu Asp Phe Val
    130                 135                 140

Ser Glu Asn Ser Asn Asn Lys Arg Ala Pro Tyr Trp Thr Asn Thr Glu
145                 150                 155                 160

Lys Met Glu Lys Arg Leu His Ala Val Pro Ala Ala Asn Thr Val Lys
                165                 170                 175

Phe Arg Cys Pro Ala Gly Gly Asn Pro Met Pro Thr Met Arg Trp Leu
                180                 185                 190

Lys Asn Gly Lys Glu Phe Lys Gln Glu His Arg Ile Gly Gly Tyr Lys
                195                 200                 205

Val Arg Asn Gln His Trp Ser Leu Ile Met Glu Ser Val Val Pro Ser
    210                 215                 220

Asp Lys Gly Asn Tyr Thr Cys Val Val Glu Asn Glu Tyr Gly Ser Ile
225                 230                 235                 240

Asn His Thr Tyr His Leu Asp Val Val Glu Arg Ser Pro His Arg Pro
                245                 250                 255

Ile Leu Gln Ala Gly Leu Pro Ala Asn Ala Ser Thr Val Val Gly Gly
                260                 265                 270

Asp Val Glu Phe Val Cys Lys Val Tyr Ser Asp Ala Gln Pro His Ile
                275                 280                 285

Gln Trp Ile Lys His Val Glu Lys Asn Gly Ser Lys Tyr Gly Pro Asp
    290                 295                 300

Gly Leu Pro Tyr Leu Lys Val Leu Lys Ala Ala Gly Val Asn Thr Thr
305                 310                 315                 320

Asp Lys Glu Ile Glu Val Leu Tyr Ile Arg Asn Val Thr Phe Glu Asp
                325                 330                 335

Ala Gly Glu Tyr Thr Cys Leu Ala Gly Asn Ser Ile Gly Ile Ser Phe
                340                 345                 350

His Ser Ala Trp Leu Thr Val Leu Pro Ala Pro Gly Arg Glu Lys Glu
                355                 360                 365

Ile Thr Ala Ser Pro Asp Tyr Leu Glu Ile Ala Ile Tyr Cys Ile Gly
                370                 375                 380

Val Phe Leu Ile Ala Cys Met Val Val Thr Val Ile Leu Cys Arg Met
385                 390                 395                 400

Lys Asn Thr Thr Lys Lys Pro Asp Phe Ser Ser Gln Pro Ala Val His
                405                 410                 415

Lys Leu Thr Lys Arg Ile Pro Leu Arg Arg Gln Val Thr Val Ser Ala
```

```
            420                 425                 430
Glu Ser Ser Ser Met Asn Ser Asn Thr Pro Leu Val Arg Ile Thr
            435                 440                 445

Thr Arg Leu Ser Ser Thr Ala Asp Thr Pro Met Leu Ala Gly Val Ser
450                 455                 460

Glu Tyr Glu Leu Pro Glu Asp Pro Lys Trp Glu Phe Pro Arg Asp Lys
465                 470                 475                 480

Leu Thr Leu Gly Lys Pro Leu Gly Glu Gly Cys Phe Gly Gln Val Val
            485                 490                 495

Met Ala Glu Ala Val Gly Ile Asp Lys Asp Lys Pro Lys Glu Ala Val
            500                 505                 510

Thr Val Ala Val Lys Met Leu Lys Asp Asp Ala Thr Glu Lys Asp Leu
            515                 520                 525

Ser Asp Leu Val Ser Glu Met Glu Met Met Lys Met Ile Gly Lys His
            530                 535                 540

Lys Asn Ile Ile Asn Leu Leu Gly Ala Cys Thr Gln Asp Gly Pro Leu
545                 550                 555                 560

Tyr Val Ile Val Glu Tyr Ala Ser Lys Gly Asn Leu Arg Glu Tyr Leu
            565                 570                 575

Arg Ala Arg Arg Pro Pro Gly Met Glu Tyr Ser Tyr Asp Ile Asn Arg
            580                 585                 590

Val Pro Glu Glu Gln Met Thr Phe Lys Asp Leu Val Ser Cys Thr Tyr
            595                 600                 605

Gln Leu Ala Arg Gly Met Glu Tyr Leu Ala Ser Gln Lys Cys Ile His
            610                 615                 620

Arg Asp Leu Ala Ala Arg Asn Val Leu Val Thr Glu Asn Asn Val Met
625                 630                 635                 640

Lys Ile Ala Asp Phe Gly Leu Ala Arg Asp Ile Asn Asn Ile Asp Tyr
            645                 650                 655

Tyr Lys Lys Thr Thr Asn Gly Arg Leu Pro Val Lys Trp Met Ala Pro
            660                 665                 670

Glu Ala Leu Phe Asp Arg Val Tyr Thr His Gln Ser Asp Val Trp Ser
            675                 680                 685

Phe Gly Val Leu Met Trp Glu Ile Phe Thr Leu Gly Gly Ser Pro Tyr
            690                 695                 700

Pro Gly Ile Pro Val Glu Glu Leu Phe Lys Leu Leu Lys Glu Gly His
705                 710                 715                 720

Arg Met Asp Lys Pro Ala Asn Cys Thr Asn Glu Leu Tyr Met Met Met
            725                 730                 735

Arg Asp Cys Trp His Ala Val Pro Ser Gln Arg Pro Thr Phe Lys Gln
            740                 745                 750

Leu Val Glu Asp Leu Asp Arg Ile Leu Thr Leu Thr Thr Asn Glu Glu
            755                 760                 765

Tyr Leu Asp Leu Ser Gln Pro Leu Glu Gln Tyr Ser Pro Ser Tyr Pro
            770                 775                 780

Asp Thr Arg Ser Ser Cys Ser Ser Gly Asp Asp Ser Val Phe Ser Pro
785                 790                 795                 800

Asp Pro Met Pro Tyr Glu Pro Cys Leu Pro Gln Tyr Pro His Ile Asn
            805                 810                 815

Gly Ser Val Lys Thr
            820

<210> SEQ ID NO 46
```

<211> LENGTH: 840
<212> TYPE: PRT
<213> ORGANISM: Mus musculus
<220> FEATURE:
<223> OTHER INFORMATION: murine FGFR2

<400> SEQUENCE: 46

```
Met Gly Leu Pro Ser Thr Trp Arg Tyr Gly Arg Gly Pro Gly Ile Gly
1               5                   10                  15

Thr Val Thr Met Val Ser Trp Gly Arg Phe Ile Cys Leu Val Leu Val
            20                  25                  30

Thr Met Ala Thr Leu Ser Leu Ala Arg Pro Ser Phe Ser Leu Val Glu
        35                  40                  45

Asp Thr Thr Leu Glu Pro Glu Glu Pro Pro Thr Lys Tyr Gln Ile Ser
50                  55                  60

Gln Pro Glu Ala Tyr Val Val Ala Pro Gly Glu Ser Leu Glu Leu Gln
65                  70                  75                  80

Cys Met Leu Lys Asp Ala Ala Val Ile Ser Trp Thr Lys Asp Gly Val
                85                  90                  95

His Leu Gly Pro Asn Asn Arg Thr Val Leu Ile Gly Glu Tyr Leu Gln
            100                 105                 110

Ile Lys Gly Ala Thr Pro Arg Asp Ser Gly Leu Tyr Ala Cys Thr Ala
        115                 120                 125

Ala Arg Thr Val Asp Ser Glu Thr Trp Tyr Phe Met Val Asn Val Thr
130                 135                 140

Asp Ala Ile Ser Ser Gly Asp Asp Glu Asp Thr Asp Ser Ser Glu
145                 150                 155                 160

Asp Val Val Ser Glu Asn Arg Ser Asn Gln Arg Ala Pro Tyr Trp Thr
                165                 170                 175

Asn Thr Glu Lys Met Glu Lys Arg Leu His Ala Val Pro Ala Ala Asn
            180                 185                 190

Thr Val Lys Phe Arg Cys Pro Ala Gly Gly Asn Pro Thr Pro Thr Met
        195                 200                 205

Arg Trp Leu Lys Asn Gly Lys Glu Phe Lys Gln Glu His Arg Ile Gly
210                 215                 220

Gly Tyr Lys Val Arg Asn Gln His Trp Ser Leu Ile Met Glu Ser Val
225                 230                 235                 240

Val Pro Ser Asp Lys Gly Asn Tyr Thr Cys Leu Val Glu Asn Glu Tyr
                245                 250                 255

Gly Ser Ile Asn His Thr Tyr His Leu Asp Val Val Glu Arg Ser Pro
            260                 265                 270

His Arg Pro Ile Leu Gln Ala Gly Leu Pro Ala Asn Ala Ser Thr Val
        275                 280                 285

Val Gly Gly Asp Val Glu Phe Val Cys Lys Val Tyr Ser Asp Ala Gln
290                 295                 300

Pro His Ile Gln Trp Ile Lys His Val Glu Lys Asn Gly Ser Lys Tyr
305                 310                 315                 320

Gly Pro Asp Gly Leu Pro Tyr Leu Lys Val Leu Lys Ala Ala Gly Val
                325                 330                 335

Asn Thr Thr Asp Lys Glu Ile Glu Val Leu Tyr Ile Arg Asn Val Thr
            340                 345                 350

Phe Glu Asp Ala Gly Glu Tyr Thr Cys Leu Ala Gly Asn Ser Ile Gly
        355                 360                 365

Ile Ser Phe His Ser Ala Trp Leu Thr Val Leu Pro Ala Pro Val Arg
370                 375                 380
```

```
Glu Lys Glu Ile Thr Ala Ser Pro Asp Tyr Leu Glu Ile Ala Ile Tyr
385                 390                 395                 400

Cys Ile Gly Val Phe Leu Ile Ala Cys Met Val Thr Val Ile Phe
                405                 410                 415

Cys Arg Met Lys Thr Thr Thr Lys Lys Pro Asp Phe Ser Ser Gln Pro
            420                 425                 430

Ala Val His Lys Leu Thr Lys Arg Ile Pro Leu Arg Arg Gln Val Thr
            435                 440                 445

Val Ser Ala Glu Ser Ser Ser Met Asn Ser Asn Thr Pro Leu Val
450                 455                 460

Arg Ile Thr Thr Arg Leu Ser Ser Thr Ala Asp Thr Pro Met Leu Ala
465                 470                 475                 480

Gly Val Ser Glu Tyr Glu Leu Pro Glu Asp Pro Lys Trp Glu Phe Pro
                485                 490                 495

Arg Asp Lys Leu Thr Leu Gly Lys Pro Leu Gly Glu Gly Cys Phe Gly
            500                 505                 510

Gln Val Val Met Ala Glu Ala Val Gly Ile Asp Lys Asp Lys Pro Lys
            515                 520                 525

Glu Ala Val Thr Val Ala Val Lys Met Leu Lys Asp Asp Ala Thr Glu
530                 535                 540

Lys Asp Leu Ser Asp Leu Val Ser Glu Met Glu Met Met Lys Met Ile
545                 550                 555                 560

Gly Lys His Lys Asn Ile Ile Asn Leu Leu Gly Ala Cys Thr Gln Asp
                565                 570                 575

Gly Pro Leu Tyr Val Ile Val Glu Tyr Ala Ser Lys Gly Asn Leu Arg
                580                 585                 590

Glu Tyr Leu Arg Ala Arg Arg Pro Pro Gly Met Glu Tyr Ser Tyr Asp
            595                 600                 605

Ile Asn Arg Val Pro Glu Glu Gln Met Thr Phe Lys Asp Leu Val Ser
            610                 615                 620

Cys Thr Tyr Gln Leu Ala Arg Gly Met Glu Tyr Leu Ala Ser Gln Lys
625                 630                 635                 640

Cys Ile His Arg Asp Leu Ala Ala Arg Asn Val Leu Val Thr Glu Asn
                645                 650                 655

Asn Val Met Lys Ile Ala Asp Phe Gly Leu Ala Arg Asp Ile Asn Asn
                660                 665                 670

Ile Asp Tyr Tyr Lys Lys Thr Thr Asn Gly Arg Leu Pro Val Lys Trp
            675                 680                 685

Met Ala Pro Glu Ala Leu Phe Asp Arg Val Tyr Thr His Gln Ser Asp
            690                 695                 700

Val Trp Ser Phe Gly Val Leu Met Trp Glu Ile Phe Thr Leu Gly Gly
705                 710                 715                 720

Ser Pro Tyr Pro Gly Ile Pro Val Glu Glu Leu Phe Lys Leu Leu Lys
                725                 730                 735

Glu Gly His Arg Met Asp Lys Pro Thr Asn Cys Thr Asn Glu Leu Tyr
            740                 745                 750

Met Met Met Arg Asp Cys Trp His Ala Val Pro Ser Gln Arg Pro Thr
            755                 760                 765

Phe Lys Gln Leu Val Glu Asp Leu Asp Arg Ile Leu Thr Leu Thr Thr
            770                 775                 780

Asn Glu Glu Tyr Leu Asp Leu Thr Gln Pro Leu Glu Gln Tyr Ser Pro
785                 790                 795                 800
```

```
Ser Tyr Pro Asp Thr Arg Ser Ser Cys Ser Ser Gly Asp Asp Ser Val
                805                 810                 815

Phe Ser Pro Asp Pro Met Pro Tyr Glu Pro Cys Leu Pro Gln Tyr Pro
            820                 825                 830

His Ile Asn Gly Ser Val Lys Thr
            835                 840

<210> SEQ ID NO 47
<211> LENGTH: 806
<212> TYPE: PRT
<213> ORGANISM: Homo sapiens
<220> FEATURE:
<223> OTHER INFORMATION: human FGFR3

<400> SEQUENCE: 47

Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val
                20                  25                  30

Gly Arg Ala Ala Glu Val Pro Gly Pro Glu Pro Gly Gln Gln Glu Gln
            35                  40                  45

Leu Val Phe Gly Ser Gly Asp Ala Val Glu Leu Ser Cys Pro Pro Pro
    50                  55                  60

Gly Gly Gly Pro Met Gly Pro Thr Val Trp Val Lys Asp Gly Thr Gly
65                  70                  75                  80

Leu Val Pro Ser Glu Arg Val Leu Val Gly Pro Gln Arg Leu Gln Val
                85                  90                  95

Leu Asn Ala Ser His Glu Asp Ser Gly Ala Tyr Ser Cys Arg Gln Arg
            100                 105                 110

Leu Thr Gln Arg Val Leu Cys His Phe Ser Val Arg Val Thr Asp Ala
        115                 120                 125

Pro Ser Ser Gly Asp Asp Glu Asp Gly Glu Asp Glu Ala Glu Asp Thr
    130                 135                 140

Gly Val Asp Thr Gly Ala Pro Tyr Trp Thr Arg Pro Glu Arg Met Asp
145                 150                 155                 160

Lys Lys Leu Leu Ala Val Pro Ala Ala Asn Thr Val Arg Phe Arg Cys
                165                 170                 175

Pro Ala Ala Gly Asn Pro Thr Pro Ser Ile Ser Trp Leu Lys Asn Gly
            180                 185                 190

Arg Glu Phe Arg Gly Glu His Arg Ile Gly Gly Ile Lys Leu Arg His
        195                 200                 205

Gln Gln Trp Ser Leu Val Met Glu Ser Val Val Pro Ser Asp Arg Gly
    210                 215                 220

Asn Tyr Thr Cys Val Val Glu Asn Lys Phe Gly Ser Ile Arg Gln Thr
225                 230                 235                 240

Tyr Thr Leu Asp Val Leu Glu Arg Ser Pro His Arg Pro Ile Leu Gln
                245                 250                 255

Ala Gly Leu Pro Ala Asn Gln Thr Ala Val Leu Gly Ser Asp Val Glu
            260                 265                 270

Phe His Cys Lys Val Tyr Ser Asp Ala Gln Pro His Ile Gln Trp Leu
        275                 280                 285

Lys His Val Glu Val Asn Gly Ser Lys Val Gly Pro Asp Gly Thr Pro
    290                 295                 300

Tyr Val Thr Val Leu Lys Thr Ala Gly Ala Asn Thr Thr Asp Lys Glu
305                 310                 315                 320
```

```
Leu Glu Val Leu Ser Leu His Asn Val Thr Phe Glu Asp Ala Gly Glu
            325                 330                 335

Tyr Thr Cys Leu Ala Gly Asn Ser Ile Gly Phe Ser His His Ser Ala
            340                 345                 350

Trp Leu Val Val Leu Pro Ala Glu Glu Leu Val Glu Ala Asp Glu
            355                 360                 365

Ala Gly Ser Val Tyr Ala Gly Ile Leu Ser Tyr Gly Val Gly Phe Phe
            370                 375                 380

Leu Phe Ile Leu Val Val Ala Ala Val Thr Leu Cys Arg Leu Arg Ser
385                 390                 395                 400

Pro Pro Lys Lys Gly Leu Gly Ser Pro Thr Val His Lys Ile Ser Arg
            405                 410                 415

Phe Pro Leu Lys Arg Gln Val Ser Leu Glu Ser Asn Ala Ser Met Ser
            420                 425                 430

Ser Asn Thr Pro Leu Val Arg Ile Ala Arg Leu Ser Ser Gly Glu Gly
            435                 440                 445

Pro Thr Leu Ala Asn Val Ser Glu Leu Glu Leu Pro Ala Asp Pro Lys
            450                 455                 460

Trp Glu Leu Ser Arg Ala Arg Leu Thr Leu Gly Lys Pro Leu Gly Glu
465                 470                 475                 480

Gly Cys Phe Gly Gln Val Val Met Ala Glu Ala Ile Gly Ile Asp Lys
            485                 490                 495

Asp Arg Ala Ala Lys Pro Val Thr Val Ala Val Lys Met Leu Lys Asp
            500                 505                 510

Asp Ala Thr Asp Lys Asp Leu Ser Asp Leu Val Ser Glu Met Glu Met
            515                 520                 525

Met Lys Met Ile Gly Lys His Lys Asn Ile Ile Asn Leu Leu Gly Ala
            530                 535                 540

Cys Thr Gln Gly Gly Pro Leu Tyr Val Leu Val Glu Tyr Ala Ala Lys
545                 550                 555                 560

Gly Asn Leu Arg Glu Phe Leu Arg Ala Arg Arg Pro Pro Gly Leu Asp
            565                 570                 575

Tyr Ser Phe Asp Thr Cys Lys Pro Pro Glu Glu Gln Leu Thr Phe Lys
            580                 585                 590

Asp Leu Val Ser Cys Ala Tyr Gln Val Ala Arg Gly Met Glu Tyr Leu
            595                 600                 605

Ala Ser Gln Lys Cys Ile His Arg Asp Leu Ala Ala Arg Asn Val Leu
            610                 615                 620

Val Thr Glu Asp Asn Val Met Lys Ile Ala Asp Phe Gly Leu Ala Arg
625                 630                 635                 640

Asp Val His Asn Leu Asp Tyr Tyr Lys Lys Thr Thr Asn Gly Arg Leu
            645                 650                 655

Pro Val Lys Trp Met Ala Pro Glu Ala Leu Phe Asp Arg Val Tyr Thr
            660                 665                 670

His Gln Ser Asp Val Trp Ser Phe Gly Val Leu Leu Trp Glu Ile Phe
            675                 680                 685

Thr Leu Gly Gly Ser Pro Tyr Pro Gly Ile Pro Val Glu Glu Leu Phe
            690                 695                 700

Lys Leu Leu Lys Glu Gly His Arg Met Asp Lys Pro Ala Asn Cys Thr
705                 710                 715                 720

His Asp Leu Tyr Met Ile Met Arg Glu Cys Trp His Ala Ala Pro Ser
            725                 730                 735

Gln Arg Pro Thr Phe Lys Gln Leu Val Glu Asp Leu Asp Arg Val Leu
```

```
                    740             745             750
Thr Val Thr Ser Thr Asp Glu Tyr Leu Asp Leu Ser Ala Pro Phe Glu
            755                 760             765

Gln Tyr Ser Pro Gly Gly Gln Asp Thr Pro Ser Ser Ser Ser Ser Gly
770             775                 780

Asp Asp Ser Val Phe Ala His Asp Leu Leu Pro Ala Pro Pro Ser
785             790             795             800

Ser Gly Gly Ser Arg Thr
            805

<210> SEQ ID NO 48
<211> LENGTH: 782
<212> TYPE: PRT
<213> ORGANISM: Mus musculus
<220> FEATURE:
<223> OTHER INFORMATION: murine FGFR3

<400> SEQUENCE: 48

Met Val Val Pro Ala Cys Val Leu Val Phe Cys Val Ala Val Val Ala
1               5                   10                  15

Gly Ala Thr Ser Glu Pro Pro Gly Pro Glu Gln Arg Val Val Arg Arg
            20                  25                  30

Ala Ala Glu Val Pro Gly Pro Glu Pro Ser Gln Gln Glu Gln Val Ala
        35                  40                  45

Phe Gly Ser Gly Asp Thr Val Glu Leu Ser Cys His Pro Pro Gly Gly
    50                  55                  60

Ala Pro Thr Gly Pro Thr Val Trp Ala Lys Asp Gly Thr Gly Leu Val
65                  70                  75                  80

Ala Ser His Arg Ile Leu Val Gly Pro Gln Arg Leu Gln Val Leu Asn
                85                  90                  95

Ala Ser His Glu Asp Ala Gly Val Tyr Ser Cys Gln His Arg Leu Thr
            100                 105                 110

Arg Arg Val Leu Cys His Phe Ser Val Arg Val Thr Gly Ala Pro Tyr
        115                 120                 125

Trp Thr Arg Pro Glu Arg Met Asp Lys Lys Leu Leu Ala Val Pro Ala
    130                 135                 140

Ala Asn Thr Val Arg Phe Arg Cys Pro Ala Ala Gly Asn Pro Thr Pro
145                 150                 155                 160

Ser Ile Ser Trp Leu Lys Asn Gly Lys Glu Phe Arg Gly Glu His Arg
                165                 170                 175

Ile Gly Gly Ile Lys Leu Arg His Gln Gln Trp Ser Leu Val Met Glu
            180                 185                 190

Ser Val Val Pro Ser Asp Arg Gly Asn Tyr Thr Cys Val Val Glu Asn
        195                 200                 205

Lys Phe Gly Ser Ile Arg Gln Thr Tyr Thr Leu Asp Val Leu Glu Arg
    210                 215                 220

Ser Pro His Arg Pro Ile Leu Gln Ala Gly Leu Pro Ala Asn Gln Thr
225                 230                 235                 240

Ala Ile Leu Gly Ser Asp Val Glu Phe His Cys Lys Val Tyr Ser Asp
                245                 250                 255

Ala Gln Pro His Ile Gln Trp Leu Lys His Val Glu Val Asn Gly Ser
            260                 265                 270

Lys Val Gly Pro Asp Gly Thr Pro Tyr Val Thr Val Leu Lys Thr Ala
        275                 280                 285

Gly Ala Asn Thr Thr Asp Lys Glu Leu Glu Val Leu Ser Leu His Asn
```

```
                290             295             300
Val Thr Phe Glu Asp Ala Gly Glu Tyr Thr Cys Leu Ala Gly Asn Ser
305                 310             315                 320

Ile Gly Phe Ser His His Ser Ala Trp Leu Val Val Leu Pro Ala Glu
                325             330             335

Glu Glu Leu Met Glu Thr Asp Glu Ala Gly Ser Val Tyr Ala Gly Val
                340             345             350

Leu Ser Tyr Gly Val Val Phe Phe Leu Phe Ile Leu Val Val Ala Ala
            355             360             365

Val Ile Leu Cys Arg Leu Arg Ser Pro Lys Lys Gly Leu Gly Ser
370             375             380

Pro Thr Val His Lys Val Ser Arg Phe Pro Leu Lys Arg Gln Val Ser
385             390             395             400

Leu Glu Ser Asn Ser Ser Met Asn Ser Asn Thr Pro Leu Val Arg Ile
                405             410             415

Ala Arg Leu Ser Ser Gly Glu Gly Pro Val Leu Ala Asn Val Ser Glu
                420             425             430

Leu Glu Leu Pro Ala Asp Pro Lys Trp Glu Leu Ser Arg Thr Arg Leu
            435             440             445

Thr Leu Gly Lys Pro Leu Gly Glu Gly Cys Phe Gly Gln Val Val Met
            450             455             460

Ala Glu Ala Ile Gly Ile Asp Lys Asp Arg Thr Ala Lys Pro Val Thr
465             470             475             480

Val Ala Val Lys Met Leu Lys Asp Asp Ala Thr Asp Lys Asp Leu Ser
                485             490             495

Asp Leu Val Ser Glu Met Glu Met Met Lys Met Ile Gly Lys His Lys
                500             505             510

Asn Ile Ile Asn Leu Leu Gly Ala Cys Thr Gln Gly Gly Pro Leu Tyr
            515             520             525

Val Leu Val Glu Tyr Ala Ala Lys Gly Asn Leu Arg Glu Phe Leu Arg
            530             535             540

Ala Arg Arg Pro Pro Gly Met Asp Tyr Ser Phe Asp Ala Cys Arg Leu
545             550             555             560

Pro Glu Glu Gln Leu Thr Cys Lys Asp Leu Val Ser Cys Ala Tyr Gln
                565             570             575

Val Ala Arg Gly Met Glu Tyr Leu Ala Ser Gln Lys Cys Ile His Arg
            580             585             590

Asp Leu Ala Ala Arg Asn Val Leu Val Thr Glu Asp Asn Val Met Lys
            595             600             605

Ile Ala Asp Phe Gly Leu Ala Arg Asp Val His Asn Leu Asp Tyr Tyr
610             615             620

Lys Lys Thr Thr Asn Gly Arg Leu Pro Val Lys Trp Met Ala Pro Glu
625             630             635             640

Ala Leu Phe Asp Arg Val Tyr Thr His Gln Ser Asp Val Trp Ser Phe
                645             650             655

Gly Val Leu Leu Trp Glu Ile Phe Thr Leu Gly Gly Ser Pro Tyr Pro
            660             665             670

Gly Ile Pro Val Glu Glu Leu Phe Lys Leu Leu Lys Glu Gly His Arg
            675             680             685

Met Asp Lys Pro Ala Ser Cys Thr His Asp Leu Tyr Met Ile Met Arg
            690             695             700

Glu Cys Trp His Ala Val Pro Ser Gln Arg Pro Thr Phe Lys Gln Leu
705             710             715             720
```

Val Glu Asp Leu Asp Arg Ile Leu Thr Val Thr Ser Thr Asp Glu Tyr
                    725                 730                 735

Leu Asp Leu Ser Val Pro Phe Glu Gln Tyr Ser Pro Gly Gly Gln Asp
                740                 745                 750

Thr Pro Ser Ser Ser Ser Gly Asp Asp Ser Val Phe Thr His Asp
            755                 760                 765

Leu Leu Pro Pro Gly Pro Pro Ser Asn Gly Gly Pro Arg Thr
770                 775                 780

<210> SEQ ID NO 49
<211> LENGTH: 802
<212> TYPE: PRT
<213> ORGANISM: Homo sapiens
<220> FEATURE:
<223> OTHER INFORMATION: human FGFR4

<400> SEQUENCE: 49

Met Arg Leu Leu Leu Ala Leu Leu Gly Val Leu Leu Ser Val Pro Gly
1               5                   10                  15

Pro Pro Val Leu Ser Leu Glu Ala Ser Glu Glu Val Glu Leu Glu Pro
                20                  25                  30

Cys Leu Ala Pro Ser Leu Glu Gln Gln Glu Gln Glu Leu Thr Val Ala
            35                  40                  45

Leu Gly Gln Pro Val Arg Leu Cys Cys Gly Arg Ala Glu Arg Gly Gly
        50                  55                  60

His Trp Tyr Lys Glu Gly Ser Arg Leu Ala Pro Ala Gly Arg Val Arg
65                  70                  75                  80

Gly Trp Arg Gly Arg Leu Glu Ile Ala Ser Phe Leu Pro Glu Asp Ala
                85                  90                  95

Gly Arg Tyr Leu Cys Leu Ala Arg Gly Ser Met Ile Val Leu Gln Asn
            100                 105                 110

Leu Thr Leu Ile Thr Gly Asp Ser Leu Thr Ser Ser Asn Asp Asp Glu
        115                 120                 125

Asp Pro Lys Ser His Arg Asp Pro Ser Asn Arg His Ser Tyr Pro Gln
130                 135                 140

Gln Ala Pro Tyr Trp Thr His Pro Gln Arg Met Glu Lys Lys Leu His
145                 150                 155                 160

Ala Val Pro Ala Gly Asn Thr Val Lys Phe Arg Cys Pro Ala Ala Gly
                165                 170                 175

Asn Pro Thr Pro Thr Ile Arg Trp Leu Lys Asp Gly Gln Ala Phe His
            180                 185                 190

Gly Glu Asn Arg Ile Gly Gly Ile Arg Leu Arg His Gln His Trp Ser
        195                 200                 205

Leu Val Met Glu Ser Val Val Pro Ser Asp Arg Gly Thr Tyr Thr Cys
210                 215                 220

Leu Val Glu Asn Ala Val Gly Ser Ile Arg Tyr Asn Tyr Leu Leu Asp
225                 230                 235                 240

Val Leu Glu Arg Ser Pro His Arg Pro Ile Leu Gln Ala Gly Leu Pro
                245                 250                 255

Ala Asn Thr Thr Ala Val Val Gly Ser Asp Val Glu Leu Leu Cys Lys
            260                 265                 270

Val Tyr Ser Asp Ala Gln Pro His Ile Gln Trp Leu Lys His Ile Val
        275                 280                 285

Ile Asn Gly Ser Ser Phe Gly Ala Asp Gly Phe Pro Tyr Val Gln Val
290                 295                 300

```
Leu Lys Thr Ala Asp Ile Asn Ser Ser Glu Val Glu Val Leu Tyr Leu
305                 310                 315                 320

Arg Asn Val Ser Ala Glu Asp Ala Gly Glu Tyr Thr Cys Leu Ala Gly
                325                 330                 335

Asn Ser Ile Gly Leu Ser Tyr Gln Ser Ala Trp Leu Thr Val Leu Pro
            340                 345                 350

Glu Glu Asp Pro Thr Trp Thr Ala Ala Pro Glu Ala Arg Tyr Thr
        355                 360                 365

Asp Ile Ile Leu Tyr Ala Ser Gly Ser Leu Ala Leu Ala Val Leu Leu
370                 375                 380

Leu Leu Ala Gly Leu Tyr Arg Gly Gln Ala Leu His Gly Arg His Pro
385                 390                 395                 400

Arg Pro Pro Ala Thr Val Gln Lys Leu Ser Arg Phe Pro Leu Ala Arg
                405                 410                 415

Gln Phe Ser Leu Glu Ser Gly Ser Gly Lys Ser Ser Ser Ser Leu
            420                 425                 430

Val Arg Gly Val Arg Leu Ser Ser Ser Gly Pro Ala Leu Leu Ala Gly
                435                 440                 445

Leu Val Ser Leu Asp Leu Pro Leu Asp Pro Leu Trp Glu Phe Pro Arg
450                 455                 460

Asp Arg Leu Val Leu Gly Lys Pro Leu Gly Glu Gly Cys Phe Gly Gln
465                 470                 475                 480

Val Val Arg Ala Glu Ala Phe Gly Met Asp Pro Ala Arg Pro Asp Gln
                485                 490                 495

Ala Ser Thr Val Ala Val Lys Met Leu Lys Asp Asn Ala Ser Asp Lys
                500                 505                 510

Asp Leu Ala Asp Leu Val Ser Glu Met Glu Val Met Lys Leu Ile Gly
                515                 520                 525

Arg His Lys Asn Ile Ile Asn Leu Leu Gly Val Cys Thr Gln Glu Gly
                530                 535                 540

Pro Leu Tyr Val Ile Val Glu Cys Ala Ala Lys Gly Asn Leu Arg Glu
545                 550                 555                 560

Phe Leu Arg Ala Arg Arg Pro Pro Gly Pro Asp Leu Ser Pro Asp Gly
                565                 570                 575

Pro Arg Ser Ser Glu Gly Pro Leu Ser Phe Pro Val Leu Val Ser Cys
            580                 585                 590

Ala Tyr Gln Val Ala Arg Gly Met Gln Tyr Leu Glu Ser Arg Lys Cys
        595                 600                 605

Ile His Arg Asp Leu Ala Ala Arg Asn Val Leu Val Thr Glu Asp Asn
        610                 615                 620

Val Met Lys Ile Ala Asp Phe Gly Leu Ala Arg Gly Val His His Ile
625                 630                 635                 640

Asp Tyr Tyr Lys Lys Thr Ser Asn Gly Arg Leu Pro Val Lys Trp Met
                645                 650                 655

Ala Pro Glu Ala Leu Phe Asp Arg Val Tyr Thr His Gln Ser Asp Val
                660                 665                 670

Trp Ser Phe Gly Ile Leu Leu Trp Glu Ile Phe Thr Leu Gly Gly Ser
            675                 680                 685

Pro Tyr Pro Gly Ile Pro Val Glu Glu Leu Phe Ser Leu Leu Arg Glu
        690                 695                 700

Gly His Arg Met Asp Arg Pro Pro His Cys Pro Pro Glu Leu Tyr Gly
705                 710                 715                 720
```

-continued

```
Leu Met Arg Glu Cys Trp His Ala Ala Pro Ser Gln Arg Pro Thr Phe
            725                 730                 735

Lys Gln Leu Val Glu Ala Leu Asp Lys Val Leu Leu Ala Val Ser Glu
        740                 745                 750

Glu Tyr Leu Asp Leu Arg Leu Thr Phe Gly Pro Tyr Ser Pro Ser Gly
    755                 760                 765

Gly Asp Ala Ser Ser Thr Cys Ser Ser Ser Asp Ser Val Phe Ser His
770                 775                 780

Asp Pro Leu Pro Leu Gly Ser Ser Ser Phe Pro Phe Gly Ser Gly Val
785                 790                 795                 800

Gln Thr

<210> SEQ ID NO 50
<211> LENGTH: 799
<212> TYPE: PRT
<213> ORGANISM: Mus musculus
<220> FEATURE:
<223> OTHER INFORMATION: murine FGFR4

<400> SEQUENCE: 50

Met Trp Leu Leu Leu Ala Leu Leu Ser Ile Phe Gln Gly Thr Pro Ala
1               5                   10                  15

Leu Ser Leu Glu Ala Ser Glu Glu Met Glu Gln Glu Pro Cys Leu Ala
            20                  25                  30

Pro Ile Leu Glu Gln Gln Glu Gln Val Leu Thr Val Ala Leu Gly Gln
        35                  40                  45

Pro Val Arg Leu Cys Cys Gly Arg Thr Glu Arg Gly Arg His Trp Tyr
    50                  55                  60

Lys Glu Gly Ser Arg Leu Ala Ser Ala Gly Arg Val Arg Gly Trp Arg
65                  70                  75                  80

Gly Arg Leu Glu Ile Ala Ser Phe Leu Pro Glu Asp Ala Gly Arg Tyr
                85                  90                  95

Leu Cys Leu Ala Arg Gly Ser Met Thr Val Val His Asn Leu Thr Leu
            100                 105                 110

Leu Met Asp Asp Ser Leu Thr Ser Ile Ser Asn Asp Glu Asp Pro Lys
        115                 120                 125

Thr Leu Ser Ser Ser Ser Gly His Val Tyr Pro Gln Gln Ala Pro
    130                 135                 140

Tyr Trp Thr His Pro Gln Arg Met Glu Lys Lys Leu His Ala Val Pro
145                 150                 155                 160

Ala Gly Asn Thr Val Lys Phe Arg Cys Pro Ala Ala Gly Asn Pro Met
                165                 170                 175

Pro Thr Ile His Trp Leu Lys Asp Gly Gln Ala Phe His Gly Glu Asn
            180                 185                 190

Arg Ile Gly Gly Ile Arg Leu Arg His Gln His Trp Ser Leu Val Met
        195                 200                 205

Glu Ser Val Val Pro Ser Asp Arg Gly Thr Tyr Thr Cys Leu Val Glu
    210                 215                 220

Asn Ser Leu Gly Ser Ile Arg Tyr Ser Tyr Leu Leu Asp Val Leu Glu
225                 230                 235                 240

Arg Ser Pro His Arg Pro Ile Leu Gln Ala Gly Leu Pro Ala Asn Thr
                245                 250                 255

Thr Ala Val Val Gly Ser Asp Val Glu Leu Leu Cys Lys Val Tyr Ser
            260                 265                 270

Asp Ala Gln Pro His Ile Gln Trp Leu Lys His Val Val Ile Asn Gly
```

```
                275                 280                 285
Ser Ser Phe Gly Ala Asp Gly Phe Pro Tyr Val Gln Val Leu Lys Thr
290                 295                 300
Thr Asp Ile Asn Ser Ser Glu Val Glu Val Leu Tyr Leu Arg Asn Val
305                 310                 315                 320
Ser Ala Glu Asp Ala Gly Glu Tyr Thr Cys Leu Ala Gly Asn Ser Ile
                325                 330                 335
Gly Leu Ser Tyr Gln Ser Ala Trp Leu Thr Val Leu Pro Glu Glu Asp
            340                 345                 350
Leu Thr Trp Thr Thr Ala Thr Pro Glu Ala Arg Tyr Thr Asp Ile Ile
                355                 360                 365
Leu Tyr Val Ser Gly Ser Leu Val Leu Val Leu Leu Leu Leu Leu Ala
370                 375                 380
Gly Val Tyr His Arg Gln Val Ile Arg Gly His Tyr Ser Arg Gln Pro
385                 390                 395                 400
Val Thr Ile Gln Lys Leu Ser Arg Phe Pro Leu Ala Arg Gln Phe Ser
                405                 410                 415
Leu Glu Ser Arg Ser Ser Gly Lys Ser Ser Leu Ser Leu Val Arg Gly
            420                 425                 430
Val Arg Leu Ser Ser Ser Gly Pro Leu Leu Thr Gly Leu Val Asn
                435                 440                 445
Leu Asp Leu Pro Leu Asp Pro Leu Trp Glu Phe Pro Arg Asp Arg Leu
450                 455                 460
Val Leu Gly Lys Pro Leu Gly Glu Gly Cys Phe Gly Gln Val Val Arg
465                 470                 475                 480
Ala Glu Ala Phe Gly Met Asp Pro Ser Arg Pro Asp Gln Thr Ser Thr
                485                 490                 495
Val Ala Val Lys Met Leu Lys Asp Asn Ala Ser Asp Lys Asp Leu Ala
            500                 505                 510
Asp Leu Val Ser Glu Met Glu Val Met Lys Leu Ile Gly Arg His Lys
                515                 520                 525
Asn Ile Ile Asn Leu Leu Gly Val Cys Thr Gln Glu Gly Pro Leu Tyr
530                 535                 540
Val Ile Val Glu Cys Ala Ala Lys Gly Asn Leu Arg Glu Phe Leu Arg
545                 550                 555                 560
Ala Arg Arg Pro Pro Gly Pro Asp Leu Ser Pro Asp Gly Pro Arg Ser
                565                 570                 575
Ser Glu Gly Pro Leu Ser Phe Pro Ala Leu Val Ser Cys Ala Tyr Gln
            580                 585                 590
Val Ala Arg Gly Met Gln Tyr Leu Glu Ser Arg Lys Cys Ile His Arg
                595                 600                 605
Asp Leu Ala Ala Arg Asn Val Leu Val Thr Glu Asp Asp Val Met Lys
610                 615                 620
Ile Ala Asp Phe Gly Leu Ala Arg Gly Val His His Ile Asp Tyr Tyr
625                 630                 635                 640
Lys Lys Thr Ser Asn Gly Arg Leu Pro Val Lys Trp Met Ala Pro Glu
                645                 650                 655
Ala Leu Phe Asp Arg Val Tyr Thr His Gln Ser Asp Val Trp Ser Phe
            660                 665                 670
Gly Ile Leu Leu Trp Glu Ile Phe Thr Leu Gly Gly Ser Pro Tyr Pro
                675                 680                 685
Gly Ile Pro Val Glu Glu Leu Phe Ser Leu Leu Arg Glu Gly His Arg
690                 695                 700
```

```
Met Glu Arg Pro Pro Asn Cys Pro Ser Glu Leu Tyr Gly Leu Met Arg
705                 710                 715                 720

Glu Cys Trp His Ala Ala Pro Ser Gln Arg Pro Thr Phe Lys Gln Leu
            725                 730                 735

Val Glu Ala Leu Asp Lys Val Leu Leu Ala Val Ser Glu Glu Tyr Leu
        740                 745                 750

Asp Leu Arg Leu Thr Phe Gly Pro Phe Ser Pro Ser Asn Gly Asp Ala
            755                 760                 765

Ser Ser Thr Cys Ser Ser Ser Asp Ser Val Phe Ser His Asp Pro Leu
        770                 775                 780

Pro Leu Glu Pro Ser Pro Phe Pro Phe Ser Asp Ser Gln Thr Thr
785                 790                 795
```

<210> SEQ ID NO 51
<211> LENGTH: 20
<212> TYPE: DNA
<213> ORGANISM: Artificial Sequence
<220> FEATURE:
<223> OTHER INFORMATION: Primer sequence Actb

<400> SEQUENCE: 51
agagggaaat cgtgcgtgac                                            20

<210> SEQ ID NO 52
<211> LENGTH: 21
<212> TYPE: DNA
<213> ORGANISM: Artificial Sequence
<220> FEATURE:
<223> OTHER INFORMATION: Primer sequence Actb

<400> SEQUENCE: 52
caatagtgat gacctggccg t                                          21

<210> SEQ ID NO 53
<211> LENGTH: 21
<212> TYPE: DNA
<213> ORGANISM: Artificial Sequence
<220> FEATURE:
<223> OTHER INFORMATION: Primer sequence Cidea

<400> SEQUENCE: 53
tgctcttctg tatcgcccag t                                          21

<210> SEQ ID NO 54
<211> LENGTH: 21
<212> TYPE: DNA
<213> ORGANISM: Artificial Sequence
<220> FEATURE:
<223> OTHER INFORMATION: Primer sequence Cidea

<400> SEQUENCE: 54
gccgtgttaa ggaatctgct g                                          21

<210> SEQ ID NO 55
<211> LENGTH: 20
<212> TYPE: DNA
<213> ORGANISM: Artificial Sequence
<220> FEATURE:
<223> OTHER INFORMATION: Primer sequence Cox7a1

<400> SEQUENCE: 55
ccgacaatga cctcccagta                                            20

<210> SEQ ID NO 56
<211> LENGTH: 20
<212> TYPE: DNA
<213> ORGANISM: Artificial Sequence
<220> FEATURE:
<223> OTHER INFORMATION: Primer sequence Cox7a1

<400> SEQUENCE: 56
tgtttgtcca agtcctccaa                                                   20

<210> SEQ ID NO 57
<211> LENGTH: 21
<212> TYPE: DNA
<213> ORGANISM: Artificial Sequence
<220> FEATURE:
<223> OTHER INFORMATION: Primer Sequence Elovl3

<400> SEQUENCE: 57
tccgcgttct catgtaggtc t                                                 21

<210> SEQ ID NO 58
<211> LENGTH: 21
<212> TYPE: DNA
<213> ORGANISM: Artificial Sequence
<220> FEATURE:
<223> OTHER INFORMATION: Primer sequence Elovl3

<400> SEQUENCE: 58
ggacctgatg caaccctatg a                                                 21

<210> SEQ ID NO 59
<211> LENGTH: 20
<212> TYPE: DNA
<213> ORGANISM: Artificial Sequence
<220> FEATURE:
<223> OTHER INFORMATION: Primer sequence Foxc2

<400> SEQUENCE: 59
acgagtgcgg atttgtaacc                                                   20

<210> SEQ ID NO 60
<211> LENGTH: 20
<212> TYPE: DNA
<213> ORGANISM: Artificial Sequence
<220> FEATURE:
<223> OTHER INFORMATION: Primer sequence Foxc2

<400> SEQUENCE: 60
cagtttgggg agggacctat                                                   20

<210> SEQ ID NO 61
<211> LENGTH: 20
<212> TYPE: DNA
<213> ORGANISM: Artificial Sequence
<220> FEATURE:
<223> OTHER INFORMATION: Primer sequence Hsp90

<400> SEQUENCE: 61
aggagggtca aggaagtggt                                                   20

<210> SEQ ID NO 62
<211> LENGTH: 20
<212> TYPE: DNA
<213> ORGANISM: Artificial Sequence
<220> FEATURE:
<223> OTHER INFORMATION: Primer sequence Hsp90

```
<400> SEQUENCE: 62
tttttcttgt ctttgccgct                                              20

<210> SEQ ID NO 63
<211> LENGTH: 21
<212> TYPE: DNA
<213> ORGANISM: Artificial Sequence
<220> FEATURE:
<223> OTHER INFORMATION: Primer sequence Otop1

<400> SEQUENCE: 63
ggacctgatg caaccctatg a                                            21

<210> SEQ ID NO 64
<211> LENGTH: 20
<212> TYPE: DNA
<213> ORGANISM: Artificial Sequence
<220> FEATURE:
<223> OTHER INFORMATION: Primer sequence Otop1

<400> SEQUENCE: 64
accatgctct acgtgctgtg                                              20

<210> SEQ ID NO 65
<211> LENGTH: 20
<212> TYPE: DNA
<213> ORGANISM: Artificial Sequence
<220> FEATURE:
<223> OTHER INFORMATION: Primer sequence Ppargc1a

<400> SEQUENCE: 65
ggacggaagc aattttttcaa                                             20

<210> SEQ ID NO 66
<211> LENGTH: 20
<212> TYPE: DNA
<213> ORGANISM: Artificial Sequence
<220> FEATURE:
<223> OTHER INFORMATION: Primer sequence Ppargc1a

<400> SEQUENCE: 66
gagtcttggg aaaggacacg                                              20

<210> SEQ ID NO 67
<211> LENGTH: 20
<212> TYPE: DNA
<213> ORGANISM: Artificial Sequence
<220> FEATURE:
<223> OTHER INFORMATION: Primer sequence Prb

<400> SEQUENCE: 67
taaacatctc ccagcggagt                                              20

<210> SEQ ID NO 68
<211> LENGTH: 20
<212> TYPE: DNA
<213> ORGANISM: Artificial Sequence
<220> FEATURE:
<223> OTHER INFORMATION: Primer sequence Prb

<400> SEQUENCE: 68
acaaccatga gccaggagtc                                              20

<210> SEQ ID NO 69
```

```
<211> LENGTH: 20
<212> TYPE: DNA
<213> ORGANISM: Artificial Sequence
<220> FEATURE:
<223> OTHER INFORMATION: Primer sequence Prdm16

<400> SEQUENCE: 69
ctgttagctt tggagccgac                                              20

<210> SEQ ID NO 70
<211> LENGTH: 20
<212> TYPE: DNA
<213> ORGANISM: Artificial Sequence
<220> FEATURE:
<223> OTHER INFORMATION: Primer sequence Prdm16

<400> SEQUENCE: 70
gacgagggtc ctgtgatgtt                                              20

<210> SEQ ID NO 71
<211> LENGTH: 20
<212> TYPE: DNA
<213> ORGANISM: Artificial Sequence
<220> FEATURE:
<223> OTHER INFORMATION: Primer sequence Ucp1

<400> SEQUENCE: 71
tctctgccag gacagtaccc                                              20

<210> SEQ ID NO 72
<211> LENGTH: 20
<212> TYPE: DNA
<213> ORGANISM: Artificial Sequence
<220> FEATURE:
<223> OTHER INFORMATION: Primer sequence Ucp1

<400> SEQUENCE: 72
agaagcccaa tgatgttcag                                              20

<210> SEQ ID NO 73
<211> LENGTH: 20
<212> TYPE: DNA
<213> ORGANISM: Artificial Sequence
<220> FEATURE:
<223> OTHER INFORMATION: Primer sequence Fgfr1

<400> SEQUENCE: 73
ccggatctac acacaccaga                                              20

<210> SEQ ID NO 74
<211> LENGTH: 20
<212> TYPE: DNA
<213> ORGANISM: Artificial Sequence
<220> FEATURE:
<223> OTHER INFORMATION: Primer sequence Fgfr1

<400> SEQUENCE: 74
ccaccaactg cttgaacgta                                              20

<210> SEQ ID NO 75
<211> LENGTH: 20
<212> TYPE: DNA
<213> ORGANISM: Artificial Sequence
<220> FEATURE:
<223> OTHER INFORMATION: Primer sequence Fgfr2

<400> SEQUENCE: 75
```
agggacacag gatggacaag                                              20

<210> SEQ ID NO 76
<211> LENGTH: 20
<212> TYPE: DNA
<213> ORGANISM: Artificial Sequence
<220> FEATURE:
<223> OTHER INFORMATION: Primer sequence Fgfr2

<400> SEQUENCE: 76
aaacacagaa tcgtcccctg                                              20

<210> SEQ ID NO 77
<211> LENGTH: 20
<212> TYPE: DNA
<213> ORGANISM: Artificial Sequence
<220> FEATURE:
<223> OTHER INFORMATION: Primer sequence Fgfr3

<400> SEQUENCE: 77
accgagtcta cacccaccag                                              20

<210> SEQ ID NO 78
<211> LENGTH: 20
<212> TYPE: DNA
<213> ORGANISM: Artificial Sequence
<220> FEATURE:
<223> OTHER INFORMATION: Primer sequence Fgfr3

<400> SEQUENCE: 78
tgaggatgcg gtctaaatcc                                              20

<210> SEQ ID NO 79
<211> LENGTH: 20
<212> TYPE: DNA
<213> ORGANISM: Artificial Sequence
<220> FEATURE:
<223> OTHER INFORMATION: Primer sequence Fgfr4

<400> SEQUENCE: 79
tggaagctct ggacaaggtc                                              20

<210> SEQ ID NO 80
<211> LENGTH: 20
<212> TYPE: DNA
<213> ORGANISM: Artificial Sequence
<220> FEATURE:
<223> OTHER INFORMATION: Primer sequence Fgfr4

<400> SEQUENCE: 80
atacaacatt gctgctcccc                                              20

<210> SEQ ID NO 81
<211> LENGTH: 20
<212> TYPE: DNA
<213> ORGANISM: Artificial Sequence
<220> FEATURE:
<223> OTHER INFORMATION: Primer sequence aklotho

<400> SEQUENCE: 81
ggctcaactc tcccagtcag                                              20

<210> SEQ ID NO 82
<211> LENGTH: 20
<212> TYPE: DNA

```
<213> ORGANISM: Artificial Sequence
<220> FEATURE:
<223> OTHER INFORMATION: Primer sequence aklotho

<400> SEQUENCE: 82
cgcaaactag ccacaaaggt                                                     20

<210> SEQ ID NO 83
<211> LENGTH: 20
<212> TYPE: DNA
<213> ORGANISM: Artificial Sequence
<220> FEATURE:
<223> OTHER INFORMATION: Primer sequence bklotho

<400> SEQUENCE: 83
atgtccagga ggctctgaaa                                                     20

<210> SEQ ID NO 84
<211> LENGTH: 20
<212> TYPE: DNA
<213> ORGANISM: Artificial Sequence
<220> FEATURE:
<223> OTHER INFORMATION: Primer sequence bklotho

<400> SEQUENCE: 84
agcaaatggt gcagtctgtg                                                     20

<210> SEQ ID NO 85
<211> LENGTH: 2421
<212> TYPE: DNA
<213> ORGANISM: Homo sapiens
<220> FEATURE:
<223> OTHER INFORMATION: human FGFR3 spliceform 3c

<400> SEQUENCE: 85
atgggcgccc ctgcctgcgc cctcgcgctc tgcgtggccg tggccatcgt ggccggcgcc         60
tcctcggagt ccttggggac ggagcagcgc gtcgtgggcg agcggcagag agtcccgggc        120
ccagagcccg ccagcaggag cagttggtc ttcggcagcg gggatgctgt ggagctgagc         180
tgtccccccg ccggggggtgg tcccatgggg cccactgtct gggtcaagga tggcacaggg        240
ctggtgccct cggagcgtgt cctggtgggg ccccagcggc tgcaggtgct gaatgcctcc        300
cacgaggact ccgggcccta cagctgccgg cagcggctca cgcagcgcgt actgtgccac        360
ttcagtgtgc gggtgacaga cgctccatcc tcgggagatg acgaagacgg ggaggacgag        420
gctgaggaca caggtgtgga cacaggggcc ccttactgga cacggcccga gcggatggac        480
aagaagctgc tggccgtgcc ggccgccaac accgtccgct tccgctgccc agccgctggc        540
aaccccactc cctccatctc ctggctgaag aacggcaggg agttccgcgg cgagcaccgc        600
attggaggca tcaagctgcg gcatcagcag tggagcctgg tcatggaaag cgtggtgccc        660
tcggaccgcg gcaactacac ctgcgtcgtg gagaacaagt ttggcagcat ccggcagacg        720
tacacgctgg acgtgctgga gcgctcccg caccggccca tcctgcaggc ggggctgccg        780
gccaaccaga cggcggtgct gggcagcgac gtggagttcc actgcaaggt gtacagtgac        840
gcacagcccc acatccagtg gctcaagcac gtggaggtga atggcagcaa ggtgggcccg        900
gacggcacac cctacgttac cgtgctcaag acggcgggcg ctaacaccac cgacaaggag        960
ctagaggttc tctccttgca caacgtcacc tttgaggacg ccggggagta cacctgcctg       1020
gcgggcaatt ctattgggtt ttctcatcac tctgcgtggc tggtggtgct gccagccgag       1080
gaggagctgg tggaggctga cgaggcgggc agtgtgtatg caggcatcct cagctacggg       1140
```

```
gtgggcttct tcctgttcat cctggtggtg gcggctgtga cgctctgccg cctgcgcagc    1200
cccccaaga aaggcctggg ctcccccacc gtgcacaaga tctcccgctt cccgctcaag    1260
cgacaggtgt ccctggagtc caacgcgtcc atgagctcca acacaccact ggtgcgcatc    1320
gcaaggctgt cctcagggga gggcccacg ctggccaatg tctccgagct cgagctgcct    1380
gccgacccca atgggagct gtctcggggcc cggctgaccc tgggcaagcc ccttggggag    1440
ggctgcttcg gccaggtggt catggcgag gccatcggca ttgacaagga ccgggccgcc    1500
aagcctgtca ccgtagccgt gaagatgctg aaagacgatg ccactgacaa ggacctgtcg    1560
gacctggtgt ctgagatgga gatgatgaag atgatcggga acacaaaaa catcatcaac    1620
ctgctgggcg cctgcacgca gggcgggccc ctgtacgtgc tggtggagta cgcggccaag    1680
ggtaacctgc gggagtttct gcgggcgcgg cggcccccgg gcctggacta ctccttcgac    1740
acctgcaagc cgcccgagga gcagctcacc ttcaaggacc tggtgtcctg tgcctaccag    1800
gtggcccggg gcatggagta cttggcctcc cagaagtgca tccacaggga cctggctgcc    1860
cgcaatgtgc tggtgaccga ggacaacgtg atgaagatcg cagacttcgg gctggcccgg    1920
gacgtgcaca acctcgacta ctacaagaag acgaccaacg gccggctgcc cgtgaagtgg    1980
atggcgcctg aggccttgtt tgaccgagtc tacactcacc agagtgacgt ctggtccttt    2040
ggggtcctgc tctgggagat cttcacgctg ggggctccc cgtacccgg catccctgtg    2100
gaggagctct tcaagctgct gaaggagggc caccgcatgg acaagcccgc caactgcaca    2160
cacgacctgt acatgatcat gcgggagtgc tggcatgccg cgccctccca gaggcccacc    2220
ttcaagcagc tggtggagga cctggaccgt gtccttaccg tgacgtccac cgacgagtac    2280
ctggacctgt cggcgccttt cgagcagtac tccccggtg gccaggacac ccccagctcc    2340
agctcctcag gggacgactc cgtgtttgcc cacgacctgc tgccccggc cccacccagc    2400
agtgggggct cgcggacgtg a                                              2421
```

<210> SEQ ID NO 86
<211> LENGTH: 2403
<212> TYPE: DNA
<213> ORGANISM: Mus musculus
<220> FEATURE:
<223> OTHER INFORMATION: murine FGF3 spliceform c

<400> SEQUENCE: 86

```
atggtagtcc cggcctgcgt gctagtgttc tgcgtggcgg tcgtggctgg agctacttcc      60
gagcctcctg gtccagagca gcgagttgtg cggagagcgg cagaggttcc agggcctgaa    120
cctagccagc aggagcaggt ggccttcggc agtggggaca ccgtggagct gagctgccat    180
cctcctggag gtgcccccac agggcccacg gtctgggcta aggatggtac aggtctggtg    240
gcctcccacc gcatcctggt ggggcctcag aggctgcaag tgctaaatgc ctcccacgaa    300
gatgcagggg tctacagctg ccagcaccgg ctcactcggc gtgtgctgtg ccacttcagt    360
gtgcgtgtaa cagatgctcc atcctcagga gatgacgaag atgggagga cgtggctgaa    420
gacacagggg ctccttattg gactcgcccg gagcgaatgg ataagaaact gctggctgtg    480
ccagccgcaa acactgtccg cttccgctgc ccagctgctg caaccctac cccctccatc    540
tcctggctga agaatggcaa agaattccga ggggagcatc gcattggggg catcaagctc    600
cggcaccagc agtggagctt ggtcatggaa agtgtggtac cctccgatcg tggcaactat    660
acctgtgtag ttgagaacaa gtttggcagc atccggcaga catacacact ggatgtgctg    720
```

```
gagcgctccc cacaccggcc catcctgcag gctgggctgc cggccaacca gacagccatt    780
ctaggcagtg acgtggagtt ccactgcaag gtgtacagcg atgcacagcc acacatccag    840
tggctgaagc acgtggaagt gaacggcagc aaggtgggcc ctgacggcac gccctacgtc    900
actgtactca agactgcagg cgctaacacc accgacaagg agctagaggt tctgtccttg    960
cacaatgtca cctttgagga cgcgggggag tacacctgcc tggcgggcaa ttctattggg   1020
ttttcccatc actctgcgtg gctggtggtg ctgccagctg aggaggagct gatggaaact   1080
gatgaggctg gcagcgtgta cgcaggcgtc ctcagctacg gggtggtctt cttcctcttc   1140
atcctggtgg tggcagctgt gatactctgc cgcctgcgca gtccccccaa gaagggcttg   1200
ggctcgccca ccgtgcacaa ggtctctcgc ttcccgctta agcacaggt gtccttggaa    1260 tctaactcct ctatgaactc caacacaccc cttgtccgga ttgcccggct gtcctcagga   1320
gaaggtcctg ttctggccaa tgtttctgaa cttgagctgc ctgctgaccc caagtgggag   1380
ctatccagga cccggctgac acttggtaag cctcttggag aaggctgctt tggacaggtg   1440
gtcatggcag aagctattgg catcgacaag gaccgtactg ccaagcctgt caccgtggcc   1500
gtgaagatgc tgaaagatga tgcgactgac aaggacctgt cggacctggt atctgagatg   1560
gagatgatga aatgattgg caagcacaag aacatcatta acctgctggg ggcgtgcaca   1620
cagggtgggc ccctgtatgt gctggtggag tacgcagcca agggcaatct ccgggagttc   1680
cttcgggcgc ggcggcctcc aggcatggac tactcctttg atgcctgcag gctgccagag   1740
gaacagctca cctgcaagga tctagtgtcc tgtgcctacc aggtggcacg gggcatggaa   1800
tacttggctt ctcagaagtg tattcacaga gacttggctg ccagaaacgt cctggtgacc   1860
gaggacaatg tgatgaagat tgcggacttt ggcctggctc gagatgtgca acctggac    1920 tactacaaga gaccacaaa tggccggcta cctgtgaagt ggatggcacc agaggccctt   1980
tttgaccgag tctacaccca ccagagtgat gtttggtctt ttggtgtcct cctctgggag   2040
atctttacgc tggggggctc accgtatcct ggcatcccag tggaagagct tttcaagctg   2100
ttgaaagagg gccaccgcat ggacaagcca gccagctgca cacatgacct gtacatgatc   2160
atgcgggaat gttggcatgc ggtgccttca cagaggccca ccttcaagca gttggtagag   2220
gatttagacc gcatcctcac tgtgacatca accgacgagt acttggacct ctccgtgccg   2280
tttgagcagt actcgccagg tggccaggac acgcctagct ccagctcgtc cggagatgac   2340
tcggtgttca cccatgacct gctaccccca ggtccacccca gtaacggggg acctcggacg   2400
tga                                                                 2403
```

<210> SEQ ID NO 87
<211> LENGTH: 806
<212> TYPE: PRT
<213> ORGANISM: Homo sapiens
<220> FEATURE:
<223> OTHER INFORMATION: human FGFR3 spliceform c

<400> SEQUENCE: 87

```
Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val
            20                  25                  30

Gly Arg Ala Ala Glu Val Pro Gly Pro Glu Pro Gly Gln Gln Glu Gln
        35                  40                  45

Leu Val Phe Gly Ser Gly Asp Ala Val Glu Leu Ser Cys Pro Pro Pro
    50                  55                  60
```

Gly Gly Gly Pro Met Gly Pro Thr Val Trp Val Lys Asp Gly Thr Gly
65                  70                  75                  80

Leu Val Pro Ser Glu Arg Val Leu Val Gly Pro Gln Arg Leu Gln Val
                85                  90                  95

Leu Asn Ala Ser His Glu Asp Ser Gly Ala Tyr Ser Cys Arg Gln Arg
                100                 105                 110

Leu Thr Gln Arg Val Leu Cys His Phe Ser Val Arg Val Thr Asp Ala
            115                 120                 125

Pro Ser Ser Gly Asp Asp Glu Asp Gly Glu Asp Ala Glu Asp Thr
            130                 135                 140

Gly Val Asp Thr Gly Ala Pro Tyr Trp Thr Arg Pro Glu Arg Met Asp
145                 150                 155                 160

Lys Lys Leu Leu Ala Val Pro Ala Ala Asn Thr Val Arg Phe Arg Cys
                165                 170                 175

Pro Ala Ala Gly Asn Pro Thr Pro Ser Ile Ser Trp Leu Lys Asn Gly
                180                 185                 190

Arg Glu Phe Arg Gly Glu His Arg Ile Gly Gly Ile Lys Leu Arg His
            195                 200                 205

Gln Gln Trp Ser Leu Val Met Glu Ser Val Val Pro Ser Asp Arg Gly
210                 215                 220

Asn Tyr Thr Cys Val Val Glu Asn Lys Phe Gly Ser Ile Arg Gln Thr
225                 230                 235                 240

Tyr Thr Leu Asp Val Leu Glu Arg Ser Pro His Arg Pro Ile Leu Gln
            245                 250                 255

Ala Gly Leu Pro Ala Asn Gln Thr Ala Val Leu Gly Ser Asp Val Glu
            260                 265                 270

Phe His Cys Lys Val Tyr Ser Asp Ala Gln Pro His Ile Gln Trp Leu
            275                 280                 285

Lys His Val Glu Val Asn Gly Ser Lys Val Gly Pro Asp Gly Thr Pro
            290                 295                 300

Tyr Val Thr Val Leu Lys Thr Ala Gly Ala Asn Thr Thr Asp Lys Glu
305                 310                 315                 320

Leu Glu Val Leu Ser Leu His Asn Val Thr Phe Glu Asp Ala Gly Glu
                325                 330                 335

Tyr Thr Cys Leu Ala Gly Asn Ser Ile Gly Phe Ser His His Ser Ala
            340                 345                 350

Trp Leu Val Val Leu Pro Ala Glu Glu Leu Val Glu Ala Asp Glu
            355                 360                 365

Ala Gly Ser Val Tyr Ala Gly Ile Leu Ser Tyr Gly Val Gly Phe Phe
            370                 375                 380

Leu Phe Ile Leu Val Val Ala Ala Val Thr Leu Cys Arg Leu Arg Ser
385                 390                 395                 400

Pro Pro Lys Lys Gly Leu Gly Ser Pro Thr Val His Lys Ile Ser Arg
                405                 410                 415

Phe Pro Leu Lys Arg Gln Val Ser Leu Glu Ser Asn Ala Ser Met Ser
            420                 425                 430

Ser Asn Thr Pro Leu Val Arg Ile Ala Arg Leu Ser Ser Gly Glu Gly
            435                 440                 445

Pro Thr Leu Ala Asn Val Ser Glu Leu Glu Leu Pro Ala Asp Pro Lys
        450                 455                 460

Trp Glu Leu Ser Arg Ala Arg Leu Thr Leu Gly Lys Pro Leu Gly Glu
465                 470                 475                 480

Gly Cys Phe Gly Gln Val Val Met Ala Glu Ala Ile Gly Ile Asp Lys
            485                 490                 495

Asp Arg Ala Ala Lys Pro Val Thr Val Ala Val Lys Met Leu Lys Asp
        500                 505                 510

Asp Ala Thr Asp Lys Asp Leu Ser Asp Leu Val Ser Glu Met Glu Met
    515                 520                 525

Met Lys Met Ile Gly Lys His Lys Asn Ile Ile Asn Leu Leu Gly Ala
530                 535                 540

Cys Thr Gln Gly Gly Pro Leu Tyr Val Leu Val Glu Tyr Ala Ala Lys
545                 550                 555                 560

Gly Asn Leu Arg Glu Phe Leu Arg Ala Arg Arg Pro Pro Gly Leu Asp
                565                 570                 575

Tyr Ser Phe Asp Thr Cys Lys Pro Pro Glu Glu Gln Leu Thr Phe Lys
            580                 585                 590

Asp Leu Val Ser Cys Ala Tyr Gln Val Ala Arg Gly Met Glu Tyr Leu
        595                 600                 605

Ala Ser Gln Lys Cys Ile His Arg Asp Leu Ala Ala Arg Asn Val Leu
    610                 615                 620

Val Thr Glu Asp Asn Val Met Lys Ile Ala Asp Phe Gly Leu Ala Arg
625                 630                 635                 640

Asp Val His Asn Leu Asp Tyr Tyr Lys Lys Thr Thr Asn Gly Arg Leu
                645                 650                 655

Pro Val Lys Trp Met Ala Pro Glu Ala Leu Phe Asp Arg Val Tyr Thr
            660                 665                 670

His Gln Ser Asp Val Trp Ser Phe Gly Val Leu Leu Trp Glu Ile Phe
        675                 680                 685

Thr Leu Gly Gly Ser Pro Tyr Pro Gly Ile Pro Val Glu Glu Leu Phe
    690                 695                 700

Lys Leu Leu Lys Glu Gly His Arg Met Asp Lys Pro Ala Asn Cys Thr
705                 710                 715                 720

His Asp Leu Tyr Met Ile Met Arg Glu Cys Trp His Ala Ala Pro Ser
                725                 730                 735

Gln Arg Pro Thr Phe Lys Gln Leu Val Glu Asp Leu Asp Arg Val Leu
            740                 745                 750

Thr Val Thr Ser Thr Asp Glu Tyr Leu Asp Leu Ser Ala Pro Phe Glu
        755                 760                 765

Gln Tyr Ser Pro Gly Gly Gln Asp Thr Pro Ser Ser Ser Ser Ser Gly
    770                 775                 780

Asp Asp Ser Val Phe Ala His Asp Leu Leu Pro Pro Ala Pro Pro Ser
785                 790                 795                 800

Ser Gly Gly Ser Arg Thr
                805

<210> SEQ ID NO 88
<211> LENGTH: 800
<212> TYPE: PRT
<213> ORGANISM: Mus musculus
<220> FEATURE:
<223> OTHER INFORMATION: murine FGFR3 spliceform c

<400> SEQUENCE: 88

Met Val Val Pro Ala Cys Val Leu Val Phe Cys Val Ala Val Val Ala
1               5                   10                  15

Gly Ala Thr Ser Glu Pro Pro Gly Pro Glu Gln Arg Val Val Arg Arg
            20                  25                  30

-continued

```
Ala Ala Glu Val Pro Gly Pro Glu Pro Ser Gln Gln Glu Gln Val Ala
         35                  40                  45
Phe Gly Ser Gly Asp Thr Val Glu Leu Ser Cys His Pro Pro Gly Gly
 50                  55                  60
Ala Pro Thr Gly Pro Thr Val Trp Ala Lys Asp Gly Thr Gly Leu Val
 65                  70                  75                  80
Ala Ser His Arg Ile Leu Val Gly Pro Gln Arg Leu Gln Val Leu Asn
                 85                  90                  95
Ala Ser His Glu Asp Ala Gly Val Tyr Ser Cys Gln His Arg Leu Thr
             100                 105                 110
Arg Arg Val Leu Cys His Phe Ser Val Arg Val Thr Asp Ala Pro Ser
         115                 120                 125
Ser Gly Asp Asp Glu Asp Gly Glu Asp Val Ala Glu Asp Thr Gly Ala
 130                 135                 140
Pro Tyr Trp Thr Arg Pro Glu Arg Met Asp Lys Lys Leu Leu Ala Val
145                 150                 155                 160
Pro Ala Ala Asn Thr Val Arg Phe Arg Cys Pro Ala Ala Gly Asn Pro
                 165                 170                 175
Thr Pro Ser Ile Ser Trp Leu Lys Asn Gly Lys Glu Phe Arg Gly Glu
             180                 185                 190
His Arg Ile Gly Gly Ile Lys Leu Arg His Gln Gln Trp Ser Leu Val
         195                 200                 205
Met Glu Ser Val Val Pro Ser Asp Arg Gly Asn Tyr Thr Cys Val Val
 210                 215                 220
Glu Asn Lys Phe Gly Ser Ile Arg Gln Thr Tyr Thr Leu Asp Val Leu
225                 230                 235                 240
Glu Arg Ser Pro His Arg Pro Ile Leu Gln Ala Gly Leu Pro Ala Asn
                 245                 250                 255
Gln Thr Ala Ile Leu Gly Ser Asp Val Glu Phe His Cys Lys Val Tyr
             260                 265                 270
Ser Asp Ala Gln Pro His Ile Gln Trp Leu Lys His Val Glu Val Asn
         275                 280                 285
Gly Ser Lys Val Gly Pro Asp Gly Thr Pro Tyr Val Thr Val Leu Lys
 290                 295                 300
Thr Ala Gly Ala Asn Thr Thr Asp Lys Glu Leu Glu Val Leu Ser Leu
305                 310                 315                 320
His Asn Val Thr Phe Glu Asp Ala Gly Glu Tyr Thr Cys Leu Ala Gly
                 325                 330                 335
Asn Ser Ile Gly Phe Ser His His Ser Ala Trp Leu Val Val Leu Pro
             340                 345                 350
Ala Glu Glu Glu Leu Met Glu Thr Asp Glu Ala Gly Ser Val Tyr Ala
         355                 360                 365
Gly Val Leu Ser Tyr Gly Val Val Phe Phe Leu Phe Ile Leu Val Val
 370                 375                 380
Ala Ala Val Ile Leu Cys Arg Leu Arg Ser Pro Lys Lys Gly Leu
385                 390                 395                 400
Gly Ser Pro Thr Val His Lys Val Ser Arg Phe Pro Leu Lys Arg Gln
                 405                 410                 415
Val Ser Leu Glu Ser Asn Ser Ser Met Asn Ser Asn Thr Pro Leu Val
             420                 425                 430
Arg Ile Ala Arg Leu Ser Ser Gly Glu Gly Pro Val Leu Ala Asn Val
         435                 440                 445
Ser Glu Leu Glu Leu Pro Ala Asp Pro Lys Trp Glu Leu Ser Arg Thr
```

```
                450             455             460
Arg Leu Thr Leu Gly Lys Pro Leu Gly Glu Gly Cys Phe Gly Gln Val
465                 470             475                 480

Val Met Ala Glu Ala Ile Gly Ile Asp Lys Asp Arg Thr Ala Lys Pro
                485             490             495

Val Thr Val Ala Val Lys Met Leu Lys Asp Asp Ala Thr Asp Lys Asp
            500             505             510

Leu Ser Asp Leu Val Ser Glu Met Glu Met Met Lys Met Ile Gly Lys
        515             520             525

His Lys Asn Ile Ile Asn Leu Leu Gly Ala Cys Thr Gln Gly Gly Pro
    530             535             540

Leu Tyr Val Leu Val Glu Tyr Ala Ala Lys Gly Asn Leu Arg Glu Phe
545             550             555                 560

Leu Arg Ala Arg Arg Pro Pro Gly Met Asp Tyr Ser Phe Asp Ala Cys
                565             570             575

Arg Leu Pro Glu Glu Gln Leu Thr Cys Lys Asp Leu Val Ser Cys Ala
            580             585             590

Tyr Gln Val Ala Arg Gly Met Glu Tyr Leu Ala Ser Gln Lys Cys Ile
        595             600             605

His Arg Asp Leu Ala Ala Arg Asn Val Leu Val Thr Glu Asp Asn Val
    610             615             620

Met Lys Ile Ala Asp Phe Gly Leu Ala Arg Asp Val His Asn Leu Asp
625             630             635             640

Tyr Tyr Lys Lys Thr Thr Asn Gly Arg Leu Pro Val Lys Trp Met Ala
                645             650             655

Pro Glu Ala Leu Phe Asp Arg Val Tyr Thr His Gln Ser Asp Val Trp
            660             665             670

Ser Phe Gly Val Leu Leu Trp Glu Ile Phe Thr Leu Gly Gly Ser Pro
        675             680             685

Tyr Pro Gly Ile Pro Val Glu Glu Leu Phe Lys Leu Leu Lys Glu Gly
    690             695             700

His Arg Met Asp Lys Pro Ala Ser Cys Thr His Asp Leu Tyr Met Ile
705             710             715             720

Met Arg Glu Cys Trp His Ala Val Pro Ser Gln Arg Pro Thr Phe Lys
                725             730             735

Gln Leu Val Glu Asp Leu Asp Arg Ile Leu Thr Val Thr Ser Thr Asp
            740             745             750

Glu Tyr Leu Asp Leu Ser Val Pro Phe Glu Gln Tyr Ser Pro Gly Gly
        755             760             765

Gln Asp Thr Pro Ser Ser Ser Ser Gly Asp Asp Ser Val Phe Thr
    770             775             780

His Asp Leu Leu Pro Pro Gly Pro Pro Ser Asn Gly Gly Pro Arg Thr
785             790             795             800

<210> SEQ ID NO 89
<211> LENGTH: 820
<212> TYPE: PRT
<213> ORGANISM: Homo sapiens
<220> FEATURE:
<223> OTHER INFORMATION: human FGFR1b based on Transcript FGFR1-020
      ENST00000397108

<400> SEQUENCE: 89

Met Trp Ser Trp Lys Cys Leu Leu Phe Trp Ala Val Leu Val Thr Ala
1               5                   10                  15
```

-continued

```
Thr Leu Cys Thr Ala Arg Pro Ser Pro Thr Leu Pro Glu Gln Ala Gln
         20                  25                  30

Pro Trp Gly Ala Pro Val Glu Val Ser Phe Leu Val His Pro Gly
     35                  40                  45

Asp Leu Leu Gln Leu Arg Cys Arg Leu Arg Asp Val Gln Ser Ile
 50                  55                  60

Asn Trp Leu Arg Asp Gly Val Gln Leu Ala Glu Ser Asn Arg Thr Arg
 65                  70                  75                  80

Ile Thr Gly Glu Glu Val Glu Val Gln Asp Ser Val Pro Ala Asp Ser
                 85                  90                  95

Gly Leu Tyr Ala Cys Val Thr Ser Ser Pro Ser Gly Ser Asp Thr Thr
                100                 105                 110

Tyr Phe Ser Val Asn Val Ser Asp Ala Leu Pro Ser Ser Glu Asp Asp
         115                 120                 125

Asp Asp Asp Asp Asp Ser Ser Ser Glu Glu Lys Glu Thr Asp Asn Thr
130                 135                 140

Lys Pro Asn Pro Val Ala Pro Tyr Trp Thr Ser Pro Glu Lys Met Glu
145                 150                 155                 160

Lys Lys Leu His Ala Val Pro Ala Ala Lys Thr Val Lys Phe Lys Cys
                 165                 170                 175

Pro Ser Ser Gly Thr Pro Asn Pro Thr Leu Arg Trp Leu Lys Asn Gly
             180                 185                 190

Lys Glu Phe Lys Pro Asp His Arg Ile Gly Gly Tyr Lys Val Arg Tyr
         195                 200                 205

Ala Thr Trp Ser Ile Ile Met Asp Ser Val Val Pro Ser Asp Lys Gly
 210                 215                 220

Asn Tyr Thr Cys Ile Val Glu Asn Glu Tyr Gly Ser Ile Asn His Thr
225                 230                 235                 240

Tyr Gln Leu Asp Val Val Glu Arg Ser Pro His Arg Pro Ile Leu Gln
                 245                 250                 255

Ala Gly Leu Pro Ala Asn Lys Thr Val Ala Leu Gly Ser Asn Val Glu
             260                 265                 270

Phe Met Cys Lys Val Tyr Ser Asp Pro Gln Pro His Ile Gln Trp Leu
         275                 280                 285

Lys His Ile Glu Val Asn Gly Ser Lys Ile Gly Pro Asp Asn Leu Pro
 290                 295                 300

Tyr Val Gln Ile Leu Lys Thr Ala Gly Val Asn Thr Thr Asp Lys Glu
305                 310                 315                 320

Met Glu Val Leu His Leu Arg Asn Val Ser Phe Glu Asp Ala Gly Glu
                 325                 330                 335

Tyr Thr Cys Leu Ala Gly Asn Ser Ile Gly Leu Ser His His Ser Ala
             340                 345                 350

Trp Leu Thr Val Leu Glu Ala Leu Glu Glu Arg Pro Ala Val Met Thr
         355                 360                 365

Ser Pro Leu Tyr Leu Glu Ile Ile Ile Tyr Cys Thr Gly Ala Phe Leu
 370                 375                 380

Ile Ser Cys Met Val Gly Ser Val Ile Val Tyr Lys Met Lys Ser Gly
385                 390                 395                 400

Thr Lys Lys Ser Asp Phe His Ser Gln Met Ala Val His Lys Leu Ala
                 405                 410                 415

Lys Ser Ile Pro Leu Arg Arg Gln Val Thr Val Ser Ala Asp Ser Ser
             420                 425                 430

Ala Ser Met Asn Ser Gly Val Leu Leu Val Arg Pro Ser Arg Leu Ser
```

```
                    435                 440                 445
Ser Ser Gly Thr Pro Met Leu Ala Gly Val Ser Glu Tyr Glu Leu Pro
450                     455                 460

Glu Asp Pro Arg Trp Glu Leu Pro Arg Asp Arg Leu Val Leu Gly Lys
465                 470                  475                 480

Pro Leu Gly Glu Gly Cys Phe Gly Gln Val Leu Ala Glu Ala Ile
                485                 490                 495

Gly Leu Asp Lys Asp Lys Pro Asn Arg Val Thr Lys Val Ala Val Lys
                500                 505                 510

Met Leu Lys Ser Asp Ala Thr Glu Lys Asp Leu Ser Asp Leu Ile Ser
            515                 520                 525

Glu Met Glu Met Met Lys Met Ile Gly Lys His Lys Asn Ile Ile Asn
530                     535                 540

Leu Leu Gly Ala Cys Thr Gln Asp Gly Pro Leu Tyr Val Ile Val Glu
545                     550                 555                 560

Tyr Ala Ser Lys Gly Asn Leu Arg Glu Tyr Leu Gln Ala Arg Arg Pro
                565                 570                 575

Pro Gly Leu Glu Tyr Cys Tyr Asn Pro Ser His Asn Pro Glu Glu Gln
                580                 585                 590

Leu Ser Ser Lys Asp Leu Val Ser Cys Ala Tyr Gln Val Ala Arg Gly
            595                 600                 605

Met Glu Tyr Leu Ala Ser Lys Lys Cys Ile His Arg Asp Leu Ala Ala
610                     615                 620

Arg Asn Val Leu Val Thr Glu Asp Asn Val Met Lys Ile Ala Asp Phe
625                     630                 635                 640

Gly Leu Ala Arg Asp Ile His His Ile Asp Tyr Tyr Lys Lys Thr Thr
                645                 650                 655

Asn Gly Arg Leu Pro Val Lys Trp Met Ala Pro Glu Ala Leu Phe Asp
                660                 665                 670

Arg Ile Tyr Thr His Gln Ser Asp Val Trp Ser Phe Gly Val Leu Leu
            675                 680                 685

Trp Glu Ile Phe Thr Leu Gly Gly Ser Pro Tyr Pro Gly Val Pro Val
690                     695                 700

Glu Glu Leu Phe Lys Leu Leu Lys Glu Gly His Arg Met Asp Lys Pro
705                     710                 715                 720

Ser Asn Cys Thr Asn Glu Leu Tyr Met Met Met Arg Asp Cys Trp His
                725                 730                 735

Ala Val Pro Ser Gln Arg Pro Thr Phe Lys Gln Leu Val Glu Asp Leu
                740                 745                 750

Asp Arg Ile Val Ala Leu Thr Ser Asn Gln Glu Tyr Leu Asp Leu Ser
            755                 760                 765

Met Pro Leu Asp Gln Tyr Ser Pro Ser Phe Pro Asp Thr Arg Ser Ser
            770                 775                 780

Thr Cys Ser Ser Gly Glu Asp Ser Val Phe Ser His Glu Pro Leu Pro
785                     790                 795                 800

Glu Glu Pro Cys Leu Pro Arg His Pro Ala Gln Leu Ala Asn Gly Gly
                805                 810                 815

Leu Lys Arg Arg
            820

<210> SEQ ID NO 90
<211> LENGTH: 733
<212> TYPE: PRT
<213> ORGANISM: Homo sapiens
```

<220> FEATURE:
<223> OTHER INFORMATION: human FGFR1c based on transcript FGFR1-011
      ENST00000397103

<400> SEQUENCE: 90

```
Met Trp Ser Trp Lys Cys Leu Leu Phe Trp Ala Val Leu Val Thr Ala
1               5                   10                  15

Thr Leu Cys Thr Ala Arg Pro Ser Pro Thr Leu Pro Glu Gln Asp Ala
            20                  25                  30

Leu Pro Ser Ser Glu Asp Asp Asp Asp Asp Asp Ser Ser Ser Glu Glu
        35                  40                  45

Glu Lys Glu Thr Asp Asn Thr Lys Pro Asn Pro Val Ala Pro Tyr Trp
    50                  55                  60

Thr Ser Pro Glu Lys Met Glu Lys Lys Leu His Ala Val Pro Ala Ala
65                  70                  75                  80

Lys Thr Val Lys Phe Lys Cys Pro Ser Ser Gly Thr Pro Asn Pro Thr
                85                  90                  95

Leu Arg Trp Leu Lys Asn Gly Lys Glu Phe Lys Pro Asp His Arg Ile
            100                 105                 110

Gly Gly Tyr Lys Val Arg Tyr Ala Thr Trp Ser Ile Ile Met Asp Ser
        115                 120                 125

Val Val Pro Ser Asp Lys Gly Asn Tyr Thr Cys Ile Val Glu Asn Glu
    130                 135                 140

Tyr Gly Ser Ile Asn His Thr Tyr Gln Leu Asp Val Val Glu Arg Ser
145                 150                 155                 160

Pro His Arg Pro Ile Leu Gln Ala Gly Leu Pro Ala Asn Lys Thr Val
                165                 170                 175

Ala Leu Gly Ser Asn Val Glu Phe Met Cys Lys Val Tyr Ser Asp Pro
            180                 185                 190

Gln Pro His Ile Gln Trp Leu Lys His Ile Glu Val Asn Gly Ser Lys
        195                 200                 205

Ile Gly Pro Asp Asn Leu Pro Tyr Val Gln Ile Leu Lys His Ser Gly
    210                 215                 220

Ile Asn Ser Ser Asp Ala Glu Val Leu Thr Leu Phe Asn Val Thr Glu
225                 230                 235                 240

Ala Gln Ser Gly Glu Tyr Val Cys Lys Val Ser Asn Tyr Ile Gly Glu
                245                 250                 255

Ala Asn Gln Ser Ala Trp Leu Thr Val Thr Arg Pro Val Ala Lys Ala
            260                 265                 270

Leu Glu Glu Arg Pro Ala Val Met Thr Ser Pro Leu Tyr Leu Glu Ile
        275                 280                 285

Ile Ile Tyr Cys Thr Gly Ala Phe Leu Ile Ser Cys Met Val Gly Ser
    290                 295                 300

Val Ile Val Tyr Lys Met Lys Ser Gly Thr Lys Lys Ser Asp Phe His
305                 310                 315                 320

Ser Gln Met Ala Val His Lys Leu Ala Lys Ser Ile Pro Leu Arg Arg
                325                 330                 335

Gln Val Thr Val Ser Ala Asp Ser Ser Ala Ser Met Asn Ser Gly Val
            340                 345                 350

Leu Leu Val Arg Pro Ser Arg Leu Ser Ser Ser Gly Thr Pro Met Leu
        355                 360                 365

Ala Gly Val Ser Glu Tyr Glu Leu Pro Glu Asp Pro Arg Trp Glu Leu
    370                 375                 380

Pro Arg Asp Arg Leu Val Leu Gly Lys Pro Leu Gly Glu Gly Cys Phe
```

```
                385                 390                 395                 400
        Gly Gln Val Val Leu Ala Glu Ala Ile Gly Leu Asp Lys Asp Lys Pro
                        405                 410                 415

Asn Arg Val Thr Lys Val Ala Val Lys Met Leu Lys Ser Asp Ala Thr
                        420                 425                 430

Glu Lys Asp Leu Ser Asp Leu Ile Ser Glu Met Glu Met Met Lys Met
                        435                 440                 445

Ile Gly Lys His Lys Asn Ile Ile Asn Leu Leu Gly Ala Cys Thr Gln
                        450                 455                 460

Asp Gly Pro Leu Tyr Val Ile Val Glu Tyr Ala Ser Lys Gly Asn Leu
        465                 470                 475                 480

Arg Glu Tyr Leu Gln Ala Arg Arg Pro Pro Gly Leu Glu Tyr Cys Tyr
                        485                 490                 495

Asn Pro Ser His Asn Pro Glu Glu Gln Leu Ser Ser Lys Asp Leu Val
                        500                 505                 510

Ser Cys Ala Tyr Gln Val Ala Arg Gly Met Glu Tyr Leu Ala Ser Lys
                        515                 520                 525

Lys Cys Ile His Arg Asp Leu Ala Ala Arg Asn Val Leu Val Thr Glu
                        530                 535                 540

Asp Asn Val Met Lys Ile Ala Asp Phe Gly Leu Ala Arg Asp Ile His
        545                 550                 555                 560

His Ile Asp Tyr Tyr Lys Lys Thr Thr Asn Gly Arg Leu Pro Val Lys
                        565                 570                 575

Trp Met Ala Pro Glu Ala Leu Phe Asp Arg Ile Tyr Thr His Gln Ser
                        580                 585                 590

Asp Val Trp Ser Phe Gly Val Leu Leu Trp Glu Ile Phe Thr Leu Gly
                        595                 600                 605

Gly Ser Pro Tyr Pro Gly Val Pro Val Glu Glu Leu Phe Lys Leu Leu
                        610                 615                 620

Lys Glu Gly His Arg Met Asp Lys Pro Ser Asn Cys Thr Asn Glu Leu
        625                 630                 635                 640

Tyr Met Met Met Arg Asp Cys Trp His Ala Val Pro Ser Gln Arg Pro
                        645                 650                 655

Thr Phe Lys Gln Leu Val Glu Asp Leu Asp Arg Ile Val Ala Leu Thr
                        660                 665                 670

Ser Asn Gln Glu Tyr Leu Asp Leu Ser Met Pro Leu Asp Gln Tyr Ser
                        675                 680                 685

Pro Ser Phe Pro Asp Thr Arg Ser Ser Thr Cys Ser Ser Gly Glu Asp
                        690                 695                 700

Ser Val Phe Ser His Glu Pro Leu Pro Glu Glu Pro Cys Leu Pro Arg
        705                 710                 715                 720

His Pro Ala Gln Leu Ala Asn Gly Gly Leu Lys Arg Arg
                        725                 730

<210> SEQ ID NO 91
<211> LENGTH: 821
<212> TYPE: PRT
<213> ORGANISM: Homo sapiens
<220> FEATURE:
<223> OTHER INFORMATION: human FGFR2b based on transcript FGFR2-201
      ENST00000351936

<400> SEQUENCE: 91

Met Val Ser Trp Gly Arg Phe Ile Cys Leu Val Val Val Thr Met Ala
1               5                   10                  15
```

-continued

Thr Leu Ser Leu Ala Arg Pro Ser Phe Ser Leu Val Glu Asp Thr Thr
            20                  25                  30

Leu Glu Pro Glu Glu Pro Pro Thr Lys Tyr Gln Ile Ser Gln Pro Glu
            35                  40                  45

Val Tyr Val Ala Ala Pro Gly Glu Ser Leu Glu Val Arg Cys Leu Leu
        50                  55                  60

Lys Asp Ala Ala Val Ile Ser Trp Thr Lys Asp Gly Val His Leu Gly
65                  70                  75                  80

Pro Asn Asn Arg Thr Val Leu Ile Gly Glu Tyr Leu Gln Ile Lys Gly
                85                  90                  95

Ala Thr Pro Arg Asp Ser Gly Leu Tyr Ala Cys Thr Ala Ser Arg Thr
            100                 105                 110

Val Asp Ser Glu Thr Trp Tyr Phe Met Val Asn Val Thr Asp Ala Ile
        115                 120                 125

Ser Ser Gly Asp Asp Glu Asp Asp Thr Asp Gly Ala Glu Asp Phe Val
    130                 135                 140

Ser Glu Asn Ser Asn Asn Lys Arg Ala Pro Tyr Trp Thr Asn Thr Glu
145                 150                 155                 160

Lys Met Glu Lys Arg Leu His Ala Val Pro Ala Ala Asn Thr Val Lys
                165                 170                 175

Phe Arg Cys Pro Ala Gly Gly Asn Pro Met Pro Thr Met Arg Trp Leu
            180                 185                 190

Lys Asn Gly Lys Glu Phe Lys Gln Glu His Arg Ile Gly Gly Tyr Lys
        195                 200                 205

Val Arg Asn Gln His Trp Ser Leu Ile Met Glu Ser Val Val Pro Ser
    210                 215                 220

Asp Lys Gly Asn Tyr Thr Cys Val Val Glu Asn Glu Tyr Gly Ser Ile
225                 230                 235                 240

Asn His Thr Tyr His Leu Asp Val Val Glu Arg Ser Pro His Arg Pro
                245                 250                 255

Ile Leu Gln Ala Gly Leu Pro Ala Asn Ala Ser Thr Val Val Gly Gly
            260                 265                 270

Asp Val Glu Phe Val Cys Lys Val Tyr Ser Asp Ala Gln Pro His Ile
        275                 280                 285

Gln Trp Ile Lys His Val Glu Lys Asn Gly Ser Lys Tyr Gly Pro Asp
    290                 295                 300

Gly Leu Pro Tyr Leu Lys Val Leu Lys Val Phe Ala Ala Gly Val Asn
305                 310                 315                 320

Thr Thr Asp Lys Glu Ile Glu Val Leu Tyr Ile Arg Asn Val Thr Phe
                325                 330                 335

Glu Asp Ala Gly Glu Tyr Thr Cys Leu Ala Gly Asn Ser Ile Gly Ile
            340                 345                 350

Ser Phe His Ser Ala Trp Leu Thr Val Leu Pro Ala Pro Gly Arg Glu
        355                 360                 365

Lys Glu Ile Thr Ala Ser Pro Asp Tyr Leu Glu Ile Ala Ile Tyr Cys
    370                 375                 380

Ile Gly Val Phe Leu Ile Ala Cys Met Val Val Thr Val Ile Leu Cys
385                 390                 395                 400

Arg Met Lys Asn Thr Thr Lys Lys Pro Asp Phe Ser Ser Gln Pro Ala
                405                 410                 415

Val His Lys Leu Thr Lys Arg Ile Pro Leu Arg Arg Gln Val Ser Ala
            420                 425                 430

Glu Ser Ser Ser Ser Met Asn Ser Asn Thr Pro Leu Val Arg Ile Thr

```
                    435                 440                 445
Thr Arg Leu Ser Ser Thr Ala Asp Thr Pro Met Leu Ala Gly Val Ser
450                 455                 460

Glu Tyr Glu Leu Pro Glu Asp Pro Lys Trp Glu Phe Pro Arg Asp Lys
465                 470                 475                 480

Leu Thr Leu Gly Lys Pro Leu Gly Glu Gly Cys Phe Gly Gln Val Val
                485                 490                 495

Met Ala Glu Ala Val Gly Ile Asp Lys Asp Lys Pro Lys Glu Ala Val
            500                 505                 510

Thr Val Ala Val Lys Met Leu Lys Asp Asp Ala Thr Glu Lys Asp Leu
515                 520                 525

Ser Asp Leu Val Ser Glu Met Glu Met Met Lys Met Ile Gly Lys His
530                 535                 540

Lys Asn Ile Ile Asn Leu Leu Gly Ala Cys Thr Gln Asp Gly Pro Leu
545                 550                 555                 560

Tyr Val Ile Val Glu Tyr Ala Ser Lys Gly Asn Leu Arg Glu Tyr Leu
                565                 570                 575

Arg Ala Arg Arg Pro Pro Gly Met Glu Tyr Ser Tyr Asp Ile Asn Arg
            580                 585                 590

Val Pro Glu Glu Gln Met Thr Phe Lys Asp Leu Val Ser Cys Thr Tyr
595                 600                 605

Gln Leu Ala Arg Gly Met Glu Tyr Leu Ala Ser Gln Lys Cys Ile His
610                 615                 620

Arg Asp Leu Ala Ala Arg Asn Val Leu Val Thr Glu Asn Asn Val Met
625                 630                 635                 640

Lys Ile Ala Asp Phe Gly Leu Ala Arg Asp Ile Asn Asn Ile Asp Tyr
                645                 650                 655

Tyr Lys Lys Thr Thr Asn Gly Arg Leu Pro Val Lys Trp Met Ala Pro
            660                 665                 670

Glu Ala Leu Phe Asp Arg Val Tyr Thr His Gln Ser Asp Val Trp Ser
675                 680                 685

Phe Gly Val Leu Met Trp Glu Ile Phe Thr Leu Gly Gly Ser Pro Tyr
690                 695                 700

Pro Gly Ile Pro Val Glu Glu Leu Phe Lys Leu Leu Lys Glu Gly His
705                 710                 715                 720

Arg Met Asp Lys Pro Ala Asn Cys Thr Asn Glu Leu Tyr Met Met Met
                725                 730                 735

Arg Asp Cys Trp His Ala Val Pro Ser Gln Arg Pro Thr Phe Lys Gln
            740                 745                 750

Leu Val Glu Asp Leu Asp Arg Ile Leu Thr Leu Thr Thr Asn Glu Glu
755                 760                 765

Tyr Leu Asp Leu Ser Gln Pro Leu Glu Gln Tyr Ser Pro Ser Tyr Pro
770                 775                 780

Asp Thr Arg Ser Ser Cys Ser Ser Gly Asp Asp Ser Val Phe Ser Pro
785                 790                 795                 800

Asp Pro Met Pro Tyr Glu Pro Cys Leu Pro Gln Tyr Pro His Ile Asn
                805                 810                 815

Gly Ser Val Lys Thr
            820

<210> SEQ ID NO 92
<211> LENGTH: 822
<212> TYPE: PRT
<213> ORGANISM: Homo sapiens
```

<220> FEATURE:
<223> OTHER INFORMATION: human FGFR2c based on transcript FGFR2-010
      ENST00000457416

<400> SEQUENCE: 92

```
Met Val Ser Trp Gly Arg Phe Ile Cys Leu Val Val Thr Met Ala
1               5                   10                  15

Thr Leu Ser Leu Ala Arg Pro Ser Phe Ser Leu Val Glu Asp Thr Thr
            20                  25                  30

Leu Glu Pro Glu Glu Pro Thr Lys Tyr Gln Ile Ser Gln Pro Glu
        35                  40                  45

Val Tyr Val Ala Ala Pro Gly Glu Ser Leu Glu Val Arg Cys Leu Leu
50                  55                  60

Lys Asp Ala Ala Val Ile Ser Trp Thr Lys Asp Gly Val His Leu Gly
65                  70                  75                  80

Pro Asn Asn Arg Thr Val Leu Ile Gly Glu Tyr Leu Gln Ile Lys Gly
                85                  90                  95

Ala Thr Pro Arg Asp Ser Gly Leu Tyr Ala Cys Thr Ala Ser Arg Thr
            100                 105                 110

Val Asp Ser Glu Thr Trp Tyr Phe Met Val Asn Val Thr Asp Ala Ile
        115                 120                 125

Ser Ser Gly Asp Asp Glu Asp Asp Thr Asp Gly Ala Glu Asp Phe Val
130                 135                 140

Ser Glu Asn Ser Asn Asn Lys Arg Ala Pro Tyr Trp Thr Asn Thr Glu
145                 150                 155                 160

Lys Met Glu Lys Arg Leu His Ala Val Pro Ala Ala Asn Thr Val Lys
                165                 170                 175

Phe Arg Cys Pro Ala Gly Gly Asn Pro Met Pro Thr Met Arg Trp Leu
            180                 185                 190

Lys Asn Gly Lys Glu Phe Lys Gln Glu His Arg Ile Gly Gly Tyr Lys
        195                 200                 205

Val Arg Asn Gln His Trp Ser Leu Ile Met Glu Ser Val Val Pro Ser
210                 215                 220

Asp Lys Gly Asn Tyr Thr Cys Val Val Glu Asn Glu Tyr Gly Ser Ile
225                 230                 235                 240

Asn His Thr Tyr His Leu Asp Val Val Glu Arg Ser Pro His Arg Pro
                245                 250                 255

Ile Leu Gln Ala Gly Leu Pro Ala Asn Ala Ser Thr Val Val Gly Gly
            260                 265                 270

Asp Val Glu Phe Val Cys Lys Val Tyr Ser Asp Ala Gln Pro His Ile
        275                 280                 285

Gln Trp Ile Lys His Val Glu Lys Asn Gly Ser Lys Tyr Gly Pro Asp
290                 295                 300

Gly Leu Pro Tyr Leu Lys Val Leu Lys His Ser Gly Ile Asn Ser Ser
305                 310                 315                 320

Asn Ala Glu Val Leu Ala Leu Phe Asn Val Thr Glu Ala Asp Ala Gly
                325                 330                 335

Glu Tyr Ile Cys Lys Val Ser Asn Tyr Ile Gly Gln Ala Asn Gln Ser
            340                 345                 350

Ala Trp Leu Thr Val Leu Pro Lys Gln Gln Ala Pro Gly Arg Glu Lys
        355                 360                 365

Glu Ile Thr Ala Ser Pro Asp Tyr Leu Glu Ile Ala Ile Tyr Cys Ile
370                 375                 380

Gly Val Phe Leu Ile Ala Cys Met Val Val Thr Val Ile Leu Cys Arg
```

-continued

```
            385                 390                 395                 400
Met Lys Asn Thr Thr Lys Lys Pro Asp Phe Ser Ser Gln Pro Ala Val
                        405                 410                 415

His Lys Leu Thr Lys Arg Ile Pro Leu Arg Arg Gln Val Thr Val Ser
                420                 425                 430

Ala Glu Ser Ser Ser Met Asn Ser Asn Thr Pro Leu Val Arg Ile
            435                 440                 445

Thr Thr Arg Leu Ser Ser Thr Ala Asp Thr Pro Met Leu Ala Gly Val
        450                 455                 460

Ser Glu Tyr Glu Leu Pro Glu Asp Pro Lys Trp Glu Phe Pro Arg Asp
465                 470                 475                 480

Lys Leu Thr Leu Gly Lys Pro Leu Gly Glu Gly Cys Phe Gly Gln Val
                485                 490                 495

Val Met Ala Glu Ala Val Gly Ile Asp Lys Asp Lys Pro Lys Glu Ala
                500                 505                 510

Val Thr Val Ala Val Lys Met Leu Lys Asp Asp Ala Thr Glu Lys Asp
            515                 520                 525

Leu Ser Asp Leu Val Ser Glu Met Glu Met Met Lys Met Ile Gly Lys
        530                 535                 540

His Lys Asn Ile Ile Asn Leu Leu Gly Ala Cys Thr Gln Asp Gly Pro
545                 550                 555                 560

Leu Tyr Val Ile Val Glu Tyr Ala Ser Lys Gly Asn Leu Arg Glu Tyr
                565                 570                 575

Leu Arg Ala Arg Arg Pro Pro Gly Met Glu Tyr Ser Tyr Asp Ile Asn
                580                 585                 590

Arg Val Pro Glu Glu Gln Met Thr Phe Lys Asp Leu Val Ser Cys Thr
            595                 600                 605

Tyr Gln Leu Ala Arg Gly Met Glu Tyr Leu Ala Ser Gln Lys Cys Ile
        610                 615                 620

His Arg Asp Leu Ala Ala Arg Asn Val Leu Val Thr Glu Asn Asn Val
625                 630                 635                 640

Met Lys Ile Ala Asp Phe Gly Leu Ala Arg Asp Ile Asn Asn Ile Asp
                645                 650                 655

Tyr Tyr Lys Lys Thr Thr Asn Gly Arg Leu Pro Val Lys Trp Met Ala
                660                 665                 670

Pro Glu Ala Leu Phe Asp Arg Val Tyr Thr His Gln Ser Asp Val Trp
            675                 680                 685

Ser Phe Gly Val Leu Met Trp Glu Ile Phe Thr Leu Gly Gly Ser Pro
        690                 695                 700

Tyr Pro Gly Ile Pro Val Glu Glu Leu Phe Lys Leu Leu Lys Glu Gly
705                 710                 715                 720

His Arg Met Asp Lys Pro Ala Asn Cys Thr Asn Glu Leu Tyr Met Met
                725                 730                 735

Met Arg Asp Cys Trp His Ala Val Pro Ser Gln Arg Pro Thr Phe Lys
                740                 745                 750

Gln Leu Val Glu Asp Leu Asp Arg Ile Leu Thr Leu Thr Thr Asn Glu
            755                 760                 765

Glu Tyr Leu Asp Leu Ser Gln Pro Leu Glu Gln Tyr Ser Pro Ser Tyr
        770                 775                 780

Pro Asp Thr Arg Ser Ser Cys Ser Ser Gly Asp Asp Ser Val Phe Ser
785                 790                 795                 800

Pro Asp Pro Met Pro Tyr Glu Pro Cys Leu Pro Gln Tyr Pro His Ile
                805                 810                 815
```

Asn Gly Ser Val Lys Thr
            820

<210> SEQ ID NO 93
<211> LENGTH: 808
<212> TYPE: PRT
<213> ORGANISM: Homo sapiens
<220> FEATURE:
<223> OTHER INFORMATION: human FGFR3b based on transcript FGFR3-201
      ENST00000340107

<400> SEQUENCE: 93

Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val
                20                  25                  30

Gly Arg Ala Ala Glu Val Pro Gly Pro Glu Pro Gly Gln Gln Glu Gln
            35                  40                  45

Leu Val Phe Gly Ser Gly Asp Ala Val Glu Leu Ser Cys Pro Pro Pro
    50                  55                  60

Gly Gly Gly Pro Met Gly Pro Thr Val Trp Val Lys Asp Gly Thr Gly
65                  70                  75                  80

Leu Val Pro Ser Glu Arg Val Leu Val Gly Pro Gln Arg Leu Gln Val
                85                  90                  95

Leu Asn Ala Ser His Glu Asp Ser Gly Ala Tyr Ser Cys Arg Gln Arg
            100                 105                 110

Leu Thr Gln Arg Val Leu Cys His Phe Ser Val Arg Val Thr Asp Ala
        115                 120                 125

Pro Ser Ser Gly Asp Asp Glu Asp Gly Glu Asp Glu Ala Glu Asp Thr
    130                 135                 140

Gly Val Asp Thr Gly Ala Pro Tyr Trp Thr Arg Pro Glu Arg Met Asp
145                 150                 155                 160

Lys Lys Leu Leu Ala Val Pro Ala Ala Asn Thr Val Arg Phe Arg Cys
                165                 170                 175

Pro Ala Ala Gly Asn Pro Thr Pro Ser Ile Ser Trp Leu Lys Asn Gly
            180                 185                 190

Arg Glu Phe Arg Gly Glu His Arg Ile Gly Gly Ile Lys Leu Arg His
        195                 200                 205

Gln Gln Trp Ser Leu Val Met Glu Ser Val Val Pro Ser Asp Arg Gly
    210                 215                 220

Asn Tyr Thr Cys Val Val Glu Asn Lys Phe Gly Ser Ile Arg Gln Thr
225                 230                 235                 240

Tyr Thr Leu Asp Val Leu Glu Arg Ser Pro His Arg Pro Ile Leu Gln
                245                 250                 255

Ala Gly Leu Pro Ala Asn Gln Thr Ala Val Leu Gly Ser Asp Val Glu
            260                 265                 270

Phe His Cys Lys Val Tyr Ser Asp Ala Gln Pro His Ile Gln Trp Leu
        275                 280                 285

Lys His Val Glu Val Asn Gly Ser Lys Val Gly Pro Asp Gly Thr Pro
    290                 295                 300

Tyr Val Thr Val Leu Lys Ser Trp Ile Ser Glu Ser Val Glu Ala Asp
305                 310                 315                 320

Val Arg Leu Arg Leu Ala Asn Val Ser Glu Arg Asp Gly Gly Glu Tyr
                325                 330                 335

Leu Cys Arg Ala Thr Asn Phe Ile Gly Val Ala Glu Lys Ala Phe Trp

```
                340             345             350
Leu Ser Val His Gly Pro Arg Ala Glu Glu Leu Val Glu Ala
        355             360             365
Asp Glu Ala Gly Ser Val Tyr Ala Gly Ile Leu Ser Tyr Gly Val Gly
    370             375             380
Phe Phe Leu Phe Ile Leu Val Val Ala Val Thr Leu Cys Arg Leu
385             390             395             400
Arg Ser Pro Pro Lys Lys Gly Leu Gly Ser Pro Thr Val His Lys Ile
                405             410             415
Ser Arg Phe Pro Leu Lys Arg Gln Val Ser Leu Glu Ser Asn Ala Ser
                420             425             430
Met Ser Ser Asn Thr Pro Leu Val Arg Ile Ala Arg Leu Ser Ser Gly
        435             440             445
Glu Gly Pro Thr Leu Ala Asn Val Ser Glu Leu Glu Leu Pro Ala Asp
    450             455             460
Pro Lys Trp Glu Leu Ser Arg Ala Arg Leu Thr Leu Gly Lys Pro Leu
465             470             475             480
Gly Glu Gly Cys Phe Gly Gln Val Val Met Ala Glu Ala Ile Gly Ile
                485             490             495
Asp Lys Asp Arg Ala Ala Lys Pro Val Thr Val Ala Val Lys Met Leu
                500             505             510
Lys Asp Asp Ala Thr Asp Lys Asp Leu Ser Asp Leu Val Ser Glu Met
                515             520             525
Glu Met Met Lys Met Ile Gly Lys His Lys Asn Ile Ile Asn Leu Leu
        530             535             540
Gly Ala Cys Thr Gln Gly Gly Pro Leu Tyr Val Leu Val Glu Tyr Ala
545             550             555             560
Ala Lys Gly Asn Leu Arg Glu Phe Leu Arg Ala Arg Arg Pro Pro Gly
                565             570             575
Leu Asp Tyr Ser Phe Asp Thr Cys Lys Pro Pro Glu Glu Gln Leu Thr
                580             585             590
Phe Lys Asp Leu Val Ser Cys Ala Tyr Gln Val Ala Arg Gly Met Glu
        595             600             605
Tyr Leu Ala Ser Gln Lys Cys Ile His Arg Asp Leu Ala Ala Arg Asn
    610             615             620
Val Leu Val Thr Glu Asp Asn Val Met Lys Ile Ala Asp Phe Gly Leu
625             630             635             640
Ala Arg Asp Val His Asn Leu Asp Tyr Tyr Lys Lys Thr Thr Asn Gly
                645             650             655
Arg Leu Pro Val Lys Trp Met Ala Pro Glu Ala Leu Phe Asp Arg Val
                660             665             670
Tyr Thr His Gln Ser Asp Val Trp Ser Phe Gly Val Leu Leu Trp Glu
        675             680             685
Ile Phe Thr Leu Gly Gly Ser Pro Tyr Pro Gly Ile Pro Val Glu Glu
    690             695             700
Leu Phe Lys Leu Leu Lys Glu Gly His Arg Met Asp Lys Pro Ala Asn
705             710             715             720
Cys Thr His Asp Leu Tyr Met Ile Met Arg Glu Cys Trp His Ala Ala
                725             730             735
Pro Ser Gln Arg Pro Thr Phe Lys Gln Leu Val Glu Asp Leu Asp Arg
                740             745             750
Val Leu Thr Val Thr Ser Thr Asp Glu Tyr Leu Asp Leu Ser Ala Pro
        755             760             765
```

Phe Glu Gln Tyr Ser Pro Gly Gly Gln Asp Thr Pro Ser Ser Ser
            770                 775                 780

Ser Gly Asp Asp Ser Val Phe Ala His Asp Leu Leu Pro Pro Ala Pro
785                 790                 795                 800

Pro Ser Ser Gly Gly Ser Arg Thr
                805

<210> SEQ ID NO 94
<211> LENGTH: 806
<212> TYPE: PRT
<213> ORGANISM: Homo sapiens
<220> FEATURE:
<223> OTHER INFORMATION: human FGFR3c based on transcript FGFR3-203:
      ENST00000440486

<400> SEQUENCE: 94

Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val
            20                  25                  30

Gly Arg Ala Ala Glu Val Pro Gly Pro Glu Pro Gly Gln Gln Glu Gln
        35                  40                  45

Leu Val Phe Gly Ser Gly Asp Ala Val Glu Leu Ser Cys Pro Pro Pro
    50                  55                  60

Gly Gly Gly Pro Met Gly Pro Thr Val Trp Val Lys Asp Gly Thr Gly
65                  70                  75                  80

Leu Val Pro Ser Glu Arg Val Leu Val Gly Pro Gln Arg Leu Gln Val
                85                  90                  95

Leu Asn Ala Ser His Glu Asp Ser Gly Ala Tyr Ser Cys Arg Gln Arg
            100                 105                 110

Leu Thr Gln Arg Val Leu Cys His Phe Ser Val Arg Val Thr Asp Ala
        115                 120                 125

Pro Ser Ser Gly Asp Asp Glu Asp Gly Glu Asp Glu Ala Glu Asp Thr
    130                 135                 140

Gly Val Asp Thr Gly Ala Pro Tyr Trp Thr Arg Pro Glu Arg Met Asp
145                 150                 155                 160

Lys Lys Leu Leu Ala Val Pro Ala Ala Asn Thr Val Arg Phe Arg Cys
                165                 170                 175

Pro Ala Ala Gly Asn Pro Thr Pro Ser Ile Ser Trp Leu Lys Asn Gly
            180                 185                 190

Arg Glu Phe Arg Gly Glu His Arg Ile Gly Gly Ile Lys Leu Arg His
        195                 200                 205

Gln Gln Trp Ser Leu Val Met Glu Ser Val Val Pro Ser Asp Arg Gly
    210                 215                 220

Asn Tyr Thr Cys Val Val Glu Asn Lys Phe Gly Ser Ile Arg Gln Thr
225                 230                 235                 240

Tyr Thr Leu Asp Val Leu Glu Arg Ser Pro His Arg Pro Ile Leu Gln
                245                 250                 255

Ala Gly Leu Pro Ala Asn Gln Thr Ala Val Leu Gly Ser Asp Val Glu
            260                 265                 270

Phe His Cys Lys Val Tyr Ser Asp Ala Gln Pro His Ile Gln Trp Leu
        275                 280                 285

Lys His Val Glu Val Asn Gly Ser Lys Val Gly Pro Asp Gly Thr Pro
    290                 295                 300

Tyr Val Thr Val Leu Lys Thr Ala Gly Ala Asn Thr Thr Asp Lys Glu

```
                305                 310                 315                 320
        Leu Glu Val Leu Ser Leu His Asn Val Thr Phe Glu Asp Ala Gly Glu
                        325                 330                 335

Tyr Thr Cys Leu Ala Gly Asn Ser Ile Gly Phe Ser His His Ser Ala
                        340                 345                 350

Trp Leu Val Val Leu Pro Ala Glu Glu Leu Val Glu Ala Asp Glu
                        355                 360                 365

Ala Gly Ser Val Tyr Ala Gly Ile Leu Ser Tyr Gly Val Gly Phe Phe
                370                 375                 380

Leu Phe Ile Leu Val Val Ala Ala Val Thr Leu Cys Arg Leu Arg Ser
        385                 390                 395                 400

Pro Pro Lys Lys Gly Leu Gly Ser Pro Thr Val His Lys Ile Ser Arg
                        405                 410                 415

Phe Pro Leu Lys Arg Gln Val Ser Leu Glu Ser Asn Ala Ser Met Ser
                        420                 425                 430

Ser Asn Thr Pro Leu Val Arg Ile Ala Arg Leu Ser Ser Gly Glu Gly
                        435                 440                 445

Pro Thr Leu Ala Asn Val Ser Glu Leu Glu Leu Pro Ala Asp Pro Lys
                450                 455                 460

Trp Glu Leu Ser Arg Ala Arg Leu Thr Leu Gly Lys Pro Leu Gly Glu
        465                 470                 475                 480

Gly Cys Phe Gly Gln Val Val Met Ala Glu Ala Ile Gly Ile Asp Lys
                        485                 490                 495

Asp Arg Ala Ala Lys Pro Val Thr Val Ala Val Lys Met Leu Lys Asp
                        500                 505                 510

Asp Ala Thr Asp Lys Asp Leu Ser Asp Leu Val Ser Glu Met Glu Met
                        515                 520                 525

Met Lys Met Ile Gly Lys His Lys Asn Ile Ile Asn Leu Leu Gly Ala
                530                 535                 540

Cys Thr Gln Gly Gly Pro Leu Tyr Val Leu Val Glu Tyr Ala Ala Lys
        545                 550                 555                 560

Gly Asn Leu Arg Glu Phe Leu Arg Ala Arg Arg Pro Pro Gly Leu Asp
                        565                 570                 575

Tyr Ser Phe Asp Thr Cys Lys Pro Pro Glu Glu Gln Leu Thr Phe Lys
                        580                 585                 590

Asp Leu Val Ser Cys Ala Tyr Gln Val Ala Arg Gly Met Glu Tyr Leu
                        595                 600                 605

Ala Ser Gln Lys Cys Ile His Arg Asp Leu Ala Ala Arg Asn Val Leu
                610                 615                 620

Val Thr Glu Asp Asn Val Met Lys Ile Ala Asp Phe Gly Leu Ala Arg
        625                 630                 635                 640

Asp Val His Asn Leu Asp Tyr Tyr Lys Lys Thr Thr Asn Gly Arg Leu
                        645                 650                 655

Pro Val Lys Trp Met Ala Pro Glu Ala Leu Phe Asp Arg Val Tyr Thr
                        660                 665                 670

His Gln Ser Asp Val Trp Ser Phe Gly Val Leu Leu Trp Glu Ile Phe
                        675                 680                 685

Thr Leu Gly Gly Ser Pro Tyr Pro Gly Ile Pro Val Glu Glu Leu Phe
                        690                 695                 700

Lys Leu Leu Lys Glu Gly His Arg Met Asp Lys Pro Ala Asn Cys Thr
        705                 710                 715                 720

His Asp Leu Tyr Met Ile Met Arg Glu Cys Trp His Ala Ala Pro Ser
                        725                 730                 735
```

-continued

```
Gln Arg Pro Thr Phe Lys Gln Leu Val Glu Asp Leu Asp Arg Val Leu
            740                 745                 750

Thr Val Thr Ser Thr Asp Glu Tyr Leu Asp Leu Ser Ala Pro Phe Glu
            755                 760                 765

Gln Tyr Ser Pro Gly Gly Gln Asp Thr Pro Ser Ser Ser Ser Ser Gly
            770                 775                 780

Asp Asp Ser Val Phe Ala His Asp Leu Leu Pro Pro Ala Pro Pro Ser
785                 790                 795                 800

Ser Gly Gly Ser Arg Thr
            805

<210> SEQ ID NO 95
<211> LENGTH: 733
<212> TYPE: PRT
<213> ORGANISM: Mus musculus
<220> FEATURE:
<223> OTHER INFORMATION: murine FGFR1b based on transcript FGFR1-201
      ENSMUST00000178276

<400> SEQUENCE: 95

Met Trp Gly Trp Lys Cys Leu Leu Phe Trp Ala Val Leu Val Thr Ala
1               5                   10                  15

Thr Leu Cys Thr Ala Arg Pro Ala Pro Thr Leu Pro Glu Gln Asp Ala
            20                  25                  30

Leu Pro Ser Ser Glu Asp Asp Asp Asp Asp Asp Ser Ser Ser Glu
            35                  40                  45

Glu Lys Glu Thr Asp Asn Thr Lys Pro Asn Pro Val Ala Pro Tyr Trp
50                  55                  60

Thr Ser Pro Glu Lys Met Glu Lys Lys Leu His Ala Val Pro Ala Ala
65                  70                  75                  80

Lys Thr Val Lys Phe Lys Cys Pro Ser Ser Gly Thr Pro Asn Pro Thr
            85                  90                  95

Leu Arg Trp Leu Lys Asn Gly Lys Glu Phe Lys Pro Asp His Arg Ile
            100                 105                 110

Gly Gly Tyr Lys Val Arg Tyr Ala Thr Trp Ser Ile Ile Met Asp Ser
            115                 120                 125

Val Val Pro Ser Asp Lys Gly Asn Tyr Thr Cys Ile Val Glu Asn Glu
            130                 135                 140

Tyr Gly Ser Ile Asn His Thr Tyr Gln Leu Asp Val Val Glu Arg Ser
145                 150                 155                 160

Pro His Arg Pro Ile Leu Gln Ala Gly Leu Pro Ala Asn Lys Thr Val
            165                 170                 175

Ala Leu Gly Ser Asn Val Glu Phe Met Cys Lys Val Tyr Ser Asp Pro
            180                 185                 190

Gln Pro His Ile Gln Trp Leu Lys His Ile Glu Val Asn Gly Ser Lys
            195                 200                 205

Ile Gly Pro Asp Asn Leu Pro Tyr Val Gln Ile Leu Lys His Ser Gly
            210                 215                 220

Ile Asn Ser Ser Asp Ala Glu Val Leu Thr Leu Phe Asn Val Thr Glu
225                 230                 235                 240

Ala Gln Ser Gly Glu Tyr Val Cys Lys Val Ser Asn Tyr Ile Gly Glu
            245                 250                 255

Ala Asn Gln Ser Ala Trp Leu Thr Val Thr Arg Pro Val Ala Lys Ala
            260                 265                 270

Leu Glu Glu Arg Pro Ala Val Met Thr Ser Pro Leu Tyr Leu Glu Ile
```

```
                275                 280                 285
Ile Ile Tyr Cys Thr Gly Ala Phe Leu Ile Ser Cys Met Leu Gly Ser
290                 295                 300

Val Ile Ile Tyr Lys Met Lys Ser Gly Thr Lys Lys Ser Asp Phe His
305                 310                 315                 320

Ser Gln Met Ala Val His Lys Leu Ala Lys Ser Ile Pro Leu Arg Arg
                325                 330                 335

Gln Val Thr Val Ser Ala Asp Ser Ser Ala Ser Met Asn Ser Gly Val
            340                 345                 350

Leu Leu Val Arg Pro Ser Arg Leu Ser Ser Ser Gly Thr Pro Met Leu
        355                 360                 365

Ala Gly Val Ser Glu Tyr Glu Leu Pro Glu Asp Pro Arg Trp Glu Leu
370                 375                 380

Pro Arg Asp Arg Leu Val Leu Gly Lys Pro Leu Gly Glu Gly Cys Phe
385                 390                 395                 400

Gly Gln Val Val Leu Ala Glu Ala Ile Gly Leu Asp Lys Asp Lys Pro
                405                 410                 415

Asn Arg Val Thr Lys Val Ala Val Lys Met Leu Lys Ser Asp Ala Thr
            420                 425                 430

Glu Lys Asp Leu Ser Asp Leu Ile Ser Glu Met Glu Met Met Lys Met
        435                 440                 445

Ile Gly Lys His Lys Asn Ile Ile Asn Leu Leu Gly Ala Cys Thr Gln
450                 455                 460

Asp Gly Pro Leu Tyr Val Ile Val Glu Tyr Ala Ser Lys Gly Asn Leu
465                 470                 475                 480

Arg Glu Tyr Leu Gln Ala Arg Arg Pro Pro Gly Leu Glu Tyr Cys Tyr
                485                 490                 495

Asn Pro Ser His Asn Pro Glu Glu Gln Leu Ser Ser Lys Asp Leu Val
            500                 505                 510

Ser Cys Ala Tyr Gln Val Ala Arg Gly Met Glu Tyr Leu Ala Ser Lys
        515                 520                 525

Lys Cys Ile His Arg Asp Leu Ala Ala Arg Asn Val Leu Val Thr Glu
530                 535                 540

Asp Asn Val Met Lys Ile Ala Asp Phe Gly Leu Ala Arg Asp Ile His
545                 550                 555                 560

His Ile Asp Tyr Tyr Lys Lys Thr Thr Asn Gly Arg Leu Pro Val Lys
                565                 570                 575

Trp Met Ala Pro Glu Ala Leu Phe Asp Arg Ile Tyr Thr His Gln Ser
            580                 585                 590

Asp Val Trp Ser Phe Gly Val Leu Leu Trp Glu Ile Phe Thr Leu Gly
        595                 600                 605

Gly Ser Pro Tyr Pro Gly Val Pro Val Glu Glu Leu Phe Lys Leu Leu
610                 615                 620

Lys Glu Gly His Arg Met Asp Lys Pro Ser Asn Cys Thr Asn Glu Leu
625                 630                 635                 640

Tyr Met Met Met Arg Asp Cys Trp His Ala Val Pro Ser Gln Arg Pro
                645                 650                 655

Thr Phe Lys Gln Leu Val Glu Asp Leu Asp Arg Ile Val Ala Leu Thr
            660                 665                 670

Ser Asn Gln Glu Tyr Leu Asp Leu Ser Ile Pro Leu Asp Gln Tyr Ser
        675                 680                 685

Pro Ser Phe Pro Asp Thr Arg Ser Ser Thr Cys Ser Ser Gly Glu Asp
690                 695                 700
```

```
Ser Val Phe Ser His Glu Pro Leu Pro Glu Glu Pro Cys Leu Pro Arg
705                 710                 715                 720

His Pro Thr Gln Leu Ala Asn Ser Gly Leu Lys Arg Arg
                725                 730
```

<210> SEQ ID NO 96
<211> LENGTH: 833
<212> TYPE: PRT
<213> ORGANISM: Mus musculus
<220> FEATURE:
<223> OTHER INFORMATION: murine FGFR1c based on transcript FGFR1-202
      ENSMUST00000179592

<400> SEQUENCE: 96

```
Met Trp Gly Trp Lys Cys Leu Leu Phe Trp Ala Val Leu Val Thr Ala
1               5                   10                  15

Thr Leu Cys Thr Ala Arg Pro Ala Pro Thr Leu Pro Glu Gln Val Gly
                20                  25                  30

Ser Ser Ser Trp Pro Leu Trp Val Ala Ala Ala Gln Pro Trp Gly
            35                  40                  45

Val Pro Val Glu Val Glu Ser Leu Leu Val His Pro Gly Asp Leu Leu
50                  55                  60

Gln Leu Arg Cys Arg Leu Arg Asp Asp Val Gln Ser Ile Asn Trp Leu
65                  70                  75                  80

Arg Asp Gly Val Gln Leu Val Glu Ser Asn Arg Thr Arg Ile Thr Gly
                85                  90                  95

Glu Glu Val Glu Val Arg Asp Ser Ile Pro Ala Asp Ser Gly Leu Tyr
            100                 105                 110

Ala Cys Val Thr Ser Ser Pro Ser Gly Ser Asp Thr Thr Tyr Phe Ser
        115                 120                 125

Val Asn Val Ser Asp Ala Leu Pro Ser Ser Glu Asp Asp Asp Asp Asp
130                 135                 140

Asp Asp Ser Ser Ser Glu Glu Lys Glu Thr Asp Asn Thr Lys Pro Asn
145                 150                 155                 160

Pro Val Ala Pro Tyr Trp Thr Ser Pro Glu Lys Met Glu Lys Lys Leu
                165                 170                 175

His Ala Val Pro Ala Ala Lys Thr Val Lys Phe Lys Cys Pro Ser Ser
            180                 185                 190

Gly Thr Pro Asn Pro Thr Leu Arg Trp Leu Lys Asn Gly Lys Glu Phe
        195                 200                 205

Lys Pro Asp His Arg Ile Gly Gly Tyr Lys Val Arg Tyr Ala Thr Trp
210                 215                 220

Ser Ile Ile Met Asp Ser Val Val Pro Ser Asp Lys Gly Asn Tyr Thr
225                 230                 235                 240

Cys Ile Val Glu Asn Glu Tyr Gly Ser Ile Asn His Thr Tyr Gln Leu
                245                 250                 255

Asp Val Val Glu Arg Ser Pro His Arg Pro Ile Leu Gln Ala Gly Leu
            260                 265                 270

Pro Ala Asn Lys Thr Val Ala Leu Gly Ser Asn Val Glu Phe Met Cys
        275                 280                 285

Lys Val Tyr Ser Asp Pro Gln Pro His Ile Gln Trp Leu Lys His Ile
        290                 295                 300

Glu Val Asn Gly Ser Lys Ile Gly Pro Asp Asn Leu Pro Tyr Val Gln
305                 310                 315                 320

Ile Leu Lys Thr Ala Gly Val Asn Thr Thr Asp Lys Glu Met Glu Val
```

-continued

```
                325                 330                 335
Leu His Leu Arg Asn Val Ser Phe Glu Asp Ala Gly Glu Tyr Thr Cys
            340                 345                 350
Leu Ala Gly Asn Ser Ile Gly Leu Ser His His Ser Ala Trp Leu Thr
            355                 360                 365
Val Leu Glu Ala Leu Glu Arg Pro Ala Val Met Thr Ser Pro Leu
        370                 375                 380
Tyr Leu Glu Ile Ile Ile Tyr Cys Thr Gly Ala Phe Leu Ile Ser Cys
385                 390                 395                 400
Met Leu Gly Ser Val Ile Ile Tyr Lys Met Lys Ser Gly Thr Lys Lys
                405                 410                 415
Ser Asp Phe His Ser Gln Met Ala Val His Lys Leu Ala Lys Ser Ile
            420                 425                 430
Pro Leu Arg Arg Gln Val Thr Val Ser Ala Asp Ser Ser Ala Ser Met
        435                 440                 445
Asn Ser Gly Val Leu Leu Val Arg Pro Ser Arg Leu Ser Ser Ser Gly
        450                 455                 460
Thr Pro Met Leu Ala Gly Val Ser Glu Tyr Glu Leu Pro Glu Asp Pro
465                 470                 475                 480
Arg Trp Glu Leu Pro Arg Asp Arg Leu Val Leu Gly Lys Pro Leu Gly
                485                 490                 495
Glu Gly Cys Phe Gly Gln Val Val Leu Ala Glu Ala Ile Gly Leu Asp
                500                 505                 510
Lys Asp Lys Pro Asn Arg Val Thr Lys Val Ala Val Lys Met Leu Lys
            515                 520                 525
Ser Asp Ala Thr Glu Lys Asp Leu Ser Asp Leu Ile Ser Glu Met Glu
        530                 535                 540
Met Met Lys Met Ile Gly Lys His Lys Asn Ile Ile Asn Leu Leu Gly
545                 550                 555                 560
Ala Cys Thr Gln Asp Gly Pro Leu Tyr Val Ile Val Glu Tyr Ala Ser
                565                 570                 575
Lys Gly Asn Leu Arg Glu Tyr Leu Gln Ala Arg Arg Pro Pro Gly Leu
            580                 585                 590
Glu Tyr Cys Tyr Asn Pro Ser His Asn Pro Glu Glu Gln Leu Ser Ser
        595                 600                 605
Lys Asp Leu Val Ser Cys Ala Tyr Gln Val Ala Arg Gly Met Glu Tyr
        610                 615                 620
Leu Ala Ser Lys Lys Cys Ile His Arg Asp Leu Ala Ala Arg Asn Val
625                 630                 635                 640
Leu Val Thr Glu Asp Asn Val Met Lys Ile Ala Asp Phe Gly Leu Ala
                645                 650                 655
Arg Asp Ile His His Ile Asp Tyr Tyr Lys Lys Thr Thr Asn Gly Arg
            660                 665                 670
Leu Pro Val Lys Trp Met Ala Pro Glu Ala Leu Phe Asp Arg Ile Tyr
        675                 680                 685
Thr His Gln Ser Asp Val Trp Ser Phe Gly Val Leu Leu Trp Glu Ile
        690                 695                 700
Phe Thr Leu Gly Gly Ser Pro Tyr Pro Gly Val Pro Val Glu Glu Leu
705                 710                 715                 720
Phe Lys Leu Leu Lys Glu Gly His Arg Met Asp Lys Pro Ser Asn Cys
                725                 730                 735
Thr Asn Glu Leu Tyr Met Met Met Arg Asp Cys Trp His Ala Val Pro
            740                 745                 750
```

```
Ser Gln Arg Pro Thr Phe Lys Gln Leu Val Glu Asp Leu Asp Arg Ile
        755                 760                 765

Val Ala Leu Thr Ser Asn Gln Glu Tyr Leu Asp Leu Ser Ile Pro Leu
    770                 775                 780

Asp Gln Tyr Ser Pro Ser Phe Pro Asp Thr Arg Ser Ser Thr Cys Ser
785                 790                 795                 800

Ser Gly Glu Asp Ser Val Phe Ser His Glu Pro Leu Pro Glu Pro
                805                 810                 815

Cys Leu Pro Arg His Pro Thr Gln Leu Ala Asn Ser Gly Leu Lys Arg
                820                 825                 830

Arg

<210> SEQ ID NO 97
<211> LENGTH: 819
<212> TYPE: PRT
<213> ORGANISM: Mus musculus
<220> FEATURE:
<223> OTHER INFORMATION: murine FGFR2b based on transcript FGFR2-011
      ENSMUST00000119260

<400> SEQUENCE: 97

Met Val Ser Trp Gly Arg Phe Ile Cys Leu Val Leu Val Thr Met Ala
1               5                   10                  15

Thr Leu Ser Leu Ala Arg Pro Ser Phe Ser Leu Val Glu Asp Thr Thr
            20                  25                  30

Leu Glu Pro Glu Glu Pro Pro Thr Lys Tyr Gln Ile Ser Gln Pro Glu
        35                  40                  45

Ala Tyr Val Val Ala Pro Gly Glu Ser Leu Glu Leu Gln Cys Met Leu
    50                  55                  60

Lys Asp Ala Ala Val Ile Ser Trp Thr Lys Asp Gly Val His Leu Gly
65                  70                  75                  80

Pro Asn Asn Arg Thr Val Leu Ile Gly Glu Tyr Leu Gln Ile Lys Gly
                85                  90                  95

Ala Thr Pro Arg Asp Ser Gly Leu Tyr Ala Cys Thr Ala Ala Arg Thr
            100                 105                 110

Val Asp Ser Glu Thr Trp Tyr Phe Met Val Asn Val Thr Asp Ala Ile
        115                 120                 125

Ser Ser Gly Asp Asp Glu Asp Asp Thr Asp Ser Ser Glu Asp Val Val
    130                 135                 140

Ser Glu Asn Arg Ser Asn Gln Arg Ala Pro Tyr Trp Thr Asn Thr Glu
145                 150                 155                 160

Lys Met Glu Lys Arg Leu His Ala Val Pro Ala Ala Asn Thr Val Lys
                165                 170                 175

Phe Arg Cys Pro Ala Gly Gly Asn Pro Thr Pro Thr Met Arg Trp Leu
            180                 185                 190

Lys Asn Gly Lys Glu Phe Lys Gln Glu His Arg Ile Gly Gly Tyr Lys
        195                 200                 205

Val Arg Asn Gln His Trp Ser Leu Ile Met Glu Ser Val Val Pro Ser
    210                 215                 220

Asp Lys Gly Asn Tyr Thr Cys Leu Val Glu Asn Glu Tyr Gly Ser Ile
225                 230                 235                 240

Asn His Thr Tyr His Leu Asp Val Val Glu Arg Ser Pro His Arg Pro
                245                 250                 255

Ile Leu Gln Ala Gly Leu Pro Ala Asn Ala Ser Thr Val Val Gly Gly
            260                 265                 270
```

```
Asp Val Glu Phe Val Cys Lys Val Tyr Ser Asp Ala Gln Pro His Ile
        275                 280                 285

Gln Trp Ile Lys His Val Glu Lys Asn Gly Ser Lys Tyr Gly Pro Asp
    290                 295                 300

Gly Leu Pro Tyr Leu Lys Val Leu Lys Ala Ala Gly Val Asn Thr Thr
305                 310                 315                 320

Asp Lys Glu Ile Glu Val Leu Tyr Ile Arg Asn Val Thr Phe Glu Asp
                325                 330                 335

Ala Gly Glu Tyr Thr Cys Leu Ala Gly Asn Ser Ile Gly Ile Ser Phe
            340                 345                 350

His Ser Ala Trp Leu Thr Val Leu Pro Ala Pro Val Arg Glu Lys Glu
        355                 360                 365

Ile Thr Ala Ser Pro Asp Tyr Leu Glu Ile Ala Ile Tyr Cys Ile Gly
    370                 375                 380

Val Phe Leu Ile Ala Cys Met Val Val Thr Val Ile Phe Cys Arg Met
385                 390                 395                 400

Lys Thr Thr Thr Lys Lys Pro Asp Phe Ser Ser Gln Pro Ala Val His
                405                 410                 415

Lys Leu Thr Lys Arg Ile Pro Leu Arg Arg Gln Val Ser Ala Glu Ser
            420                 425                 430

Ser Ser Ser Met Asn Ser Asn Thr Pro Leu Val Arg Ile Thr Thr Arg
        435                 440                 445

Leu Ser Ser Thr Ala Asp Thr Pro Met Leu Ala Gly Val Ser Glu Tyr
    450                 455                 460

Glu Leu Pro Glu Asp Pro Lys Trp Glu Phe Pro Arg Asp Lys Leu Thr
465                 470                 475                 480

Leu Gly Lys Pro Leu Gly Glu Gly Cys Phe Gly Gln Val Val Met Ala
                485                 490                 495

Glu Ala Val Gly Ile Asp Lys Asp Lys Pro Lys Glu Ala Val Thr Val
            500                 505                 510

Ala Val Lys Met Leu Lys Asp Asp Ala Thr Glu Lys Asp Leu Ser Asp
        515                 520                 525

Leu Val Ser Glu Met Glu Met Met Lys Met Ile Gly Lys His Lys Asn
    530                 535                 540

Ile Ile Asn Leu Leu Gly Ala Cys Thr Gln Asp Gly Pro Leu Tyr Val
545                 550                 555                 560

Ile Val Glu Tyr Ala Ser Lys Gly Asn Leu Arg Glu Tyr Leu Arg Ala
                565                 570                 575

Arg Arg Pro Pro Gly Met Glu Tyr Ser Tyr Asp Ile Asn Arg Val Pro
            580                 585                 590

Glu Glu Gln Met Thr Phe Lys Asp Leu Val Ser Cys Thr Tyr Gln Leu
        595                 600                 605

Ala Arg Gly Met Glu Tyr Leu Ala Ser Gln Lys Cys Ile His Arg Asp
    610                 615                 620

Leu Ala Ala Arg Asn Val Leu Val Thr Glu Asn Asn Val Met Lys Ile
625                 630                 635                 640

Ala Asp Phe Gly Leu Ala Arg Asp Ile Asn Asn Ile Asp Tyr Tyr Lys
                645                 650                 655

Lys Thr Thr Asn Gly Arg Leu Pro Val Lys Trp Met Ala Pro Glu Ala
            660                 665                 670

Leu Phe Asp Arg Val Tyr Thr His Gln Ser Asp Val Trp Ser Phe Gly
        675                 680                 685
```

```
Val Leu Met Trp Glu Ile Phe Thr Leu Gly Gly Ser Pro Tyr Pro Gly
    690                 695                 700

Ile Pro Val Glu Glu Leu Phe Lys Leu Leu Lys Glu Gly His Arg Met
705                 710                 715                 720

Asp Lys Pro Thr Asn Cys Thr Asn Glu Leu Tyr Met Met Arg Asp
                725                 730                 735

Cys Trp His Ala Val Pro Ser Gln Arg Pro Thr Phe Lys Gln Leu Val
                740                 745                 750

Glu Asp Leu Asp Arg Ile Leu Thr Leu Thr Thr Asn Glu Glu Tyr Leu
                755                 760                 765

Asp Leu Thr Gln Pro Leu Glu Gln Tyr Ser Pro Ser Tyr Pro Asp Thr
770                 775                 780

Arg Ser Ser Cys Ser Ser Gly Asp Asp Ser Val Phe Ser Pro Asp Pro
785                 790                 795                 800

Met Pro Tyr Glu Pro Cys Leu Pro Gln Tyr Pro His Ile Asn Gly Ser
                805                 810                 815

Val Lys Thr

<210> SEQ ID NO 98
<211> LENGTH: 820
<212> TYPE: PRT
<213> ORGANISM: Mus musculus
<220> FEATURE:
<223> OTHER INFORMATION: murine FGFR2c based on transcript FGFR2-012
      ENSMUST00000117089

<400> SEQUENCE: 98

Met Val Ser Trp Gly Arg Phe Ile Cys Leu Val Leu Val Thr Met Ala
1               5                   10                  15

Thr Leu Ser Leu Ala Arg Pro Ser Phe Ser Leu Val Glu Asp Thr Thr
                20                  25                  30

Leu Glu Pro Glu Glu Pro Pro Thr Lys Tyr Gln Ile Ser Gln Pro Glu
            35                  40                  45

Ala Tyr Val Val Ala Pro Gly Glu Ser Leu Glu Leu Gln Cys Met Leu
    50                  55                  60

Lys Asp Ala Ala Val Ile Ser Trp Thr Lys Asp Gly Val His Leu Gly
65                  70                  75                  80

Pro Asn Asn Arg Thr Val Leu Ile Gly Glu Tyr Leu Gln Ile Lys Gly
                85                  90                  95

Ala Thr Pro Arg Asp Ser Gly Leu Tyr Ala Cys Thr Ala Ala Arg Thr
                100                 105                 110

Val Asp Ser Glu Thr Trp Tyr Phe Met Val Asn Val Thr Asp Ala Ile
            115                 120                 125

Ser Ser Gly Asp Asp Glu Asp Asp Thr Asp Ser Ser Glu Asp Val Val
    130                 135                 140

Ser Glu Asn Arg Ser Asn Gln Arg Ala Pro Tyr Trp Thr Asn Thr Glu
145                 150                 155                 160

Lys Met Glu Lys Arg Leu His Ala Val Pro Ala Ala Asn Thr Val Lys
                165                 170                 175

Phe Arg Cys Pro Ala Gly Gly Asn Pro Thr Pro Thr Met Arg Trp Leu
                180                 185                 190

Lys Asn Gly Lys Glu Phe Lys Gln Glu His Arg Ile Gly Gly Tyr Lys
            195                 200                 205

Val Arg Asn Gln His Trp Ser Leu Ile Met Glu Ser Val Val Pro Ser
    210                 215                 220
```

```
Asp Lys Gly Asn Tyr Thr Cys Leu Val Glu Asn Glu Tyr Gly Ser Ile
225                 230                 235                 240

Asn His Thr Tyr His Leu Asp Val Val Glu Arg Ser Pro His Arg Pro
            245                 250                 255

Ile Leu Gln Ala Gly Leu Pro Ala Asn Ala Ser Thr Val Val Gly Gly
            260                 265                 270

Asp Val Glu Phe Val Cys Lys Val Tyr Ser Asp Ala Gln Pro His Ile
        275                 280                 285

Gln Trp Ile Lys His Val Glu Lys Asn Gly Ser Lys Tyr Gly Pro Asp
    290                 295                 300

Gly Leu Pro Tyr Leu Lys Val Leu Lys His Ser Gly Ile Asn Ser Ser
305                 310                 315                 320

Asn Ala Glu Val Leu Ala Leu Phe Asn Val Thr Glu Met Asp Ala Gly
                325                 330                 335

Glu Tyr Ile Cys Lys Val Ser Asn Tyr Ile Gly Gln Ala Asn Gln Ser
                340                 345                 350

Ala Trp Leu Thr Val Leu Pro Lys Gln Gln Ala Pro Val Arg Glu Lys
            355                 360                 365

Glu Ile Thr Ala Ser Pro Asp Tyr Leu Glu Ile Ala Ile Tyr Cys Ile
        370                 375                 380

Gly Val Phe Leu Ile Ala Cys Met Val Val Thr Val Ile Phe Cys Arg
385                 390                 395                 400

Met Lys Thr Thr Thr Lys Lys Pro Asp Phe Ser Ser Gln Pro Ala Val
                405                 410                 415

His Lys Leu Thr Lys Arg Ile Pro Leu Arg Arg Gln Val Ser Ala Glu
            420                 425                 430

Ser Ser Ser Ser Met Asn Ser Asn Thr Pro Leu Val Arg Ile Thr Thr
        435                 440                 445

Arg Leu Ser Ser Thr Ala Asp Thr Pro Met Leu Ala Gly Val Ser Glu
    450                 455                 460

Tyr Glu Leu Pro Glu Asp Pro Lys Trp Glu Phe Pro Arg Asp Lys Leu
465                 470                 475                 480

Thr Leu Gly Lys Pro Leu Gly Glu Gly Cys Phe Gly Gln Val Val Met
                485                 490                 495

Ala Glu Ala Val Gly Ile Asp Lys Asp Lys Pro Lys Glu Ala Val Thr
                500                 505                 510

Val Ala Val Lys Met Leu Lys Asp Asp Ala Thr Glu Lys Asp Leu Ser
            515                 520                 525

Asp Leu Val Ser Glu Met Glu Met Met Lys Met Ile Gly Lys His Lys
530                 535                 540

Asn Ile Ile Asn Leu Leu Gly Ala Cys Thr Gln Asp Gly Pro Leu Tyr
545                 550                 555                 560

Val Ile Val Glu Tyr Ala Ser Lys Gly Asn Leu Arg Glu Tyr Leu Arg
                565                 570                 575

Ala Arg Arg Pro Pro Gly Met Glu Tyr Ser Tyr Asp Ile Asn Arg Val
            580                 585                 590

Pro Glu Glu Gln Met Thr Phe Lys Asp Leu Val Ser Cys Thr Tyr Gln
        595                 600                 605

Leu Ala Arg Gly Met Glu Tyr Leu Ala Ser Gln Lys Cys Ile His Arg
    610                 615                 620

Asp Leu Ala Ala Arg Asn Val Leu Val Thr Glu Asn Asn Val Met Lys
625                 630                 635                 640

Ile Ala Asp Phe Gly Leu Ala Arg Asp Ile Asn Asn Ile Asp Tyr Tyr
```

```
                        645                 650                 655
Lys Lys Thr Thr Asn Gly Arg Leu Pro Val Lys Trp Met Ala Pro Glu
            660                 665                 670
Ala Leu Phe Asp Arg Val Tyr Thr His Gln Ser Asp Val Trp Ser Phe
            675                 680                 685
Gly Val Leu Met Trp Glu Ile Phe Thr Leu Gly Gly Ser Pro Tyr Pro
            690                 695                 700
Gly Ile Pro Val Glu Glu Leu Phe Lys Leu Leu Lys Glu Gly His Arg
705                 710                 715                 720
Met Asp Lys Pro Thr Asn Cys Thr Asn Glu Leu Tyr Met Met Met Arg
            725                 730                 735
Asp Cys Trp His Ala Val Pro Ser Gln Arg Pro Thr Phe Lys Gln Leu
            740                 745                 750
Val Glu Asp Leu Asp Arg Ile Leu Thr Leu Thr Thr Asn Glu Glu Tyr
            755                 760                 765
Leu Asp Leu Thr Gln Pro Leu Glu Gln Tyr Ser Pro Ser Tyr Pro Asp
            770                 775                 780
Thr Arg Ser Ser Cys Ser Ser Gly Asp Asp Ser Val Phe Ser Pro Asp
785                 790                 795                 800
Pro Met Pro Tyr Glu Pro Cys Leu Pro Gln Tyr Pro His Ile Asn Gly
            805                 810                 815
Ser Val Lys Thr
            820

<210> SEQ ID NO 99
<211> LENGTH: 802
<212> TYPE: PRT
<213> ORGANISM: Mus musculus
<220> FEATURE:
<223> OTHER INFORMATION: murine FGFR3b based on transcript FGFR3-201
      ENSMUST00000114411

<400> SEQUENCE: 99

Met Val Val Pro Ala Cys Val Leu Val Phe Cys Val Ala Val Val Ala
1               5                   10                  15
Gly Ala Thr Ser Glu Pro Pro Gly Pro Glu Gln Arg Val Val Arg Arg
            20                  25                  30
Ala Ala Glu Val Pro Gly Pro Glu Pro Ser Gln Gln Glu Gln Val Ala
        35                  40                  45
Phe Gly Ser Gly Asp Thr Val Glu Leu Ser Cys His Pro Pro Gly Gly
    50                  55                  60
Ala Pro Thr Gly Pro Thr Val Trp Ala Lys Asp Gly Thr Gly Leu Val
65                  70                  75                  80
Ala Ser His Arg Ile Leu Val Gly Pro Gln Arg Leu Gln Val Leu Asn
                85                  90                  95
Ala Ser His Glu Asp Ala Gly Val Tyr Ser Cys Gln His Arg Leu Thr
            100                 105                 110
Arg Arg Val Leu Cys His Phe Ser Val Arg Val Thr Asp Ala Pro Ser
            115                 120                 125
Ser Gly Asp Asp Glu Asp Gly Glu Asp Val Ala Glu Asp Thr Gly Ala
            130                 135                 140
Pro Tyr Trp Thr Arg Pro Glu Arg Met Asp Lys Lys Leu Leu Ala Val
145                 150                 155                 160
Pro Ala Ala Asn Thr Val Arg Phe Arg Cys Pro Ala Ala Gly Asn Pro
                165                 170                 175
```

```
Thr Pro Ser Ile Ser Trp Leu Lys Asn Gly Lys Glu Phe Arg Gly Glu
            180                 185                 190

His Arg Ile Gly Gly Ile Lys Leu Arg His Gln Gln Trp Ser Leu Val
            195                 200             205

Met Glu Ser Val Val Pro Ser Asp Arg Gly Asn Tyr Thr Cys Val Val
210                 215                 220

Glu Asn Lys Phe Gly Ser Ile Arg Gln Thr Tyr Thr Leu Asp Val Leu
225                 230                 235                 240

Glu Arg Ser Pro His Arg Pro Ile Leu Gln Ala Gly Leu Pro Ala Asn
                245                 250                 255

Gln Thr Ala Ile Leu Gly Ser Asp Val Glu Phe His Cys Lys Val Tyr
            260                 265                 270

Ser Asp Ala Gln Pro His Ile Gln Trp Leu Lys His Val Glu Val Asn
            275                 280             285

Gly Ser Lys Val Gly Pro Asp Gly Thr Pro Tyr Val Thr Val Leu Lys
            290                 295                 300

Ser Trp Ile Ser Glu Asn Val Glu Ala Asp Ala Arg Leu Arg Leu Ala
305                 310                 315                 320

Asn Val Ser Glu Arg Asp Gly Gly Glu Tyr Leu Cys Arg Ala Thr Asn
                325                 330                 335

Phe Ile Gly Val Ala Glu Lys Ala Phe Trp Leu Arg Val His Gly Pro
            340                 345                 350

Gln Ala Ala Glu Glu Glu Leu Met Glu Thr Asp Glu Ala Gly Ser Val
            355                 360             365

Tyr Ala Gly Val Leu Ser Tyr Gly Val Val Phe Phe Leu Phe Ile Leu
            370                 375                 380

Val Val Ala Ala Val Ile Leu Cys Arg Leu Arg Ser Pro Pro Lys Lys
385                 390                 395                 400

Gly Leu Gly Ser Pro Thr Val His Lys Val Ser Arg Phe Pro Leu Lys
                405                 410                 415

Arg Gln Val Ser Leu Glu Ser Asn Ser Ser Met Asn Ser Asn Thr Pro
            420                 425                 430

Leu Val Arg Ile Ala Arg Leu Ser Ser Gly Glu Gly Pro Val Leu Ala
            435                 440             445

Asn Val Ser Glu Leu Glu Leu Pro Ala Asp Pro Lys Trp Glu Leu Ser
450                 455                 460

Arg Thr Arg Leu Thr Leu Gly Lys Pro Leu Gly Glu Gly Cys Phe Gly
465                 470                 475                 480

Gln Val Val Met Ala Glu Ala Ile Gly Ile Asp Lys Asp Arg Thr Ala
                485                 490                 495

Lys Pro Val Thr Val Ala Val Lys Met Leu Lys Asp Asp Ala Thr Asp
            500                 505                 510

Lys Asp Leu Ser Asp Leu Val Ser Glu Met Glu Met Met Lys Met Ile
            515                 520             525

Gly Lys His Lys Asn Ile Ile Asn Leu Leu Gly Ala Cys Thr Gln Gly
            530                 535                 540

Gly Pro Leu Tyr Val Leu Val Glu Tyr Ala Ala Lys Gly Asn Leu Arg
545                 550                 555                 560

Glu Phe Leu Arg Ala Arg Arg Pro Pro Gly Met Asp Tyr Ser Phe Asp
                565                 570                 575

Ala Cys Arg Leu Pro Glu Glu Gln Leu Thr Cys Lys Asp Leu Val Ser
            580                 585                 590

Cys Ala Tyr Gln Val Ala Arg Gly Met Glu Tyr Leu Ala Ser Gln Lys
```

```
                    595                 600                 605
Cys Ile His Arg Asp Leu Ala Ala Arg Asn Val Leu Val Thr Glu Asp
            610                 615                 620
Asn Val Met Lys Ile Ala Asp Phe Gly Leu Ala Arg Asp Val His Asn
625                 630                 635                 640
Leu Asp Tyr Tyr Lys Lys Thr Thr Asn Gly Arg Leu Pro Val Lys Trp
                645                 650                 655
Met Ala Pro Glu Ala Leu Phe Asp Arg Val Tyr Thr His Gln Ser Asp
            660                 665                 670
Val Trp Ser Phe Gly Val Leu Leu Trp Glu Ile Phe Thr Leu Gly Gly
                675                 680                 685
Ser Pro Tyr Pro Gly Ile Pro Val Glu Glu Leu Phe Lys Leu Leu Lys
            690                 695                 700
Glu Gly His Arg Met Asp Lys Pro Ala Ser Cys Thr His Asp Leu Tyr
705                 710                 715                 720
Met Ile Met Arg Glu Cys Trp His Ala Val Pro Ser Gln Arg Pro Thr
                725                 730                 735
Phe Lys Gln Leu Val Glu Asp Leu Asp Arg Ile Leu Thr Val Thr Ser
            740                 745                 750
Thr Asp Glu Tyr Leu Asp Leu Ser Val Pro Phe Glu Gln Tyr Ser Pro
                755                 760                 765
Gly Gly Gln Asp Thr Pro Ser Ser Ser Ser Ser Gly Asp Asp Ser Val
            770                 775                 780
Phe Thr His Asp Leu Leu Pro Pro Gly Pro Pro Ser Asn Gly Gly Pro
785                 790                 795                 800
Arg Thr

<210> SEQ ID NO 100
<211> LENGTH: 800
<212> TYPE: PRT
<213> ORGANISM: Mus musculus
<220> FEATURE:
<223> OTHER INFORMATION: murine FGFR3c based on transcript FGFR3-202
      ENSMUST00000169212

<400> SEQUENCE: 100

Met Val Val Pro Ala Cys Val Leu Val Phe Cys Val Ala Val Val Ala
1               5                   10                  15
Gly Ala Thr Ser Glu Pro Pro Gly Pro Glu Gln Arg Val Val Arg Arg
                20                  25                  30
Ala Ala Glu Val Pro Gly Pro Glu Pro Ser Gln Gln Glu Gln Val Ala
            35                  40                  45
Phe Gly Ser Gly Asp Thr Val Glu Leu Ser Cys His Pro Pro Gly Gly
        50                  55                  60
Ala Pro Thr Gly Pro Thr Val Trp Ala Lys Asp Gly Thr Gly Leu Val
65                  70                  75                  80
Ala Ser His Arg Ile Leu Val Gly Pro Gln Arg Leu Gln Val Leu Asn
                85                  90                  95
Ala Ser His Glu Asp Ala Gly Val Tyr Ser Cys Gln His Arg Leu Thr
            100                 105                 110
Arg Arg Val Leu Cys His Phe Ser Val Arg Val Thr Asp Ala Pro Ser
        115                 120                 125
Ser Gly Asp Asp Glu Asp Gly Glu Asp Val Ala Glu Asp Thr Gly Ala
    130                 135                 140
Pro Tyr Trp Thr Arg Pro Glu Arg Met Asp Lys Lys Leu Leu Ala Val
```

-continued

```
            145                 150                 155                 160
        Pro Ala Ala Asn Thr Val Arg Phe Arg Cys Pro Ala Ala Gly Asn Pro
                            165                 170                 175
        Thr Pro Ser Ile Ser Trp Leu Lys Asn Gly Lys Glu Phe Arg Gly Glu
                            180                 185                 190
        His Arg Ile Gly Gly Ile Lys Leu Arg His Gln Gln Trp Ser Leu Val
                            195                 200                 205
        Met Glu Ser Val Val Pro Ser Asp Arg Gly Asn Tyr Thr Cys Val Val
                            210                 215                 220
        Glu Asn Lys Phe Gly Ser Ile Arg Gln Thr Tyr Thr Leu Asp Val Leu
        225                 230                 235                 240
        Glu Arg Ser Pro His Arg Pro Ile Leu Gln Ala Gly Leu Pro Ala Asn
                            245                 250                 255
        Gln Thr Ala Ile Leu Gly Ser Asp Val Glu Phe His Cys Lys Val Tyr
                            260                 265                 270
        Ser Asp Ala Gln Pro His Ile Gln Trp Leu Lys His Val Glu Val Asn
                            275                 280                 285
        Gly Ser Lys Val Gly Pro Asp Gly Thr Pro Tyr Val Thr Val Leu Lys
                            290                 295                 300
        Thr Ala Gly Ala Asn Thr Thr Asp Lys Glu Leu Glu Val Leu Ser Leu
        305                 310                 315                 320
        His Asn Val Thr Phe Glu Asp Ala Gly Glu Tyr Thr Cys Leu Ala Gly
                            325                 330                 335
        Asn Ser Ile Gly Phe Ser His His Ser Ala Trp Leu Val Val Leu Pro
                            340                 345                 350
        Ala Glu Glu Glu Leu Met Glu Thr Asp Glu Ala Gly Ser Val Tyr Ala
                            355                 360                 365
        Gly Val Leu Ser Tyr Gly Val Val Phe Phe Leu Phe Ile Leu Val Val
                            370                 375                 380
        Ala Ala Val Ile Leu Cys Arg Leu Arg Ser Pro Pro Lys Lys Gly Leu
        385                 390                 395                 400
        Gly Ser Pro Thr Val His Lys Val Ser Arg Phe Pro Leu Lys Arg Gln
                            405                 410                 415
        Val Ser Leu Glu Ser Asn Ser Ser Met Asn Ser Asn Thr Pro Leu Val
                            420                 425                 430
        Arg Ile Ala Arg Leu Ser Ser Gly Glu Gly Pro Val Leu Ala Asn Val
                            435                 440                 445
        Ser Glu Leu Glu Leu Pro Ala Asp Pro Lys Trp Glu Leu Ser Arg Thr
                            450                 455                 460
        Arg Leu Thr Leu Gly Lys Pro Leu Gly Glu Gly Cys Phe Gly Gln Val
        465                 470                 475                 480
        Val Met Ala Glu Ala Ile Gly Ile Asp Lys Asp Arg Thr Ala Lys Pro
                            485                 490                 495
        Val Thr Val Ala Val Lys Met Leu Lys Asp Asp Ala Thr Asp Lys Asp
                            500                 505                 510
        Leu Ser Asp Leu Val Ser Glu Met Glu Met Met Lys Met Ile Gly Lys
                            515                 520                 525
        His Lys Asn Ile Ile Asn Leu Leu Gly Ala Cys Thr Gln Gly Gly Pro
                            530                 535                 540
        Leu Tyr Val Leu Val Glu Tyr Ala Ala Lys Gly Asn Leu Arg Glu Phe
        545                 550                 555                 560
        Leu Arg Ala Arg Arg Pro Pro Gly Met Asp Tyr Ser Phe Asp Ala Cys
                            565                 570                 575
```

```
Arg Leu Pro Glu Glu Gln Leu Thr Cys Lys Asp Leu Val Ser Cys Ala
            580                 585                 590

Tyr Gln Val Ala Arg Gly Met Glu Tyr Leu Ala Ser Gln Lys Cys Ile
        595                 600                 605

His Arg Asp Leu Ala Ala Arg Asn Val Leu Val Thr Glu Asp Asn Val
    610                 615                 620

Met Lys Ile Ala Asp Phe Gly Leu Ala Arg Asp Val His Asn Leu Asp
625                 630                 635                 640

Tyr Tyr Lys Lys Thr Thr Asn Gly Arg Leu Pro Val Lys Trp Met Ala
                645                 650                 655

Pro Glu Ala Leu Phe Asp Arg Val Tyr Thr His Gln Ser Asp Val Trp
            660                 665                 670

Ser Phe Gly Val Leu Leu Trp Glu Ile Phe Thr Leu Gly Gly Ser Pro
        675                 680                 685

Tyr Pro Gly Ile Pro Val Glu Glu Leu Phe Lys Leu Leu Lys Glu Gly
    690                 695                 700

His Arg Met Asp Lys Pro Ala Ser Cys Thr His Asp Leu Tyr Met Ile
705                 710                 715                 720

Met Arg Glu Cys Trp His Ala Val Pro Ser Gln Arg Pro Thr Phe Lys
                725                 730                 735

Gln Leu Val Glu Asp Leu Asp Arg Ile Leu Thr Val Thr Ser Thr Asp
            740                 745                 750

Glu Tyr Leu Asp Leu Ser Val Pro Phe Glu Gln Tyr Ser Pro Gly Gly
        755                 760                 765

Gln Asp Thr Pro Ser Ser Ser Ser Gly Asp Asp Ser Val Phe Thr
    770                 775                 780

His Asp Leu Leu Pro Pro Gly Pro Pro Ser Asn Gly Gly Pro Arg Thr
785                 790                 795                 800

<210> SEQ ID NO 101
<211> LENGTH: 15
<212> TYPE: DNA
<213> ORGANISM: Artificial Sequence
<220> FEATURE:
<223> OTHER INFORMATION: primer sequence fgfr3c rev

<400> SEQUENCE: 101
ctccttgtcg gtggt                                                    15

<210> SEQ ID NO 102
<211> LENGTH: 15
<212> TYPE: DNA
<213> ORGANISM: Artificial Sequence
<220> FEATURE:
<223> OTHER INFORMATION: primer sequence fgfr3c fwd

<400> SEQUENCE: 102
acggcacgcc ctacg                                                    15

<210> SEQ ID NO 103
<211> LENGTH: 11
<212> TYPE: PRT
<213> ORGANISM: Artificial Sequence
<220> FEATURE:
<223> OTHER INFORMATION: FGF fragment

<400> SEQUENCE: 103

Val Thr Val Gln Ser Ser Pro Asn Phe Thr Gln
1               5                   10
```

<210> SEQ ID NO 104
<211> LENGTH: 33
<212> TYPE: DNA
<213> ORGANISM: Artificial Sequence
<220> FEATURE:
<223> OTHER INFORMATION: FGF fragment

<400> SEQUENCE: 104
gtaactgttc agtcctcacc taattttaca cag                                   33

<210> SEQ ID NO 105
<211> LENGTH: 12
<212> TYPE: PRT
<213> ORGANISM: Artificial Sequence
<220> FEATURE:
<223> OTHER INFORMATION: FGF fragment

<400> SEQUENCE: 105

Gln Val Thr Val Gln Ser Ser Pro Asn Phe Thr Gln
1               5                   10

<210> SEQ ID NO 106
<211> LENGTH: 11
<212> TYPE: PRT
<213> ORGANISM: Artificial Sequence
<220> FEATURE:
<223> OTHER INFORMATION: FGF fragment

<400> SEQUENCE: 106

Gln Val Thr Val Gln Ser Ser Pro Asn Phe Thr
1               5                   10

<210> SEQ ID NO 107
<211> LENGTH: 4
<212> TYPE: PRT
<213> ORGANISM: Artificial Sequence
<220> FEATURE:
<223> OTHER INFORMATION: FGF fragment

<400> SEQUENCE: 107

Ser Pro Asn Phe
1

<210> SEQ ID NO 108
<211> LENGTH: 6
<212> TYPE: PRT
<213> ORGANISM: Artificial Sequence
<220> FEATURE:
<223> OTHER INFORMATION: FGF fragment
<220> FEATURE:
<221> NAME/KEY: VARIANT
<222> LOCATION: 5
<223> OTHER INFORMATION: X may be T or N

<400> SEQUENCE: 108

Ser Pro Asn Phe Xaa Gln
1               5

<210> SEQ ID NO 109
<211> LENGTH: 15
<212> TYPE: PRT
<213> ORGANISM: Artificial Sequence
<220> FEATURE:
<223> OTHER INFORMATION: FGF fragment

<400> SEQUENCE: 109

```
Val Thr Val Gln Ser Ser Pro Asn Phe Thr Gln Ser Pro Asn Phe
1               5                   10                  15

<210> SEQ ID NO 110
<211> LENGTH: 12
<212> TYPE: PRT
<213> ORGANISM: Artificial Sequence
<220> FEATURE:
<223> OTHER INFORMATION: FGF fragment

<400> SEQUENCE: 110

Gln Val Thr Val Gln Ser Ser Pro Asn Phe Asn Gln
1               5                   10

<210> SEQ ID NO 111
<211> LENGTH: 4
<212> TYPE: PRT
<213> ORGANISM: Artificial Sequence
<220> FEATURE:
<223> OTHER INFORMATION: Cluster of basic amino acids
<220> FEATURE:
<221> NAME/KEY: VARIANT
<222> LOCATION: 1
<223> OTHER INFORMATION: Xaa may be any amino acid
<220> FEATURE:
<221> NAME/KEY: VARIANT
<222> LOCATION: 4
<223> OTHER INFORMATION: Xaa may be any amino acid

<400> SEQUENCE: 111

Xaa Asx Asx Xaa
1

<210> SEQ ID NO 112
<211> LENGTH: 5
<212> TYPE: PRT
<213> ORGANISM: Artificial Sequence
<220> FEATURE:
<223> OTHER INFORMATION: Cluster of basic amino acids
<220> FEATURE:
<221> NAME/KEY: VARIANT
<222> LOCATION: 1
<223> OTHER INFORMATION: Xaa may be any amino acid
<220> FEATURE:
<221> NAME/KEY: VARIANT
<222> LOCATION: 5
<223> OTHER INFORMATION: Xaa may be any amino acid

<400> SEQUENCE: 112

Xaa Asx Asx Asx Xaa
1               5
```